US012790326B2

(12) United States Patent
Bartolozzi et al.

(10) Patent No.: US 12,790,326 B2
(45) Date of Patent: Nov. 10, 2026

(54) PYRIDOPYRIMIDINONE DERIVATIVES AS AHR ANTAGONISTS

(71) Applicant: Sail Biomedicines, Inc., Cambridge, MA (US)

(72) Inventors: Alessandra Bartolozzi, Gladwyne, PA (US); John Robert Proudfoot, Newtown, CT (US); Timothy Briggs, Waltham, MA (US); John Mancuso, Sainte-Marthe-sur-le-Lac (CA); Karunakar Reddy Bonepally, Montreal (CA); Patrick Bureau, Kirkland (CA); Tianlin Guo, Montreal (CA); Maxence Bos, Montreal (CA); Anna Blois, Chestnut Hill, MA (US); Bernard Lanter, Somerville, MA (US); Steven John Taylor, Winchester, MA (US); Leonard Buckbinder, East Greenwich, RI (US); Francesca Barone, Solihull (GB)

(73) Assignee: Sail Biomedicines, Inc., Cambridge, MA (US)

( * ) Notice: Subject to any disclaimer, the term of this patent is extended or adjusted under 35 U.S.C. 154(b) by 1182 days.

(21) Appl. No.: 17/756,243

(22) PCT Filed: Nov. 20, 2020

(86) PCT No.: PCT/US2020/061548

§ 371 (c)(1),
(2) Date: May 19, 2022

(87) PCT Pub. No.: WO2021/102288

PCT Pub. Date: May 27, 2021

(65) Prior Publication Data

US 2023/0295152 A1 Sep. 21, 2023

Related U.S. Application Data

(60) Provisional application No. 63/091,192, filed on Oct. 13, 2020, provisional application No. 63/050,416, (Continued)

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC ...... C07D 471/04; A61P 35/00; A61K 31/519
See application file for complete search history.

(56) References Cited

U.S. PATENT DOCUMENTS

| | | | |
|---|---|---|---|
| 3,646,049 | A | 2/1972 | Hoff et al. |
| 10,570,138 | B2 | 2/2020 | Castro et al. |

(Continued)

FOREIGN PATENT DOCUMENTS

| | | | |
|---|---|---|---|
| CN | 101547922 | A | 9/2009 |
| CN | 115443276 | A | 12/2022 |

(Continued)

OTHER PUBLICATIONS

Haarmann-Stemmann, Thomas et al. "The Janus-facedness of the aryl hydrocarbon receptor pathway Report of the 6th International AHR Meeting: Research, Prevention, Therapy." Biochemical pharmacology vol. 234 (2025): 116808. doi: 10.1016/j.bcp.2025.116808 (Year: 2025).*

(Continued)

*Primary Examiner* — Sarah Pihonak
*Assistant Examiner* — Jackson J Hernandez
(74) *Attorney, Agent, or Firm* — McNeill PLLC

(57) ABSTRACT

The present disclosure relates to compounds of formula (Ia) and pharmaceutically acceptable salts thereof, pharmaceu- (Continued)

tical compositions comprising the same, methods of preparing the same, intermediate compounds useful for preparing the same, and methods for treating or prophylaxis of diseases, in particular cancer or conditions with dysregulated immune responses or other disorders associated with aberrant AHR signaling. These compounds may also be useful in treating cancer when administered in combination with at least one additional therapy.

(Ia)

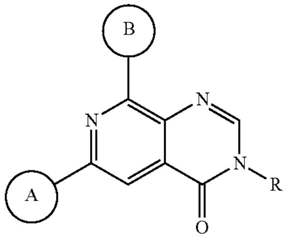

23 Claims, 17 Drawing Sheets

Related U.S. Application Data filed on Jul. 10, 2020, provisional application No. 62/939,377, filed on Nov. 22, 2019.

(56) References Cited

U.S. PATENT DOCUMENTS

| | | | |
|---|---|---|---|
| 10,696,650 | B2 | 6/2020 | Castro et al. |
| 11,040,035 | B2 | 6/2021 | Schmees et al. |
| 11,304,946 | B2 | 4/2022 | Lefranc et al. |
| 11,459,312 | B2 | 10/2022 | Zorn et al. |
| 2005/0288311 | A1 | 12/2005 | Rault et al. |
| 2012/0295904 | A1 | 11/2012 | Zhi et al. |
| 2020/0283395 | A1 | 9/2020 | Lefranc et al. |
| 2021/0017153 | A1 | 1/2021 | Castro et al. |
| 2022/0195533 | A1 | 6/2022 | Opitz et al. |
| 2022/0233513 | A1 | 7/2022 | Li et al. |
| 2023/0121195 | A1 | 4/2023 | Gutcher et al. |
| 2023/0234967 | A1 | 7/2023 | Bartolozzi et al. |

FOREIGN PATENT DOCUMENTS

| | | | |
|---|---|---|---|
| EP | 3713923 | A1 | 9/2020 |
| EP | 3974422 | A1 | 3/2022 |
| WO | 2004/077058 | A1 | 9/2004 |
| WO | 200841118 | A2 | 4/2008 |
| WO | 2010/008843 | A1 | 1/2010 |
| WO | 2010/008847 | A2 | 1/2010 |
| WO | 2010/100144 | A1 | 9/2010 |
| WO | 2010/144909 | A1 | 12/2010 |
| WO | 2016/046530 | A1 | 3/2016 |
| WO | WO 2017/202816 | A1 | 11/2017 |
| WO | 2018/141857 | A1 | 8/2018 |
| WO | WO 2018/146010 | A1 | 8/2018 |
| WO | WO 2018/195397 | A2 | 10/2018 |
| WO | WO 2019/036657 | A1 | 2/2019 |
| WO | 2019/101643 | A1 | 5/2019 |
| WO | WO 2019/156987 | A1 | 8/2019 |
| WO | 2019/178542 | A1 | 9/2019 |
| WO | 2020/021024 | A1 | 1/2020 |
| WO | 2020/051207 | A2 | 3/2020 |
| WO | 2020/081636 | A1 | 4/2020 |
| WO | WO 2020/233641 | A1 | 11/2020 |
| WO | 2021/028382 | A1 | 2/2021 |
| WO | 2021/102288 | A1 | 5/2021 |
| WO | 2021/108469 | A1 | 6/2021 |
| WO | 2021/108528 | A1 | 6/2021 |
| WO | 2021/122434 | A1 | 6/2021 |
| WO | 2021/127301 | A1 | 6/2021 |
| WO | 2021/127302 | A1 | 6/2021 |
| WO | 2021/142180 | A1 | 7/2021 |
| WO | 2021/210970 | A1 | 10/2021 |
| WO | 2021/236717 | A1 | 11/2021 |
| WO | 2021/242955 | A1 | 12/2021 |
| WO | 2022/029063 | A1 | 2/2022 |
| WO | 2022/081649 | A1 | 4/2022 |
| WO | 2022/094567 | A1 | 5/2022 |
| WO | 2022/133480 | A1 | 6/2022 |

OTHER PUBLICATIONS

Adis Insight, "BAY 218" Drug Profile; Bayer, Last Updated: May 3, 2019; 9 pages.

Adis Insight, "BAY 2416964" Drug Profile; Bayer, Last Updated: Oct. 2, 2021; 12 pages.

Adis Insight, "HP 163" Drug Profile; Hercules Pharmaceuticals, Last Updated: Sep. 21, 2020; 10 pages.

Adis Insight, "IK 175" Drug Profile; Ikena Oncology, Last Updated: Aug. 20, 2021; 18 pages.

Adis Insight, "IK 175" Drug Profile; Ikena Oncology, Last Updated: May 6, 2022; 14 pages.

Adis Insight, "Research programme: immuno-oncology therapies—Jaguahr Therapeutics," Drug Profile; Jaguahr Therapeutics, Last Updated: Jun. 24, 2021; 8 pages.

Aggen, D.H. et al., "(661) Initial Results from a Phase 1a/b Study of IK-175, an Oral AHR Inhibitor, as Single Agent and in Combination with Nivolumab in Patients with Advanced Solid Tumors and Urothelial Cancer," Ikena Oncology, Poster, Nov. 7, 2022.

Andersson, P. et al., "A constitutively active dioxin/aryl hydrocarbon receptor induces stomach tumors," PNAS, vol. 99; No. 15; 9990-9995 (2002).

Antonia, S.J. et al., "Durvalumab after Chemoradiotherapy in Stage III Non-Small-Cell Lung Cancer," N Engl J Med, vol. 377; No. 20; 1919-1929 (2017).

Bayer Pharmaceuticals, "BAY 2416964: The first Aryl Hydrocarbon Receptor (AhR) inhibitor to enter phase I clinical development as a novel cancer immunotherapy," Photograph of Powerpoint Slide 19, 1 Page, Presented at AACR Virtual Annual Meeting | 2020 (Apr. 27, 2020).

Bayer Pharmaceuticals, "BAY 2416964 Is a Highly Selective AhR Inhibitor," Powerpoint Slide, 1 Page (2020).

Bayer Pharmaceuticals, "Identification of BAY-218, a potent and selective small-molecule AhR inhibitor, as a new modality to counteract tumor immunosuppression," Powerpoint Slide 10, 1 Page, Presented at AACR Annual Meeting 2019 (Apr. 2, 2019).

Bui, L. et al., "Nedd9/Hef1/Cas-L mediates the effects of environmental pollutants on cell migration and plasticity," Oncogene, vol. 28; 3642-3651 (2009).

Campesato, L.F. et al., "Blockade of the AHR restricts a Treg-macrophage suppressive axis induced by L-Kynurenine," Nature Communications, vol. 11; 4011; 11 pages (2020).

Campesato, L.F. et al., "Blockade of the AHR restricts a Treg-macrophage suppressive axis induced by L-Kynurenine," Nature Communications, vol. 11; 4011; Reporting Summary (2020).

Campesato, L.F. et al., "Blockade of the AHR restricts a Treg-macrophage suppressive axis induced by L-Kynurenine," Nature Communications, vol. 11; 4011; Supplementary Data (2020).

Cella, D. et al., "Patient-reported outcomes of patients with advanced renal cell carcinoma treated with nivolumab plus ipilimumab versus sunitinib (CheckMate 214): a randomised, phase 3 trial," Lancet Oncol., vol. 20; No. 2; 297-310 (2019).

Chamoto et al., "Role of PD-1 in Immunity and Diseases," Curr Top Microbiol Immunol., 2017, 410, 75-97.

Das, S. and Johnson, D.B., "Immune-related adverse events and anti-tumor efficacy of immune checkpoint inhibitors," Journal of Immuno Therapy of Cancer, vol. 7; 306; 11 Pages (2019).

(56) References Cited

OTHER PUBLICATIONS

Di Meglio, P. et al., "Activation of the Aryl Hydrocarbon Receptor Dampens the Severity of Inflammatory Skin Conditions," Immunity, vol. 40; 989-1001 (2014).
Di Meglio, P. et al., "Activation of the Aryl Hydrocarbon Receptor Dampens the Severity of Inflammatory Skin Conditions," Immunity, vol. 40; 989-1001; Supplemental Information (2014).
Dieterich, W. et al., "Microbiota in the Gastrointestinal Tract," Med. Sci., vol. 6; No. 4; 116; 15 Pages (2018).
Dietrich, C. and Kaina, B., "The aryl hydrocarbon receptor (AhR) in the regulation of cell-cell contract and tumor growth," Carcinogenesis, vol. 31; No. 8; 1319-1328 (2010).
DiNatale, B.C. et al., "Kynurenic Acid is a Potent Endogenous Aryl Hydrocarbon Receptor Ligand that Synergistically Induces Interleukin-6 in the Presence of Inflammatory Signaling," Toxicol. Sci, vol. 115; No. 1; 89-97 (2010).
Donaldson, G.P. et al., "Gut biogeography of the bacterial microbiota," Nat Rev Microbiol, vol. 14; No. 1; 20-32 (2016).
Esser, C. et al., "The aryl hydrocarbon receptor in immunity," Trends Immunol., 2009, 30, 447-454.
Fallarino, F. et al., "T cell apoptosis by tryptophan catabolism" Cell Death Differ, 2002, 9(10), 1069-1077.
Ferns, D.M. et al., "Indoleamine-2,3-dioxygenase (IDO) metabolic activity is detrimental for cervical cancer patient survival," Oncoimmunology, 2015, 4(2); e981457-2.
Fife, B.T. and Bluestone, J.A., "Control of peripheral T-cell tolerance and autoimmunity via the CTLA-4 and PD-1 pathways," Immunol Rev., 2008, 224, 166-182.
Funatake et al., "Cutting Edge: Activation of the Aryl Hydrocarbon Receptor by 2,3,7,8-Tetrachlorodibenzo-p-dioxin Generates a Population of CD4+CD25+ Cells with Characteristics of Regulatory T Cells," J Immunol, 2005, 175(7), 4184-4188.
G. Kulkarni Ravindra et al: "Synthesis, p38 kinase inhibitory and anti-inflammatory activity of new substituted benzimidazole derivatives." Medicinal Chemistry vol. 9. No. 1 (2013): pp. 91-99.
Gandhi, L. et al., "Pembrolizumab plus Chemotherapy in Metastatic Non-Small-Cell Lung Cancer," N Engl J Med, 2018, 378(22) 2078-2092.
Gargaro, M. et al., "Indoleamine 2,3-dioxygenase 1 activation in mature cDC1 promotes tolerogenic education of inflammatory cDC2 via metabolic communication," Immunity, vol. 55; 1032-1050 (2022).
Gopalakrishnan et al., "Gut microbiome modulates response to anti-PD-1 immunotherapy in melanoma patients," Science, 2018, 359(6371), 97-103.
Gramatzki, D. et al., "Aryl hydrocarbon receptor inhibition downregulates the TGF-B/Smad pathway in human glioblastoma cells," Oncogene, 2009, 28, 28, 2593-2605.
Gutcher Ilona et al.: "Blocking tumor-associated immune suppression with BAY-218, a novel, selective aryl hydrocarbon receptor (AhR) inhibitor." Cancer Research 79.13_Supplement (2019): 1288-1288.
Hankinson et al., "Role of coactivators in transcriptional activation by the aryl hydrocarbon receptor," Arch Biochem Biophys, 2005, 433(2), 379-386.
Hezaveh, K. et al., "Tryptophan-derived microbial metabolites activate the aryl hydrocarbon receptor in tumor-associated macrophages to suppress anti-tumor immunity," Immunity, vol. 55; 324-340 (2022).
Hidaka, T. et al., "Aryl Hydrocarbon Receptor Modulates Carcinogenesis and Maintenance of Skin Cancers," Frontiers in Medicine, vol. 6; Article 194; 7 pages (2019).
Hoffman, T., "Discovery of Small Molecule Aryl Hydrocarbon Receptor (AhR) Antagonists for Cancer Immunotherapy," Discovery on Target, Boston Massachusetts, Presentation; 30 pages (2019).
Horsman, M.R. et al., "Tumors Resistant to Checkpoint Inhibitors Can Become Sensitive after Treatment with Vascular Disrupting Agents," Int J Mol Sci, 2020, 21(13). 4778.
Ikena Oncology. (2022) Form 10-K 2021. U.S. Securities and Exchange Commission.
Ikena Oncology. (2022) Form 8-K Apr. 6, 2022. U.S. Securities and Exchange Commission.
Karayama M et al.: "Comprehensive assessment of multiple tryptophan metabolites as potential biomarkers for immune checkpoint inhibitors in patients with non-small cell lung cancer." Clinical and Translational Oncology 2, 3 (2021): pp. 418-423.
Kenison, J.E. et al., "The aryl hydrocarbon receptor suppresses immunity to oral squamous cell carcinoma through immune checkpoint regulation," PNAS, vol. 118; No. 19; e2012692118; 12 pages (2021).
Kim, N. et al., "Discovery of novel HCV polymerase inhibitors using pharmacophore-based virtual screening," Bioorganic & medicinal chemistry letters vol. 21.No. 11 (2011): pp. 3329-3334.
Kim, S. et al., "Novel Compound 2-Methyl-2H-pyrazole-3-carboxylic Acid (2-methyl-4-o-tolylazo-phenyl)-amide (CH-223191) Prevents 2,3,7,8-TCDD-Induced Toxicity by Antagonizing the Aryl Hydrocarbon Receptor," Molecular Pharmacology, vol. 69; No. 6; 1871-1878 (2006).
Lin, L. and Zhang, J., "Role of intestinal microbiota and metabolites on gut homeostasis and human diseases," BMC Immunol., 2017, 18(1), 2.
Liu, X. et al., "Selective inhibition of IDO1 effectively regulates mediators of antitumor immunity," Blood, vol. 115; No. 17; 3520-3530 (2010).
Liu, X. et al., "The serratus anterior plan block for analgesia after thoracic surgery," Medicine, vol. 99; No. 21; 8 pages (2020).
Matson et al., "The commensal microbiome is associated with anti-PD-1 efficacy in metastatic melanoma patients," Science, 2018, 359(6371) 104-108.
McGovern, K. et al., "Discovery and characterization of a novel aryl hydrocarbon receptor inhibitor, IK-175, and its inhibitory activity on tumor immune suppression," Mol Cancer Ther (2022) 21 (8): 1261-1272.
McKean, M.A. et al., "A Phase 1a/b Study of IK-175, an Oral AHR Inhibitor, Alone and in Combination with Nivolumab in Patients with Locally Advanced or Metastatic Solid Tumors and Urothelial Carcinoma," Ikena Oncology, SITC 36th Annual Meeting, Poster #550, Nov. 13, 2021.
Metz, R. et al., "Novel Tryptophan Catabolic Enzyme IDO2 Is the Preferred Biochemical Target of the Antitumor Indoleamine 2,3-Dioxygenase Inhibitory Compound D-1-Methyl-Tryptophan," Cancer Res, 2007, 67, 15; 7082-7087.
Mezrich, J.D. et al., "An Interaction between Kynurenine and the Aryl Hydrocarbon Receptor Can Generate Regulatory T Cells," J Immunol, 2010, 185, 6, 3190-3198.
Mo, Z. et al., "A Comprehensive Pan-Cancer Analysis of 33 Human Cancers Reveals the Immunotherapeutic Value of Aryl Hydrocarbon Receptor," Frontiers in Immunology, vol. 12; Article 564948; 13 pages (2021).
Muller, A.J. et al., "Inhibiting IDO pathways to treat cancer: lessons from the ECHO-301 trial and beyond," Semin Immunopathol., 2019, 41(1), 9 pages.
Muller, A.J. et al., "Inhibition of indoleamine 2,3-dioxygenase, an immunoregulatory target of the cancer suppression gene Bin 1, potentiates cancer chemotherapy," Nat Med, 11, 3, 312-319 (No date available).
Nguyen, L.P. and Bradfield, C.A., "The Search for Endogenous Activators of the Hydrocarbon Receptor," Chem Res Toxicol, vol. 21; No. 1; 102-116 (2008).
Nguyen, N.T. et al., "Aryl hydrocarbon receptor and kynurenine: recent advances in autoimmune disease research," Front. Immunol., vol. 5; Article 551; 6 Pages (2014).
Nguyen, N.T. et al., "Aryl hydrocarbon receptor negatively regulates dendritic cell immunogenicity via a kynurenine-dependent mechanism," PNAS, vol. 107; No. 46; 19961-19966 (2010).
Notification Concerning Transmittal of International Preliminary Report on Patentability for International Application No. PCT/US2020/061548, mailed Jun. 2, 2022.
Notification of Transmittal of the International Search Report and Written Opinion for International Application No. PCT/US2021/054698, mailed Feb. 4, 2022.

(56) References Cited

OTHER PUBLICATIONS

Opitz Christiane A et al: "The therapeutic potential of targeting tryptophan catabolismin cancer." British journal of cancer vol. 122.No. 1 (2020): pp. 30-44.
Opitz, C.A. et al., "An endogenous tumour-promoting ligand of the human aryl hydrocarbon receptor," Nature, vol. 478; 197-203 (2011).
Pandiyan, P. et al., "Microbiome Dependent Regulation of Tregs and Th17 Cells in Mucosa," Front Immunol, vol. 10; Article 426; 17 Pages (2019).
Paris, A. et al., "AhR and Cancer: From Gene Profiling to Targeted Therapy," International Journal of Molecular Sciences, vol. 22; 752; 22 pages (2021).
Platten, M. et al., "Cancer immunotherapy by targeting IDO1/TDO and their downstream effectors," Front Immunol., vol. 5; Article 673; 7 Pages (2015).
Qin, S. et al., "Novel immune checkpoint targets: moving beyond PD-1 and CTLA-4," Molecular Cancer, vol. 18; 155; 14 Pages (2019).
Quintana, F.J. and Weiner, H.L., "Environmental control of Th17 differentiation," Eur J Immunol., vol. 39; No. 3; 655-657 (2009).
Quintana, F.J. et al., "Control of Treg and Th17 cell differentiation by the aryl hydrocarbon receptor," Nature, vol. 453; 65-71 (2008).
Reyes, H. et al., "Identification of the Ah receptor nuclear translocator protein (Arnt) as a component of the DNA binding form of the Ah receptor," Science, 1992, 256, 5060, 1193-1195.
Richards M L et al: "Substituted 2-phenyl-benzimidazole derivatives: novel compounds that suppress key markers of allergy." European journal of medicinal chemistry vol. 41. No. 8 (2006): pp. 950-969.
Rossi, M. and Bot, A., "The Th17 Cell Population and the Immune Homeostasis of the Gastrointestinal Tract," Int Rev Immunol, 2013, 32(5-6), 471-474.
Rothhammer, V. and Quintana, F.J., "The aryl hydrocarbon receptor: an environmental sensor integrating immune responses in health and disease," Nat Rev Immunol., 2019, 19(3), 184-197.
Routy, B. et al., "Gut microbiome influences efficacy of PD-1-based immunotherapy against epithelial tumors," Science, 2018, 359(6371), 91-97.
Safe, Stephen, et al. "Aryl hydrocarbon receptor (AHR) ligands as selective AHR modulators (SAhRMs)." International journal of molecular sciences vol. 21. No. 6654 (2020).
Sanchez-Martin, M. et al., "Computational Biology and Tissue-based Approaches to Inform Indication Selection for Novel AHR Inhibitor," Presented in Boston, Massachusetts, SITC 36th Annual Meeting, Abstract 15472; Poster# 93, Nov. 12, 2021.
Socinski, M.A. et al., "Atezolizumab for First-Line Treatment of Metastatic Nonsquamous NSCLC," N Engl J Med, vol. 378; No. 24; 2288-2301 (2018).
Suzuki, Y. et al., "Increased serum kynurenine/tryptophan ratio correlates with disease progression in lung cancer," et al., Lung Cancer, 2010, 67(3), 361-365.
Tsai, H. and Hsu, P., "Cancer immunotherapy by targeting immune checkpoints: mechanism of T cell dysfunction in cancer immunity and new therapeutic targets," Journal of Biomedical Science, vol. 24; No. 35; 8 Pages (2017).
Uyttenhove, C. et al., "Evidence for a tumoral immune resistance mechanism based on tryptophan degradation by indoleamine 2,3-dioxygenase," Nat Med, 2003, 9, 10, 1269-1274.
Veldhoen, M. et al., "Natural agonists for aryl hydrocarbon receptor in culture medium are essential for optimal differentiation of Th17 T cells," J. Exp. Med., vol. 206; No. 1; 43-49 (2009).
Veldhoen, M. et al., "Natural agonists for aryl hydrocarbon receptor in culture medium are essential for optimal differentiation of Th17 T cells," J. Exp. Med., vol. 206; No. 1; 43-49; Supplemental Material (2009).
Veldhoen, M. et al., "The aryl hydrocarbon receptor links TH17-cell-mediated autoimmunity to environmental toxins," Nature, vol. 453; 106-109 (2008).
Veldhoen, M. et al., "The aryl hydrocarbon receptor links TH17-cell-mediated autoimmunity to environmental toxins," Nature, vol. 453; 106-110 (2008). (Supplementary Information).
Vlaar, J. et al., "Recurrent activating mutations in AHR act as drivers of urinary tract cancer," BioRxiv 10.1101/2021.11.09.468005, 25 pages (2021).
Wang, C. et al., "Activation of the aryl hydrocarbon receptor affects activation and function of human monocyte-derived dendritic cells," Clin Exp Immunol., vol. 177; 521-530 (2014).
Wang, L. et al., "Analytical validation of a novel immunohistochemistry assay to determine nuclear AHR expression in human bladder cancer," Ikena Oncology, Inc., SITC 36th Annual Meeting, Poster #58; Nov. 13, 2021.
Wang, Z. et al., "How the AHR Became Important in Cancer: The Role of Chronically Active AHR in Cancer Aggression," International Journal of Molecular Sciences, vol. 22; 387; 22 pages (2021).
Wei, P. et al., "An aryl hydrocarbon receptor ligand acts on dendritic cells and T cells to suppress the Th17 response in allergic rhinitis patients," Lab Invest, vol. 94; No. 5; 528-535 (2014).
Wolchok, J.D. et al., "Overall Survival with Combined Nivolumab and Ipilimumab in Advanced Melanoma," N. Engl. J. Med., vol. 377; No. 14; 1345-1356 (2017).
Xiong, J. et al., "Aryl hydrocarbon receptor mediates Jak2/STAT3 signaling for non-small cell lung cancer stem cell maintenance," Exp Cell Res, 2020, 112288, 13 pages.
Yamada, T. et al., "Constitutive aryl hydrocarbon receptor signaling constrains type I interferon-mediated antiviral innate defense," Nat Immunol., vol. 17; No. 6; 687-694 (2016).
Yeste, A. et al., "IL-21 induces IL-22 production in CD4+ T-cells," Nat Commun, vol. 5; 3753; 29 pages (2014).
Yuan Xu et al.: "Design, synthesis and in vitro evaluation of 6-amide-2-aryl benzoxazole/benzimidazole derivatives against tumor cells by inhibiting VEGFR-2 kinase." European journal of medicinal chemistry vol. 179 (2019): pp. 147-165.
Zierer, J. et al., "The fecal metabolome as a functional readout of the gut microbiome," Nat Genet, vol. 50; No. 6; 790-795 (2018).
Chen, et al. "IDO, TDO, and AHR overexpression is associated with poor outcome in diffuse large B-cell lymphoma patients in the rituximab era", Medicine (Baltimore), May 22, 2020; 99(21), 8 pages.
International Search Report and Written Opinion received for PCT Patent Application No. PCT/US2021/034413, mailed on Oct. 14, 2021, 19 pages.
International Search Report issued for PCT Application No. PCT/US2021/033078, mailed Sep. 21, 2021 (6 pages).
Notification Concerning Transmittal of International Preliminary Report on Patentability for International Application No. PCT/US2021/033078, mailed Dec. 1, 2022.
Notification Concerning Transmittal of the International Preliminary Report on Patentability for International Application No. PCT/US2021/034413, mailed Dec. 8, 2022.
Gelling, I.R. et al., "Pyridopyrimidines. Part V. Syntheses and Properties of Pyrido[3,4-d]-pyrimidin-4(3H)-ones and -pyrimidine-2,4-(1H,3H)-diones", Journal of the Chemical Society C: Organic, No. 6, Jan. 1, 1969, p. 931, XP055058943.
International Search Report for International Application No. PCT/US2020/061548 dated Feb. 17, 2021, 4 pages.
Written Opinion for International Application No. PCT/US2020/061548 dated Feb. 17, 2021, 7 pages.
Bavetsias, V., Lanigan, R. M., Ruda, G. F., Atrash, B., Mclaughlin, M. G., Tumber, A., Blagg, J. (2016). 8-Substituted Pyrido[3,4-d]pyrimidin-4(3H)-one Derivatives as Potent, Cell Permeable, KDM4 (JMJD2) and KDM5 (JARID1) Histone Lysine Demethylase Inhibitors. Journal of Medicinal Chemistry, 59(4), 1388-1409.
Le Bihan, Yann-Vaï et al. "C8-substituted pyrido[3,4-d]pyrimidin-4(3H)-ones: Studies towards the identification of potent, cell penetrant Jumonji C domain containing histone lysine demethylase 4 subfamily (KDM4) inhibitors, compound profiling in cell-based target engagement assays." European journal of medicinal chemistry vol. 177 (2019): 316-337.
Li et. al. "Aryl Hydrocarbon Receptor Signaling Cell-intrinsically Inhibits Intestinal Group 2 Innate Lymphoid Cell Function" Immunity. 2018, 49, 5, 915-928 DOI: 10.1016/j.immuni.2018.09.015.

(56) References Cited

OTHER PUBLICATIONS

Roberts et. al. “Characterization of the Ah Receptor Mediating Aryl Hydrocarbon Hydroxylase Induction in the Human Liver Cell Line Hep GZ” Archives of Biochemistry and Biophysics, 1990, 276, 2, 442-450. DOI: 10.1016/0003-9861(90) 90743-1.
Wright et. al. “The Chemistry of the Benzimidazoles” Chem. Rev. 1951, 48, 397-541. DOI: 10.1021/cr60151a002. Only pp. 397-401.
Cushing T.D., et al. Journal of Medicinal Chemistry, “PI3Kdelta and PI3Kgamma as Targets for Autoimmune and Inflammatory Diseases,” Aug. 27, 2012, pp. 8559-8581.

* cited by examiner

PYRIDOPYRIMIDINONE DERIVATIVES AS AHR ANTAGONISTS

The present application is a national stage filing under 35 U.S.C. § 371 of International Application No. PCT/US2020/061548, filed on Nov. 20, 2020, which claims the benefit of priority to U.S. Patent Application No. 62/939,377 filed Nov. 22, 2019, U.S. Patent Application No. 63/050,416 filed Jul. 10, 2020, and U.S. Patent Application No. 63/091,192 filed Oct. 13, 2020. The disclosure of all which are hereby incorporated by reference in their entirety.

Disclosed herein are novel 3,6,8-trisubstituted pyrido[3,4-d]pyrimidin-4(3H)-one compounds of formula (Ia) and pharmaceutically acceptable salts thereof, methods of preparing said compounds and salts, intermediate compounds useful for preparing said compounds and salts, pharmaceutical compositions comprising said compounds and salts, and methods of using said compounds and salts for the treatment or prophylaxis of diseases, in particular of cancer or conditions with dysregulated immune responses or other disorders associated with aberrant AHR signaling. Also disclosed herein are compositions comprising at least one such compound and/or pharmaceutically acceptable salt thereof and at least one additional therapy and methods of treating cancer comprising administering at least one such compound and/or pharmaceutically acceptable salt thereof and at least one additional therapy.

(Ia)

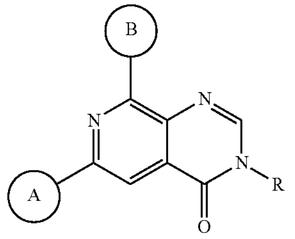

The Aryl Hydrocarbon Receptor (AHR) is a ligand-activated transcription factor, belonging to the basic helix-loop-helix/Per-Arnt-Sim (bHLH/PAS) family that is located in the cytosol. Upon ligand binding, the AHR translocates to the nucleus where it heterodimerises with ARNT (AHR Nuclear Translocator) upon which it interacts with DREs (Dioxin Response Elements) of AHR-responsive genes to regulate their transcription. The AHR is best known for binding to environmental toxins and inducing the metabolic machinery, such as cytochrome P 450 enzymes (eg. CYP1A1, CYP1A2 and CYP1B1), required for their elimination (Reyes et al., Science, 1992, 256(5060):1 193-5). Activation of AHR by xenobiotics has demonstrated its role in numerous cellular processes such as embryogenesis, tumorigenesis and inflammation.

AHR is expressed in many cells of the immune system, including dendritic cells (DCs), macrophages, T cells and NK cells, and plays an important role in immunoregulation (Nguyen et al., *Front. Immunol.,* 2014, 5:551). The classic exogenous AHR ligands TCDD and 3-methylcholanthrene, for example, are known to induce profound immunosuppression, promote carcinogenesis and induce tumour growth (Gramatzki et al., *Oncogene,* 2009, 28(28):2593-605; Bui et al., *Oncogene,* 2009, 28(41):3642-51; Esser et al., *Trends Immunol.,* 2009, 30:447-454). In the context of immunosuppression, AHR activation promotes regulatory T cell generation, inhibits Th1 and Th17 differentiation, directly and indirectly, and decreases the activation and maturation of DCs (Wang et al., *Clin. Exp. Immunol.,* 2014, 177(2):521-30; Mezrich et al., *J. Immunol.,* 2010, 185(6):3190-8; Wei et al., *Lab. Invest.,* 2014, 94(5):528-35; Nguyen et al., *PNAS,* 2010, 107(46):19961-6). AHR activation modulates the innate immune response and constitutive AHR expression has been shown to negatively regulate the type-1 interferon response to viral infection (Yamada et al., *Nat. Immunol.,* 2016, 17(6):687-94). Additionally, mice with a constitutively active AHR spontaneously develop tumours (Andersson et al., *PNAS,* 2002, 99(15):9990-5).

In addition to xenobiotics, the AHR can also bind metabolic products of tryptophan degradation. Tryptophan metabolites, such as kynurenine and kynurenic acid, are endogenous AHR ligands that activate the AHR under physiological conditions (DiNatale et al., *Toxicol. Sci.,* 2010, 115(1):89-97; Mezrich et al., *J. Immunol.,* 2010, 185(6):3190-8; Opitz et al., *Nature,* 2011, 478(7368):197-203). Other endogenous ligands are known to bind the AHR, although their physiological roles are currently unknown (Nguyen & Bradfield, *Chem. Res. Toxicol.,* 2008, 21(1):102-116).

The immunosuppressive properties of kynurenine and tryptophan degradation are well described and are implicated in cancer-associated immunosuppression. The enzymes indoleamine-2,3-dioxygenases 1 and 2 (IDO1/IDO2) as well as tryptophan-2,3-dioxygenase 2 (TDO2) are responsible for catalysing the first and rate-limiting step of tryptophan metabolism. IDO1/2-mediated degradation of tryptophan in tumours and tumour-draining lymph nodes reduces anti-tumour immune responses and inhibition of IDO can suppress tumour formation in animal models (Uyttenhove et al., *Nat. Med.,* 2003, 9(10):1269-74; Liu et al., *Blood,* 2005, 115(17): 3520-30; Muller et al., *Nat. Med.,* 11(3):312-9; Metz, *Cancer Res.,* 2007, 67(15):7082-7).

TDO2 is also strongly expressed in cancer and can lead to the production of Immunosuppressive kynurenine. In glioma, activation of the AHR by kynurenine, downstream of TDO-mediated tryptophan degradation, enhances tumour growth as a consequence of inhibiting anti-tumour immune responses as well as directly promoting tumour cell survival and motility (Opitz et al., Nature, 2011, 478(7368):197-203). AHR ligands generated by tumour cells therefore act in both an autocrine and paracrine fashion on tumour cells and lymphocytes, respectively, to promote tumour growth.

Additional therapies may be useful in the treatment of cancer in combination with AhR. Immune checkpoint inhibitors (ICIs) have been used in cancer treatment to enhance the immune response of the host. Non-limiting examples of ICI targets include programmed death 1 (PD-1), ligand for PD-1 (PD-L1) and Cytotoxic T lymphocyte antigen 4 (CTLA-4).

PD-1 is highly expressed by activated T cells, B cells, dendritic cells (DC), and natural killer cells (NK), whereas PD-L1 can be expressed on several types of tumor cells.

ICIs are currently approved by the Food and Drug Administration to treat melanoma, non-small cell lung cancer, renal cell carcinoma, head and neck squamous cell carcinoma, Hodgkin's lymphoma, urothelial carcinoma, small cell lung cancer, esophageal squamous cell carcinoma, cervical cancer, primary mediastinal large B-cell lymphoma, MSI-H/dMMR colorectal cancer, hepatocellular carcinoma, Merkel cell carcinoma, triple-negative breast cancer, and cutaneous squamous cell carcinoma.

The present disclosure is drawn to novel 3,6,8-trisubstituted pyrido[3,4-d]pyrimidin-4(3H)-one of formula (I) or formula (Ia) and/or pharmaceutically acceptable salts thereof. Compounds of the present disclosure have surprisingly been found to effectively inhibit AHR and may therefore be used for treatment or prophylaxis of cancer and/or other conditions where exogenous and endogenous AHR ligands induce dysregulated immune responses, uncontrolled cell growth, proliferation and/or survival of tumor cells, immunosuppression in the context of cancer, inappropriate cellular immune responses, or inappropriate cellular inflammatory responses or diseases that are accompanied by uncontrolled cell growth, proliferation and/or survival of tumor cells, immunosuppression in the context of cancer inappropriate cellular immune responses, or inappropriate cellular inflammatory responses, particularly in which the uncontrolled cell growth, proliferation and/or survival of tumor cells, immunosuppression in the context of cancer, inappropriate cellular immune responses, or inappropriate cellular inflammatory responses is mediated by AHR, such as, for example, liquid and solid tumors, and/or metastases thereof, e.g. head and neck tumors including brain tumors and brain metastases, tumors of the thorax including non-small cell and small cell lung tumors, gastrointestinal tumors including colon, colorectal and pancreatic tumors, liver tumors, endocrine tumors, mammary and other gynecological tumors, urological tumors including renal, bladder and prostate tumors, skin tumors, and sarcomas, and/or metastases thereof.

The present disclosure also relates to pharmaceutical compositions comprising at least one entity chosen from compounds of formula (I) or formula (Ia) and pharmaceutically acceptable salts thereof. The present disclosure also relates to methods of treatment comprising administering at least one compound, pharmaceutically acceptable salt thereof, and/or pharmaceutical composition of the present disclosure. In some embodiments, the disclosure provides a method of treating a disease or condition mediated by AHR signaling. In some embodiments, the disclosure provides a method of treating a disease or condition associated with aberrant AHR signaling. In some embodiments, the disclosure provides a method of inhibiting cancer cell proliferation mediated by AHR signaling.

Figure 1:
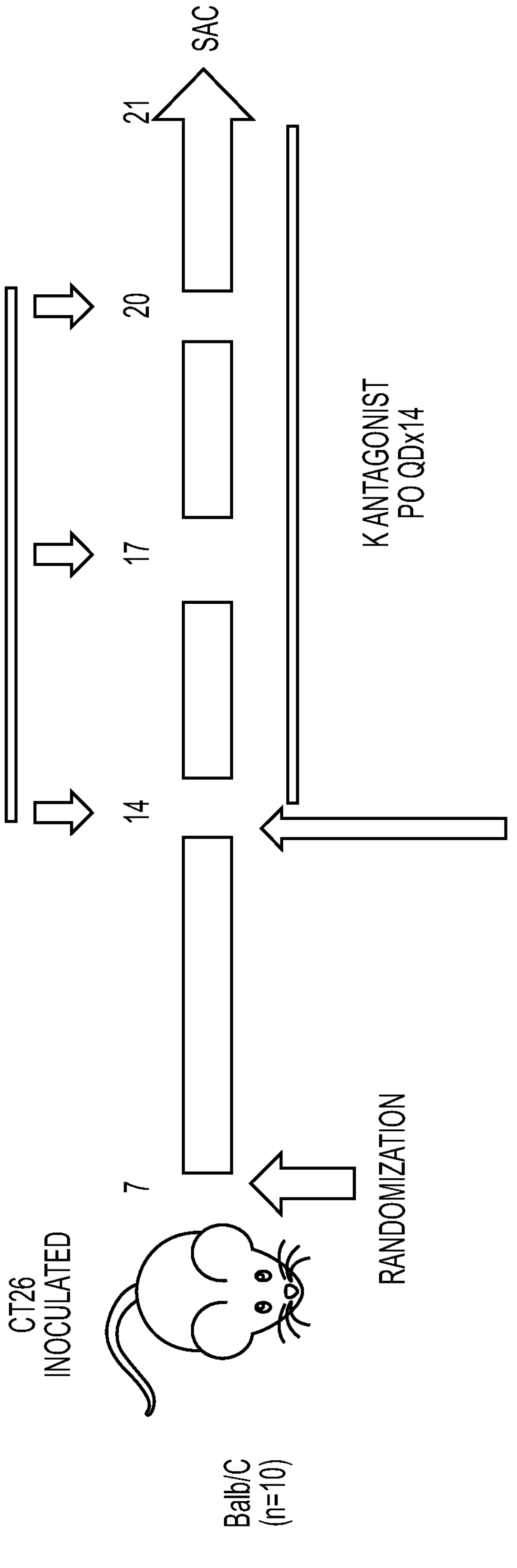
FIG. 1 shows the dosing regimen for the in vivo syngeneic model study using CT26 Balb/C mice.

As used herein, the term "pharmaceutically acceptable salt" refers to a salt that is pharmaceutically acceptable as defined herein and that has the desired pharmacological activity of the parent compound. Non-limiting examples of pharmaceutically acceptable salts include those derived from inorganic acids, non-limiting examples of which include hydrochloric acid, hydrobromic acid, hydroiodic acid, sulfuric acid, nitric acid, and phosphoric acid, and those derived from organic acids, non-limiting examples of which include acetic acid, trifluoroacetic acid, propionic acid, glycolic acid, pyruvic acid, oxalic acid, stearic acid, malic acid, maleic acid, malonic acid, salicylic acid, succinic acid, fumaric acid, tartaric acid, citric acid, benzoic acid, cinnamic acid, mandelic acid, p-toluenesulfonic acid, methanesulfonic acid, ethanesulfonic acid, and lactic acid.

Additional non-limiting examples of pharmaceutically acceptable salts include those formed when an acidic proton in a parent compound is replaced by a metal ion, non-limiting examples of which include an alkali metal ion and an alkaline earth metal ion, and those formed when an acidic proton present in a parent compound is replaced by a ammonium ion, a primary ammonium ion, a secondary ammonium ion, a tertiary ammonium ion, or a quaternary ammonium ion. Non-limiting examples of alkali metals and alkaline earth metals include sodium, potassium, lithium, calcium, aluminum, magnesium, copper, zinc, iron, and manganese. Additional non-limiting examples of pharmaceutically acceptable salts include those comprising one or more counterions and zwitterions.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. The same rule applies for any other ranges described herein, even if the values within the range are not specifically called out in this disclosure.

As used herein, the terms "checkpoint inhibitor" and "checkpoint inhibitor therapy" are used interchangeably to refer to any therapeutic agent, including any small molecule chemical compound, antibody, nucleic acid molecule, or polypeptide, or any fragments thereof, that inhibits one or more inhibitory pathways, thereby allowing more extensive immune activity. In some embodiments, a checkpoint inhibitor therapy comprises administering at least one checkpoint inhibitor to a patient in need of such treatment.

The term "compound," as used herein unless otherwise indicated, refers to a collection of molecules having an identical chemical structure as a collection of stereoisomers (for example, a collection of racemates, a collection of cis/trans stereoisomers, or a collection of (E) and (Z) stereoisomers). Therefore, geometric and conformational mixtures of the present compounds and salts are within the scope of the disclosure. Unless otherwise stated, all tautomeric forms of the compounds of the disclosure are within the scope of the disclosure.

"Stereoisomer" as used herein refers to enantiomers and diastereomers.

The term "tautomer," as used herein, refers to one of two or more isomers of a compound that exist together in equilibrium, and are readily interchanged by migration of an atom or group within the molecule.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a chemical group is described by its chemical formula or structure having a terminal bond moiety indicated by "—", it will be understood that the "—" represents the point of attachment. In some embodiments, a wavy line (i.e., ) depicts the point of attachment.

As used herein, an "acyl" or "alkanoyl" is a functional group with formula RCO— where R is bound to the carbon atom of the carbonyl functional group by a single bond and the "—" denotes the point of attachment to the rest of the molecule. Non-limiting examples of acyls include formyl (HC(O)—, also called methanoyl), acetyl ($CH_3C(O)$—, also called ethanoyl), and benzoyl (PhC(O)—).

The term "alkyl" or "aliphatic" as used herein, means a straight-chain (i.e., unbranched) or branched, substituted or unsubstituted hydrocarbon chain that is completely saturated and that has a single point of attachment to the rest of the molecule. Unless otherwise specified, an alkyl group is a hydrocarbon chain of 1 to 20 alkyl carbon atoms. In some embodiments, an alkyl group contains one to twelve carbon atoms ($C_1$-$C_{12}$). In some embodiments, an alkyl group contains one to eight carbon atoms ($C_1$-$C_8$). In some embodiments, an alkyl group contains one to six carbon atoms ($C_1$-$C_6$). In some embodiments, an alkyl group contains one to four carbon atoms ($C_1$-$C_4$). In some embodiments, a cyclic alkyl group contains three to six carbon atoms ($C_3$-$C_6$). Non-limiting examples of substituted and unsubstituted linear, branched, and cyclic alkyl groups include methyl, ethyl, n-propyl, iso-propyl, cyclopropyl, n-butyl, sec-butyl, iso-butyl, tert-butyl, cyclobutyl, cyclopentyl, cyclohexyl, hydroxymethyl, chloromethyl, fluoromethyl, trifluoromethyl, aminomethyl, 2-aminoethyl, 3-aminopropyl, 4-aminobutyl, dimethylaminomethyl, 2-dimethylaminoethyl, 3-dimethylaminopropyl, 4-dimethylaminobutyl, cyclopropylmethyl, cyclobutylmethyl, cyclopentylmethyl, trifluoroethyl, and trifluoropropyl.

"Alkoxy," as used herein, refers to an alkyl group, as previously defined, attached to the principal carbon chain through an oxygen ("alkoxy") atom.

"Halo" and "halogen," as used herein, are interchangeable and refer to halogen atoms such as fluoro (F), chloro (Cl), bromo (Br), and iodo (I).

"Haloalkyl" refers to an alkyl group substituted with one or more halo atoms (F, Cl, Br, I). For example, "fluoromethyl" refers to a methyl group substituted with one or more fluoro atoms (e.g., monofluoromethyl, difluoromethyl, or trifluoromethyl).

"Haloalkoxy" refers to an alkoxy group substituted with one or more halo atoms (F, Cl, Br, I). For example, "fluoromethoxy" refers to a methoxy group substituted with one or more fluoro atoms (e.g., monofluoromethoxy, difluoromethoxy, or trifluoromethoxy).

"Hydroxyalkyl" refers to an alkyl group substituted with one or more hydroxy groups (—OH).

The terms "cycloalkyl" and "cycloalkyl group" as used interchangeably herein refer to a cyclic saturated monovalent hydrocarbon radical of three to twelve carbon atoms that has a single point of attachment to the rest of the molecule. Cycloalkyl groups may be unsubstituted or substituted. In some embodiments, a cycloalkyl group comprises three to eight carbon atoms ($C_3$-$C_8$). In some embodiments, a cycloalkyl group comprises three to six carbon atoms ($C_3$-$C_6$). Non-limiting examples of substituted and unsubstituted cycloalkyls include cyclopropyl, cyclopropylmethyl, cyclobutyl, cyclobutylmethyl, cyclopentyl, cyclopentylmethyl, cyclohexyl, cycloheptyl, and cyclooctyl.

The terms "alkylene" and "alkylene group" as used interchangeably herein refer to a saturated divalent (i.e., having two points of attachment to the rest of the molecule) hydrocarbon radical comprising one to twelve carbon atoms ($C_1$-$C_{12}$). Alkylene groups may be linear, branched, or cyclic. Alkylene groups may be unsubstituted or substituted. In some embodiments, an alkylene group comprises one to eight carbon atoms ($C_1$-$C_8$). In some embodiments, an alkylene group comprises one to six carbon atoms ($C_1$-$C_6$). In some embodiments, an alkylene group comprises one to four carbon atoms ($C_1$-$C_4$). Non-limiting examples of alkylene groups include methylene and ethylene.

The terms "alkenyl" and "alkenyl group" as used interchangeably herein refer to a monovalent (i.e., having a single point of attachment to the rest of the molecule) hydrocarbon radical comprising two to eight carbon atoms ($C_2$-$C_8$) with at least one site of unsaturation (i.e., an sp2 carbon-carbon double bond). Alkenyl groups may be linear, branched, or cyclic. Alkenyl groups may be unsubstituted or substituted. In some embodiments, an alkenyl group contains two to six carbon atoms ($C_2$-$C_6$). In some embodiments, an alkenyl group contains two to four carbon atoms ($C_2$-$C_4$). Alkenyl groups may have E or Z orientations. Non-limiting examples of alkenyl groups include ethenyl (also called vinyl), 1-propenyl, iso-propenyl, and 2-chloroethenyl.

The terms "alkenylene" and "alkenylene group" as used interchangeably herein refer to a divalent (i.e., having two points of attachment to the rest of the molecule) hydrocarbon radical of two to eight carbon atoms ($C_2$-$C_8$) with at least one site of unsaturation (e.g., an sp2 carbon-carbon double bond). Alkenylene groups may be linear, branched, or cyclic. Alkenylene groups may be unsubstituted or substituted. In some embodiments, an alkylene group contains two to six carbon atoms ($C_2$-$C_6$). In some embodiments, an alkylene group contains two to four carbon atoms ($C_2$-$C_4$). Alkylene groups may have E or Z orientations. A non-limiting example of an alkenyl group is ethenylene (also called vinylene).

The terms "alkynyl" and "alkynyl group" as used interchangeably herein refer to a monovalent (i.e., having a single point of attachment to the rest of the molecule) hydrocarbon radical of two to eight carbon atoms ($C_2$-$C_8$) with at least one site of unsaturation (i.e., an sp carbon-carbon triple bond). Alkynyl groups may be linear or branched. Alkynyl groups may be unsubstituted or substituted. In some embodiments, an alkynyl group contains two to six carbon atoms ($C_2$-$C_6$). In some embodiments, an alkynyl group contains two to four carbon atoms ($C_2$-$C_4$). A non-limiting example of an alkynyl group is ethynyl.

The terms "alkynylene" and "alkynylene group" as used interchangeably herein refer to a divalent (i.e., having two points of attachment to the rest of the molecule) hydrocarbon radical of two to eight carbon atoms ($C_2$-$C_8$) with at least one site of unsaturation (i.e., an sp carbon-carbon triple bond). Alkynylene groups may be linear or branched. Alkynylene groups may be unsubstituted or substituted. In some embodiments, an alkynylene group contains two to six carbon atoms ($C_2$-$C_6$). In some embodiments, an alkynylene group contains two to four carbon atoms ($C_2$-$C_4$). A non-limiting example of an alkynylene group is ethynylene.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Nonlimiting examples of aromatic groups include aryl and heteroaryl groups.

The terms "aryl" and "aryl group" as used interchangeably herein refer to a monovalent (i.e., having a single point of attachment to the rest of the molecule) aromatic hydrocarbon radical of 6-20 carbon atoms ($C_6$-$C_{20}$). Aryl groups can be unsubstituted or substituted. Non-limiting examples of unsubstituted and substituted aryl groups include phenyl, 2-fluorophenyl, 3-fluorophenyl, 4-fluorophenyl, 2-methylphenyl, 3-methylphenyl, 4-methylphenyl, 2-chlorophenyl, 3-chlorophenyl, 4-chlorophenyl, 2,6-dichlorophenyl, 3,4-difluorophenyl, 2-hydroxyphenyl, 3-hydroxyphenyl, 4-hydroxyphenyl, 2-methoxyphenyl, 3-methoxyphenyl, 4-methoxyphenyl, 2-phenoxyphenyl, 3-phenoxyphenyl, 4-phenoxyphenyl, 2-cyanophenyl, 3-cyanophenyl, 4-cyanophenyl, 2-dimethylaminophenyl, 3-dimethylaminophenyl, 4-dimethylaminophenyl, 3-methylsulfonylphenyl, 4-methylsulfonylphenyl, 3-aminophenyl, 3-methylaminophenyl, 3-(2-hydroxyethoxy)phenyl, 2-trifluoromethylphenyl, 3-trifluoromethylphenyl, 4-trifluoromethylphenyl, 2-isopropylphenyl, 3-isopropylphenyl, 4-isopropylphenyl, 1-naphthyl and 2-naphthyl.

The term "heteroalkyl" as used herein refers to an alkyl group wherein at least one of the carbon atoms in the chain is replaced by a heteroatom, such as nitrogen, oxygen, phosphorous, and sulfur. A heteroalkyl group may be unsubstituted or substituted.

The terms "heterocycloalkyl," "heterocycle," "heterocyclyl," and "heterocyclic group" as used interchangeably herein refer to a saturated or partially unsaturated ring system of 3 to 20 atoms, wherein at least one of the ring atoms is a heteroatom, such as nitrogen, oxygen, phosphorous, and sulfur. A heterocycloalkyl group may be unsubstituted or substituted. In some embodiments, a heterocycloalkyl group comprises 3 to 10 atoms. In some embodiments, a heterocycloalkyl group contains 3 to 7 atoms. In some embodiments, a heterocycloalkyl group is monocyclic. In some embodiments, a heterocycloalkyl group is bicyclic. In some embodiments, a heterocycloalkyl group comprises fused rings. Non-limiting examples of unsubstituted and substituted heterocycloalkyl groups include pyrrolidinyl, N-methylpyrrolidinyl, azetidinyl, dihydrofuranyl, tetrahydrofuranyl, tetrahydropyranyl, 3-hydroxypyrrolidinyl, 3-methoxypyrrolidinyl, and benzodioxolyl.

The terms "heteroaryl" and "heteroaryl group" as used interchangeably herein refer to an aromatic ring system of 3 to 20 atoms, wherein at least one of the ring atoms is a heteroatom, such as nitrogen, oxygen, phosphorous, and sulfur. A heteroaryl group may be unsubstituted or substituted. In some embodiments, a heteroaryl group contains 5 to 20 atoms. In some embodiments, a heteroaryl group contains 5 to 9 atoms. In some embodiments, a heteroaryl group contains 5 atoms. In some embodiments, a heteroaryl group contains 6 atoms. In some embodiments, a heteroaryl group contains 7 atoms. In some embodiments, a heteroaryl group is monocyclic. In some embodiments, a heteroaryl group is bicyclic. In some embodiments, a heteroaryl group contains fused rings. Non-limiting examples of heteroaryl groups include pyridinyl, imidazolyl, imidazopyridinyl, pyrimidinyl, pyrazolyl, triazolyl, pyrazinyl, tetrazolyl, furyl, 2-thienyl, 3-thienyl, isoxazolyl, thiazolyl, oxadiazolyl, 3-methyl-1,2,4-oxadiazolyl, 3-phenyl-1,2,4-oxadiazolyl, oxazolyl, isothiazolyl, pyrrolyl, quinolinyl, isoquinolinyl, tetrahydroisoquinolinyl, indolyl, benzimidazolyl, benzofuranyl, indazolyl, indolizinyl, phthalazinyl, pyridazinyl, triazinyl, thiadiazolyl, furazanyl, benzofurazanyl, benzothiophenyl, benzothiazolyl, benzoxazolyl, quinazolinyl, quinoxalinyl, naphthyridinyl, furopyridinyl, and 1H-pyrrolo[2,3-b]pyridinyl. Non-limiting examples of heteroaryl groups include:

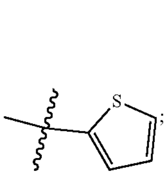 ; 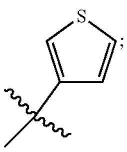 ; 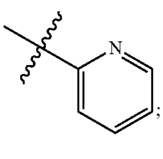 ;

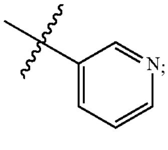 ; 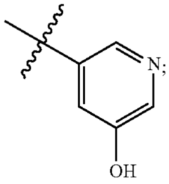 ;

-continued

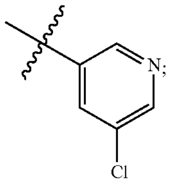

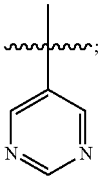

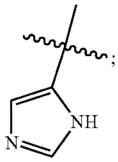

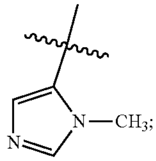

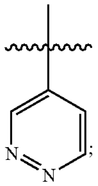

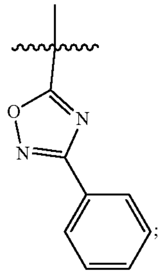

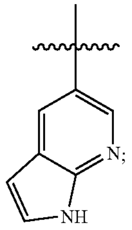

and

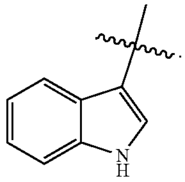

The phrase "optionally substituted" as used herein means may or may not be "substituted." The term "substituted" as used herein refers to the replacement of one or more hydrogen atoms on a group (such as on an alkyl group, alkylene group, alkenyl group, alkenylene group, alkynyl group, alkynylene group, aryl group, heterocycloalkyl group, or heteroaryl group) by one or more substituents. Non-limiting examples of substituents that replace a single hydrogen atom include halogen, hydroxyl, and amino. Non-limiting examples of substituents that replace two hydrogen atoms include oxo and methene. Non-limiting examples of substituents that replace three hydrogen atoms include nitrile.

Additional non-limiting examples of substituents include:

$C_1$-$C_6$ linear, branched, and cyclic alkyl groups, non-limiting examples of which include methyl, ethyl, n-propyl, iso-propyl, cyclopropyl, n-butyl sec-butyl, iso-butyl, tert-butyl, cyclobutyl, cyclopentyl, and cyclohexyl;

$C_2$-$C_8$ linear, branched, and cyclic alkenyl groups, non-limiting examples of which include ethenyl (also called vinyl), 1-propenyl, and iso-propenyl;

$C_2$-$C_8$ linear and branched alkynyl groups, non-limiting examples of which include ethynyl;

substituted and unsubstituted aryl groups, non-limiting examples of which include phenyl, 2-fluorophenyl, 3-methylphenyl, 4-chlorophenyl, 2,6-dichlorophenyl, 3,4-difluorophenyl, 3-hydroxyphenyl, 4-cyanophenyl, 2-dimethylaminophenyl, 3-methylsulfonylphenyl, 4-trifluoromethylphenyl, 3-isopropylphenyl, 1-naphthyl, and 2-naphthyl;

substituted and unsubstituted heterocyclic groups, non-limiting examples of which include pyrrolidinyl, N-methylpyrrolidinyl, azetidinyl, dihydrofuranyl, tetrahydrofuranyl, tetrahydropyranyl, 3-hydroxypyrrolidinyl, and 3-methoxypyrrolidinyl;

substituted and unsubstituted heteroaryl groups, non-limiting examples of which include pyridinyl, imidazolyl, pyrimidinyl, pyrazolyl, furyl, 2-thienyl, 3-thienyl, isoxazolyl, thiazolyl, oxadiazolyl, 3-methyl-1,2,4-oxadiazolyl, 3-phenyl-1,2,4-oxadiazolyl, indolyl, benzothiazolyl, and 1H-pyrrolo[2,3-b]pyridinyl;

$-(CR_aR_b)_zOR_c$, non-limiting examples of which include $-OH$, $-OCH_3$, $-OCH_2OH$, and $-OCH_2CH_3$;

$-(CR_aR_b)_zN(R_c)(R_d)$, non-limiting examples of which include $-NH_2$, $-NHCH_3$, $-N(CH_3)_2$, $-CH_2NH_2$, $-CH_2NHCH_3$, a halogen atom, non-limiting examples of which include a fluorine atom (—F) and a chlorine atom (—Cl);

$-(CR^aR^b)_zCN$;

$-(CR^aR^b)_zNO_2$;

$-CH_xX_y$, wherein X is a halogen atom and x+y sum to 3, non-limiting examples of which include $-CH_2F$, $-CHF_2$, and $-CF_3$;

$-(CR^aR^b)_zC(O)R^c$, non-limiting examples of which include $-COCH_3$, $-COCH_2CH_3$, and $-CH_2COCH_3$;

$-(CR^aR^b)_zC(O)OR^c$, non-limiting examples include $CO_2H$, $-CO_2CH_3$, $-CO_2CH_2CH_3$, and $-CH_2CO_2CH_3$, $-(CR^aR^b)_zC(O)N(R)(R^d)$, non-limiting examples of which include $-CONH_2$, $-CONHCH_3$, $-CON(CH_3)_2$, $-CH_2CONH_2$, $-CH_2CONHCH_3$, $-CH_2CON(C H_3)_2$;

$-(CR^aR^b)_zSO_2R^c$; non-limiting examples of which include $-SO_2H$, $-SO_2CH_3$, $-CH_2SO_2H$, $-CH_2SO_2CH_3$, $-SO_2C_6H_5$, and $-CH_2SO_2C_6H_5$; and $-(CR^aR^b)_zSO_3R^c$; non-limiting examples of which include $-SO_3H$, $-SO_3CH_3$, $-CH_2SO_3H$, $-CH_2SO_3CH_3$, $-SO_3C_6H_5$, and $-CH_2SO_3C_6H_5$;

wherein each of $R^a$ and $R^b$ is independently chosen from hydrogen and substituted or unsubstituted $C_1$-$C_6$ linear, branched, or cyclic alkyl, each of $R^c$ and $R^d$ is independently chosen from hydrogen, substituted or unsubstituted $C_1$-$C_6$ linear, branched, or cyclic alkyl, and aryl, or wherein $R^c$ and $R^d$ together form a ring system comprising 3 to 7 atoms, and z is chosen from 0, 1, 2, 3, and 4.

As used herein, the term "pharmaceutical composition" refers to a preparation that is in such form as to permit the biological activity of the active ingredient to be effective, and that contains no additional components that are unacceptably toxic to a subject to which the composition would be administered. In some embodiments, such compositions may be sterile.

The term "pharmaceutically acceptable," as used herein in "pharmaceutically acceptable salt" and "pharmaceutically acceptable excipient," refers to a component that is, within the scope of sound medical judgment, suitable for use in contact with the tissues of humans and other mammals without undue toxicity, irritation, allergic response and the like, and are commensurate with a reasonable benefit/risk ratio.

The phrase "pharmaceutically acceptable excipient" is employed herein to refer to a pharmaceutically acceptable material chosen from a solvent, dispersion media, diluent, dispersion, suspension aid, surface active agent, isotonic agent, thickening or emulsifying agent, preservative, polymer, peptide, protein, cell, hyaluronidase, and mixtures thereof. In some embodiments, the solvent is an aqueous solvent.

"Treatment," "treat," and "treating" refer to reversing, alleviating (e.g., alleviating one or more symptoms), and/or delaying the progression of a medical condition or disorder described herein.

The terms "disease" and "disorder" are used interchangeably herein and refer to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, sickness, illness, complaint, indisposition, or affection.

"Subject," as used herein, means an animal subject, such as a mammalian subject, and particularly human beings.

As used herein, the term "administering" refers to the placement of a compound, pharmaceutically acceptable salt thereof, and/or a pharmaceutical composition comprising into a mammalian tissue or a subject by a method or route that results in at least partial localization of the compound, salt, and/or composition at a desired site or tissue location.

The term "therapeutically effective amount" as used herein refers to an amount of a compound or salt that produces a desired effect for which it is administered (e.g., improvement in symptoms of a disease or condition mediated by AhR signaling, lessening the severity of such a disease or condition or a symptom thereof, and/or reducing progression any one of the foregoing). The exact amount of an effective dose will depend on the purpose of the treatment and will be ascertainable by one skilled in the art using known techniques (see, e.g., Lloyd (1999) The Art, Science and Technology of Pharmaceutical Compounding).

One of ordinary skill in the art would recognize that, when an amount of a compound is disclosed, the relevant amount of a pharmaceutically acceptable salt form of the compound is an amount equivalent to the amount of the free base of the compound. The amounts of the compounds and pharmaceutically acceptable salts disclosed herein are based upon the free base form of the relevant compound. For example, "10 mg of at least one entity chosen from compounds of Formulas I or Ia and pharmaceutically acceptable salts thereof" refers to 10 mg of a compound of Formulas I or Ia or an amount of a pharmaceutically acceptable salt of the compound of Formulas I or Ia equivalent to 10 mg of the relevant compound of Formulas I or Ia.

The "effectiveness" of a compound or composition of the disclosure can be assessed by any method known to one of ordinary skill in the art, including those described in the examples of this disclosure. Effectiveness can be established in vitro (biochemical and/or biological in cultured cells) and/or in vivo. Effectiveness in vitro may be used to extrapolate or predict some degree of effectiveness in vivo, in an animal or in a human subject. A reference or standard or comparison may be used. The term "effective" at inhibiting a receptor (such as AhR), and/or signaling mediated by the enzyme in the context of this disclosure and claims means reducing/activating the activity of the receptor and/or the activation and propagation of the signaling pathway in terms of activation of a downstream molecule or known biological effect by a detectable or measurable amount relative to the baseline activity. This can be assessed in vitro or in vivo and, in some cases, extrapolated to what an activity or benefit in vivo might be by one of ordinary skill in the art. In some embodiments, the reduction or activation is measured in terms of percentage reduction or activation, relative to the activity in the absence of exposure to the compound of the disclosure, including, for example, at least 5%, at least 10%, 20%, at least 30%, at least 40%, at least 50%, at least 60%, at least 70%, at least 80%, at least 90%, or about 100%. The activity might also fall within a range, e.g., 5-10%, 10-20%, and any other range interval between 1% and 100%. An amount is "effective" in vivo if it produces any benefit to the subject to whom the compound or salt is administered.

Disclosed herein are compounds of Formula (I):

(I)

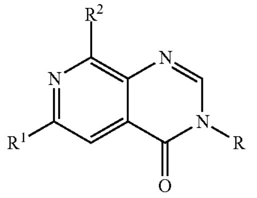

and pharmaceutically acceptable salts thereof, wherein:

each of $R^1$ and $R^2$ is independently chosen from optionally substituted alkyls, optionally substituted esters, optionally substituted heteroalkyls, optionally substituted acyls, optionally substituted amides, optionally substituted aryls, optionally substituted heteroaryls, optionally substituted cycloalkyls, optionally substituted amines and optionally substituted heterocycloalkyls; and $R^3$ is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, optionally substituted amines, cyano, halos, hydroxy, and —C(O)H.

In some embodiments $R^2$ is a dialkyl amine. In some embodiments $R^2$ is a diethyl amine.

Also disclosed herein are compounds of Formula Ia:

(Ia)

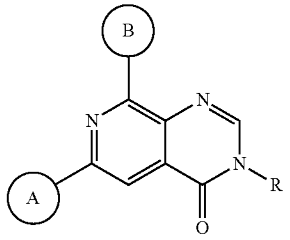

and pharmaceutically acceptable salts thereof, wherein:

ring A is chosen from optionally substituted aryls, optionally substituted heteroaryls, optionally substituted cycloalkyls, and optionally substituted heterocycloalkyls;

ring B is chosen from optionally substituted aryls, optionally substituted heteroaryls, optionally substituted cycloalkyls, and optionally substituted heterocycloalkyls; and R is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, amino, cyano, halos, hydroxy, and —C(O)H.

In some embodiments, ring A is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$.

In some embodiments, ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$.

In some embodiments, R is chosen from hydrogen, $C_1$-$C_{10}$ alkyls, 6-10 membered aryls, —C(O)R', —C(O)NR'R', 3-10 membered cycloalkyls, —C(O)OR', $C_1$-$C_{10}$ heteroalkyls, 5-10 membered heteroaryls, 3-10 membered heterocycloalkyls, amino, cyano, halos, hydroxy, and —C(O)H, wherein each $C_1$-$C_{10}$ alkyl, 6-10 membered aryl, 3-10 membered cycloalkyl, $C_1$-$C_{10}$ heteroalkyl, 5-10 membered heteroaryl, and 3-10 membered heterocycloalkyl is independently optionally substituted with 1 to 5 instances of $R^C$.

In some embodiments, each R' is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R".

In some embodiments, each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R".

In some embodiments, each $R^C$ is independently chosen from halos, hydroxy, cyano, $C_1$-$C_{10}$ alkyls, $C_1$-$C_{10}$ alkoxys, $C_1$-$C_{10}$ haloalkyls, 3-10 membered cycloalkyls, 3-10 membered heterocycloalkyls, 6-10 membered aryls, and 5-10 membered heteroaryls.

In some embodiments, each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, ring A is chosen from 6-10 membered aryls, 5-8 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$;

ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$;

R is chosen from hydrogen, $C_1$-$C_{10}$ alkyls, 6-10 membered aryls, —C(O)R', —C(O)NR'R', 3-10 membered cycloalkyls, —C(O)OR', $C_1$-$C_{10}$ heteroalkyls, 5-10 membered heteroaryls, 3-10 membered heterocycloalkyls, amino, cyano, halos, hydroxy, and —C(O)H, wherein each $C_1$-$C_{10}$ alkyl, 6-10 membered aryl, 3-10 membered cycloalkyl, $C_1$-$C_{10}$ heteroalkyl, 5-10 membered heteroaryl, and 3-10 membered heterocycloalkyl is independently optionally substituted with 1 to 5 instances of $R^c$;

each R' is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls;

each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^C$ is independently chosen from halos, hydroxy, cyano, $C_1$-$C_{10}$ alkyls, $C_1$-$C_{10}$ alkoxys, $C_1$-$C_{10}$ haloalkyls, 3-10 membered cycloalkyls, 3-10 membered heterocycloalkyls, 6-10 membered aryls, and 5-10 membered heteroaryls; and each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

In some embodiments, ring A is chosen from 3-10 membered cycloalkyl optionally substituted with 1 to 5 instances of $R^A$. In some embodiments, ring A is chosen from cyclopropyl, cyclobutyl, cyclopentyl, cyclohexyl, cycloheptyl, and cyclooctyl optionally substituted with 1 to 5 instances of $R^A$. In some embodiments, ring A is chosen from 6-8 membered aryls optionally substituted with 1 to 5 instances of $R^A$. In some embodiments, ring A is phenyl optionally substituted with 1 to 3 instances of $R^A$. In some embodiments, ring A is chosen from 5-8 membered heteroaryls optionally substituted with 1 to 5 instances of $R^A$.

In some embodiments, ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$.

In some embodiments, ring A is pyridinyl optionally substituted with 1 to 3 instances of $R^A$. In some embodiments, ring A is chosen from 5-8 membered heterocycloalkyls optionally substituted with 1 to 5 instances of $R^A$. In some embodiments, ring A is chosen from pyrrolidinyl, pyrazolidinyl, piperidinyl, piperazinyl, morpholino, azepinyl, tetrahydropyranyl, and tetrahydrofuranyl, wherein each of pyrrolidinyl, pyrazolidinyl, piperidinyl, piperazinyl, morpholino, azepinyl, tetrahydropyranyl, and tetrahydrofuranyl is independently optionally substituted with 1 to 3 instances of $R^A$. In some embodiments, ring A is piperidinyl or morpholino optionally substituted with 1 to 3 instances of $R^A$.

In some embodiments, each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and NR"R". In some embodiments, each $R^B$ is independently chosen from halos, $C_1$-$C_{10}$ alkyls, and $C_1$-$C_{10}$ haloalkyls. In some embodiments, each $R^C$ is independently chosen from halos, hydroxy, cyano, $C_1$-$C_{10}$ alkyls, $C_1$-$C_{10}$ alkoxys, 3-8 membered cycloalkyls, 3-8 membered heterocycloalkyls, and 6-8 membered aryls. In some embodiments, each R" is independently chosen from hydrogen and $C_1$-$C_{10}$ alkyls.

In some embodiments, each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and NR"R";

each $R^B$ is independently chosen from halos, $C_1$-$C_{10}$ alkyls, and $C_1$-$C_{10}$ haloalkyls;

each $R^C$ is independently chosen from halos, hydroxy, cyano, $C_1$-$C_{10}$ alkyls, $C_1$-$C_{10}$ alkoxys, 3-8 membered cycloalkyls, 3-8 membered heterocycloalkyls, and 6-8 membered aryls; and each R" is independently chosen from hydrogen and $C_1$-$C_{10}$ alkyls.

In some embodiments, ring B is chosen from 6-8 membered aryls optionally substituted with 1 to 5 instances of $R^B$. In some embodiments, ring B is phenyl optionally substituted with 1 to 3 instances of $R^B$. In some embodiments, ring B is chosen from 5-8 membered heteroaryls optionally substituted with 1 to 5 instances of $R^B$. In some embodiments, ring B is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, pyridinonyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^B$. In some embodiments, ring B is chosen from pyrazolyl, isothiazoyl, isoxazolyl, pyridinyl, pyrimidinyl, and thiophenyl, wherein each of pyrazolyl, isothiazoyl, isoxazolyl, pyridinyl, pyrimidinyl, and thiophenyl is independently optionally substituted with 1 to 3 instances of $R^B$.

In some embodiments, ring A is chosen from

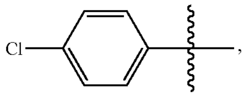,

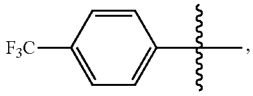, 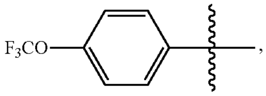,

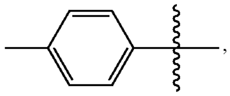, 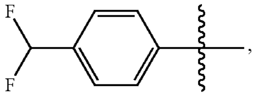,

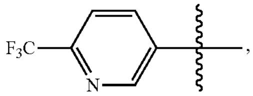, 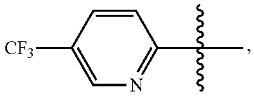,

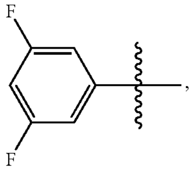, 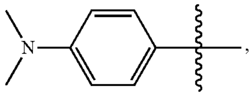,

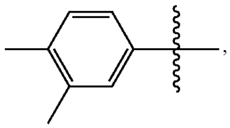, 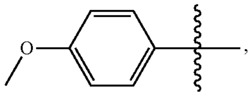,

-continued

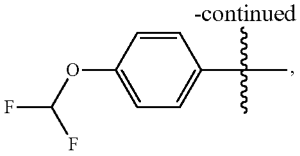,

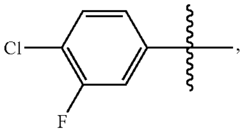, 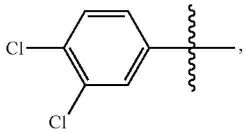,

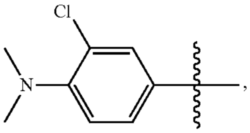, 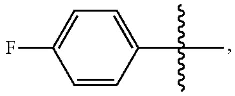,

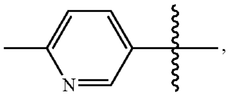, 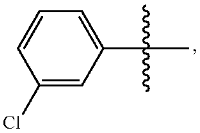,

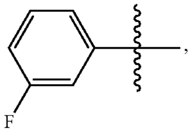, 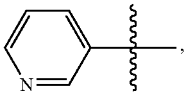,

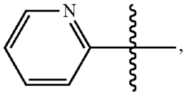,

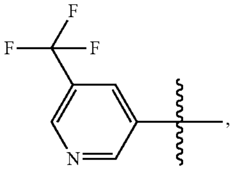, 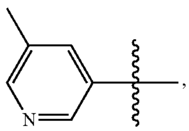,

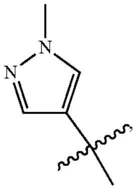 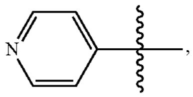,

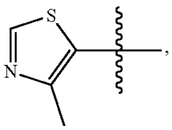, 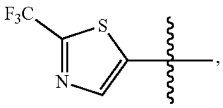,

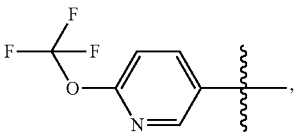, 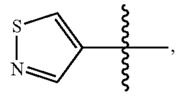,

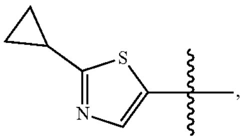, 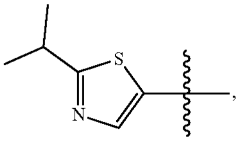,

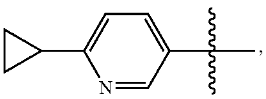,

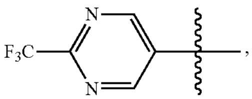, 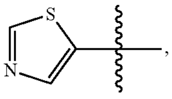,

-continued
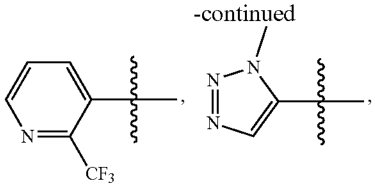,
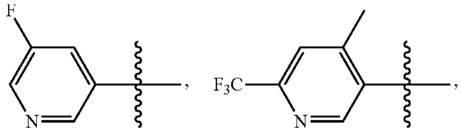,
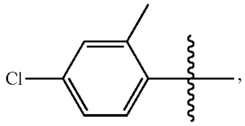,
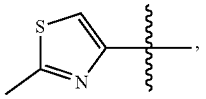, and
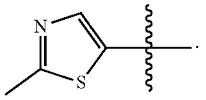.
In some embodiments, ring A is chosen from
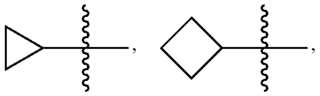,
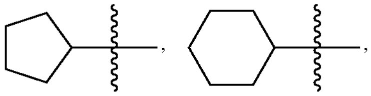,
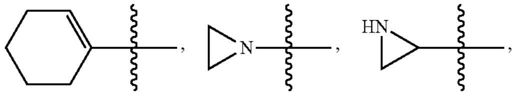,
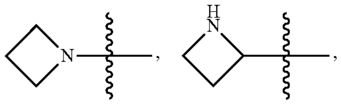,
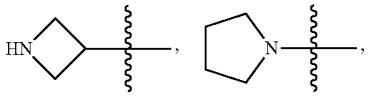,
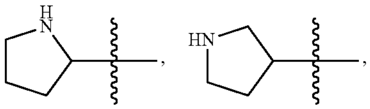,
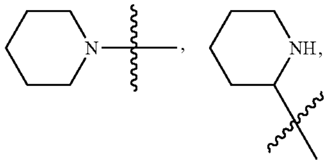,
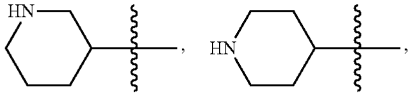,
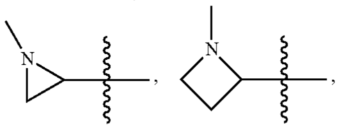,
-continued
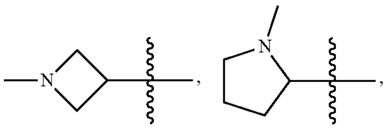,
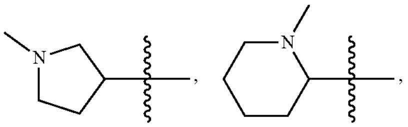,
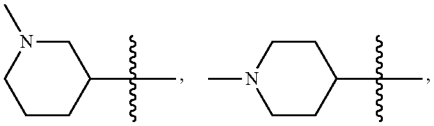,
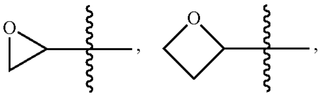,
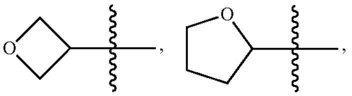,
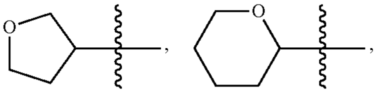,
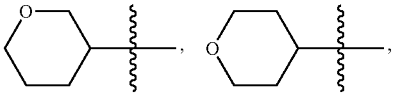, and
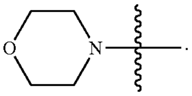.
In some embodiments, ring A is chosen from
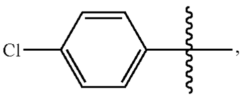,
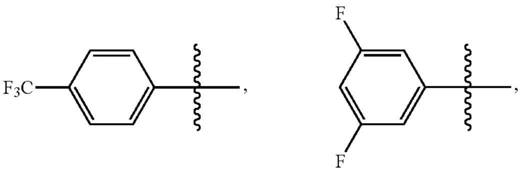,
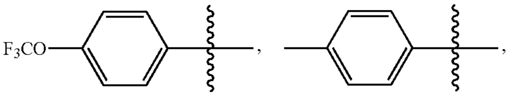,
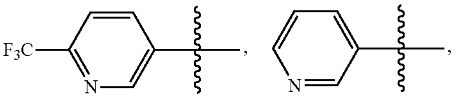, -continued
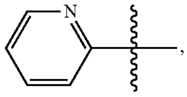,
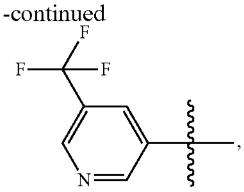,
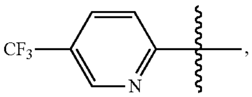,
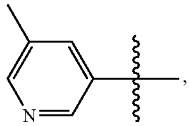,
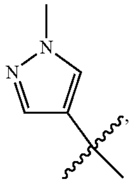,
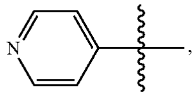, and
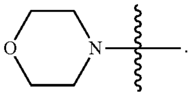.
In some embodiments, ring B is chosen from
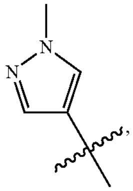,
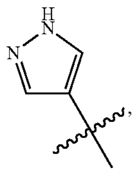,
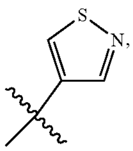,
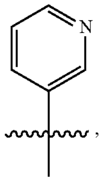,
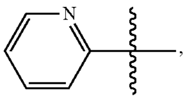,
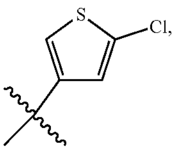,
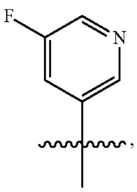,
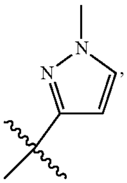,
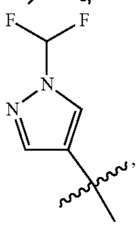,
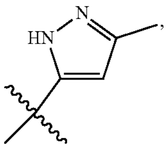,
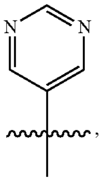,
-continued
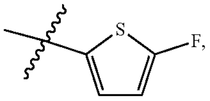,
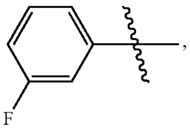,
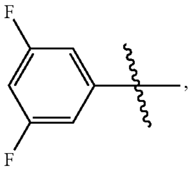,
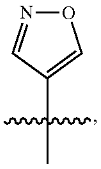,
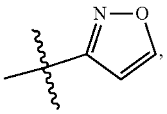,
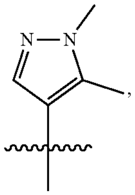,
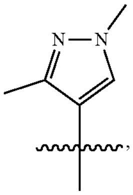,
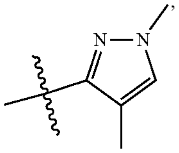,
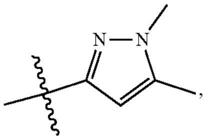,
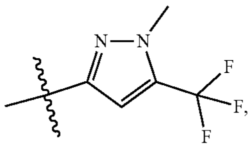,
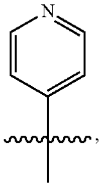,
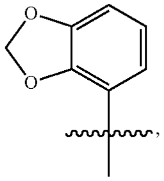,
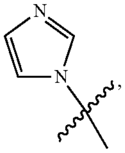,
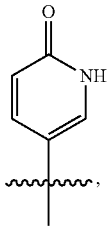,
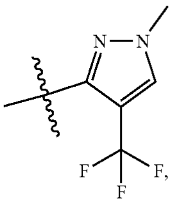,
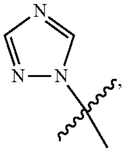,
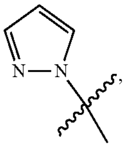, -continued
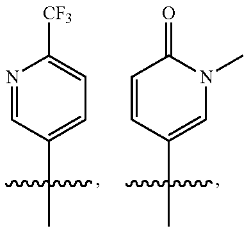,
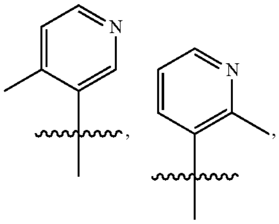, and
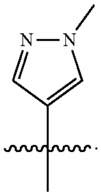.
In some embodiments, ring B is from
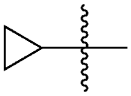, 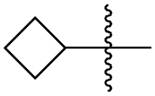, 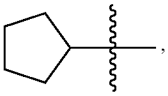,
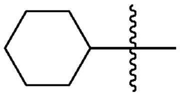, 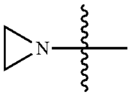, 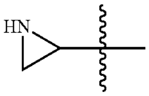,
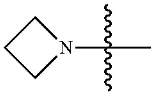, 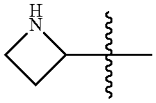, 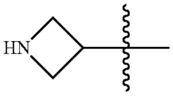,
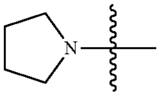, 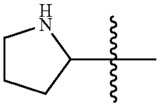,
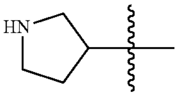, 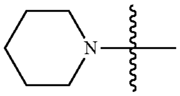,
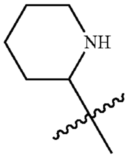, 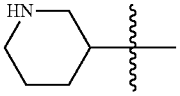,
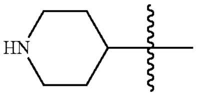, 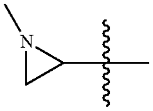,
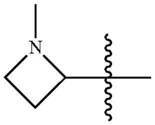, 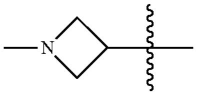,
-continued
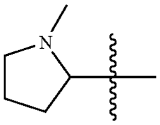, 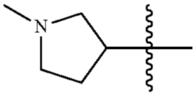,
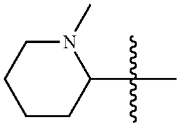, 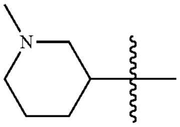,
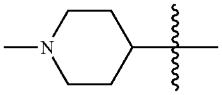, 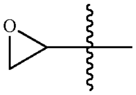,
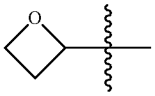, 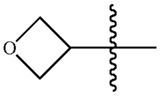,
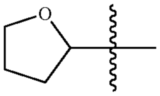, 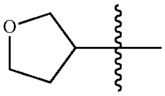,
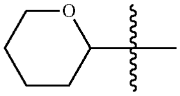, 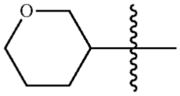,
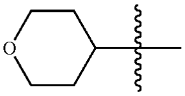, and 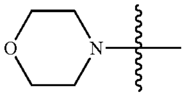.
In some embodiments, ring B is chosen from
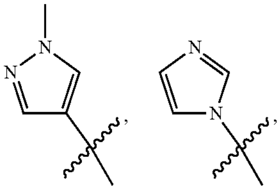,
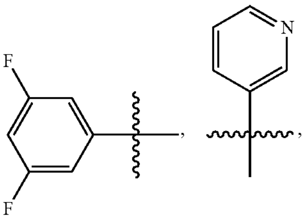,
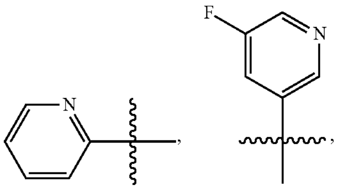,
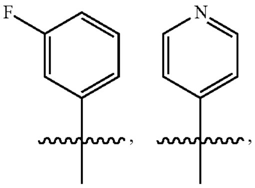, -continued
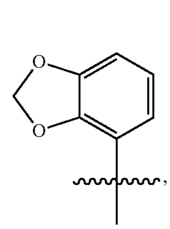
and
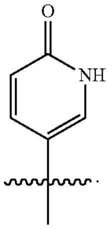
In some embodiments, R is chosen from methyl,
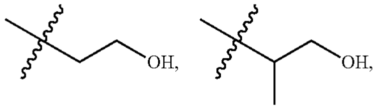
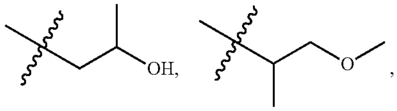
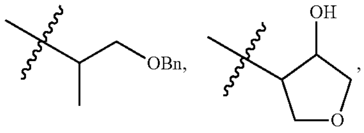
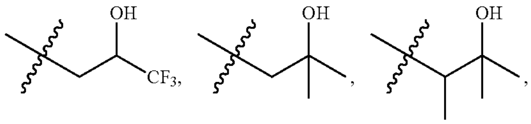
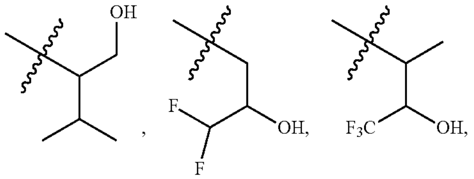
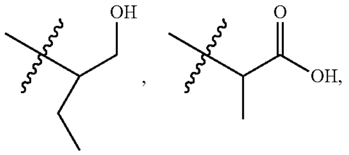
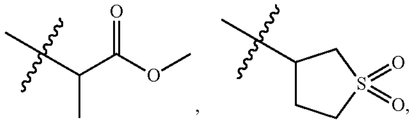
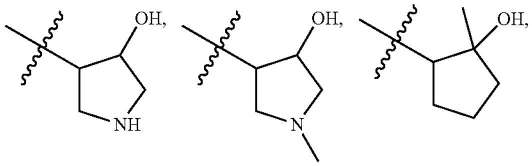
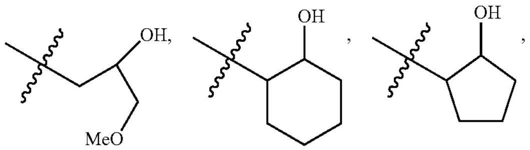
-continued
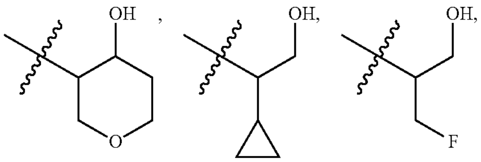
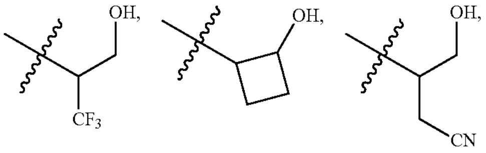
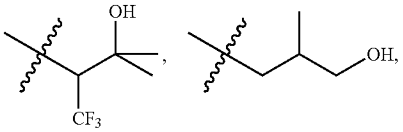
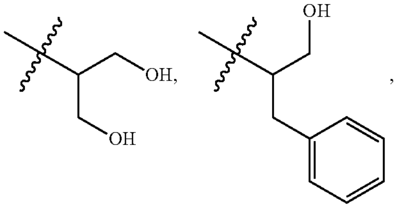
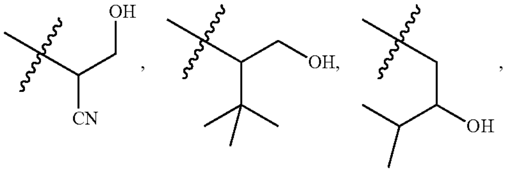
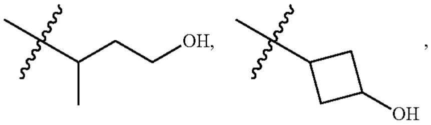
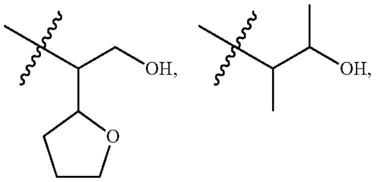
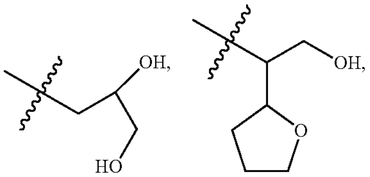
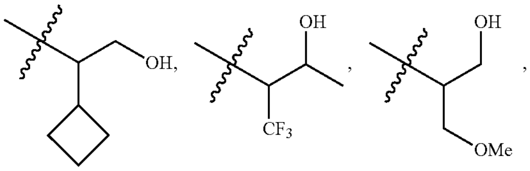
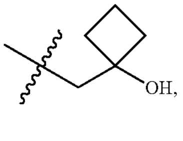
and
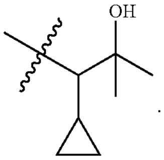
In some embodiments, R is chosen from methyl,

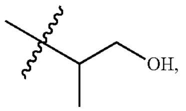 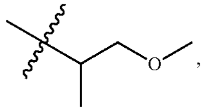

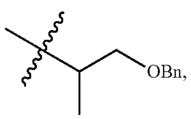 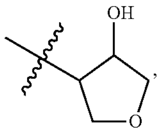

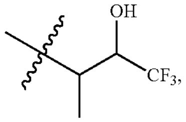 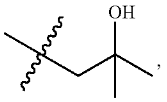

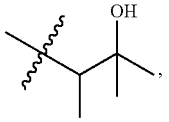 and 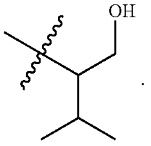

Also disclosed herein are compounds of Formula Ib:

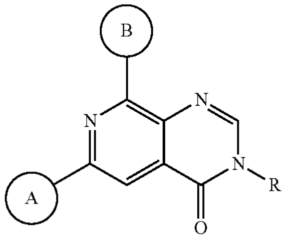

(Ib)

and pharmaceutically acceptable salts thereof, wherein:

ring A is chosen from optionally substituted heteroaryls and optionally substituted heterocycloalkyls;

ring B is chosen from optionally substituted heteroaryls and optionally substituted heterocycloalkyls; and R is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, amino, cyano, halos, hydroxy, and —C(O)H.

In some embodiments, the present disclosure is drawn to one or more compounds recited in Table 1.

TABLE 1

| Compound No. | Structure and name |
| --- | --- |
| 1 | 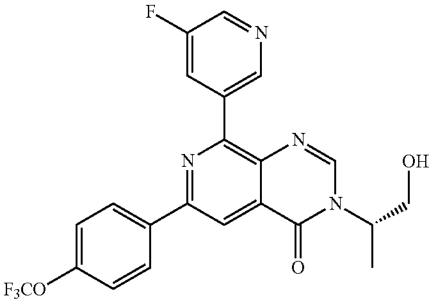 8-(5-fluoropyridin-3-yl)-3-[(2S)-1-hydroxypropan-2-yl]-6-[4-(trifluoromethoxy)phenyl]-3H,4H-pyrido[3,4-d]pyrimidin-4-one |
| 2 | 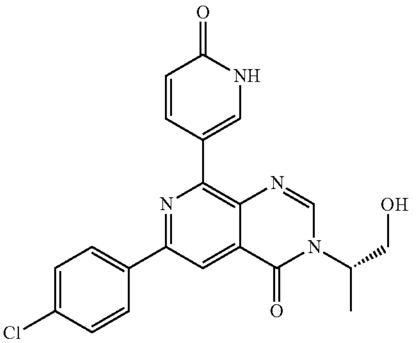 5-[6-(4-chlorophenyl)-3-[(2S)-1-hydroxypropan-2-yl]-4-oxo-3H,4H-pyrido[3,4-d]pyrimidin-8-yl]-1,2-dihydropyridin-2-one |
| 3 | 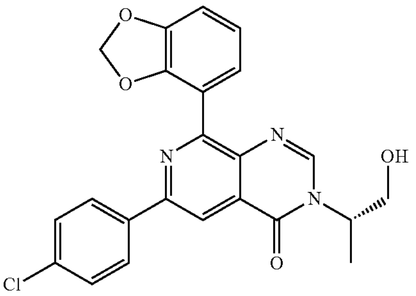 8-(2H-1,3-benzodioxol-4-yl)-6-(4-chlorophenyl)-3-[(2S)-1-hydroxypropan-2-yl]-3H,4H-pyrido[3,4-d]pyrimidin-4-one |

TABLE 1-continued

| Compound No. | Structure and name |
|---|---|
| 4 | 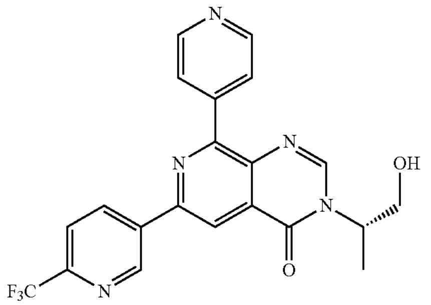 3-[(2S)-1-hydroxypropan-2-yl]-8-(pyridin-4-yl)-6-[6-(trifluoromethyl)pyridin-3-yl]-3H,4H-pyrido[3,4-d]pyrimidin-4-one |
| 5 | 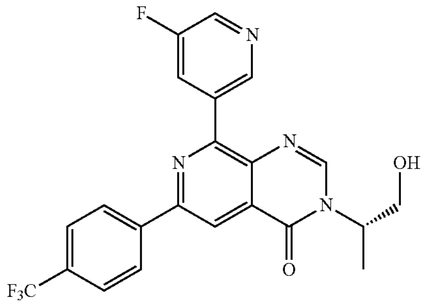 8-(5-fluoropyridin-3-yl)-3-[(2S)-1-hydroxypropan-2-yl]-6-[4-(trifluoromethyl)phenyl]-3H,4H-pyrido[3,4-d]pyrimidin-4-one |
| 6 | 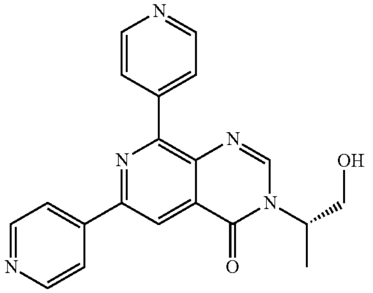 3-[(2S)-1-hydroxypropan-2-yl]-6,8-bis(pyridin-4-yl)-3H,4H-pyrido[3,4-d]pyrimidin-4-one |

TABLE 1-continued

| Compound No. | Structure and name |
|---|---|
| 7 | 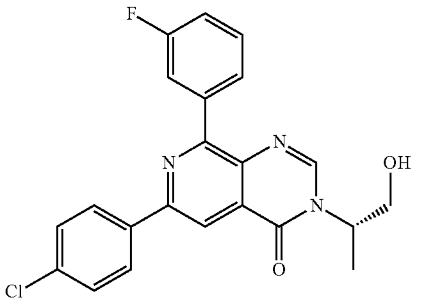 6-(4-chlorophenyl)-8-(3-fluorophenyl)-3-[(2S)-1-hydroxypropan-2-yl]-3H,4H-pyrido[3,4-d]pyrimidin-4-one |
| 8 | 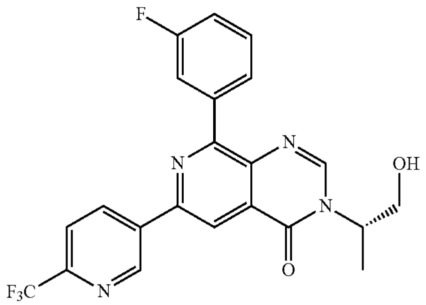 8-(3-fluorophenyl)-3-[(2S)-1-hydroxypropan-2-yl]-6-[6-(trifluoromethyl)pyridin-3-yl]-3H,4H-pyrido[3,4-d]pyrimidin-4-one |
| 9 | 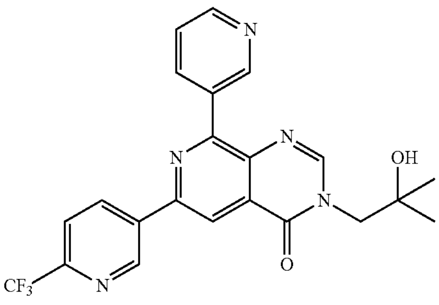 3-(2-hydroxy-2-methylpropyl)-8-(pyridin-3-yl)-6-(6-(trifluoromethyl)pyridin-3-yl)pyrido[3,4-d]pyrimidin-4(3H)-one |

TABLE 1-continued

| Compound No. | Structure and name |
|---|---|
| 10 | 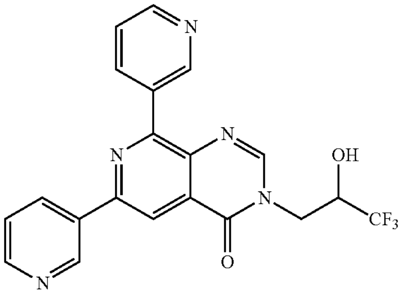 6,8-di(pyridin-3-yl)-3-(3,3,3-trifluoro-2-hydroxypropyl)pyrido[3,4-d]pyrimidin-4(3H)-one |
| 11 | 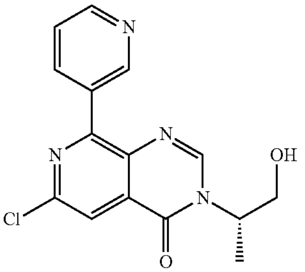 (S)-6-chloro-3-(1-hydroxypropan-2-yl)-8-(pyridin-3-yl)pyrido[3,4-d]pyrimidin-4(3H)-one |
| 12 | 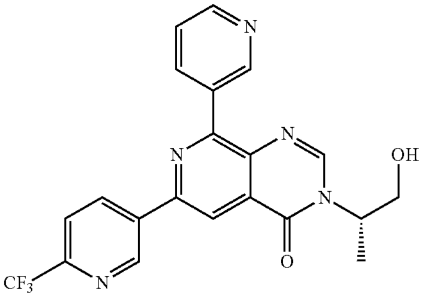 (S)-3-(1-hydroxypropan-2-yl)-8-(pyridin-3-yl)-6-(6-(trifluoromethyl)pyridin-3-yl)pyrido[3,4-d]pyrimidin-4(3H)-one |

TABLE 1-continued

| Compound No. | Structure and name |
|---|---|
| 13 | 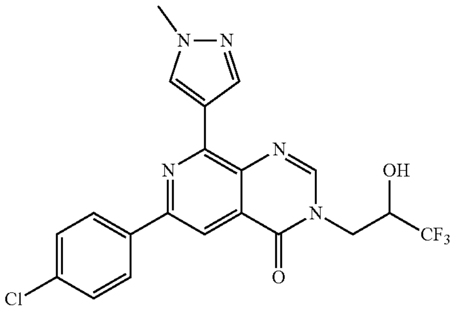 6-(4-chlorophenyl)-8-(pyridin-3-yl)-3-(3,3,3-trifluoro-2-hydroxypropyl)pyrido[3,4-d]pyrimidin-4(3H)-one |
| 14 | 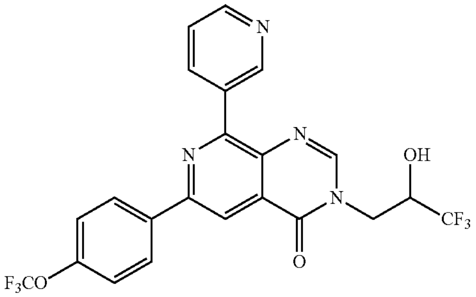 8-(pyridin-3-yl)-3-(3,3,3-trifluoro-2-hydroxypropyl)-6-(4-(trifluoromethoxy)phenyl) pyrido[3,4-d]pyrimidin-4(3H)-one |
| 15 | 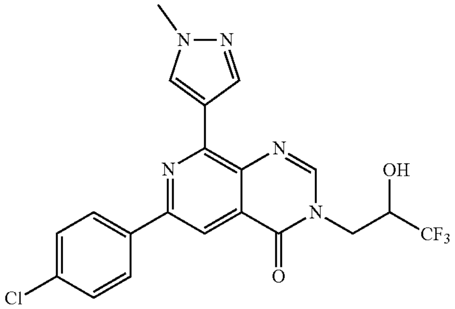 6-(4-chlorophenyl)-8-(1-methyl-1H-pyrazol-4-yl)-3-(3,3,3-trifluoro-2-hydroxypropyl)pyrido[3,4-d]pyrimidin-4(3H)-one |

TABLE 1-continued

| Compound No. | Structure and name |
|---|---|
| 16 | 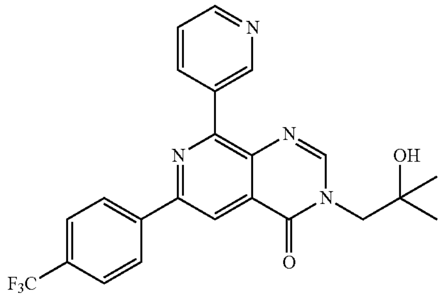 3-(2-hydroxy-2-methylpropyl)-8-(pyridin-3-yl)-6-(4-(trifluoromethyl)phenyl)pyrido[3,4-d]pyrimidin-4(3H)-one |
| 17 | 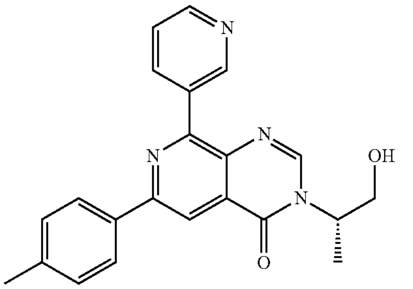 (S)-3-(1-hydroxypropan-2-yl)-8-(pyridin-3-yl)-6-(p-tolyl)pyrido[3,4-d]pyrimidin-4(3H)-one |
| 18 | 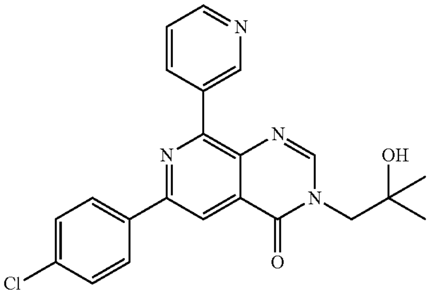 6-(4-chlorophenyl)-3-(2-hydroxy-2-methylpropyl)-8-(pyridin-3-yl)pyrido[3,4-d]pyrimidin-4(3H)-one |
| 19 | 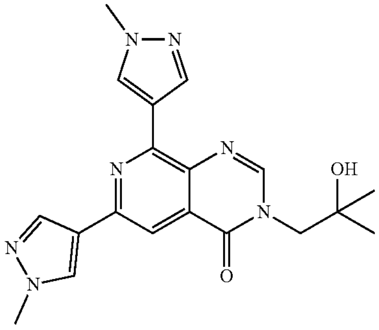 3-(2-hydroxy-2-methylpropyl)-6,8-bis(1-methyl-1H-pyrazol-4-yl)pyrido[3,4-d]pyrimidin-4(3H)-one |
| 20 | 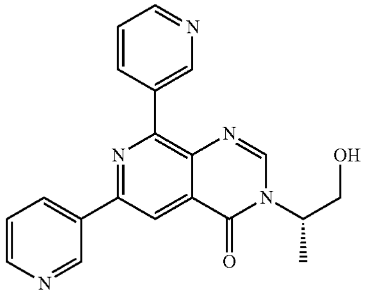 (S)-3-(1-hydroxypropan-2-yl)-6,8-di(pyridin-3-yl)pyrido[3,4-d]pyrimidin-4(3H)-one |
| 21 | 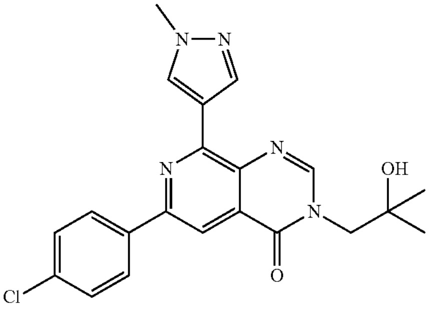 6-(4-chlorophenyl)-3-(2-hydroxy-2-methylpropyl)-8-(1-methyl-1H-pyrazol-4-yl)pyrido[3,4-d]pyrimidin-4(3H)-one |

TABLE 1-continued

| Compound No. | Structure and name |
|---|---|
| 22 | 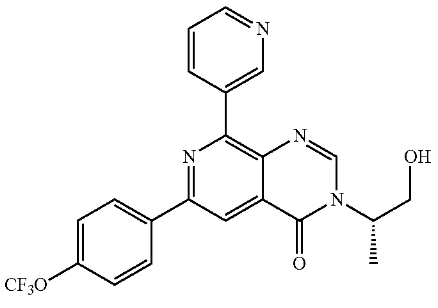 (S)-3-(1-hydroxypropan-2-yl)-8-(pyridin-3-yl)-6-(4-(trifluoromethoxy)phenyl)pyrido[3,4-d]pyrimidin-4(3H)-one |
| 23 | 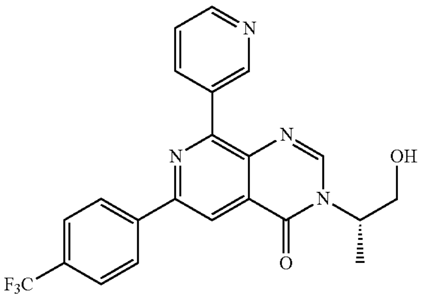 (S)-3-(1-hydroxypropan-2-yl)-8-(pyridin-3-yl)-6-(4-(trifluoromethyl)phenyl)pyrido[3,4-d]pyrimidin-4(3H)-one |
| 24 | 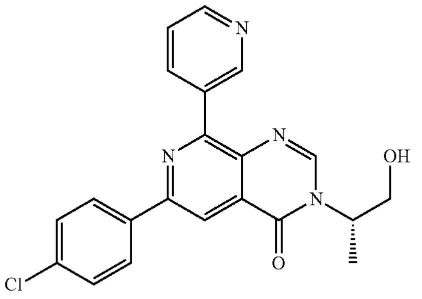 (S)-6-(4-chlorophenyl)-3-(1-hydroxypropan-2-yl)-8-(pyridin-3-yl)pyrido[3,4-d]pyrimidin-4(3H)-one |

TABLE 1-continued

| Compound No. | Structure and name |
|---|---|
| 25 | 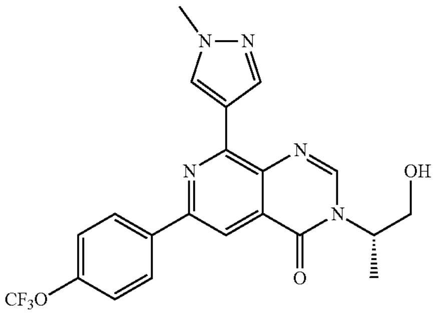 (S)-3-(1-hydroxypropan-2-yl)-8-(1-methyl-1H-pyrazol-4-yl)-6-(4-(trifluoromethoxy)phenyl)pyrido[3,4-d]pyrimidin-4(3H)-one |
| 26 | 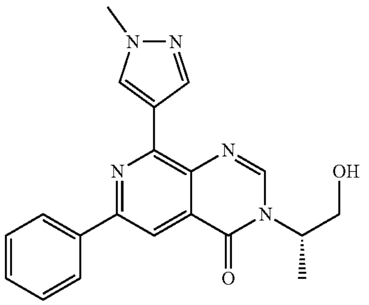 (S)-3-(1-hydroxypropan-2-yl)-8-(1-methyl-1H-pyrazol-4-yl)-6-phenylpyrido[3,4-d]pyrimidin-4(3H)-one |
| 27 | 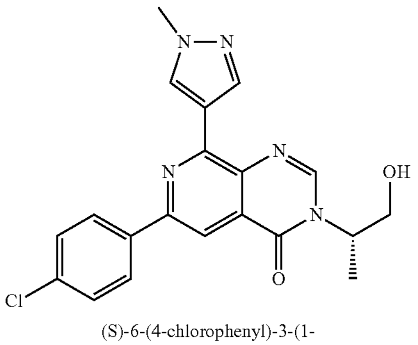 (S)-6-(4-chlorophenyl)-3-(1-hydroxypropan-2-yl)-8-(1-methyl-1H-pyrazol-4-yl)pyrido[3,4-d]pyrimidin-4(3H)-one |

TABLE 1-continued

| Compound No. | Structure and name |
|---|---|
| 28 | 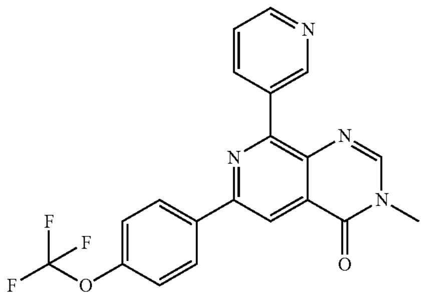 3-methyl-8-(pyridin-3-yl)-6-(4-(trifluoromethoxy)phenyl)pyrido[3,4-d]pyrimidin-4(3H)-one |
| 29 | 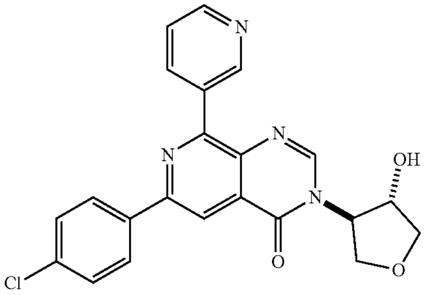 rac-6-(4-chlorophenyl)-3-((trans)-4-hydroxytetrahydrofuran-3-yl)-8-(pyridin-3-yl)pyrido[3,4-d]pyrimidin-4(3H)-one |
| 30 | 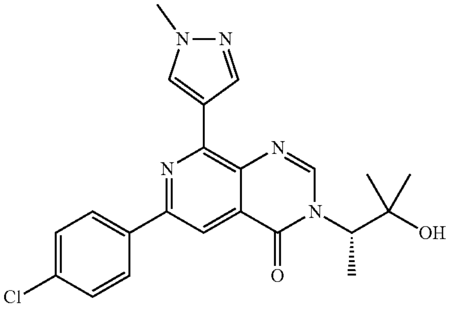 (S)-6-(4-chlorophenyl)-3-(3-hydroxy-3-methylbutan-2-yl)-8-(1-methyl-1H-pyrazol-4-yl)pyrido[3,4-d]pyrimidin-4(3H)-one |

TABLE 1-continued

| Compound No. | Structure and name |
|---|---|
| 31 | 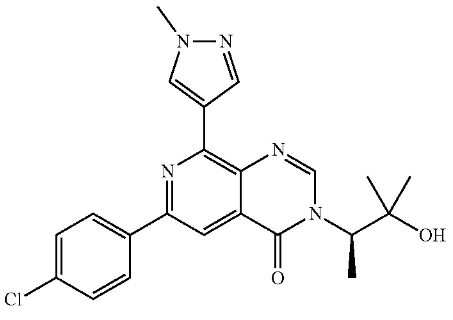 (R)-6-(4-chlorophenyl)-3-(3-hydroxy-3-methylbutan-2-yl)-8-(1-methyl-1H-pyrazol-4-yl)pyrido[3,4-d]pyrimidin-4(3H)-one |
| 32 | 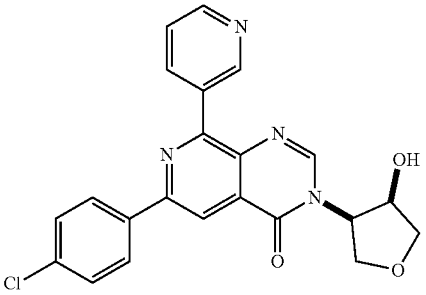 rac-6-(4-chlorophenyl)-3-((cis)-4-hydroxytetrahydrofuran-3-yl)-8-(pyridin-3-yl)pyrido[3,4-d]pyrimidin-4(3H)-one |
| 33 | 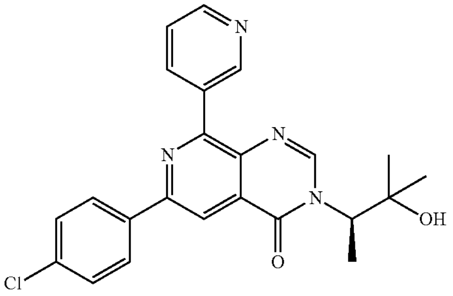 (R)-6-(4-chlorophenyl)-3-(3-hydroxy-3-methylbutan-2-yl)-8-(pyridin-3-yl)pyrido[3,4-d]pyrimidin-4(3H)-one |

TABLE 1-continued

| Compound No. | Structure and name |
| --- | --- |
| 34 | 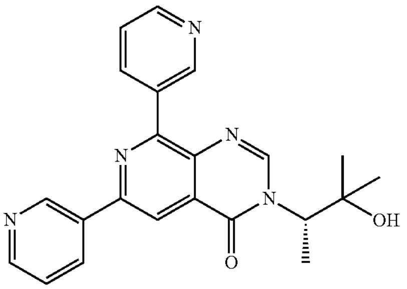 (S)-3-(3-hydroxy-3-methylbutan-2-yl)-6,8-di(pyridin-3-yl)pyrido[3,4-d]pyrimidin-4(3H)-one |
| 35 | 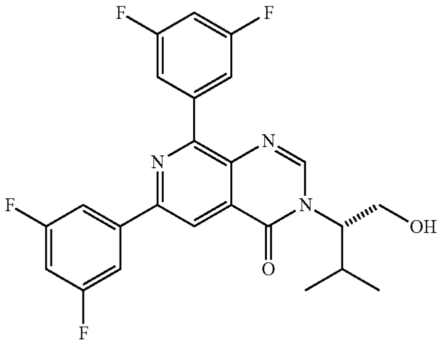 (S)-6,8-bis(3,5-difluorophenyl)-3-(1-hydroxy-3-methylbutan-2-yl)pyrido[3,4-d]pyrimidin-4(3H)-one |
| 36 | 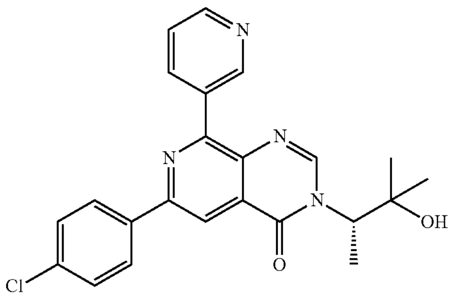 (S)-6-(4-chlorophenyl)-3-(3-hydroxy-3-methylbutan-2-yl)-8-(pyridin-3-yl)pyrido[3,4-d]pyrimidin-4(3H)-one |

TABLE 1-continued

| Compound No. | Structure and name |
| --- | --- |
| 37 | 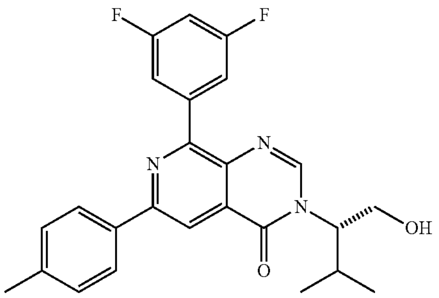 (S)-8-(3,5-difluorophenyl)-3-(1-hydroxy-3-methylbutan-2-yl)-6-(p-tolyl)pyrido[3,4-d]pyrimidin-4(3H)-one |
| 38 | 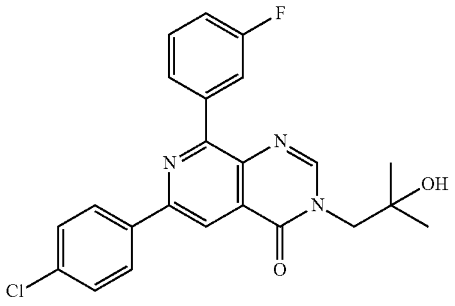 6-(4-chlorophenyl)-8-(3-fluorophenyl)-3-(2-hydroxy-2-methylpropyl)pyrido[3,4-d]pyrimidin-4(3H)-one |
| 39 | 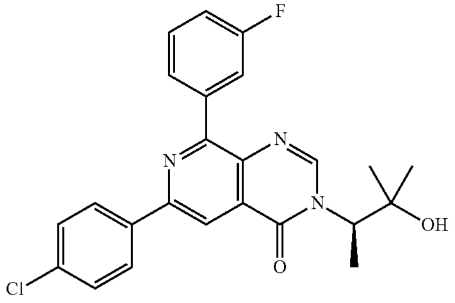 (R)-6-(4-chlorophenyl)-8-(3-fluorophenyl)-3-(3-hydroxy-3-methylbutan-2-yl)pyrido[3,4-d]pyrimidin-4(3H)-one |

| Compound No. | Structure and name |
|---|---|
| 40 | 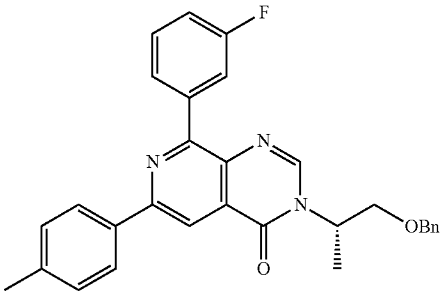 (S)-3-(1-(benzyloxy)propan-2-yl)-8-(3-fluorophenyl)-6-(p-tolyl)pyrido[3,4-d]pyrimidin-4(3H)-one |
| 41 | 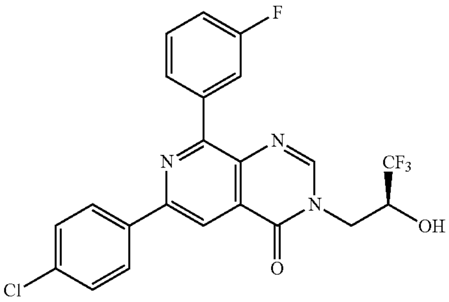 6-(4-chlorophenyl)-8-(3-fluorophenyl)-3-(3,3,3-trifluoro-2-hydroxypropyl)pyrido[3,4-d]pyrimidin-4(3H)-one, enantiomer 1 |
| 42 | 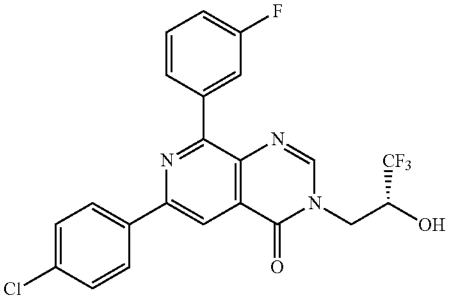 6-(4-chlorophenyl)-8-(3-fluorophenyl)-3-(3,3,3-trifluoro-2-hydroxypropyl)pyrido[3,4-d]pyrimidin-4(3H)-one, enantiomer 2 |

| Compound No. | Structure and name |
|---|---|
| 43 | 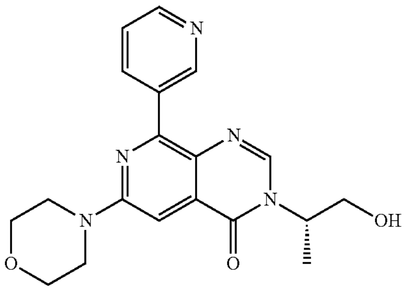 (S)-3-(1-hydroxypropan-2-yl)-6-morpholino-8-(pyridin-3-yl)pyrido[3,4-d]pyrimidin-4(3H)-one |
| 44 | 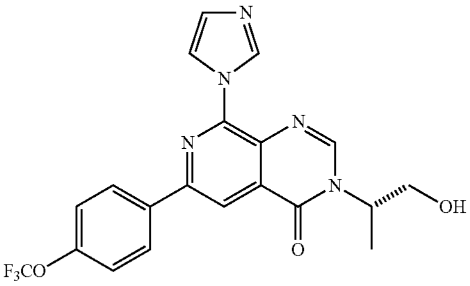 (S)-3-(1-hydroxypropan-2-yl)-8-(1H-imidazol-1-yl)-6-(4-(trifluoromethoxy)phenyl)pyrido[3,4-d]pyrimidin-4(3H)-one |
| 45 | 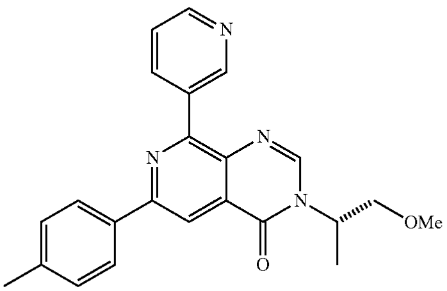 (S)-3-(1-methoxypropan-2-yl)-8-(pyridin-3-yl)-6-(p-tolyl)pyrido[3,4-d]pyrimidin-4(3H)-one |

TABLE 1-continued

| Compound No. | Structure and name |
| --- | --- |
| 46 | 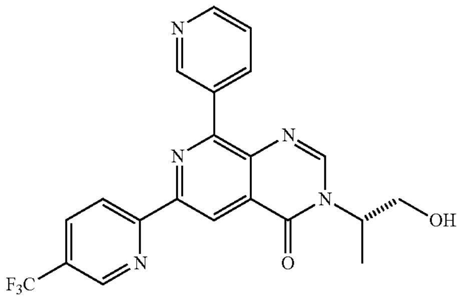 (S)-3-(1-hydroxypropan-2-yl)-8-(pyridin-3-yl)-6-(5-(trifluoromethyl)pyridin-2-yl)pyrido[3,4-d]pyrimidin-4(3H)-one |
| 47 | 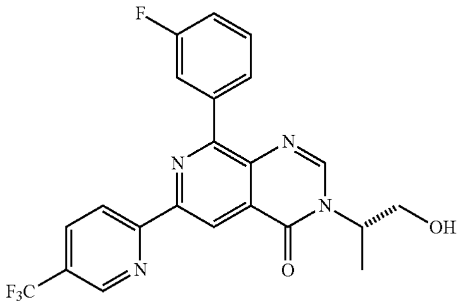 (S)-8-(3-fluorophenyl)-3-(1-hydroxypropan-2-yl)-6-(5-(trifluoromethyl)pyridin-2-yl)pyrido[3,4-d]pyrimidin-4(3H)-one |
| 48 | 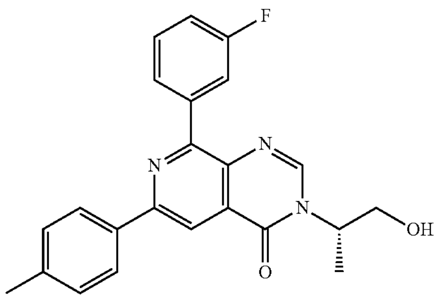 (S)-8-(3-fluorophenyl)-3-(1-hydroxypropan-2-yl)-6-(p-tolyl)pyrido[3,4-d]pyrimidin-4(3H)-one |

TABLE 1-continued

| Compound No. | Structure and name |
| --- | --- |
| 49 | 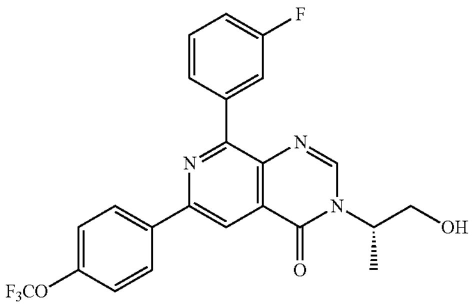 (S)-8-(3-fluorophenyl)-3-(1-hydroxypropan-2-yl)-6-(4-(trifluoromethoxy)phenyl)pyrido[3,4-d]pyrimidin-4(3H)-one |
| 50 | 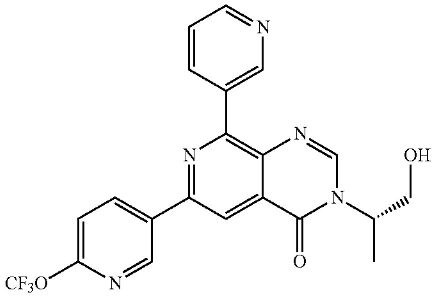 (S)-3-(1-hydroxypropan-2-yl)-8-(pyridin-3-yl)-6-(6-(trifluoromethoxy)pyridin-3-yl)pyrido[3,4-d]pyrimidin-4(3H)-one |
| 51 | 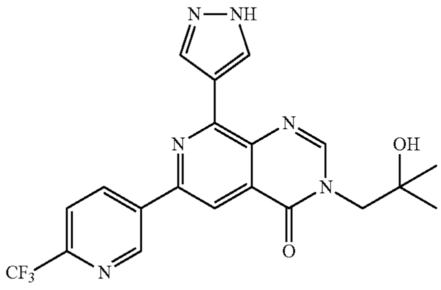 (S)-3-(2-hydroxy-2-methylpropyl)-8-(1H-pyrazol-4-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 52 | 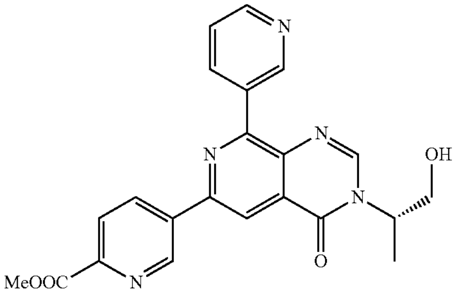 methyl (S)-5-(3-(1-hydroxypropan-2-yl)-4-oxo-8-(pyridin-3-yl)-3,4-dihydropyrido[3,4-d]pyrimidin-6-yl)picolinate |
| 53 | 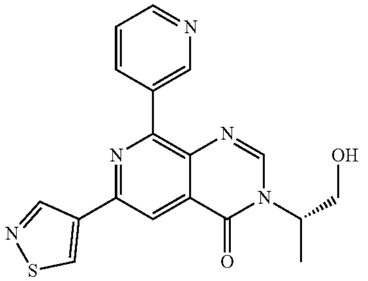 (S)-3-(1-hydroxypropan-2-yl)-6-(isothiazol-4-yl)-8-(pyridin-3-yl)pyrido[3,4-d]pyrimidin-4(3H)-one |
| 54 | 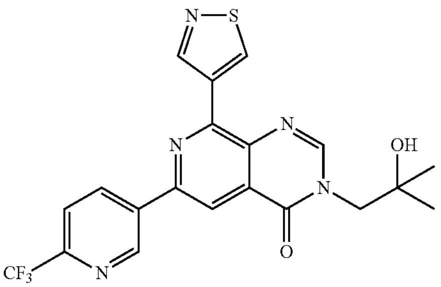 3-(2-hydroxy-2-methylpropyl)-8-(isothiazol-4-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 55 | 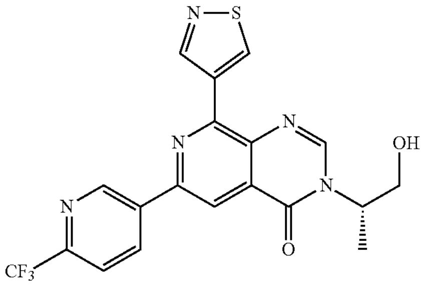 (S)-3-(1-hydroxypropan-2-yl)-8-( isothiazol-4-yl)-6-(6-(trifluoromethyl)pyridin-3-yl)pyrido[3,4-d]pyrimidin-4(3H)-one |
| 56 | 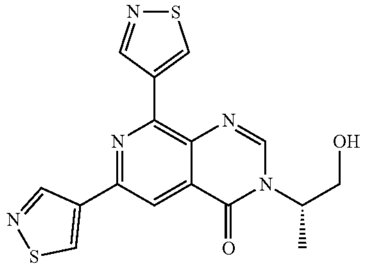 (S)-3-(1-hydroxypropan-2-yl)-6,8-di(isothiazol-4-yl)pyrido[3,4-d]pyrimidin-4(3H)-one |
| 57 | 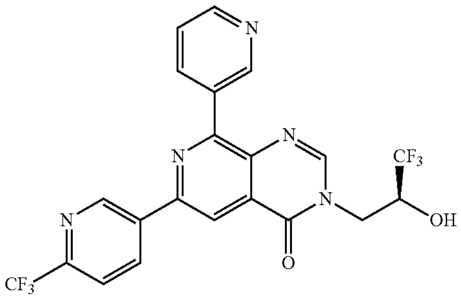 (S)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one |

TABLE 1-continued

| Compound No. | Structure and name |
| --- | --- |
| 58 | 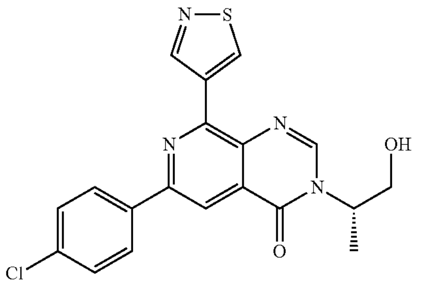 (S)-6-(4-chlorophenyl)-3-(1-hydroxypropan-2-yl)-8-(isothiazol-4-yl)pyrido[3,4-d]pyrimidin-4(3H)-one |
| 59 | 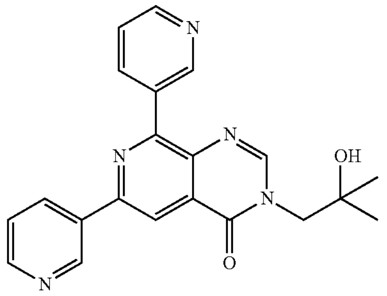 3-(2-hydroxy-2-methylpropyl)-6,8-di(pyridin-3-yl)pyrido[3,4-d]pyrimidin-4(3H)-one |
| 60 | 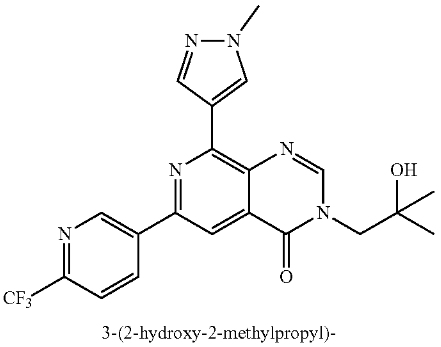 3-(2-hydroxy-2-methylpropyl)-8-(1-methyl-1H-pyrazol-4-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 61 | 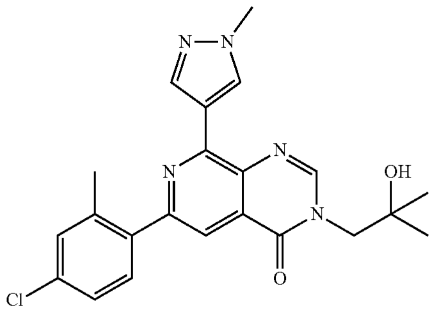 6-(4-chloro-2-methylphenyl)-3-(2-hydroxy-2-methylpropyl)-8-(1-methyl-1H-pyrazol-4-yl)pyrido[3,4-d]pyrimidin-4(3H)-one |
| 62 | 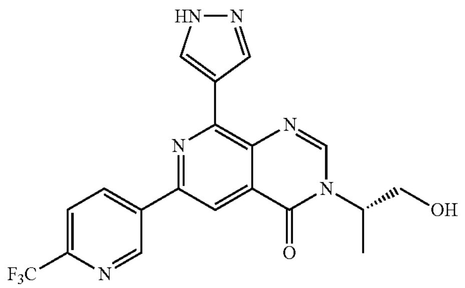 (S)-3-(1-hydroxypropan-2-yl)-8-(1H-pyrazol-4-yl)-6-(6-(trifluoromethyl)pyridin-3-yl)pyrido[3,4-d]pyrimidin-4(3H)-one |
| 63 | 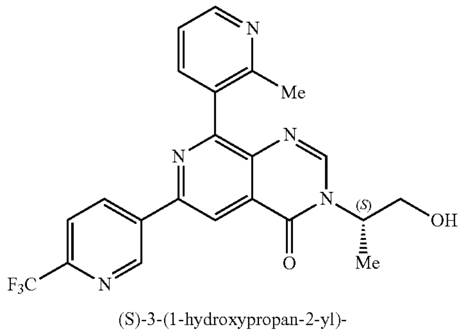 (S)-3-(1-hydroxypropan-2-yl)-8-(2-methylpyridin-3-yl)-6-(6-(trifluoromethyl)pyridin-3-yl)pyrido[3,4-d]pyrimidin-4(3H)-one |

TABLE 1-continued

| Compound No. | Structure and name |
|---|---|
| 64 | 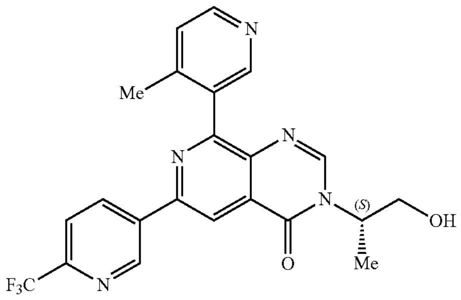<br>(S)-3-(1-hydroxypropan-2-yl)-8-(4-methylpyridin-3-yl)-6-(6-(trifluoromethyl)pyridin-3-yl)pyrido[3,4-d]pyrimidin-4(3H)-one |
| 65 | 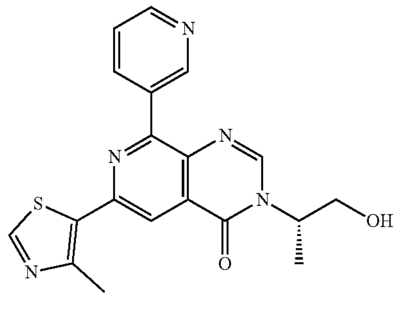<br>(S)-3-(1-hydroxypropan-2-yl)-6-(4-methylthiazol-5-yl)-8-(pyridin-3-yl)pyrido[3,4-d]pyrimidin-4(3H)-one |
| 66 | 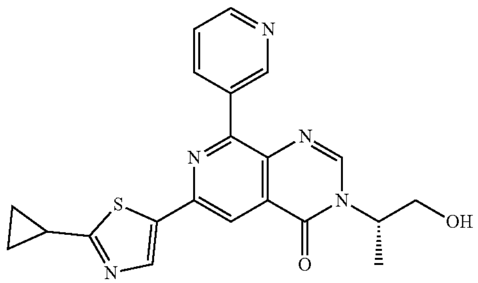<br>(S)-6-(2-cyclopropylthiazol-5-yl)-3-(1-hydroxypropan-2-yl)-8-(pyridin-3-yl)pyrido[3,4-d]pyrimidin-4(3H)-one |

TABLE 1-continued

| Compound No. | Structure and name |
|---|---|
| 67 | 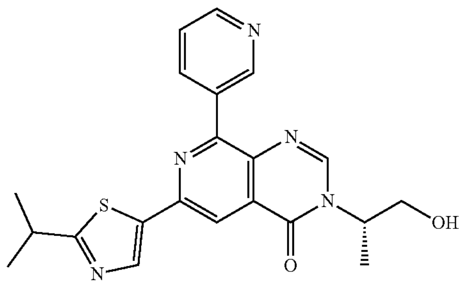<br>(S)-3-(1-hydroxypropan-2-yl)-6-(2-isopropylthiazol-5-yl)-8-(pyridin-3-yl)pyrido[3,4-d]pyrimidin-4(3H)-one |
| 68 | 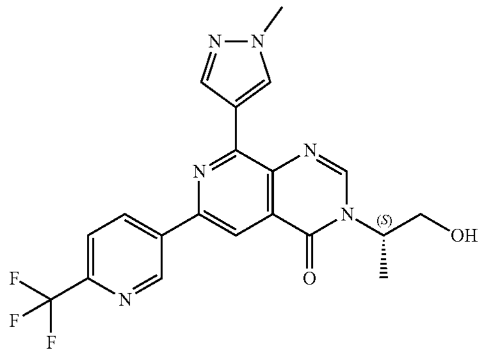<br>(S)-3-(1-hydroxypropan-2-yl)-8-(1-methyl-1H-pyrazol-4-yl)-6-(6-(trifluoromethyl)pyridin-3-yl)pyrido[3,4-d]pyrimidin-4(3H)-one |
| 69 | 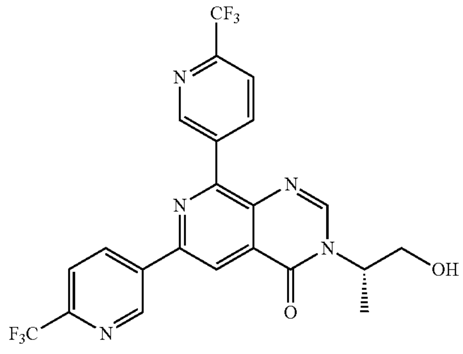<br>(S)-3-(1-hydroxypropan-2-yl)-6,8-bis(6-(trifluoromethyl)pyridin-3-yl)pyrido[3,4-d]pyrimidin-4(3H)-one |

TABLE 1-continued

| Compound No. | Structure and name |
| --- | --- |
| 70 | 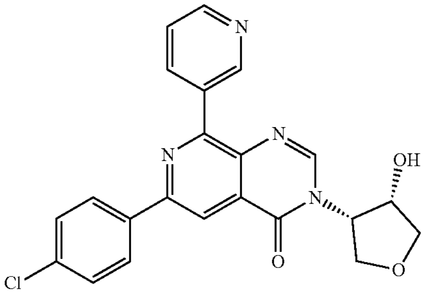 6-(4-chlorophenyl)-3-((3S,4S)-4-hydroxytetrahydrofuran-3-yl)-8-(pyridin-3-yl)pyrido[3,4-d]pyrimidin-4(3H)-one. |
| 71 | 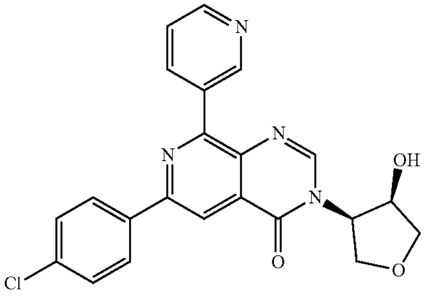 6-(4-chlorophenyl)-3-((3R,4R)-4-hydroxytetrahydrofuran-3-yl)-8-(pyridin-3-yl)pyrido[3,4-d]pyrimidin-4(3H)-one |
| 72 | 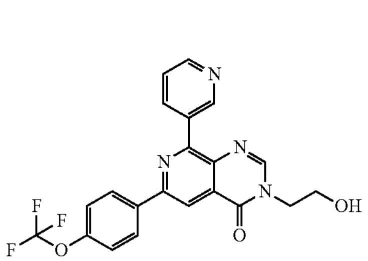 3-(2-hydroxyethyl)-8-(pyridin-3-yl)-6-(4-(trifluoromethoxy)phenyl)pyrido[3,4-d]pyrimidin-4(3H)-one |

TABLE 1-continued

| Compound No. | Structure and name |
| --- | --- |
| 73 | 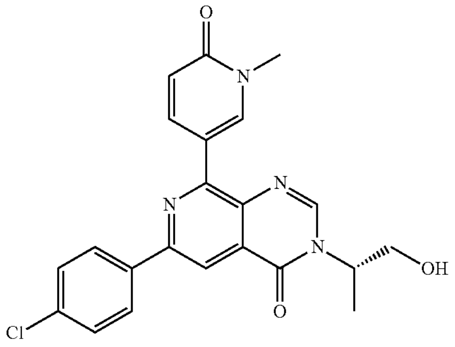 (S)-6-(4-chlorophenyl)-3-(1-hydroxypropan-2-yl)-8-(1-methyl-6-oxo-1,6-dihydropyridin-3-yl)pyrido[3,4-d]pyrimidin-4(3H)-one |
| 74 | 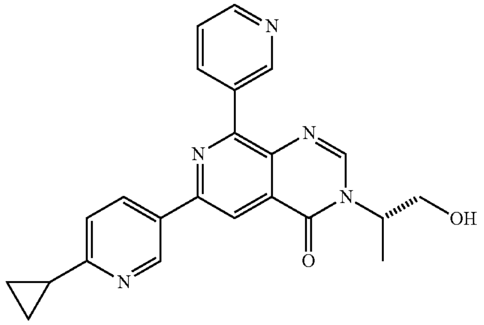 (S)-6-(6-cyclopropylpyridin-3-yl)-3-(1-hydroxypropan-2-yl)-8-(pyridin-3-yl)pyrido[3,4-d]pyrimidin-4(3H)-one |
| 75 | 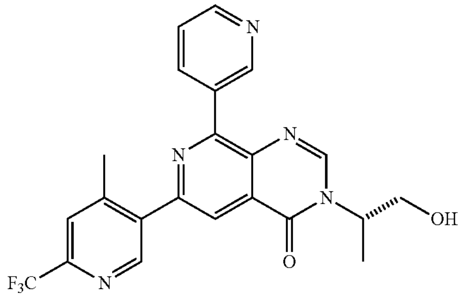 (S)-3-(1-hydroxypropan-2-yl)-6-(4-methyl-6-(trifluoromethyl)pyridin-3-yl)-8-(pyridin-3-yl)pyrido[3,4-d]pyrimidin-4(3H)-one |

TABLE 1-continued

| Compound No. | Structure and name |
|---|---|
| 76 | 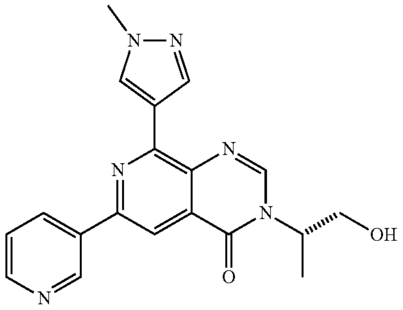 (S)-3-(1-hydroxypropan-2-yl)-8-(1-methyl-1H-pyrazol-4-yl)-6-(pyridin-3-yl)pyrido[3,4-d]pyrimidin-4(3H)-one |
| 77 | 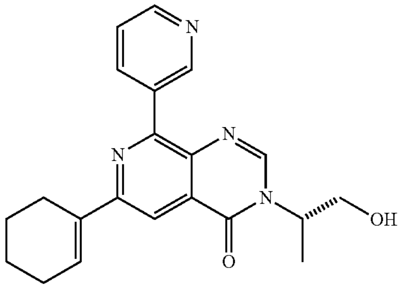 (S)-6-(cyclohex-1-en-1-yl)-3-(1-hydroxypropan-2-yl)-8-(pyridin-3-yl)pyrido[3,4-d]pyrimidin-4(3H)-one |
| 78 | 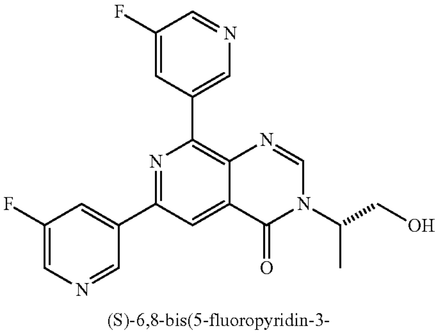 (S)-6,8-bis(5-fluoropyridin-3-yl)-3-(1-hydroxypropan-2-yl)pyrido[3,4-d]pyrimidin-4(3H)-one |

TABLE 1-continued

| Compound No. | Structure and name |
|---|---|
| 79 | 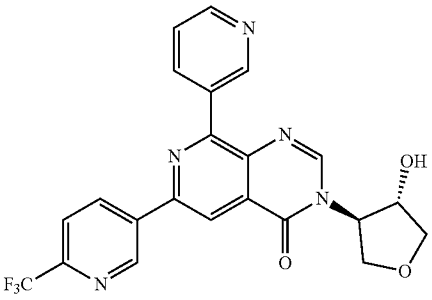 3-((3R,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one |
| 80 | 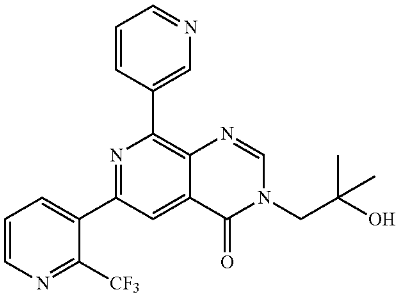 3-(2-hydroxy-2-methylpropyl)-8-(pyridin-3-yl)-6-(2-(trifluoromethyl)pyridin-3-yl)pyrido[3,4-d]pyrimidin-4(3H)-one |
| 81 | 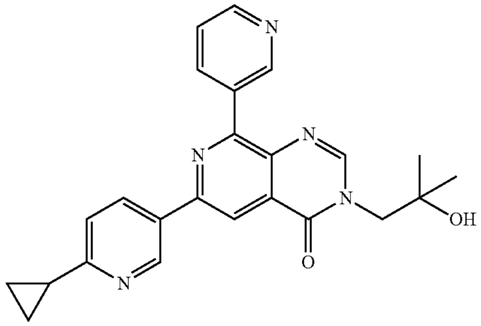 6-(6-cyclopropylpyridin-3-yl)-3-(2-hydroxy-2-methylpropyl)-8-(pyridin-3-yl)pyrido[3,4-d]pyrimidin-4(3H)-one |

TABLE 1-continued

| Compound No. | Structure and name |
|---|---|
| 82 | 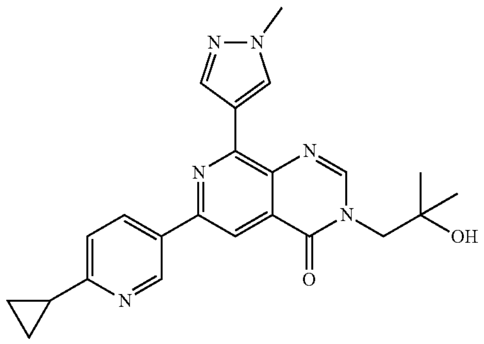 6-(6-cyclopropylpyridin-3-yl)-3-(2-hydroxy-2-methylpropyl)-8-(1-methyl-1H-pyrazol-4-yl)pyrido[3,4-d]pyrimidin-4(3H)-one |
| 83 | 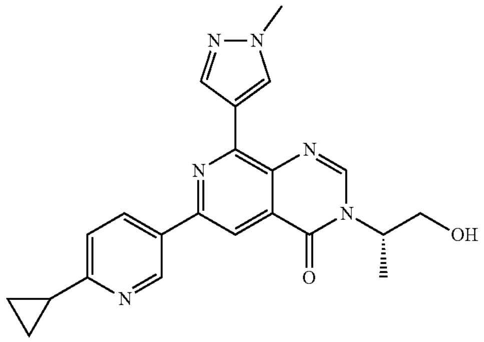 (S)-6-(6-cyclopropylpyridin-3-yl)-3-(1-hydroxypropan-2-yl)-8-(1-methyl-1H-pyrazol-4-yl)pyrido[3,4-d]pyrimidin-4(3H)-one |
| 84 | 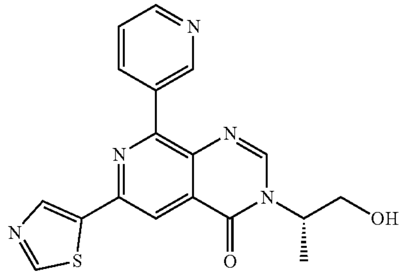 (S)-3-(1-hydroxypropan-2-yl)-8-(pyridin-3-yl)-6-(thiazol-5-yl)pyrido[3,4-d]pyrimidin-4(3H)-one |

TABLE 1-continued

| Compound No. | Structure and name |
|---|---|
| 85 | 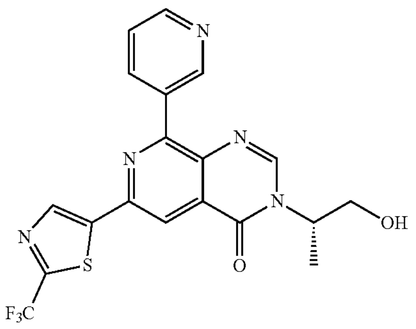 (S)-3-(1-hydroxypropan-2-yl)-8-(pyridin-3-yl)-6-(2-(trifluoromethyl)thiazol-5-yl)pyrido[3,4-d]pyrimidin-4(3H)-one |
| 86 | 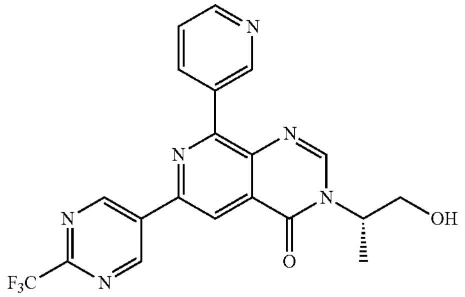 (S)-3-(1-hydroxypropan-2-yl)-8-(pyridin-3-yl)-6-(2-(trifluoromethyl)pyrimidin-5-yl)pyrido[3,4-d]pyrimidin-4(3H)-one |
| 87 | 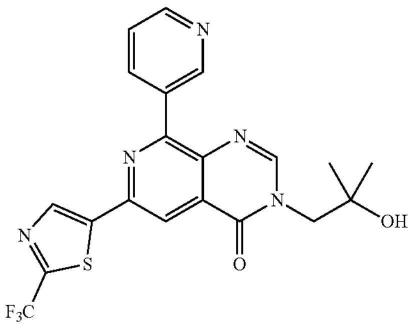 3-(2-hydroxy-2-methylpropyl)-8-(pyridin-3-yl)-6-(2-(trifluoromethyl)thiazol-5-yl)pyrido[3,4-d]pyrimidin-4(3H)-one |

TABLE 1-continued

| Compound No. | Structure and name |
| --- | --- |
| 88 | 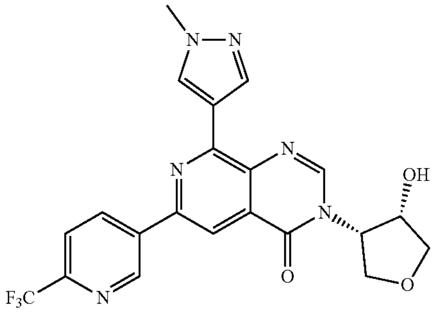 3-((3S,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one |
| 89 | 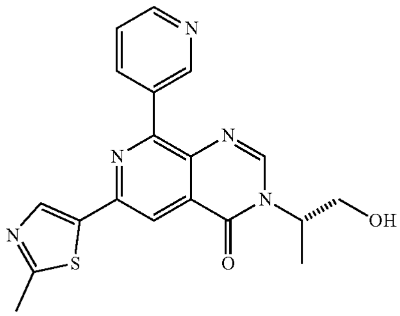 (S)-3-(1-hydroxypropan-2-yl)-6-(2-methylthiazol-5-yl)-8-(pyridin-3-yl)pyrido[3,4-d]pyrimidin-4(3H)-one |
| 90 | 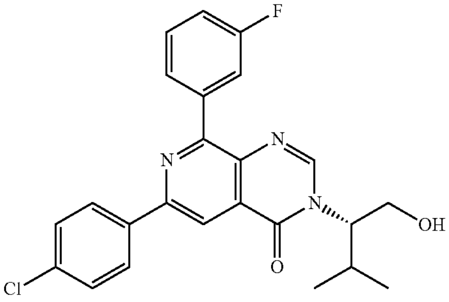 (S)-6-(4-chlorophenyl)-8-(3-fluorophenyl)-3-(1-hydroxy-3-methylbutan-2-yl)pyrido[3,4-d]pyrimidin-4(3H)-one |

TABLE 1-continued

| Compound No. | Structure and name |
| --- | --- |
| 91 | 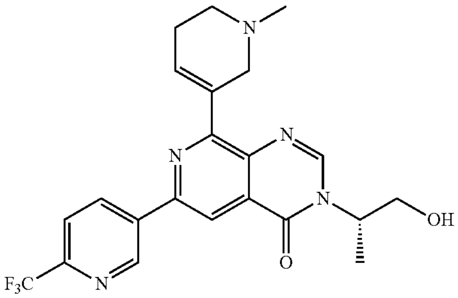 (S)-3-(1-hydroxypropan-2-yl)-8-(1-methyl-1,2,5,6-tetrahydropyridin-3-yl)-6-(6-(trifluoromethyl)pyridin-3-yl)pyrido[3,4-d]pyrimidin-4(3H)-one |
| 92 | 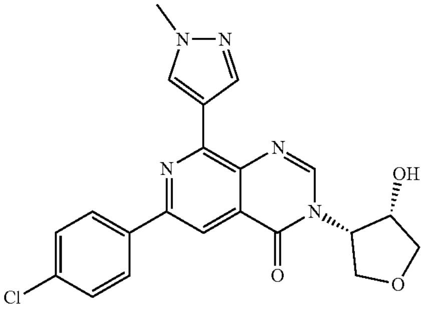 6-(4-chlorophenyl)-3-((3S,4S)-4-hydroxytetrahydrofuran-3-yl)-8-(1-methyl-1H-pyrazol-4-yl)pyrido[3,4-d]pyrimidin-4(3H)-one |
| 93 | 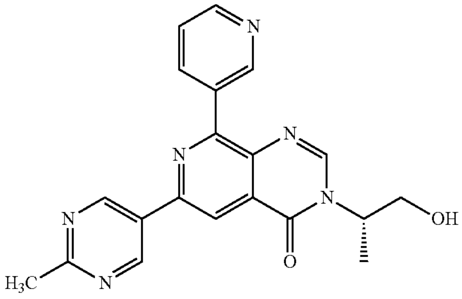 (S)-3-(1-hydroxypropan-2-yl)-6-(2-methylpyrimidin-5-yl)-8-(pyridin-3-yl)pyrido[3,4-d]pyrimidin-4(3H)-one |

TABLE 1-continued

| Compound No. | Structure and name |
|---|---|
| 94 | 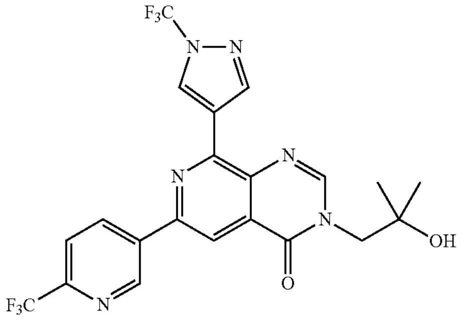 3-(2-hydroxy-2-methylpropyl)-8-(1-(trifluoromethyl)-1H-pyrazol-4-yl)-6-(6-(trifluoromethyl)pyridin-3-yl)pyrido[3,4-d]pyrimidin-4(3H)-one |
| 95 | 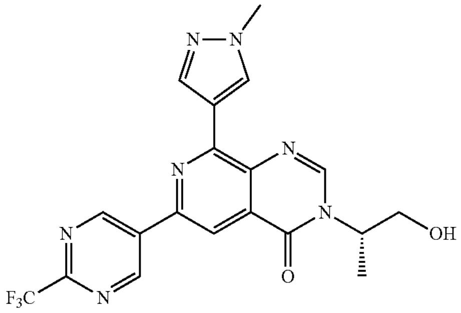 (S)-3-(1-hydroxypropan-2-yl)-8-(1-methyl-1H-pyrazol-4-yl)-6-(2-(trifluoromethyl)pyrimidin-5-yl)pyrido[3,4-d]pyrimidin-4(3H)-one |
| 96 | 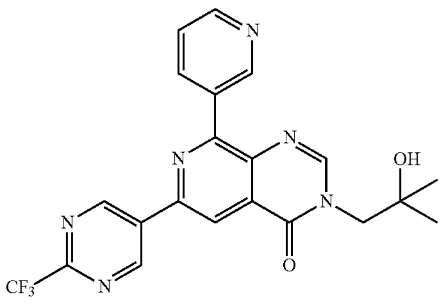 3-(2-hydroxy-2-methylpropyl)-8-(pyridin-3-yl)-6-(2-(trifluoromethyl)pyrimidin-5-yl)pyrido[3,4-d]pyrimidin-4(3H)-one |

TABLE 1-continued

| Compound No. | Structure and name |
|---|---|
| 97 | 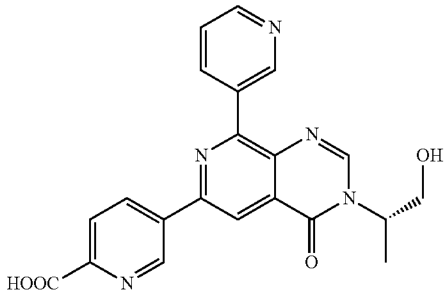 (S)-5-(3-(1-hydroxypropan-2-yl)-4-oxo-8-(pyridin-3-yl)-3,4-dihydropyrido[3,4-d]pyrimidin-6-yl)picolinic acid |
| 98 | 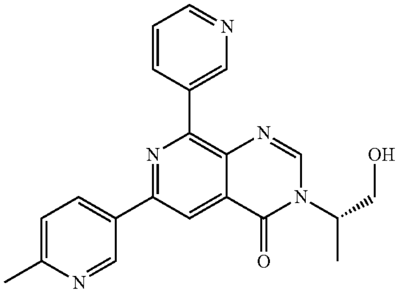 (S)-3-(1-hydroxypropan-2-yl)-6-(6-methylpyridin-3-yl)-8-(pyridin-3-yl)pyrido[3,4-d]pyrimidin-4(3H)-one |
| 99 | 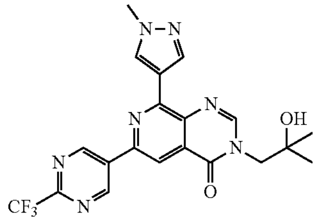 3-(2-hydroxy-2-methylpropyl)-8-(1-methyl-1H-pyrazol-4-yl)-6-(2-(trifluoromethyl)pyrimidin-5-yl)pyrido[3,4-d]pyrimidin-4(3H)-one |
| 100 | 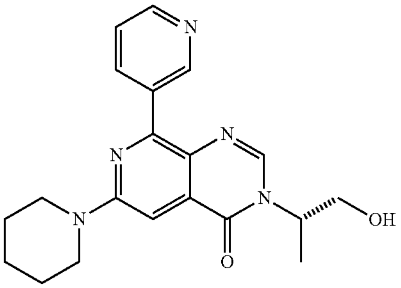 (S)-3-(1-hydroxypropan-2-yl)-6-(piperidin-1-yl)-8-(pyridin-3-yl)pyrido[3,4-d]pyrimidin-4(3H)-one |

TABLE 1-continued

| Compound No. | Structure and name |
|---|---|
| 101 | 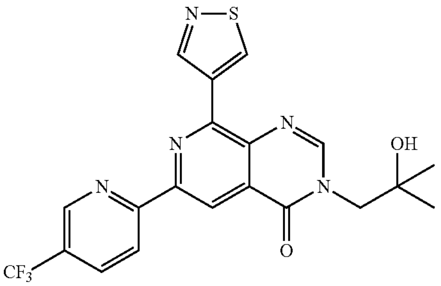 3-(2-hydroxy-2-methylpropyl)-8-( isothiazol-4-yl)-6-(5-(trifluoromethyl)pyridin-2-yl)pyrido[3,4-d]pyrimidin-4(3H)-one |
| 102 | 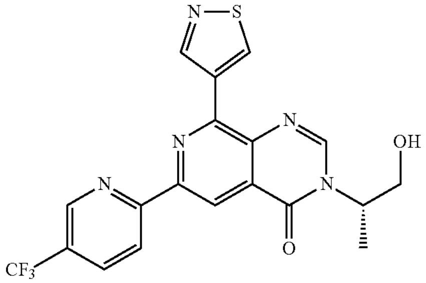 (S)-3-(1-hydroxypropan-2-yl)-8-( isothiazol-4-yl)-6-(5-(trifluoromethyl)pyridin-2-yl)pyrido[3,4-d]pyrimidin-4(3H)-one |
| 103 | 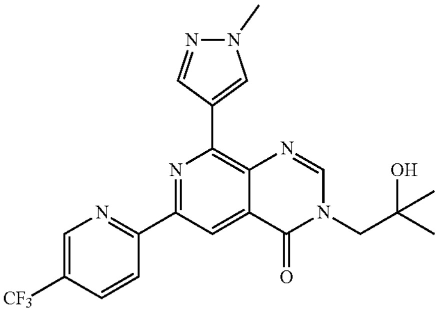 3-(2-hydroxy-2-methylpropyl)-8-(1-methyl-1H-pyrazol-4-yl)-6-(5-(trifluoromethyl)pyridin-2-yl)pyrido[3,4-d]pyrimidin-4(3H)-one |

TABLE 1-continued

| Compound No. | Structure and name |
|---|---|
| 104 | 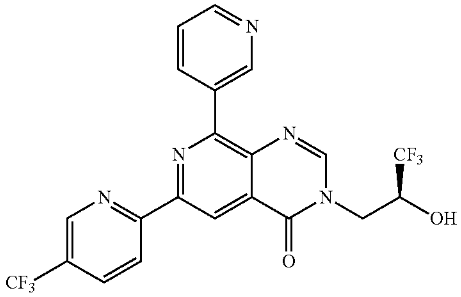 (S)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one |
| 105 | 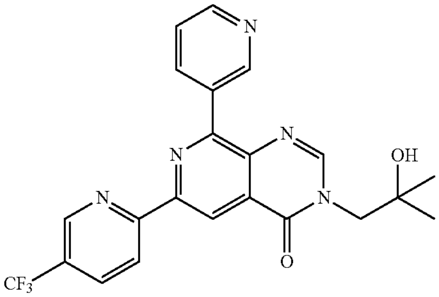 (3-(2-hydroxy-2-methylpropyl)-8-(pyridin-3-yl)-6-(5-(trifluoromethyl)pyridin-2-yl)pyrido[3,4-d]pyrimidin-4(3H)-one |
| 106 | 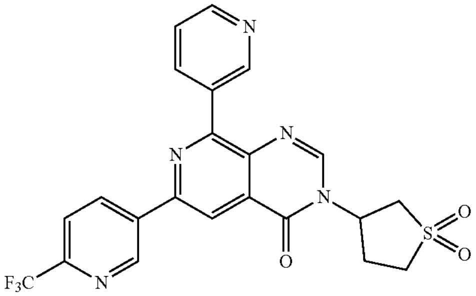 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 107 | 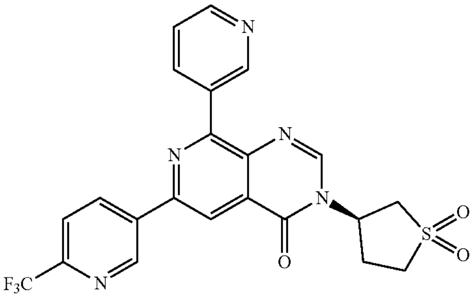 (R)-3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one |
| 108 | 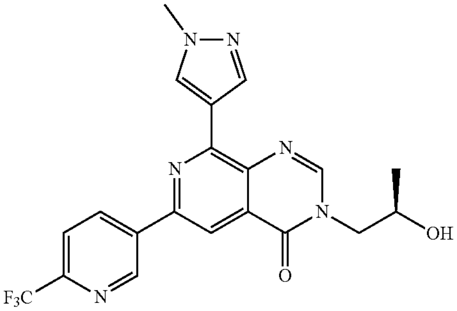 (R)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one |
| 1090 | 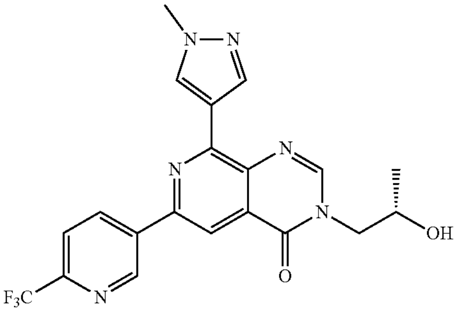 (S)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 110 | 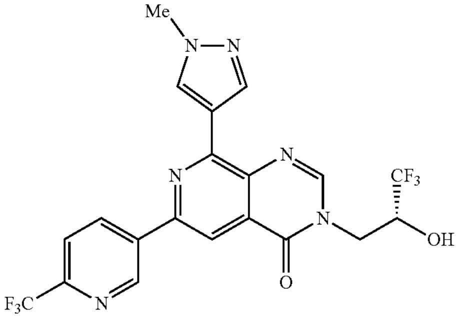 (R)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one |
| 111 | 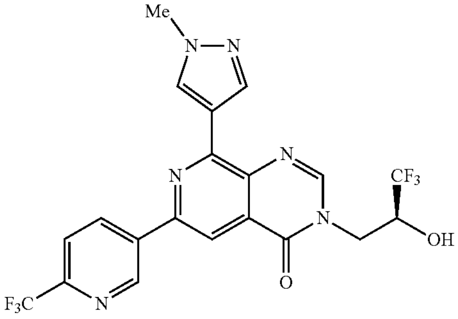 (S)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one |
| 112 | 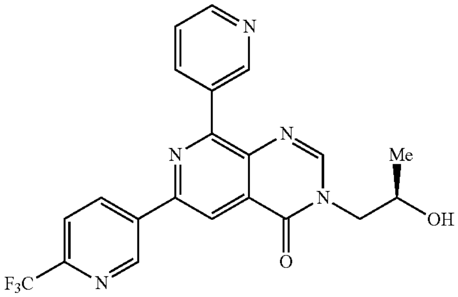 (R)-3-(2-hydroxypropyl)-8-(pyridin-3-yl)-6-(6-(trifluoromethyl)pyridin-3-yl)pyrido[3,4-d]pyrimidin-4(3H)-one |

TABLE 1-continued

| Compound No. | Structure and name |
|---|---|
| 113 | 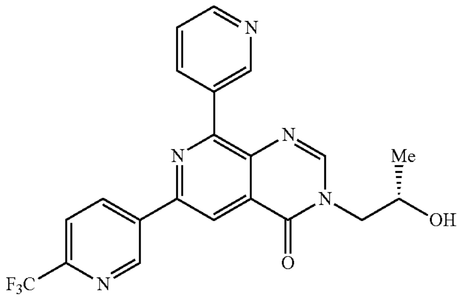<br>(R)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one |
| 114 | 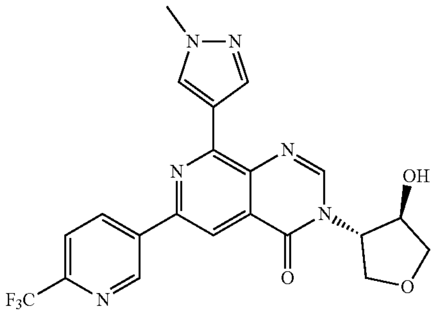<br>3-((3S,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one |
| 115 | 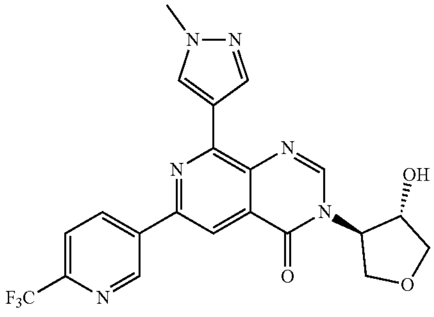<br>3-((3R,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one |
| 116 | 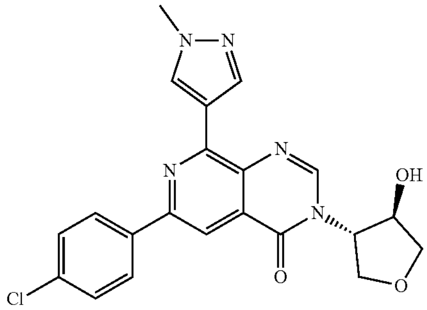<br>6-(4-chlorophenyl)-3-((3S,4R)-4-hydroxytetrahydrofuran-3-yl)-8-(1-methyl-1H-pyrazol-4-yl)pyrido[3,4-d]pyrimidin-4(3H)-one |
| 117 | 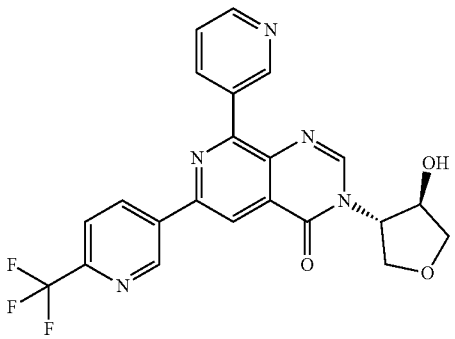<br>3-((3S,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one |
| 118 | 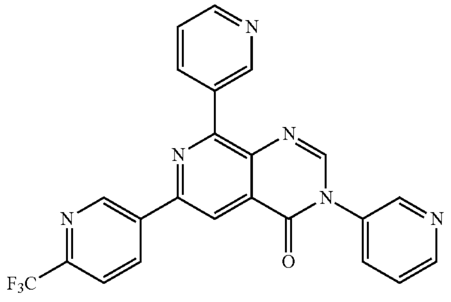<br>3,8-di(pyridin-3-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 119 | 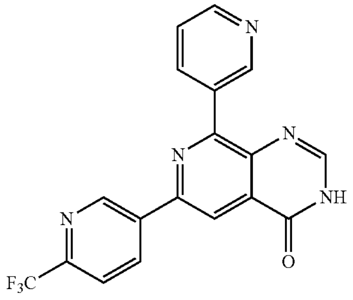 8-(pyridin-3-yl)-6-(6-(trifluoromethyl)pyridin-3-yl)pyrido[3,4-d]pyrimidin-4(3H)-one |
| 120 | 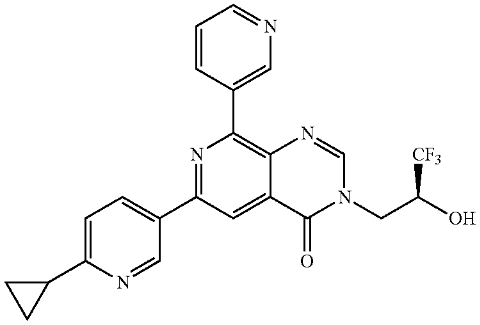 (S)-6-(6-cyclopropylpyridin-3-yl)-8-(pyridin-3-yl)-3-(3,3,3-trifluoro-2-hydroxypropyl)pyrido[3,4-d]pyrimidin-4(3H)-one |
| 121 | 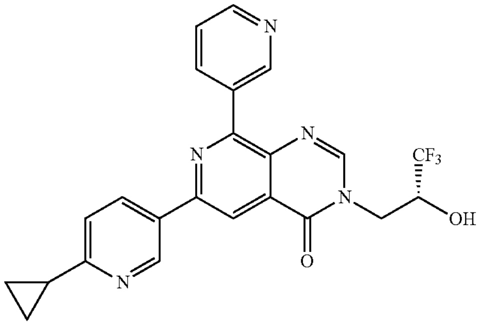 (R)-6-(6-cyclopropylpyridin-3-yl)-8-(pyridin-3-yl)-3-(3,3,3-trifluoro-2-hydroxypropyl)pyrido[3,4-d]pyrimidin-4(3H)-one |
| 122 | 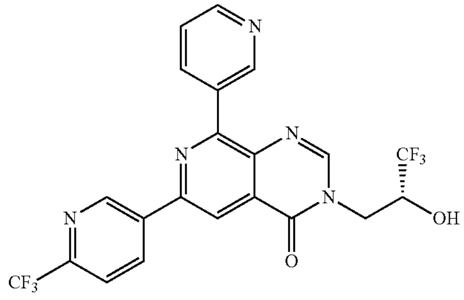 (R)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one |
| 123 | 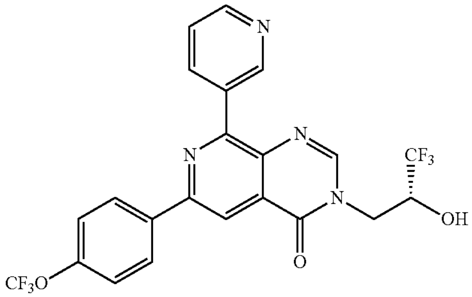 (R)-8-(pyridin-3-yl)-3-(3,3,3-trifluoro-2-hydroxypropyl)-6-(4-(trifluoromethoxy)phenyl) pyrido[3,4-d]pyrimidin-4(3H)-one |
| 124 | 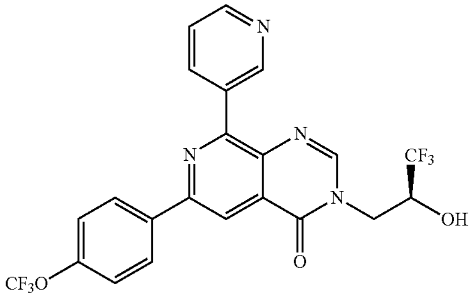 (S)-8-(pyridin-3-yl)-3-(3,3,3-trifluoro-2-hydroxypropyl)-6-(4-(trifluoromethoxy)phenyl) pyrido[3,4-d]pyrimidin-4(3H)-one |

TABLE 1-continued

| Compound No. | Structure and name |
| --- | --- |
| 125 | 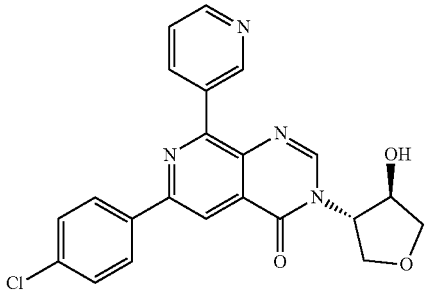 6-(4-chlorophenyl)-3-((3S,4R)-4-hydroxytetrahydrofuran-3-yl)-8-(pyridin-3-yl)pyrido[3,4-d]pyrimidin-4(3H)-one |
| 126 | 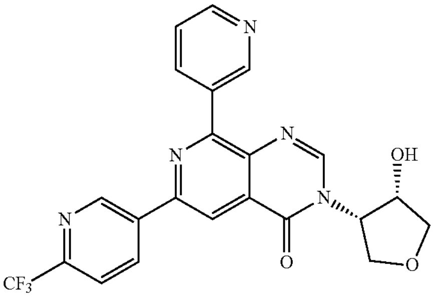 3-((3S,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one |
| 127 | 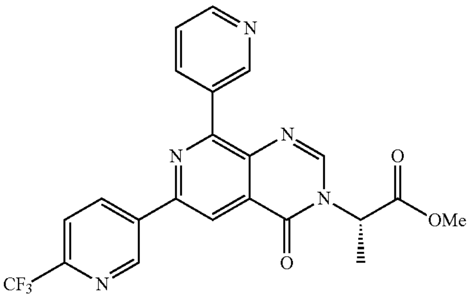 methyl (S)-2-(4-oxo-8-(pyridin-3-yl)-6-(6-(trifluoromethyl)pyridin-3-yl)pyrido[3,4-d]pyrimidin-3(4H)-yl)propanoate |

TABLE 1-continued

| Compound No. | Structure and name |
| --- | --- |
| 128 | 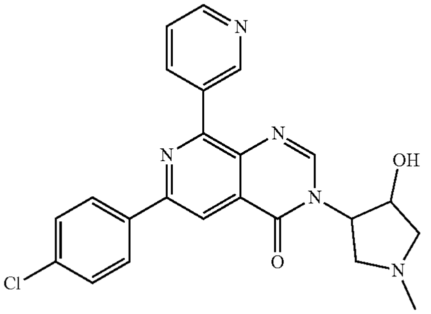 6-(4-chlorophenyl)-3-(4-hydroxy-1-methylpyrrolidin-3-yl)-8-(pyridin-3-yl)pyrido[3,4-d]pyrimidin-4(3H)-one |
| 129 | 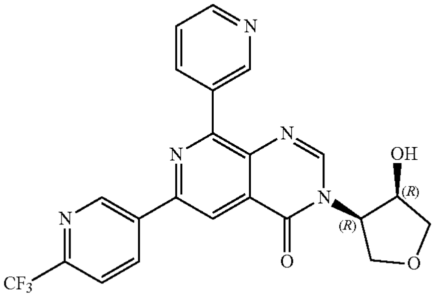 3-((3R,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one |
| 130 | 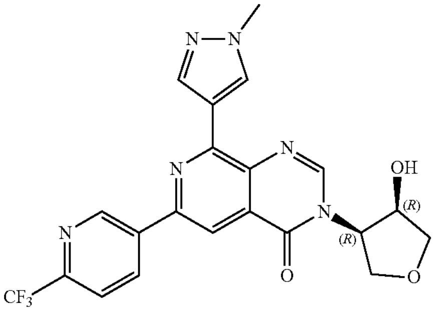 3-((3R,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 131 | 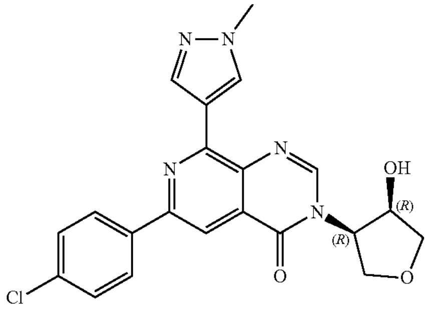 6-(4-chlorophenyl)-3-((3R,4R)-4-hydroxytetrahydrofuran-3-yl)-8-(1-methyl-1H-pyrazol-4-yl)pyrido[3,4-d]pyrimidin-4(3H)-one |
| 132 | 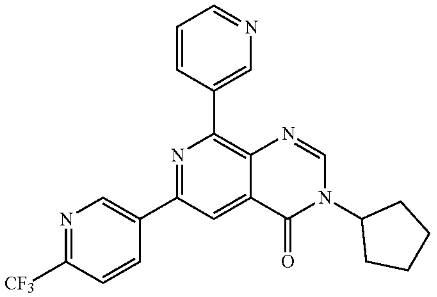 3-cyclopentyl-8-(pyridin-3-yl)-6-(6-(trifluoromethyl)pyridin-3-yl)pyrido[3,4-d]pyrimidin-4(3H)-one |
| 133 | 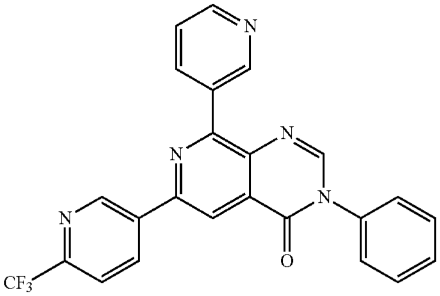 3-phenyl-8-(pyridin-3-yl)-6-(6-(trifluoromethyl)pyridin-3-yl)pyrido[3,4-d]pyrimidin-4(3H)-one |
| 134 | 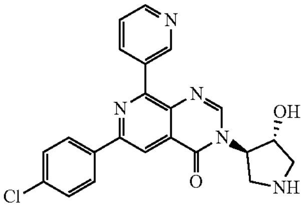 6-(4-chlorophenyl)-3-((3R,4R)-4-hydroxypyrrolidin-3-yl)-8-(pyridin-3-yl)pyrido[3,4-d]pyrimidin-4(3H)-one |

TABLE 1-continued

| Compound No. | Structure and name |
| --- | --- |
| 135 | 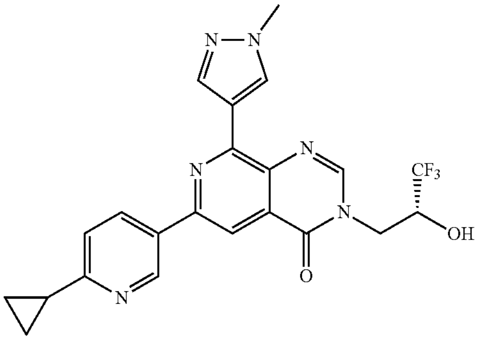 (R)-6-(6-cyclopropylpyridin-3-yl)-8-(1-methyl-1H-pyrazol-4-yl)-3-(3,3,3-trifluoro-2-hydroxypropyl)pyrido[3,4-d]pyrimidin-4(3H)-one |
| 136 | 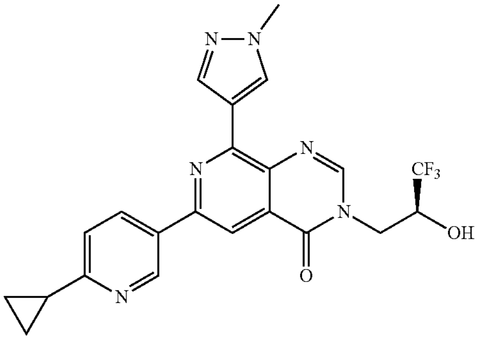 (S)-6-(6-cyclopropylpyridin-3-yl)-8-(1-methyl-1H-pyrazol-4-yl)-3-(3,3,3-trifluoro-2-hydroxypropyl)pyrido[3,4-d]pyrimidin-4(3H)-one |
| 137 | 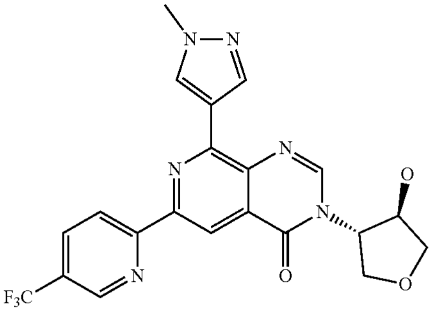 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one |

TABLE 1-continued

| Compound No. | Structure and name |
|---|---|
| 138 | 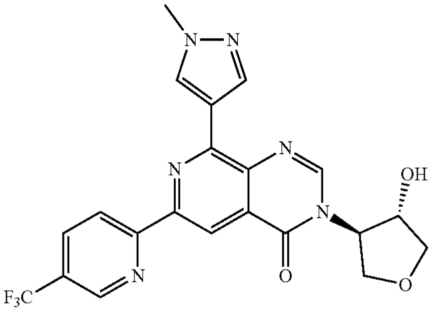 3-((3R,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one |
| 139 | 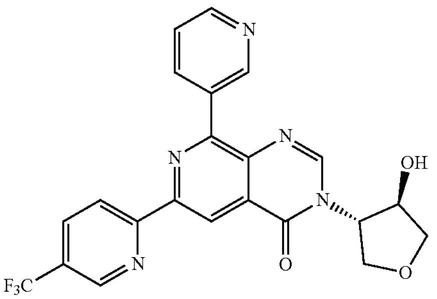 3-((3S,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one |
| 140 | 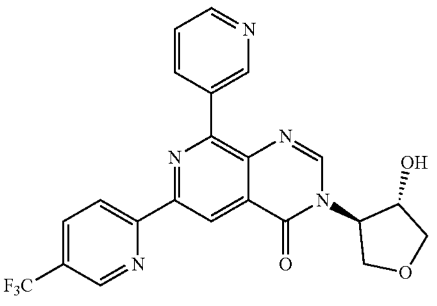 3-((3R,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one |
| 141 | 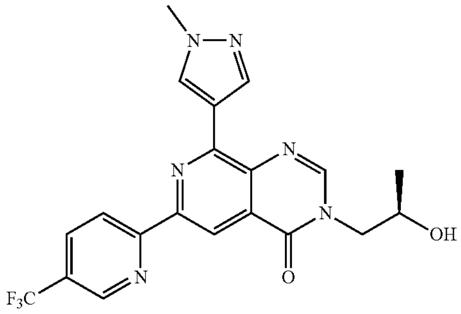 (R)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one |
| 142 | 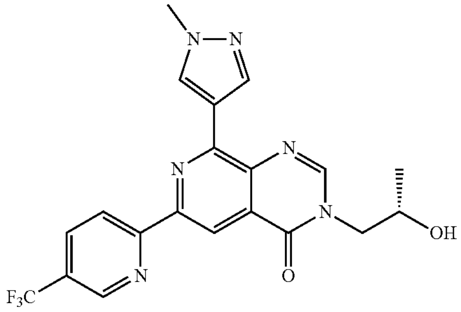 (S)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one |
| 143 | 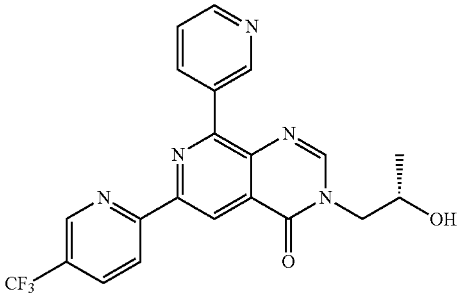 (S)-3-(2-hydroxypropyl)-8-(pyridin-3-yl)-6-(5-(trifluoromethyl)pyridin-2-yl)pyrido[3,4-d]pyrimidin-4(3H)-one |

TABLE 1-continued

| Compound No. | Structure and name |
|---|---|
| 144 | 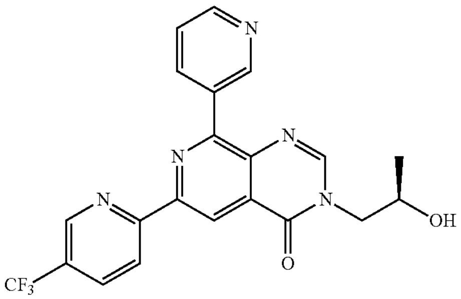<br>(R)-3-(2-hydroxypropyl)-8-(pyridin-3-yl)-6-(5-(trifluoromethyl)pyridin-2-yl)pyrido[3,4-d]pyrimidin-4(3H)-one |
| 145 | 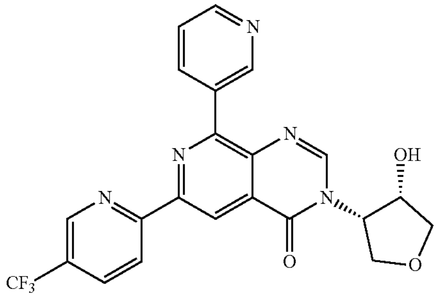<br>3-((3S,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one |
| 146 | 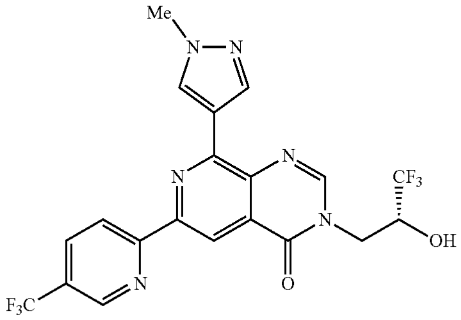<br>(S)-3-(2-hydroxypropyl)-8-(pyridin-3-yl)-6-(6-(trifluoromethyl)pyridin-3-yl)pyrido[3,4-d]pyrimidin-4(3H)-one |

TABLE 1-continued

| Compound No. | Structure and name |
|---|---|
| 147 | 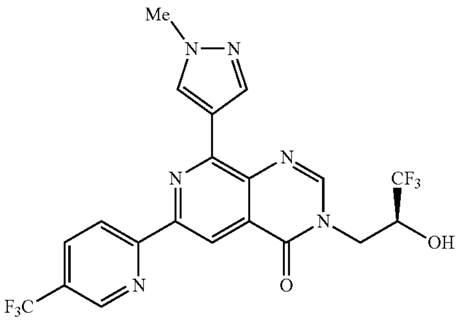<br>(S)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one |
| 148 | 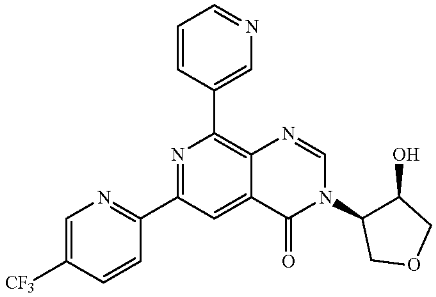<br>3-((3R,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one |
| 149 | 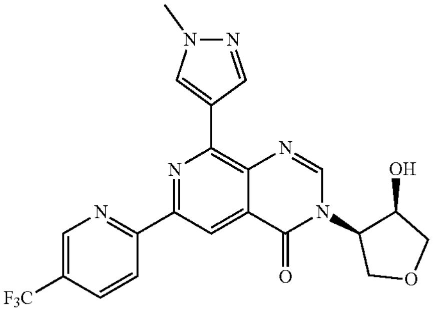<br>3-((3R,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one |

TABLE 1-continued

| Compound No. | Structure and name |
|---|---|
| 150 | 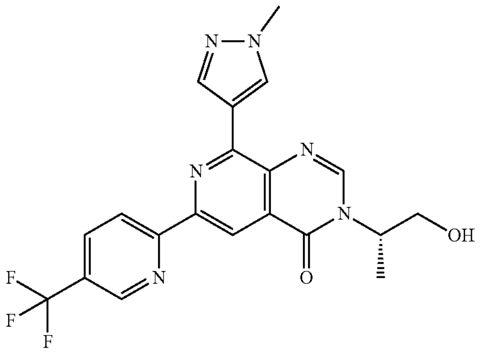 (S)-3-(1-hydroxypropan-2-yl)-8-(1-methyl-1H-pyrazol-4-yl)-6-(5-(trifluoromethyl)pyridin-2-yl)pyrido[3,4-d]pyrimidin-4(3H)-one |
| 151 | 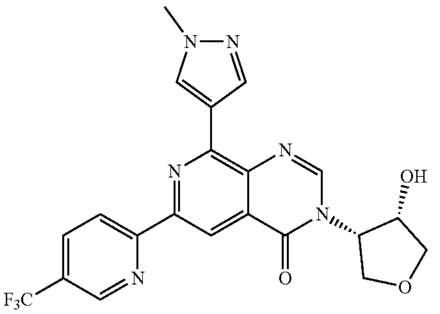 3-((3S,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one |
| 152 | 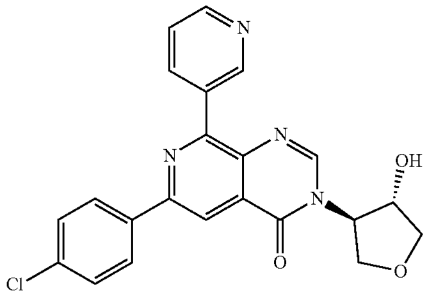 6-(4-chlorophenyl)-3-((3R,4S)-4-hydroxytetrahydrofuran-3-yl)-8-(pyridin-3-yl)pyrido[3,4-d]pyrimidin-4(3H)-one |
| 153 | 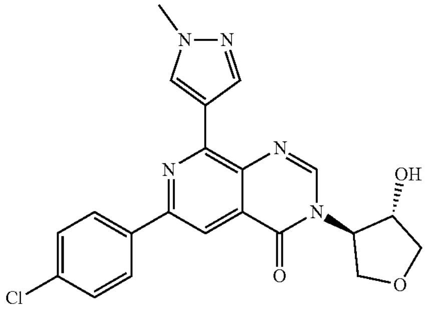 6-(4-Chlorophenyl)-3-((3R,4S)-4-hydroxytetrahydrofuran-3-yl)-8-(1-methyl-1H-pyrazol-4-yl)pyrido[3,4-d]pyrimidin-4(3H)-one |
| 154 | 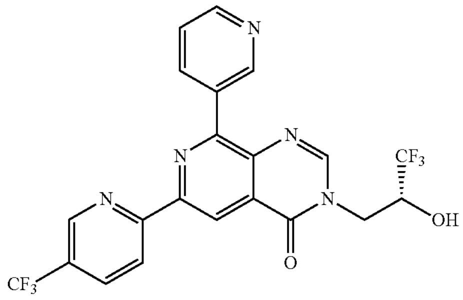 (R)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one |
| 155 | 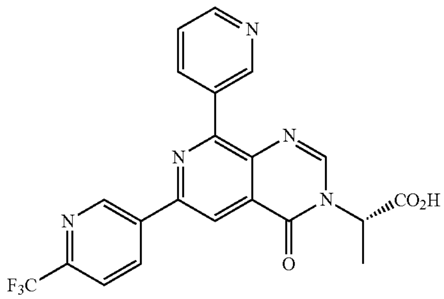 (S)-2-(4-oxo-8-(pyridin-3-yl)-6-(6-(trifluoromethyl)pyridin-3-yl)pyrido[3,4-d]pyrimidin-3(4H)-yl)propanoic acid |

TABLE 1-continued

| Compound No. | Structure and name |
| --- | --- |
| 156 | 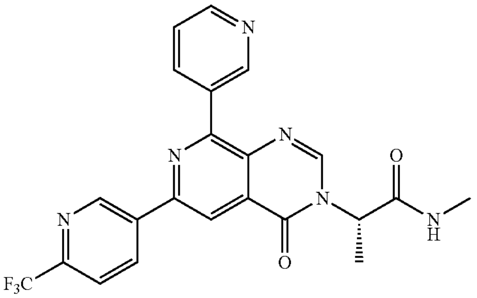<br>(S)-N-methyl-2-(4-oxo-8-(pyridin-3-yl)-6-(6-(trifluoromethyl)pyridin-3-yl)pyrido[3,4-d]pyrimidin-3(4H)-yl)propanamide |
| 157 | 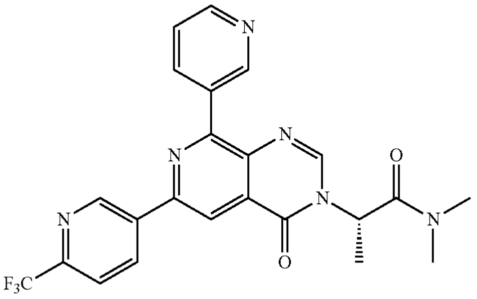<br>(S)-N,N-dimethyl-2-(4-oxo-8-(pyridin-3-yl)-6-(6-(trifluoromethyl)pyridin-3-yl)pyrido[3,4-d]pyrimidin-3(4H)-yl)propenamide |
| 158 | 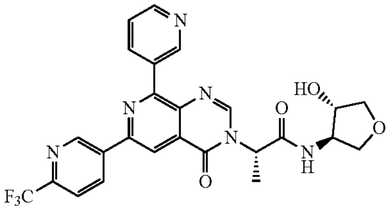<br>(S)-N-((3R,4S)-4-hydroxytetrahydrofuran-3-yl)-2-(4-oxo-8-(pyridin-3-yl)-6-(6-(trifluoromethyl)pyridin-3-yl)pyrido[3,4-d]pyrimidin-3(4H)-yl)propanamide |
| 159 | 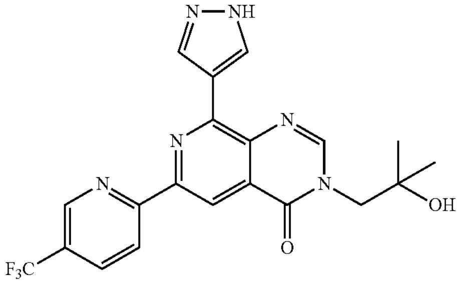<br>3-(2-hydroxy-2-methylpropyl)-8-(1H-pyrazol-4-yl)-6-(5-(trifluoromethyl)pyridin-2-yl)pyrido[3,4-d]pyrimidin-4(3H)-one |

TABLE 1-continued

| Compound No. | Structure and name |
| --- | --- |
| 160 | 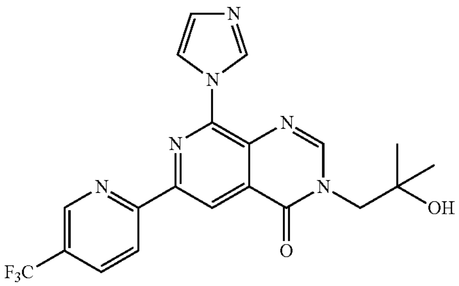<br>3-(2-hydroxy-2-methylpropyl)-8-(1H-imidazol-1-yl)-6-(5-(trifluoromethyl)pyridin-2-yl)pyrido[3,4-d]pyrimidin-4(3H)-one |
| 161 | 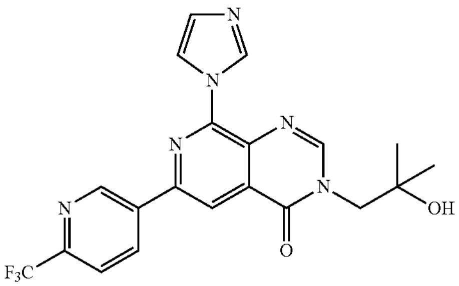<br>3-(2-hydroxy-2-methylpropyl)-8-(1H-imidazol-1-yl)-6-(6-(trifluoromethyl)pyridin-2-yl)pyrido[3,4-d]pyrimidin-4(3H)-one |
| 162 | 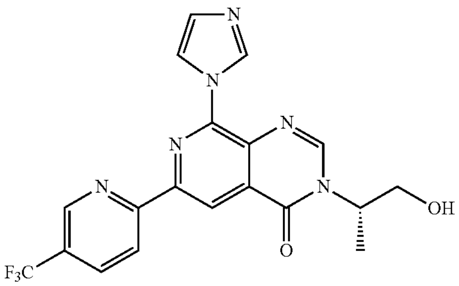<br>(S)-3-(1-hydroxypropan-2-yl)-8-(1H-imidazol-1-yl)-6-(5-(trifluoromethyl)pyridin-2-yl)pyrido[3,4-d]pyrimidin-4(3H)-one |

TABLE 1-continued

| Compound No. | Structure and name |
| --- | --- |
| 163 | 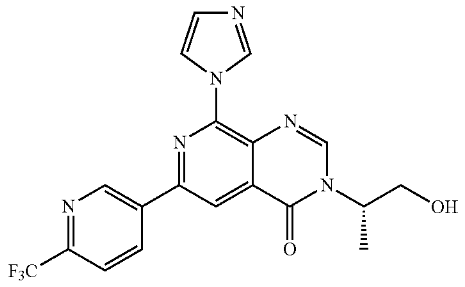 (S)-3-(1-hydroxypropan-2-yl)-8-(1H-imidazol-1-yl)-6-(6-(trifluoromethyl)pyridin-3-yl)pyrido[3,4-d]pyrimidin-4(3H)-one |
| 164 | 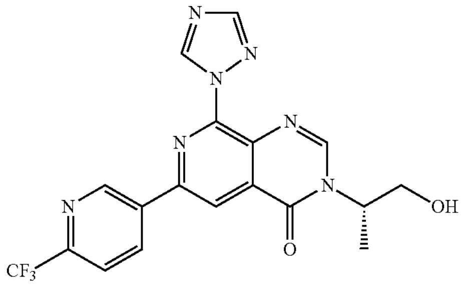 (S)-3-(1-hydroxypropan-2-yl)-8-(1H-1,2,4-triazol-1-yl)-6-(6-(trifluoromethyl)pyridin-3-yl)pyrido[3,4-d]pyrimidin-4(3H)-one |
| 165 | 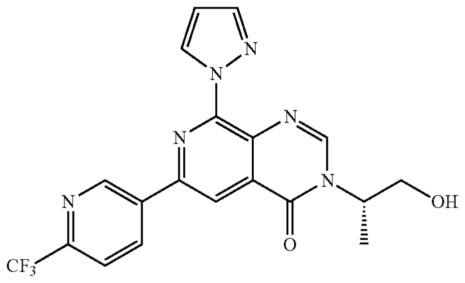 (S)-3-(1-hydroxypropan-2-yl)-8-(1H-pyrazol-1-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 166 | 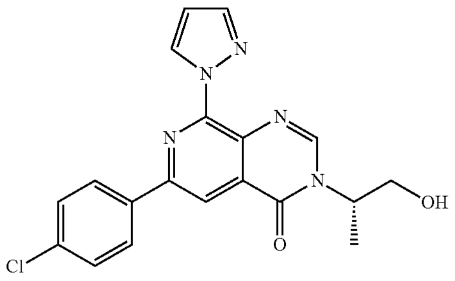 (S)-6-(4-chlorophenyl)-3-(1-hydroxypropan-2-yl)-8-(1H-pyrazol-1-yl)pyrido[3,4-d]pyrimidin-4(3H)-one |
| 167 | 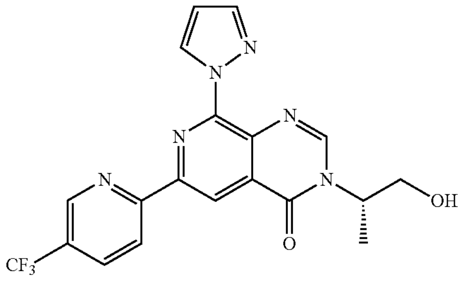 (S)-3-(1-hydroxypropan-2-yl)-8-(1H-pyrazol-1-yl)-6-(5-(trifluoromethyl)pyridin-2-yl)pyrido[3,4-d]pyrimidin-4(3H)-one |
| 168 | 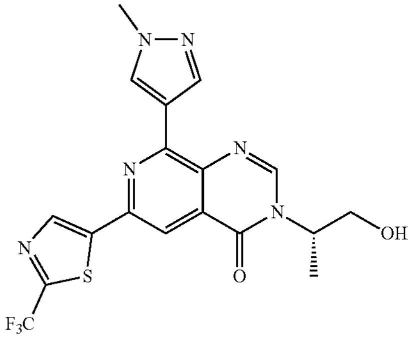 S)-3-(1-hydroxypropan-2-yl)-8-(1-methyl-1H-pyrazol-4-yl)-6-(2-(trifluoromethyl)thiazol-5-yl)pyrido[3,4-d]pyrimidin-4(3H)-one |

TABLE 1-continued

| Compound No. | Structure and name |
| --- | --- |
| 169 | 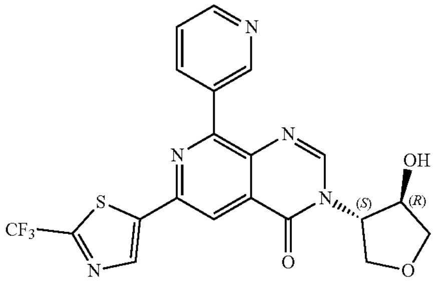<br>3-((3S,4R)-4-hydroxytetrahydrofuran-3-yl)-8-(pyridin-3-yl)-6-(2-(trifluoromethyl)thiazol-5-yl)pyrido[3,4-d]pyrimidin-4(3H)-one |
| 170 | 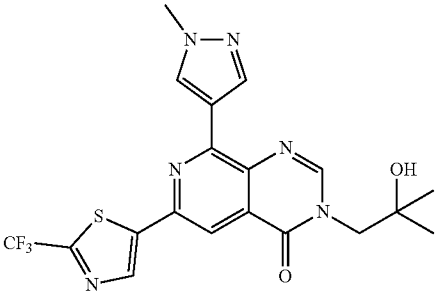<br>3-(2-hydroxy-2-methylpropyl)-8-(1-methyl-1H-pyrazol-4-yl)-6-(2-(trifluoromethyl)thiazol-5-yl)pyrido[3,4-d]pyrimidin-4(3H)-one |
| 171 | 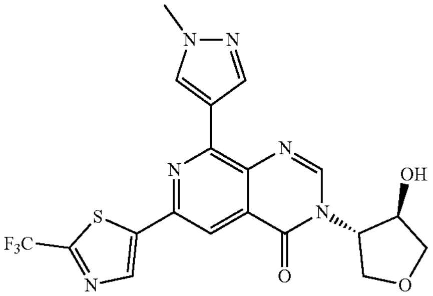<br>3-((3S,4R)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one |
| 172 | 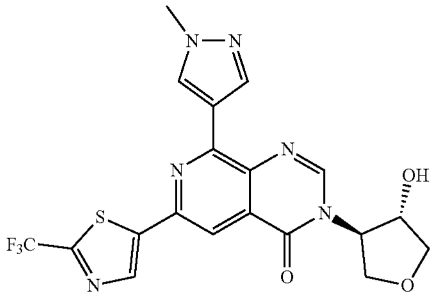<br>3-((3R,4S)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one |
| 173 | 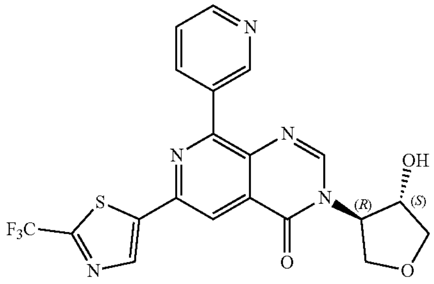<br>3-((3R,4S)-4-hydroxytetrahydrofuran-3-yl)-8-(pyridin-3-yl)-6-(2-(trifluoromethyl)thiazol-5-yl)pyrido[3,4-d]pyrimidin-4(3H)-one |
| 174 | 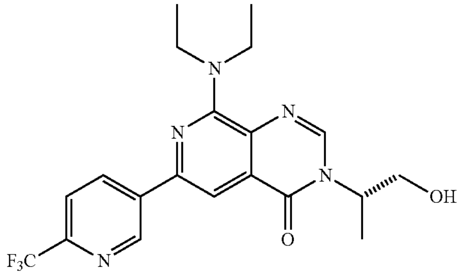<br>(S)-8-(diethylamino)-3-(1-hydroxypropan-2-yl)-6-(6-(trifluoromethyl)pyridin-3-yl)pyrido[3,4-d]pyrimidin-4(3H)-one |

TABLE 1-continued

| Compound No. | Structure and name |
| --- | --- |
| 175 | 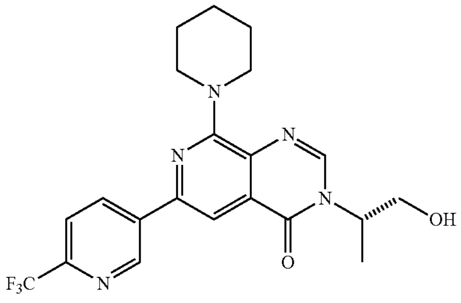 (S)-3-(1-hydroxypropan-2-yl)-8-(piperidin-1-yl)-6-(6-(trifluoromethyl)pyridin-3-yl)pyrido[3,4-d]pyrimidin-4(3H)-one |
| 176 | 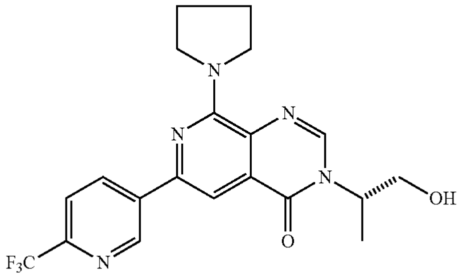 (S)-3-(1-hydroxypropan-2-yl)-8-(pyrrolidin-1-yl)-6-(6-(trifluoromethyl)pyridin-3-yl)pyrido[3,4-d]pyrimidin-4(3H)-one |
| 177 | 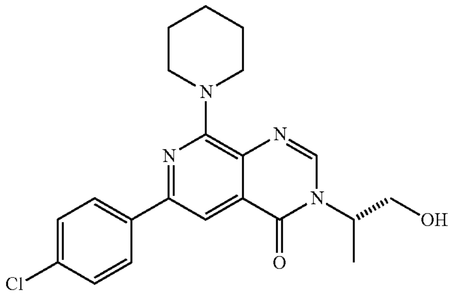 (S)-6-(4-chlorophenyl)-3-(1-hydroxypropan-2-yl)-8-(piperidin-1-yl)pyrido[3,4-d]pyrimidin-4(3H)-one |

TABLE 1-continued

| Compound No. | Structure and name |
| --- | --- |
| 178 | 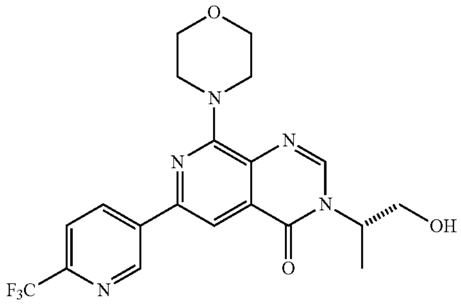 (S)-3-(1-hydroxypropan-2-yl)-8-morpholino-6-(6-(trifluoromethyl)pyridin-3-yl)pyrido[3,4-d]pyrimidin-4(3H)-one |
| 179 | 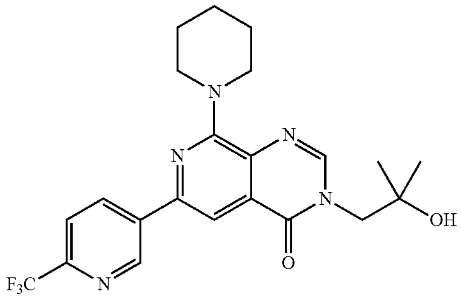 3-(2-hydroxy-2-methylpropyl)-8-(piperidin-1-yl)-6-(6-(trifluoromethyl)pyridin-3-yl)pyrido[3,4-d]pyrimidin-4(3H)-one |
| 180 | 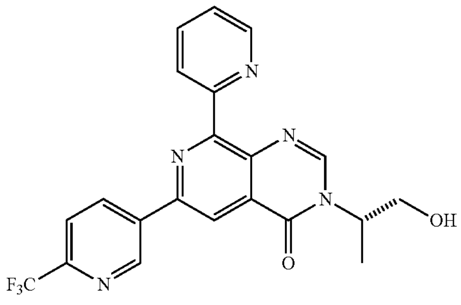 (S)-3-(1-hydroxypropan-2-yl)-8-(pyridin-2-yl)-6-(6-(trifluoromethyl)pyridin-3-yl)pyrido[3,4-d]pyrimidin-4(3H)-one |

TABLE 1-continued

| Compound No. | Structure and name |
|---|---|
| 181 | 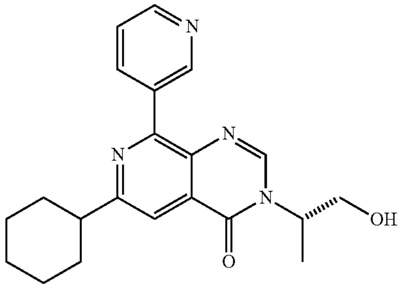 (S)-6-cyclohexyl-3-(1-hydroxypropan-2-yl)-8-(pyridin-3-yl)pyrido[3,4-d]pyrimidin-4(3H)-one |
| 182 | 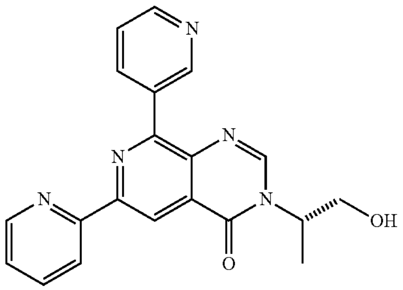 (S)-3-(1-hydroxypropan-2-yl)-6-(pyridin-2-yl)-8-(pyridin-3-yl)pyrido[3,4-d]pyrimidin-4(3H)-one |
| 183 | 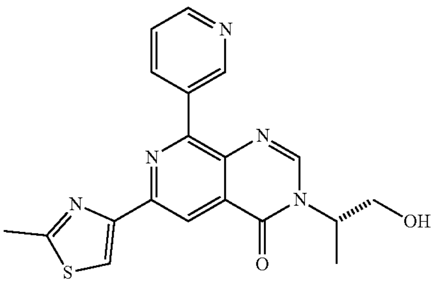 (S)-3-(1-hydroxypropan-2-yl)-6-(2-methylthiazol-4-yl)-8-(pyridin-3-yl)pyrido[3,4-d]pyrimidin-4(3H)-one |
| 184 | 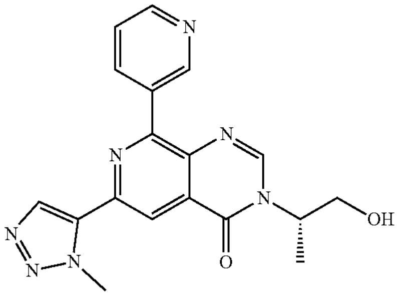 (S)-3-(1-hydroxypropan-2-yl)-6-(1-methyl-1H-1,2,3-triazol-5-yl)-8-(pyridin-3-yl)pyrido[3,4-d]pyrimidin-4(3H)-one |
| 185 enantiomer 1 and 185 enantiomer 2 | 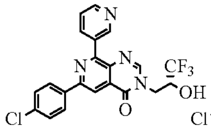 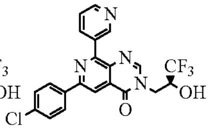 (R)-6-(4-chlorophenyl)-8-(pyridin-3-yl)-3-(3,3,3-trifluoro-2-hydroxypropyl)pyrido[3,4-d]pyrimidin-4(3H)-one and (S)-6-(4-chlorophenyl)-8-(pyridin-3-yl)-3-(3,3,3-trifluoro-2-hydroxypropyl)pyrido[3,4-d]pyrimidin-4(3H)-one |
| 186 | 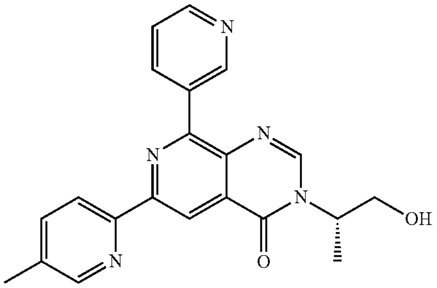 (S)-3-(1-hydroxypropan-2-yl)-6-(5-methylpyridin-2-yl)-8-(pyridin-3-yl)pyrido[3,4-d]pyrimidin-4(3H)-one |
| 187 | 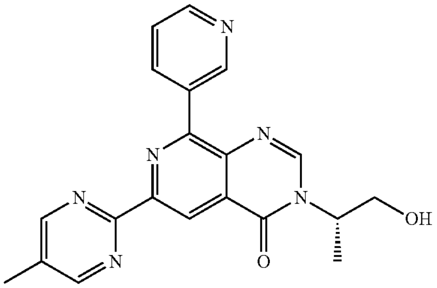 (S)-3-(1-hydroxypropan-2-yl)-6-(5-methylpyrimidin-2-yl)-8-(pyridin-3-yl)pyrido[3,4-d]pyrimidin-4(3H)-one |

TABLE 1-continued

| Compound No. | Structure and name |
|---|---|
| 188 | 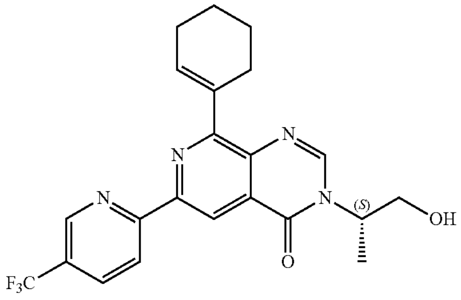 (S)-8-(cyclohex-1-en-1-yl)-3-(1-hydroxypropan-2-yl)-6-(5-(trifluoromethyl)pyridin-2-yl)pyrido[3,4-d]pyrimidin-4(3H)-one |
| 189 | 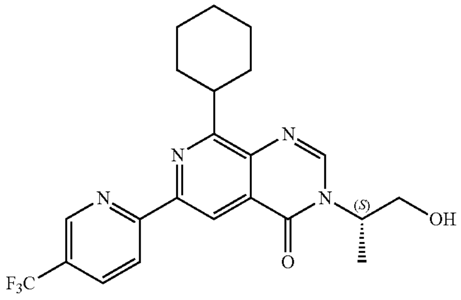 (S)-8-cyclohexyl-3-(1-hydroxypropan-2-yl)-6-(5-(trifluoromethyl)pyridin-2-yl)pyrido[3,4-d]pyrimidin-4(3H)-one |
| 190 | 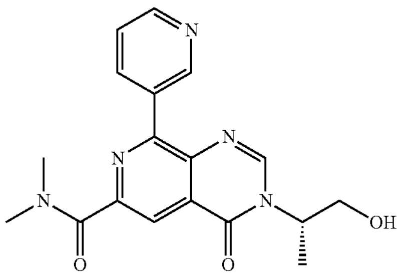 (S)-3-(1-hydroxypropan-2-yl)-N,N-dimethyl-4-oxo-8-(pyridin-3-yl)-3,4-dihydropyrido[3,4-d]pyrimidine-6-carboxamide |

TABLE 1-continued

| Compound No. | Structure and name |
|---|---|
| 191 | 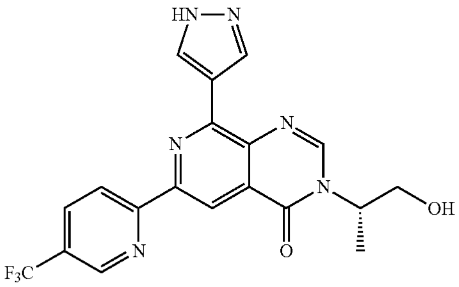 (S)-3-(1-hydroxypropan-2-yl)-8-(1H-pyrazol-4-yl)-6-(5-(trifluoromethyl)pyridin-2-yl)pyrido[3,4-d]pyrimidin-4(3H)-one |
| 192 | 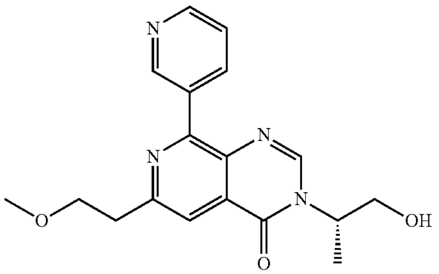 (S)-3-(1-hydroxypropan-2-yl)-6-(2-methoxyethyl)-8-(pyridin-3-yl)pyrido[3,4-d]pyrimidin-4(3H)-one |
| 193 | 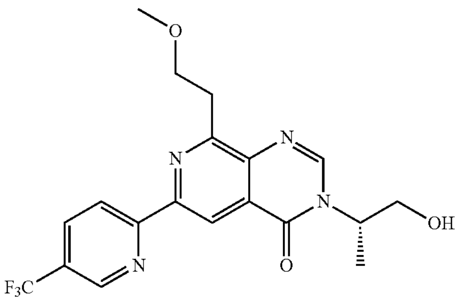 (S)-3-(1-hydroxypropan-2-yl)-8-(2-methoxyethyl)-6-(5-(trifluoromethyl)pyridin-2-yl)pyrido[3,4-d]pyrimidin-4(3H)-one |

In some embodiments, the present disclosure is drawn to one or more compounds chosen from the compounds below and pharmaceutically acceptable salts thereof:

(i) (S)-8-(5-fluoropyridin-3-yl)-3-(1-hydroxypropan-2-yl)-6-(4-(trifluoromethoxy)phenyl)pyrido[3,4-d]pyrimidin-4(3H)-one;

(ii) (S)-6-(4-chlorophenyl)-3-(1-hydroxypropan-2-yl)-8-(6-oxo-1,6-dihydropyridin-3-yl)pyrido[3,4-d]pyrimidin-4(3H)-one;

(iii) (S)-8-(benzo[d][1,3]dioxol-4-yl)-6-(4-chlorophenyl)-3-(1-hydroxypropan-2-yl)pyrido[3,4-d]pyrimidin-4(3H)-one;

(iv) (S)-3-(1-hydroxypropan-2-yl)-8-(pyridin-4-yl)-6-(6-(trifluoromethyl)pyridin-3-yl)pyrido[3,4-d]pyrimidin-4(3H)-one;

(v) (S)-8-(5-fluoropyridin-3-yl)-3-(1-hydroxypropan-2-yl)-6-(4-(trifluoromethyl)phenyl)pyrido[3,4-d]pyrimidin-4(3H)-one;

(vi) (S)-3-(1-hydroxypropan-2-yl)-6,8-di(pyridin-4-yl)pyrido[3,4-d]pyrimidin-4(3H)-one;

(vii) (S)-6-(4-chlorophenyl)-8-(3-fluorophenyl)-3-(1-hydroxypropan-2-yl)pyrido[3,4-d]pyrimidin-4(3H)-one;

(viii) (S)-8-(3-fluorophenyl)-3-(1-hydroxypropan-2-yl)-6-(6-(trifluoromethyl)pyridin-3-yl)pyrido[3,4-d]pyrimidin-4(3H)-one;

(ix) 3-(2-hydroxy-2-methylpropyl)-8-(pyridin-3-yl)-6-(6-(trifluoromethyl)pyridin-3-yl)pyrido[3,4-d]pyrimidin-4(3H)-one;

(x) 6,8-di(pyridin-3-yl)-3-(3,3,3-trifluoro-2-hydroxypropyl)pyrido[3,4-d]pyrimidin-4(3H)-one;

(xi) (S)-6-chloro-3-(1-hydroxypropan-2-yl)-8-(pyridin-3-yl)pyrido[3,4-d]pyrimidin-4(3H)-one;

(xii) (S)-3-(1-hydroxypropan-2-yl)-8-(pyridin-3-yl)-6-(6-(trifluoromethyl)pyridin-3-yl)pyrido[3,4-d]pyrimidin-4(3H)-one;

(xiii) 6-(4-chlorophenyl)-8-(pyridin-3-yl)-3-(3,3,3-trifluoro-2-hydroxypropyl)pyrido[3,4-d]pyrimidin-4(3H)-one;

(xiv) 8-(pyridin-3-yl)-3-(3,3,3-trifluoro-2-hydroxypropyl)-6-(4-(trifluoromethoxy)phenyl)pyrido[3,4-d]pyrimidin-4(3H)-one;

(xv) 6-(4-chlorophenyl)-8-(1-methyl-1H-pyrazol-4-yl)-3-(3,3,3-trifluoro-2-hydroxypropyl)pyrido[3,4-d]pyrimidin-4(3H)-one;

(xvi) 3-(2-hydroxy-2-methylpropyl)-8-(pyridin-3-yl)-6-(4-(trifluoromethyl)phenyl)pyrido[3,4-d]pyrimidin-4(3H)-one;

(xvii) (S)-3-(1-hydroxypropan-2-yl)-8-(pyridin-3-yl)-6-(p-tolyl)pyrido[3,4-d]pyrimidin-4(3H)-one;

(xviii) 6-(4-chlorophenyl)-3-(2-hydroxy-2-methylpropyl)-8-(pyridin-3-yl)pyrido[3,4-d]pyrimidin-4(3H)-one;

(xix) 3-(2-hydroxy-2-methylpropyl)-6,8-bis(1-methyl-1H-pyrazol-4-yl)pyrido[3,4-d]pyrimidin-4(3H)-one;

(xx) (S)-3-(1-hydroxypropan-2-yl)-6,8-di(pyridin-3-yl)pyrido[3,4-d]pyrimidin-4(3H)-one;

(xxi) 6-(4-chlorophenyl)-3-(2-hydroxy-2-methylpropyl)-8-(1-methyl-1H-pyrazol-4-yl)pyrido[3,4-d]pyrimidin-4(3H)-one;

(xxii) (S)-3-(1-hydroxypropan-2-yl)-8-(pyridin-3-yl)-6-(4-(trifluoromethoxy)phenyl)pyrido[3,4-d]pyrimidin-4(3H)-one;

(xxiii) (S)-3-(1-hydroxypropan-2-yl)-8-(pyridin-3-yl)-6-(4-(trifluoromethyl)phenyl)pyrido[3,4-d]pyrimidin-4(3H)-one;

(xxiv) (S)-6-(4-chlorophenyl)-3-(1-hydroxypropan-2-yl)-8-(pyridin-3-yl)pyrido[3,4-d]pyrimidin-4(3H)-one;

(xxv) (S)-3-(1-hydroxypropan-2-yl)-8-(1-methyl-1H-pyrazol-4-yl)-6-(4-(trifluoromethoxy)phenyl)pyrido[3,4-d]pyrimidin-4(3H)-one;

(xxvi) (S)-3-(1-hydroxypropan-2-yl)-8-(1-methyl-1H-pyrazol-4-yl)-6-phenylpyrido[3,4-d]pyrimidin-4(3H)-one;

(xxvii) (S)-6-(4-chlorophenyl)-3-(1-hydroxypropan-2-yl)-8-(1-methyl-1H-pyrazol-4-yl)pyrido[3,4-d]pyrimidin-4(3H)-one;

(xxviii) 3-methyl-8-(pyridin-3-yl)-6-(4-(trifluoromethoxy)phenyl)pyrido[3,4-d]pyrimidin-4(3H)-one;

(xxix) Rac-6-(4-chlorophenyl)-3-((trans)-4-hydroxytetrahydrofuran-3-yl)-8-(pyridin-3-yl)pyrido[3,4-d]pyrimidin-4(3H)-one;

(xxx) (S)-6-(4-chlorophenyl)-3-(3-hydroxy-3-methylbutan-2-yl)-8-(1-methyl-1H-pyrazol-4-yl)pyrido[3,4-d]pyrimidin-4(3H)-one;

(xxxi) (R)-6-(4-chlorophenyl)-3-(3-hydroxy-3-methylbutan-2-yl)-8-(1-methyl-1H-pyrazol-4-yl)pyrido[3,4-d]pyrimidin-4(3H)-one;

(xxxii) rac-6-(4-chlorophenyl)-3-((cis)-4-hydroxytetrahydrofuran-3-yl)-8-(pyridin-3-yl)pyrido[3,4-d]pyrimidin-4(3H)-one;

(xxxiii) (R)-6-(4-chlorophenyl)-3-(3-hydroxy-3-methylbutan-2-yl)-8-(pyridin-3-yl)pyrido[3,4-d]pyrimidin-4(3H)-one;

(xxxiv) (S)-3-(3-hydroxy-3-methylbutan-2-yl)-6,8-di(pyridin-3-yl)pyrido[3,4-d]pyrimidin-4(3H)-one;

(xxxv) (S)-6,8-bis(3,5-difluorophenyl)-3-(1-hydroxy-3-methylbutan-2-yl)pyrido[3,4-d]pyrimidin-4(3H)-one;

(xxxvi) (S)-6-(4-chlorophenyl)-3-(3-hydroxy-3-methylbutan-2-yl)-8-(pyridin-3-yl)pyrido[3,4-d]pyrimidin-4(3H)-one;

(xxxvii) (S)-8-(3,5-difluorophenyl)-3-(1-hydroxy-3-methylbutan-2-yl)-6-(p-tolyl)pyrido[3,4-d]pyrimidin-4(3H)-one;

(xxxviii) 6-(4-chlorophenyl)-8-(3-fluorophenyl)-3-(2-hydroxy-2-methylpropyl)pyrido[3,4-d]pyrimidin-4(3H)-one;

(xxxix) (R)-6-(4-chlorophenyl)-8-(3-fluorophenyl)-3-(3-hydroxy-3-methylbutan-2-yl)pyrido[3,4-d]pyrimidin-4(3H)-one;

(xl) (S)-3-(1-(benzyloxy)propan-2-yl)-8-(3-fluorophenyl)-6-(p-tolyl)pyrido[3,4-d]pyrimidin-4(3H)-one;

(xli) (R)-6-(4-chlorophenyl)-8-(3-fluorophenyl)-3-(3,3,3-trifluoro-2-hydroxypropyl)pyrido[3,4-d]pyrimidin-4(3H)-one;

(xlii) (S)-6-(4-chlorophenyl)-8-(3-fluorophenyl)-3-(3,3,3-trifluoro-2-hydroxypropyl)pyrido[3,4-d]pyrimidin-4(3H)-one;

(xliii) (S)-3-(1-hydroxypropan-2-yl)-6-morpholino-8-(pyridin-3-yl)pyrido[3,4-d]pyrimidin-4(3H)-one;

(xliv) (S)-3-(1-hydroxypropan-2-yl)-8-(1H-imidazol-1-yl)-6-(4-(trifluoromethoxy)phenyl)pyrido[3,4-d]pyrimidin-4(3H)-one;

(xlv) (S)-3-(1-methoxypropan-2-yl)-8-(pyridin-3-yl)-6-(p-tolyl)pyrido[3,4-d]pyrimidin-4(3H)-one;

(xlvi) (S)-3-(1-hydroxypropan-2-yl)-8-(pyridin-3-yl)-6-(5-(trifluoromethyl)pyridin-2-yl)pyrido[3,4-d]pyrimidin-4(3H)-one;

(xlvii) (S)-8-(3-fluorophenyl)-3-(1-hydroxypropan-2-yl)-6-(5-(trifluoromethyl)pyridin-2-yl)pyrido[3,4-d]pyrimidin-4(3H)-one;

(xlviii) (S)-8-(3-fluorophenyl)-3-(1-hydroxypropan-2-yl)-6-(p-tolyl)pyrido[3,4-d]pyrimidin-4(3H)-one;

(xlix) (S)-8-(3-fluorophenyl)-3-(1-hydroxypropan-2-yl)-6-(4-(trifluoromethoxy)phenyl)pyrido[3,4-d]pyrimidin-4(3H)-one;

(l) (S)-3-(1-hydroxypropan-2-yl)-8-(pyridin-3-yl)-6-(6-(trifluoromethoxy)pyridin-3-yl)pyrido[3,4-d]pyrimidin-4(3H)-one (li) (S)-3-(2-hydroxy-2-methylpropyl)-8-(1H-pyrazol-4-yl)-6-(6-(trifluoromethyl)pyridin-3-yl)pyrido[3,4-d]pyrimidin-4(3H)-one (lii)methyl (S)-5-(3-(1-hydroxypropan-2-yl)-4-oxo-8-(pyridin-3-yl)-3,4-dihydropyrido[3,4-d]pyrimidin-6-yl)picolinate (liii) (S)-3-(1-hydroxypropan-2-yl)-6-(isothiazol-4-yl)-8-(pyridin-3-yl)pyrido[3,4-d]pyrimidin-4(3H)-one (liv) 3-(2-hydroxy-2-methylpropyl)-8-(isothiazol-4-yl)-6-(6-(trifluoromethyl)pyridin-3-yl)pyrido[3,4-d]pyrimidin-4(3H)-one
(lv) (S)-3-(1-hydroxypropan-2-yl)-8-(isothiazol-4-yl)-6-(6-(trifluoromethyl)pyridin-3-yl)pyrido[3,4-d]pyrimidin-4(3H)-one
(lvi) (S)-3-(1-hydroxypropan-2-yl)-6,8-di(isothiazol-4-yl)pyrido[3,4-d]pyrimidin-4(3H)-one
(lvii) (S)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one
(lviii) (S)-6-(4-chlorophenyl)-3-(1-hydroxypropan-2-yl)-8-(isothiazol-4-yl)pyrido[3,4-d]pyrimidin-4(3H)-one
(lix) 3-(2-hydroxy-2-methylpropyl)-6,8-di(pyridin-3-yl)pyrido[3,4-d]pyrimidin-4(3H)-one
(lx) 3-(2-hydroxy-2-methylpropyl)-8-(1-methyl-1H-pyrazol-4-yl)-6-(6-(trifluoromethyl)pyridin-3-yl)pyrido[3,4-d]pyrimidin-4(3H)-one
(lxi) 6-(4-chloro-2-methylphenyl)-3-(2-hydroxy-2-methylpropyl)-8-(1-methyl-1H-pyrazol-4-yl)pyrido[3,4-d]pyrimidin-4(3H)-one
(lxii) (S)-3-(1-hydroxypropan-2-yl)-8-(1H-pyrazol-4-yl)-6-(6-(trifluoromethyl)pyridin-3-yl)pyrido[3,4-d]pyrimidin-4(3H)-one
(lxiii) (S)-3-(1-hydroxypropan-2-yl)-8-(2-methylpyridin-3-yl)-6-(6-(trifluoromethyl)pyridin-3-yl)pyrido[3,4-d]pyrimidin-4(3H)-one
(lxiv) (S)-3-(1-hydroxypropan-2-yl)-8-(4-methylpyridin-3-yl)-6-(6-(trifluoromethyl)pyridin-3-yl)pyrido[3,4-d]pyrimidin-4(3H)-one
(lxv) (S)-3-(1-hydroxypropan-2-yl)-6-(4-methylthiazol-5-yl)-8-(pyridin-3-yl)pyrido[3,4-d]pyrimidin-4(3H)-one
(lxvi) (S)-6-(2-cyclopropylthiazol-5-yl)-3-(1-hydroxypropan-2-yl)-8-(pyridin-3-yl)pyrido[3,4-d]pyrimidin-4(3H)-one
(lxvii) (S)-3-(1-hydroxypropan-2-yl)-6-(2-isopropylthiazol-5-yl)-8-(pyridin-3-yl)pyrido[3,4-d]pyrimidin-4(3H)-one
(lxviii) (S)-3-(1-hydroxypropan-2-yl)-8-(1-methyl-1H-pyrazol-4-yl)-6-(6-(trifluoromethyl)pyridin-3-yl)pyrido[3,4-d]pyrimidin-4(3H)-one
(lxix) (S)-3-(1-hydroxypropan-2-yl)-6,8-bis(6-(trifluoromethyl)pyridin-3-yl)pyrido[3,4-d]pyrimidin-4(3H)-one
(lxx) 6-(4-chlorophenyl)-3-((3S,4S)-4-hydroxytetrahydrofuran-3-yl)-8-(pyridin-3-yl)pyrido[3,4-d]pyrimidin-4(3H)-one.
(lxxi) 6-(4-chlorophenyl)-3-((3R,4R)-4-hydroxytetrahydrofuran-3-yl)-8-(pyridin-3-yl)pyrido[3,4-d]pyrimidin-4(3H)-one
(lxxii) 3-(2-hydroxyethyl)-8-(pyridin-3-yl)-6-(4-(trifluoromethoxy)phenyl)pyrido[3,4-d]pyrimidin-4(3H)-one
(lxxiii) (S)-6-(4-chlorophenyl)-3-(1-hydroxypropan-2-yl)-8-(1-methyl-6-oxo-1,6-dihydropyridin-3-yl)pyrido[3,4-d]pyrimidin-4(3H)-one
(lxxiv) (S)-6-(6-cyclopropylpyridin-3-yl)-3-(1-hydroxypropan-2-yl)-8-(pyridin-3-yl)pyrido[3,4-d]pyrimidin-4(3H)-one
(lxxv) (S)-3-(1-hydroxypropan-2-yl)-6-(4-methyl-6-(trifluoromethyl)pyridin-3-yl)-8-(pyridin-3-yl)pyrido[3,4-d]pyrimidin-4(3H)-one
(lxxvi) (S)-3-(1-hydroxypropan-2-yl)-8-(1-methyl-1H-pyrazol-4-yl)-6-(pyridin-3-yl)pyrido[3,4-d]pyrimidin-4(3H)-one
(lxxvii) (S)-6-(cyclohex-1-en-1-yl)-3-(1-hydroxypropan-2-yl)-8-(pyridin-3-yl)pyrido[3,4-d]pyrimidin-4(3H)-one
(lxxviii) (S)-6,8-bis(5-fluoropyridin-3-yl)-3-(1-hydroxypropan-2-yl)pyrido[3,4-d]pyrimidin-4(3H)-one
(lxxix) 3-((3R,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one
(lxxx) 3-(2-hydroxy-2-methylpropyl)-8-(pyridin-3-yl)-6-(2-(trifluoromethyl)pyridin-3-yl)pyrido[3,4-d]pyrimidin-4(3H)-one
(lxxxi) 6-(6-cyclopropylpyridin-3-yl)-3-(2-hydroxy-2-methylpropyl)-8-(pyridin-3-yl)pyrido[3,4-d]pyrimidin-4(3H)-one
(lxxxii) 6-(6-cyclopropylpyridin-3-yl)-3-(2-hydroxy-2-methylpropyl)-8-(1-methyl-1H-pyrazol-4-yl)pyrido[3,4-d]pyrimidin-4(3H)-one
(lxxxiii) (S)-6-(6-cyclopropylpyridin-3-yl)-3-(1-hydroxypropan-2-yl)-8-(1-methyl-1H-pyrazol-4-yl)pyrido[3,4-d]pyrimidin-4(3H)-one
(lxxxiv) (S)-3-(1-hydroxypropan-2-yl)-8-(pyridin-3-yl)-6-(thiazol-5-yl)pyrido[3,4-d]pyrimidin-4(3H)-one
(lxxxv) (S)-3-(1-hydroxypropan-2-yl)-8-(pyridin-3-yl)-6-(2-(trifluoromethyl)thiazol-5-yl)pyrido[3,4-d]pyrimidin-4(3H)-one
(lxxxvi) (S)-3-(1-hydroxypropan-2-yl)-8-(pyridin-3-yl)-6-(2-(trifluoromethyl)pyrimidin-5-yl)pyrido[3,4-d]pyrimidin-4(3H)-one
(lxxxvii) 3-(2-hydroxy-2-methylpropyl)-8-(pyridin-3-yl)-6-(2-(trifluoromethyl)thiazol-5-yl)pyrido[3,4-d]pyrimidin-4(3H)-one
(lxxxviii) 3-((3S,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one
(lxxxix) (S)-3-(1-hydroxypropan-2-yl)-6-(2-methylthiazol-5-yl)-8-(pyridin-3-yl)pyrido[3,4-d]pyrimidin-4(3H)-one
(xc) (S)-6-(4-chlorophenyl)-8-(3-fluorophenyl)-3-(1-hydroxy-3-methylbutan-2-yl)pyrido[3,4-d]pyrimidin-4(3H)-one
(xci) (S)-3-(1-hydroxypropan-2-yl)-6-(piperidin-1-yl)-8-(pyridin-3-yl)pyrido[3,4-d]pyrimidin-4(3H)-one
(xcii) 3-(2-hydroxy-2-methylpropyl)-8-(isothiazol-4-yl)-6-(5-(trifluoromethyl)pyridin-2-yl)pyrido[3,4-d]pyrimidin-4(3H)-one
(xciii) (S)-3-(1-hydroxypropan-2-yl)-8-(isothiazol-4-yl)-6-(5-(trifluoromethyl)pyridin-2-yl)pyrido[3,4-d]pyrimidin-4(3H)-one
(xciv) 3-(2-hydroxy-2-methylpropyl)-8-(1-methyl-1H-pyrazol-4-yl)-6-(5-(trifluoromethyl)pyridin-2-yl)pyrido[3,4-d]pyrimidin-4(3H)-one
(xcv) (S)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one
(xcvi) (3-(2-hydroxy-2-methylpropyl)-8-(pyridin-3-yl)-6-(5-(trifluoromethyl)pyridin-2-yl)pyrido[3,4-d]pyrimidin-4(3H)-one
(xcvii) 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one
(xcviii) (R)-3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one
(xcix) (R)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one
(c) (S)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one
(ci)(R)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one (cii) (S)-8-(1-methyl-1H-pyrazol-4-yl)-3-(3,3,3-trifluoro-2-hydroxypropyl)-6-(6-(trifluoromethyl)pyridin-3-yl) pyrido[3,4-d]pyrimidin-4(3H)-one
(ciii) (R)-3-(2-hydroxypropyl)-8-(pyridin-3-yl)-6-(6-(trifluoromethyl)pyridin-3-yl)pyrido[3,4-d]pyrimidin-4(3H)-one
(civ) (R)-8-(1-methyl-1H-pyrazol-4-yl)-3-(3,3,3-trifluoro-2-hydroxypropyl)-6-(5-(trifluoromethyl)pyridin-2-yl) pyrido[3,4-d]pyrimidin-4(3H)-one
(cv) 3-((3S,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one
(cvi) 3-((3R,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one
(cvii) 6-(4-chlorophenyl)-3-((3S,4R)-4-hydroxytetrahydrofuran-3-yl)-8-(1-methyl-1H-pyrazol-4-yl)pyrido[3,4-d] pyrimidin-4(3H)-one
(cviii) 3-((3S,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one
(cix) (S)-6-(6-cyclopropylpyridin-3-yl)-8-(pyridin-3-yl)-3-(3,3,3-trifluoro-2-hydroxypropyl)pyrido[3,4-d]pyrimidin-4(3H)-one
(cx) (R)-6-(6-cyclopropylpyridin-3-yl)-8-(pyridin-3-yl)-3-(3,3,3-trifluoro-2-hydroxypropyl)pyrido[3,4-d]pyrimidin-4(3H)-one
(cxi) (R)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one
(cxii) (R)-8-(pyridin-3-yl)-3-(3,3,3-trifluoro-2-hydroxypropyl)-6-(4-(trifluoromethoxy)phenyl)pyrido[3,4-d]pyrimidin-4(3H)-one
(cxiii) (S)-8-(pyridin-3-yl)-3-(3,3,3-trifluoro-2-hydroxypropyl)-6-(4-(trifluoromethoxy)phenyl)pyrido[3,4-d]pyrimidin-4(3H)-one
(cxiv) 6-(4-chlorophenyl)-3-((3S,4R)-4-hydroxytetrahydrofuran-3-yl)-8-(pyridin-3-yl)pyrido[3,4-d]pyrimidin-4 (3H)-one
(cxv) 3-((3S,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one
(cxvi) methyl (S)-2-(4-oxo-8-(pyridin-3-yl)-6-(6-(trifluoromethyl)pyridin-3-yl)pyrido[3,4-d]pyrimidin-3(4H)-yl) propanoate
(cxvii) 6-(4-chlorophenyl)-3-(4-hydroxy-1-methylpyrrolidin-3-yl)-8-(pyridin-3-yl)pyrido[3,4-d]pyrimidin-4(3H)-one
(cxviii) 6-(4-chlorophenyl)-3-((3R,4R)-4-hydroxypyrrolidin-3-yl)-8-(pyridin-3-yl)pyrido[3,4-d]pyrimidin-4(3H)-one
(cxix) (R)-6-(6-cyclopropylpyridin-3-yl)-8-(1-methyl-1H-pyrazol-4-yl)-3-(3,3,3-trifluoro-2-hydroxypropyl)pyrido [3,4-d]pyrimidin-4(3H)-one
(cxx) (S)-6-(6-cyclopropylpyridin-3-yl)-8-(1-methyl-1H-pyrazol-4-yl)-3-(3,3,3-trifluoro-2-hydroxypropyl)pyrido [3,4-d]pyrimidin-4(3H)-one
(cxxi) 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one
(cxxii) 3-((3R,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one
(cxxiii) 3-((3S,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one
(cxxiv) 3-((3R,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one
(cxxv) (R)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one
(cxxvi) (S)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one
(cxxvii) (S)-3-(2-hydroxypropyl)-8-(pyridin-3-yl)-6-(5-(trifluoromethyl)pyridin-2-yl)pyrido[3,4-d]pyrimidin-4 (3H)-one
(cxxviii) (R)-3-(2-hydroxypropyl)-8-(pyridin-3-yl)-6-(5-(trifluoromethyl)pyridin-2-yl)pyrido[3,4-d]pyrimidin-4 (3H)-one
(cxxix) 3-((3S,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one
(cxxx) (S)-3-(2-hydroxypropyl)-8-(pyridin-3-yl)-6-(6-(trifluoromethyl)pyridin-3-yl)pyrido[3,4-d]pyrimidin-4(3H)-one
(cxxxi) (S)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one
(cxxxii) (S)-3-(1-hydroxypropan-2-yl)-8-(1-methyl-1H-pyrazol-4-yl)-6-(5-(trifluoromethyl)pyridin-2-yl)pyrido [3,4-d]pyrimidin-4(3H)-one
(cxxxiii) 3-((3S,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one
(cxxxiv) 6-(4-chlorophenyl)-3-((3R,4S)-4-hydroxytetrahydrofuran-3-yl)-8-(pyridin-3-yl)pyrido[3,4-d]pyrimidin-4 (3H)-one
(cxxxv) 6-(4-Chlorophenyl)-3-((3R,4S)-4-hydroxytetrahydrofuran-3-yl)-8-(1-methyl-1H-pyrazol-4-yl)pyrido[3,4-d]pyrimidin-4(3H)-one
(cxxxvi) (R)-8-(pyridin-3-yl)-3-(3,3,3-trifluoro-2-hydroxypropyl)-6-(5-(trifluoromethyl)pyridin-2-yl)pyrido[3,4-d] pyrimidin-4(3H)-one
(cxxxvii) (S)-2-(4-oxo-8-(pyridin-3-yl)-6-(6-(trifluoromethyl)pyridin-3-yl)pyrido[3,4-d]pyrimidin-3(4H)-yl)propanoic acid
(cxxxviii) (S)—N-methyl-2-(4-oxo-8-(pyridin-3-yl)-6-(6-(trifluoromethyl)pyridin-3-yl)pyrido[3,4-d]pyrimidin-3 (4H)-yl)propanamide
(cxxxix) (S)—N,N-dimethyl-2-(4-oxo-8-(pyridin-3-yl)-6-(6-(trifluoromethyl)pyridin-3-yl)pyrido[3,4-d]pyrimidin-3(4H)-yl)propenamide
(cxl) 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one
(cxli) 3-(2-hydroxy-2-methylpropyl)-8-(1H-imidazol-1-yl)-6-(5-(trifluoromethyl)pyridin-2-yl)pyrido[3,4-d]pyrimidin-4(3H)-one
(cxlii) 3-(2-hydroxy-2-methylpropyl)-8-(1H-imidazol-1-yl)-6-(6-(trifluoromethyl)pyridin-2-yl)pyrido[3,4-d]pyrimidin-4(3H)-one
(cxliii) (S)-3-(1-hydroxypropan-2-yl)-8-(1H-imidazol-1-yl)-6-(5-(trifluoromethyl)pyridin-2-yl)pyrido[3,4-d]pyrimidin-4(3H)-one
(cxliv) (S)-3-(1-hydroxypropan-2-yl)-8-(1H-imidazol-1-yl)-6-(6-(trifluoromethyl)pyridin-3-yl)pyrido[3,4-d]pyrimidin-4(3H)-one
(cxlv) (S)-3-(1-hydroxypropan-2-yl)-8-(1H-1,2,4-triazol-1-yl)-6-(6-(trifluoromethyl)pyridin-3-yl)pyrido[3,4-d]pyrimidin-4(3H)-one (cxlvi) (S)-3-(1-hydroxypropan-2-yl)-8-(1H-pyrazol-1-yl)-6-(6-(trifluoromethyl)pyridin-3-yl)pyrido[3,4-d]pyrimidin-4(3H)-one (cxlvii) (S)-3-(1-hydroxypropan-2-yl)-8-(1-methyl-1H-pyrazol-4-yl)-6-(2-(trifluoromethyl)thiazol-5-yl)pyrido[3,4-d]pyrimidin-4(3H)-one (cxlviii) (S)-8-(diethylamino)-3-(1-hydroxypropan-2-yl)-6-(6-(trifluoromethyl)pyridin-3-yl)pyrido[3,4-d]pyrimidin-4(3H)-one (cxlix) (S)-3-(1-hydroxypropan-2-yl)-8-(piperidin-1-yl)-6-(6-(trifluoromethyl)pyridin-3-yl)pyrido[3,4-d]pyrimidin-4(3H)-one (cl) (S)-3-(1-hydroxypropan-2-yl)-8-(pyrrolidin-1-yl)-6-(6-(trifluoromethyl)pyridin-3-yl)pyrido[3,4-d]pyrimidin-4(3H)-one (cli) (S)-6-(4-chlorophenyl)-3-(1-hydroxypropan-2-yl)-8-(piperidin-1-yl)pyrido[3,4-d]pyrimidin-4(3H)-one (clii) (S)-3-(1-hydroxypropan-2-yl)-8-(pyridin-2-yl)-6-(6-(trifluoromethyl)pyridin-3-yl)pyrido[3,4-d]pyrimidin-4(3H)-one (cliii) (S)-6-cyclohexyl-3-(1-hydroxypropan-2-yl)-8-(pyridin-3-yl)pyrido[3,4-d]pyrimidin-4(3H)-one (cliv) (S)-3-(1-hydroxypropan-2-yl)-6-(pyridin-2-yl)-8-(pyridin-3-yl)pyrido[3,4-d]pyrimidin-4(3H)-one (clv) (S)-3-(1-hydroxypropan-2-yl)-6-(2-methylthiazol-4-yl)-8-(pyridin-3-yl)pyrido[3,4-d]pyrimidin-4(3H)-one (clvi) (S)-3-(1-hydroxypropan-2-yl)-6-(1-methyl-1H-1,2,3-triazol-5-yl)-8-(pyridin-3-yl)pyrido[3,4-d]pyrimidin-4(3H)-one (clvii) (R)-6-(4-chlorophenyl)-8-(pyridin-3-yl)-3-(3,3,3-trifluoro-2-hydroxypropyl)pyrido[3,4-d]pyrimidin-4(3H)-one (clviii) (S)-6-(4-chlorophenyl)-8-(pyridin-3-yl)-3-(3,3,3-trifluoro-2-hydroxypropyl)pyrido[3,4-d]pyrimidin-4(3H)-one (clix) (S)-3-(1-hydroxypropan-2-yl)-8-(1-methyl-1,2,5,6-tetrahydropyridin-3-yl)-6-(6-(trifluoromethyl)pyridin-3-yl)pyrido[3,4-d]pyrimidin-4(3H)-one (clx) 6-(4-chlorophenyl)-3-((3S,4S)-4-hydroxytetrahydrofuran-3-yl)-8-(1-methyl-1H-pyrazol-4-yl)pyrido[3,4-d]pyrimidin-4(3H)-one (clxi) (S)-3-(1-hydroxypropan-2-yl)-6-(2-methylpyrimidin-5-yl)-8-(pyridin-3-yl)pyrido[3,4-d]pyrimidin-4(3H)-one (clxii) 3-(2-hydroxy-2-methylpropyl)-8-(1-(trifluoromethyl)-1H-pyrazol-4-yl)-6-(6-(trifluoromethyl)pyridin-3-yl)pyrido[3,4-d]pyrimidin-4(3H)-one (clxiii) (S)-3-(1-hydroxypropan-2-yl)-8-(1-methyl-1H-pyrazol-4-yl)-6-(2-(trifluoromethyl)pyrimidin-5-yl)pyrido[3,4-d]pyrimidin-4(3H)-one (clxiv) 3-(2-hydroxy-2-methylpropyl)-8-(pyridin-3-yl)-6-(2-(trifluoromethyl)pyrimidin-5-yl)pyrido[3,4-d]pyrimidin-4(3H)-one (clxv) (S)-5-(3-(1-hydroxypropan-2-yl)-4-oxo-8-(pyridin-3-yl)-3,4-dihydropyrido[3,4-d]pyrimidin-6-yl)picolinic acid (clxvi) (S)-3-(1-hydroxypropan-2-yl)-6-(6-methylpyridin-3-yl)-8-(pyridin-3-yl)pyrido[3,4-d]pyrimidin-4(3H)-one (clxvii) 3-(2-hydroxy-2-methylpropyl)-8-(1-methyl-1H-pyrazol-4-yl)-6-(2-(trifluoromethyl)pyrimidin-5-yl)pyrido[3,4-d]pyrimidin-4(3H)-one (clxviii) 3,8-di(pyridin-3-yl)-6-(6-(trifluoromethyl)pyridin-3-yl)pyrido[3,4-d]pyrimidin-4(3H)-one (clxix) 8-(pyridin-3-yl)-6-(6-(trifluoromethyl)pyridin-3-yl)pyrido[3,4-d]pyrimidin-4(3H)-one (clxx) 3-((3R,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one (clxxi) 3-((3R,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one (clxxii) 6-(4-chlorophenyl)-3-((3R,4R)-4-hydroxytetrahydrofuran-3-yl)-8-(1-methyl-1H-pyrazol-4-yl)pyrido[3,4-d]pyrimidin-4(3H)-one (clxxiii) 3-cyclopentyl-8-(pyridin-3-yl)-6-(6-(trifluoromethyl)pyridin-3-yl)pyrido[3,4-d]pyrimidin-4(3H)-one (clxxiv) 3-phenyl-8-(pyridin-3-yl)-6-(6-(trifluoromethyl)pyridin-3-yl)pyrido[3,4-d]pyrimidin-4(3H)-one (clxxv) 3-((3R,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one (clxxvi) 3-((3R,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (clxxvii) (S)-3-(1-hydroxypropan-2-yl)-8-(1-methyl-1H-pyrazol-4-yl)-6-(5-(trifluoromethyl)pyridin-2-yl)pyrido[3,4-d]pyrimidin-4(3H)-one (clxxviii) (S)—N-((3R,4S)-4-hydroxytetrahydrofuran-3-yl)-2-(4-oxo-8-(pyridin-3-yl)-6-(6-(trifluoromethyl)pyridin-3-yl)pyrido[3,4-d]pyrimidin-3(4H)-yl)propanamide (clxxix) 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one (clxxx) (S)-6-(4-chlorophenyl)-3-(1-hydroxypropan-2-yl)-8-(1H-pyrazol-1-yl)pyrido[3,4-d]pyrimidin-4(3H)-one (clxxxi) (S)-3-(1-hydroxypropan-2-yl)-8-(1H-pyrazol-1-yl)-6-(5-(trifluoromethyl)pyridin-2-yl)pyrido[3,4-d]pyrimidin-4(3H)-one (clxxxii) 3-((3S,4R)-4-hydroxytetrahydrofuran-3-yl)-8-(pyridin-3-yl)-6-(2-(trifluoromethyl)thiazol-5-yl)pyrido[3,4-d]pyrimidin-4(3H)-one (clxxxiii) 3-(2-hydroxy-2-methylpropyl)-8-(1-methyl-1H-pyrazol-4-yl)-6-(2-(trifluoromethyl)thiazol-5-yl)pyrido[3,4-d]pyrimidin-4(3H)-one (clxxxiv) 3-((3S,4R)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one (clxxxv) 3-((3R,4S)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one (clxxxvi) 3-((3R,4S)-4-hydroxytetrahydrofuran-3-yl)-8-(pyridin-3-yl)-6-(2-(trifluoromethyl)thiazol-5-yl)pyrido[3,4-d]pyrimidin-4(3H)-one (clxxxvii) (S)-3-(1-hydroxypropan-2-yl)-8-morpholino-6-(6-(trifluoromethyl)pyridin-3-yl)pyrido[3,4-d]pyrimidin-4(3H)-one (clxxxviii) 3-(2-hydroxy-2-methylpropyl)-8-(piperidin-1-yl)-6-(6-(trifluoromethyl)pyridin-3-yl)pyrido[3,4-d]pyrimidin-4(3H)-one (clxxxix) (S)-3-(1-hydroxypropan-2-yl)-6-(5-methylpyridin-2-yl)-8-(pyridin-3-yl)pyrido[3,4-d]pyrimidin-4(3H)-one (cxc) (S)-3-(1-hydroxypropan-2-yl)-6-(5-methylpyrimidin-2-yl)-8-(pyridin-3-yl)pyrido[3,4-d]pyrimidin-4(3H)-one (cxci) (S)-8-(cyclohex-1-en-1-yl)-3-(1-hydroxypropan-2-yl)-6-(5-(trifluoromethyl)pyridin-2-yl)pyrido[3,4-d]pyrimidin-4(3H)-one (cxcii) (S)-8-cyclohexyl-3-(1-hydroxypropan-2-yl)-6-(5-(trifluoromethyl)pyridin-2-yl)pyrido[3,4-d]pyrimidin-4(3H)-one (cxciii) (S)-3-(1-hydroxypropan-2-yl)-N,N-dimethyl-4-oxo-8-(pyridin-3-yl)-3,4-dihydropyrido[3,4-d]pyrimidine-6-carboxamide (cxciv) (S)-3-(1-hydroxypropan-2-yl)-8-(1H-pyrazol-4-yl)-6-(5-(trifluoromethyl)pyridin-2-yl)pyrido[3,4-d]pyrimidin-4(3H)-one (cxcv) (S)-3-(1-hydroxypropan-2-yl)-6-(2-methoxyethyl)-8-(pyridin-3-yl)pyrido[3,4-d]pyrimidin-4(3H)-one (cxcvi) (S)-3-(1-hydroxypropan-2-yl)-8-(2-methoxyethyl)-6-(5-(trifluoromethyl)pyridin-2-yl)pyrido[3,4-d]pyrimidin-4(3H)-one.

The compounds of formula I or formula Ia and pharmaceutically acceptable salts thereof can be incorporated into pharmaceutical compositions. In some embodiments, the disclosure is drawn to a pharmaceutical composition comprising at least one entity chosen from compounds of formula I or formula Ia and pharmaceutically acceptable salts thereof. In some embodiments, the disclosure is drawn to a pharmaceutical composition consisting essentially of at least one entity chosen from compounds of formula I or formula Ia and pharmaceutically acceptable salts thereof.

In some embodiments, the at least one entity chosen from compounds of formula I or formula Ia and pharmaceutically acceptable salts thereof can be administered in combination with at least one additional therapy. In some embodiments, the at least one additional therapy is chosen from immune checkpoint inhibitors (ICIs).

In some embodiments, the at least one additional therapy is chosen from anti-CTLA-4 compounds, anti-PD-1 compounds, and anti-PDL-1 compounds. In some embodiments, the at least one additional therapy is chosen from Pembrolizumab (Keytruda); Nivolumab (Opdivo); Ipilimumab (Yervoy); Avelumab (Bavencio); Atezolizumab (Tecentriq); Durvalumab (Imfinzi); Cemiplimab (LBTAYO); Sintilimab (Tyvyt); Toripalimab (Tuoyi); Camrelizumab (AiRuiKa); Spartalizumab; and Tislelizumab. In some embodiments, the at least one additional therapy is chosen from anti-LAG-3 (lymphocyte activation gene-3) compounds; anti-TIM-3 (T-cell immunoglobulin and mucin-domain containing-3) compounds; anti-TIGIT (T-cell immunoglobulin and ITIM domain) compounds; anti-VISTA (V-domain Ig suppressor of T-cell activation) compounds; or a combination thereof. Non-limiting examples of anti-LAG-3 compounds include IMP321 (Eftilagimod alpha), Relatlimab (BMS-986016), LAG525, MK-4280, REGN3767, TSR-033, BI754111, Sym022, FS118, and MGD013. Non-limiting examples of anti-TIM-3 compounds include TSR-022, MBG453, Sym023, INCAGN2390, LY3321367, BMS-986258, SHR-1702, RO7121661. Non-limiting examples of anti-TIGIT compounds include MK-7684, Etigilimab (OMP-313), Tiragolumab (MTIG7192A, RG-6058), BMS-986207, AB-154, and ASP-8374. Non-limiting examples of anti-VISTA compounds include JNJ-61610588 and CA-170.

In some embodiments, the pharmaceutical composition comprises at least one entity chosen from compounds of formula I or formula Ia and pharmaceutically acceptable salts thereof and at least one pharmaceutically acceptable excipient. Pharmaceutically acceptable excipients are well-known to persons having ordinary skill in the art and are described in, as a non-limiting example, Remington: The Science and Practice of Pharmacy, 22nd Edition, Lippincott Williams & Wilkins, Philadelphia, Pa. (2013) and any other editions, which are hereby incorporated by reference. In some embodiments, the pharmaceutical composition further comprises at least one at least one additional therapy.

Compounds of the disclosure, pharmaceutically acceptable salts thereof, and/or pharmaceutical compositions comprising said at least one entity chosen from compounds of formula I or formula Ia and pharmaceutically acceptable salts thereof, and optionally further comprising at least one at least one additional therapy, can be used in therapeutic treatments.

The compounds, pharmaceutically acceptable salts, additional therapies, and/or pharmaceutical compositions can be administered in unit forms of administration to mammalian subjects, including human beings. Suitable non-limiting examples of unit forms of administration include orally administered forms and forms administered via a parenteral/systemic route, non-limiting examples of which including inhalation, subcutaneous administration, intramuscular administration, intravenous administration, intradermal administration, and intravitreal administration.

In some embodiments, pharmaceutical compositions suitable for oral administration can be in the form of tablets, pills, powders, hard gelatine capsules, soft gelatine capsules, and/or granules. In some embodiments of such pharmaceutical compositions, a compound of the disclosure and/or a pharmaceutically acceptable salt of a compound of the disclosure is (or are) mixed with one or more inert diluents, non-limiting examples of which including starch, cellulose, sucrose, lactose, and silica. In some embodiments, such pharmaceutical compositions may further comprise one or more substances other than diluents, such as (as non-limiting examples), lubricants, coloring agents, coatings, or varnishes. In some embodiments, such pharmaceutical compositions may further comprise at least one at least one additional therapy.

In some embodiments, pharmaceutical compositions for parenteral administration can be in the form of aqueous solutions, non-aqueous solutions, suspensions, emulsions, drops, or any combination(s) thereof. In some embodiments, such pharmaceutical compositions may comprise one or more of water, pharmaceutically acceptable glycol(s), pharmaceutically acceptable oil(s), pharmaceutically acceptable organic esters, or other pharmaceutically acceptable solvents. In some embodiments, such pharmaceutical compositions may further comprise at least one at least one additional therapy.

In some embodiments, disclosed herein is a method of inhibiting AhR comprising administering to a subject in need thereof at least one entity chosen from compounds of formula I or formula Ia and pharmaceutically acceptable salts thereof. In some embodiments, disclosed herein is a method of reducing the activity of AhR comprising administering to a subject in need thereof at least one entity chosen from compounds of formula I or formula Ia and pharmaceutically acceptable salts thereof. In some embodiments, such pharmaceutical compositions may further comprise at least one at least one additional therapy.

In some embodiments, disclosed herein is a method of treating a cancer comprising administering to a subject in need thereof at least one entity chosen from compounds of formula I or formula Ia and pharmaceutically acceptable salts thereof. In some embodiments, the cancers are chosen from liquid tumors and solid tumors. In some embodiments, the cancer is chosen from breast cancers, respiratory tract cancers, brain cancers, cancers of reproductive organs, digestive tract cancers, urinary tract cancers, eye cancers, liver cancers, skin cancers, head and neck cancers, thyroid cancers, parathyroid cancers, and metastases of any of the foregoing. In some embodiments, the cancers are chosen from breast cancers, pancreatic cancers, prostate cancers, and colon cancers. In some embodiments, the cancers are chosen from lymphomas, sarcomas, and leukemias.

In some embodiments, disclosed herein is a method of treating cancer comprising administering to a subject in need thereof at least one entity chosen from compounds of formula I or formula Ia and pharmaceutically acceptable salts thereof and at least one additional therapy. In some embodiments, the cancer is chosen from non-small cell lung cancer (NSCLC); small cell lung cancer; head and neck squamous cell carcinoma; renal cell carcinoma; gastric adenocarcinoma; nasopharyngeal neoplasms; urothelial carcinoma; colorectal cancer; pleural mesothelioma; triple-negative breast cancer (TNBC); esophageal neoplasms; multiple myeloma; gastric and gastroesophageal junction cancer; melanoma; Hodgkin lymphoma; hepatocellular carcinoma; lung cancer; head and neck cancer; non-Hodgkin lymphoma; metastatic clear cell renal carcinoma; squamous cell lung carcinoma; mesothelioma; gastric cancer; gastroesophageal junction cancer; metastatic melanoma; metastatic non-cutaneous melanoma; urothelial cancer; diffuse large B-cell lymphoma; renal cell cancer; ovarian cancer, fallopian tube cancer; peritoneal neoplasms; extensive stage small cell lung cancer; bladder cancer; transitional cell carcinoma; prostatic neoplasms; recurrent or metastatic PD-L1 positive or negative squamous cell carcinoma of the head and neck (SCCHN); recurrent squamous cell lung cancer; advanced solid malignancies; SCCHN; hypo pharyngeal squamous cell carcinoma; laryngeal squamous cell carcinoma; unresectable or metastatic melanoma; biliary tract neoplasms; esophageal squamous cell carcinoma, breast cancer, pancreatic cancer, glioblastoma, metastatic cancer, prostatic cancer, solid organ cancer; stomach cancer; colon cancer; and liver cancer.

In some embodiments, disclosed herein is a method of treating ocular disorders comprising administering to a subject in need thereof at least one entity chosen from compounds of formula I or formula Ia and pharmaceutically acceptable salts thereof and optionally at least one additional therapy.

With regard to the methods disclosed herein, the mode (or modes) of administration, dose (or doses), and pharmaceutical form (or forms) can be determined according to criteria generally considered during the establishment of a treatment of a patient, such as, by way of non-limiting examples, the potency of the compound(s) and/or pharmaceutically acceptable salts of the compound(s), the at least one additional therapy (if present), the age of the patient, the body weight of the patient, the severity of the patient's condition (or conditions), the patient's tolerance to the treatment, and secondary effects observed in treatment. Determination of doses effective to provide therapeutic benefit for specific modes and frequency of administration is within the capabilities of those skilled in the art.

In some embodiments, a compound of formula I or formula Ia and/or pharmaceutically acceptable salt thereof is present in a pharmaceutical composition in an amount ranging from 5 μg to 2,000 mg. In some embodiments, a compound of the disclosure and/or pharmaceutically acceptable salt thereof is present in a pharmaceutical composition in an amount ranging from 5 μg to 1,000 mg. In some embodiments, a compound of the disclosure and/or pharmaceutically acceptable salt thereof is present in a pharmaceutical composition in an amount ranging from 5 μg to 500 mg. In some embodiments, a compound of the disclosure and/or pharmaceutically acceptable salt thereof is present in a pharmaceutical composition in an amount ranging from 5 μg to 250 mg. In some embodiments, a compound of the disclosure and/or pharmaceutically acceptable salt thereof is present in a pharmaceutical composition in an amount ranging from 5 μg to 100 mg. In some embodiments, a compound of the disclosure and/or pharmaceutically acceptable salt thereof is present in a pharmaceutical composition in an amount ranging from 5 μg to 50 mg.

In some embodiments, a compound of the disclosure and/or pharmaceutically acceptable salt thereof is present in a pharmaceutical composition in an amount ranging from 1 mg to 5,000 mg. In some embodiments, a compound of the disclosure and/or pharmaceutically acceptable salt thereof is present in a pharmaceutical composition in an amount ranging from 1 mg to 3,000 mg. In some embodiments, a compound of the disclosure and/or pharmaceutically acceptable salt thereof is present in a pharmaceutical composition in an amount ranging from 1 mg to 2,000 mg. In some embodiments, a compound of the disclosure and/or pharmaceutically acceptable salt thereof is present in a pharmaceutical composition in an amount ranging from 1 mg to 1,000 mg. In some embodiments, a compound of the disclosure and/or pharmaceutically acceptable salt thereof is present in a pharmaceutical composition in an amount ranging from 1 mg to 500 mg. In some embodiments, a compound of the disclosure and/or pharmaceutically acceptable salt thereof is present in a pharmaceutical composition in an amount ranging from 1 mg to 250 mg. In some embodiments, a compound of the disclosure and/or pharmaceutically acceptable salt thereof is present in a pharmaceutical composition in an amount ranging from 1 mg to 100 mg. In some embodiments, a compound of the disclosure and/or pharmaceutically acceptable salt thereof is present in a pharmaceutical composition in an amount ranging from 1 mg to 50 mg.

In some embodiments, a compound of the disclosure and/or pharmaceutically acceptable salt thereof is present in a pharmaceutical composition in an amount of 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 125 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1,000 mg, 1,100 mg, 1,200 mg, 1,300 mg, 1,400 mg, 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,100 mg, 3,200 mg, 3,300 mg, 3,400 mg, 3,500 mg, 3,600 mg, 3,700 mg, 3,800 mg, 3,900 mg, 4,000 mg, 4,100 mg, 4,200 mg, 4,300 mg, 4,400 mg, 4,500 mg, 4,600 mg, 4,700 mg, 4,800 mg, 4,900 mg, or 5,000 mg.

Effective amounts and dosages can be estimated initially from in vitro assays. For example, an initial dosage for use in animals can be formulated to achieve a circulating blood or serum concentration of active compound that is at or above an $IC_{50}$ of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," in *Goodman and Gilman's The Pharmaceutical Basis of Therapeutics*, Chapter 1, pp. 1-46, latest edition, Pergamagon Press, and the references cited therein, which methods are incorporated herein by reference in their entirety. Initial dosages can also be estimated from in vivo data, such as animal models. Animal models useful for testing the efficacy of compounds to treat or prevent the various diseases described in this disclosure are well-known in the art.

In some embodiments, the administered dose ranges from 0.0001 or 0.001 or 0.01 mg/kg/day to 100 mg/kg/day, but can be higher or lower, depending upon, among other factors, the activity of the compound, its bioavailability, the mode of administration and various factors discussed above. Doses and intervals can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Non-limiting embodiments of the present disclosure include:

1. A compound of Formula I:

(I)

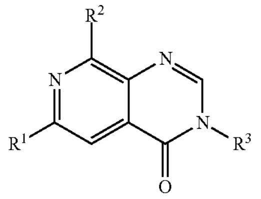

and pharmaceutically acceptable salts thereof,
wherein:

each of $R^1$ and $R^2$ is independently chosen from optionally substituted alkyls, optionally substituted esters, optionally substituted heteroalkyls, optionally substituted acyls, optionally substituted amides, optionally substituted aryls, optionally substituted heteroaryls, optionally substituted cycloalkyls, optionally substituted amines and optionally substituted heterocycloalkyls; and $R^3$ is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, optionally substituted amines, cyano, halos, hydroxy, and —C(O)H.

2. A compound of Formula Ia (Ia)

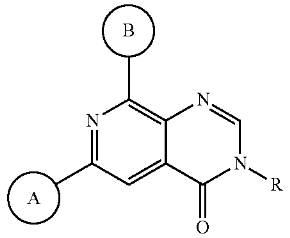

or a pharmaceutically acceptable salt thereof,
wherein:

ring A is chosen from optionally substituted aryls, optionally substituted heteroaryls, optionally substituted cycloalkyls, and optionally substituted heterocycloalkyls;

ring B is chosen from optionally substituted aryls, optionally substituted heteroaryls, optionally substituted cycloalkyls, and optionally substituted heterocycloalkyls; and R is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, amino, cyano, halos, hydroxy, and —C(O)H.

3. The compound of embodiment 2, or a pharmaceutically acceptable salt thereof, wherein:

ring A is chosen from optionally substituted 6-10 membered aryls, optionally substituted 5-10 membered heteroaryls, optionally substituted 3-10 membered cycloalkyls, and optionally substituted 3-10 membered heterocycloalkyls;

ring B is chosen from optionally substituted 6-10 membered aryls, optionally substituted 5-10 membered heteroaryls, optionally substituted 3-10 membered cycloalkyls, and optionally substituted 3-10 membered heterocycloalkyls;

R is chosen from hydrogen, optionally substituted $C_1$-$C_{10}$ alkyls, optionally substituted 6-10 membered aryls, —C(O)R', —C(O)NR'R', optionally substituted 3-10 membered cycloalkyls, —C(O)OR', optionally substituted $C_1$-$C_{10}$ heteroalkyls, optionally substituted 5-10 membered heteroaryls, optionally substituted 3-10 membered heterocycloalkyls, amino, cyano, halos, hydroxy, and —C(O)H; and each R' is independently chosen from hydrogen, optionally substituted $C_1$-$C_{10}$ alkyls, and optionally substituted $C_1$-$C_{10}$ heteroalkyls.

4. The compound of embodiment 2 or 3, or a pharmaceutically acceptable salt thereof, wherein:

ring A is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$;

ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$;

R is chosen from hydrogen, $C_1$-$C_{10}$ alkyls, 6-10 membered aryls, —C(O)R', —C(O)NR'R', 3-10 membered cycloalkyls, —C(O)OR', $C_1$-$C_{10}$ heteroalkyls, 5-10 membered heteroaryls, 3-10 membered heterocycloalkyls, amino, cyano, halos, hydroxy, and —C(O)H, wherein each $C_1$-$C_{10}$ alkyl, 6-10 membered aryl, 3-10 membered cycloalkyl, $C_1$-$C_{10}$ heteroalkyl, 5-10 membered heteroaryl, and 3-10 membered heterocycloalkyl is independently optionally substituted with 1 to 5 instances of $R^c$;

each R' is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls;

each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^C$ is independently chosen from halos, hydroxy, cyano, $C_1$-$C_{10}$ alkyls, $C_1$-$C_{10}$ alkoxys, $C_1$-$C_{10}$ haloalkyls, 3-10 membered cycloalkyls, 3-10 membered heterocycloalkyls, 6-10 membered aryls, and 5-10 membered heteroaryls; and each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

5. The compound of embodiment 4, or a pharmaceutically acceptable salt thereof, wherein ring A is chosen from 3-10 membered cycloalkyl optionally substituted with 1 to 5 instances of $R^A$.

6. The compound of embodiment 4 or 5, or a pharmaceutically acceptable salt thereof, wherein ring A is chosen from cyclopropyl, cyclobutyl, cyclopentyl, cyclohexyl, cycloheptyl, and cyclooctyl optionally substituted with 1 to 5 instances of $R^A$.

7. The compound of embodiment 4, or a pharmaceutically acceptable salt thereof, wherein ring A is chosen from 6-8 membered aryls optionally substituted with 1 to 5 instances of $R^A$.

8. The compound of embodiment 4 or 7, or a pharmaceutically acceptable salt thereof, wherein ring A is phenyl optionally substituted with 1 to 3 instances of $R^A$.

9. The compound of embodiment 4, or a pharmaceutically acceptable salt thereof, wherein ring A is chosen from 5-8 membered heteroaryls optionally substituted with 1 to 5 instances of $R^A$.

10. The compound of embodiment 4 or 9, or a pharmaceutically acceptable salt thereof, wherein ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$.

11. The compound of any one of embodiments 4, 9, or 10, or a pharmaceutically acceptable salt thereof, wherein ring A is pyridinyl optionally substituted with 1 to 3 instances of $R^A$.

12. The compound of embodiment 4, or a pharmaceutically acceptable salt thereof, wherein ring A is chosen from 5-8 membered heterocycloalkyls optionally substituted with 1 to 5 instances of $R^A$.

13. The compound of embodiment 4 or 12, or a pharmaceutically acceptable salt thereof, wherein ring A is chosen from pyrrolidinyl, pyrazolidinyl, piperidinyl, piperazinyl, morpholino, azepinyl, tetrahydropyranyl, and tetrahydrofuranyl, wherein each of pyrrolidinyl, pyrazolidinyl, piperidinyl, piperazinyl, morpholino, azepinyl, tetrahydropyranyl, and tetrahydrofuranyl is independently optionally substituted with 1 to 3 instances of $R^A$.

14. The compound of any one of embodiments 4, 12, or 13, or a pharmaceutically acceptable salt thereof, wherein ring A is piperidinyl or morpholino optionally substituted with 1 to 3 instances of $R^A$.

15. The compound of embodiment 4, or a pharmaceutically acceptable salt thereof, wherein ring B is chosen from 6-8 membered aryls optionally substituted with 1 to 5 instances of $R^B$.

16. The compound of embodiment 4 or 15, or a pharmaceutically acceptable salt thereof, wherein ring B is phenyl optionally substituted with 1 to 3 instances of $R^B$.

17. The compound of embodiment 4, or a pharmaceutically acceptable salt thereof, wherein ring B is chosen from benzodioxolyl and 5-8 membered heteroaryls optionally substituted with 1 to 5 instances of $R^B$.

18. The compound of embodiment 4 or 17, or a pharmaceutically acceptable salt thereof, wherein ring B is chosen from benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, pyridinonyl, and pyrimidinyl, wherein each of benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^B$.

19. The compound of any one of embodiments 4, 17, or 18, or a pharmaceutically acceptable salt thereof, wherein ring B is chosen from pyrazolyl, isothiazoyl, isoxazolyl, pyridinyl, pyrimidinyl, and thiophenyl, wherein each of pyrazolyl, isothiazoyl, isoxazolyl, pyridinyl, pyrimidinyl, and thiophenyl is independently optionally substituted with 1 to 3 instances of $R^B$.

20. The compound of any one of embodiments 4 to 19, or a pharmaceutically acceptable salt thereof, wherein:

each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and NR"R";

each $R^B$ is independently chosen from halos, $C_1$-$C_{10}$ alkyls, and $C_1$-$C_{10}$ haloalkyls;

each $R^C$ is independently chosen from halos, hydroxy, cyano, $C_1$-$C_{10}$ alkyls, $C_1$-$C_{10}$ alkoxys, 3-8 membered cycloalkyls, 3-8 membered heterocycloalkyls, and 6-8 membered aryls; and each R" is independently chosen from hydrogen and $C_1$-$C_{10}$ alkyls.

21. The compound of any one of embodiments 2 to 4, and 7 to 20, or a pharmaceutically acceptable salt thereof, wherein ring A is chosen from

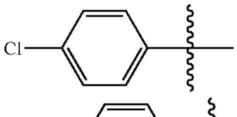, 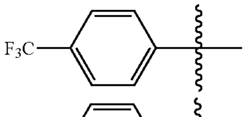,

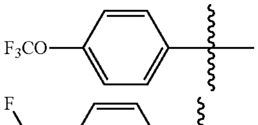, 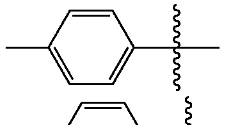,

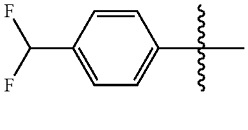, 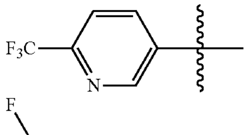,

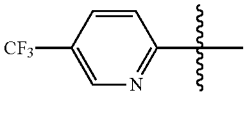, 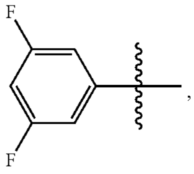,

-continued
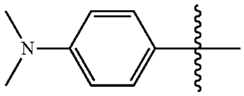, 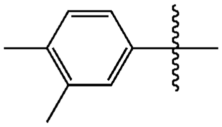,
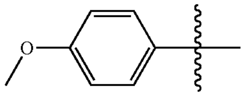,
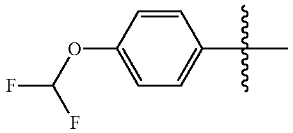,
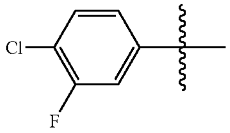, 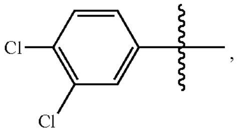,
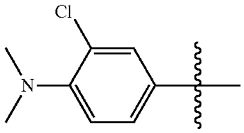, 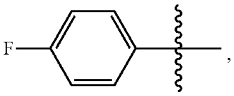,
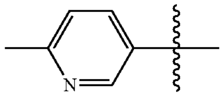, 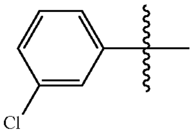,
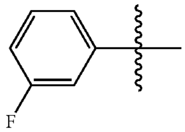, 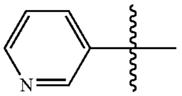,
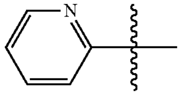, 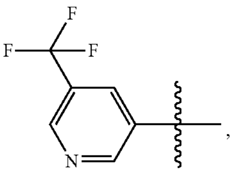,
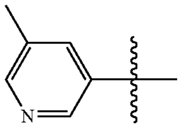, 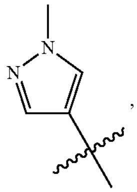,
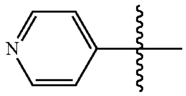, 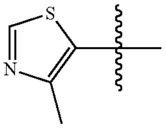,
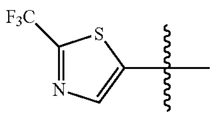,
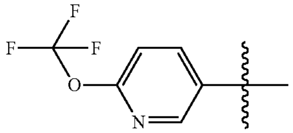, 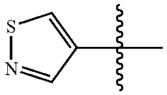,
-continued
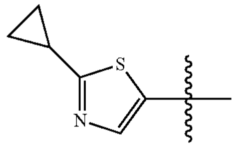, 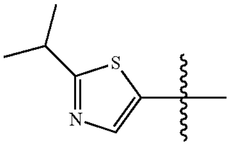,
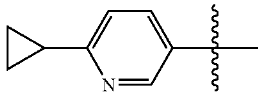,
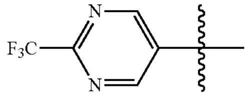, 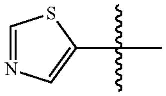,
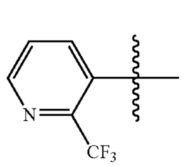, 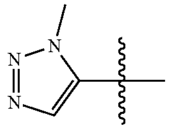,
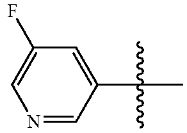, 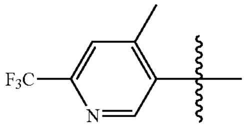,
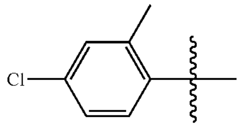, 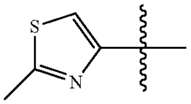, and
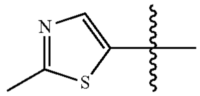.
22. The compound of any one of embodiments 2 to 6 and 15 to 20, or a pharmaceutically acceptable salt thereof, wherein ring A is chosen from
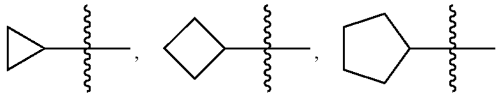,
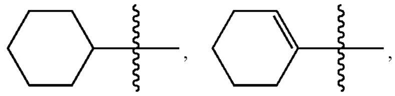,
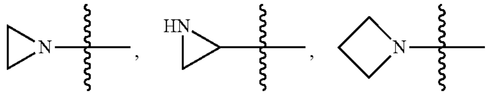,
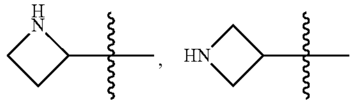,
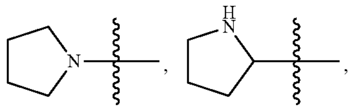,
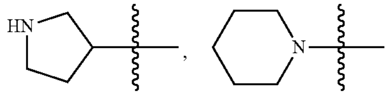, -continued
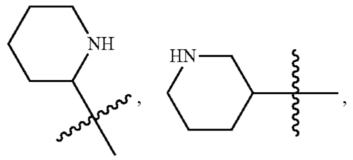
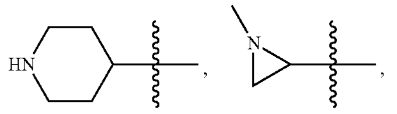
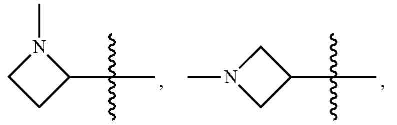
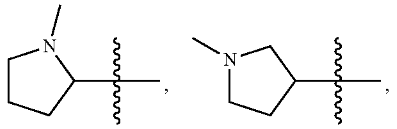
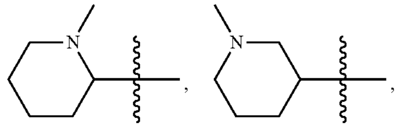
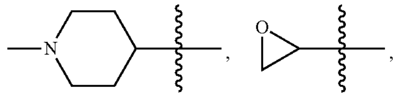
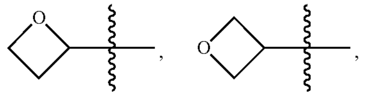
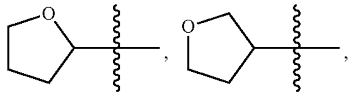
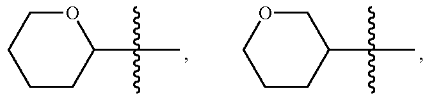
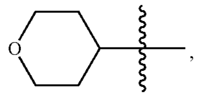
and
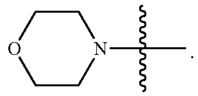
23. The compound of any one of embodiments 2 to 4, and 7 to 20, or a pharmaceutically acceptable salt thereof, wherein ring A is chosen from
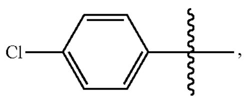
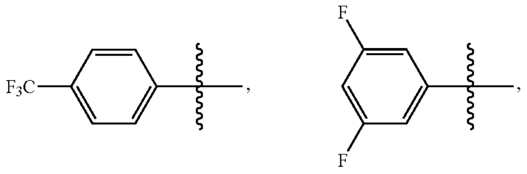
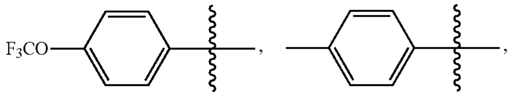
-continued
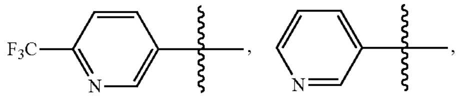
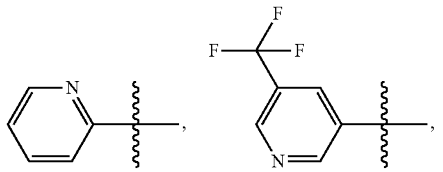
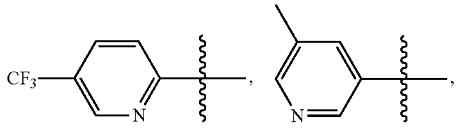
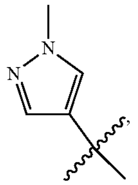
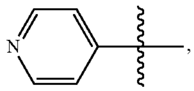
and
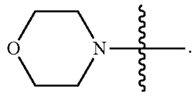
24. The compound of any one of embodiments 2 to 4, and 7 to 20, or a pharmaceutically acceptable salt thereof, wherein ring B is chosen from
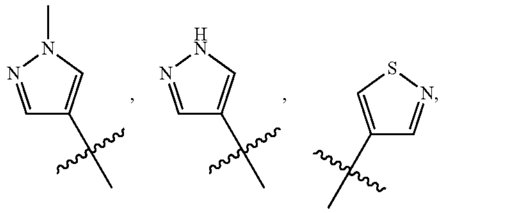
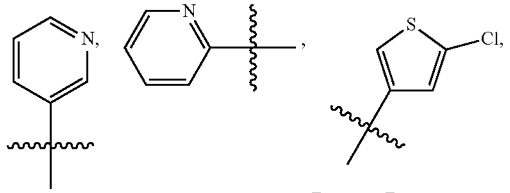
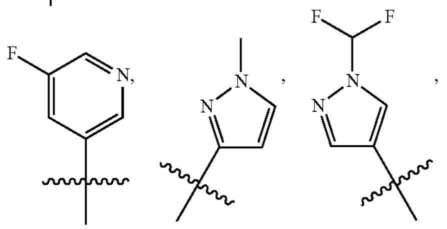
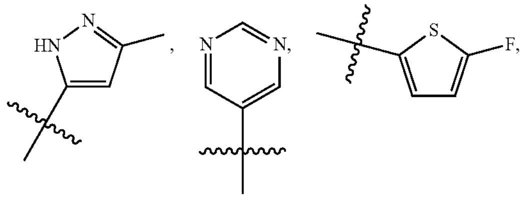

-continued
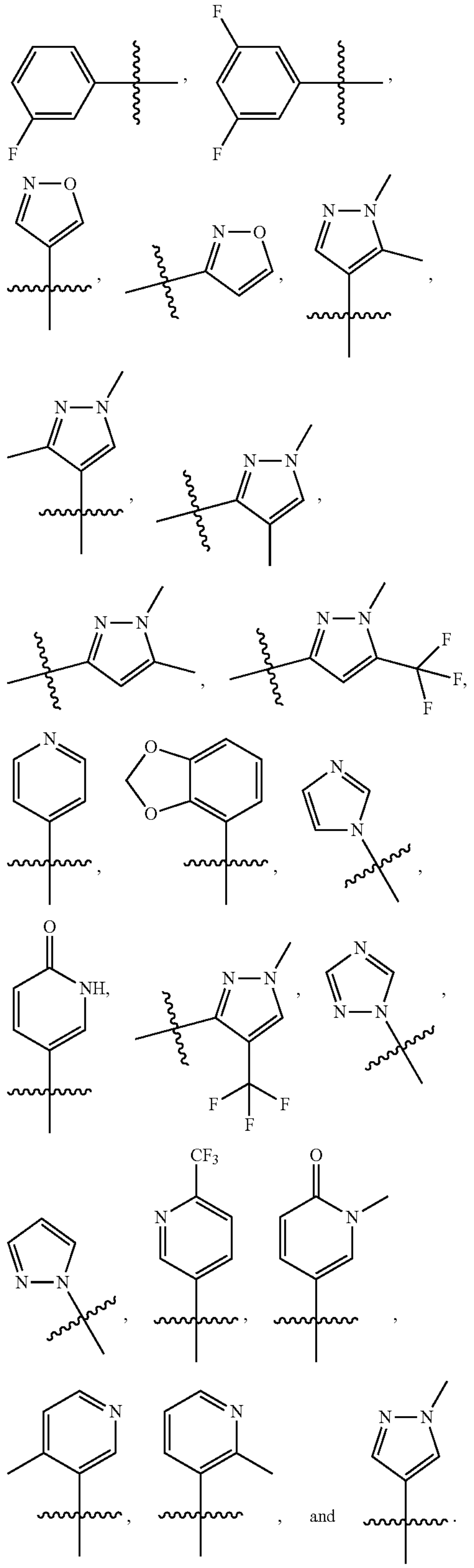
and
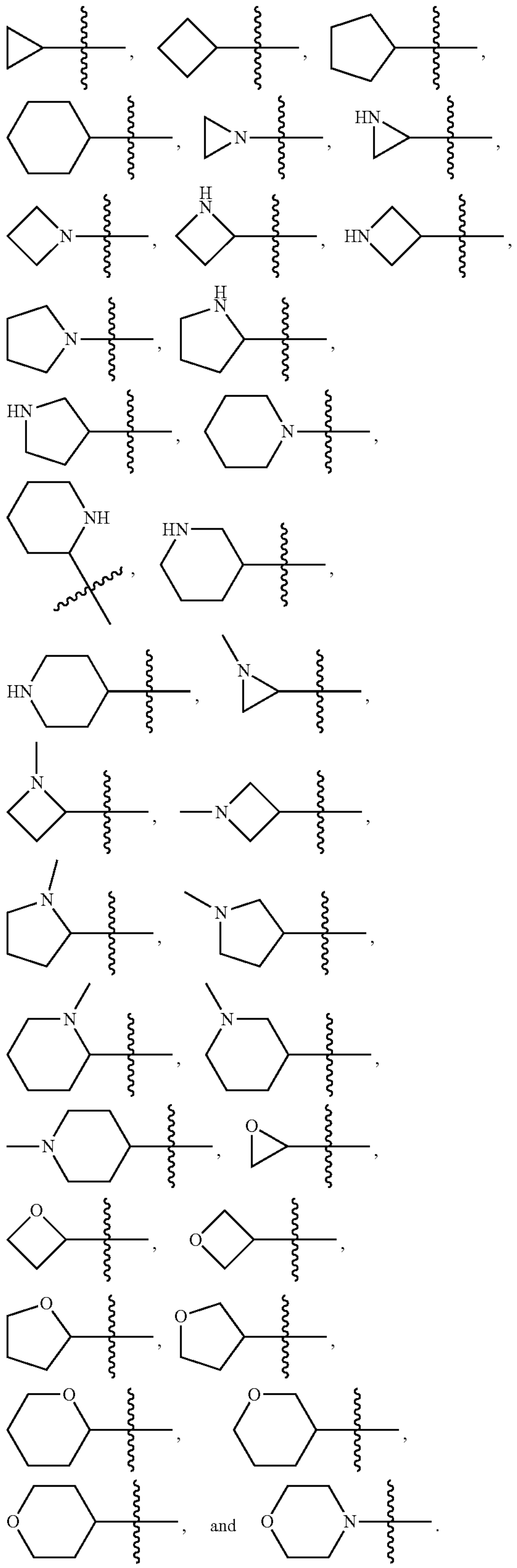
and
25. The compound of any one of embodiments 2 to 14 and 20, or a pharmaceutically acceptable salt thereof, wherein ring B is chosen from
26. The compound of any one of embodiments 2 to 4, and 7 to 20, or a pharmaceutically acceptable salt thereof, wherein ring B is chosen from

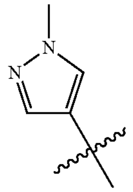 , 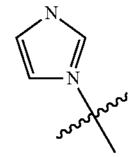 , 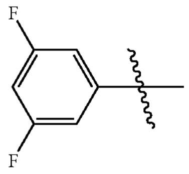 , 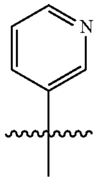 , 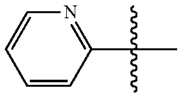 , 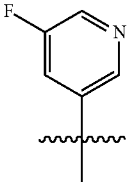 , 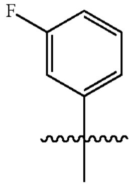 , 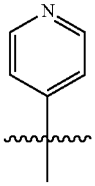 , 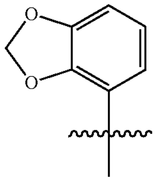 , and 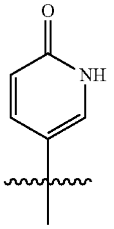 .
27. The compound of any one of embodiments 2 to 26, or a pharmaceutically acceptable salt thereof, wherein R is chosen from methyl,
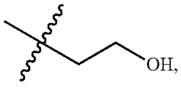 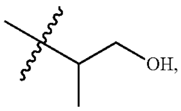 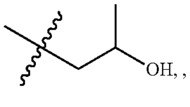 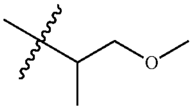 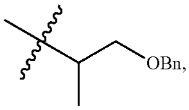 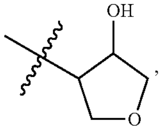 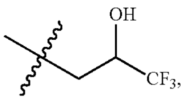 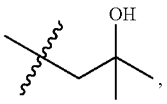
-continued
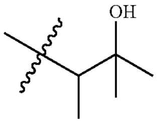 , 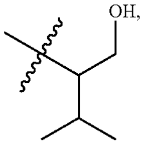 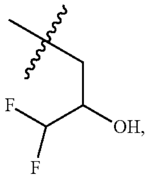 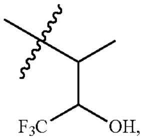 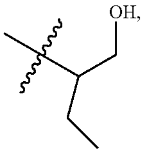 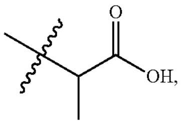 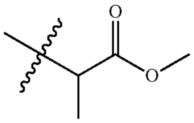 , 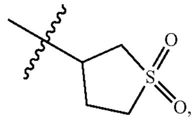 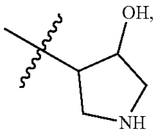 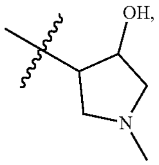 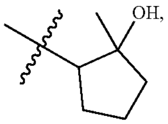 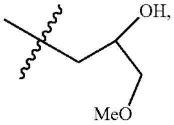 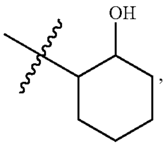 , 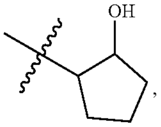 , 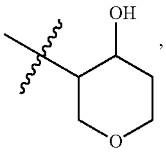 , 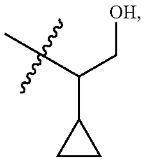 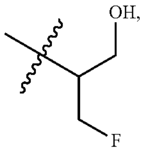 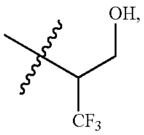 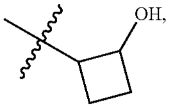 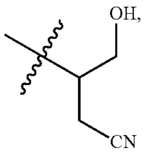 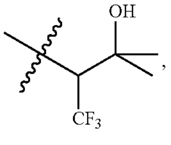 , 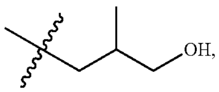

-continued

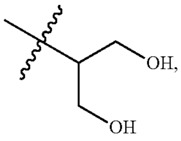 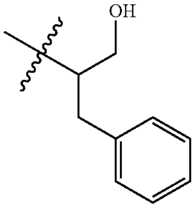,

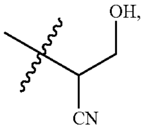 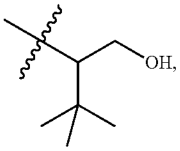 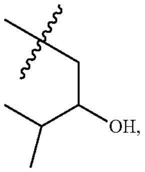

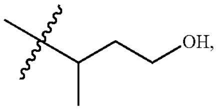 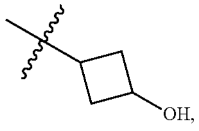

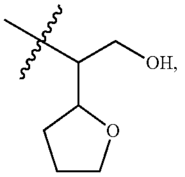 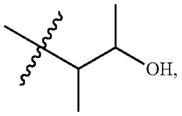

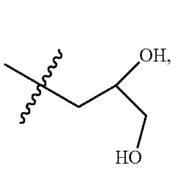 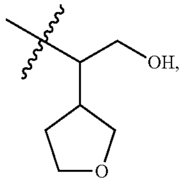

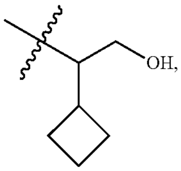 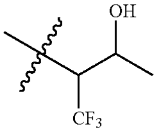, 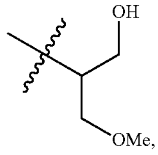

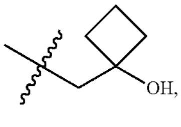 and 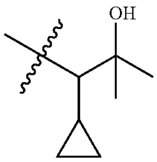.

28. The compound of any one of embodiments 2 to 27, or a pharmaceutically acceptable salt thereof, wherein R is chosen from methyl,

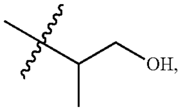 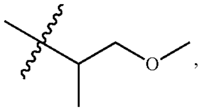,

-continued

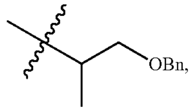 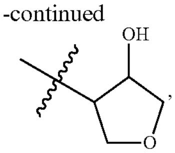,

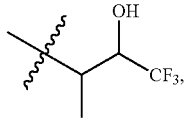 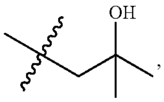,

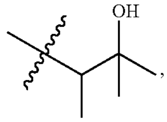, and 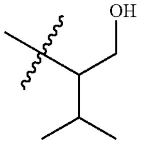.

29. At least one entity chosen from the compounds below and pharmaceutically acceptable salts thereof:

(i) (S)-8-(5-fluoropyridin-3-yl)-3-(1-hydroxypropan-2-yl)-6-(4-(trifluoromethoxy)phenyl)pyrido[3,4-d]pyrimidin-4(3H)-one;

(ii) (S)-6-(4-chlorophenyl)-3-(1-hydroxypropan-2-yl)-8-(6-oxo-1,6-dihydropyridin-3-yl)pyrido[3,4-d]pyrimidin-4(3H)-one;

(iii) (S)-8-(benzo[d][1,3]dioxol-4-yl)-6-(4-chlorophenyl)-3-(1-hydroxypropan-2-yl)pyrido[3,4-d]pyrimidin-4(3H)-one;

(iv) (S)-3-(1-hydroxypropan-2-yl)-8-(pyridin-4-yl)-6-(6-(trifluoromethyl)pyridin-3-yl)pyrido[3,4-d]pyrimidin-4(3H)-one;

(v) (S)-8-(5-fluoropyridin-3-yl)-3-(1-hydroxypropan-2-yl)-6-(4-(trifluoromethyl)phenyl)pyrido[3,4-d]pyrimidin-4(3H)-one;

(vi) (S)-3-(1-hydroxypropan-2-yl)-6,8-di(pyridin-4-yl)pyrido[3,4-d]pyrimidin-4(3H)-one;

(vii) (S)-6-(4-chlorophenyl)-8-(3-fluorophenyl)-3-(1-hydroxypropan-2-yl)pyrido[3,4-d]pyrimidin-4(3H)-one;

(viii) (S)-8-(3-fluorophenyl)-3-(1-hydroxypropan-2-yl)-6-(6-(trifluoromethyl)pyridin-3-yl)pyrido[3,4-d]pyrimidin-4(3H)-one;

(ix) 3-(2-hydroxy-2-methylpropyl)-8-(pyridin-3-yl)-6-(6-(trifluoromethyl)pyridin-3-yl)pyrido[3,4-d]pyrimidin-4(3H)-one;

(x) 6,8-di(pyridin-3-yl)-3-(3,3,3-trifluoro-2-hydroxypropyl)pyrido[3,4-d]pyrimidin-4(3H)-one;

(xi) (S)-6-chloro-3-(1-hydroxypropan-2-yl)-8-(pyridin-3-yl)pyrido[3,4-d]pyrimidin-4(3H)-one;

(xii) (S)-3-(1-hydroxypropan-2-yl)-8-(pyridin-3-yl)-6-(6-(trifluoromethyl)pyridin-3-yl)pyrido[3,4-d]pyrimidin-4(3H)-one;

(xiii) 6-(4-chlorophenyl)-8-(pyridin-3-yl)-3-(3,3,3-trifluoro-2-hydroxypropyl)pyrido[3,4-d]pyrimidin-4(3H)-one;

(xiv) 8-(pyridin-3-yl)-3-(3,3,3-trifluoro-2-hydroxypropyl)-6-(4-(trifluoromethoxy)phenyl)pyrido[3,4-d]pyrimidin-4(3H)-one;

(xv) 6-(4-chlorophenyl)-8-(1-methyl-1H-pyrazol-4-yl)-3-(3,3,3-trifluoro-2-hydroxypropyl)pyrido[3,4-d]pyrimidin-4(3H)-one;

(xvi) 3-(2-hydroxy-2-methylpropyl)-8-(pyridin-3-yl)-6-(4-(trifluoromethyl)phenyl)pyrido[3,4-d]pyrimidin-4(3H)-one;

(xvii) (S)-3-(1-hydroxypropan-2-yl)-8-(pyridin-3-yl)-6-(p-tolyl)pyrido[3,4-d]pyrimidin-4(3H)-one;

(xviii) 6-(4-chlorophenyl)-3-(2-hydroxy-2-methylpropyl)-8-(pyridin-3-yl)pyrido[3,4-d]pyrimidin-4(3H)-one;

(xix) 3-(2-hydroxy-2-methylpropyl)-6,8-bis(1-methyl-1H-pyrazol-4-yl)pyrido[3,4-d]pyrimidin-4(3H)-one;

(xx) (S)-3-(1-hydroxypropan-2-yl)-6,8-di(pyridin-3-yl)pyrido[3,4-d]pyrimidin-4(3H)-one;

(xxi) 6-(4-chlorophenyl)-3-(2-hydroxy-2-methylpropyl)-8-(1-methyl-1H-pyrazol-4-yl)pyrido[3,4-d]pyrimidin-4(3H)-one;

(xxii) (S)-3-(1-hydroxypropan-2-yl)-8-(pyridin-3-yl)-6-(4-(trifluoromethoxy)phenyl)pyrido[3,4-d]pyrimidin-4(3H)-one;

(xxiii) (S)-3-(1-hydroxypropan-2-yl)-8-(pyridin-3-yl)-6-(4-(trifluoromethyl)phenyl)pyrido[3,4-d]pyrimidin-4(3H)-one;

(xxiv) (S)-6-(4-chlorophenyl)-3-(1-hydroxypropan-2-yl)-8-(pyridin-3-yl)pyrido[3,4-d]pyrimidin-4(3H)-one;

(xxv) (S)-3-(1-hydroxypropan-2-yl)-8-(1-methyl-1H-pyrazol-4-yl)-6-(4-(trifluoromethoxy)phenyl)pyrido[3,4-d]pyrimidin-4(3H)-one;

(xxvi) (S)-3-(1-hydroxypropan-2-yl)-8-(1-methyl-1H-pyrazol-4-yl)-6-phenylpyrido[3,4-d]pyrimidin-4(3H)-one;

(xxvii) (S)-6-(4-chlorophenyl)-3-(1-hydroxypropan-2-yl)-8-(1-methyl-1H-pyrazol-4-yl)pyrido[3,4-d]pyrimidin-4(3H)-one;

(xxviii) 3-methyl-8-(pyridin-3-yl)-6-(4-(trifluoromethoxy)phenyl)pyrido[3,4-d]pyrimidin-4(3H)-one;

(xxix) Rac-6-(4-chlorophenyl)-3-((trans)-4-hydroxytetrahydrofuran-3-yl)-8-(pyridin-3-yl)pyrido[3,4-d]pyrimidin-4(3H)-one;

(xxx) (S)-6-(4-chlorophenyl)-3-(3-hydroxy-3-methylbutan-2-yl)-8-(1-methyl-1H-pyrazol-4-yl)pyrido[3,4-d]pyrimidin-4(3H)-one;

(xxxi) (R)-6-(4-chlorophenyl)-3-(3-hydroxy-3-methylbutan-2-yl)-8-(1-methyl-1H-pyrazol-4-yl)pyrido[3,4-d]pyrimidin-4(3H)-one;

(xxxii) rac-6-(4-chlorophenyl)-3-((cis)-4-hydroxytetrahydrofuran-3-yl)-8-(pyridin-3-yl)pyrido[3,4-d]pyrimidin-4(3H)-one;

(xxxiii) (R)-6-(4-chlorophenyl)-3-(3-hydroxy-3-methylbutan-2-yl)-8-(pyridin-3-yl)pyrido[3,4-d]pyrimidin-4(3H)-one;

(xxxiv) (S)-3-(3-hydroxy-3-methylbutan-2-yl)-6,8-di(pyridin-3-yl)pyrido[3,4-d]pyrimidin-4(3H)-one;

(xxxv) (S)-6,8-bis(3,5-difluorophenyl)-3-(1-hydroxy-3-methylbutan-2-yl)pyrido[3,4-d]pyrimidin-4(3H)-one;

(xxxvi) (S)-6-(4-chlorophenyl)-3-(3-hydroxy-3-methylbutan-2-yl)-8-(pyridin-3-yl)pyrido[3,4-d]pyrimidin-4(3H)-one;

(xxxvii) (S)-8-(3,5-difluorophenyl)-3-(1-hydroxy-3-methylbutan-2-yl)-6-(p-tolyl)pyrido[3,4-d]pyrimidin-4(3H)-one;

(xxxviii) 6-(4-chlorophenyl)-8-(3-fluorophenyl)-3-(2-hydroxy-2-methylpropyl)pyrido[3,4-d]pyrimidin-4(3H)-one;

(xxxix) (R)-6-(4-chlorophenyl)-8-(3-fluorophenyl)-3-(3-hydroxy-3-methylbutan-2-yl)pyrido[3,4-d]pyrimidin-4(3H)-one;

(xl) (S)-3-(1-(benzyloxy)propan-2-yl)-8-(3-fluorophenyl)-6-(p-tolyl)pyrido[3,4-d]pyrimidin-4(3H)-one;

(xli) (R)-6-(4-chlorophenyl)-8-(3-fluorophenyl)-3-(3,3,3-trifluoro-2-hydroxypropyl)pyrido[3,4-d]pyrimidin-4(3H)-one;

(xlii) (S)-6-(4-chlorophenyl)-8-(3-fluorophenyl)-3-(3,3,3-trifluoro-2-hydroxypropyl)pyrido[3,4-d]pyrimidin-4(3H)-one;

(xliii) (S)-3-(1-hydroxypropan-2-yl)-6-morpholino-8-(pyridin-3-yl)pyrido[3,4-d]pyrimidin-4(3H)-one;

(xliv) (S)-3-(1-hydroxypropan-2-yl)-8-(1H-imidazol-1-yl)-6-(4-(trifluoromethoxy)phenyl)pyrido[3,4-d]pyrimidin-4(3H)-one;

(xlv) (S)-3-(1-methoxypropan-2-yl)-8-(pyridin-3-yl)-6-(p-tolyl)pyrido[3,4-d]pyrimidin-4(3H)-one;

(xlvi) (S)-3-(1-hydroxypropan-2-yl)-8-(pyridin-3-yl)-6-(5-(trifluoromethyl)pyridin-2-yl)pyrido[3,4-d]pyrimidin-4(3H)-one;

(xlvii) (S)-8-(3-fluorophenyl)-3-(1-hydroxypropan-2-yl)-6-(5-(trifluoromethyl)pyridin-2-yl)pyrido[3,4-d]pyrimidin-4(3H)-one;

(xlviii) (S)-8-(3-fluorophenyl)-3-(1-hydroxypropan-2-yl)-6-(p-tolyl)pyrido[3,4-d]pyrimidin-4(3H)-one;

(xlix) (S)-8-(3-fluorophenyl)-3-(1-hydroxypropan-2-yl)-6-(4-(trifluoromethoxy)phenyl)pyrido[3,4-d]pyrimidin-4(3H)-one;

(l) (S)-3-(1-hydroxypropan-2-yl)-8-(pyridin-3-yl)-6-(6-(trifluoromethoxy)pyridin-3-yl)pyrido[3,4-d]pyrimidin-4(3H)-one (li) (S)-3-(2-hydroxy-2-methylpropyl)-8-(1H-pyrazol-4-yl)-6-(6-(trifluoromethyl)pyridin-3-yl)pyrido[3,4-d]pyrimidin-4(3H)-one (lii) methyl (S)-5-(3-(1-hydroxypropan-2-yl)-4-oxo-8-(pyridin-3-yl)-3,4-dihydropyrido[3,4-d]pyrimidin-6-yl)picolinate (liii) (S)-3-(1-hydroxypropan-2-yl)-6-(isothiazol-4-yl)-8-(pyridin-3-yl)pyrido[3,4-d]pyrimidin-4(3H)-one (liv) 3-(2-hydroxy-2-methylpropyl)-8-(isothiazol-4-yl)-6-(6-(trifluoromethyl)pyridin-3-yl)pyrido[3,4-d]pyrimidin-4(3H)-one (lv) (S)-3-(1-hydroxypropan-2-yl)-8-(isothiazol-4-yl)-6-(6-(trifluoromethyl)pyridin-3-yl)pyrido[3,4-d]pyrimidin-4(3H)-one (lvi) (S)-3-(1-hydroxypropan-2-yl)-6,8-di(isothiazol-4-yl)pyrido[3,4-d]pyrimidin-4(3H)-one (lvii) (S)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one (lviii) (S)-6-(4-chlorophenyl)-3-(1-hydroxypropan-2-yl)-8-(isothiazol-4-yl)pyrido[3,4-d]pyrimidin-4(3H)-one (lix) 3-(2-hydroxy-2-methylpropyl)-6,8-di(pyridin-3-yl)pyrido[3,4-d]pyrimidin-4(3H)-one (lx) 3-(2-hydroxy-2-methylpropyl)-8-(1-methyl-1H-pyrazol-4-yl)-6-(6-(trifluoromethyl)pyridin-3-yl)pyrido[3,4-d]pyrimidin-4(3H)-one (lxi) 6-(4-chloro-2-methylphenyl)-3-(2-hydroxy-2-methylpropyl)-8-(1-methyl-1H-pyrazol-4-yl)pyrido[3,4-d]pyrimidin-4(3H)-one (lxii) (S)-3-(1-hydroxypropan-2-yl)-8-(1H-pyrazol-4-yl)-6-(6-(trifluoromethyl)pyridin-3-yl)pyrido[3,4-d]pyrimidin-4(3H)-one (lxiii) (S)-3-(1-hydroxypropan-2-yl)-8-(2-methylpyridin-3-yl)-6-(6-(trifluoromethyl)pyridin-3-yl)pyrido[3,4-d]pyrimidin-4(3H)-one (lxiv) (S)-3-(1-hydroxypropan-2-yl)-8-(4-methylpyridin-3-yl)-6-(6-(trifluoromethyl)pyridin-3-yl)pyrido[3,4-d]pyrimidin-4(3H)-one (lxv) (S)-3-(1-hydroxypropan-2-yl)-6-(4-methylthiazol-5-yl)-8-(pyridin-3-yl)pyrido[3,4-d]pyrimidin-4(3H)-one (lxvi) (S)-6-(2-cyclopropylthiazol-5-yl)-3-(1-hydroxypropan-2-yl)-8-(pyridin-3-yl)pyrido[3,4-d]pyrimidin-4(3H)-one (lxvii) (S)-3-(1-hydroxypropan-2-yl)-6-(2-isopropylthiazol-5-yl)-8-(pyridin-3-yl)pyrido[3,4-d]pyrimidin-4(3H)-one (lxviii) (S)-3-(1-hydroxypropan-2-yl)-8-(1-methyl-1H-pyrazol-4-yl)-6-(6-(trifluoromethyl)pyridin-3-yl)pyrido[3,4-d]pyrimidin-4(3H)-one (lxix) (S)-3-(1-hydroxypropan-2-yl)-6,8-bis(6-(trifluoromethyl)pyridin-3-yl)pyrido[3,4-d]pyrimidin-4(3H)-one (lxx) 6-(4-chlorophenyl)-3-((3S,4S)-4-hydroxytetrahydrofuran-3-yl)-8-(pyridin-3-yl)pyrido[3,4-d]pyrimidin-4(3H)-one.

(lxxi) 6-(4-chlorophenyl)-3-((3R,4R)-4-hydroxytetrahydrofuran-3-yl)-8-(pyridin-3-yl)pyrido[3,4-d]pyrimidin-4(3H)-one (lxxii) 3-(2-hydroxyethyl)-8-(pyridin-3-yl)-6-(4-(trifluoromethoxy)phenyl)pyrido[3,4-d]pyrimidin-4(3H)-one (lxxiii) (S)-6-(4-chlorophenyl)-3-(1-hydroxypropan-2-yl)-8-(1-methyl-6-oxo-1,6-dihydropyridin-3-yl)pyrido[3,4-d]pyrimidin-4(3H)-one (lxxiv) (S)-6-(6-cyclopropylpyridin-3-yl)-3-(1-hydroxypropan-2-yl)-8-(pyridin-3-yl)pyrido[3,4-d]pyrimidin-4(3H)-one (lxxv) (S)-3-(1-hydroxypropan-2-yl)-6-(4-methyl-6-(trifluoromethyl)pyridin-3-yl)-8-(pyridin-3-yl)pyrido[3,4-d]pyrimidin-4(3H)-one (lxxvi) (S)-3-(1-hydroxypropan-2-yl)-8-(1-methyl-1H-pyrazol-4-yl)-6-(pyridin-3-yl)pyrido[3,4-d]pyrimidin-4(3H)-one (lxxvii) (S)-6-(cyclohex-1-en-1-yl)-3-(1-hydroxypropan-2-yl)-8-(pyridin-3-yl)pyrido[3,4-d]pyrimidin-4(3H)-one (lxxviii) (S)-6,8-bis(5-fluoropyridin-3-yl)-3-(1-hydroxypropan-2-yl)pyrido[3,4-d]pyrimidin-4(3H)-one (lxxix) 3-((3R,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one (lxxx) 3-(2-hydroxy-2-methylpropyl)-8-(pyridin-3-yl)-6-(2-(trifluoromethyl)pyridin-3-yl)pyrido[3,4-d]pyrimidin-4(3H)-one (lxxxi) 6-(6-cyclopropylpyridin-3-yl)-3-(2-hydroxy-2-methylpropyl)-8-(pyridin-3-yl)pyrido[3,4-d]pyrimidin-4(3H)-one (lxxxii) 6-(6-cyclopropylpyridin-3-yl)-3-(2-hydroxy-2-methylpropyl)-8-(1-methyl-1H-pyrazol-4-yl)pyrido[3,4-d]pyrimidin-4(3H)-one (lxxxiii) (S)-6-(6-cyclopropylpyridin-3-yl)-3-(1-hydroxypropan-2-yl)-8-(1-methyl-1H-pyrazol-4-yl)pyrido[3,4-d]pyrimidin-4(3H)-one (lxxxiv) (S)-3-(1-hydroxypropan-2-yl)-8-(pyridin-3-yl)-6-(thiazol-5-yl)pyrido[3,4-d]pyrimidin-4(3H)-one (lxxxv) (S)-3-(1-hydroxypropan-2-yl)-8-(pyridin-3-yl)-6-(2-(trifluoromethyl)thiazol-5-yl)pyrido[3,4-d]pyrimidin-4(3H)-one (lxxxvi) (S)-3-(1-hydroxypropan-2-yl)-8-(pyridin-3-yl)-6-(2-(trifluoromethyl)pyrimidin-5-yl)pyrido[3,4-d]pyrimidin-4(3H)-one (lxxxvii) 3-(2-hydroxy-2-methylpropyl)-8-(pyridin-3-yl)-6-(2-(trifluoromethyl)thiazol-5-yl)pyrido[3,4-d]pyrimidin-4(3H)-one (lxxxviii) 3-((3S,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one (lxxxix) (S)-3-(1-hydroxypropan-2-yl)-6-(2-methylthiazol-5-yl)-8-(pyridin-3-yl)pyrido[3,4-d]pyrimidin-4(3H)-one (xc) (S)-6-(4-chlorophenyl)-8-(3-fluorophenyl)-3-(1-hydroxy-3-methylbutan-2-yl)pyrido[3,4-d]pyrimidin-4(3H)-one (xci) (S)-3-(1-hydroxypropan-2-yl)-6-(piperidin-1-yl)-8-(pyridin-3-yl)pyrido[3,4-d]pyrimidin-4(3H)-one (xcii) 3-(2-hydroxy-2-methylpropyl)-8-(isothiazol-4-yl)-6-(5-(trifluoromethyl)pyridin-2-yl)pyrido[3,4-d]pyrimidin-4(3H)-one (xciii) (S)-3-(1-hydroxypropan-2-yl)-8-(isothiazol-4-yl)-6-(5-(trifluoromethyl)pyridin-2-yl)pyrido[3,4-d]pyrimidin-4(3H)-one (xciv) 3-(2-hydroxy-2-methylpropyl)-8-(1-methyl-1H-pyrazol-4-yl)-6-(5-(trifluoromethyl)pyridin-2-yl)pyrido[3,4-d]pyrimidin-4(3H)-one (xcv) (S)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one (xcvi) (3-(2-hydroxy-2-methylpropyl)-8-(pyridin-3-yl)-6-(5-(trifluoromethyl)pyridin-2-yl)pyrido[3,4-d]pyrimidin-4(3H)-one (xcvii) 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (xcviii) (R)-3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (xcix) (R)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one (c) (S)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one (ci)(R)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one (cii) (S)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one (ciii) (R)-3-(2-hydroxypropyl)-8-(pyridin-3-yl)-6-(6-(trifluoromethyl)pyridin-3-yl)pyrido[3,4-d]pyrimidin-4(3H)-one (civ) (R)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one (cv) 3-((3S,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one (cvi) 3-((3R,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one (cvii) 6-(4-chlorophenyl)-3-((3S,4R)-4-hydroxytetrahydrofuran-3-yl)-8-(1-methyl-1H-pyrazol-4-yl)pyrido[3,4-d]pyrimidin-4(3H)-one (cviii) 3-((3S,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one (cix) (S)-6-(6-cyclopropylpyridin-3-yl)-8-(pyridin-3-yl)-3-(3,3,3-trifluoro-2-hydroxypropyl)pyrido[3,4-d]pyrimidin-4(3H)-one (cx) (R)-6-(6-cyclopropylpyridin-3-yl)-8-(pyridin-3-yl)-3-(3,3,3-trifluoro-2-hydroxypropyl)pyrido[3,4-d]pyrimidin-4(3H)-one (cxi) (R)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one (cxii) (R)-8-(pyridin-3-yl)-3-(3,3,3-trifluoro-2-hydroxypropyl)-6-(4-(trifluoromethoxy)phenyl)pyrido[3,4-d]pyrimidin-4(3H)-one (cxiii) (S)-8-(pyridin-3-yl)-3-(3,3,3-trifluoro-2-hydroxypropyl)-6-(4-(trifluoromethoxy)phenyl)pyrido[3,4-d]pyrimidin-4(3H)-one (cxiv) 6-(4-chlorophenyl)-3-((3S,4R)-4-hydroxytetrahydrofuran-3-yl)-8-(pyridin-3-yl)pyrido[3,4-d]pyrimidin-4(3H)-one (cxv) 3-((3S,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one (cxvi) methyl (S)-2-(4-oxo-8-(pyridin-3-yl)-6-(6-(trifluoromethyl)pyridin-3-yl)pyrido[3,4-d]pyrimidin-3(4H)-yl) propanoate (cxvii) 6-(4-chlorophenyl)-3-(4-hydroxy-1-methylpyrrolidin-3-yl)-8-(pyridin-3-yl)pyrido[3,4-d]pyrimidin-4(3H)-one (cxviii) 6-(4-chlorophenyl)-3-((3R,4R)-4-hydroxypyrrolidin-3-yl)-8-(pyridin-3-yl)pyrido[3,4-d]pyrimidin-4(3H)-one (cxix) (R)-6-(6-cyclopropylpyridin-3-yl)-8-(1-methyl-1H-pyrazol-4-yl)-3-(3,3,3-trifluoro-2-hydroxypropyl)pyrido [3,4-d]pyrimidin-4(3H)-one (cxx) (S)-6-(6-cyclopropylpyridin-3-yl)-8-(1-methyl-1H-pyrazol-4-yl)-3-(3,3,3-trifluoro-2-hydroxypropyl)pyrido [3,4-d]pyrimidin-4(3H)-one (cxxi) 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (cxxii) 3-((3R,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (cxxiii) 3-((3S,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one (cxxiv) 3-((3R,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one (cxxv)(R)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one (cxxvi) (S)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one (cxxvii) (S)-3-(2-hydroxypropyl)-8-(pyridin-3-yl)-6-(5-(trifluoromethyl)pyridin-2-yl)pyrido[3,4-d]pyrimidin-4 (3H)-one (cxxviii) (R)-3-(2-hydroxypropyl)-8-(pyridin-3-yl)-6-(5-(trifluoromethyl)pyridin-2-yl)pyrido[3,4-d]pyrimidin-4 (3H)-one (cxxix) 3-((3S,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one (cxxx) (S)-3-(2-hydroxypropyl)-8-(pyridin-3-yl)-6-(6-(trifluoromethyl)pyridin-3-yl)pyrido[3,4-d]pyrimidin-4(3H)-one (cxxxi) (S)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one (cxxxii) (S)-3-(1-hydroxypropan-2-yl)-8-(1-methyl-1H-pyrazol-4-yl)-6-(5-(trifluoromethyl)pyridin-2-yl)pyrido [3,4-d]pyrimidin-4(3H)-one (cxxxiii) 3-((3S,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (cxxxiv) 6-(4-chlorophenyl)-3-((3R,4S)-4-hydroxytetrahydrofuran-3-yl)-8-(pyridin-3-yl)pyrido[3,4-d]pyrimidin-4 (3H)-one (cxxxv) 6-(4-Chlorophenyl)-3-((3R,4S)-4-hydroxytetrahydrofuran-3-yl)-8-(1-methyl-1H-pyrazol-4-yl)pyrido[3,4-d]pyrimidin-4(3H)-one (cxxxvi) (R)-8-(pyridin-3-yl)-3-(3,3,3-trifluoro-2-hydroxypropyl)-6-(5-(trifluoromethyl)pyridin-2-yl)pyrido[3,4-d] pyrimidin-4(3H)-one (cxxxvii) (S)-2-(4-oxo-8-(pyridin-3-yl)-6-(6-(trifluoromethyl)pyridin-3-yl)pyrido[3,4-d]pyrimidin-3(4H)-yl)propanoic acid (cxxxviii) (S)—N-methyl-2-(4-oxo-8-(pyridin-3-yl)-6-(6-(trifluoromethyl)pyridin-3-yl)pyrido[3,4-d]pyrimidin-3 (4H)-yl)propanamide (cxxxix) (S)—N,N-dimethyl-2-(4-oxo-8-(pyridin-3-yl)-6-(6-(trifluoromethyl)pyridin-3-yl)pyrido[3,4-d]pyrimidin-3(4H)-yl)propenamide (cxl) 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one (cxli) 3-(2-hydroxy-2-methylpropyl)-8-(1H-imidazol-1-yl)-6-(5-(trifluoromethyl)pyridin-2-yl)pyrido[3,4-d]pyrimidin-4(3H)-one (cxlii) 3-(2-hydroxy-2-methylpropyl)-8-(1H-imidazol-1-yl)-6-(6-(trifluoromethyl)pyridin-2-yl)pyrido[3,4-d]pyrimidin-4(3H)-one (cxliii) (S)-3-(1-hydroxypropan-2-yl)-8-(1H-imidazol-1-yl)-6-(5-(trifluoromethyl)pyridin-2-yl)pyrido[3,4-d]pyrimidin-4(3H)-one (cxliv) (S)-3-(1-hydroxypropan-2-yl)-8-(1H-imidazol-1-yl)-6-(6-(trifluoromethyl)pyridin-3-yl)pyrido[3,4-d]pyrimidin-4(3H)-one (cxlv) (S)-3-(1-hydroxypropan-2-yl)-8-(1H-1,2,4-triazol-1-yl)-6-(6-(trifluoromethyl)pyridin-3-yl)pyrido[3,4-d]pyrimidin-4(3H)-one (cxlvi) (S)-3-(1-hydroxypropan-2-yl)-8-(1H-pyrazol-1-yl)-6-(6-(trifluoromethyl)pyridin-3-yl)pyrido[3,4-d]pyrimidin-4(3H)-one (cxlvii) (S)-3-(1-hydroxypropan-2-yl)-8-(1-methyl-1H-pyrazol-4-yl)-6-(2-(trifluoromethyl)thiazol-5-yl)pyrido [3,4-d]pyrimidin-4(3H)-one (cxlviii) (S)-8-(diethylamino)-3-(1-hydroxypropan-2-yl)-6-(6-(trifluoromethyl)pyridin-3-yl)pyrido[3,4-d]pyrimidin-4(3H)-one (cxlix) (S)-3-(1-hydroxypropan-2-yl)-8-(piperidin-1-yl)-6-(6-(trifluoromethyl)pyridin-3-yl)pyrido[3,4-d]pyrimidin-4(3H)-one (cl) (S)-3-(1-hydroxypropan-2-yl)-8-(pyrrolidin-1-yl)-6-(6-(trifluoromethyl)pyridin-3-yl)pyrido[3,4-d]pyrimidin-4 (3H)-one (cli) (S)-6-(4-chlorophenyl)-3-(1-hydroxypropan-2-yl)-8-(piperidin-1-yl)pyrido[3,4-d]pyrimidin-4(3H)-one (clii) (S)-3-(1-hydroxypropan-2-yl)-8-(pyridin-2-yl)-6-(6-(trifluoromethyl)pyridin-3-yl)pyrido[3,4-d]pyrimidin-4 (3H)-one (cliii) (S)-6-cyclohexyl-3-(1-hydroxypropan-2-yl)-8-(pyridin-3-yl)pyrido[3,4-d]pyrimidin-4(3H)-one (cliv) (S)-3-(1-hydroxypropan-2-yl)-6-(pyridin-2-yl)-8-(pyridin-3-yl)pyrido[3,4-d]pyrimidin-4(3H)-one (clv) (S)-3-(1-hydroxypropan-2-yl)-6-(2-methylthiazol-4-yl)-8-(pyridin-3-yl)pyrido[3,4-d]pyrimidin-4(3H)-one (clvi) (S)-3-(1-hydroxypropan-2-yl)-6-(1-methyl-1H-1,2,3-triazol-5-yl)-8-(pyridin-3-yl)pyrido[3,4-d]pyrimidin-4 (3H)-one (clvii) (R)-6-(4-chlorophenyl)-8-(pyridin-3-yl)-3-(3,3,3-trifluoro-2-hydroxypropyl)pyrido[3,4-d]pyrimidin-4(3H)-one;

(clviii) (S)-6-(4-chlorophenyl)-8-(pyridin-3-yl)-3-(3,3,3-trifluoro-2-hydroxypropyl)pyrido[3,4-d]pyrimidin-4(3H)-one;

(clix) (S)-3-(1-hydroxypropan-2-yl)-8-(1-methyl-1,2,5,6-tetrahydropyridin-3-yl)-6-(6-(trifluoromethyl)pyridin-3-yl)pyrido[3,4-d]pyrimidin-4(3H)-one;

(clx) 6-(4-chlorophenyl)-3-((3S,4S)-4-hydroxytetrahydrofuran-3-yl)-8-(1-methyl-1H-pyrazol-4-yl)pyrido[3,4-d]pyrimidin-4(3H)-one;

(clxi) (S)-3-(1-hydroxypropan-2-yl)-6-(2-methylpyrimidin-5-yl)-8-(pyridin-3-yl)pyrido[3,4-d]pyrimidin-4(3H)-one;

(clxii) 3-(2-hydroxy-2-methylpropyl)-8-(1-(trifluoromethyl)-1H-pyrazol-4-yl)-6-(6-(trifluoromethyl)pyridin-3-yl)pyrido[3,4-d]pyrimidin-4(3H)-one;

(clxiii) (S)-3-(1-hydroxypropan-2-yl)-8-(1-methyl-1H-pyrazol-4-yl)-6-(2-(trifluoromethyl)pyrimidin-5-yl)pyrido[3,4-d]pyrimidin-4(3H)-one;

(clxiv) 3-(2-hydroxy-2-methylpropyl)-8-(pyridin-3-yl)-6-(2-(trifluoromethyl)pyrimidin-5-yl)pyrido[3,4-d]pyrimidin-4(3H)-one;

(clxv) (S)-5-(3-(1-hydroxypropan-2-yl)-4-oxo-8-(pyridin-3-yl)-3,4-dihydropyrido[3,4-d]pyrimidin-6-yl)picolinic acid;

(clxvi) (S)-3-(1-hydroxypropan-2-yl)-6-(6-methylpyridin-3-yl)-8-(pyridin-3-yl)pyrido[3,4-d]pyrimidin-4(3H)-one;

(clxvii) 3-(2-hydroxy-2-methylpropyl)-8-(1-methyl-1H-pyrazol-4-yl)-6-(2-(trifluoromethyl)pyrimidin-5-yl)pyrido[3,4-d]pyrimidin-4(3H)-one;

(clxviii) 3,8-di(pyridin-3-yl)-6-(6-(trifluoromethyl)pyridin-3-yl)pyrido[3,4-d]pyrimidin-4(3H)-one;

(clxix) 8-(pyridin-3-yl)-6-(6-(trifluoromethyl)pyridin-3-yl)pyrido[3,4-d]pyrimidin-4(3H)-one;

(clxx) 3-((3R,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one;

(clxxi) 3-((3R,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one;

(clxxii) 6-(4-chlorophenyl)-3-((3R,4R)-4-hydroxytetrahydrofuran-3-yl)-8-(1-methyl-1H-pyrazol-4-yl)pyrido[3,4-d]pyrimidin-4(3H)-one;

(clxxiii) 3-cyclopentyl-8-(pyridin-3-yl)-6-(6-(trifluoromethyl)pyridin-3-yl)pyrido[3,4-d]pyrimidin-4(3H)-one;

(clxxiv) 3-phenyl-8-(pyridin-3-yl)-6-(6-(trifluoromethyl)pyridin-3-yl)pyrido[3,4-d]pyrimidin-4(3H)-one;

(clxxv) 3-((3R,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one;

(clxxvi) 3-((3R,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one;

(clxxvii) (S)-3-(1-hydroxypropan-2-yl)-8-(1-methyl-1H-pyrazol-4-yl)-6-(5-(trifluoromethyl)pyridin-2-yl)pyrido[3,4-d]pyrimidin-4(3H)-one;

(clxxviii) (S)—N-((3R,4S)-4-hydroxytetrahydrofuran-3-yl)-2-(4-oxo-8-(pyridin-3-yl)-6-(6-(trifluoromethyl)pyridin-3-yl)pyrido[3,4-d]pyrimidin-3(4H)-yl)propanamide (clxxix) 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one;

(clxxx) (S)-6-(4-chlorophenyl)-3-(1-hydroxypropan-2-yl)-8-(1H-pyrazol-1-yl)pyrido[3,4-d]pyrimidin-4(3H)-one;

(clxxxi) (S)-3-(1-hydroxypropan-2-yl)-8-(1H-pyrazol-1-yl)-6-(5-(trifluoromethyl)pyridin-2-yl)pyrido[3,4-d]pyrimidin-4(3H)-one;

(clxxxii) 3-((3S,4R)-4-hydroxytetrahydrofuran-3-yl)-8-(pyridin-3-yl)-6-(2-(trifluoromethyl)thiazol-5-yl)pyrido[3,4-d]pyrimidin-4(3H)-one;

(clxxxiii) 3-(2-hydroxy-2-methylpropyl)-8-(1-methyl-1H-pyrazol-4-yl)-6-(2-(trifluoromethyl)thiazol-5-yl)pyrido[3,4-d]pyrimidin-4(3H)-one;

(clxxxiv) 3-((3S,4R)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one;

(clxxxv) 3-((3R,4S)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one;

(clxxxvi) 3-((3R,4S)-4-hydroxytetrahydrofuran-3-yl)-8-(pyridin-3-yl)-6-(2-(trifluoromethyl)thiazol-5-yl)pyrido[3,4-d]pyrimidin-4(3H)-one;

(clxxxvii) (S)-3-(1-hydroxypropan-2-yl)-8-morpholino-6-(6-(trifluoromethyl)pyridin-3-yl)pyrido[3,4-d]pyrimidin-4(3H)-one;

(clxxxviii) 3-(2-hydroxy-2-methylpropyl)-8-(piperidin-1-yl)-6-(6-(trifluoromethyl)pyridin-3-yl)pyrido[3,4-d]pyrimidin-4(3H)-one;

(clxxxix) (S)-3-(1-hydroxypropan-2-yl)-6-(5-methylpyridin-2-yl)-8-(pyridin-3-yl)pyrido[3,4-d]pyrimidin-4(3H)-one;

(cxc) (S)-3-(1-hydroxypropan-2-yl)-6-(5-methylpyrimidin-2-yl)-8-(pyridin-3-yl)pyrido[3,4-d]pyrimidin-4(3H)-one;

(cxci) (S)-8-(cyclohex-1-en-1-yl)-3-(1-hydroxypropan-2-yl)-6-(5-(trifluoromethyl)pyridin-2-yl)pyrido[3,4-d]pyrimidin-4(3H)-one;

(cxcii) (S)-8-cyclohexyl-3-(1-hydroxypropan-2-yl)-6-(5-(trifluoromethyl)pyridin-2-yl)pyrido[3,4-d]pyrimidin-4(3H)-one;

(cxciii) (S)-3-(1-hydroxypropan-2-yl)-N,N-dimethyl-4-oxo-8-(pyridin-3-yl)-3,4-dihydropyrido[3,4-d]pyrimidine-6-carboxamide;

(cxciv) (S)-3-(1-hydroxypropan-2-yl)-8-(1H-pyrazol-4-yl)-6-(5-(trifluoromethyl)pyridin-2-yl)pyrido[3,4-d]pyrimidin-4(3H)-one;

(cxcv) (S)-3-(1-hydroxypropan-2-yl)-6-(2-methoxyethyl)-8-(pyridin-3-yl)pyrido[3,4-d]pyrimidin-4(3H)-one; and (cxcvi) (S)-3-(1-hydroxypropan-2-yl)-8-(2-methoxyethyl)-6-(5-(trifluoromethyl)pyridin-2-yl)pyrido[3,4-d]pyrimidin-4(3H)-one.

(cxcvii)

30. A pharmaceutical composition comprising at least one entity chosen from the compounds of any one of embodiment 1 to 29 and pharmaceutically acceptable salts thereof, and at least one pharmaceutically acceptable excipient.

31. A method of treating a disease or condition mediated by AhR signaling in a subject in need thereof comprising administering to the subject a therapeutically effective amount of at least one entity chosen from the compounds of any one of embodiments 1 to 29 and pharmaceutically acceptable salts thereof, or at least one pharmaceutical composition of embodiment 30.

32. A method of treating a disease or condition associated with aberrant AhR signaling in a subject in need thereof comprising administering to the subject a therapeutically effective amount of at least one entity chosen from the compounds of any one of embodiments 1 to 29 and pharmaceutically acceptable salts thereof, or at least one pharmaceutical composition of embodiment 30.

33. The method of embodiment 31 or 32, wherein the disease is chosen from cancers.

34. The method of embodiment 31 or 32, wherein the disease is chosen from liquid tumors and solid tumors.

35. The method of any one of embodiments 31 to 34, wherein the disease is chosen from breast cancers, respiratory tract cancers, brain cancers, cancers of reproductive organs, digestive tract cancers, urinary tract cancers, eye cancers, liver cancers, skin cancers, head and neck cancers, thyroid cancers, parathyroid cancers, and metastases of any of the foregoing.

36. The method of any one of embodiments 31 to 35, wherein the disease is chosen from breast cancers, pancreatic cancers, prostate cancers, and colon cancers.

37. The method of any one of embodiments 31 to 34, wherein the disease is chosen from lymphomas, sarcomas, melanomas, glioblastomas, and leukemias.

38. A method of inhibiting cancer cell proliferation mediated by AhR signaling in a subject in need thereof comprising administering to the subject a therapeutically effective amount of at least one entity chosen from the compounds of any one of embodiments 1 to 29 and pharmaceutically acceptable salts thereof, or at least one pharmaceutical composition of embodiment 30.

39. A method of inhibiting tumor cell invasion or metastasis mediated by AhR signaling in a subject in need thereof comprising administering to the subject a therapeutically effective amount of at least one entity chosen from the compounds of any one of embodiments 1 to 29 and pharmaceutically acceptable salts thereof, or at least one pharmaceutical composition of embodiment 30.

40. A method of treating cancer in a subject in need thereof comprising administering to said subject a therapeutically effective amount of i) at least one entity chosen from the compounds of any one of embodiments 1 to 29 and pharmaceutically acceptable salts thereof or at least one pharmaceutical composition of embodiment 30, and ii) a therapeutically effective amount of at least one additional therapy.

41. The method of embodiment 40, wherein the at least one additional therapy comprises at least two, at least three, at least four, or at least five additional therapies.

42. The method of embodiment 40, wherein administration of the at least one entity chosen from the compounds of any one of embodiments 1 to 29 and pharmaceutically acceptable salts thereof or at least one pharmaceutical composition of embodiment 30, is initiated before administration of the at least one additional therapy.

43. The method of embodiment 40, wherein the at least one entity chosen from the compounds of any one of embodiments 1 to 29 and pharmaceutically acceptable salts thereof or at least one pharmaceutical composition of embodiment 30, is administered after administration of the at least one additional therapy.

44. The method of embodiment 40, wherein the at least one entity chosen from the compounds of any one of embodiments 1 to 29 and pharmaceutically acceptable salts thereof or at least one pharmaceutical composition of embodiment 30, is administered concurrently with administration of the at least one additional therapy.

45. The method of any one of embodiments 40 to 44, wherein the at least one additional therapy is chosen from checkpoint inhibitors.

46. The method of embodiment 45, wherein the subject is intolerant, non-responsive, and/or poorly responsive to the at least one additional therapy when administered alone.

47. The method of embodiment 46, wherein the at least one additional therapy is chosen from checkpoint inhibitors that target CTLA-4, PD-1, PD-L1, LAG-3, TIM-3, TIGIT and/or VISTA.

48. The method of embodiment 46, wherein the at least one additional therapy is chosen from checkpoint inhibitors that target CTLA-4, PD-1, and/or PD-L1.

49. The method of embodiment 46, wherein the at least one additional therapy is chosen from cytotoxic T-lymphocyte-associated antigen 4 pathway inhibitors.

50. The method of embodiment 49, wherein the cytotoxic T-lymphocyte-associated antigen 4 pathway inhibitors are chosen from anti-CTLA-4 antibodies.

51. The method of embodiment 50, wherein the anti-CTLA-4 antibody is ipilimumab.

52. The method of embodiment 46, wherein the at least one additional therapy is chosen from programmed death-1 pathway inhibitors.

53. The method of embodiment 52, wherein the programmed death-1 pathway inhibitors are chosen from anti-PD-1 antibodies.

54. The method of embodiment 52, wherein the anti-PD-1 antibody is nivolumab.

55. The method of embodiment 52, wherein the anti-PD-1 antibody is pembrolizumab.

56. The method of embodiment 52, wherein the anti-PD-1 antibody is cemiplimab

57. The method of embodiment 52, wherein the anti-PD-1 antibody is camrelizumab.

58. The method of embodiment 52, wherein the anti-PD-1 antibody is sintilimab.

59. The method of embodiment 52, wherein the anti-PD-1 antibody is spartalizumab.

60. The method of embodiment 52, wherein the anti-PD-1 antibody is tislelizumab.

61. The method of embodiment 52, wherein the anti-PD-1 antibody is BCD-100.

62. The method of embodiment 52, wherein the anti-PD-1 antibody is JS001.

63. The method of embodiment 52, wherein the programmed death-1 pathway inhibitors are chosen from anti-PD-L1 antibodies.

64. The method of embodiment 63, wherein the anti-PD-L1 antibody is atezolizumab.

65. The method of embodiment 63, wherein the anti-PD-L1 antibody is avelumab.

66. The method of embodiment 63, wherein the anti-PD-L1 antibody is durvalumab.

67. The method of embodiment 63, wherein the anti-PD-L1 antibody is KN035.

68. The method of embodiment 46, wherein the at least one additional therapy is chosen from lymphocyte activation gene-3 (LAG-3) inhibitors.

69. The method of embodiment 68, wherein the LAG-3 inhibitors are chosen from anti-LAG-3 antibodies.

70. The method of embodiment 46, wherein the at least one additional therapy is chosen from T-cell immunoglobulin and mucin-domain containing-3 (TIM-3) inhibitors.

71. The method of embodiment 70, wherein the TIM-3 inhibitors are chosen from anti-TIM-3 antibodies.

72. The method of embodiment 46, wherein the at least one additional therapy is chosen from T-cell immunoglobulin and ITIM domain (TIGIT) inhibitors.

73. The method of embodiment 72, wherein the TIGIT inhibitors are chosen from TIGIT antibodies.

74. The method of embodiment 46, wherein the at least one additional therapy is chosen from V-domain Ig suppressor of T-cell activation (VISTA) inhibitors.

75. The method of embodiment 74, wherein the VISTA inhibitors are chosen from anti-VISTA antibodies.

76. The method of any one of embodiments 40 to 75, wherein the cancer is chosen from non-small cell lung cancer (NSCLC); small cell lung cancer; head and neck squamous cell carcinoma; renal cell carcinoma; gastric adenocarcinoma; nasopharyngeal neoplasms; urothelial carcinoma; colorectal cancer; pleural mesothelioma; triple-negative breast cancer (TNBC); esophageal neoplasms;

multiple myeloma; gastric and gastroesophageal junction cancer; melanoma; Hodgkin lymphoma; hepatocellular carcinoma; lung cancer; head and neck cancer; non-Hodgkin lymphoma; metastatic clear cell renal carcinoma; squamous cell lung carcinoma; mesothelioma; gastric cancer; gastroesophageal junction cancer; metastatic melanoma; metastatic non-cutaneous melanoma; urothelial cancer; diffuse large B-cell lymphoma; renal cell cancer; ovarian cancer, fallopian tube cancer; peritoneal neoplasms; extensive stage small cell lung cancer; bladder cancer; transitional cell carcinoma; prostatic neoplasms; recurrent or metastatic PD-L1 positive or negative squamous cell carcinoma of the head and neck (SCCHN); recurrent squamous cell lung cancer; advanced solid malignancies; SCCHN; hypo pharyngeal squamous cell carcinoma; laryngeal squamous cell carcinoma; unresectable or metastatic melanoma; biliary tract neoplasms; esophageal squamous cell carcinoma, breast cancer, pancreatic cancer, glioblastoma, metastatic cancer, prostatic cancer, solid organ cancer; stomach cancer; colon cancer; and liver cancer.

EXAMPLES

The following non-limiting examples and data illustrate various aspects and features relating to the compounds and/or methods of the present disclosure, including the preparation of various compounds, as are available through the synthetic methodologies described herein. In comparison with the prior art, in some embodiments, the present compounds and/or methods provide results and data which are surprising, unexpected and contrary thereto. While the utility of this disclosure is illustrated through the use of several compounds and moieties/groups which can be used therewith, it will be understood by those skilled in the art that comparable results are obtainable with various other compounds, moieties and/or groups, as are commensurate with the scope of this disclosure.

Example 1. Synthesis of Pyridopyrimidinone Compounds

The compounds encompassed within the present disclosure can be prepared by the procedure outlined in Scheme I and described in the Examples herein below.

Scheme I

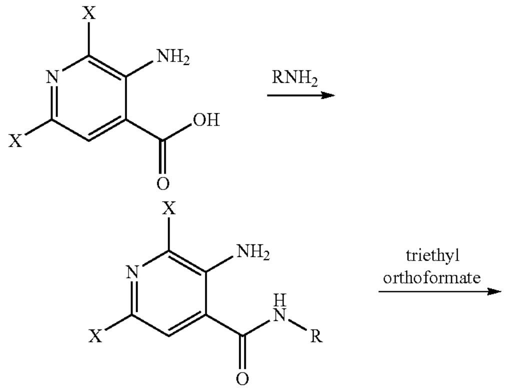

-continued

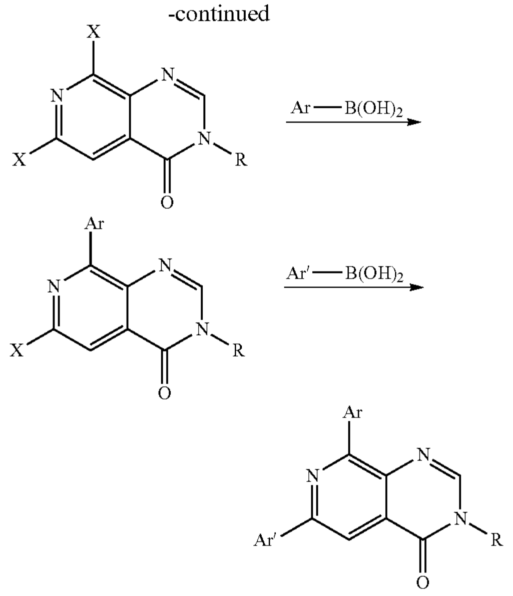

Preparation of tert-butyl N-[(1S)-2-benzyloxy-1-methyl-ethyl]carbamate

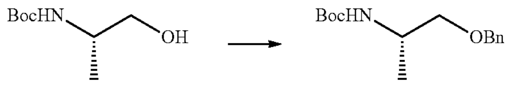 [SMILES: C[C@@H](CO)NC(=O)OC(C)(C)C ; C[C@@H](COCc1ccccc1)NC(=O)OC(C)(C)C]

To a solution of tert-butyl N-[(1S)-2-hydroxy-1-methyl-ethyl]carbamate (8, 10 g, 57 mmol, 1 eq) in THE (300 mL) was added NaH (2.51 g, 62.78 mmol, 60% purity, 1.1 eq) at 0° C. and the mixture was stirred at 0° C. for 30 min. The BnBr (11.71 g, 68.48 mmol, 8.13 mL, 1.2 eq) and tetrabutylammonium iodide (210.80 mg, 570.69 umol, 0.01 eq) was added to the mixture at 0° C. and then the mixture was stirred at 25° C. for 3 hr. The reaction mixture was quenched by addition MeOH (50 mL) at 0° C., and then filtered, and the filtrate was concentrated under reduced pressure to give a residue. The residue was purified by column chromatography (SiO2, Petroleum ether/Ethyl acetate=1/0 to 0/1) to get the title compound (12 g, 45.22 mmol, 79% yield) 1H NMR (400 MHz, CDCl3), δ ppm 1.20 (d, J=6.8 Hz, 3H), 1.45 (s, 9H), 3.35-3.48 (m, 2H), 3.80-3.94 (m, 1H), 4.48 (q, J=12.0, 17.6 Hz, 2H), 4.67-4.80 (m, 1H), 7.27-7.38 (m, 5H).

Preparation of (2S)-1-benzyloxypropan-2-amine trifluoroacetic acid

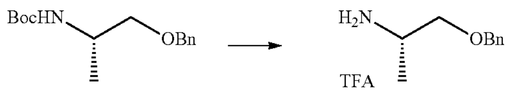 [SMILES: C[C@@H](COCc1ccccc1)NC(=O)OC(C)(C)C ; C[C@H](N)COCc1ccccc1]

To a solution of tert-butyl N-[(1S)-2-benzyloxy-1-methyl-ethyl]carbamate (9, 12 g, 45.22 mmol, 1 eq) in DCM (100 mL) was added dropwise TFA (30.80 g, 270.12 mmol, 20 mL, 5.97 eq). The mixture was stirred at 25° C. for 3 hr. The reaction mixture was concentrated under reduced pressure to get the title compound (10, 10 g, 35.81 mmol, 79.18% yield, TFA) which was used directly.

Preparation of (S)-8-(5-fluoropyridin-3-yl)-3-(1-hydroxypropan-2-yl)-6-(4-(trifluoromethoxy)phenyl) pyrido[3,4-d]pyrimidin-4(3H)-one (1)

Step 1. Preparation of (S)-3-amino-2,6-dichloro-N-(1-hydroxypropan-2-yl)isonicotinamide (Intermediate A1

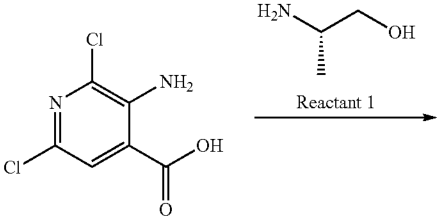

-continued

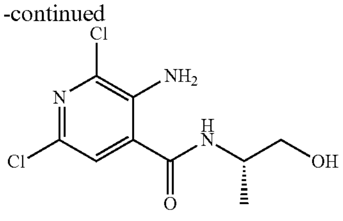

A1

A mixture of 3-amino-2,6-dichloroisonicotinic acid (2.0 g, 9.66 mmol) and (S)-2-aminopropan-1-ol (Reactant 1, 0.80 g, 10.63 mmol) were dissolved in DMF (32.2 mL) and the reaction mixture was cooled to 0° C. Diisopropylethylamine (3.37 mL, 19.3 mmol) and HATU (4.41 g, 11.59 mmol) were added and the reaction was stirred at 0° C. for 1 hour. The reaction was quenched with water and partitioned between ethyl acetate and water. The organic phase was separated, washed with saturated aqueous ammonium chloride and then with saturated aqueous sodium bicarbonate, dried over anhydrous magnesium sulfate, filtered and evaporated. The residue was purified by silica gel chromatography with ethyl acetate/hexane to afford the title compound (1.82 g, 6.89 mmol, 71% yield). $^1$H NMR ($CH_3OH$-d4, 400 MHz) δ 1.21 (3H, d, J=6.8 Hz), 3.58-3.56 (2H, m), 4.17-4.12 (1H, m), 7.49 (1H, s); MS (m/z): 265.1 $[M+H]^+$.

Table 2 lists intermediates that were made via a procedure similar to that described in Step 1 above.

TABLE 2

| Intermediate ID | Structure and name | $^1$H-NMR | MS (m/z) [M + H]+; Purity (%) |
| --- | --- | --- | --- |
| A2 | 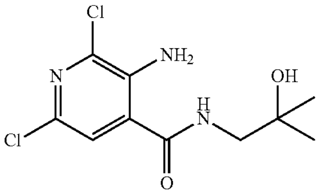 3-amino-2,6-dichloro-N-(2-hydroxy-2-methylpropyl)isonicotinamide | ($CH3OH-d_4$, 400 MHz): δ 1.22 (6H, s), 3.36 (2H, t, J = 6.1 Hz), 7.51 (1H, s), 7.67 (2H, s). | 278.1; NA |
| A3 | 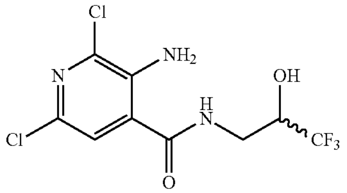 3-amino-2,6-dichloro-N-(3,3,3-trifluoro-2-hydroxypropyl)-isonicotinamide | N/A | 318.0; NA |

TABLE 2-continued

| Intermediate ID | Structure and name | $^1$H-NMR | MS (m/z) [M + H]+; Purity (%) |
|---|---|---|---|
| A4 | 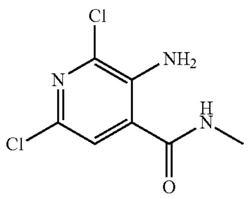 3-amino-2,6-dichloro-N-(3,3,3-trifluoro-2-hydroxypropyl)-isonicotinamide | N/A | 220.0; NA |
| A5 | 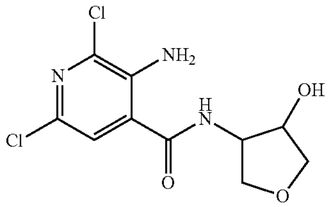 3-amino-2,6-dichloro-N-(4-hydroxytetrahydrofuran-3-yl)isonicotinamide, trans racemic mixture | (DMSO-$d_6$, 400 MHz): δ 0.97 (3H, s), 1.27 (3H, s), 1.48 (3H, d, J = 7.2 Hz), 3.95 (3H, s), 4.97 (1H, m), 5.07 (1H, s), 7.57 (2H, d, J = 8.4 Hz), 8.31-8.28 (3H, m), 8.48 (1H, s), 8.56 (1H, s), 8.82 (1H, s). | 424.1; 99 |
| A6 | 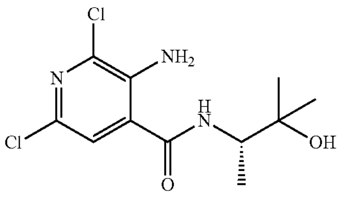 (S)-3-amino-2,6-dichloro-N-(3-hydroxy-3-methylbutan-2-yl)isonicotinamide | ($CHCl_3$-d, 400 MHz): δ 1.25 (3H, d, J = 6.7 Hz), 1.30 (6H, s), 1.78 (1H, s), 4.08 (1H, dd, J = 15.4, 7.7 Hz), 5.93 (2H, br s), 6.50 (1H, br s), 7.17 (1H, s). | 292.0; >90 |
| A7 | 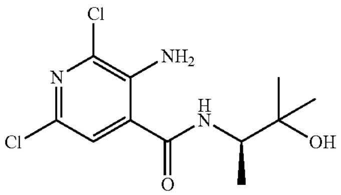 (R)-3-amino-2,6-dichloro-N-(3-hydroxy-3-methylbutan-2-yl)isonicotinamide | ($CHCl_3$-d, 400 MHz): δ 1.25 (3H, d, J = 6.6 Hz), 1.29 (6H, s), 4.14-4.05 (1H, m), 5.93 (2H, br s), 6.55 (1H, br s), 7.18 (1H, s), 7.26 (1H, s). | 292.0; >90 |
| A8 | 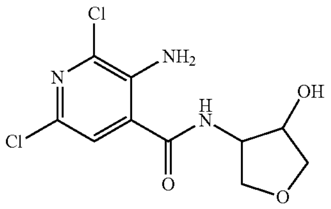 3-amino-2,6-dichloro-N-(4-hydroxytetrahydrofuran-3-yl)isonicotinamide, cis racemic mixture | (DMSO-$d_6$, 400 MHz): δ 3.88 (2H, m), 4.23 (1H, m), 4.32 (1H, m), 5.28 (1H, d, J = 4.4 Hz), 6.53 (2H, s), 7.66 (1H, s), 8.51 (1H, d, J = 7.4 Hz). | 292.0; >90 |

TABLE 2-continued

| Intermediate ID | Structure and name | $^1$H-NMR | MS (m/z) [M + H]+; Purity (%) |
|---|---|---|---|
| A9 | 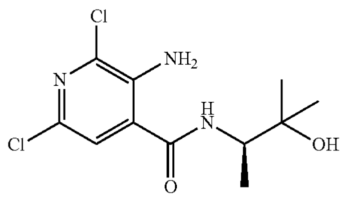 (R)-3-amino-2,6-dichloro-N-(3-hydroxy-3-methylbutan-2-yl)isonicotinamide | ($CHCl_3$-d, 400 MHz): δ 1.25 (3H, d, J = 6.6 Hz), 1.29 (6H, s), 4.14-4.05 (1H, m), 5.93 (2H, br s), 6.55 (1H, br s), 7.18 (1H, s), 7.26 (1H, s). | 292.0; >90 |
| A10 | 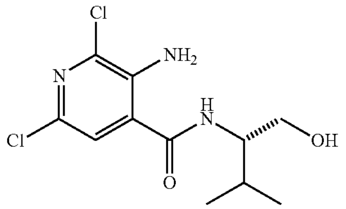 (S)-3-amino-2,6-dichloro-N-(1-hydroxy-3-methylbutan-2-yl)isonicotinamide | ($CH_3OH$-$d_4$, 400 MHz): δ 0.94 (6H, dd, J = 14.4, 6.8 Hz), 1.92-1.87 (1H, m), 3.66 (2H, d, J = 4.7 Hz), 3.80 (2H, br s), 7.37 (1H, s), 7.62 (1H, br s). | 292.0; >90 |
| A11 | 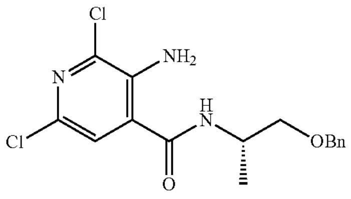 3-amino-N-[(1S)-2-benzyloxy-1-methyl-ethyl]-2,6-dichloro-pyridine-4-carboxamide | N/A | 354.0; NA |
| A12 | 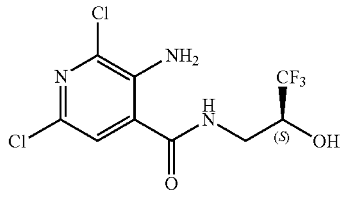 (S)-3-amion-2,6-dichloro-N-(3,3,3-trifluoro-2-hydroxypropyl)isonicotinamide | ($CH_3OH$-$d_4$, 300 MHz): $\delta_H$ 3.44 (1H, dd, J = 14.1, 8.7 Hz), 3.74 (1H, dd, J = 13.8, 4.0 Hz), 4.23 (1H, s), 7.48 (1H, s). | 317.9; NA |
| A13 | 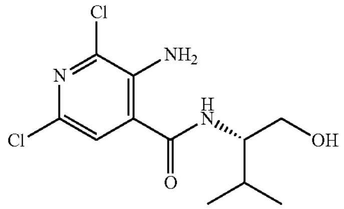 (S)-3-amino-2,6-dichloro-N-(1-hydroxy-3-methylbutan-2-yl)isonicotinamide | NA | 292.0; 90.0 |

TABLE 2-continued

| Intermediate ID | Structure and name | $^1$H-NMR | MS (m/z) [M + H]+; Purity (%) |
| --- | --- | --- | --- |
| A14 | 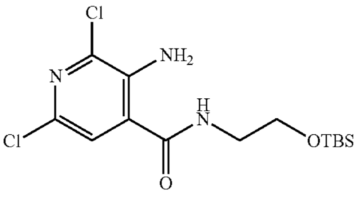 3-amino-N-(2-((tert-butyldimethylsilyl) oxy)ethyl)-2,6-dichloroisonicotinamide | NA | 364.1; NA |
| A15 | 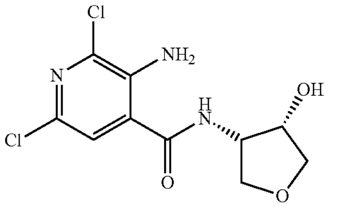 | NA | 293.10; NA |

NA = Not available

Preparation of 3-amino-2,6-dichloro-N-((3R,4S)-4-hydroxytetrahydrofuran-3-yl)isonicotinamide (A16)

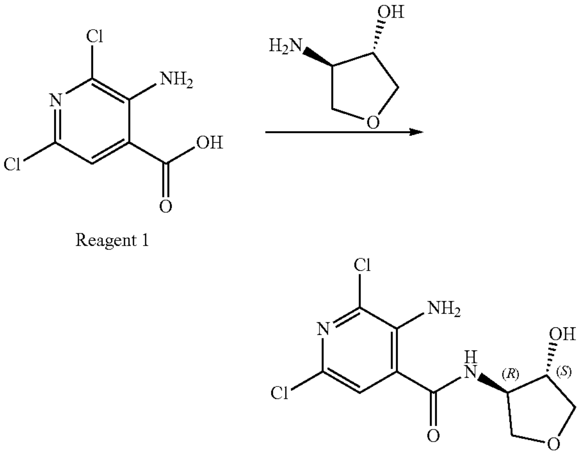

Reagent 1

A16

Propylphosphonic anhydride (T3P, 64.6 g, 101 mmol, 60.3 mL, 50% purity, 1.05 eq) was added in one portion to a solution of 3-amino-2,6-dichloroisonicotinic acid (Reagent 1, 20 g, 96.6 mmol, 1 eq), (3S,4R)-4-aminotetrahydrofuran-3-ol (10.5 g, 101 mmol, 1.05 eq) and triethylamine (29.3 g, 290 mmol, 40.3 mL, 3 eq) in EtOAc (150 mL). The resulting solution was stirred at 25° C. for 1 h. The reaction was poured into water (100 mL). The organic phase was collected and the aqueous phase was extracted by EtOAc (30 mL×2). The combined organic phase was washed with brine (100 mL) and concentrated under vacuum to afford the title compound 3-amino-2,6-dichloro-N-((3R,4S)-4-hydroxytetrahydrofuran-3-yl)isonicotinamide (A16, 25 g, 85.6 mmol, 88.6% yield) as off-white solid. The crude product was used for the next step without purification. $^1$H-NMR (400 MHz, $CD_3OD$): $\delta_H$ ppm 7.49 (s, 1H), 4.28-4.34 (m, 2H), 4.10-4.17 (m, 1H), 4.02 (dd, J=10.0 Hz, J=4.4 Hz, 1H), 3.73-3.78 (m, 1H), 3.65-3.70 (m, 1H); MS (m/z): 290.0 $[M+H]^+$.

Step 2. Preparation of (S)-6,8-dichloro-3-(1-hydroxypropan-2-yl)pyrido[3,4-d]pyrimidin-4(3H)-one (Intermediate B1)

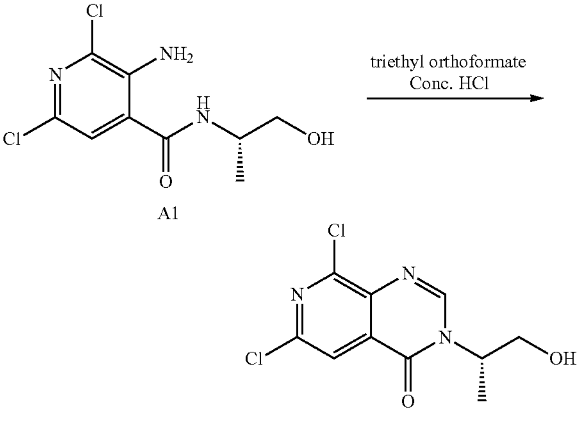

A1

B1

To (S)-3-amino-2,6-dichloro-N-(1-hydroxypropan-2-yl) isonicotinamide (A1, 2.54 g, 9.66 mmol) in a flask was added triethyl orthoformate (20 mL). Concentrated hydrochloric acid (0.8 mL, 9.7 mmol) was added dropwise slowly at room temperature and the resulting mixture was stirred for 2 hours. The mixture was concentrated and the solid was collected by vacuum filtration, washed with water and dried under high vacuum to afford the title compound (B1, 1.82 g, 6.64 mmol, 69% yield). $^1$H NMR (CH3OH-d4, 400 MHz) δ 1.51 (3H, d, J=7.1 Hz), 3.80 (1H, dd, J=11.9, 4.2 Hz), 3.92

(1H, dd, J=11.9, 6.9 Hz), 4.93-4.88 (1H, m), 8.05 (1H, s), 8.45 (1H, s); MS (m/z): 274.0[M+H]$^+$.

Preparation of 3-[(1S)-2-benzyloxy-1-methyl-ethyl]-6,8-dichloro-pyrido[3,4-d]pyrimidin-4-one (Intermediate Bit)

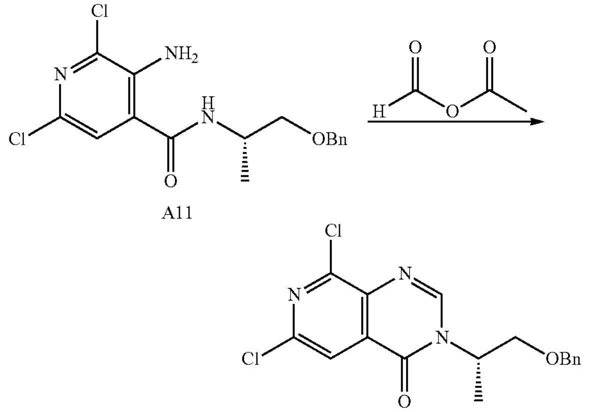

A11

B11

Formic acid (18.94 g, 411.41 mmol, 15.52 mL, 1.5 eq) was added dropwise into acetyl acetate (28 g, 274.27 mmol, 25.69 mL, 1 eq) at 0° C. and stirred at 60° C. for 2 hr under $N_2$ atmosphere. The solution was obtained as a colorless liquid (41 mL, 6.65 M) and used into the next step without further purification. To a solution of 3-amino-N-[(1S)-2-benzyloxy-1-methyl-ethyl]-2,6-dichloro-pyridine-4-carboxamide (A11, 4.5 g, 12.70 mmol, 1 eq) in THE (50 mL) was added formyl acetate solution (6.65 M, 41 mL, 21.47 eq,) at 25° C. and stirred at 60° C. for 30 min. Then the mixture was stirred at 100° C. for 9.5 hr. LCMS showed desired compound was detected. The reaction mixture was concentrated under reduced pressure to give a residue. The residue was diluted with EtOAc (50 mL) and washed with sat. $NaHCO_3$ (200 mL), water (50 mL) and brine (50 mL) sequentially, dried over $Na_2SO_4$, filtered and the filtrate was concentrated under reduced pressure to give a residue. The residue was purified by column chromatography (SiO2, Petroleum ether/Ethyl acetate=1/0 to 1/1) to get the title compound (B11, 2.4 g, 6.59 mmol, 51.88% yield). $^1$H NMR (400 MHz, CDCl3) δ ppm 1.56 (d, J=7.2 Hz, 3H), 3.65-3.79 (m, 2H), 4.50 (q, J=12.4, 18.8 Hz, 2H), 5.08-5.20 (m, 1H), 7.20-7.31 (m, 5H), 8.02 (s, 1H), 8.41 (s, 1H); MS: M+H$^+$, 364.0.

Table 3 lists intermediates that were made via a procedure similar to that described for the synthesis of Intermediate B1 above.

TABLE 3

| Intermediate ID | Structure and name | $^1$H-NMR | MS (m/z) [M + H]+; Purity (%) |
|---|---|---|---|
| B2 | 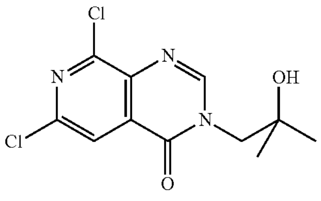 6,8-dichloro-3-(2-hydroxy-2-methylpropyl)pyrido[3,4-d]pyrimidin-4(3H)-one | ($CHCl_3$-d, 400 MHz): δ 1.31 (6H, s), 1.90 (1H, s), 4.08 (2H, s), 8.06 (1H, s), 8.36 (1H, s). | 288.0; NA |
| B3 | 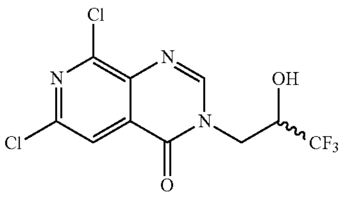 6,8-dichloro-3-(3,3,3-trifluoro-2-hydroxypropyl)pyrido[3,4-d]pyrimidin-4(3H)-one | ($CH_3OH$-$d_4$, 400 MHz): δ 3.97 (1H, dd, J = 13.7, 9.7 Hz), 4.36 (1H, t, J = 8.0 Hz), 4.56 (1H, dd, J = 13.7, 2.9 Hz), 8.08 (1H, s), 8.38 (1H, s). | 328.0; NA |

TABLE 3-continued

| Intermediate ID | Structure and name | $^1$H-NMR | MS (m/z) [M + H]+; Purity (%) |
|---|---|---|---|
| B4 | 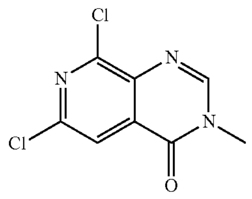 6,8-dichloro-3-methylpyrido[3,4-d]pyrimidin-4(3H)-one | ($CHCl_3$-d, 400 MHz): δ 3.64 (3H, s), 8.07 (1H, s), 8.18 (1H, s). | 23.0.0; >90 |
| B5 | 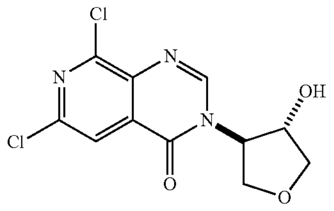 [SMILES: O=c1c2cc(Cl)nc(Cl)c2ncn1[C@@H]1COC[C@H]1O] 6,8-dichloro-3-(4-hydroxytetrahydrofuran-3-yl)pyrido[3,4-d]pyrimidin-4(3H)-one, trans racemic mixture | NA | 302.0; >90 |
| B6 | 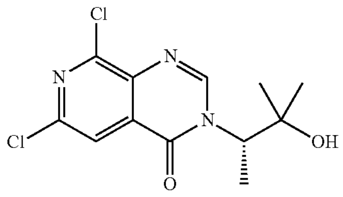 (S)-6,8-dichloro-3-(3-hydroxy-3-methylbutan-2-yl)pyrido[3,4-d]pyrimidin-4(3H)-one | ($CH_3OH$-$d_4$, 400 MHz): δ 1.05 (3H, s), 1.35 (3H, s), 1.53 (3H, d, J = 7.2 Hz), 5.03 (1H, br s), 8.05 (1H, s), 8.62 (1H, s). | 302.0; >90 |
| B7 | 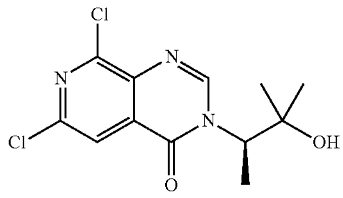 (R)-6,8-dichloro-3-(3-hydroxy-3-methylbutan-2-yl)pyrido[3,4-d]pyrimidin-4(3H)-one | ($CHCl_3$-d, 400 MHz): δ 1.15 (3H, s), 1.41 (3H, s), 1.55 (3H, d, J = 7.2 Hz), 5.03 (1H, br s), 8.06 (1H, s), 8.59 (1H, s). | 302.0; >90 |
| B8 | 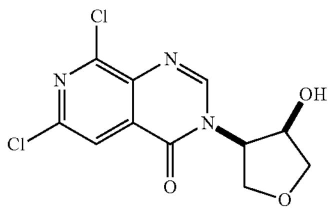 6,8-dichloro-3-(4-hydroxytetrahydrofuran-3-yl)pyrido[3,4-d]pyrimidin-4(3H)-one, cis racemic mixture | NA | 302.0; >90 |

TABLE 3-continued

| Intermediate ID | Structure and name | $^{1}$H-NMR | MS (m/z) [M + H]+; Purity (%) |
|---|---|---|---|
| B9 | 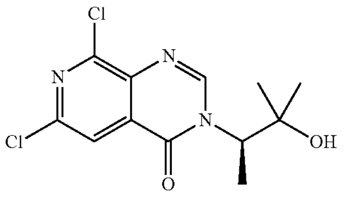 (R)-6,8-dichloro-3-(3-hydroxy-3-methylbutan-2-yl)pyrido[3,4-d]pyrimidin-4(3H)-one | ($CHCl_3$-d, 400 MHz): δ 1.15 (3H, s), 1.41 (3H, s), 1.55 (3H, d, J = 7.2 Hz), 5.03 (1H, br s), 8.06 (1H, s), 8.59 (1H, s). | 302.0; >90 |
| B10 | 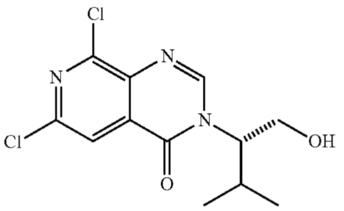 (S)-6,8-dichloro-3-(1-hydroxy-3-methylbutan-2-yl)pyrido[3,4-d]pyrimidin-4(3H)-one | ($CHCl_3$-d, 400 MHz): δ 0.84 (3H, d, J = 6.7 Hz), 1.16 (3H, d, J = 6.5 Hz), 2.45-2.36 (1H, m), 2.67 (1H, br s), 3.91 (1H, dd, J = 11.8, 2.8 Hz), 4.14 (1H, dd, J = 11.9, 5.5 Hz), 4.50 (1H, br s), 8.03 (1H, s), 8.40 (1H, s). | 302.0; >90 |
| B11 | 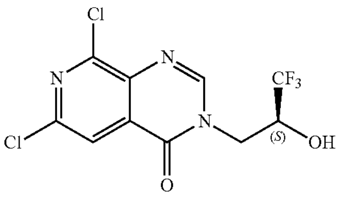 (S)-6,8-dichloro-3-(3,3,3-trifluoro-2-hydroxypropyl)pyrido[3,4-d]pyrimidin-4(3H)-one | $^{1}$H NMR ($CHCl_3$-d, 300 MHz): $\delta_H$ 3.96 (1H, dd, J = 13.7, 9.6 Hz), 4.36 (1H, t, J = 7.6 Hz), 4.56 (1H, dd, J = 13.4, 3.0 Hz), 5.48 (1H, s), 8.07 (1H, s), 8.37 (1H, s). | 327.8; NA |
| B12* | 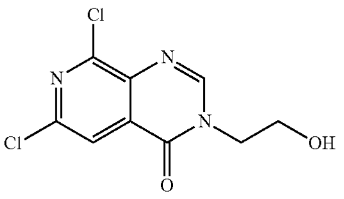 6,8-dichloro-3-(2-hydroxyethyl)pyrido[3,4-d]pyrimidin-4(3H)-one | NA | 260.0; 90.0 |
| B13 | 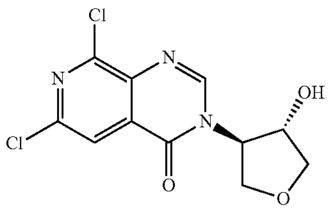 | (DMSO-$d_6$, 400 MHz): δ 3.60 (1H, dd, J = 9.6, 3.2 Hz), 4.06-4.03 (1H, m), 4.18-4.09 (2H, m), 4.52 (1H, s), 4.90 (1H, s), 5.70 (1H, d, J = 4.3 Hz), 8.07 (1H, s), 8.40 (1H, s). | 302.0; NA |

TABLE 3-continued

| Intermediate ID | Structure and name | $^1$H-NMR | MS (m/z) [M + H]+; Purity (%) |
|---|---|---|---|
| B14 | 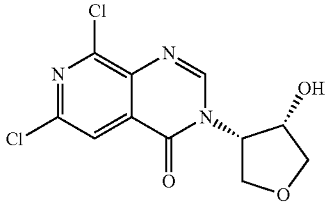 [SMILES: O=c1c2cc(Cl)nc(Cl)c2ncn1[C@H]1COC[C@H]1O] | (DMSO-$d_6$, 400 MHz): $\delta_H$ 3.76 (2H, d, J = 9.8 Hz), 3.98-3.88 (3H, m), 4.15 (2H, dd, J = 10.0, 5.7 Hz), 4.47-4.44 (2H, m), 5.32 (2H, q, J = 6.6 Hz), 8.06 (1H, s), 8.37 (1H, s). | 302.0; NA |

NA = Not available;

*The TBS group is cleaved during the cyclization conditions.

Preparation of (S)-6,8-dichloro-3-(1-hydroxy-3-methylbutan-2-yl)pyrido[3,4-d]pyrimidin-4(3H)-one (B10)

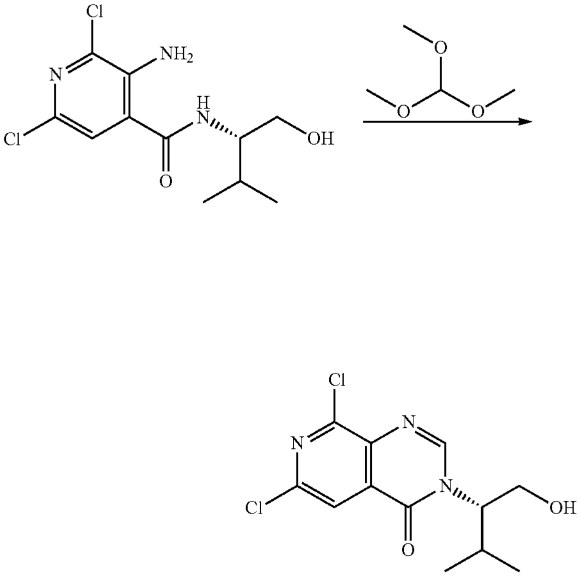

B10

4-Methylbenzenesulfonic acid (141.46 mg, 821.46 mmol) was added to a mixture of (S)-3-amino-2,6-dichloro-N-(1-hydroxy-3-methylbutan-2-yl)isonicotinamide (1.2 g, 4.11 mmol) in trimethyl orthoformate (10 mL) and was degassed and purged with nitrogen for 3 times. The mixture was stirred at 120° C. for 8 hours under nitrogen atmosphere. TLC indicated the starting reactant was remained and two new spots formed. The solvent is evaporated and the residue is taken up in ethyl acetate (20 mL), washed three times with brine (10 mL), dried over anhydrous sodium sulfate, filtered and evaporated. The residue was purified by prep-HPLC to afford the title compound (S)-6,8-dichloro-3-(1-hydroxy-3-methylbutan-2-yl)pyrido[3,4-d]pyrimidin-4(3H)-one (600 mg, 1.99 mmol, 48% yield). $^1$H-NMR (400 MHz, DMSO-$d_6$): $\delta_H$ ppm 8.60 (s, 1H), 8.05 (s, 1H), 5.02 (d, J=3.2 Hz, 1H), 4.19-4.56 (m, 1H), 3.85-3.97 (m, 1H), 3.74 (q, J=11.8 Hz, J=3.4 Hz, 1H), 2.23-2.38 (m, 1H), 1.04 (d, J=6.6 Hz, 3H), 0.75 (d, J=6.6 Hz, 3H); MS (m/z): 302.0 $[M+H]^+$; 90% purity.

Step 3. Preparation of (S)-6-chloro-8-(5-fluoropyridin-3-yl)-3-(1-2-yl)pyrido[3,4-d]pyrimidin-4(3H)-one (Intermediate C1)

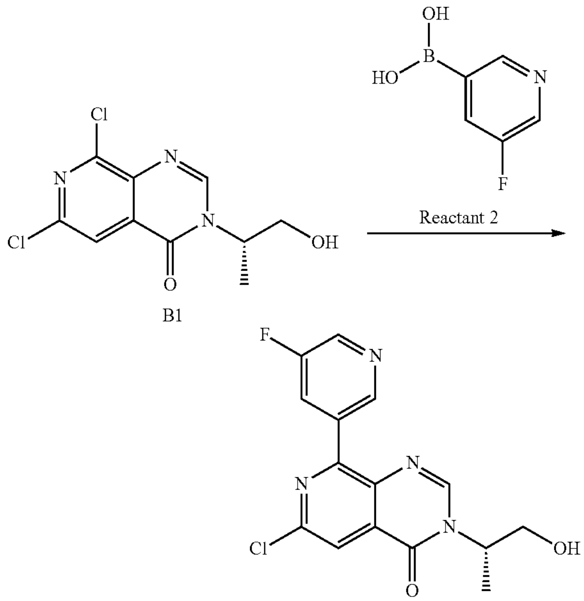

C1

A mixture of(S)-6,8-dichloro-3-(1-hydroxypropan-2-yl)pyrido[3,4-d]pyrimidin-4(3H)-one (B1, 0.10 g, 0.37 mmol), (5-fluoropyridin-3-yl)boronic acid (Reactant 2, 0.057 g, 0.401 mmol), sodium carbonate (0.16 g, 1.46 mmol) and tetrakis(triphenylphosphine)palladium (0.042 g, 0.036 mmol) in a sealed tube was purged with argon. Toluene (3.0 mL) and ethanol (1.5 mL) were added and the resulting mixture was stirred at 75° C. for 15 hours. The mixture was cooled to room temperature, filtered through Celite and the Celite pad was washed with ethyl acetate and filtrate was concentrated to dryness. Purification of the residue by silica gel chromatography with methanol/dichloromethane afforded the title compound (C1, 0.078 g, 0.19 mmol, 53% yield). $^1$H NMR (DMSO-d6, 300 MHz): δ 1.41 (3H, d, J=7.0 Hz), 3.69-3.62 (1H, m), 3.82-3.74 (1H, m), 4.89-4.83 (1H, m), 5.06 (1H, t, J=5.6 Hz), 8.12 (1H, s), 8.38 (1H, ddd, J=10.2, 2.8, 1.7 Hz), 8.60 (1H, s), 8.73 (1H, d, J=2.8 Hz), 9.14 (1H, s); MS (m/z): 335.1$[M+H]^+$.

Table 4 lists intermediates that were made via a procedure similar to that described in Step 3 above.

TABLE 4

| Intermediate name | Structure and name | $^1$H-NMR chemical shifts | MS (m/z) $[M + H]^+$; Purity (%) |
|---|---|---|---|
| C2 | 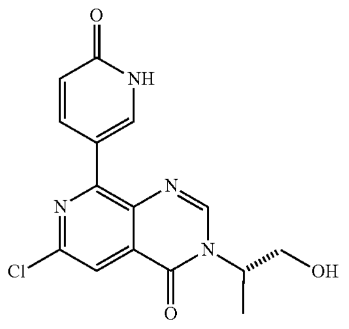 S)-6-chloro-3-(1-hydroxypropan-2-yl)-8-(6-oxo-1,6-dihydropyridin-3-yl)pyrido[3,4-d]pyrimidin-4(3H)-one | (DMSO-$d_6$, 400 MHz): δ 1.41 (3H, d, J = 7.0 Hz), 3.68-3.62 (1H, m), 3.81-3.75 (1H, m), 4.87-4.82 (1H, m), 5.06 (1H, t, J = 5.7 Hz), 6.48 (1H, d, J = 9.7 Hz), 7.87 (1H, s), 8.32 (1H, dd, J = 9.7, 2.7 Hz), 8.57 (1H, s), 8.78 (1H, s), 12.08 (1H, s). | 333.0; NA |
| C3 | 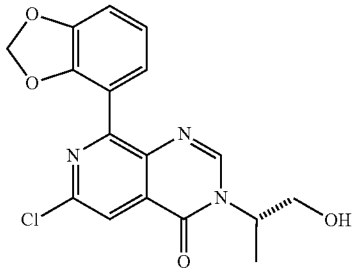 (S)-8-(benzo[d][1,3]dioxol-4-yl)-6-chloro-3-(1-hydroxypropan-2-yl)pyrido[3,4-d]pyrimidin-4(3H)-one | (DMSO-$d_6$, 400 MHz): δ 1.39 (3H, d, J = 7.1 Hz), 3.67-3.61 (1H, m), 3.77-3.72 (1H, m), 4.85-4.80 (1H, m), 5.05 (1H, t, J = 5.7 Hz), 6.03 (2H, s), 6.99-6.93 (1H, m), 7.07 (2H, t, J = 8.1 Hz), 8.06 (1H, s), 8.47 (1H, s). | 360.0; NA |
| C4 | 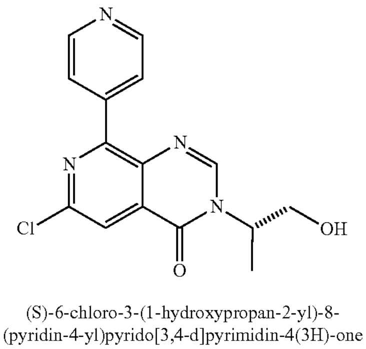 [SMILES: C[C@@H](CO)n1cnc2c(-c3ccncc3)nc(Cl)cc2c1=O] (S)-6-chloro-3-(1-hydroxypropan-2-yl)-8-(pyridin-4-yl)pyrido[3,4-d]pyrimidin-4(3H)-one | (DMSO-$d_6$, 400 MHz): δ 1.41 (3H, d, J = 7.0 Hz), 3.68-3.62 (1H, m), 3.80-3.74 (1H, m), 4.87-4.82 (1H, m), 5.06 (1H, t, J = 5.7 Hz), 8.04 (2H, dd, J = 4.8, 1.5 Hz), 8.13 (1H, s), 8.57 (1H, s), 8.76-8.74 (2H, m). | 316.9; NA |

TABLE 4-continued

| Intermediate name | Structure and name | $^1$H-NMR chemical shifts | MS (m/z) [M + H]$^+$; Purity (%) |
|---|---|---|---|
| C5 | 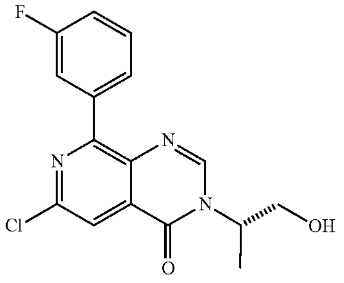 (S)-6-chloro-8-(3-fluorophenyl)-3-(1-hydroxypropan-2-yl)pyrido[3,4-d]pyrimidin-4(3H)-one | ($CH_3OH-d_4$, 400 MHz): δ 1.52 (3H, d, J = 7.1 Hz), 3.82 (1H, dd, J = 11.9, 4.3 Hz), 3.93 (1H, dd, J = 11.9, 7.0 Hz), 4.96-4.91 (1H, m), 7.22 (1H, dd, J = 10.1, 7.8 Hz), 7.52-7.47 (1H, m), 7.98-7.92 (2H, m), 8.07 (1H, s), 8.40 (1H, s). | 334.1; NA |
| C6 | 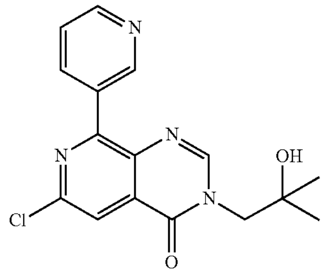 6-chloro-3-(2-hydroxy-2-methylpropyl)-8-(pyridin-3-yl)pyrido[3,4-d]pyrimidin-4(3H)-one | ($CH_3OH-d_4$, 400 MHz): δ 1.25 (6H, s), 4.10 (2H, s), 7.59 (1H, t, J = 6.5 Hz), 8.13 (1H, s), 8.34 (1H, s), 8.62 (2H, d, J = 7.3 Hz), 9.32 (1H, s). | 331.1; NA |
| C7 | 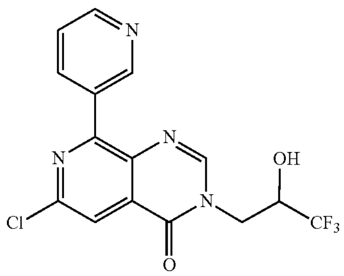 6-chloro-8-(pyridin-3-yl)-3-(3,3,3-trifluoro-2-hydroxypropyl)pyrido[3,4-d]pyrimidin-4(3H)-one | ($CHCl_3$-d + 10% $CH_3OH-d_4$, 400 MHz): δ 3.75 (1H, dd, J = 13.7, 9.6 Hz), 4.29 (1H, s), 4.60 (1H, dd, J = 13.7, 2.9 Hz), 7.44 (1H, dd, J = 8.0, 4.9 Hz), 8.08 (1H, s), 8.14 (1H, s), 8.44 (1H, d, J = 8.0 Hz), 8.59 (1H, d, J = 4.9 Hz), 9.27 (1H, s). | 371.0; NA |
| C8 | 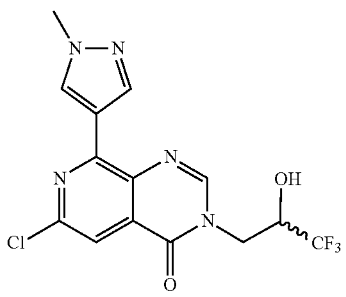 6-chloro-8-(1-methyl-1H-pyrazol-4-yl)-3-(3,3,3-trifluoro-2-hydroxypropyl)pyrido[3,4-d]pyrimidin-4(3H)-one | ($CHCl_3$-d + 10% $CH_3OH-d_4$, 400 MHz): δ 3.72 (1H, dd, J = 13.7, 9.5 Hz), 3.91 (3H, s), 4.28 (1H, t, J = 7.9 Hz), 4.57 (1H, dd, J = 13.7, 3.0 Hz), 7.78 (1H, s), 8.11 (1H, s), 8.40 (1H, s), 8.48 (1H, s). | 374.1; NA |

TABLE 4-continued

| Intermediate name | Structure and name | $^1$H-NMR chemical shifts | MS (m/z) [M + H]$^+$; Purity (%) |
|---|---|---|---|
| C9 | 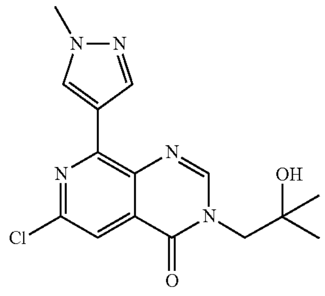 6-chloro-3-(2-hydroxy-2-methylpropyl)-8-(1-methyl-1H-pyrazol-4-yl)pyrido[3,4-d]pyrimidin-4(3H)-one | ($CH_3OH-d_4$, 400 MHz): δ 1.24 (6H, s), 3.98 (3H, s), 4.09 (2H, s), 7.83 (1H, s), 8.36 (1H, s), 8.43 (1H, s), 8.73 (1H, s). | 334.1; NA |
| C10 | 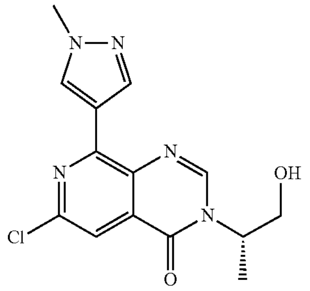 (S)-6-chloro-3-(1-hydroxypropan-2-yl)-8-(1-methyl-1H-pyrazol-4-yl)pyrido[3,4-d]pyrimidin-4(3H)-one | ($CH_3OH-d_4$, 400 MHz): δH 1.53-1.50 (3H, m), 3.82 (1H, dd, J = 11.9, 4.3 Hz), 3.88 (3H, s), 3.94-3.91 (1H, m), 4.96-4.91 (1H, m), 7.71 (1H, s), 7.79 (1H, s), 8.43 (1H, s), 8.69 (1H, s). | 320.1; NA |
| C11 | 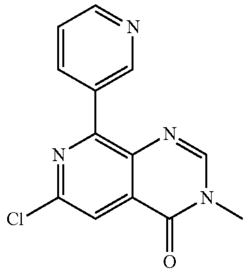 6-chloro-3-methyl-8-(pyridin-3-yl)pyrido[3,4-d]pyrimidin-4(3H)-one | Not available | 273.0; >90 |
| C12 | 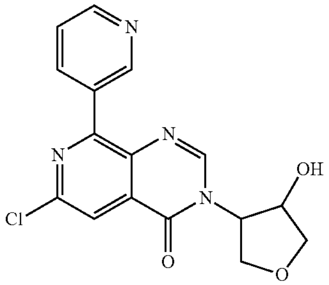 6-chloro-3-((3R,4S)-4-hydroxytetrahydrofuran-3-yl)-8-(pyridin-3-yl)pyrido[3,4-d]pyrimidin-4(3H)-one, trans racemic mixture | (DMSO-$d_6$, 400 MHz): δ 3.59 (1H, dd, J = 9.6, 3.3 Hz), 4.03 (1H, dd, J = 10.1, 4.0 Hz), 4.18-4.09 (2H, m), 4.53 (1H, s), 4.93 (1H, s), 5.68 (1H, d, J = 4.4 Hz), 7.56 (1H, dd, J = 8.0, 4.9 Hz), 8.08 (1H, s), 8.35 (1H, d, J = 0.6 Hz), 8.40 (1H, dt, J = 8.0, 2.0 Hz), 8.68 (1H, dd, J = 4.8, 1.7 Hz), 9.20 (1H, d, J = 2.2 Hz). | 345.0; >90 |

TABLE 4-continued

| Intermediate name | Structure and name | $^1$H-NMR chemical shifts | MS (m/z) [M + H]$^+$; Purity (%) |
|---|---|---|---|
| C13 | 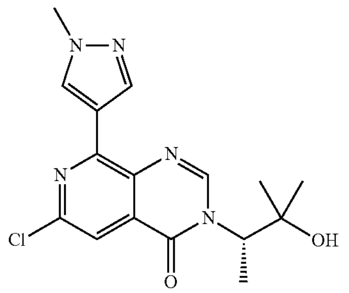 (S)-6-chloro-3-(3-hydroxy-3-methylbutan-2-yl)-8-(1-methyl-1H-pyrazol-4-yl)pyrido[3,4-d]pyrimidin-4(3H)-one | ($CHCl_3$-d, 400 MHz): δ 1.04 (3H, s), 1.31 (3H, s), 1.48 (3H, d, J = 7.2 Hz), 3.33 (1H, s), 3.90 (3H, s), 4.96 (1H, br s), 7.80 (1H, s), 8.41 (1H, s), 8.47 (1H, s), 8.50 (1H, s). | 348.1; >90 |
| C14 | 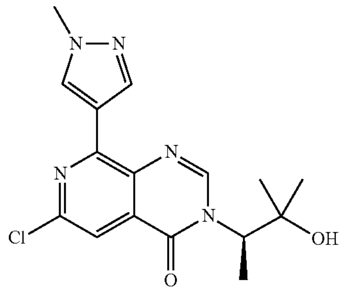 (R)-6-chloro-3-(3-hydroxy-3-methylbutan-2-yl)-8-(1-methyl-1H-pyrazol-4-yl)pyrido[3,4-d]pyrimidin-4(3H)-one | NA | 348.1; >90 |
| C15 | 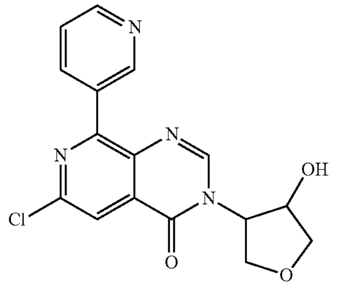 6-chloro-3-(4-hydroxytetrahydrofuran-3-yl)-8-(pyridin-3-yl)pyrido[3,4-d]pyrimidin-4(3H)-one, cis racemic | (DMSO-$d_6$, 400 MHz): δ 3.75 (1H, dd, J = 9.7, 2.3 Hz), 3.98 (2H, m), 4.15 (1H, dd, J = 9.8, 5.9 Hz), 4.48 (1H, m), 5.33 (1H, q, J = 6.7 Hz), 5.44 (1H, d, J = 4.3 Hz), 7.56 (1H, dd, J = 8.0, 4.8 Hz), 8.08 (1H, s), 8.34 (1H, s), 8.42 (1H, dt, J = 8.0, 2.0 Hz), 8.68 (1H, dd, J = 4.8, 1.7 Hz), 9.21 (1H, s). | 345.0 >90 |
| C16 | 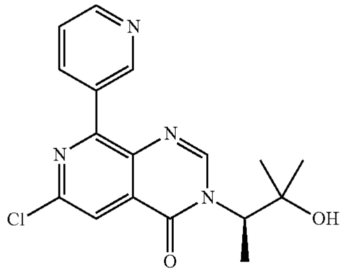 (R)-6-chloro-3-(3-hydroxy-3-methylbutan-2-yl)-8-(pyridin-3-yl)pyrido[3,4-d]pyrimidin-4(3H)-one | NA | 345.1; >90 |

TABLE 4-continued

| Intermediate name | Structure and name | $^1$H-NMR chemical shifts | MS (m/z) [M + H]$^+$; Purity (%) |
|---|---|---|---|
| C17 | 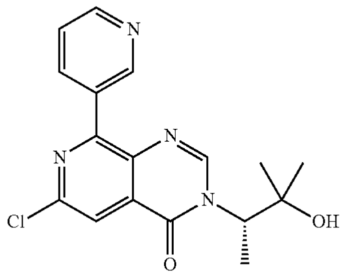 (S)-6-chloro-3-(3-hydroxy-3-methylbutan-2-yl)-8-(pyridin-3-yl)pyrido[3,4-d]pyrimidin-4(3H)-one | ($CHCl_3$-d, 400 MHz): δ 1.06 (3H, s), 1.32 (3H, s), 1.47 (3H, d, J = 7.2 Hz), 4.99 (1H, br s), 5.25 (1H, s), 7.43 (1H, dd, J = 8.0, 4.9 Hz), 8.08 (1H, s), 8.44 (1H, d, J = 8.1 Hz), 8.49-8.48 (1H, m), 8.57 (1H, dd, J = 4.9, 1.7 Hz), 9.27 (1H, d, J = 2.2 Hz). | 345.1; >90 |
| C18 | 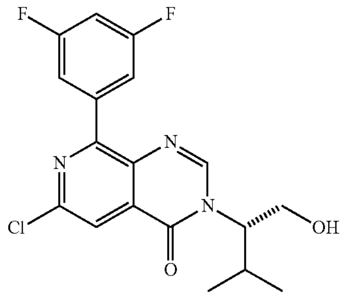 (S)-6-chloro-8-(3,5-difluorophenyl)-3-(1-hydroxy-3-methylbutan-2-yl)pyrido[3,4-d]pyrimidin-4(3H)-one | NA | 380.0; >90 |
| C19 | 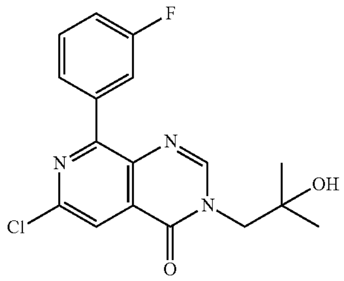 6-chloro-8-(3-fluorophenyl)-3-(2-hydroxy-2-methylpropyl)pyrido[3,4-d]pyrimidin-4(3H)-one | (400 MHz, DMSO-d6) δ ppm 1.14 (s, 6H), 4.01 (s, 2H), 4.86 (s, 1H), 7.37 (t, d = 6.8 Hz, 1H), 7.55-7.61 (m, 1H), 7.90-7.95 (m, 2H), 8.07 (s, 1H), 8.38 (s, 1H) | NA |

TABLE 4-continued

| Intermediate name | Structure and name | $^1$H-NMR chemical shifts | MS (m/z) [M + H]$^+$; Purity (%) |
|---|---|---|---|
| C20 | 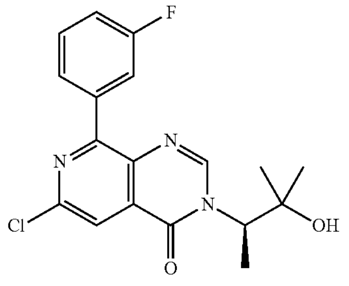 (R)-6-chloro-8-(3-fluorophenyl)-3-(3-hydroxy-3-methylbutan-2-yl)pyrido[3,4-d]pyrimidin-4(3H)-one | (400 MHz, DMSO-d6) δ ppm 0.97 (s, 3H), 1.25 (s, 3H), 1.46 (d, J = 7.2 Hz, 3H), 4.92 (d, J = 7.2 Hz, 1H), 5.04 (s, 1H), 7.37 (t, J = 7.67 Hz, 1H), 7.54-7.60 (m, 1H), 7.95 (d, J = 7.6 Hz, 2H), 8.06 (s, 1H), 8.54 (s, 1H) | NA |
| C21 | 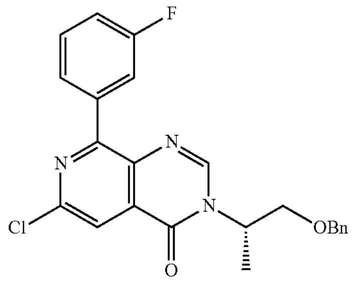 3-[(1S)-2-benzyloxy-1-methyl-ethyl]-6-chloro-8-(3-fluorophenyl)pyrido[3,4-d]pyrimidin-4-one | (400 MHz, $CDCl_3$) δ ppm 1.45-1.58 (m, 3H), 3.65-3.76 (m, 2H), 4.48 (q, J = 12.0, 20.0 Hz, 2H), 5.05-5.17 (m, 1H), 7.13-7.28 (m, 6H), 7.40-7.50 (m, 1H), 7.86-7.95 (m, 2H), 8.06 (s, 1H), 8.28 (s, 1H) | 424.0; NA |
| C22 | 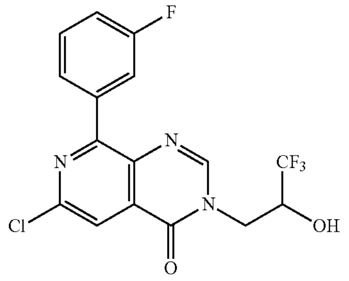 6-chloro-8-(3-fluorophenyl)-3-(3,3,3-trifluoro-2-hydroxypropyl)pyrido[3,4-d]pyrimidin-4(3H)-one | NA | 388.0; 90 |
| C23 | 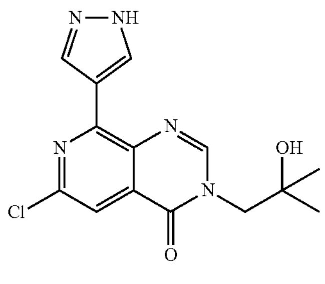 6-chloro-3-(2-hydroxy-2-methylpropyl)-8-(1H-pyrazol-4-yl)pyrido[3,4-d]pyrimidin-4(3H)-one | (DMSO-$d_6$, 400 MHz): $\delta_H$ 1.03 (6H, s), 3.99 (2H, s), 4.87 (1H, s), 7.77 (1H, s), 8.38 (2H, d, J = 11.2 Hz), 8.75 (1H, s), 13.27 (1H, s). | 320.0; NA |

TABLE 4-continued

| Intermediate name | Structure and name | $^1$H-NMR chemical shifts | MS (m/z) [M + H]$^+$; Purity (%) |
|---|---|---|---|
| C24 | 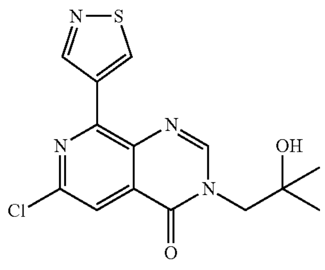 6-chloro-3-(2-hydroxy-2-methylpropyl)-8-(isothiazol-4-yl)pyrido[3,4-d]pyrimidin-4(3H)-one | (DMSO-d$_6$, 300 MHz): $\delta_H$ 1.15 (6H, s), 4.03 (2H, s), 4.89 (1H, s), 8.01 (1H, s), 8.45 (1H, s), 9.40 (1H, s), 10.06 (1H, s). | 336.9; NA |
| C25 | 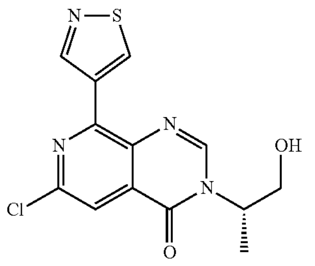 (S)-6-chloro-3-(1-hydroxypropan-2-yl)-8-(isothiazol-4-yl)pyrido[3,4-d]pyrimidin-4(3H)-one | (CH$_3$OH-d$_4$, 400 MHz): $\delta_H$ 1.54 (3H, d, J = 7.1 Hz), 3.83 (1H, dd, J = 11.9, 4.3 Hz), 3.94 (1H, dd, J = 11.9, 7.0 Hz), 4.98-4.93 (1H, m), 8.03 (1H, s), 8.50 (1H, s), 9.49 (1H, s), 10.09 (1H, s). | 322.9 NA |
| C26 | 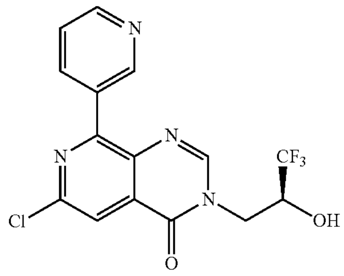 (S)-6-chloro-8-(pyridin-3-yl)-3-(3,3,3-trifluoro-2-hydroxypropyl)pyrido[3,4-d]pyrimidin-4(3H)-one | (CH$_3$OH-d$_4$, 300 MHz): $\delta_H$ 4.04-3.94 (1H, m), 4.41 (1H, brs), 4.64-4.57 (1H, m), 7.60 (1H, brs), 8.17-8.16 (1H, m), 8.35-8.35 (1H, m), 8.68-8.62 (2H, m), 9.35-9.32 (1H, m). | 370.9 NA |
| C27 | 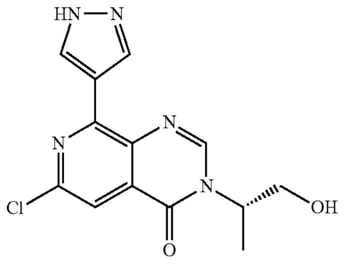 (S)-6-chloro-3-(1-hydroxypropan-2-yl)-8-(1H-pyrazol-4-yl)pyrido[3,4-d]pyrimidin-4(3H)-one | (DMSO-d$_6$, 400 MHz): $\delta_H$ 1.40 (4H, d, J = 7.0 Hz), 3.65-3.62 (1H, m), 3.78-3.73 (1H, m), 4.85-4.80 (1H, m), 5.06 (1H, t, J = 5.7 Hz), 7.76 (1H, s), 8.38 (1H, s), 8.55 (1H, s), 8.74 (1H, s), 13.28 (1H, s). | 306.0; >90 |

TABLE 4-continued

| Intermediate name | Structure and name | $^1$H-NMR chemical shifts | MS (m/z) [M + H]$^+$; Purity (%) |
|---|---|---|---|
| C28 | 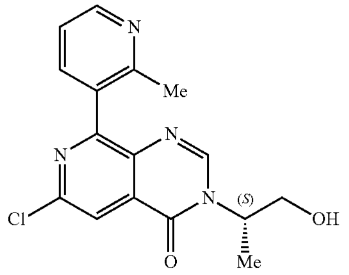 (S)-6-chloro-3-(1-hydroxypropan-2-yl)-8-(2-methylpyridin-3-yl)pyrido[3,4-d]pyrimidin-4(3H)-one | NA | 331.9; NA |
| C29 | 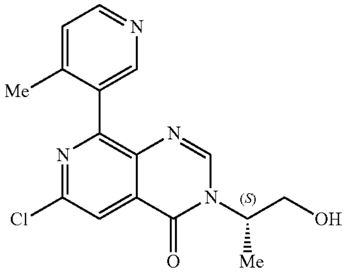 (S)-6-chloro-3-(1-hydroxypropan-2-yl)-8-(4-methylpyridin-3-yl)pyrido[3,4-d]pyrimidin-4(3H)-one | NA | 331.0; NA |
| C30 | 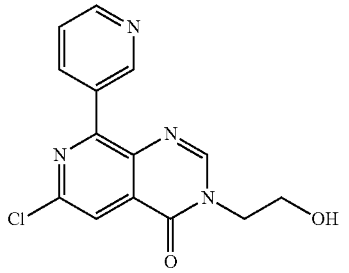 6-chloro-3-(2-hydroxyethyl)-8-(pyridin-3-yl)pyrido[3,4-d]pyrimidin-4(3H)-one | NA | 303.0; 95 |
| C31 | 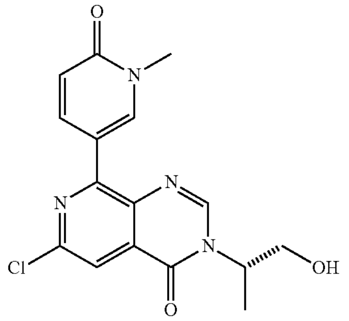 (S)-6-chloro-3-(1-hydroxypropan-2-yl)-8-(1-methyl-6-oxo-1,6-dihydropyridin-3-yl)pyrido[3,4-d]pyrimidin-4(3H)-one | (DMSO-$d_6$, 400 MHz): δ 1.41 (3H, d, J = 7.0 Hz), 3.57-3.55 (3H, m), 3.68-3.64 (1H, m), 3.79-3.74 (1H, m), 4.87-4.82 (1H, m), 5.06 (1H, t, J = 5.6 Hz), 6.53 (1H, d, J = 9.6 Hz), 7.89 (1H, s), 8.30 (1H, dd, J = 9.6, 2.6 Hz), 8.57-8.56 (1H, s), 8.93 (1H, d, J = 2.6 Hz). | 347.1; NA |

TABLE 4-continued

| Intermediate name | Structure and name | $^1$H-NMR chemical shifts | MS (m/z) [M + H]$^+$; Purity (%) |
| --- | --- | --- | --- |
| C32 | 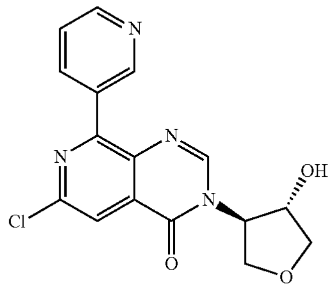 6-chloro-3-((3R,4S)-4-hydroxytetrahydrofuran-3-yl)-8-(pyridin-3-yl)pyrido[3,4-d]pyrimidin-4(3H)-one | (DMSO-$d_6$, 400 MHz): δ 3.61 (1H, dd, J = 9.6, 3.3 Hz), 4.04 (1H, dd, J = 10.1, 3.9 Hz), 4.19-4.10 (2H, m), 4.56-4.53 (1H, m), 4.95-4.92 (1H, m), 5.71 (1H, d, J = 4.4 Hz), 7.58 (1H, dd, J = 9.0, 4.8 Hz), 8.09 (1H, s), 8.36 (1H, s), 8.41 (1H, d, J = 8.0 Hz), 8.69 (1H, d, J = 4.7 Hz), 9.21 (1H, s). | 345.1; NA |
| C33 | 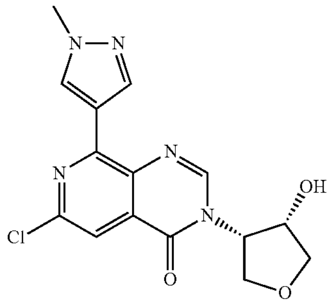 6-chloro-3-((3S,4S)-4-hydroxytetrahydrofuran-3-yl)-8-(1-methyl-1H-pyrazol-4-yl)pyrido[3,4-d]pyrimidin-4(3H)-one | (DMSO-$d_6$, 400 MHz): δ 3.79 (1H, t, J = 9.3 Hz), 4.00-3.90 (5H, m), 4.18 (1H, dd, J = 9.9, 5.4 Hz), 4.52-4.48 (1H, m), 5.37 (1H, q, J = 6.4 Hz), 5.48 (1H, d, J = 4.3 Hz), 7.79 (1H, s), 8.34 (2H, d, J = 2.4 Hz), 8.78 (1H, s). | 348.0; NA |
| C34 | 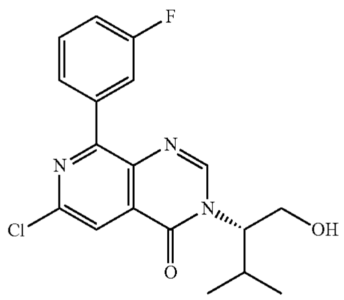 (S)-6-chloro-8-(3-fluorophenyl)-3-(1-hydroxy-3-methylbutan-2-yl)pyrido[3,4-d]pyrimidin-4(3H)-one | (400 MHz, DMSO-d6) δ ppm δ 8.56 (s, 1H), 8.06 (s, 1H), 7.88-7.99 (m, 2H), 7.50-7.63 (m, 1H), 7.26-7.44 (m, 1 H), 5.01 (t, J = 5.3 Hz, 1H), 4.29-4.57 (m, 1H), 3.84-3.98 (m, 1H), 3.32-3.78 (m, 1H), 2.18-2.38 (m, 1H), 0.99-1.10 (m, 3H), 0.76 (d, J = 6.6 Hz, 3H). | 362.1; 90.0 |

TABLE 4-continued

| Intermediate name | Structure and name | $^1$H-NMR chemical shifts | MS (m/z) [M + H]$^+$; Purity (%) |
|---|---|---|---|
| C35 | 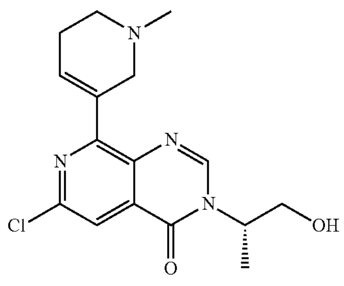 (S)-6-chloro-3-(1-hydroxypropan-2-yl)-8-(1-methyl-1,2,5,6-tetrahydropyridin-3-yl)pyrido[3,4-d]pyrimidin-4(3H)-one | NA | 335.1; NA |
| C36 | 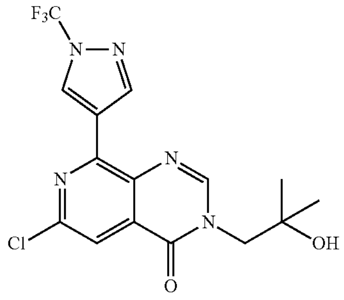 6-chloro-3-(2-hydroxy-2-methylpropyl)-8-(1-(trifluoromethyl)-1H-pyrazol-4-yl)pyrido[3,4-d]pyrimidin-4(3H)-one | $^1$H NMR (DMSO-$d_6$, 400 MHz): δ 1.16-1.14 (6H, m), 4.02 (2H, s), 4.91 (1H, s), 7.97 (1H, s), 8.46 (1H, s), 8.74 (1H, s), 9.33 (1H, s). | 387.9 |

NA = Not available

Step 4. Preparation of (S)-8-(5-fluoropyridin-3-yl)-3-(1-hydroxypropan-2-yl)-6-(4-(trifluoromethoxy)phenyl)pyrido[3,4-d]pyrimidin-4(3H)-one (1)

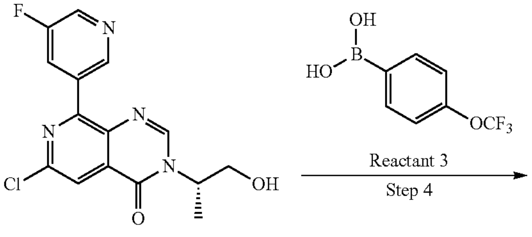

C1

-continued

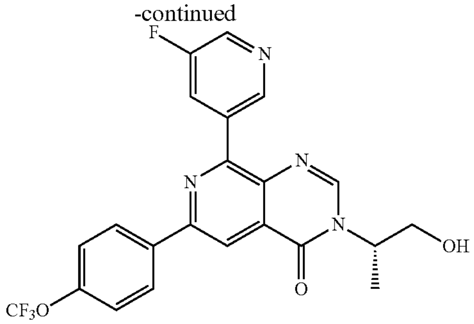

1

A mixture of (S)-6-chloro-8-(5-fluoropyridin-3-yl)-3-(1-hydroxypropan-2-yl)pyrido[3,4-d]pyrimidin-4(3H)-one (C1, 0.023 g, 0.069 mmol), (4-(trifluoromethoxy)phenyl)boronic acid (Reactant 3, 0.016 g, 0.076 mmol), sodium carbonate (0.029 g, 0.275 mmol) and tetrakis(triphenylphosphine)palladium (0.008 g, 0.007 mmol) in a sealed tube was purged with argon. Toluene (1.0 mL) and ethanol (0.5 mL) were added and the resulting mixture was stirred at 75° C.

for 15 hours. The mixture was cooled to room temperature, filtered through Celite and the Celite pad was washed with ethyl acetate and filtrate was evaporated. Purification of the residue by silica gel chromatography with methanol/dichloromethane afforded the title compound (0.022 g, 0.047 mmol, 68% yield). $^1$H NMR (DMSO-$d_6$, 400 MHz): δ 1.44 (3H, d, J=7.0 Hz), 3.72-3.66 (1H, m), 3.84-3.78 (1H, m), 4.91 (1H, s), 5.08 (1H, t, J=5.6 Hz), 7.53 (2H, d, J=8.4 Hz), 8.43 (2H, d, J=8.6 Hz), 8.53 (1H, ddd, J=10.3, 2.9, 1.7 Hz), 8.60 (2H, d, J=3.7 Hz), 8.73 (1H, d, J=2.8 Hz), 9.29 (1H, s); MS (m/z): 461.1 $[M+H]^+$; >99% purity.

Table 5 lists compounds made via procedures similar to that described for 1, replacing reactants 1, 2, and 3 with the indicated groups.

TABLE 5

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 2 | 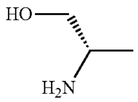 | 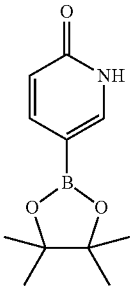 | 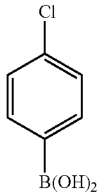 | 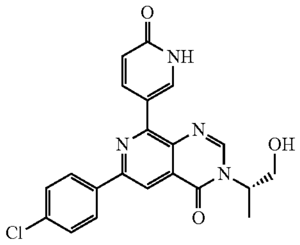 (S)-6-(4-chlorophenyl)-3-(1-hydroxypropan-2-yl)-8-(6-oxo-1,6-dihydropyridin-3-yl)pyrido[3,4-d]pyrimidin-4(3H)-one | (DMSO-$d_6$, 400 MHz): $\delta_H$ 1.43 (3H, d, J = 7.0 Hz), 3.70-3.65 (1H, m), 3.83-3.77 (1H, m), 4.91-4.86 (1H, m), 5.08 (1H, t, J = 5.6 Hz), 6.51 (1H, d, J = 9.7 Hz), 7.60 (2H, d, J = 8.4 Hz), 8.28 (2H, d, J = 8.4 Hz), 8.38 (1H, s), 8.53 (1H, dd, J = 9.7, 2.6 Hz), 8.56 (1H, s), 12.02 (1H, s). | 409.1; 96 |
| 3 | 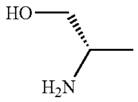 | 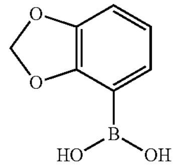 [SMILES: OB(O)c1cccc2c1OCO2] | 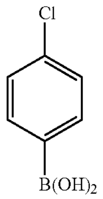 | 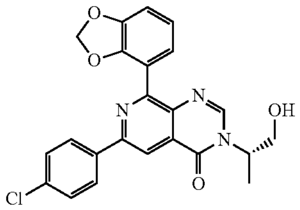 (S)-8-(benzo[d][1,3]dioxol-4-yl)-6-(4-chlorophenyl)-3-(1-hydroxypropan-2-yl)pyrido[3,4-d]pyrimidin-4(3H)-one | (DMSO-$d_6$, 400 MHz): $\delta_H$ 1.42 (3H, d, J = 7.0 Hz), 3.69-3.64 (1H, m), 3.82-3.76 (1H, m), 4.88 (1H, s), 5.08 (1H, t, J = 5.6 Hz), 6.03 (2H, s), 6.98 (1H, t, J = 7.8 Hz), 7.06 (1H, d, J = 7.6 Hz), 7.17 (1H, d, J = 7.8 Hz), 7.58 (2H, d, J = 8.4 Hz), 8.25 (2H, d, J = 8.4 Hz), 8.48 (1H, s), 8.52 (1H, s). | 435.0; >99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 4 | 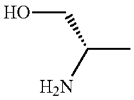 | 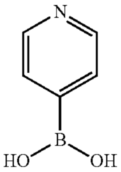 | 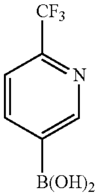 | 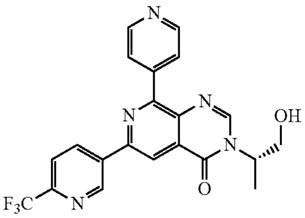 (S)-3-(1-hydroxypropan-2-yl)-8-(pyridin-4-yl)-6-(6-(trifluoromethyl)pyridin-3-yl)pyrido[3,4-d]pyrimidin-4(3H)-one | (DMSO-$d_6$, 400 MHz): $\delta_H$ 1.45 (3H, d, J = 7.0 Hz), 3.72-3.66 (1H, m), 3.84-3.78 (1H, m), 4.94-4.89 (1H, m), 5.09 (1H, t, J = 5.6 Hz), 8.07 (1H, d, J = 8.3 Hz), 8.20 (2H, d, J = 5.4 Hz), 8.63 (1H, s), 8.81-8.77 (3H, m), 8.93 (1H, d, J = 8.4 Hz), 9.64 (1H, s). | 427.9; >99 |
| 5 | 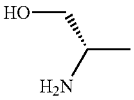 | 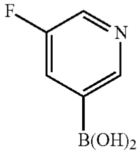 | 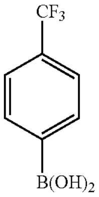 | 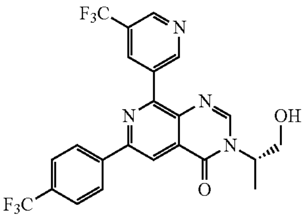 (S)-8-(5-fluoropyridin-3-yl)-3-(1-hydroxypropan-2-yl)-6-(4-(trifluoromethyl)phenyl)pyrido[3,4-d]pyrimidin-4(3H)-one | (DMSO-$d_6$, 400 MHz): $\delta_H$ 1.44 (3H, d, J = 7.0 Hz), 3.70 (1H, t, J = 5.6 Hz), 3.80 (1H, s), 4.92 (1H, s), 5.09 (1H, s), 7.91 (2H, d, J = 8.2 Hz), 8.53 (3H, d, J = 8.5 Hz), 8.63 (1H, s), 8.67 (1H, s), 8.74 (1H, d, J = 2.8 Hz), 9.30 (1H, s). | 445.1; >99 |
| 6 | 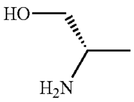 | 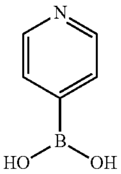 | 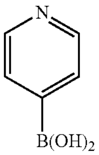 | 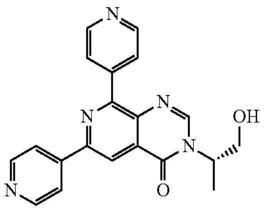 (S)-3-(1-hydroxypropan-2-yl)-6,8-di(pyridin-4-yl)pyrido[3,4-d]pyrimidin-4(3H)-one | (DMSO-$d_6$, 400 MHz): $\delta_H$ 1.44 (3H, d, J = 7.0 Hz), 3.72-3.66 (1H, m), 3.84-3.78 (1H, m), 4.93-4.88 (1H, m), 5.09 (1H, t, J = 5.6 Hz), 8.19 (2H, dd, J = 4.7, 1.6 Hz), 8.26 (2H, d, J = 5.4 Hz), 8.62 (1H, s), 8.78-8.73 (5H, m). | 360.0; >95 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 7 | 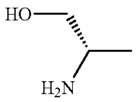 | 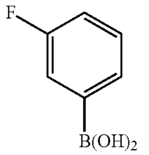 | 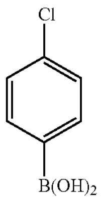 | 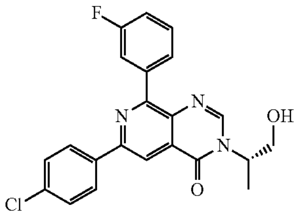 (S)-6-(4-chlorophenyl)-8-(3-fluorophenyl)-3-(1-hydroxypropan-2-yl)pyrido[3,4-d]pyrimidin-4(3H)-one | ($CHCl_3$-d, 400 MHz): δ 1.60 (3H, d, J = 7.2 Hz), 3.99 (2H, d, J = 4.8 Hz), 5.10-5.06 (1H, m), 7.20 (1H, td, J = 8.4, 2.7 Hz), 7.51-7.46 (3H, m), 7.93-7.89 (1H, m), 7.96 (1H, d, J = 7.8 Hz), 8.18-8.14 (2H, m), 8.34 (1H, s), 85.1 (1H, s). | 410.1; 98 |
| 8 | 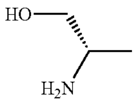 | 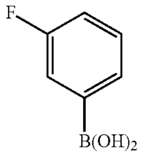 | 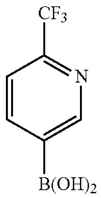 [SMILES: OB(O)c1ccc(C(F)(F)F)nc1] | 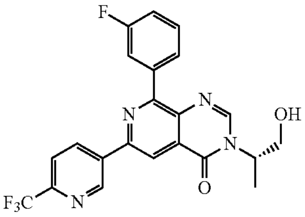 (S)-8-(3-fluorophenyl)-3-(1-hydroxypropan-2-yl)-6-(6-(trifluoromethyl)pyridin-3-yl)pyrido[3,4-d]pyrimidin-4(3H)-one | ($CH_3OH$-$d_4$, 400 MHz): δ 1.56 (3H, d, J = 7.1 Hz), 3.85 (1H, dd, J = 11.9, 4.3 Hz), 3.96 (1H, dd, J = 11.9, 6.9 Hz), 5.02-4.97 (1H, m), 7.24-7.20 (1H, m), 7.53-7.48 (1H, m), 7.95 (1H, d, J = 8.3 Hz), 8.01 (1H, d, J = 10.7 Hz), 8.06 (1H, d, J = 7.9 Hz), 8.45 (1H, s), 8.66 (1H, s), 8.81 (1H, d, J = 8.3 Hz), 9.50 (1H, s). | 444.9; 99 |
| 9 | 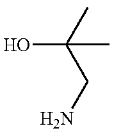 | 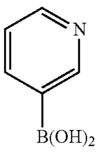 | 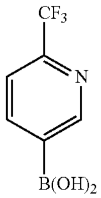 | 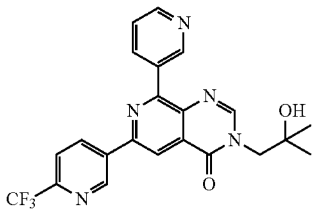 3-(2-hydroxy-2-methylpropyl)-8-(pyridin-3-yl)-6-(6-(trifluoromethyl)pyridin-3-yl)pyrido[3,4-d]pyrimidin-4(3H)-one | ($CH_3OH$-$d_4$, 400 MHz): δ 1.27 (6H, s), 4.14 (2H, s), 7.61 (1H, dd, J = 8.0, 4.9 Hz), 7.97 (1H, d, J = 8.3 Hz), 8.40 (1H, s), 8.64 (1H, d, J = 4.9 Hz), 8.73-8.70 (2H, m), 8.84 (1H, d, J = 8.4 Hz), 9.41 (1H, s), 9.54 (1H, s). | 442.2; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 10 | 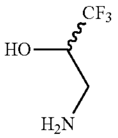 | 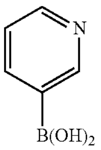 | 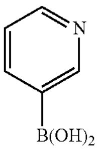 | 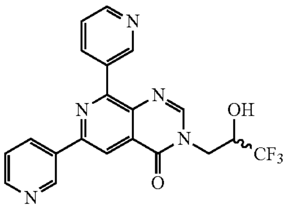 6,8-di(pyridin-3-yl)-3-(3,3,3-trifluoro-2-hydroxypropyl)pyrido[3,4-d]pyrimidin-4(3H)-one | ($CH_3OH$-$d_4$, 400 MHz): δ 3.98 (1H, dd, J = 13.7, 9.7 Hz), 4.45 (1H, d, J = 8.3 Hz), 4.61 (1H, dd, J = 13.7, 2.8 Hz), 7.57 (2H, t, J = 6.4 Hz), 8.35 (1H, s), 8.61-8.58 (4H, m), 8.67 (1H, d, J = 8.1 Hz), 9.34 (2H, d, J = 12.3 Hz). | 414.1; 97 |
| 11 | 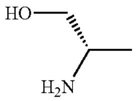 | 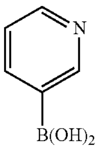 | — | 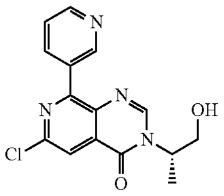 (S)-6-chloro-3-(1-hydroxypropan-2-yl)-8-(pyridin-3-yl)pyrido[3,4-d]pyrimidin-4(3H)-one | ($CH_3OH$-$d_4$, 400 MHz): δ 1.52 (3H, d, J = 7.1 Hz), 3.82 (1H, dd, J = 11.9, 4.3 Hz), 3.93 (1H, dd, J = 11.9, 7.0 Hz), 4.96-4.91 (1H, m), 7.58-7.55 (1H, m), 8.08 (1H, s), 8.41 (1H, s), 8.61-8.59 (2H, m), 9.31 (1H, s). | 317.1; 96 |
| 12 | 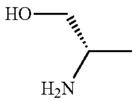 | 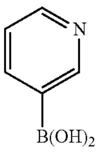 | 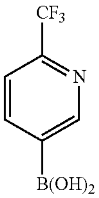 | 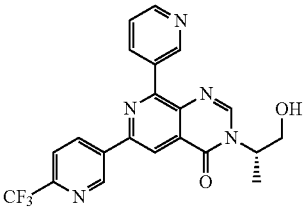 (S)-3-(1-hydroxypropan-2-yl)-8-(pyridin-3-yl)-6-(6-(trifluoromethyl)pyridin-3-yl)pyrido[3,4-d]pyrimidin-4(3H)-one | ($CH_3OH$-$d_4$, 400 MHz): $\delta_H$ 1.56 (3H, d, J = 7.1 Hz), 3.86 (1H, dd, J = 11.9, 4.3 Hz), 3.97 (1H, dd, J = 11.9, 7.0 Hz), 5.03-4.98 (1H, m), 7.62 (1H, dd, J = 8.0, 4.9 Hz), 7.98 (1H, d, J = 8.2 Hz), 8.49 (1H, s), 8.65 (1H, d, J = 4.9 Hz), 8.76-8.72 (2H, m), 8.86 (1H, d, J = 8.3 Hz), 9.43 (1H, s), 9.55 (1H, s). | 428.1; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 13 | 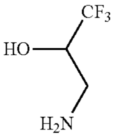 | 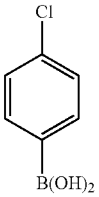 | 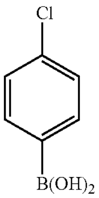 | 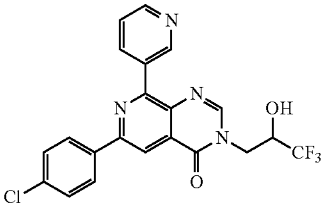 6-(4-chlorophenyl)-8-(pyridin-3-yl)-3-(3,3,3-trifluoro-2-hydroxypropyl)pyrido[3,4-d]pyrimidin-4(3H)-one | ($CH_3OH$-$d_4$, 400 MHz): $\delta_H$ 3.98 (1H, dd, J = 13.7, 9.6 Hz), 4.45-4.40 (1H, m), 4.62 (1H, dd, J = 13.8, 3.0 Hz), 7.53 (2H, d, J = 8.4 Hz), 7.60 (1H, dd, J = 8.0, 4.9 Hz), 8.23 (2H, d, J = 8.4 Hz), 8.33 (1H, s), 8.58 (1H, s), 8.63-8.62 (1H, m), 8.70 (1H, dt, J = 8.0, 1.9 Hz), 9.38 (1H, s). | 447.1; 96 |
| 14 | 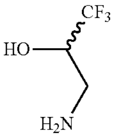 | 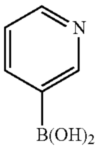 | 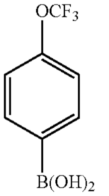 | 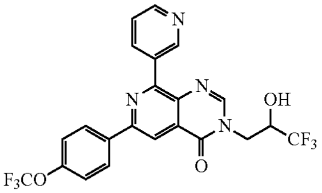 8-(pyridin-3-yl)-3-(3,3,3-trifluoro-2-hydroxypropyl)-6-(4-(trifluoromethoxy)phenyl)pyrido[3,4-d]pyrimidin-4(3H)-one | ($CH_3OH$-$d_4$, 400 MHz): $\delta_H$ 3.99 (1H, dd, J = 13.7, 9.7 Hz), 4.44 (1H, s), 4.63-4.59 (1H, m), 7.44 (2H, d, J = 8.4 Hz), 7.60 (1H, dd, J = 8.0, 4.9 Hz), 8.35 (3H, d, J = 9.1 Hz), 8.63-8.60 (2H, m), 8.71 (1H, d, J = 8.1 Hz), 9.39 (1H, s). | 497.1, 97 |
| 15 | 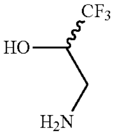 | 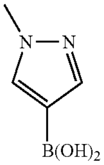 | 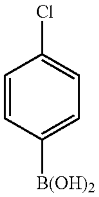 | 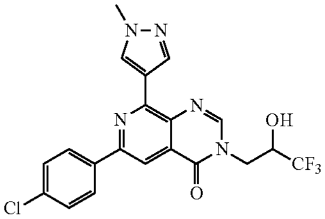 6-(4-chlorophenyl)-8-(1-methyl-1H-pyrazol-4-yl)-3-(3,3,3-trifluoro-2-hydroxypropyl)pyrido[3,4-d]pyrimidin-4(3H)-one | (DMSO-d6, 400 MHz): $\delta_H$ 3.95 (3H, s), 4.05 (1H, dd, J = 14.0, 9.7 Hz), 4.43 (2H, d, J = 13.1 Hz), 6.77 (1H, d, J = 6.5 Hz), 7.57 (2H, d, J = 8.4 Hz), 8.30-8.27 (3H, m), 8.47 (2H, s), 8.78 (1H, s). | 450.1; 97 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 16 | 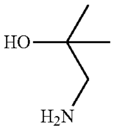 | 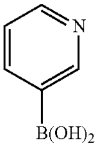 | 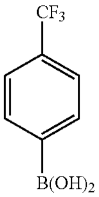 [SMILES: OB(O)c1ccc(C(F)(F)F)cc1] | 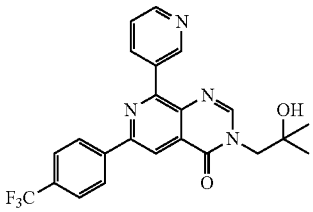 3-(2-hydroxy-2-methylpropyl)-8-(pyridin-3-yl)-6-(4-(trifluoromethyl)phenyl)pyrido[3,4-d]pyrimidin-4(3H)-one | ($CH_3$ OH-$d_4$, 400 MHz): $\delta_H$ 1.27 (6H, s), 4.14 (2H, s), 7.61 (1H, t, J = 6.4 Hz), 7.84 (2H, d, J = 8.2 Hz), 8.38 (1H, s), 8.43 (2H, d, J = 8.2 Hz), 8.64 (1H, s), 8.68 (1H, s), 8.73 (1H, d, J = 8.1 Hz), 9.41 (1H, s). | 441.2; 99 |
| 17 | 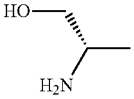 | 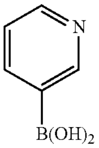 | 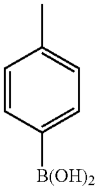 | 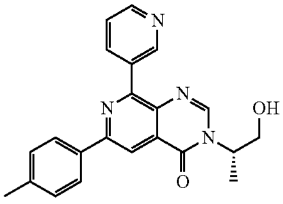 (S)-3-(1-hydroxypropan-2-yl)-8-(pyridin-3-yl)-6-(p-tolyl)pyrido[3,4-d]pyrimidin-4(3H)-one | ($CH_3OH$-$d_4$, 400 MHz): $\delta_H$ 1.55 (3H, d, J = 7.1 Hz), 2.42 (3H, s), 3.85 (1H, dd, J = 11.8, 4.3 Hz), 3.97 (1H, dd, J = 11.9, 7.0 Hz), 5.02-4.97 (1H, m), 7.36-7.34 (2H, m), 7.61-7.58 (1H, m), 8.12 (2H, d, J = 7.9 Hz), 8.40 (1H, s), 8.53 (1H, s), 8.62-8.61 (1H, m), 8.71 (1H, dt, J = 8.0, 1.9 Hz), 9.40 (1H, s). | 373.2; 99 |
| 18 | 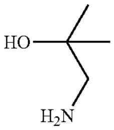 | 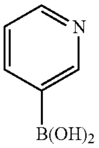 | 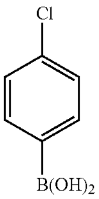 | 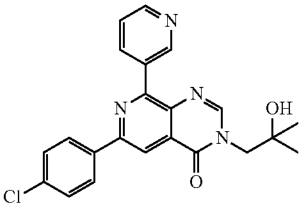 6-(4-chlorophenyl)-3-(2-hydroxy-2-methylpropyl)-8-(pyridin-3-yl)pyrido[3,4-d]pyrimidin-4(3H)-one | ($CH_3OH$-$d_4$, 400 MHz): $\delta_H$ 1.27 (6H, s), 4.13 (2H, s), 7.54-7.51 (2H, m), 7.62-7.59 (1H, m), 8.24 (2H, d, J = 8.4 Hz), 8.35 (1H, s), 8.59 (1H, s), 8.64-8.62 (1H, m), 8.71 (1H, dt, J = 8.0, 1.9 Hz), 9.40 (1H, s). | 407.1; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 19 | 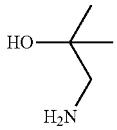 | 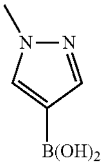 | 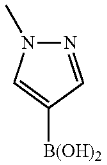 | 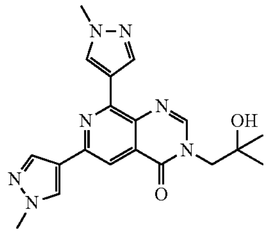 3-(2-hydroxy-2-methylpropyl)-6,8-bis(1-methyl-1H-pyrazol-4-yl)pyrido[3,4-d]pyrimidin-4(3H)-one | ($CH_3OH-d_4$, 400 MHz): $\delta_H$ 1.25 (6H, s), 3.98 (6H, d, J = 5.5 Hz), 4.10 (2H, s), 8.02 (1H, s), 8.11 (1H, s), 8.29 (2H, d, J = 3.2 Hz), 8.51 (1H, s), 8.75 (1H, s). | 380.2; 95 |
| 20 | 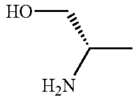 | 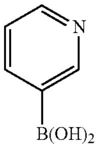 | 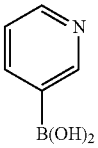 | 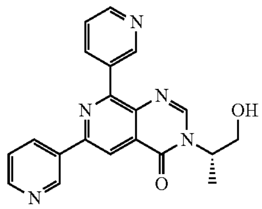 (S)-3-(1-hydroxypropan-2-yl)-6,8-di(pyridin-3-yl)pyrido[3,4-d]pyrimidin-4(3H)-one | ($CHCl_3$-d, 400 MHz): $\delta_H$ 1.60 (3H, d, J = 7.1 Hz), 4.11-4.01 (2H, m), 5.10 (1H, d, J = 7.7 Hz), 7.35 (2H, d, J = 7.0 Hz), 8.29 (1H, s), 8.36 (1H, d, J = 8.0 Hz), 8.48 (2H, s), 8.57 (2H, s), 9.22 (1H, s), 9.33 (1H, s). | 360.1; 96 |
| 21 | 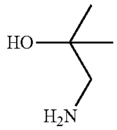 | 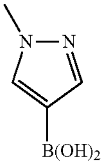 | 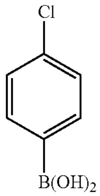 | 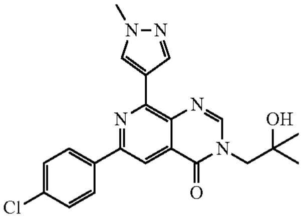 6-(4-chlorophenyl)-3-(2-hydroxy-2-methylpropyl)-8-(1-methyl-1H-pyrazol-4-yl)pyrido[3,4-d]pyrimidin-4(3H)-one | ($CH_3OH-d_4$, 400 MHz): $\delta_H$ 1.26 (6H, s), 3.99 (3H, s), 4.10 (2H, s), 7.51 (2H, d, J = 8.4 Hz), 8.19 (2H, d, J = 8.4 Hz), 8.30 (1H, s), 8.35 (1H, s), 8.52 (1H, s), 8.76 (1H, s). | 410.2; 98 |
| 22 | 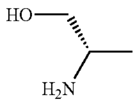 | 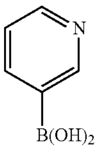 | 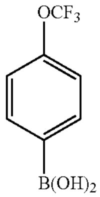 | 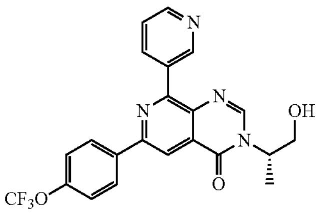 (S)-3-(1-hydroxypropan-2-yl)-8-(pyridin-3-yl)-6-(4-(trifluoromethoxy)phenyl)pyrido[3,4-d]pyrimidin-4(3H)-one | ($CH_3OH-d_4$, 400 MHz): $\delta_H$ 1.55 (3H, d, J = 7.1 Hz), 3.85 (1H, dd, J = 11.9, 4.3 Hz), 3.96 (1H, dd, J = 11.9, 6.9 Hz), 5.01-4.96 (1H, m), 7.42 (2H, d, J = 8.4 Hz), 7.59 (1H, dd, J = 8.0, 4.9 Hz), 8.31 (2H, d, J = 8.6 Hz), 8.42 (1H, s), 8.56 (1H, s), 8.62 (1H, d, | 443.2; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| | | | | | J = 4.9 Hz), 8.71-8.69 (1H, m), 9.39 (1H, s). | |
| 23 | 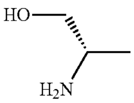 | 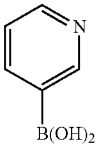 | 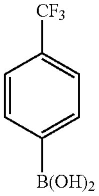 | 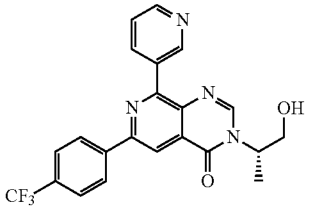 (S)-3-(1-hydroxypropan-2-yl)-8-(pyridin-3-yl)-6-(4-(trifluoromethyl)phenyl)pyrido[3,4-d]pyrimidin-4(3H)-one | ($CH_3OH-d_4$, 400 MHz): $\delta_H$ 1.56 (3H, d, J = 7.1 Hz), 3.87 (1H, t, J = 4.4 Hz), 3.96 (1H, t, J = 6.8 Hz), 4.97-5.04 (1H, m), 7.61 (1H, dd, J = 8.0, 4.9 Hz), 7.83 (2H, d, J = 8.2 Hz), 8.46-8.42 (3H, m), 8.63 (1H, s), 8.67 (1H, s), 8.73 (1H, d, J = 8.0 Hz), 9.42 (1H, s). | 427.2; 98 |
| 24 | 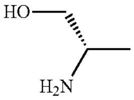 | 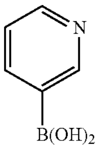 | 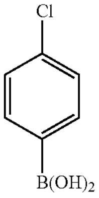 | 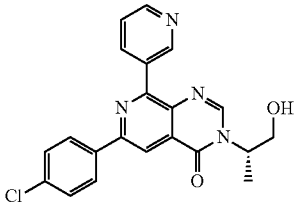 (S)-6-(4-chlorophenyl)-3-(1-hydroxypropan-2-yl)-8-(pyridin-3-yl)pyrido[3,4-d]pyrimidin-4(3H)-one | ($CH_3OH-d_4$, 400 MHz): $\delta_H$ 1.55 (3H, d, J = 7.1 Hz), 3.85 (1H, dd, J = 11.9, 4.3 Hz), 3.96 (1H, dd, J = 11.9, 7.0 Hz), 5.00 (1H, d, J = 7.7 Hz), 7.52 (2H, d, J = 8.4 Hz), 7.60 (1H, t, J = 6.4 Hz), 8.21 (2H, d, J = 8.3 Hz), 8.42 (1H, s), 8.55 (1H, s), 8.62 (1H, s), 8.71 (1H, d, J = 8.1 Hz), 9.40 (1H, s). | 393.1; 98 |
| 25 | 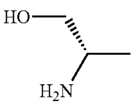 | 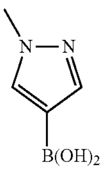 | 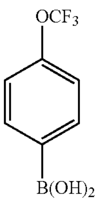 | 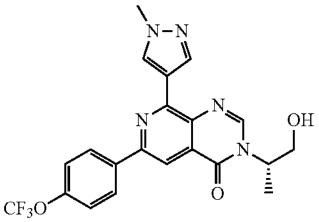 (S)-3-(1-hydroxypropan-2-yl)-8-(1-methyl-1H-pyrazol-4-yl)-6-(4-(trifluoromethoxy)phenyl)pyrido[3,4-d]pyrimidin-4(3H)-one | ($CH_3OH-d_4$, 400 MHz): $\delta_H$ 1.56 (3H, d, J = 7.1 Hz), 3.85 (1H, dd, J = 12.0, 4.3 Hz), 3.99-3.94 (4H, m), 5.02-4.97 (1H, m), 7.42 (2H, d, J = 8.3 Hz), 8.33-8.30 (3H, m), 8.46 (1H, s), 8.55 (1H, s), 8.78 (1H, s). | 446.2; 97 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 26 | 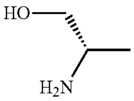 | 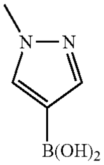 | 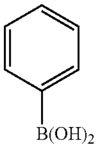 | 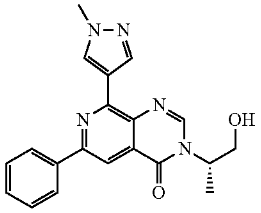 (S)-3-(1-hydroxypropan-2-yl)-8-(1-methyl-1H-pyrazol-4-yl)-6-phenylpyrido[3,4-d]pyrimidin-4(3H)-one | ($CH_3OH$-$d_4$, 400 MHz): $\delta_H$ 1.56 (3H, d, J = 7.1 Hz), 3.85 (1H, dd, J = 11.9, 4.3 Hz), 3.99-3.94 (4H, m), 4.99 (1H, d, J = 7.9 Hz), 7.45 (1H, d, J = 7.2 Hz), 7.52 (2H, t, J = 7.5 Hz), 8.20 (2H, d, J = 7.7 Hz), 8.31 (1H, s), 8.44 (1H, s), 8.55 (1H, s), 8.77 (1H, s). | 396.1; 99 |
| 27 | 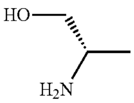 | 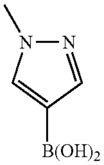 | 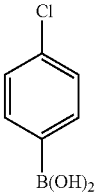 | 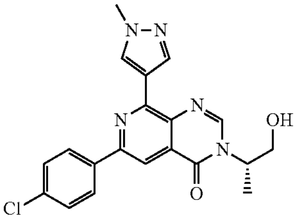 (S)-6-(4-chlorophenyl)-3-(1-hydroxypropan-2-yl)-8-(1-methyl-1H-pyrazol-4-yl)pyrido[3,4-d]pyrimidin-4(3H)-one | ($CHCl_3$-d, 400 MHz): $\delta_H$ 1.60 (3H, d, J = 7.2 Hz), 4.01-3.99 (5H, m), 5.09-5.04 (1H, m), 7.46-7.44 (2H, m), 8.10 (2H, d, J = 8.4 Hz), 8.26 (2H, d, J = 4.2 Hz), 8.51 (2H, s). | 362.2; 99 |
| 28 | 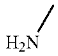 | 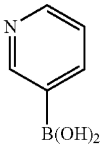 | 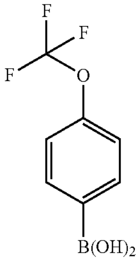 [SMILES: OB(O)c1ccc(OC(F)(F)F)cc1] | 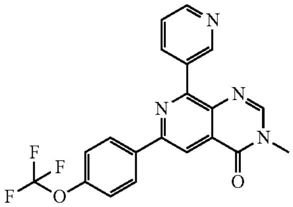 3-methyl-8-(pyridin-3-yl)-6-(4-(trifluoromethoxy)phenyl)pyrido[3,4-d]pyrimidin-4(3H)-one | (DMSO-$d_6$, 400 MHz): δ 3.55 (3H, s), 7.59-7.50 (3H, m), 8.38 (2H, d, J = 8.5 Hz), 8.52-8.50 (3H, m), 8.67 (1H, d, J = 4.8 Hz), 9.31 (1H, s). | 399.1; 98 |
| 29 | 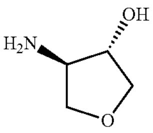 Trans, racemic mixture | 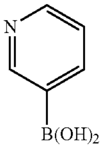 | 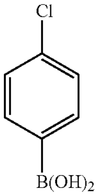 | 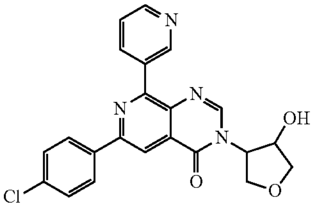 6-(4-chlorophenyl)-3-(4-hydroxytetrahydrofuran-3-yl)-8-(pyridin-3-yl)pyrido[3,4-d]pyrimidin-4(3H)-one, trans racemic mixture | (DMSO-$d_6$, 400 MHz): δ 3.61 (1H, dd, J = 9.6, 3.3 Hz), 4.05 (1H, dd, J = 10.1, 4.0 Hz), 4.20-4.11 (2H, m), 4.56 (1H, s), 4.98 (1H, s), 5.71 (1H, bs), 7.59 (2H, d, J = 8.3 Hz), 7.75 (2H, m), 8.30 (2H, d, J = 8.3 Hz), 8.35 (1H, s), 8.54 | 421.1; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| | | | | | (1H, s), 8.59 (1H, m). | |
| 30 | 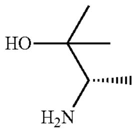 | 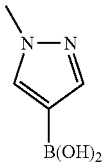 | 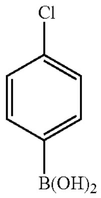 | 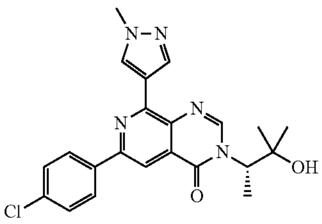 (S)-6-(4-chlorophenyl)-3-(3-hydroxy-3-methylbutan-2-yl)-8-(1-methyl-1H-pyrazol-4-yl)pyrido[3,4-d]pyrimidin-4(3H)-one | (DMSO-$d_6$, 400 MHz): δ 0.97 (3H, s), 1.27 (3H, s), 1.48 (3H, d, J = 7.2 Hz), 3.95 (3H, s), 4.97 (1H, m), 5.07 (1H, s), 7.57 (2H, d, J = 8.4 Hz), 8.31-8.28 (3H, m), 8.48 (1H, s), 85.6 (1H, s), 8.82 (1H, s). | 424.1; 99 |
| 31 | 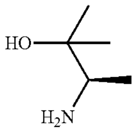 | 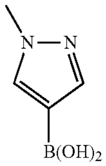 | 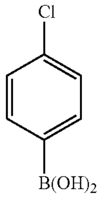 | 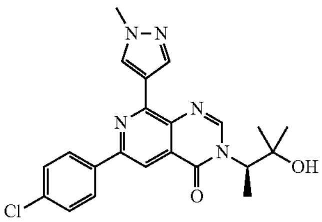 (R)-6-(4-chlorophenyl)-3-(3-hydroxy-3-methylbutan-2-yl)-8-(1-methyl-1H-pyrazol-4-yl)pyrido[3,4-d]pyrimidin-4(3H)-one | (DMSO-$d_6$, 400 MHz): δ 0.97 (3H, s), 1.27 (3H, s), 1.48 (3H, d, J = 7.2 Hz), 3.95 (3H, s), 4.96 (1H, m), 5.07 (1H, s), 7.56 (2H, d, J = 8.3 Hz), 8.29 (2H, d, J = 3.6 Hz), 8.31 (1H, s), 8.48 (1H, s), 8.55 (1H, s), 8.82 (1H, s). | 424.1; 98 |
| 32 | 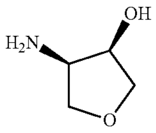 Cis, racemic mixture | 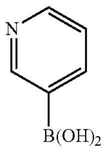 | 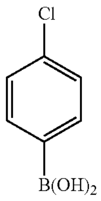 | 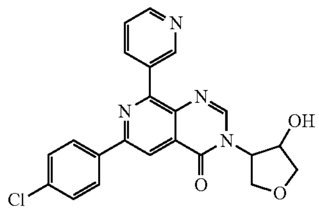 6-(4-chlorophenyl)-3-(4-hydroxytetrahydrofuran-3-yl)-8-(pyridin-3-yl)pyrido[3,4-d]pyrimidin-4(3H)-one, cis racemate | (DMSO-$d_6$, 400 MHz): δ 3.77 (1H, dd, J = 9.8, 2.3 Hz), 4.02-3.92 (2H, m), 4.18 (1H, dd, J = 9.8, 5.9 Hz), 4.50 (1H, s), 5.38 (1H, q, J = 6.7 Hz), 5.47 (1H, s), 7.59 (3H, d, J = 8.3 Hz), 8.31 (2H, d, J = 8.4 Hz), 8.34 (1H, s), 8.55-8.54 (1H, m), 8.58 (1H, s), 8.70 (1H, s), 9.35 (1H, s). | 421.1; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 33 | 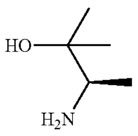 | 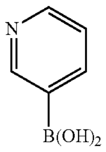 | 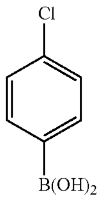 | 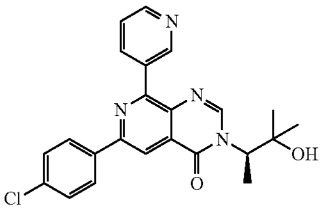 (R)-6-(4-chlorophenyl)-3-(3-hydroxy-3-methylbutan-2-yl)-8-(pyridin-3-yl)pyrido[3,4-d]pyrimidin-4(3H)-one | ($CH_3OH-d_4$, 400 MHz): δ 1.11 (3H, s), 1.39 (3H, s), 1.59 (4H, d, J = 7.2 Hz), 5.13 (1H, s), 7.54-7.52 (2H, m), 8.15 (1H, dd, J = 8.2, 5.6 Hz), 8.24 (2H, d, J = 8.3 Hz), 8.65 (2H, d, J = 5.5 Hz), 8.89 (1H, d, J = 5.5 Hz), 9.50 (1H, d, J = 8.2 Hz), 9.87 (1H, s). | 421.1; 99 |
| 34 | 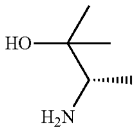 | 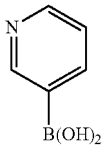 | 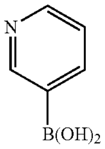 | 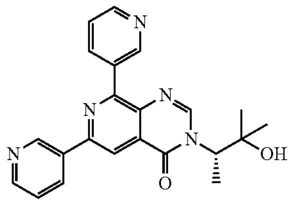 (S)-3-(3-hydroxy-3-methylbutan-2-yl)-6,8-di(pyridin-3-yl)pyrido[3,4-d]pyrimidin-4(3H)-one | ($CHCl_3$-d, 400 MHz): δ 1.22 (3H, s), 1.44 (3H, s), 1.60 (3H, d, J = 7.2 Hz), 5.17-5.07 (1H, m), 7.46 (2H, dt, J = 8.0, 4.9 Hz), 8.56-8.50 (2H, m), 8.59-8.56 (2H, m), 8.71 (2H, ddd, J = 7.7, 4.8, 1.7 Hz), 9.46 (2H, dd, J = 18.7, 2.2 Hz). | 388.1; 99 |
| 35 | 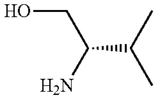 | 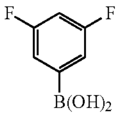 | 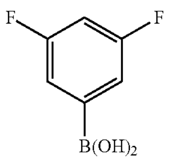 [SMILES: OB(O)c1cc(F)cc(F)c1] | 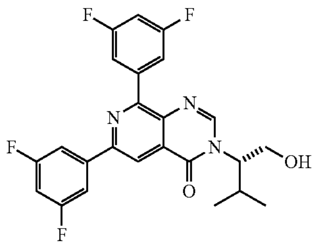 (S)-6,8-bis(3,5-difluorophenyl)-3-(1-hydroxy-3-methylbutan-2-yl)pyrido[3,4-d]pyrimidin-4(3H)-one | ($CHCl_3$-d, 400 MHz): δ 0.88 (3H, d, J = 6.6 Hz), 1.19 (3H, d, J = 6.5 Hz), 2.27 (1H, br s), 2.49-2.43 (1H, m), 3.99 (1H, d, J = 11.9 Hz), 4.17 (1H, dd, J = 11.9, 5.9 Hz), 4.53 (1H, s), 6.96-6.87 (2H, m), 7.72 (2H, d, J = 7.6 Hz), 7.86 (2H, d, J = 8.0 Hz), 8.32 (1H, s), 8.47 (1H, s). | 458.1; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 36 | 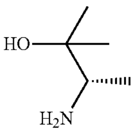 | 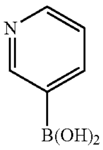 | 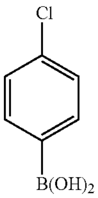 | 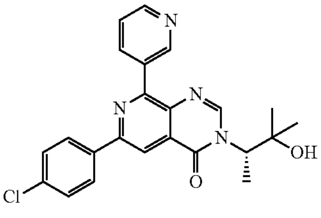 (S)-6-(4-chlorophenyl)-3-(3-hudroxy-3-methylbutan-2-yl)-8-(pyridin-3-yl)pyrido[3,4-d]pyrimidin-4(3H)-one | ($DMSO-d_6$, 400 MHz): δ 0.98 (3H, s), 1.26 (3H, s), 1.47 (3H, d, J = 7.2 Hz), 4.97 (1H, m), 5.03 (1H, s), 7.59 (3H, d, J = 8.5 Hz), 8.30 (2H, d, J = 8.3 Hz), 8.53 (3H, m), 8.67 (1H, d, J = 4.8 Hz), 9.33 (1H, s). | 421.1; 99 |
| 37 | 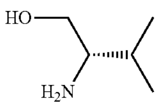 | 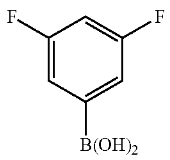 | 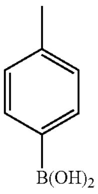 | 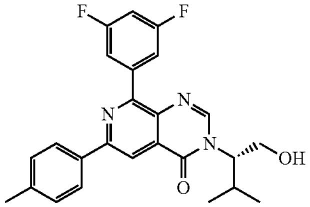 (S)-8-(3,5-difluorophenyl)-3-(1-hydroxy-3-methylbutan-2-yl)-6-(p-tolyl)pyrido[3,4-d[pyrimidin-4(3H)-one | ($CHCl_3$-d, 400 MHz): δ 0.87 (3H, d, J = 6.7 Hz), 1.16 (3H, d, J = 6.5 Hz), 2.42 (4H, m), 2.81 (1H, s), 3.95 (1H, d, J = 12.1 Hz), 4.14-4.11 (1H, m), 4.47 (1H, s), 6.91 (1H, tt, J = 8.8, 2.4 Hz), 7.29 (2H, d, J = 7.9 Hz), 7.87-7.83 (2H, m), 8.04 (2H, d, J = 7.9 Hz), 8.23 (1H, s), 8.40 (1H, s). | 436.1, 99 |
| 38 | 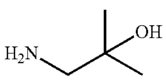 | 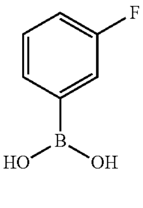 | 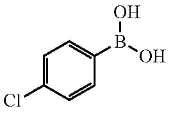 | 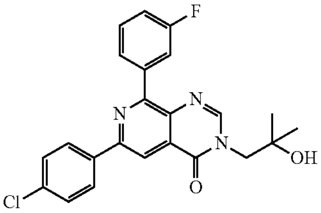 6-(4-chlorophenyl)-8-(3-fluorophenyl)-3-(2-hydroxy-2-methylpropyl)pyrido[3,4-d]pyrimidin-4(3H)-one | (400 MHz, DMSO-d6): δ ppm 1.16 (s, 6H), 4.04 (s, 2H), 4.88 (s, 1H), 7.33-7.39 (m, 1H), 7.56-7.63 (m, 3H), 8.01-8.09 (m, 2H), 8.31 (d, J = 9.2 Hz, 2H), 8.38 (s, 1H), 8.55 (s, 1H) | 424.0; 97 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 39 | TFA 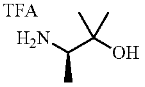 | 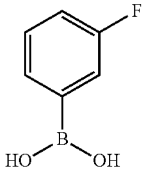 | 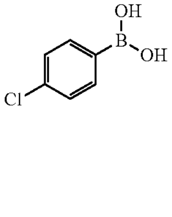 | 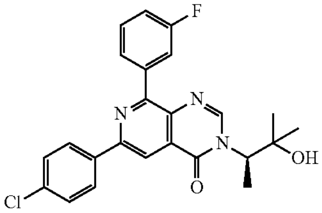 (R)-6-(4-chlorophenyl)-8-(3-fluorophenyl)-3-(3-hydroxy-3-methylbutan-2-yl)pyrido[3,4-d]pyrimidin-4(3H)-one | (400 MHz, DMSO-d6): δ ppm 0.99 (s, 3H), 1.27 (s, 3H), 1.48 (d, J = 7.2 Hz, 3H), 4.90-5.02 (m, 1H), 5.04 (s, 1H), 7.35 (t, J = 12.0 Hz, 1H), 7.54-7.63 (m, 3H), 8.06 (t, J = 8.0 Hz, 2H), 8.28 (d, J = 8.0 Hz, 2H), 8.53 (d, J = 12.0 Hz, 2H) | 464.0; 97 |
| 40 | TFA 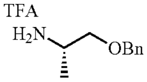 | 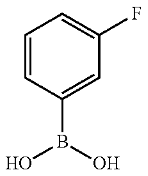 | 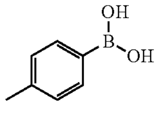 | 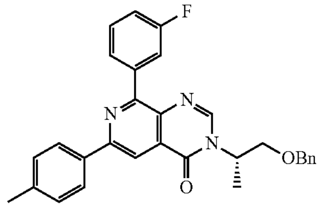 3-[(1S)-2-benzyloxy-1-methyl-ethyl]-8-(3-fluorophenyl)-6-(p-tolyl)pyrido[3,4-d]pyrimidin-4-one | (400 MHz, DMSO-d6) δ ppm 1.47 (d, J = 6.8 Hz, 3H), 2.39 (s, 3H), 3.72-3.76 (m, 1H), 3.87-3.92 (m, 1H), 4.49 (q, J = 12.4, 21.6 Hz, 2H), 5.10-5.12 (m, 1H), 7.20-7.26 (m, 5H), 7.33-7.37 (m, 3H), 7.55-7.62 (m, 1H), 8.02-8.07 (m, 2H), 8.15 (d, J = 8.0 Hz, 2H), 8.44 (s, 1H), 8.57 (s, 1H) | 480.2; 97 |
| 41** | 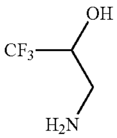 | 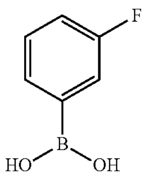 | 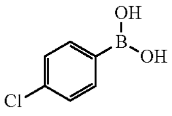 | 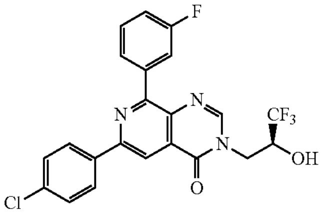 6-(4-chlorophenyl)-8-(3-fluorophenyl)-3-[3,3,3-trifluoro-2-hydroxy-propyl]pyrido[3,4-d[pyrimidin-4-one Enantiomer-1 | (400 MHz, DMSO-d6) δ ppm 4.07 (q, J = 9.6, 14.0 Hz, 1H), 4.45 (d, J = 12.0 Hz, 2H), 6.78 (d, J = 6.4 Hz, 1H), 7.34-7.41 (m, 1H), 7.56-7.64 (m, 3H), 7.96-8.06 (m, 2H), 8.31 (d, J = 8.8 Hz, 2H), 8.49 (s, 1H), 8.54 (s, 1H) | 464.0; 97 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 42** | 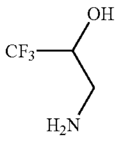 | 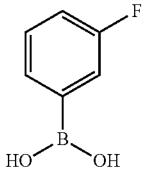 | 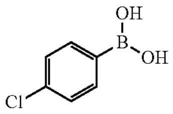 | 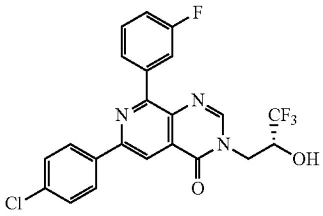 6-(4-chlorophenyl)-8-(3-fluorophenyl)-3-[(3,3,3-trifluoro-2-hydroxy-propyl]pyrido[3,4-d]pyrimidin-4-one Enantiomer-2 | (400 MHz, DMSO-d6) δ ppm 4.07 (q, J = 9.6, 14.0 Hz, 1H), 4.45 (d, J = 12.0 Hz, 2H), 6.78 (d, J = 6.4 Hz, 1H), 7.34-7.41 (m, 1H), 7.56-7.64 (m, 3H), 7.96-8.06 (m, 2H), 8.31 (d, J = 8.8 Hz, 2H), 8.49 (s, 1H), 8.54 (s, 1H). | 464.0; 97 |
| 50 | 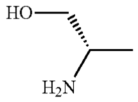 | 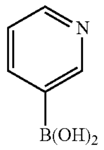 | 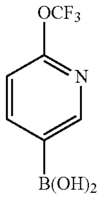 | 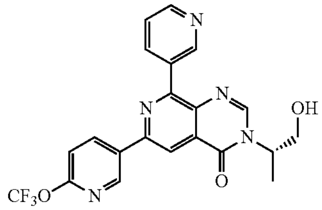 (S)-3-(1-hydroxypropan-2-yl)-8-(pyridin-3-yl)-6-(6-(trifluoromethoxy)pyridin-3-yl)pyrido[3,4-d]pyrimidin-4(3H)-one | ($CH_3OH$-$d_4$, 400 MHz): $\delta_H$ 1.56 (3H, d, J = 7.1 Hz), 3.85 (1H, dd, J = 11.9, 4.3 Hz), 3.97 (1H, dd, J = 11.9, 7.0 Hz), 5.01 (1H, td, J = 7.2, 4.5 Hz), 7.31 (1H, d, J = 8.6 Hz), 7.61 (1H, dd, J = 8.0, 5.0 Hz), 8.46 (1H, s), 8.65-8.63 (2H, m), 8.72 (1H, dd, J = 8.1, 1.7 Hz), 8.77 (1H, dd, J = 8.6, 2.5 Hz), 9.16 (1H, d, J = 2.4 Hz), 9.42 (1H, s). | 444.1; 98% |
| 51 | 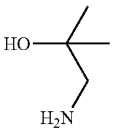 | 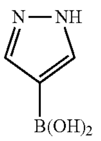 | 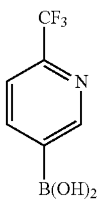 | 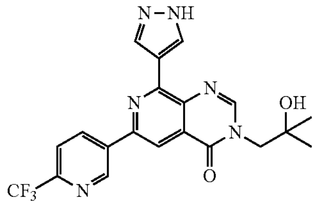 (S)-3-(2-hydroxy-2-methylpropyl)-8-(1H-pyrazol-4-yl)-6-(6-(trifluoromethyl)pyridin-3-yl)pyrido[3,4-d]pyrimidin-4(3H)-one | ($CH_3OH$-$d_4$, 400 MHz): $\delta_H$ 1.27 (6H, s), 4.15 (2H, s), 7.97 (1H, d, J = 8.2 Hz), 8.45 (1H, s), 8.53 (1H, s), 8.88-8.81 (3H, m), 9.55 (1H, s). | 431.1; 98% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 52 | 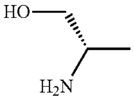 | 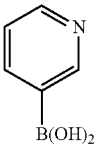 | 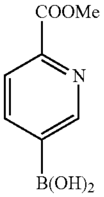 | 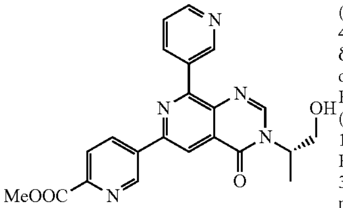 methyl (S)-5-(3-(1-hydroxypropan-2-yl)-4-oxo-8-(pyridin-3-yl)-3,4-dihydropyrido[3,4-d]pyrimidin-6-yl)picolinate | ($CH_3OH-d_4$, 400 MHz): $\delta_H$ 1.56 (3H, d, J = 7.1 Hz), 3.86 (1H, dd, J = 11.9, 4.2 Hz), 3.99-3.94 (1H, m), 4.02 (3H, s), 5.03-4.98 (1H, m), 7.63-7.60 (1H, m), 8.31 (1H, d, J = 8.2 Hz), 8.49 (1H, s), 8.65-8.64 (1H, m), 8.75-8.72 (2H, m), 8.82 (1H, dd, J = 8.2, 2.1 Hz), 9.43 (1H, s), 9.53 (1H, d, J = 2.1 Hz). | 418.1; 99% |
| 53 | 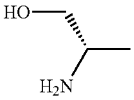 | 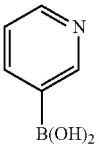 | 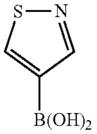 | 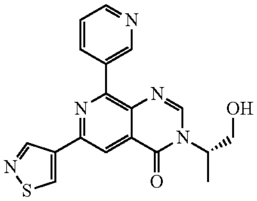 (S)-3-(1-hydroxypropan-2-yl)-6-(isothiazol-4-yl)-8-(pyridin-3-yl)pyrido[3,4-d]pyrimidin-4(3H)-one | ($CH_3OH-d_4$, 400 MHz): $\delta_H$ 1.55 (3H, d, J = 7.1 Hz), 3.85 (1H, dd, J = 11.8, 4.3 Hz), 3.96 (1H, dd, J = 11.9, 7.0 Hz), 5.01-4.97 (1H, m), 7.60 (1H, dd, J = 7.9, 4.9 Hz), 8.43 (1H, s), 8.54 (1H, s), 8.63 (1H, d, J = 4.8 Hz), 8.71 (1H, d, J = 8.1 Hz), 9.26 (1H, s), 9.40 (1H, s), 9.59 (1H, s). | 366.1; 99% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
| --- | --- | --- | --- | --- | --- | --- |
| 54 | 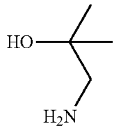 | 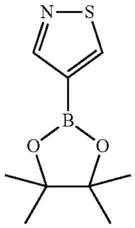 | 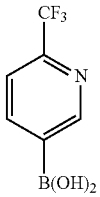 | 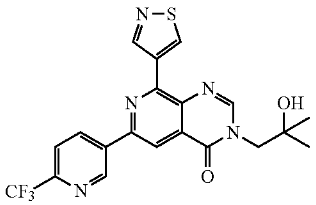 3-(2-hydroxy-2-methylpropyl)-8-(isothiazol-4-yl)-6-(6-(trifluoromethyl)pyridin-3-yl)pyrido[3,4-d]pyrimidin-4(3H)-one | ($CH_3OH-d_4$, 400 MHz): $\delta_H$ 1.30 (6H, d, J = 1.4 Hz), 4.19-4.17 (2H, m), 8.01 (1H, dd, J = 8.3, 1.6 Hz), 8.50 (1H, d, J = 1.4 Hz), 8.71 (1H, d, J = 1.3 Hz), 8.92-8.87 (1H, m), 9.59-9.58 (1H, m), 9.66 (1H, s), 10.20 (1H, d, J = 1.3 Hz). | 447.9; 98% |
| 55 | 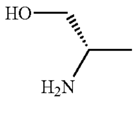 | 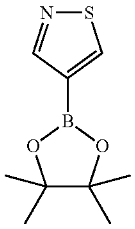 | 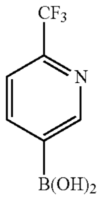 | 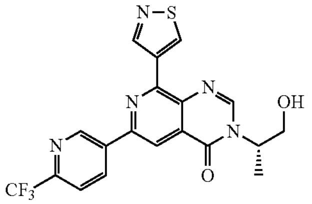 (S)-3-(1-hydroxypropan-2-yl)-8-(isothiazol-4-yl)-6-(6-(trifluoromethyl)pyridin-3-yl)pyrido[3,4-d]pyrimidin-4(3H)-one | ($CH_3OH-d_4$, 300 MHz): $\delta_H$ 1.62-1.57 (3H, m), 3.92-3.86 (1H, m), 4.03-3.96 (1H, m), 5.08-5.02 (1H, m), 8.02-7.99 (1H, m), 8.59-8.59 (1H, m), 8.70-8.70 (1H, m), 8.92-8.88 (1H, m), 95.9-9.58 (1H, m), 9.68-9.68 (1H, m), 10.21-10.20 (1H, m). | 433.9; 98% |
| 56[a] | 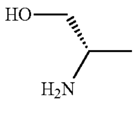 | 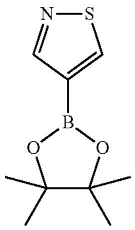 | 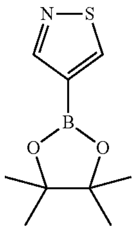 | 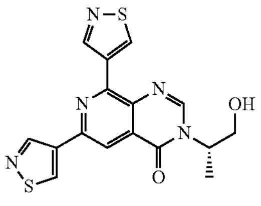 (S)-3-(1-hydroxypropan-2-yl)-6,8-di(isothiazol-4-yl)pyrido[3,4-d]pyrimidin-4(3H)-one | ($CH_3OH-d_4$, 300 MHz): $\delta_H$ 1.57 (3H, d, J = 7.1 Hz), 3.86 (1H, dd, J = 11.9, 4.3 Hz), 3.97 (1H, dd, J = 1.18, 6.9 Hz), 5.03-4.98 (1H, m), 8.45 (1H, s), 8.50-8.49 (1H, m), 9.27 (1H, s), 9.60 (1H, s), 9.63 (1H, s), 10.14 (1H, s). | 371.9; 98% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 57 | 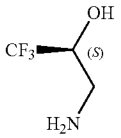 | 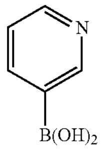 | 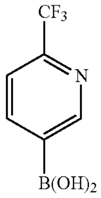 | 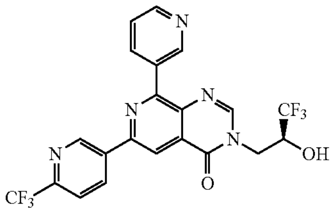 (S)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one | ($CH_3OH-d_4$, 400 MHz): $\delta_H$ 4.08-3.99 (1H, m), 4.49-4.44 (1H, m), 4.69-4.63 (1H, m), 7.67-7.63 (1H, m), 8.04-8.00 (1H, m), 8.44-8.42 (1H, m), 8.69-8.66 (1H, m), 8.77-8.72 (1H, m), 8.82-8.80 (1H, m), 8.91-8.87 (1H, m), 9.45-9.43 (1H, m), 9.60-9.58 (1H, m). | 481.9; 99% |
| 58 | 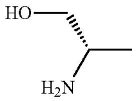 | 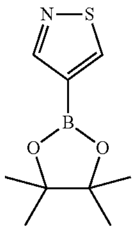 | 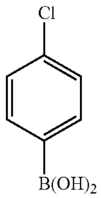 | 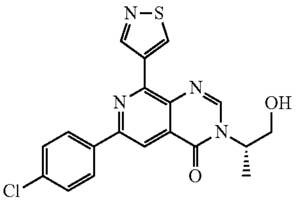 (S)-6-(4-chlorophenyl)-3-(1-hydroxypropan-2-yl)-8-(isothiazol-4-yl)pyrido[3,4-d]pyrimidin-4(3H)-one | ($CH_3O$ H-$d_4$, 400 MHz): $\delta_H$ 1.57 (3H, d, J = 7.1 Hz), 3.86 (1H, dd, J = 11.9, 4.3 Hz), 3.97 (1H, dd, J = 11.9, 6.9 Hz), 5.02-4.97 (1H, m), 7.52 (2H, d, J = 8.3 Hz), 8.21 (2H, d, J = 8.2 Hz), 8.47 (2H, d, J = 14.6 Hz), 9.59 (1H, s), 10.11 (1H, s). | 398.9; 99% |
| 59[b] | 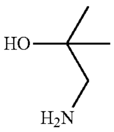 | 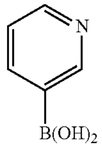 | 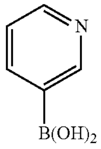 | 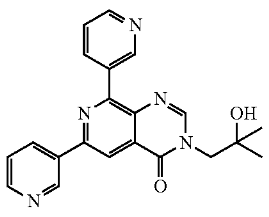 3-(2-hydroxy-2-methylpropyl)-6,8-di(pyridin-3-yl)pyrido[3,4-d]pyrimidin-4(3H)-one | ($CH_3OH-d_4$, 400 MHz): $\delta_H$ 1.27 (6H, s), 4.11 (2H, s), 7.58 (2H, t, J = 6.3 Hz), 8.35 (1H, s), 8.61 (4H, d, J = 8.1 Hz), 8.69 (1H, d, J = 8.1 Hz), 9.34 (1H, s), 9.38 (1H, s). | 374.0; 99% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 60 | 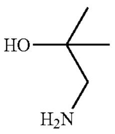 | 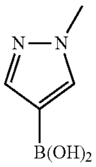 | 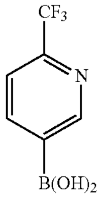 | 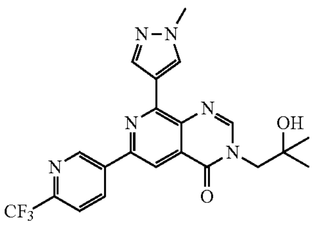 3-(2-hydroxy-2-methylpropyl)-8-(1-methyl-1H-pyrazol-4-yl)-6-(6-(trifluoromethyl)pyridin-3-yl)pyrido[3,4-d]pyrimidin-4(3H)-one | ($CH_3OH-d_4$, 400 MHz): $\delta_H$ 1.27 (6H, s), 4.00 (3H, s), 4.12 (2H, s), 7.95 (1H, d, J = 8.3 Hz), 8.41 (1H, s), 8.45 (1H, s), 8.54 (1H, s), 8.81-8.79 (2H, m), 9.50 1H, s). | 444.9; 99% |
| 61 | 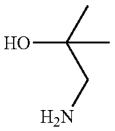 | 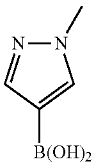 | 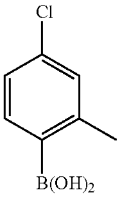 | 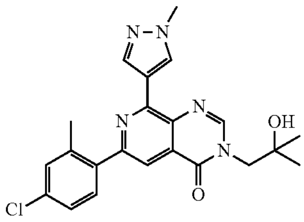 6-(4-chloro-2-methylphenyl)-3-(2-hydroxy-2-methylpropyl)-8-(1-methyl-1H-pyrazol-4-yl)pyrido[3,4-d]pyrimidin-4(3H)-one | ($CH_3OH-d_4$, 400 MHz): $\delta_H$ 1.26 (6H, s), 2.45 (3H, s), 3.97 (3H, s), 4.12 (2H, s), 7.31 (1H, d, J = 8.3 Hz), 7.36 (1H, s), 7.50 (1H, d, J = 8.2 Hz), 7.94 (1H, s), 8.40 (1H, s), 8.44 (1H, s), 8.72 (1H, s). | 423.9; 99 |
| 62 | 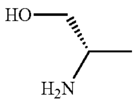 | 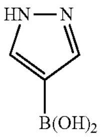 | 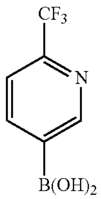 | 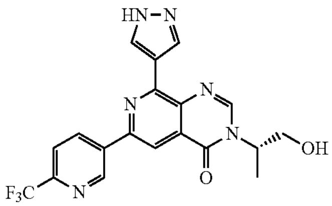 (S)-3-(1-hydroxypropan-2-yl)-8-(1H-pyrazol-4-yl)-6-(6-(trifluoromethyl)pyridin-3-yl)pyrido[3,4-d]pyrimidin-4(3H)-one | ($DMSO-d_6$, 400 MHz): $\delta_H$ 1.44 (3H, d, J = 7.0 Hz), 3.70-3.65 (1H, m), 3.82-3.77 (1H, m), 4.89 (1H, d, J = 7.7 Hz), 5.09 (1H, t, J = 5.6 Hz), 8.02 (1H, d, J = 8.3 Hz), 8.49 (1H, s), 8.59 (1H, s), 8.60 (1H, s), 8.86 (1H, s), 8.93 (1H, d, J = 8.3 Hz), 9.64 (1H, s), 13.22 (1H, s). | 417.1; >98 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 63 | 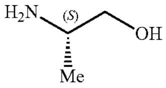 | 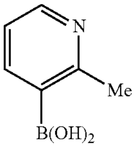 | 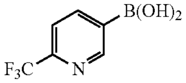 | 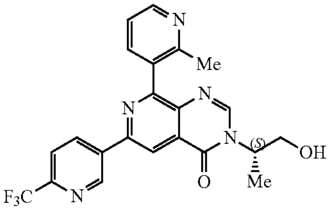 (S)-3-(1-hydroxypropan-2-yl)-8-(2-methylpyridin-3-yl)-6-(6-(trifluoromethyl)pyridin-3-yl)pyrido[3,4-d]pyrimidin-4(3H)-one | (300 MHz, DMSO-$d_6$): $\delta_H$ 9.58 (1 H, d, J 1.8), 8.90-8.84 (2 H, m), 8.76 (1 H, dd, J 5.5, 1.7), 8.52 (1 H, s), 8.23 (1 H, d, J 6.7), 8.05 (1 H, d, J 8.3), 7.69 (1 H, dd, J 8.2, 5.2), 4.95-4.85 (1 H, m), 3.79 (1 H, dd, J 11.6, 7.3), 3.68 (1 H, dd, J 11.4, 4.6), 2.51 (3 H, s), 1.43 (3 H, d, J 7.0). | 442.1; 99.6 |
| 64 | 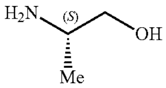 | 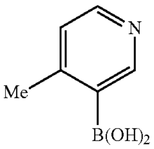 | 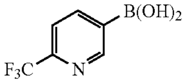 | 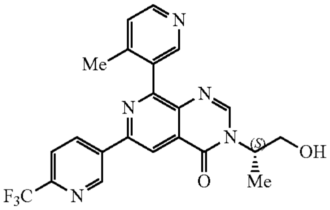 (S)-3-(1-hydroxypropan-2-yl)-8-(4-methylpyridin-3-yl)-6-(6-(trifluoromethyl)pyridin-3-yl)pyrido[3,4-d]pyrimidin-4(3H)-one | (300 MHz, DMSO-$d_6$): $\delta_H$ 9.57 (1 H, s), 8.86 (1 H, d, J 7.7), 8.80 (1 H, s), 8.58 (1 H, s), 8.54 (1 H, d, J 4.9), 8.50 (1 H, s), 8.04 (1 H, d, J 8.3), 7.42 (1 H, d, J 4.9), 5.07 (1 H, t, J 5.3), 4.90 (1 H, dd, J 12.0, 6.6), 3.84-3.74 (1 H, m), 3.72-3.63 (1 H, m), 2.24 (3H, s), 1.42 (3H, d, J 7.0). | 442.9 98.3 |
| 65 | 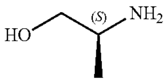 | 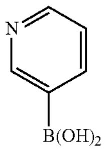 | 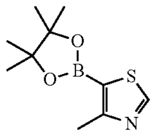 | 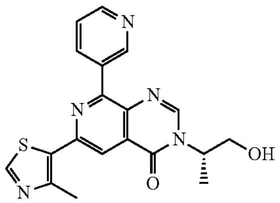 [SMILES: Cc1ncsc1-c1cc2c(=O)n([C@@H](C)CO)cnc2c(-c2cccnc2)n1] | (DMSO-$d_6$, 400 MHz): $\delta_H$ 1.42 (3H, d, J = 7.0 Hz), 3.32 (2H, s), 3.67-3.64 (1H, m), 3.81-3.77 (1H, m), 4.89-4.84 (1H, m), 5.08 (1H, s), 7.57 (1H, dd, J = 7.9, 4.8 Hz), 8.22 (1H, s), 8.47 (1H, d, J = 8.0 Hz), 8.55 (1H, s), 8.67 (1H, d, J = 4.7 Hz), 9.07 (1H, s), 9.26 (1H, s). | 380.0; >99 |

TABLE 5-continued
| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 66 | 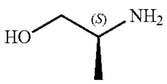 | 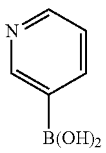 | 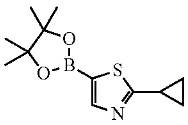 [SMILES: CC1(C)OB(c2cnc(C3CC3)s2)OC1(C)C] | 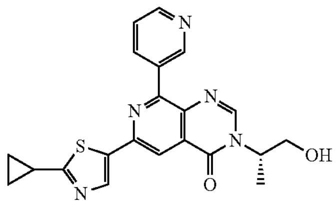 [SMILES: C[C@@H](CO)n1cnc2c(-c3cccnc3)nc(-c3cnc(C4CC4)s3)cc2c1=O] | (DMSO-$d_6$, 400 MHz): $\delta_H$ 1.04-1.01 (2H, m), 1.18-1.13 (2H, m), 1.41 (3H, d, J = 7.0 Hz), 2.45-2.40 (1H, m), 3.68-3.63 (1H, m), 3.81-3.75 (1H, m), 4.89-4.84 (1H, m), 5.06 (1H, t, J = 5.6 Hz), 7.56 (1H, dd, J = 7.9, 4.8 Hz), 8.48-8.43 (4H, m), 8.66-8.65 (1H, m), 9.25 (1H, s). | 406.1; 98 |
| 67 | 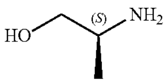 | 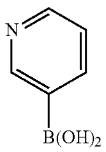 | 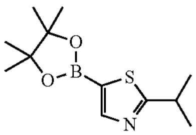 [SMILES: CC(C)c1ncc(B2OC(C)(C)C(C)(C)O2)s1] | 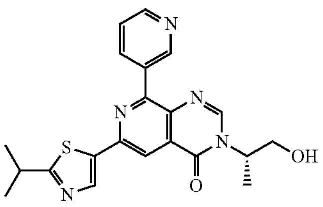 [SMILES: CC(C)c1ncc(-c2cc3c(=O)n([C@@H](C)CO)cnc3c(-c3cccnc3)n2)s1] | (DMSO-$d_6$, 400 MHz): $\delta_H$ 1.35 (3H, s), 1.37 (3H, s), 1.42 (3H, d, J = 7.0 Hz), 3.69-3.63 (1H, m), 3.81-3.75 (1H, m), 4.89-4.84 (1H, m), 5.05 (1H, t, J = 5.6 Hz), 7.56 (1H, dd, J = 7.9, 4.8 Hz), 8.46 (1H, d, J = 8.1 Hz), 8.50 (2H, d, J = 4.9 Hz), 8.55 (1H, s), 8.67-8.66 (1H, m), 9.25 (1H, d, J = 2.1 Hz). | 408.1; 99 |
| 68 | 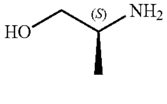 | 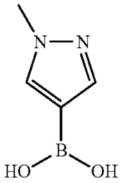 | 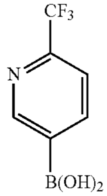 | 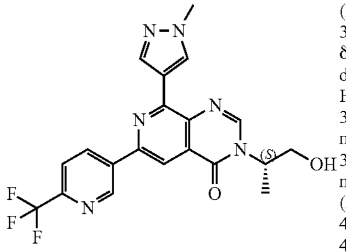 | (DMSO-$d_6$, 300 MHz): $\delta_H$ 1.47 (3H, d, J = 7.0 Hz), 3.74-3.68 (1H, m), 3.87-3.78 (1H, m), 3.98 (3H, s), 4.96-4.85 (1H, m), 5.18-5.08 (1H, m), 8.03 (1H, d, J = 8.3 Hz), 8.50 (1H, s), 8.55 | 431.1; 98 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| | | | | | (1H, s), 8.61 (1H, s), 8.85 (1H, s), 8.94 (1H, d, J = 8.4 Hz), 9.66 (1H, s). | |
| 69[a] | 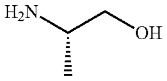 | 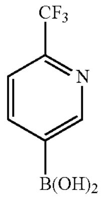 [SMILES: OB(O)c1ccc(C(F)(F)F)nc1] | 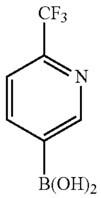 [SMILES: OB(O)c1ccc(C(F)(F)F)nc1] | 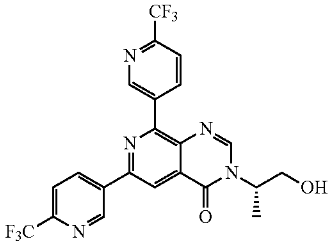 (S)-3-(1-hydroxypropan-2-yl)-6,8-bis(6-(trifluoromethyl)pyridin-3-yl)pyrido[3,4-d]pyrimidin-4(3H)-one | (DMSO-$d_6$, 300 MHz): $\delta_H$ 1.46 (3H, d, J = 7.0 Hz), 3.85-3.67 (2H, m), 4.96-4.90 (1H, m), 5.10 (1H, t, J = 5.6 Hz), 8.10 (2H, dd, J = 16.8, 8.3 Hz), 8.64 (1H, s), 8.83 (1H, s), 8.96-8.85 (2H, m), 9.55 (1H, s), 9.66 (1H, s). | 496.1; 99 |
| 70[c] | 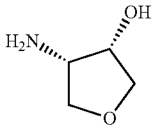 3S, 4S | 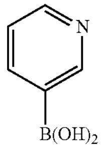 | 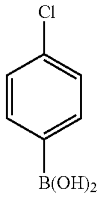 | 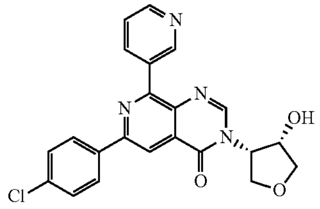 6-(4-chlorophenyl)-3-((3S,4S)-4-hydroxytetrahydrofuran-3-yl)-8-(pyridin-3-yl)pyrido[3,4-d]pyrimidin-4(3H)-one. Enantiomer 1 | (DMSO-$d_6$, 400 MHz): $\delta_H$ 3.77 (1H, d, J = 9.8 Hz), 4.02-3.92 (2H, m), 4.20-4.16 (1H, m), 4.50 (1H, s), 5.38 (1H, q, J = 6.7 Hz), 5.47 (1H, d, J = 3.8 Hz), 7.58 (3H, t, J = 8.5 Hz), 8.30 (2H, d, J = 8.4 Hz), 8.34 (1H, s), 8.54 (2H, m), 8.68 (1H, d, J = 4.8 Hz), 9.33 (1H, s). | 421.1; 99% |
| 71[c] | 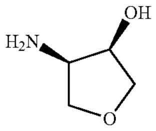 3R, 4R | 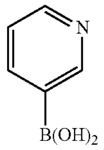 | 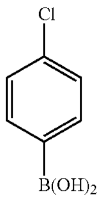 | 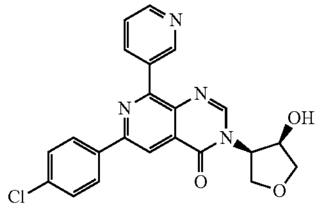 6-(4-chlorophenyl)-3-((3R,4R)-4-hydroxytetrahydrofuran-3-yl)-8-(pyridin-3-yl)pyrido[3,4-d]pyrimidin-4(3H)-one Enantiomer 2 | ($CH_3OH$-$d_4$, 400 MHz): $\delta_H$ 3.95 (1H, d, J = 10.2 Hz), 4.04-4.00 (1H, m), 4.10 (1H, t, J = 8.7 Hz), 4.22 (1H, dd, J = 10.2, 5.1 Hz), 4.67 (1H, m), 5.58 (1H, q, J = 6.2 Hz), 7.50 (2H, d, J = 8.4 Hz), 7.57 (1H, t, J = 6.4 Hz), 8.19 (2H, d, J = 8.4 Hz), | 421.1; 99 |

TABLE 5-continued

| Com-po und No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| | | | | | 8.39 (1H, s), 85.6 (1H, s), 8.61 (1H, d, J = 4.8 Hz), 8.69 (1H, d, J = 8.0 Hz), 9.38 (1H, s). | |
| 72 | 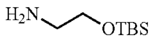 | 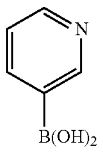 | 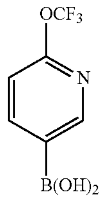 | 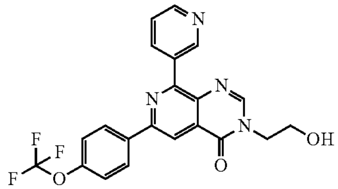 3-(2-hydroxyethyl)-8-(pyridin-3-yl)-6-(4-(trifluoromethoxy)phenyl)pyrido[3,4-d]pyrimidin-4(3H)-one | (DMSO-$d_6$, 400 MHz): $\delta_H$ 3.71-3.70 (2H, m), 4.10 (2H, t, J = 5.1 Hz), 4.99 (1H, t, J = 4.7 Hz), 7.52 (2H, d, J = 8.4 Hz), 7.58 (1H, dd, J = 8.0, 4.9 Hz), 8.41 (2H, d, J = 8.6 Hz), 8.43 (1H, s), 8.55-8.52 (2H, m), 8.68 (1H, d, J = 4.8 Hz), 9.32 (1H, s). | 429.1; 99 |
| 73 | 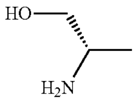 | 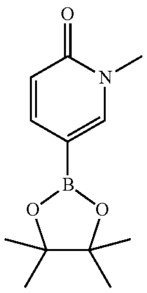 | 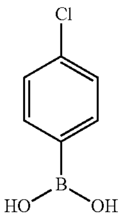 | 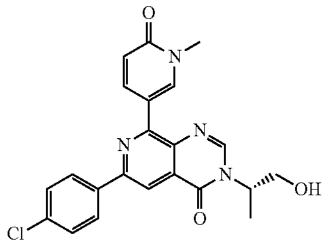 (S)-6-(4-chlorophenyl)-3-(1-hydroxypropan-2-yl)-8-(1-methyl-6-oxo-1,6-dihydropyridin-3-yl)pyrido[3,4-d]pyrimidin-4(3H)-one | (DMSO-$d_6$, 400 MHz): $\delta_H$ 1.43 (3H, d, J = 7.0 Hz), 3.59 (3H, s), 3.70-3.65 (1H, m), 3.82-3.77 (1H, m), 4.92-4.87 (1H, m), 5.08 (1H, t, J = 5.5 Hz), 6.56 (1H, d, J = 9.5 Hz), 7.60-7.57 (2H, m), 8.31-8.29 (2H, m), 8.40 (1H, s), 8.47 (1H, dd, J = 9.6, 2.6 Hz), 8.57 (1H, s), 9.01 (1H, d, J = 2.6 Hz). | 423.1; 95 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 74 | 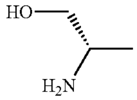 | 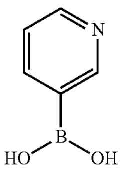 | 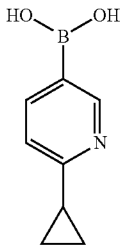 | 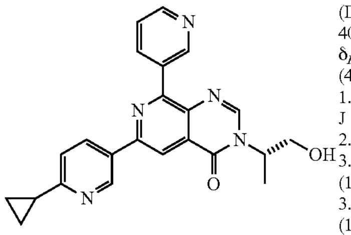 (S)-6-(6-cyclopropylpyridin-3-yl)-3-(1-hydroxypropan-2-yl)-8-(pyridin-3-yl)pyrido[3,4-d]pyrimidin-4(3H)-one | (DMSO-$d_6$, 400 MHz): $\delta_H$ 1.03-1.01 (4H, m), 1.44 (3H, d, J = 7.0 Hz), 2.20 (1H, s), 3.71-3.67 (1H, m), 3.82-3.77 (1H, m), 4.90 (1H, d, J = 7.9 Hz), 5.08 (1H, t, J = 5.6 Hz), 7.46 (1H, d, J = 8.2 Hz), 7.58 (1H, dd, J = 8.0, 4.8 Hz), 8.48 (1H, dd, J = 8.2, 2.4 Hz), 8.55 (3H, t, J = 5.3 Hz), 8.69 (1H, dd, J = 4.8, 1.7 Hz), 9.26 (1H, d, J = 2.3 Hz), 9.35 1H), d, J = 2.2 Hz). | 400.0; 99 |
| 75 | 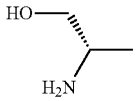 | 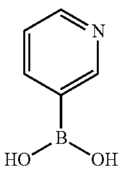 | 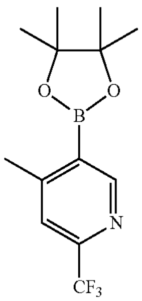 | 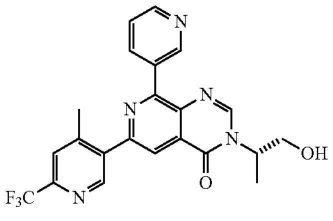 (S)-3-(1-hydroxypropan-2-yl)-6-(4-methyl-6-(trifluoromethyl)pyridin-3-yl)-8-(pyridin-3-yl)pyrido[3,4-d]pyrimidin-4(3H)-one | (DMSO-$d_6$, 400 MHz): $\delta_H$ 1.44 (3H, d, J = 7.0 Hz), 2.59 (3H, s), 3.71-3.67 (1H, m), 3.85-3.79 (1H, m), 4.93-4.87 (1H, m), 5.08 (1H, t, J = 5.6 Hz), 7.57 (1H, dd, J = 7.9, 4.8 Hz), 7.98 (1H, s), 8.33 (1H, s), 8.50-8.47 (1H, m), 8.63 (1H, s), 8.68 (1H, dd, J = 4.8, 1.7 Hz), 8.94 (1H, s), 9.29 (1H, d, J = 2.1 Hz). | 441.9; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 76 | 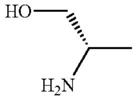 | 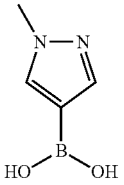 | 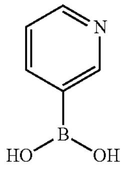 | 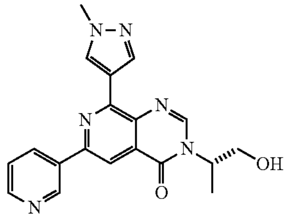 (S)-3-(1-hydroxypropan-2-yl)-8-(1-methyl-1H-pyrazol-4-yl)-6-(pyridin-3-yl)pyrido[3,4-d]pyrimidin-4(3H)-one | (DMSO-$d_6$, 400 MHz): $\delta_H$ 1.45 (3H, d, J = 7.0 Hz), 3.71-3.66 (1H, m), 3.85-3.79 (1H, m), 3.97 (3H, s), 4.92-4.87 (1H, m), 5.10 (1H, t, J = 5.6 Hz), 7.56 (1H, dd, J = 8.0, 4.8 Hz), 8.37 (1H, s), 8.53 (1H, s), 8.57 (1H, s), 8.67-8.63 (2H, m), 8.83 (1H, s), 9.46 (1H, s). | 363.0; 99 |
| 77 | 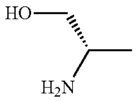 | 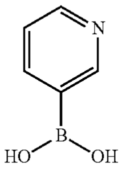 | 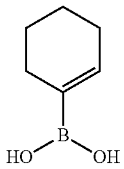 | 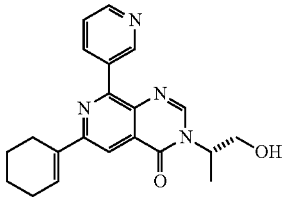 (S)-6-(cyclohex-1-en-1-yl)-3-(1-hydroxypropan-2-yl)-8-(pyridin-3-yl)pyrido[3,4-d]pyrimidin-4(3H)-one | ($CHCl_3$-d, 300 MHz): δ 1.58 (3H, d, J = 7.0 Hz), 1.76-1.70 (2H, m), 1.89-1.81 (2H, m), 2.37-2.31 (2H, m), 2.63-2.59 (2H, m), 3.98 (2H, d, J = 4.8 Hz), 5.08-5.00 (1H, m), 7.09-7.06 (1H, m), 7.40 (1H, dd, J = 8.0, 4.8 Hz), 8.07 (1H, s), 8.22 (1H, s), 8.47 (1H, dt, J = 8.0, 2.0 Hz), 8.64 (1H, d, J = 4.9 Hz), 9.37 (1H, s). | 363.0; 95 |
| 78[a] | 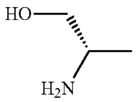 | 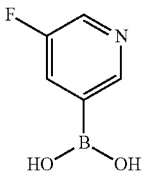 | 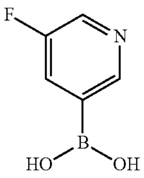 | 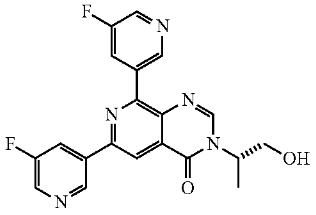 (S)-6,8-bis(5-fluoropyridin-3-yl)-3-(1-hydroxypropan-2-yl)pyrido[3,4-d]pyrimidin-4(3H)-one | (DMSO-$d_6$, 300 MHz): $\delta_H$ 1.46-1.42 (3H, m), 3.74-3.68 (1H, m), 3.82-3.77 (1H, m), 4.93-4.91 (1H, m), 5.11-5.07 (1H, m), 8.61-8.55 (1H, m), 8.66-8.61 (2H, m), 8.70-8.69 (1H, m), 8.74-8.73 (2H, m), | 395.9; 98 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| | | | | | 9.33-9.32 (1H, m), 9.38 (1H, d, J = 1.8 Hz). | |
| 79 | 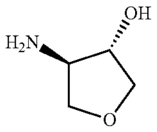 | 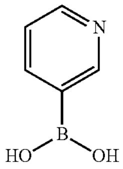 | 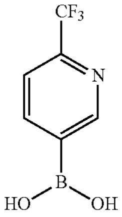 | 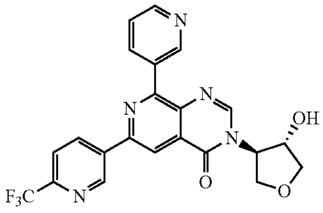 3-((3R,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one | (DMSO-d$_6$, 400 MHz): $\delta_H$ 3.64 (1H, dd, J = 9.6, 3.3 Hz), 4.08 (1H, dd, J = 10.1, 4.0 Hz), 4.23-4.14 (2H, m), 4.60 (1H, dd, J = 5.3, 2.9 Hz), 5.01-4.98 (1H, m), 5.71 (1H, d, J = 4.4 Hz), 7.60 (1H, dd, J = 8.0, 4.8 Hz), 8.07 (1H, d, J = 8.4 Hz), 8.43 (1H, s), 8.58 (1H, dt, J = 8.0, 1.9 Hz), 8.71 (1H, dd, J = 4.8, 1.7 Hz), 8.79 (1H, s), 8.95 (1H, dd, J = 8.3, 2.1 Hz), 9.37 (1H, d, J = 2.2 Hz), 9.65 (1H, s). | 466.1; 98 |
| 80 | 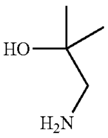 | 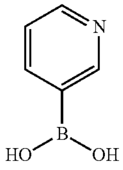 | 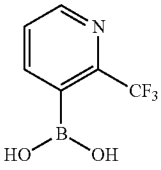 [SMILES: OB(O)c1cccnc1C(F)(F)F] | 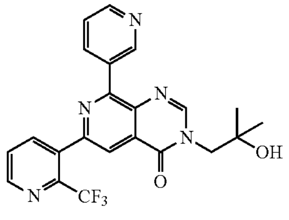 3-(2-hydroxy-2-methylpropyl)-8-(pyridin-3-yl)-6-(2-(trifluoromethyl)pyridin-3-yl)pyrido[3,4-d]pyrimidin-4(3H)-one | (DMSO-d$_6$, 300 MHz): $\delta_H$ 1.16 (6H, s), 4.05 (2H, s), 4.88 (1H, s), 7.57 (1H, dd, J = 7.9, 4.8 Hz), 7.88 (1H, dd, J = 7.9, 4.7 Hz), 8.32-8.27 (2H, m), 8.49-8.45 (2H, m), 8.68 (1H, d, J = 4.7 Hz), 8.87 (1H, d, J = 4.7 Hz), 9.28 (1H, s). | 441.9; 98 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 81 | 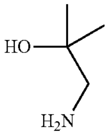 | 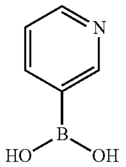 | 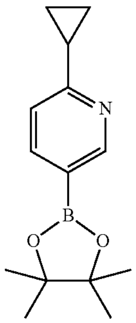 | 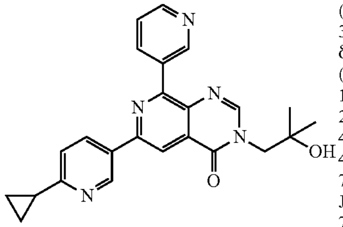 6-(6-cyclopropylpyridin-3-yl)-3-(2-hydroxy-2-methylpropyl)-8-(pyridin-3-yl)pyrido[3,4-d]pyrimidin-4(3H)-one | (DMSO-$d_6$, 300 MHz): $\delta_H$ 1.03-1.00 (4H, m), 1.16 (6H, s), 2.20 (1H, s), 4.04 (2H, s), 4.87 (1H, s), 7.45 (1H, d, J = 8.2 Hz), 7.58 (1H, dd, J = 8.0, 4.8 Hz), 8.38 (1H, s), 8.48 (1H, d, J = 8.5 Hz), 8.56-8.54 (2H, m), 8.69 (1H, d, J = 4.8 Hz), 9.26 (1H, s), 9.34 (1H, s). | 414.0; 98 |
| 82 | 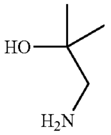 | 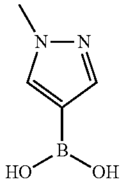 | 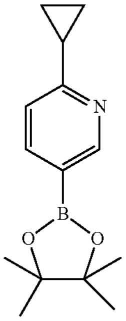 | 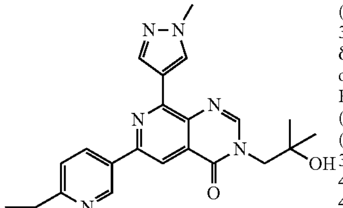 6-(6-cyclopropylpyridin-3-yl)-3-(2-hydroxy-2-methylpropyl)-8-(1-methyl-1H-pyrazol-4-yl)pyrido[3,4-d[pyrimidin-4(3H)-one | (DMSO-$d_6$, 300 MHz): $\delta_H$ 1.01 (4H, d, J = 6.6 Hz), 1.15 (6H, s), 2.20 (1H, m), 3.96 (3H, s), 4.03 (2H, s), 4.89 (1H, s), 7.44 (1H, d, J = 8.2 Hz), 8.29 (1H, s), 8.40 (1H, s), 8.49-8.46 (2H, m), 8.83 (1H, s), 9.28 (1H, s). | 417.0; 99 |
| 83 | 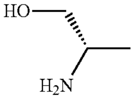 | 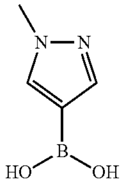 | 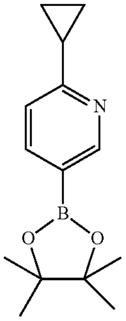 | 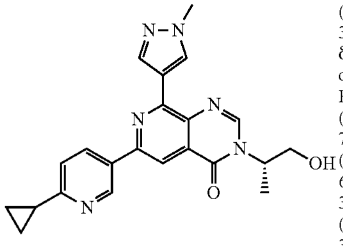 (S)-6-(6-cyclopropylpyridin-3-yl)-3-(1-hydroxypropan-2-yl)-8-(1-methyl-1H-pyrazol-4-yl)pyrido[3,4-d]pyrimidin-4(3H)-one | (DMSO-$d_6$, 300 MHz): $\delta_H$ 1.02 (4H, d, J = 6.5 Hz), 1.45 (3H, d, J = 7.0 Hz), 2.21 (1H, t, J = 6.9 Hz), 3.71-3.66 (1H, m), 3.82 (1H, d, J = 10.3 Hz), 3.97 (3H, s), 4.90 (1H, d, J = 8.1 Hz), 5.09 (1H, t, J = 5.7 Hz), 7.45 (1H, d, J = 8.3 Hz), 8.29 (1H, s), 8.53-8.46 (3H, m), 8.82 (1H, s), 9.28 (1H, s). | 403.2; 99 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 84 | 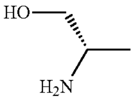 | 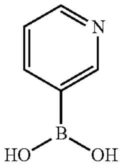 | 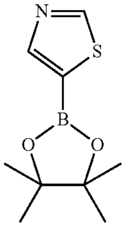 | 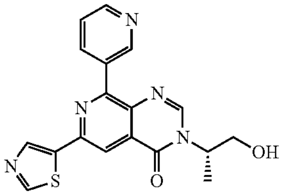 (S)-3-(1-hydroxypropan-2-yl)-8-(pyridin-3-yl)-6-(thiazol-5-yl)pyrido[3,4-d]pyrimidin-4(3H)-one | (DMSO-$d_6$, 300 MHz): $\delta_H$ 1.44 (3H, d, J = 7.0 Hz), 3.75 (2H, d, J = 33.2 Hz), 4.90 (1H, s), 5.08 (1H, s), 7.60 (1H, s), 8.60-8.48 (3H, m), 8.70 (1H, s), 8.85 (1H, s), 9.21 (1H, s), 9.29 (1H, s). | 365.9; 99 |
| 85 | 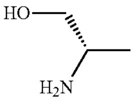 | 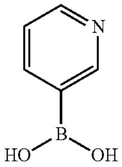 | 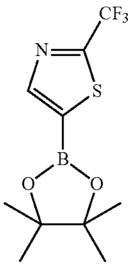 | 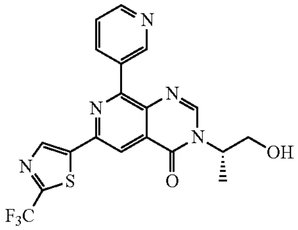 (S)-3-(1-hydroxypropan-2-yl)-8-(pyridin-3-yl)-6-(2-(trifluoromethyl)thiazol-5-yl)pyrido[3,4-d]pyrimidin-4(3H)-one | (DMSO-$d_6$, 300 MHz): $\delta_H$ 1.44 (3H, d, J = 7.0 Hz), 3.75 (2H, d, J = 32.7 Hz), 4.91 (1H, br s), 5.08 (1H, s), 7.59 (1H, s), 8.50 (1H, d, J = 8.1 Hz), 8.60 (1H, s), 8.71 (1H, s), 8.79 (1H, s), 9.10 (1H, s), 9.30 (1H, s). | 433.9; 98 |
| 86 | 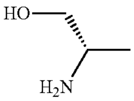 | 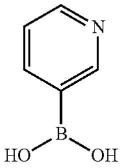 | 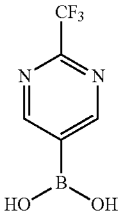 | 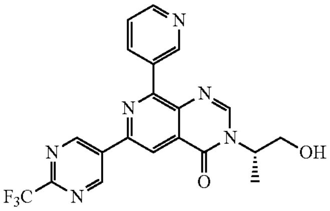 (S)-3-(1-hydroxypropan-2-yl)-8-(pyridin-3-yl)-6-(2-(trifluoromethyl)pyrimidin-5-yl)pyrido[3,4-d]pyrimidin-4(3H)-one | (DMSO-$d_6$, 400 MHz): $\delta_H$ 1.46 (3H, d, J = 7.1 Hz), 3.76 (2H, d, J = 45.5 Hz); 5.01 (2H, d, J = 72.5 Hz), 7.62 (1H, t, J = 6.3 Hz), 8.71-8.62 (3H, m), 8.89 (1H, s), 9.42 (1H, s), 9.91 (2H, s). | 429.1; 99 |
| 87 | 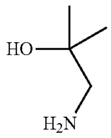 | 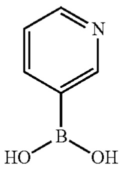 | 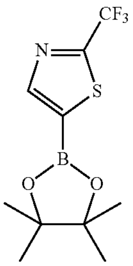 | 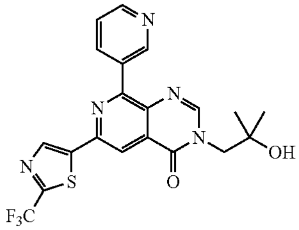 3-(2-hydroxy-2-methylpropyl)-8-(pyridin-3-yl)-6-(2-(trifluoromethyl)thiazol-5-yl)pyrido[3,4-d]pyrimidin-4(3H)-one | (DMSO-$d_6$, 400 MHz): $\delta_H$ 1.16 (6H, s), 4.05 (2H, s), 4.88 (1H, s), 7.60 (1H, dd, J = 8.0, 4.8 Hz), 8.42 (1H, s), 8.50 (1H, d, J = 8.0 Hz), 8.71 (1H, d, J = 4.8 Hz), 8.81 (1H, s), 9.10 (1H, s), 9.29 (1H, s). | 448.1; 99 |

TABLE 5-continued

| Com- po und No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 88 | 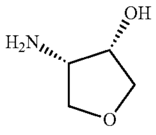 | 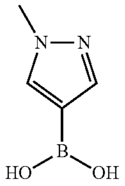 | 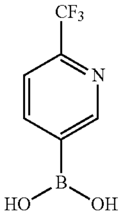 | 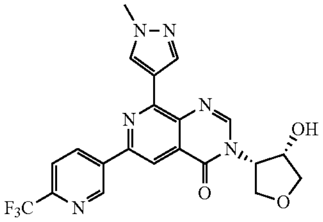 3-((3S,4S)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one | (DMSO-d$_6$, 400 MHz): $\delta_H$ 3.80 (1H, dd, J = 9.7, 2.2 Hz), 3.96-3.93 (4H, m), 4.02 (1H, dd, J = 9.9, 7.5 Hz), 4.22 (1H, dd, J = 9.9, 5.5 Hz), 4.54-4.51 (1H, m), 5.43 (1H, q, J = 6.5 Hz), 5.51 (1H, d, J = 4.4 Hz), 8.03 (1H, d, J = 8.3 Hz), 8.41 (1H, s), 8.52 (1H, s), 8.55 (1H, s), 8.89 (1H, s), 8.95 (1H, dd, J = 8.3, 2.1 Hz), 9.66 (1H, s). | 459.1; 98 |
| 89 | 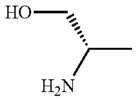 | 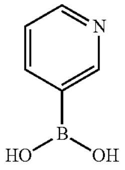 | 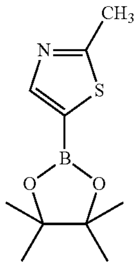 | 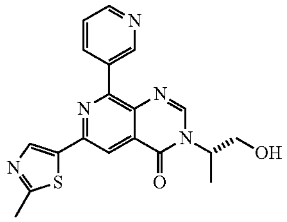 (S)-3-(1-hydroxypropan-2-yl)-6-(2-methylthiazol-5-yl)-8-(pyridin-3-yl)pyrido[3,4-d]pyrimidin-4(3H)-one | (DMSO-d$_6$, 400 MHz): $\delta_H$ 1.43 (3H, d, J = 7.0 Hz), 2.71 (3H, s), 3.69-3.64 (1H, m), 3.80 (1H, dt, J = 11.7, 6.1 Hz), 4.91-4.86 (1H, m), 5.07 (1H, t, J = 5.7 Hz), 7.58 (1H, dd, J = 8.0, 4.8 Hz), 8.55-8.47 (4H, m), 8.69 (1H, d, J = 4.8 Hz), 9.28 (1H, s). | 379.9; 95 |

TABLE 5-continued

| Com-po und No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 90[d] | 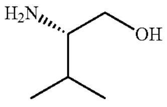 | 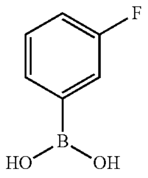 | 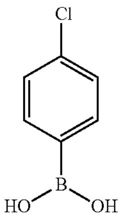 | 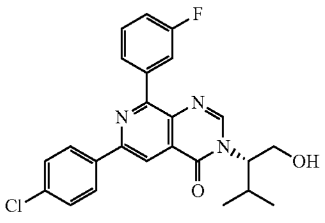 (S)-6-(4-chlorophenyl)-8-(3-fluorophenyl)-3-(1-hydroxy-3-methylbutan-2-yl)pyrido[3,4-d]pyrimidin-4(3H)-one | (400 MHz, DMSO-d6): $\delta_H$ ppm 8.40-8.61 (m, 2H), 8.19-8.35 (m, 2H), 7.97-8.14 (m, 2H), 7.53-7.67 (m, 3H), 7.33-7.38 (m, 1H), 5.02 (s, 1H), 4.18-4.70 (m, 1H), 3.88-4.00 (m, 1H), 3.79 (d, J = 11.8, 3.5 Hz, 1H), 2.20-2.42 (m, 1H), 1.07 (d, J = 6.6 Hz, 3H), 0.79 (d, J = 6.7 Hz, 3H); | 438.2; 99.9 |
| 91 | 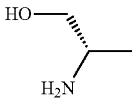 | 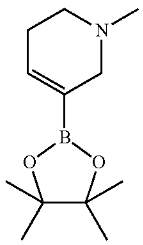 | 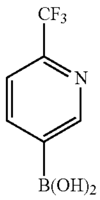 | 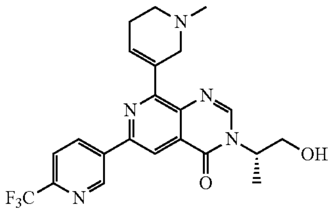 (S)-3-(1-hydroxypropan-2-yl)-8-(1-mehtyl-1,2,5,6-tetrahydropyridin-3-yl)-6-(6-(trifluoromethyl)pyridin-3-yl)pyrido[3,4-d]pyrimidin-4(3H)-one | ($CH_3OH-d_4$, 400 MHz): $\delta_H$ 1.54 (3H, d, J = 7.1 Hz), 2.51 (3H, s), 2.57 (2H, s), 2.73 (2H, t, J = 5.8 Hz), 3.72 (2H, s), 3.84 (1H, dd, J = 11.3, 4.0 Hz), 3.96 (1H, dd, J = 11.9, 6.9 Hz), 4.97 (2H, br s), 7.34 (1H, s), 7.96 (1H, d, J = 8.3 Hz), 8.43 (1H, s), 8.58 (1H, s), 8.77 (1H, d, J = 8.3 Hz), 9.48 (1H, s). | 446.2; 95% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 92 | 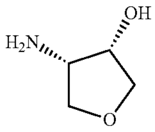 | 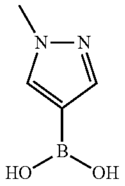 | 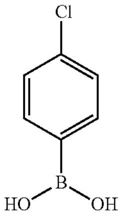 | 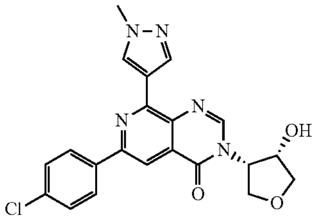 6-(4-chlorophenyl)-3-((3S,4S)-4-hydroxytetrahydrofuran-3-yl)-8-(1-methyl-1H-pyrazol-4-yl)pyrido[3,4-d]pyrimidin-4(3H)-one | (DMSO-$d_6$, 400 MHz): δ 3.79 (1H, d, J = 9.7 Hz), 4.02-3.92 (5H, m), 4.20 (1H, dd, J = 9.9, 5.6 Hz), 4.52 (1H, s), 5.41 (1H, q, J = 6.5 Hz), 5.50 (1H, d, J = 4.2 Hz), 7.59 (2H, d, J = 8.3 Hz), 8.35-8.30 (4H, m), 8.50 (1H, s), 8.84 (1H, s). | 424.; 99 |
| 93 | 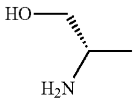 | 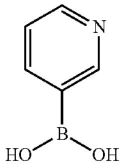 | 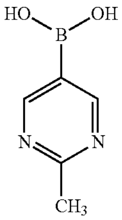 | 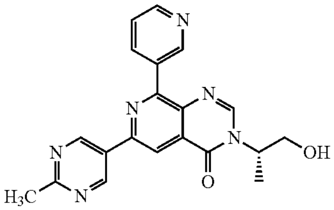 (S)-3-(1-hydroxypropan-2-yl)-6-(2-methylpyrimidin-5-yl)-8-(pyridin-3-yl)pyrido[3,4-d]pyrimidin-4(3H)-one | (DMSO-$d_6$, 400 MHz): δ 1.44 (3H, d, J = 7.0 Hz), 2.72 (3H, s), 3.71-3.65 (1H, m), 3.84-3.78 (1H, m), 4.93-4.88 (1H, m), 5.09 (1H, t, J = 5.7 Hz), 7.60 (1H, d, J = 6.8 Hz), 8.58-8.55 (2H, m), 8.70-8.69 (2H, m), 9.36 (1H, s), 9.53 (2H, s). | 375.1; 99 |
| 94 | 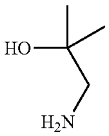 | 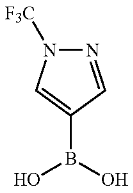 | 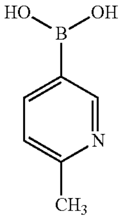 | 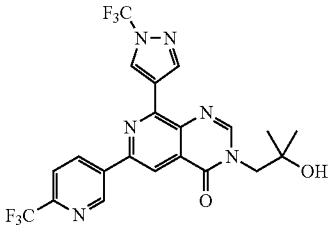 3-(2-hydroxy-2-methylpropyl)-8-(1-(trifluoromethyl)-1H-pyrazol-4-yl)-6-(6-(trifluoromethyl)pyridin-3-yl)pyrido[3,4-d]pyrimidin-4(3H)-one | (DMSO-$d_6$, 400 MHz): δ 1.16 (6H, s), 4.06 (2H, s), 4.94 (1H, s), 8.04 (1H, d, J = 8.3 Hz), 8.52 (1H, s), 8.68 (1H, s), 9.03 (2H, s), 9.48 (1H, s), 9.75 (1H, s). | 499.1; 96.6 |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 95 | 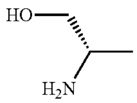 | 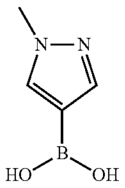 | 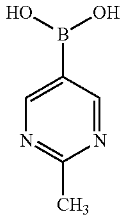 | 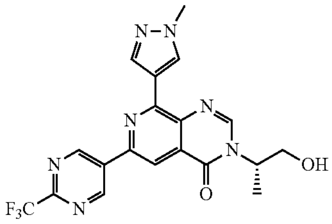 (S)-3-(1-hydroxypropan-2-yl)-8-(1-methyl-1H-pyrazol-4-yl)-6-(2-(trifluoromethyl)pyrimidin-5-yl)pyrido[3,4-d]pyrimidin-4(3H)-one | (DMSO-$d_6$, 400 MHz): δ 1.46 (3H, d, J = 7.0 Hz), 3.71-3.66 (1H, m), 3.85-3.79 (1H, m), 3.97 (3H, s), 4.93-4.88 (1H, m), 5.12 (1H, t, J = 5.6 Hz), 8.60 (1H, s), 8.62 (2H, s), 8.90 (1H, s), 9.92 (2H, s). | 432.1; 95.7 |
| 96 | 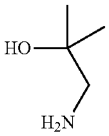 | 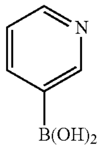 | 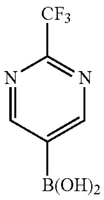 | 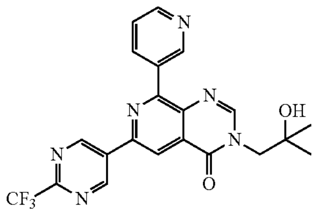 3-(2-hydroxy-2-methylpropyl)-8-(pyridin-3-yl)-6-(2-(trifluoromethyl)pyrimidin-5-yl)pyrido[3,4-d]pyrimidin-4(3H)-one | ($CH_3OH$-$d_4$, 400 MHz): $\delta_H$ 1.27 (6H, s), 4.16 (2H, s), 7.63 (1H, dd, J = 8.0, 5.0 Hz), 8.43 (1H, s), 8.65 (1H, s), 8.74 (1H, d, J = 8.0 Hz), 8.84 (1H, s), 9.43 (1H, s), 9.77 (2H, s). | 443.1; 99% |
| 97 | 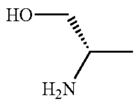 | 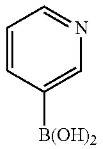 | 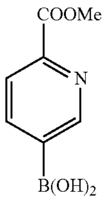 | 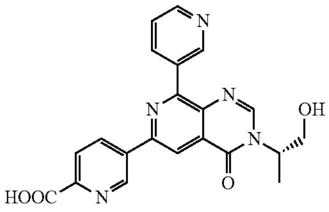 (S)-5-(3-(1-hydroxypropan-2-yl)-4-oxo-8-(pyridin-3-yl)-3,4-dihydropyrido[3,4-d]pyrimidin-6-yl)picolinic acid | ($CH_3OH$-$d_4$, 400 MHz): $\delta_H$ 1.59-1.57 (3H, m), 3.89-3.85 (1H, m), 3.98 (1H, dd, J = 11.8, 6.8 Hz), 5.07-5.00 (1H, m), 8.34-8.30 (1H, m), 8.51-8.48 (1H, m), 8.60 (1H, s), 8.99-8.96 (2H, m), 9.17-9.12 (1H, m), 9.66-9.63 (1H, m), 9.74-9.71 (1H, m), 10.01 (1H, d, J = 2.6 Hz). | 404.1; 95% |

TABLE 5-continued

| Compound No. | Reactant 1 (Step 1) | Reactant 2 (Step 3) | Reactant 3 (Step 4) | Compound Structure/Name | $^1$H-NMR | MS (m/z); Purity (%) |
|---|---|---|---|---|---|---|
| 98 | 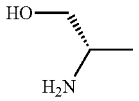 | 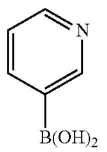 | 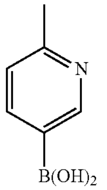 | 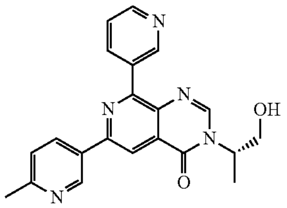 (S)-3-(1-hydroxypropan-2-yl)-6-(6-methylpyridin-3-yl)-8-(pyridin-3-yl)pyrido[3,4-d]pyrimidin-4(3H)-one | ($CH_3OH-d_4$, 400 MHz): $\delta_H$ 1.55 (3H, d, J = 7.1 Hz), 2.62 (3H, s), 3.85 (1H, dd, J = 11.9, 4.2 Hz), 3.97 (1H, dd, J = 11.9, 7.0 Hz), 5.00 (1H, s), 7.47 (1H, d, J = 8.3 Hz), 7.60 (1H, s), 8.45 (1H, s), 8.61-8.52 (3H, m), 8.70 (1H, s), 9.24 (1H, s), 9.40 (1H, s). | 374.1; 99% |
| 99 | 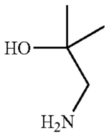 | 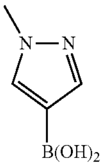 | 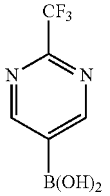 | 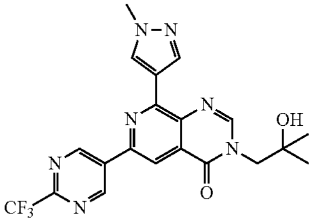 3-(2-hydroxy-2-methylpropyl)-8-(1-methyl-1H-pyrazol-4-yl)-6-(2-(trifluoromethyl)pyrimidin-5-yl)pyrido[3,4-d]pyrimidin-4(3H)-one | ($CH_3OH-d_4$, 400 MHz): $\delta_H$ 1.26 (6H, s), 3.98 (3H, s), 4.09 (2H, s), 8.39 (1H, s), 8.44 (1H, s), 8.49 (1H, s), 8.75 (1H, s), 9.66 (2H, s). | 446.1; 99% |

**Compounds 41 and 42 were obtained via SFC purification of the racemic mixture (column: DAICEL CHIRALPAK AD (250 mm*30 mm, 10 um); mobile phase: [0.1% $NH_3H_2O$ EtTOH]; B%: 40%-40% 7 min).

[a]The compound was synthesized from Intermediate B2 in one step coupling with 4-(4,4,5,5-tetramethyl-1,3,2-dioxaborolan-2-yl)isothiazole

[b]The compound was synthesized from Intermediate B1 in one step coupling with (6-(trifluoromethyl)pyridin-3-yl)boronic acid.

[c]Compounds 70 and 71 were obtained via SFC purification of the racemic mixture 29.

[d]The reaction was performed using THF/water 2/1 as solvent and $K_3CO_3$ as base.

Preparation of 3-((S)-1-hydroxypropan-2-yl)-8-(1-methylpiperidin-3-yl)-6-(6-(trifluoromethyl)pyridin-3-yl)pyrido[3,4-d]pyrimidin-4(3H)-one

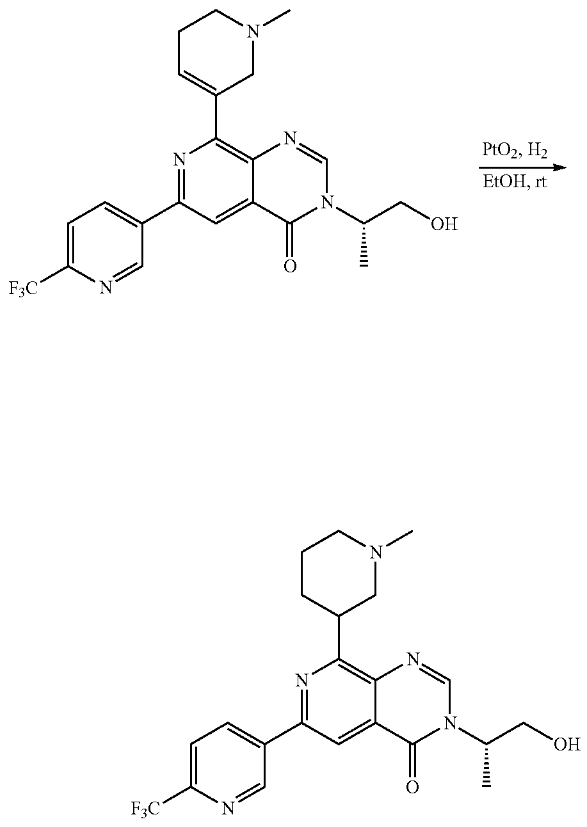

To a solution of (S)-3-(1-hydroxypropan-2-yl)-8-(1-methyl-1,2,5,6-tetrahydropyridin-3-yl)-6-(6-(trifluoromethyl)pyridin-3-yl)pyrido[3,4-d]pyrimidin-4(3H)-one (60 mg, 0.135 mmol) in EtOH (1 mL) under $N_2$, $PtO_2$ (15 mg, 0.088 mmol) was added. The flask was degassed and subjected to $H_2$ gas in balloon. After overnight, the reaction mixture was filtered through Celite®, washed well with methanol, concentrated and purified by reverse phase chromatography eluting with 0.1% formic acid in $H_2O$ and acetonitrile, to give desired product as diastereomeric mixture (4 mg, 7%). $^1$H NMR ($CH_3OH$-$d_4$, 400 MHz): $\delta_H$ 1.29 (1H, s), 1.54 (4H, d, J=7.1 Hz), 1.94 (2H, s), 2.13 (1H, s), 2.50 (3H, s), 3.13 (2H, s), 3.85 (1H, s), 3.95 (2H, s), 4.28 (1H, s), 4.62 (2H, s), 4.99 (2H, m), 7.96 (1H, d, J=8.2 Hz), 8.47 (1H, s), 8.60 (1H, s), 8.80 (1H, d, J=8.2 Hz), 9.51 (1H, s). MS (m/z): 448.2 $[M+H]^+$; >90% purity.

Preparation of (S)-3-(1-hydroxypropan-2-yl)-6-morpholino-8-(pyridin-3-yl)pyrido[3,4-d]pyrimidin-4(3H)-one (43)

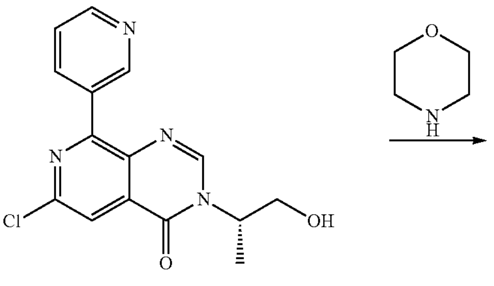

11

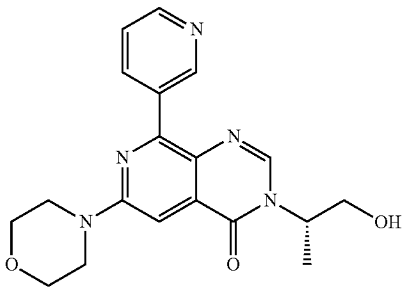

43

(S)-6-chloro-3-(1-hydroxypropan-2-yl)-8-(pyridin-3-yl)pyrido[3,4-d]pyrimidin-4(3H)-one (11, 0.060 g, 0.19 mmol), potassium carbonate (0.011 g, 0.76 mmol) in a sealed tube was added dimethylformamide (2.0 ml) followed by morpholine (0.038 g, 0.38 mmol). The resulting mixture was stirred at 120° C. After 24 hours another portion of morpholine (38.1 mg, 0.38 mmol) was added and stirring was continued for another 24 hours at 120° C. The reaction mixture was allowed to cool to room temperature and was then partitioned between water and ethyl acetate. Organic layer was separated, dried over sodium sulphate and concentrated. Purification of the residue by silica gel chromatography with methanol/dichloromethane afforded the title compound (0.026 g, 0.071 mmol, 37% yield). $^1$H NMR (DMSO-$d_6$, 400 MHz): δ 1.38 (3H, d, J=7.04 Hz), 3.58-3.65 (5H, m), 3.76 (5H, t, J=4.80 Hz), 4.82-4.87 (1H, m), 7.30 (1H, s); 5.03 (1H, s), 7.52 (1H, dd, J=7.96; 4.81 Hz), 8.23 (1H, s), 8.46 (1H, dt, J=7.97; 1.97 Hz), 8.63 (1H, dd, J=4.79; 1.75 Hz), 9.26 (1H, d, J=2.11 Hz); MS (m/z): 368.2 $[M+H]^+$; 93.6% purity.

Compounds listed in Table 6 below were made according to methods similar to 43 immediately above:

TABLE 6

| Compound No | Reactant 1 (Step 1) | Reactant 2 (Step 3) | Reactant 3 (Step 4) | Compound Structure/Name | 1H-NMR | MS (m/z) $[M + H]^+$; Purity (%) |
|---|---|---|---|---|---|---|
| 100 | 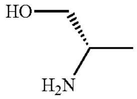 | 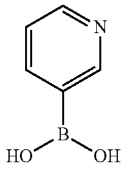 | 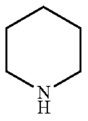 | 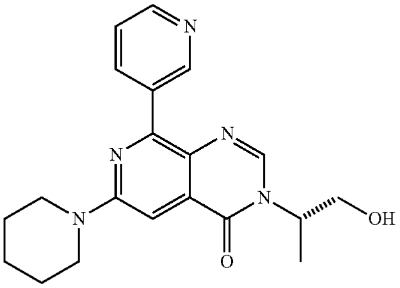 [SMILES: C[C@@H](CO)n1cnc2c(-c3cccnc3)nc(N3CCCCC3)cc2c1=O] (S)-3-(1-hydroxypropan-2-y])-6-(piperidin-1-yl)-8-(pyridin-3-yl)pyrido[3,4-d]pyrimidin-4(3H)-one | (DMSO-$d_6$, 300 MHz): $\delta_H$ 1.37 (3H, dd, J = 6.8, 3.1 Hz), 1.67-1.59 (6H, m), 3.74-3.62 (6H, m), 4.85-4.82 (1H, m), 5.04-5.00 (1H, m), 7.25 (1H, s), 7.53-7.49 (1H, m), 8.17 (1H, s), 8.43 (1H, dt, J = 8.0, 1.9 Hz), 8.62 (1H, dd, J = 4.8, 1.6 Hz), 9.24 (1H, d, J = 2.1 Hz). | 366.0; 99 |

Preparation of (S)-3-(1-hydroxypropan-2-yl)-8-(1H-imidazol-1-yl)-6-(4-(trifluoromethoxy)-phenyl) pyrido[3,4-d]pyrimidin-4(3H)-one (44)

Step 1. Preparation of (S)-6-chloro-3-(1-hydroxy-propan-2-yl)-8-(1H-imidazol-1-yl)pyrido[3,4-d]pyrimidin-4(3H)-one (C23)

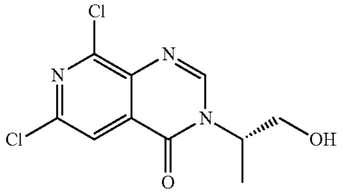

B1

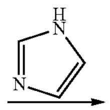

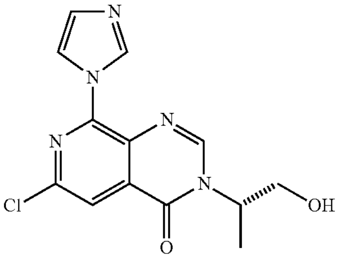

C23

To a resealable Schlenk tube, a screw-cap test tube, were added CuI (4 mg, 0.02 mmol), imidazole (25 mg, 0.37 mmol), cesium carbonate (250 mg, 0.77 mmol), and a stir bar. The tube was degassed before addition of (S)-6,8-dichloro-3-(1-hydroxypropan-2-yl)pyrido[3,4-d]pyrimidin-4(3H)-one (100 mg, 0.37 mmol), 1,10-Phenanthroline (7 mg, 0.04 mmol) and anhydrous dioxane (2 mL) under a stream of argon. The reaction tube was degassed and back-filled with argon before stirring at 90° C. for 24 h. The reaction mixture was allowed to cool to room temperature. The solution was diluted with ethyl acetate (2-3 mL), filtered through a plug of Celite, and eluted with additional ethyl acetate (10-20 mL). The filtrate was washed with water, brine, dried over $Na_2SO_4$ and concentrated. The resulting residue was purified by silica gel column chromatography ($CH_2Cl_2$/MeOH) to provide the title compound (C23, 20 mg, 0.06 mmol, 18% yield). $^1H$ NMR ($CHCl_3$-$d_3$ with 10% $CH_3OH$-$d_4$, 400 MHz): δH 1.46 (3H, dd, J=16.4, 7.1 Hz), 3.81 (2H, s), 4.94 (1H, s), 5.24 (1H, s), 7.94 (1H, s), 8.31 (1H, s); MS (m/z): 306.1 $[M+H]^+$. Imidazole protons were not observed possibly due to complexation with copper.

Step 2. Preparation of (S)-3-(1-hydroxypropan-2-yl)-8-(1H-imidazol-1-yl)-6-(4-(trifluoromethoxy) phenyl)pyrido[3,4-d]pyrimidin-4(3H)-one (44)

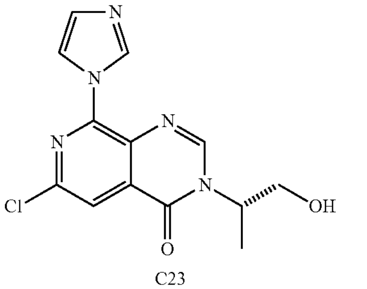

C23

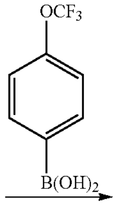

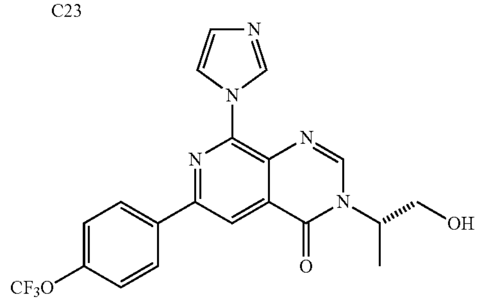

44

(S)-6-chloro-3-(1-hydroxypropan-2-yl)-8-(1H-imidazol-1-yl)pyrido[3,4-d]pyrimidin-4(3H)-one (C23, 30 mg, 0.1 mmol) and (4-(Trifluoromethoxy)phenyl)boronic acid (30 mg, 0.15 mmol) was dissolved in 1 mL toluene-EtOH (2:1), and sodium carbonate (42 mg, 0.4 mmol) was added. The suspension was degassed and refilled with argon (3 cycles). Tetrakis(triphenylphosphine)palladium (12 mg, 0.01 mmol) was added and the suspension was degassed and refilled with argon (3 cycles). The reaction mixture was stirred at 85° C. under argon overnight. The reaction mixture was allowed to cool to room temperature and diluted with ethyl acetate. The solution was washed with water, brine, dried over $Na_2SO_4$ and concentrated. The residue was purified by silica gel column chromatography ($CH_2Cl_2$/MeOH) followed by a C18 column to provide a TFA salt of (S)-3-(1-hydroxypropan-2-yl)-8-(1H-imidazol-1-yl)-6-(4-(trifluoromethoxy)phenyl)pyrido[3,4-d]pyrimidin-4(3H)-one, which was washed with sat. Na2CO3 to provide the free base of the title compound 44 (11 mg, 0.026 mmol, 26% yield). $^1$H NMR ($CH_3OH$-$d_4$, 400 MHz): δ 1.56 (3H, d, J=7.1 Hz), 3.86 (1H, dd, J=11.9, 4.3 Hz), 3.97 (1H, dd, J=11.9, 6.9 Hz), 5.02-4.97 (1H, m), 7.16 (1H, s), 7.42 (2H, d, J=8.4 Hz), 8.28 (2H, d, J=8.7 Hz), 8.36 (1H, s), 8.50 (2H, s), 9.14 (1H, s); MS (m/z): 432.2[M+H]$^+$; purity 98%.

Preparation of (S)-3-(1-methoxypropan-2-yl)-8-(pyridin-3-yl)-6-(p-tolyl)pyrido[3,4-d]pyrimidin-4(3H)-one (45)

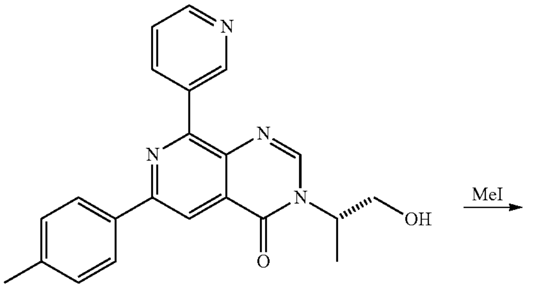

17

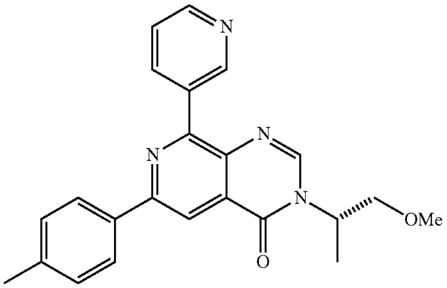

45

(S)-3-(1-hydroxypropan-2-yl)-8-(pyridin-3-yl)-6-(p-tolyl)pyrido[3,4-d]pyrimidin-4(3H)-one (17, 20 mg, 0.05 mmol) was dissolved in anhydrous THE and the resulting solution was cooled with an ice-water bath. t-BuOK (6 mg, 0.05 mmol) was then added, followed by $CH_3I$ (8 mg, 0.05 mmol). The reaction mixture was stirred for 1 h at 0° C. The reaction was quenched by addition of methanol and diluted with EtOAc. This solution washed with water, brine, dried over $Na_2SO_4$, concentrated and purified by HPLC, providing a TFA salt of (S)-3-(1-methoxypropan-2-yl)-8-(pyridin-3-yl)-6-(p-tolyl)pyrido[3,4-d]pyrimidin-4(3H)-one, which was washed with aqueous sat. $Na_2CO_3$ to provide a free base of the title compound 45. (2 mg, 0.005 mmol, 10% yield). $^1$H NMR ($CH_3OH$-$d_4$, 400 MHz): δ 1.55 (3H, d, J=7.1 Hz), 2.41 (3H, s), 3.36 (3H, s), 3.68 (1H, dd, J=10.5, 4.2 Hz), 3.85 (1H, dd, J=10.4, 7.2 Hz), 5.14 (1H, d, J=7.3 Hz), 7.33 (2H, d, J=7.9 Hz), 7.59 (1H, dd, J=8.0, 4.9 Hz), 8.09 (2H, d, J=8.0 Hz), 8.39 (1H, s), 8.50 (1H, s), 8.61 (1H, s), 8.70 (1H, d, J=8.0 Hz), 9.39 (1H, s); MS (m/z): 387.1 [M+H]$^+$; purity 97%.

Preparation of (S)-3-(1-hydroxypropan-2-yl)-8-(pyridin-3-yl)-6-(5-(trifluoromethyl)pyridin-2-yl)pyrido[3,4-d]pyrimidin-4(3H)-one (46)

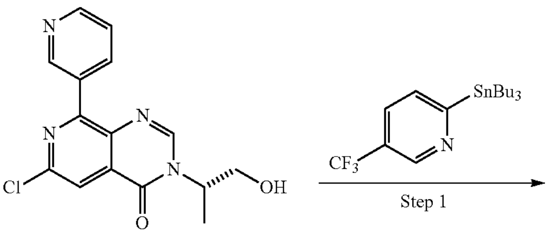

11

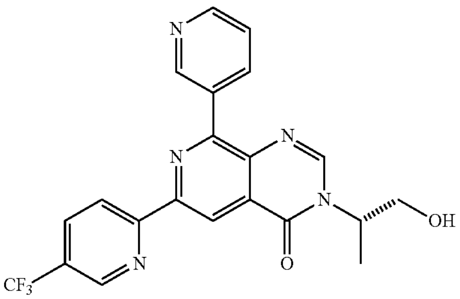

46

(S)-6-chloro-3-(1-hydroxypropan-2-yl)-8-(pyridin-3-yl)pyrido[3,4-d]pyrimidin-4(3H)-one (11, 50 mg, 0.15 mmol) was dissolved in toluene. The solution was degassed before addition of Pd(dppf)$Cl_2$·$CH_2Cl_2$ (13 mg, 0.016 mmol), LiCl (26 mg, 4 eq), CuI (6 mg, 0.032 mmol) and 2-(tributylstannyl)-5-(trifluoromethyl)pyridine (83 mg, 0.19 mmol). The solution was degassed again and stirred at 80° C. overnight. LCMS monitoring of the reaction mixture showed incomplete conversion to the expected product, thus 30 mg of CuI was added and the reaction was allowed to proceed for an additional 6 hours at 80° C. The reaction mixture was allowed to cool to room temperature and it was diluted with EtOAc. This solution was washed with water, brine and dried over $Na_2SO_4$. Solvents were removed under reduced pressure and the residue was purified by a silica gel column chromatography ($CH_2Cl_2$/MeOH) followed by a C18 column chromatography to provide a TFA salt of (S)-3-(1-hydroxypropan-2-yl)-8-(pyridin-3-yl)-6-(5-(trifluoromethyl)pyridin-2-yl)pyrido[3,4-d]pyrimidin-4(3H)-one, which was washed with aqueous sat. $Na_2CO_3$ to provide the free base of the title compound (8 mg, 0.019 mmol, 12% yield)$^1$H NMR ($CH_3OH$-$d_4$, 400 MHz): δ 1.56 (3H, d, J=7.1 Hz), 3.85 (1H, dd, J=11.9, 4.3 Hz), 3.96 (1H, dd, J=11.9, 6.9 Hz), 5.01-4.96 (1H, m), 7.60 (1H, dd, J=8.0, 4.9 Hz), 8.24 (1H, d, J=8.5 Hz), 8.46 (1H, s), 8.63 (1H, d, J=4.9 Hz), 8.74-8.70 (2H, m), 8.99 (1H, s), 9.13 (1H, s), 9.41 (1H, s); MS (m/z): 428.1 [M+H]$^+$; purity 99%.

Preparation of (S)-8-(3-fluorophenyl)-3-(1-hydroxy-propan-2-yl)-6-(5-(trifluoromethyl)pyridin-2-yl) pyrido[3,4-d]pyrimidin-4(3H)-one (47)

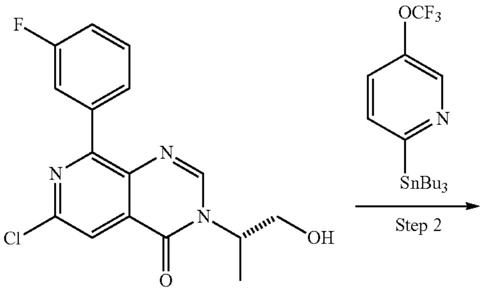

C1

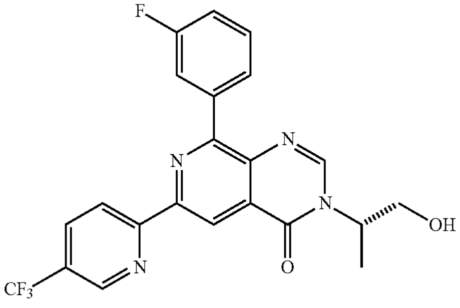

47

(S)-6-chloro-8-(3-fluorophenyl)-3-(1-hydroxypropan-2-yl)pyrido[3,4-d]pyrimidin-4(3H)-one (C1, 50 mg, 0.15 mmol) was dissolved in toluene and degassed before addition of Pd(dppf)$Cl_2$—$CH_2Cl_2$ (24 mg, 0.18 mg), LiCl (26 mg, 0.6 mmol), CuI (29 mg, 0.15 mmol) and 2-(tributyl-stannyl)-5-(trifluoromethyl)pyridine (79 mg, 0.18 mmol). The solution was degassed again and stirred at 80° C. overnight. The reaction mixture was diluted with EtOAc, washed with water, brine and dried over $Na_2SO_4$. Solvents were removed under vacuum and the residue was purified by silica gel column chromatography ($CH_2Cl_2$/MeOH) followed by a C18 column to provide a TFA salt of (S)-8-(3-fluorophenyl)-3-(1-hydroxypropan-2-yl)-6-(5-(trifluoromethyl)pyridin-2-yl)pyrido[3,4-d]pyrimidin-4(3H)-one, which was washed with sat. $Na_2CO_3$ to provide the free base of the title compound (19 mg, 0.04 mmol, 25% yield). $^1$H NMR ($CH_3OH-d_4$, 400 MHz): δH 1.56 (3H, d, J=7.1 Hz), 3.85 (1H, dd, J=11.9, 4.3 Hz), 3.96 (1H, dd, J=11.9, 6.9 Hz), 5.01-4.96 (1H, m), 7.60 (1H, dd, J=8.0, 4.9 Hz), 8.24 (1H, d, J=8.5 Hz), 8.46 (1H, s), 8.63 (1H, d, J=4.9 Hz), 8.74-8.70 (2H, m), 8.99 (1H, s), 9.13 (1H, s), 9.41 (1H, s); MS (m/z): 445.1 [M+H]+; purity 99%.

Compounds prepared in a similar manner to 47 are listed in Table 7, below:

TABLE 7

| Compound No. | Reactant 1 (Step 1) | Reactant 2 (Step 3) | Reactant 3 (Step 4) | Compound Structure/Name | $^1$H-NMR | MS (m/z) [M + H]$^+$; Purity (%) |
|---|---|---|---|---|---|---|
| 101 | 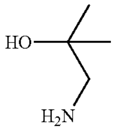 | 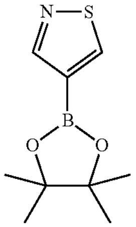 | 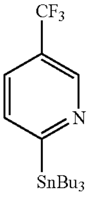 | 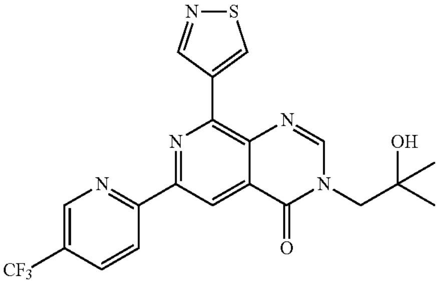 [SMILES: CC(C)(O)Cn1cnc2c(-c3cnsc3)nc(-c3ccc(C(F)(F)F)cn3)cc2c1=O] 3-(2-hydroxy-2-methylpropyl)-8-( isothiazol-4-yl)-6-(5-(trifluoromethyl)pyridin-2-yl)pyrido[3,4-d]pyrimidin-4(3H)-one | ($CH_3OH-d_4$, 300 MHZ): δH 1.29 (6H, s), 4.12 (2H, s), 8.24 (1H, d, J = 8.3 Hz), 8.43 (1H, s), 8.70 (1H, d, J = 8.2 Hz), 8.99 (2H, d, J = 8.5 Hz), 9.58 (1H, s), 10.12 (1H, s). | 447.9, 99 |
| 102 | 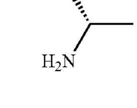 | 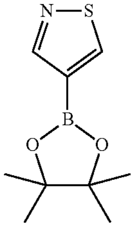 | 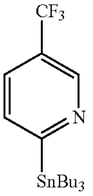 | 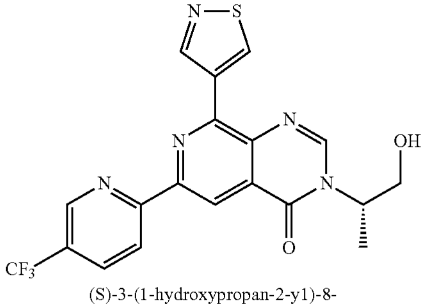 (S)-3-(1-hydroxypropan-2-yl)-8- | ($CH_3OH-d_4$, 300 MHZ): δ H 1.60 (3H, d, J = 7.1 Hz), 3.91 (1H, d, J = 4.3 Hz), 3.98 (1H, d, J = 6.8 Hz), 5.03 (1H, s), 8.30 (1H, s), 8.57 (1H, s), 8.79 (1H, d, J = 8.3 Hz), 9.02 (1H, s), 9.10 (1H, s), 9.65 | 433.9, 99 |

TABLE 7-continued

| Compound No. | Reactant 1 (Step 1) | Reactant 2 (Step 3) | Reactant 3 (Step 4) | Compound Structure/Name | $^1$H-NMR | MS (m/z) [M + H]$^+$; Purity (%) |
|---|---|---|---|---|---|---|
| | | | | ( isothiazol-4-yl)-6-(5-(trifluoromethyl)pyridin-2-yl)pyrido[3,4-d]pyrimidin-4(3H)-one | (1H, s), 10.18 (1H, s). | |
| 103 | 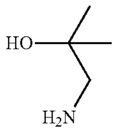 | 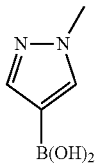 | 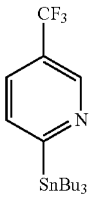 | 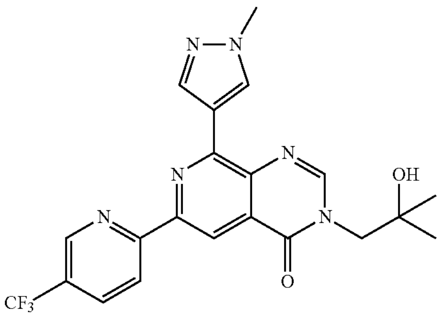 [SMILES: Cn1cc(-c2nc(-c3ccc(C(F)(F)F)cn3)cc3c(=O)n(CC(C)(C)O)cnc23)cn1] 3-(2-hydroxy-2-methylpropyl)-8-(1-methyl-1H-pyrazol-4-yl)-6-(5-(trifluoromethyl)pyridin-2-yl)pyrido[3,4-d]pyrimidin-4(3H)-one | ($CH_3OH$-$d_4$, 300 MHZ): δ H 1.29 (6H, s), 4.02 (3H, s), 4.13 (2H, s), 8.25 (1H, d, J = 8.5 Hz), 8.41 (1H, s), 8.55 (1H, s), 8.75 (1H, d, J = 8.4 Hz), 8.80 (1H, s), 8.92 (1H, s), 8.98 (1H, s). | 444.9; 99 |
| 104 | 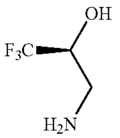 | 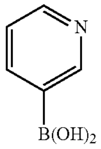 | 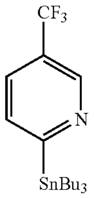 | 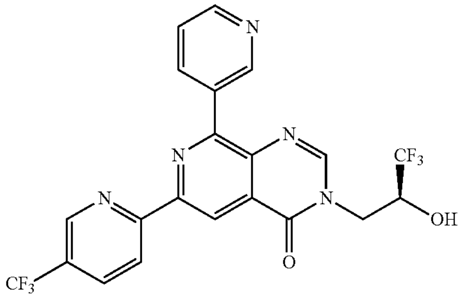 (S)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one | ($CH_3OH$-$d_4$, 400 MHZ): δ H 4.01 (1H, t, J = 11.7 Hz), 4.47 (1H, brs), 4.65 (1H, d, J = 13.9 Hz), 7.64 (1H, t, J = 6.5 Hz), 8.29 (1H, d, J = 8.5 Hz), 8.41 (1H, s), 8.67 (1H, d, J = 4.9 Hz), 8.77 (2H, t, J = 7.8 Hz), 9.04 (1H, s), 9.22 (1H, s), 9.43 (1H, s). | 481.9, 97 |
| 105 | 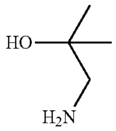 | 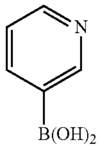 | 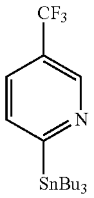 | 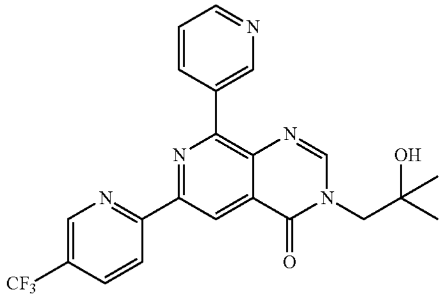 [SMILES: CC(C)(O)Cn1cnc2c(-c3cccnc3)nc(-c3ccc(C(F)(F)F)cn3)cc2c1=O] (3-(2-hydroxy-2-methylpropyl)-8-(pyridin-3-y1)-6-(5-(trifluoromethyl)pyridin-2-yl)pyrido[3,4-d]pyrimidin-4(3H)-one | ($CH_3OH$-$d_4$, 400 MHZ): 8H 1.29 (6H, s), 4.13 (2H, s), 4.61 (1H, s), 7.58 (1H, s), 8.26 (1H, d, J = 8.5 Hz), 8.39 (1H, s), 8.69 (3H, m), 9.00 (1H, s), 9.12 (1H, s), 9.38 (1H, s). | 441.9; 99 |

Preparation of 8-(3-fluorophenyl)-3-[(1S)-2-hydroxy-1-methyl-ethyl]-6-(p-tolyl)pyrido[3,4-d]pyrimidin-4-one (48)

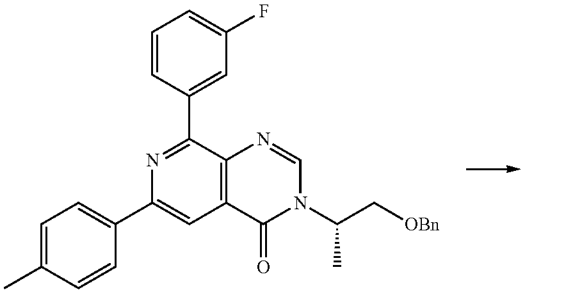

40

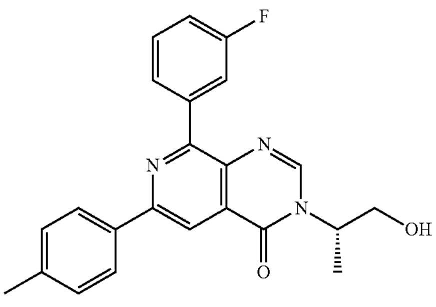

48

A mixture of 3-[(1S)-2-benzyloxy-1-methyl-ethyl]-8-(3-fluorophenyl)-6-(p-tolyl)pyrido[3,4-d]pyrimidin-4-one (40, 160 mg, 333.65 umol, 1 eq) and Pd/C (80 mg, 333.65 umol, 10% purity, 1.00 eq) in MeOH (25 mL) and EtOAc (25 mL) was degassed and purged with $H_2$ (15 psi) for 3 times, and then the mixture was stirred at 80° C. for 15 hr under $H_2$ atmosphere. LCMS showed desired compound was detected. The reaction mixture was filtered and the filtrate was concentrated under reduced pressure to give a residue. The residue was purified by prep-TLC ($SiO_2$, Petroleum ether/Ethyl acetate=1:1) to get the title compound (47 mg, 120.69 umol, 36.17% yield) $^1$H NMR (400 MHz, DMSO-$d_6$) δ ppm 1.43 (d, J=6.8 Hz, 3H), 2.39 (s, 3H), 3.62-3.71 (m, 1H), 3.76-3.84 (m, 1H), 4.84-4.96 (m, 1H), 5.07 (t, J=5.6 Hz, 1H), 7.33-7.37 (m, 3H), 7.59 (q, J=7.6, 14.0 Hz, 1H), 8.03-8.09 (m, 2H), 8.16 (d, J=8.4 Hz, 2H), 8.46 (s, 1H), 8.53 (s, 1H); MS: M+H+, 390.1; 98% purity.

Preparation of 8-(3-fluorophenyl)-3-[(1S)-2-hydroxy-1-methyl-ethyl]-6-[4-(trifluoromethoxy)phenyl]pyrido[3,4-d]pyrimidin-4-one (49)

Step 1. Preparation of 3-[(1S)-2-benzyloxy-1-methyl-ethyl]-8-(3-fluorophenyl)-6-[4-(trifluoromethoxy)phenyl]pyrido[3,4-d]pyrimidin-4-one (Precursor 1)

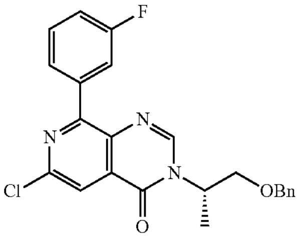

C21

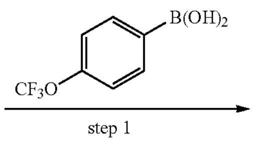

-continued

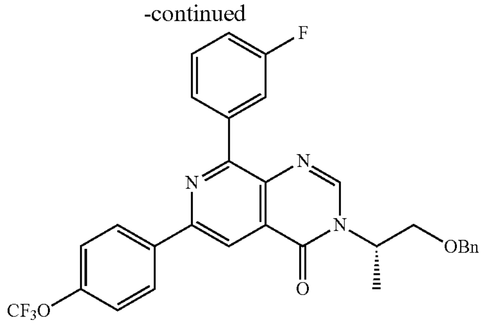

20

To a solution of 3-[(1S)-2-benzyloxy-1-methyl-ethyl]-6-chloro-8-(3-fluorophenyl)pyrido[3,4-d]pyrimidin-4-one (C21, 460 mg, 1.09 mmol, 1 eq) and [4-(trifluoromethoxy)phenyl]boronic acid (268.18 mg, 1.30 mmol, 1.2 eq) in toluene (8 mL) and EtOH (4 mL) was added $Na_2CO_3$ (460.10 mg, 4.34 mmol, 4 eq) and $Pd(PPh_3)_4$ (125.41 mg, 108.52 umol, 0.1 eq). The mixture was taken up into a microwave tube. The sealed tube was heated at 100° C. for 1 h under microwave. LCMS showed desired compound was detected. The reaction mixture was filtered and the filtrate was concentrated under reduced pressure to give a residue. The residue was purified by column chromatography ($SiO_2$, Petroleum ether/Ethyl acetate=1/0 to 0/1) to get the title compound (400 mg, 727.92 umol, 67.07% yield). MS: M+H$^+$, 550.1.

Step 2. Preparation of 8-(3-fluorophenyl)-3-[(1S)-2-hydroxy-1-methyl-ethyl]-6-[4-(trifluoromethoxy)phenyl]pyrido[3,4-d]pyrimidin-4-one (49)

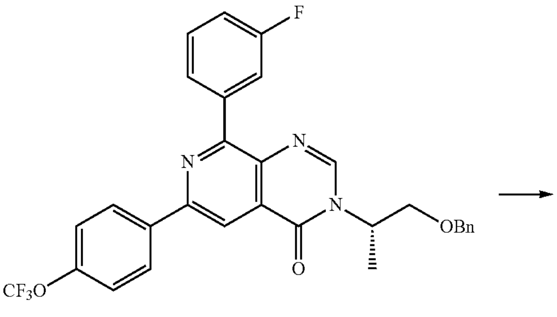

Precursor 1

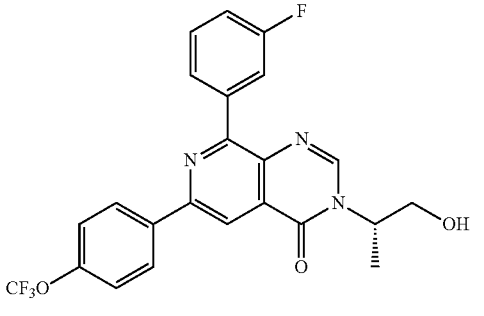

49

To a solution of 3-[(1S)-2-benzyloxy-1-methyl-ethyl]-8-(3-fluorophenyl)-6-[4-(trifluoromethoxy) phenyl]pyrido[3, 4-d]pyrimidin-4-one (Precursor 1, 290 mg, 527.74 umol, 1 eq) in EtOAc (20 mL) and MeOH (20 mL) was added $Pd(OH)_2/C$ (130 mg, 527.74 umol, 10% purity, 1.00 eq). The mixture was stirred at 25° C. for 6 hr under $H_2$ (15 psi). LCMS showed desired mass was detected. The reaction mixture was filtered and the filtrate was concentrated under reduced pressure to give a residue. The residue was purified by prep-TLC ($SiO_2$, Petroleum ether/Ethyl acetate=1:1) to get the title compound 49 (22 mg, 47.41 umol, 8.98% yield), $^1$H NMR (400 MHz, $CDCl_3$) δ ppm 1.61 (d, J=7.1 Hz, 3H), 1.94-2.05 (m, 1H), 3.95-4.04 (m, 2H), 5.04-5.15 (m, 1H), 7.17-7.25 (m, 1H), 7.36 (d, J=8.4 Hz, 2H), 7.46-7.54 (m, 1H), 7.94-8.07 (m, 2H), 8.26 (d, J=8.4 Hz, 2H), 8.32 (s, 1H), 8.53 (s, 1H). MS: M+H+, 460.1; 99% purity.

The compounds encompassed within the present disclosure can be prepared by the procedure outlined in Scheme II and described in the Examples herein below:

Scheme II

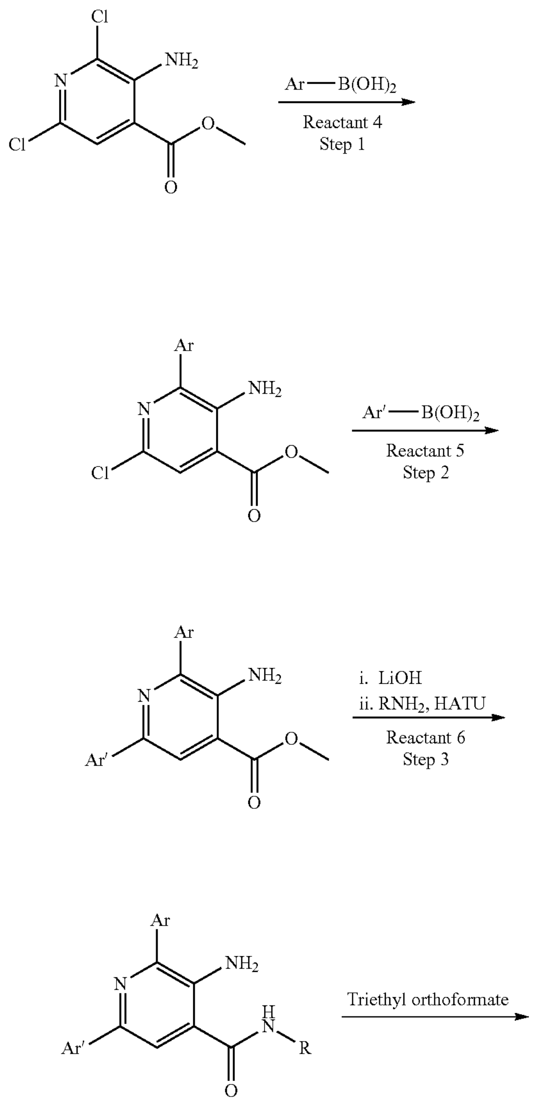

-continued

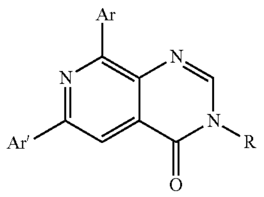

Preparation of 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (106)

Step 1. Preparation of methyl 3-amino-6-chloro-[2,3'-bipyridine]-4-carboxylate (Precursor 2)

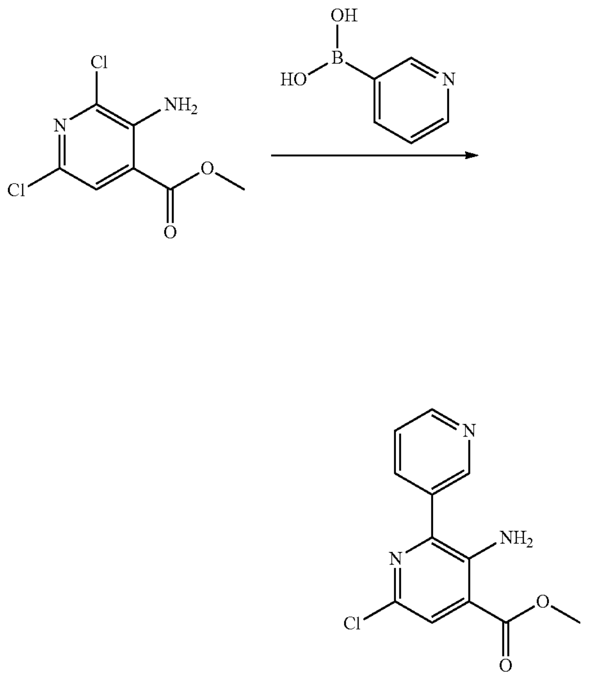

Precursor 2

Precursor 2 was prepared according to the procedure reported for Step 3 for the synthesis of 1. $^1$H NMR ($CHCl_3$-d, 400 MHz): $\delta_H$ 3.95 (3H, s), 5.91 (2H, s), 7.44 (1H, dd, J=7.9, 4.9 Hz), 7.74 (1H, s), 7.97 (1H, d, J=7.9 Hz), 8.69 (1H, dd, J=4.9, 1.7 Hz), 8.91 (1H, s); MS (m/z): 264.0 $[M+H]^+$.

Table 8 lists intermediates that were made via a procedure similar to that described in Step 1 above.

TABLE 8

| Intermediate ID | Intermediate Structure and Name | $^1$H-NMR | MS (m/z) $[M + H]^+$; Purity (%) |
|---|---|---|---|
| D1 | 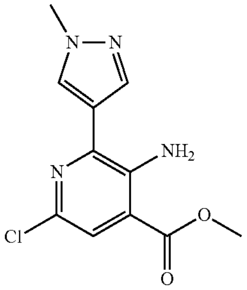 [SMILES: COC(=O)c1cc(Cl)nc(-c2cnn(C)c2)c1N] Methyl 3-amino-6-chloro-2-(1-methyl-1H-pyrazol-4-yl)isonicotinate | NA | 267.0; >95 |

Step 2. Preparation of methyl 3'-amino-6"-(trifluoromethyl)-[3,2': 6',3"-terpyridine]-4'-carboxylate (Precursor 3)

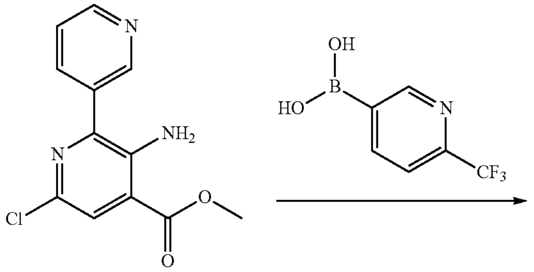

Precursor 2

-continued

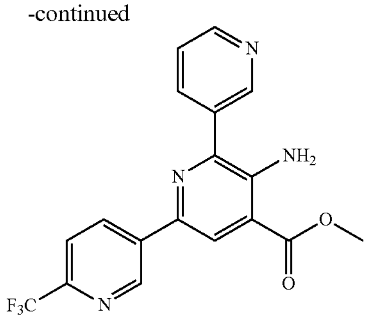

Precursor 3

Precursor 3 was prepared according to the procedure reported for Step 3 for the synthesis of 1. $^1$H NMR ($CHCl_3$-d, 400 MHz): $\delta_H$ 4.01 (3H, s), 6.20 (2H, s), 7.49 (1H, t, J=6.4 Hz), 7.73 (1H, d, J=8.2 Hz), 8.06 (1H, d, J=7.9 Hz), 8.25 (1H, s), 8.46 (1H, d, J=8.3 Hz), 8.74 (1H, d, J=4.9 Hz), 9.00 (1H, s), 9.27 (1H, s); MS (m/z): 375.0$[M+H]^+$.

Table 9 lists intermediates that were made via a procedure similar to that described in the above.

TABLE 9

| Intermediate ID | Intermediate Structure and Name | $^1$H NMR | MS (m/z) $[M + H]^+$; Purity (%) |
|---|---|---|---|
| E1 | 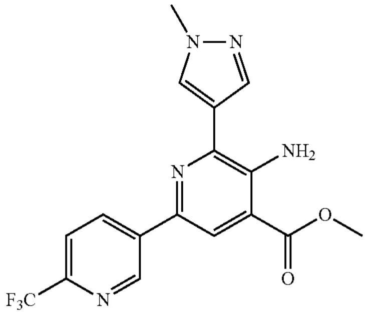 [SMILES: COC(=O)c1cc(-c2ccc(C(F)(F)F)nc2)nc(-c2cnn(C)c2)c1N] Methyl 5-amino-6-(1-methyl-1H-pyrazol-4-yl)-6'-(trifluoromethyl)-[2,3'-bipyridine]-4-carboxylate | ($CHCl_3$-d, 300 MHz): δ H 4.01 (3H, s), 4.05 (3H, s), 7.74 (1H, d, J = 8.2 Hz), 7.96 (1H, s), 8.04 (1H, s), 8.13 (1H, s), 8.46 (1H, d, J = 8.3 Hz), 9.31 (1H, s) | 378.1; >95 |

TABLE 9-continued

| Intermediate ID | Intermediate Structure and Name | $^{1}$H NMR | MS (m/z) [M + H]$^+$; Purity (%) |
|---|---|---|---|
| E2 | 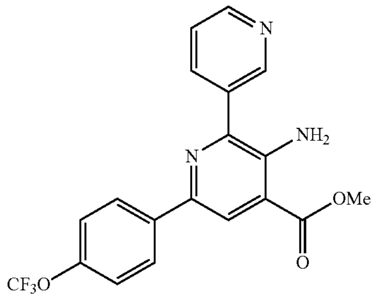 methyl 3-amino-6-(4-(trifluoromethoxy)phenyl)-[2,3'-bipyridine]-4-carboxylate | ($CH_3OH$-$d_4$, 400 MHz): δ H 3.98 (3H, s), 7.32 (2H, d, J = 8.4 Hz), 7.62 (1H, s), 8.05 (2H, d, J = 8.5 Hz), 8.22-8.21 (2H, m), 8.63 (1H, d, J = 5.0 Hz), 8.89 (1H, s). | 389.9; NA |
| E3 | 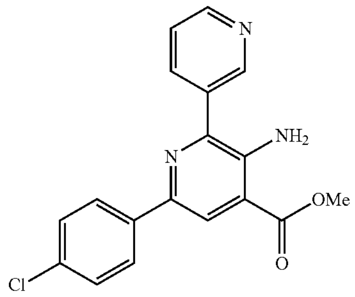 [SMILES: COC(=O)c1cc(-c2ccc(Cl)cc2)nc(-c2cccnc2)c1N] methyl 3-amino-6-(4-chlorophenyl)-[2,3'-bipyridine]-4-carboxylate | ($CHCl_3$-d, 400 MHz): δ H 3.99 (3H, s), 6.02 (2H, s), 7.40 (2H, d, J = 8.4 Hz), 7.47 (1H, t, J = 6.3 Hz), 7.93 (2H, d, J = 8.4 Hz), 8.07 (1H, d, J = 7.9 Hz), 8.15 (1H, s), 8.71 (1H, d, J = 4.8 Hz), 9.01 (1H, s). | 340.1; NA |
| E4 | 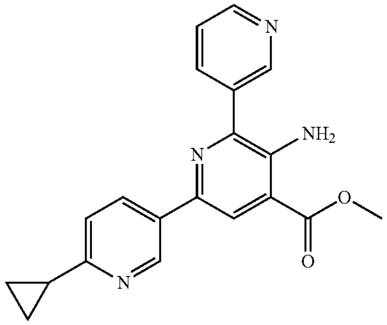 [SMILES: COC(=O)c1cc(-c2ccc(C3CC3)nc2)nc(-c2cccnc2)c1N] methyl 3'-amino-6''-cyclopropyl-[3,2':6',3''-terpyridine]-4'-carboxylate | (DMSO-$d_6$, 400 MHz): δ 0.95 (4H, t, J = 7.1 Hz), 2.15-2.09 (1H, m), 3.91 (3H, s), 6.67 (2H, s), 7.33 (1H, d, J = 8.2 Hz), 7.55 (1H, dd, J = 7.9, 4.9 Hz), 8.17-8.11 (3H, m), 8.67 (1H, d, J = 4.7 Hz), 8.89 (1H, s), 8.96 (1H, d, J = 2.2 Hz). | 347.0 NA |

TABLE 9-continued

| Intermediate ID | Intermediate Structure and Name | $^1$H NMR | MS (m/z) $[M + H]^+$; Purity (%) |
|---|---|---|---|
| E5 | 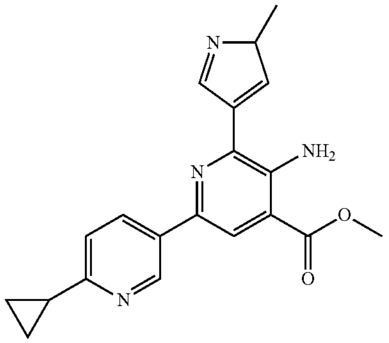 [SMILES: COC(=O)c1cc(-c2ccc(C3CC3)nc2)nc(C2=CC(C)N=C2)c1N] methyl 5-amino-6'-cyclopropyl-6-(1-methyl-1H-pyrazol-4-yl)-[2,3'-bipyridine]-4-carboxylate | (DMSO-$d_6$, 400 MHz): δ 0.97 (4H, d, J = 8.6 Hz), 2.16-2.10 (1H, m), 3.90 (3H, s), 3.93 (3H, s), 6.58 (2H, s), 7.34 (1H, d, J = 8.2 Hz), 8.01 (2H, m), 8.19 (1H, dd, J = 8.2, 2.3 Hz), 8.33 (1H, s), 9.02 (1H, s). | 350.0; NA |
| E6 | 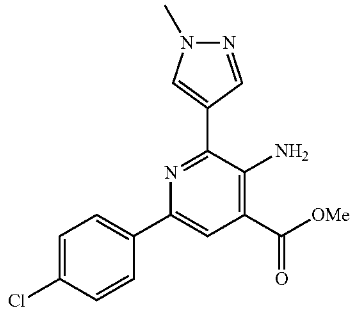 [SMILES: COC(=O)c1cc(-c2ccc(Cl)cc2)nc(-c2cnn(C)c2)c1N] methyl 3-amino-6-(4-chlorophenyl)-2-(1-methyl-1H-pyrazol-4-yl)isonicotinate | (DMSO-$d_6$, 300 MHz): δ H 3.91 (3H, s), 3.94 (3H, s), 6.60 (2H, s), 7.48 (2H, d, J = 8.4 Hz), 8.02 (3H, m), 8.06 (1H, s), 8.33 (1H, s). | 342.9; NA |

Step 3. Preparation of 3'-amino-N-(1,1-dioxidotetrahydrothiophen-3-yl)-6''-(trifluoromethyl)-[3,2': 6',3''-terpyridine]-4'-carboxamide (Precursor 4)

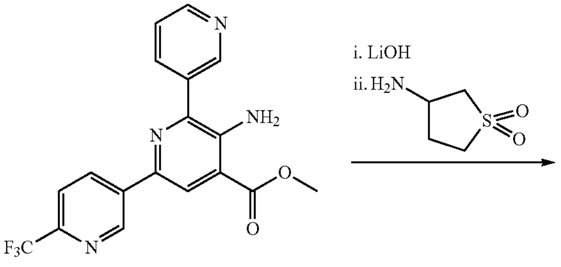

Precursor 3

-continued

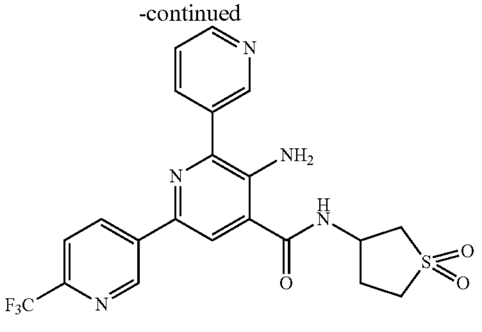

Precursor 4

A solution of methyl 3'-amino-6''-(trifluoromethyl)-[3,2': 6',3''-terpyridine]-4'-carboxylate (Precursor 3, 3.5 g, 8.32 mmol) in THF: water (42 mL:14 mL) was cooled to 0° C.; LiOH (1.05 g, 24.96 mmol) was added. The reaction was stirred at 0° C. for 1 hour and stirred at room temperature overnight. The reaction mixture was acidified with Amberlite IR120 to pH 4, followed by addition of ethyl acetate and MeOH. The solution was filtered to remove the resin and the solvent was evaporated to afford 3'-amino-6''-(trifluoromethyl)-[3,2': 6',3''-terpyridine]-4'-carboxylic acid (3.0 g, 7.91 mmol, 95% yield, >95% purity). MS (m/z): 361.1$[M+H]^+$. The acid intermediate was directly subjected to the next step.

A mixture of 3'-amino-6''-(trifluoromethyl)-[3,2':6',3''-terpyridine]-4'-carboxylic acid (0.6 g, 1.67 mmol) and 3-aminotetrahydrothiophene 1,1-dioxide·HCl (0.314 g, 1.83 mmol) were dissolved in DMF (8.0 mL) and the reaction mixture was cooled to 0° C. Diisopropylethylamine (0.87 mL, 4.5 mmol) and HATU (0.633 g, 1.67 mmol) were added. The reaction was stirred at 0° C. for 1 hour and stirred at room temperature overnight. The reaction was quenched with water and partitioned between ethyl acetate and water. The organic phase was separated, washed with saturated aqueous ammonium chloride and then with saturated aqueous sodium bicarbonate. The organic phase was dried over anhydrous magnesium sulfate, filtered and evaporated to afford the title compound 3'-amino-N-(1,1-dioxidotetrahydrothiophen-3-yl)-6"-(trifluoromethyl)-[3,2':6',3"-terpyridine]-4'-carboxamide (Precursor 4, 0.58 g, 66% yield, >90% purity). MS (m/z): 478.1[M+H]$^+$. The crude product was subjected to the next step without purification.

Table 10 lists intermediates that were made via a procedure similar to that described in the above step.

TABLE 10

| Intermediate Name | Structure and Name | 1H-NMR | MS (m/z) [M + H]$^+$; Purity (%) |
|---|---|---|---|
| F1 For 107 | 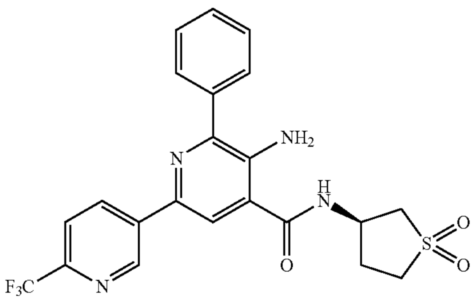 [SMILES: Nc1c(C(=O)N[C@@H]2CCS(=O)(=O)C2)cc(-c2ccc(C(F)(F)F)nc2)nc1-c1ccccc1] (R)-3'-amino-N-(1,1-dioxidotetrahydrothiophen-3-yl)-6"-(trifluoromethyl)-[3,2':6',3"-terpyridine]-4'-carboxamide | NA | 478.1; >90 |
| F2 For 108 | 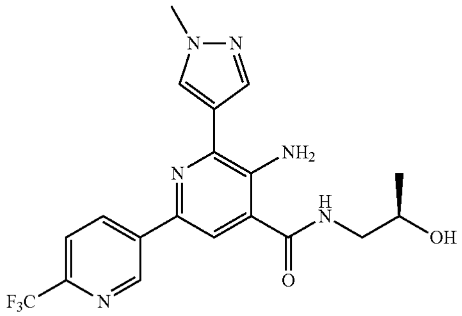 [SMILES: C[C@@H](O)CNC(=O)c1cc(-c2ccc(C(F)(F)F)nc2)nc(-c2cnn(C)c2)c1N] (R)-5-amino-N-(2-hydroxypropyl)-6-(1-methyl-1H-pyrazol-4-yl)-6'-(trifluoromethyl)-[2,3'-bipyridine]-4-carboxamide | NA | 421.1; >90 |
| F3 For 109 | 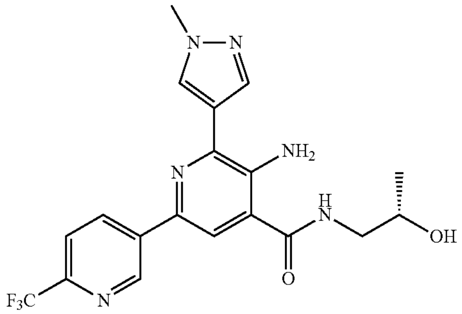 [SMILES: C[C@H](O)CNC(=O)c1cc(-c2ccc(C(F)(F)F)nc2)nc(-c2cnn(C)c2)c1N] (S)-5-amino-N-(2-hydroxypropyl)-6-(1-methyl-1H-pyrazol-4-yl)-6'-(trifluoromethyl)-[2,3'-bipyridine]-4-carboxamide | NA | 421.1; >90 |

TABLE 10-continued

| Intermediate Name | Structure and Name | 1H-NMR | MS (m/z) $[M + H]^+$; Purity (%) |
|---|---|---|---|
| F4 | 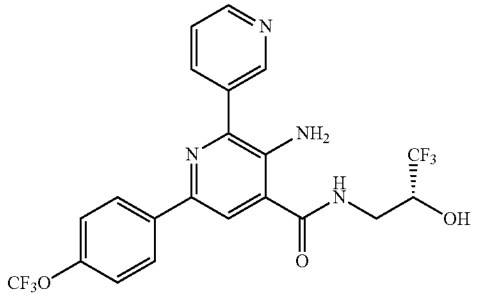 (R)-3-amino-N-(3,3,3-trifluoro-2-hydroxypropyl)-6-(4-(trifluoromethoxy)phenyl)-[2,3'-bipyridine]-4-carboxamide | ($CH_3OH-d_4$, 300 MHz): δ H 3.51 (1H, dd, J = 13.9, 8.4 Hz), 3.82 (1H, dd, J = 13.8, 4.0 Hz), 4.29 (1H, d, J = 7.8 Hz), 7.35 (2H, d, J = 8.4 Hz), 7.62 (1H, dd, J = 8.0, 4.9 Hz), 8.00 (1H, s), 8.11 (2H, d, J = 8.7 Hz), 8.25 (1H, d, J = 8.0 Hz), 8.64 (1H, s), 8.92 (1H, s). | 486.9; NA |
| F5 | 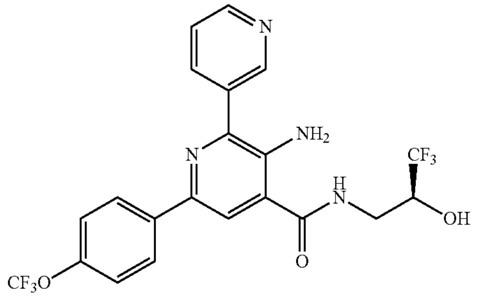 (S)-3-amino-N-(3,3,3-trifluoro-2-hydroxypropyl)-6-(4-(trifluoromethoxy)phenyl)-[2,3'-bipyridine]-4-carboxamide | ($CH_3OH-d_4$, 300 MHz): δ H 3.51 (1H, dd, J = 13.9, 8.4 Hz), 3.82 (1H, dd, J = 13.8, 4.0 Hz), 4.29 (1H, br s), 7.35 (2H, d, J = 8.4 Hz), 7.61 (1H, dd, J = 7.9, 4.9 Hz), 8.00 (1H, s), 8.11 (2H, d, J = 8.7 Hz), 8.26-8.23 (1H, m), 8.63 (1H, d, J = 5.0 Hz), 8.92 (1H, s). | 486.9; NA |
| F6 | 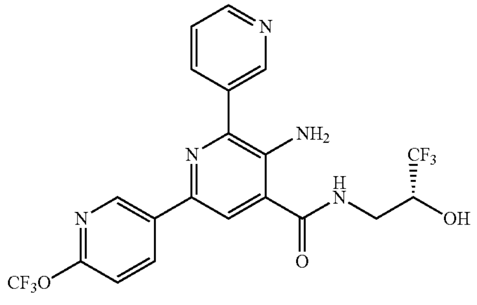 (R)-3'-amino-N-(3,3,3-trifluoro-2-hydroxypropyl)-6''-(trifluoromethyl)-[3,2':6',3''-terpyridine]-4'-carboxamide | ($CH_3OH-d_4$, 300 MHZ): δ H 3.56-3.47 (1H, m), 3.89-3.80 (1H, m), 4.34-4.26 (1H, m), 7.66-7.59 (1H, m), 7.93-7.87 (1H, m), 8.19-8.16 (1H, m), 8.29-8.22 (1H, m), 8.73-8.63 (2H, m), 9.00-8.87 (1H, m), 9.39-9.34 (1H, m). | 471.9; NA |
| F7 | 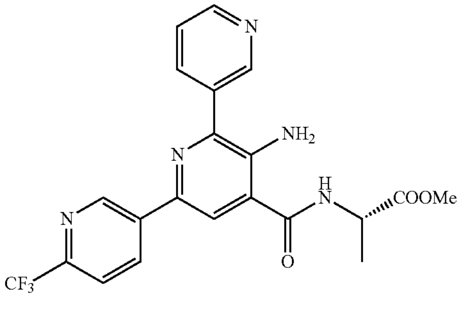 [SMILES: COC(=O)[C@H](C)NC(=O)c1cc(-c2ccc(C(F)(F)F)nc2)nc(-c2cccnc2)c1N] methyl (3'-amino-6''-(trifluoromethyl)-[3,2':6',3''-terpyridine]-4'-carbonyl)-L-alaninate | ($CH_3OH-d_4$, 400 MHz): δ H 1.55 (3H, d, J = 7.4 Hz), 3.78 (3H, s), 4.66 (1H, d, J = 7.4 Hz), 7.60 (1H, dd, J = 7.8, 4.9 Hz), 7.87 (1H, d, J = 8.3 Hz), 8.19 (1H, s), 8.25-8.23 (1H, m), 8.64 (2H, d, J = 7.6 Hz), 8.91 (1H, s), 9.35 (1H, s). | 445.9; NA |

TABLE 10-continued

| Intermediate Name | Structure and Name | 1H-NMR | MS (m/z) $[M + H]^+$; Purity (%) |
|---|---|---|---|
| F9 | 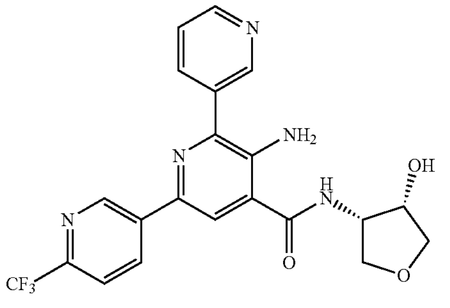 [SMILES: Nc1c(C(=O)N[C@H]2COC[C@H]2O)cc(-c2ccc(C(F)(F)F)nc2)nc1-c1cccnc1] 3'-amino-N-((3S,4S)-4-hydroxytetrahydrofuran-3-yl)-6''-(trifluoromethyl)-[3,2':6',3''-terpyridine]-4'-carboxamide | NA | 446.1; NA |
| F10 | 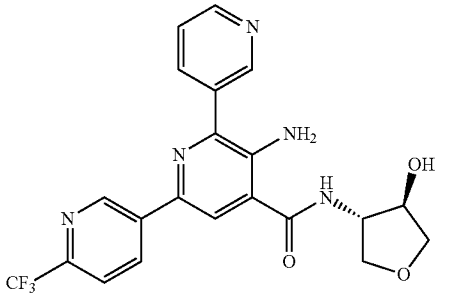 [SMILES: Nc1c(C(=O)N[C@H]2COC[C@@H]2O)cc(-c2ccc(C(F)(F)F)nc2)nc1-c1cccnc1] 3-amino-6-(4-chlorophenyl)-N-((3S,4R)-4-hydroxytetrahydrofuran-3-yl)-[2,3'-bipyridine]-4-carboxamide | (DMSO-$d_6$, 400 MHz): δ H 3.57-3.54 (1H, m), 3.71-3.69 (1H, m), 3.96-3.92 (1H, m), 4.04 (1H, dd, J = 9.1, 5.7 Hz), 4.25 (2H, s), 5.34 (1H, s), 6.42 (2H, s), 7.56-7.49 (3H, m), 8.12-8.03 (4H, m), 8.65 (1H, d, J = 4.7 Hz), 8.88 (2H, s). | 411.1; NA |
| F11 | 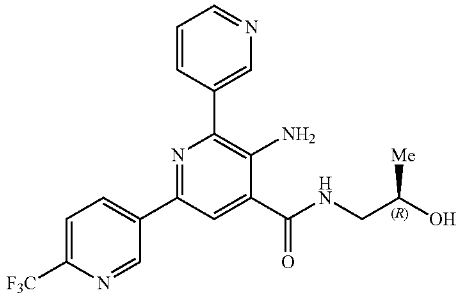 (R)-3'-amino-N-(2-hydroxypropyl)-6''-(trifluoromethyl)-[3,2':6',3''-terpyridine]-4'-carboxamide LVL-05-110 | (300 MHz, DMSO) 9.40 (1 H, s), 8.95-8.85 (2 H, m), 8.66 (1 H, d, J 3.6), 8.63 (1 H, d, J 8.8), 8.29 (1 H, s), 8.12 (1 H, d, J7.9), 7.98 (1 H, d, J 8.3), 7.55 (1 H, dd, J 7.7, 4.9), 6.71 (2 H, s), 4.86 (1 H, d, J 4.7), 3.84 (1 H, hept, J 6.7), 3.32-3.17 (2 H, m), 1.11 (3 H, d, J 6.2). | 418.1; NA |
| F12 | 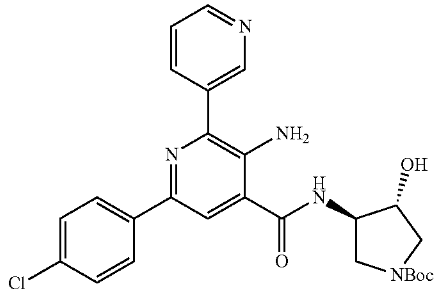 [SMILES: CC(C)(C)OC(=O)N1C[C@@H](O)[C@H](NC(=O)c2cc(-c3ccc(Cl)cc3)nc(-c3cccnc3)c2N)C1] tert-butyl (3R,4R)-3-(3-amino-6-(4-chlorophenyl)-[2,3'-bipyridine]-4-carboxamido)-4-hydroxypyrrolidine-1-carboxylate | NA | 510.2; 95 |

TABLE 10-continued

| Intermediate Name | Structure and Name | 1H-NMR | MS (m/z) [M + H]$^+$; Purity (%) |
|---|---|---|---|
| F13 | 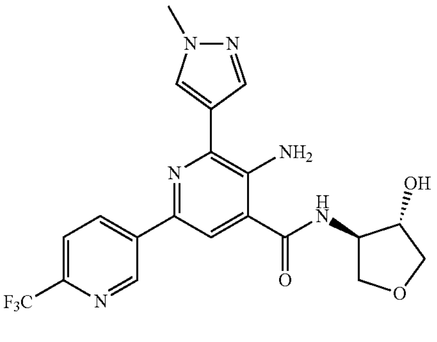 [SMILES: Cn1cc(-c2nc(-c3ccc(C(F)(F)F)nc3)cc(C(=O)N[C@@H]3COC[C@H]3O)c2N)cn1] 5-amino-N-((3R,4S)-4-hydroxytetrahydrofuran-3-yl)-6-(1-methyl-1H-pyrazol-4-yl)-6'-(trifluoromethyl)-[2,3'-bipyridine]-4-carboxamide | NA | 449.1; 90 |
| F14 | 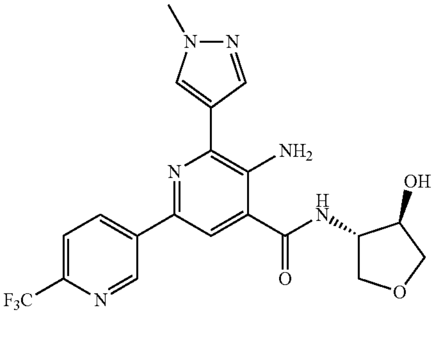 [SMILES: Cn1cc(-c2nc(-c3ccc(C(F)(F)F)nc3)cc(C(=O)N[C@H]3COC[C@@H]3O)c2N)cn1] 5-amino-N-((3S,4R)-4-hydroxytetrahydrofuran-3-yl)-6-(1-methyl-1H-pyrazol-4-yl)-6'-(trifluoromethyl)-[2,3'-bipyridine]-4-carboxamide | NA | 449.0; 95 |
| F15 | 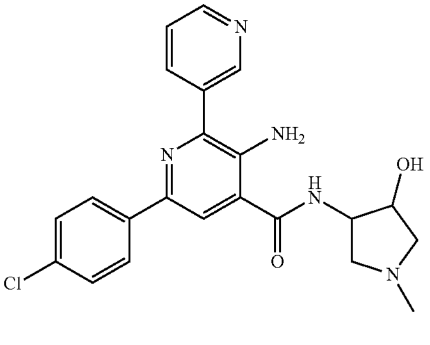 [SMILES: CN1CC(O)C(NC(=O)c2cc(-c3ccc(Cl)cc3)nc(-c3cccnc3)c2N)C1] 3-amino-6-(4-chlorophenyl)-N-((3S,4R)-4-hydroxy-1-methylpyrrolidin-3-yl)-[2,3'-bipyridine]-4-carboxamide | NA | 424.1; NA |

TABLE 10-continued

| Intermediate Name | Structure and Name | 1H-NMR | MS (m/z) [M + H]$^+$; Purity (%) |
|---|---|---|---|
| F16 | 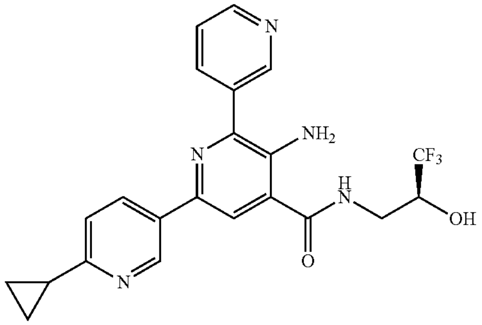 [SMILES: Nc1c(C(=O)NC[C@H](O)C(F)(F)F)cc(-c2ccc(C3CC3)nc2)nc1-c1cccnc1] (S)-3'-amino-6''-cyclopropyl-N-(3,3,3-trifluoro-2-hydroxypropyl)-[3,2':6',3''-terpyridine]-4'-carboxamide | NA | 444.0; NA |
| F17 | 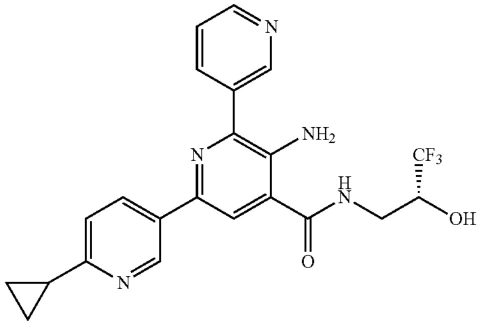 [SMILES: Nc1c(C(=O)NC[C@@H](O)C(F)(F)F)cc(-c2ccc(C3CC3)nc2)nc1-c1cccnc1] (R)-3'-amino-6''-cyclopropyl-N-(3,3,3-trifluoro-2-hydroxypropyl)-[3,2':6',3''-terpyridine]-4'-carboxamide | NA | 444.0; NA |
| F18 | 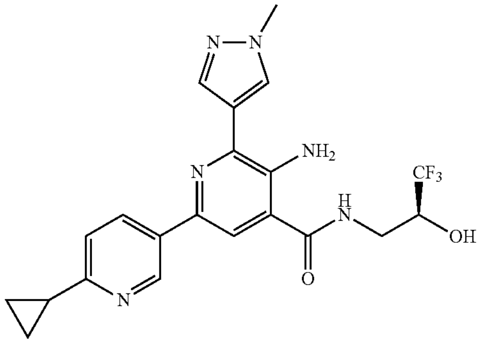 [SMILES: Cn1cc(-c2nc(-c3ccc(C4CC4)nc3)cc(C(=O)NC[C@H](O)C(F)(F)F)c2N)cn1] (S)-5-amino-6'-cyclopropyl-6-(1-methyl-1H-pyrazol-4-yl)-N-(3,3,3-trifluoro-2-hydroxypropyl)-[2,3'-bipyridine]-4-carboxamide | NA | 447.0; NA |
| F19 | 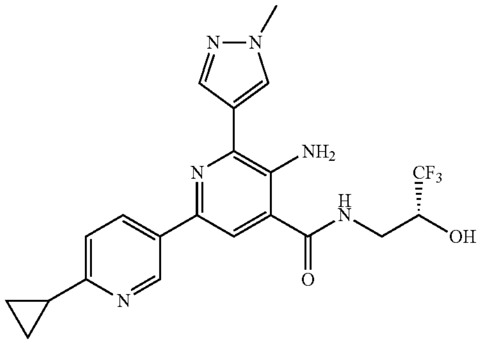 [SMILES: Cn1cc(-c2nc(-c3ccc(C4CC4)nc3)cc(C(=O)NC[C@@H](O)C(F)(F)F)c2N)cn1] | NA | 447.0; NA |

TABLE 10-continued

| Intermediate Name | Structure and Name | 1H-NMR | MS (m/z) [M + H]+; Purity (%) |
|---|---|---|---|
| | (R)-5-amino-6'-cyclopropyl-6-(1-methyl-1H-pyrazol-4-yl)-N-(3,3,3-trifluoro-2-hydroxypropyl)-[2,3'-bipyridine]-4-carboxamide | | |
| F20 | 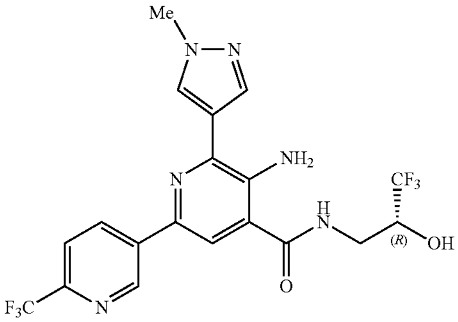 (R)-5-amino-6-(1-methyl-1H-pyrazol-4-yl)-N-(3,3,3-trifluoro-2-hydroxypropyl)-6'-(trifluoromethyl)-[2,3'-bipyridine]-4-carboxamide LVL-05-084 | (300 MHz, DMSO) 9.44 (1 H, s), 9.08 (1 H, t, J 6.1), 8.66 (1 H, d, J 7.1), 8.34 (1 H, s), 8.15 (1 H, s), 8.05 (1 H, s), 7.99 (1 H, d, J 8.2), 6.67-6.59 (2 H, m), 4.23 (1 H, s), 3.94 (3 H, s), 3.75-3.63 (1 H, m), 3.29 (1 H, s). | 475.1; NA |
| F21 | 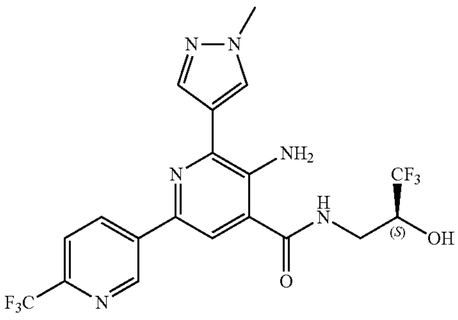 (S)-5-amino-6-(1-methyl-1H-pyrazol-4-yl)-N-(3,3,3-trifluoro-2-hydroxypropyl)-6'-(trifluoromethyl)-[2,3'-bipyridine]-4-carboxamide | NA | 475.1; NA |
| F22 | 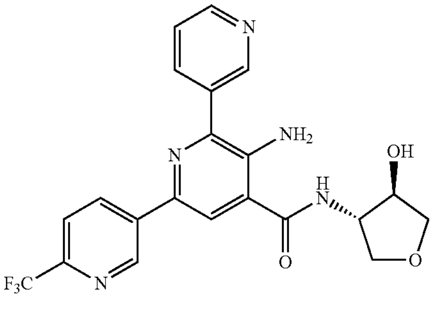 [SMILES: Nc1c(C(=O)N[C@H]2COC[C@@H]2O)cc(-c2ccc(C(F)(F)F)nc2)nc1-c1cccnc1] 3'-amino-N-((3S,4R)-4-hydroxytetrahydrofuran-3-yl)-6''-(trifluoromethyl)-[3,2':6',3''-terpyridine]-4'-carboxamide | NA | 446.10; NA |

TABLE 10-continued

| Intermediate Name | Structure and Name | 1H-NMR | MS (m/z) $[M+H]^+$; Purity (%) |
|---|---|---|---|
| F23 | 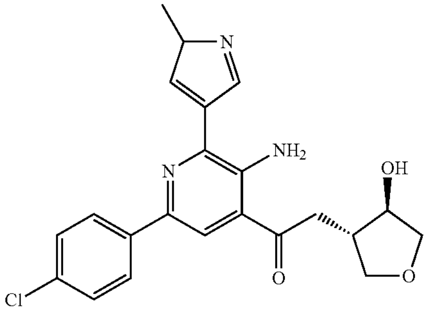 [SMILES: CC1C=C(c2nc(-c3ccc(Cl)cc3)cc(C(=O)C[C@H]3COC[C@@H]3O)c2N)C=N1] 1-(3-amino-6-(4-chlorophenyl)-2-(1-methyl-1H-pyrazol-4-yl)pyridin-4-yl)-2-((3S,4R)-4-hydroxytetrahydrofuran-3-yl)ethan-1-one | NA | 414.1; NA |
| F24 | 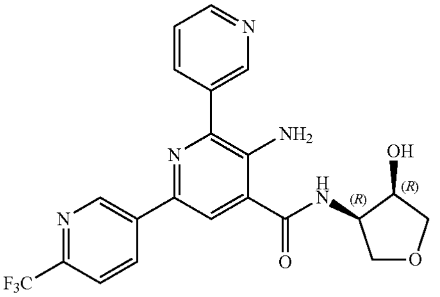 3'-amino-N-((3R,4R)-4-hydroxytetrahydrofuran-3-yl)-6''-(trifluoromethyl)-[3,2':6',3''-terpyridine]-4'-carboxamide | $^1H$ NMR (DMSO-$d_6$, 400 MHz): δ H 3.72-3.65 (2H, m), 3.94 (2H, t, J = 8.2 Hz), 4.28 (1H, s), 4.46 (1H, s), 5.34 (1H, d, J = 4.0 Hz), 6.66 (2H, s), 7.55 (1H, d, J = 6.3 Hz), 7.97 (1H, d, J = 8.3 Hz), 8.11 (1H, d, J = 7.8 Hz), 8.30 (1H, s), 8.61 (3H, t, J = 13.4 Hz), 8.89 (1H, s), 9.40 (1H, s). | 446.1; NA |
| F25 | 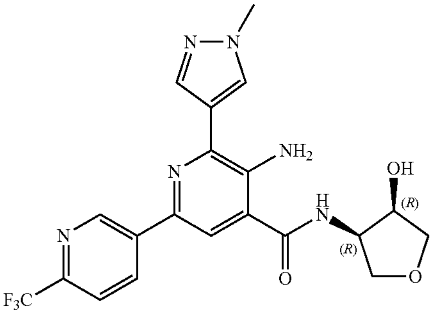 5-amino-N-((3R,4R)-4-hydroxytetrahydrofuran-3-yl)-6-(1-methyl-1H-pyrazol-4-yl)-6'-(trifluoromethyl)-[2,3'-bipyridine]-4-carboxamide | $^1H$ NMR (DMSO-$d_6$, 400 MHz): δ H 3.72-3.65 (2H, m), 3.95-3.93 (5H, m), 4.27 (1H, s), 4.45 (1H, d, J = 8.2 Hz), 5.32 (1H, d, J = 4.2 Hz), 6.55 (2H, s), 7.97 (1H, d, J = 8.3 Hz), 8.04 (1H, s), 8.16 (1H, s), 8.32 (1H, s), 8.52 (1H, d, J = 7.7 Hz), 8.66 (1H, d, J = 8.3 Hz), 9.45 (1H, s). | 449.1; NA |
| F26 | 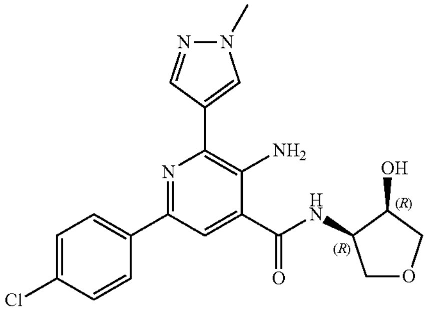 3-amino-6-(4-chlorophenyl)-N-((3R,4R)-4-hydroxytetrahydrofuran-3-yl)-2-(1-methyl-1H-pyrazol-4-yl)isonicotinamide | $^1H$ NMR (DMSO-$d_6$, 400 MHz): δ H 3.72-3.64 (2H, m), 3.95-3.91 (5H, m), 4.26 (1H, d, J = 5.0 Hz), 4.43 (1H, t, J = 7.1 Hz), 5.30 (1H, d, J = 4.1 Hz), 6.30 (2H, s), 7.49 (2H, d, J = 8.3 Hz), 7.98 (2H, d, J = 13.2 Hz), 8.11 (2H, d, J = 8.3 Hz), 8.27 (1H, s), 8.52 (1H, d, J = 7.6 Hz). | 414.1; NA |

TABLE 10-continued

| Intermediate Name | Structure and Name | 1H-NMR | MS (m/z) [M + H]+; Purity (%) |
|---|---|---|---|
| F27 | 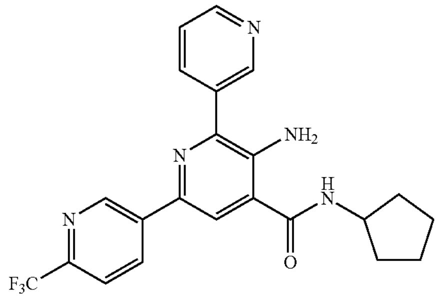 [SMILES: Nc1c(C(=O)NC2CCCC2)cc(-c2ccc(C(F)(F)F)nc2)nc1-c1cccnc1] 3'-amino-N-cyclopentyl-6''-(trifluoromethyl)-[3,2':6',3''-terpyridine]-4'-carboxamide | $^1$H NMR (DMSO-$d_6$, 400 MHz): δ H 1.61-1.53 (4H, m), 1.76-1.68 (2H, m), 1.98-1.88 (2H, m), 4.27-4.22 (1H, m), 6.66 (2H, t, J = 2.3 Hz), 7.55-7.52 (1H, m), 7.96 (1H, dd, J = 8.1, 1.6 Hz), 8.11 (1H, dd, J = 7.5, 2.3 Hz), 8.17 (1H, s), 8.65-8.60 (3H, m), 8.89 (1H, t, J = 2.2 Hz), 9.39 (1H, s). | 428.1; NA |
| F28 | 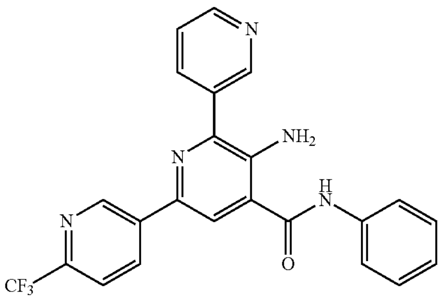 [SMILES: Nc1c(C(=O)Nc2ccccc2)cc(-c2ccc(C(F)(F)F)nc2)nc1-c1cccnc1] 3'-amino-N-phenyl-6''-(trifluoromethyl)-[3,2':6',3''-terpyridine]-4'-carboxamide | $^1$H NMR (DMSO-$d_6$, 400 MHz): δ H 6.53 (2H, s), 7.17 (1H, d, J = 7.6 Hz), 7.40 (2H, t, J = 7.6 Hz), 7.56 (1H, s), 7.74 (2H, d, J = 7.9 Hz), 7.97 (1H, d, J = 8.3 Hz), 8.14 (1H, d, J = 7.7 Hz), 8.37 (1H, s), 8.67 (2H, s), 8.92 (1H, s), 9.43 (1H, s), 10.54 (1H, s). | 436.1; NA |
| F29 | 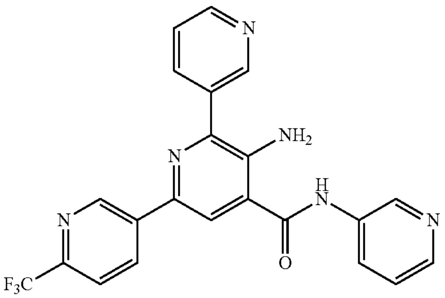 [SMILES: Nc1c(C(=O)Nc2cccnc2)cc(-c2ccc(C(F)(F)F)nc2)nc1-c1cccnc1] 3'-amino-N-(pyridin-3-yl)-6''-(trifluoromethyl)-[3,2':6',3''-terpyridine]-4'-carboxamide 3'-amino-N-(pyridin-3-y1)-6''-(trifluoromethyl)-[3,2':6',3''-terpyridine]-4'-carboxamide | NA | 437.1; NA |

Preparation of 3'-amino-6"-(trifluoromethyl)-[3,2':6',3"-terpyridine]-4'-carboxamide (F30)

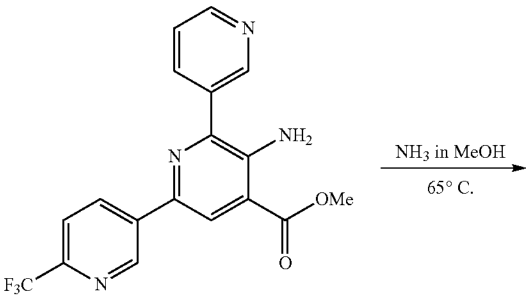

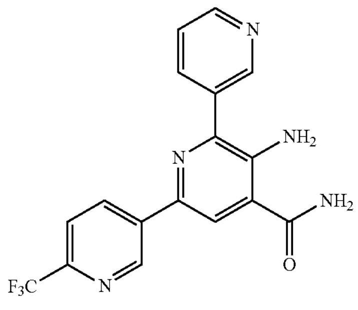

F30

To methyl 3'-amino-6"-(trifluoromethyl)-[3,2':6',3"-terpyridine]-4'-carboxylate (300 mg, 0.801 mmol) in vial was added a 7M solution of ammonia in MeOH, sealed and heated at 65° C. overnight. The solvent was evaporated and compound F30 was obtained as a white solid and was used without further purification (270 mg, 89%). MS (m/z): 488.0 $[M+H]^+$; 95% purity Step 4—Preparation of 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (106)

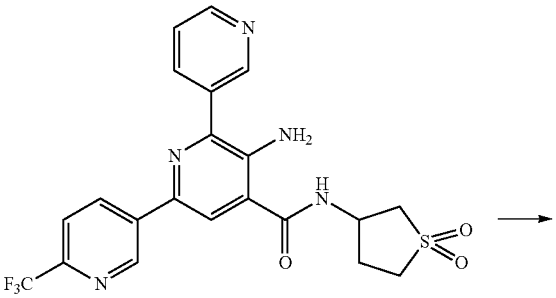

-continued

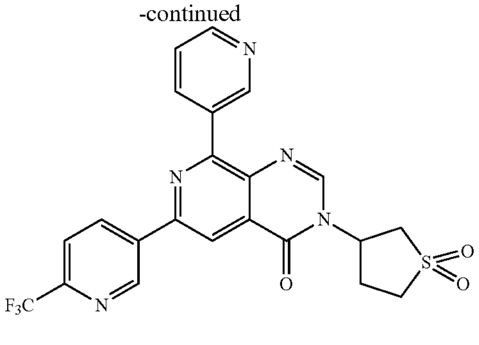

Triethyl orthoformate (10 mL) was added to 3'-amino-N-(1,1-dioxidotetrahydrothiophen-3-yl)-6"-(trifluoromethyl)-[3,2':6',3"-terpyridine]-4'-carboxamide (Precursor 4, 0.3 g, 0.618 mmol) in a sealed tube. Acetic acid (1 mL, 10% v/v) was added at room temperature and the resulting mixture was heated at 95° C. overnight. The mixture was concentrated, followed by addition of sat. $NaHCO_3$ and the solid was collected by vacuum filtration, washed with water and dried. The residue was purified by normal phase chromatography to afford the title compound 3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (106, 0.13 g, 43% yield). $^1H$ NMR (DMSO-$d_6$, 300 MHz): $\delta_H$ 2.70-2.67 (2H, m), 3.37-3.30 (1H, m), 3.70-3.57 (2H, m), 5.42 (1H, t, J=8.3 Hz), 7.62 (1H, dd, J=7.9, 4.8 Hz), 8.07 (1H, d, J=8.3 Hz), 8.58 (1H, d, J=8.1 Hz), 8.64 (1H, s), 8.72 (1H, d, J=4.7 Hz), 8.80 (1H, s), 8.96 (1H, d, J=8.4 Hz), 9.37 (1H, s), 9.66 (1H, s); MS (m/z): 488.0 $[M+H]^+$; >98% purity.

Preparation of (R)-3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (107)

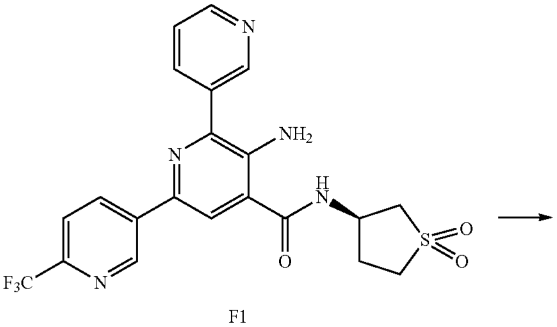

F1

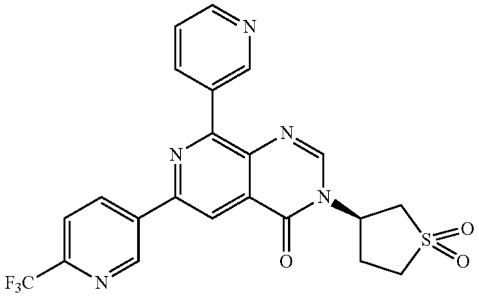

98

Dioxane (7 mL) and triethyl orthoformate (1.2 mL, 7.02 mmol) were added to intermediate (R)-3'-amino-N-(1,1-dioxidotetrahydrothiophen-3-yl)-6"-(trifluoromethyl)-[3,2':6',3"-terpyridine]-4'-carboxamide (F1, 0.67 g, 1.4 mmol) in a flask. p-Toluene sulfonic acid (0.267 mg, 1.4 mmol) was added at room temperature and the resulting mixture was stirred overnight. The mixture was concentrated, followed by addition of sat. $NaHCO_3$ and the formed solid was collected by vacuum filtration, washed with water and dried. The residue was purified by silica gel column chromatography to afford the title compound (R)-3-(1,1-dioxidotetrahydrothiophen-3-yl)-8-(pyridin-3-yl)-6-(6-(trifluoromethyl)pyridin-3-yl)pyrido[3,4-d]pyrimidin-4(3H)-one (98 1.82 g, 69% yield). $^1H$ NMR (DMSO-$d_6$, 400 MHz): $\delta_H$ 3.25-3.18 (2H, m), 3.90-3.87 (1H, m), 4.25-4.12 (3H, m), 5.96 (1H, t, J=8.5 Hz), 8.16 (1H, d, J=6.7 Hz), 8.62 (1H, d, J=8.3 Hz), 9.11 (1H, d, J=8.0 Hz), 9.18 (1H, s), 9.27 (1H, s), 9.35 (1H, s), 9.50 (1H, s), 9.90 (1H, s), 10.20 (1H, s); MS (m/z): 488.1 $[M+H]^+$; 99% purity Table 11 lists compounds made via procedures similar to that described for 98, replacing reactant 4, 5 and 6 with the indicated groups.

TABLE 11

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| 110 | 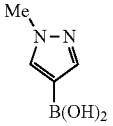 | 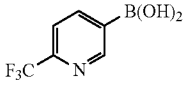 | 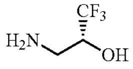 | 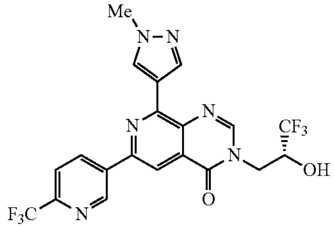 [SMILES: Cn1cc(-c2nc(-c3ccc(C(F)(F)F)nc3)cc3c(=O)n(C[C@@H](O)C(F)(F)F)cnc23)cn1] (R)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one | (300 MHz, DMSO): δ H 9.65 (1 H, s), 8.93 (1 H, d, J 7.9), 8.84 (1 H, s), 8.57-8.47 (3 H, m), 8.03 (1 H, d, J 8.1), 6.81 (1 H, bs), 4.46 (2 H, d, J 11.3), 4.09 (1 H, dd, J 13.2, 9.9), 3.97 (3 H, s). | 485.0; 98 |
| 111 | 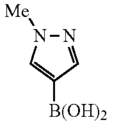 | 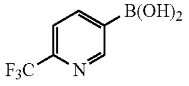 | 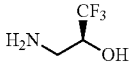 | 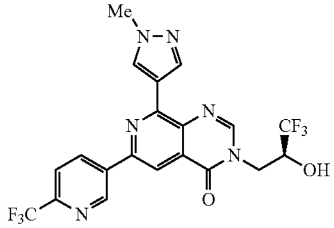 [SMILES: Cn1cc(-c2nc(-c3ccc(C(F)(F)F)nc3)cc3c(=O)n(C[C@H](O)C(F)(F)F)cnc23)cn1] (S)-8-(1-methyl-1H-pyrazol-4-yl)-3-(3,3,3-trifluoro-2-hydroxypropyl)-6-(6-(trifluoromethyl)pyridin-3-yl)pyrido[3,4-d]pyrimidin-4(3H)-one | (400 MHz, DMSO): δ H 9.65 (1 H, d, J 2.0), 8.93 (1 H, dd, J 8.1, 1.9), 8.84 (1 H, s), 8.52 (3 H, dd, J 9.6, 8.9), 8.03 (1 H, d, J 8.3), 6.81 (1 H, d, J 6.6), 4.48-4.40 (2 H, m), 4.09 (1 H, dd, J 14.2, 9.9), 3.97 (3 H, s). | 485.1; 97.8 |
| 112 | 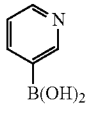 | 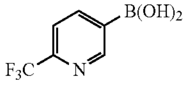 | 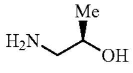 | 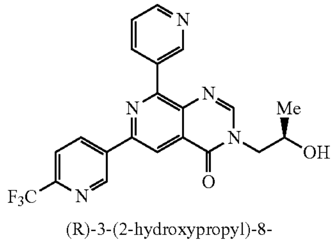 (R)-3-(2-hydroxypropyl)-8-(pyridin-3-yl)-6-(6-(trifluoromethyl)pyridin-3-yl)pyrido[3,4-d]pyrimidin-4(3H)-one | (400 MHZ, DMSO): δ H 9.63 (1 H, s), 9.36 (1 H, s), 8.93 (1 H, d, J 8.1), 8.75 (1 H, s), 8.70 (1 H, d, J 3.9), 8.59- 8.55 (1 H, m), 8.46 (1 H, s), 8.05 (1 H, d, J 8.3), 7.60 (1 H, dd, J 7.8, 4.8), 5.06 (1 H, d, J 5.0), 4.16 (1 H, dd, J 13.2, 3.2), 4.06 - 3.96 (1 H, m), 3.77 (1 H, dd, J 13.3, 8.6). | 428.1 99.2 |

TABLE 11-continued

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| 113 | 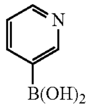 | 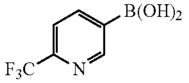 | 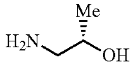 | 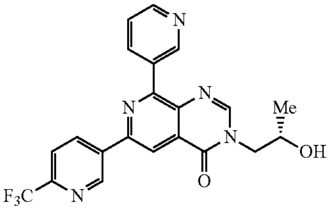 [SMILES: C[C@H](O)Cn1cnc2c(-c3cccnc3)nc(-c3ccc(C(F)(F)F)nc3)cc2c1=O] (R)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one | (400 MHz, DMSO): δ H 9.64 (1 H, d, J 1.2), 9.36 (1 H, d, J 1.6), 8.94 (1 H, dd, J 8.2, 1.5), 8.76 (1 H, s), 8.71 (1 H, dd, J 4.8, 1.4), 8.57 (1 H, dt, J 7.9, 1.8), 8.47 (1 H, s), 8.06 (1 H, d, J 8.2), 7.60 (1 H, dd, J 7.9, 4.8), 5.06 (1 H, d, J 5.0), 4.16 (1 H, dd, J 13.2, 3.2), 4.06-3.96 (1 H, m), 3.78 (1 H, dd, J 13.2, 8.6). | 428.1 99.9 |
| 114 | 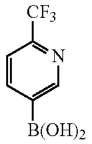 | 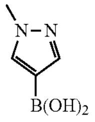 | 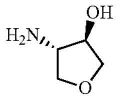 3S, 4R | 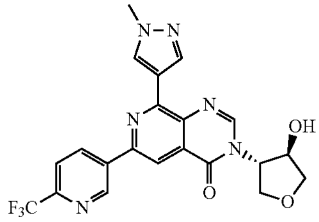 [SMILES: Cn1cc(-c2nc(-c3ccc(C(F)(F)F)nc3)cc3c(=O)n([C@H]4COC[C@@H]4O)cnc23)cn1] 3-((3S,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one | (DMSO-$d_6$, 300 MHz): δ H 3.67-3.62 (1H, m), 3.98 (3H, s), 4.18-4.14 (1H, m), 4.23-4.18 (1H, m), 4.59 (1H, bs), 5.01 (1H, bs), 5.72 (1H, d, J = 4.3 Hz), 8.04 (1H, d, J = 8.3 Hz), 8.42 (1H, s), 8.53 (2H, d, J = 7.8 Hz), 8.87 (1H, d, J = 0.9 Hz), 8.97-8.93 (1H, m), 9.67 (1H, s). | 459.1; 98% |
| 115 | 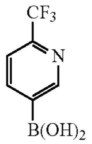 | 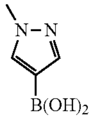 | 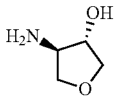 3S, 4R | 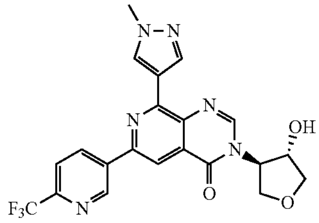 [SMILES: Cn1cc(-c2nc(-c3ccc(C(F)(F)F)nc3)cc3c(=O)n([C@@H]4COC[C@H]4O)cnc23)cn1] 3-((3R,4S)-4-hydroxytetrahydrofuran-3-y1)-8-(1-methyl-1H-pyrazol-4-y1)-6-(6-(trifluoromethyl)pyridin-3-yl)pyrido[3,4-d]pyrimidin-4(3H)-one | (DMSO-$d_6$, 300 MHz): 8H 3.65 (1H, dd, J = 9.7, 3.3 Hz), 3.98 (3H, s), 4.19-4.13 (1H, m), 4.25-4.19 (1H, m), 4.58 (1H, m), 5.03-4.98 (1H, m), 5.72 (1H, d, J = 4.3 Hz), 8.04 (1H, d, J = 8.3 Hz), 8.42 (1H, s), 8.54 (2H, d, J = 7.6 Hz), 8.87 (1H, s), 8.97-8.93 (1H, m), 9.67 (1H, s). | 459.1; 98% |
| 116 | 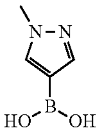 | 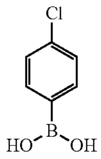 | 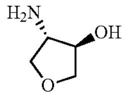 | 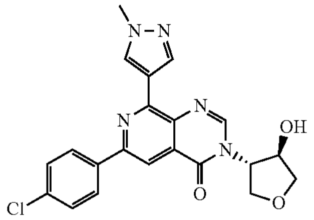 [SMILES: Cn1cc(-c2nc(-c3ccc(Cl)cc3)cc3c(=O)n([C@H]4COC[C@@H]4O)cnc23)cn1] | $^1$H NMR (DMSO-$d_6$, 400 MHz): 8H 3.62 (1H, dd, J = 9.6, 3.2 Hz), 3.95 (3H, s), 4.21-4.09 (3H, m), 4.99-4.97 (1H, m), 5.69 (1H, d, J = 4.3 Hz), 7.57 (2H, d, J = 8.4 Hz), 8.31-8.28 (3H, m), 8.35 (1H, s), 8.48 (1H, s), 8.79 (1H, s) | 424.1, 98 |

TABLE 11-continued

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| 117 | 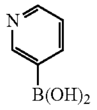 | 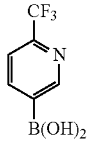 | 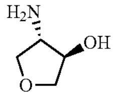 | 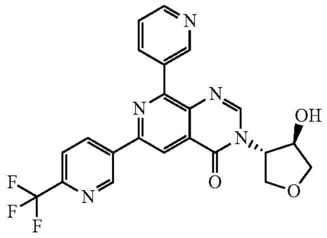 [SMILES: O=c1c2cc(-c3ccc(C(F)(F)F)nc3)nc(-c3cccnc3)c2ncn1[C@H]1COC[C@@H]1O] | (DMSO-$d_6$, 300 MHz): 8H 3.64 (1H, dd, J = 9.6, 3.2 Hz), 4.09 (1H, dd, J = 10.1, 4.1 Hz), 4.25-4.15 (2H, m), 4.60 (1H, s), 5.01 (1H, s), 5.72 (1H, d, J = 4.3 Hz), 7.60 (2H, dd, J = 8.6, 5.1 Hz), 8.06 (1H, d, J = 8.3 Hz), 8.43 (1H, s), 8.58 (1H, d, J = 8.0 Hz), 8.76-8.69 (2H, m), 8.94 (1H, d, J = 8.4 Hz), 9.37 (1H, s), 9.64 (1H, s). | 456.1; >99 |
| 118 | 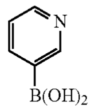 | 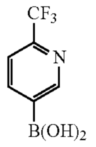 | 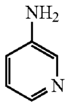 | 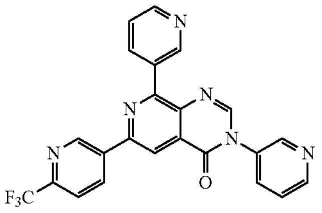 [SMILES: O=c1c2cc(-c3ccc(C(F)(F)F)nc3)nc(-c3cccnc3)c2ncn1-c1cccnc1] 3,8-di(pyridin-3-yl)-6-(6-(trifluoromethyl)pyridin-3-yl)pyrido[3,4-d]pyrimidin-4(3H)-one | (DMSO-$d_6$, 400 MHz): δ H 7.69-7.60 (2H, m), 8.07 (2H, t, J = 9.1 Hz), 8.59 (1H, d, J = 8.0 Hz), 8.66 (1H, s), 8.73 (2H, dd, J = 10.5, 4.7 Hz), 8.82 (2H, s), 8.96 (1H, d, J = 8.3 Hz), 9.38 (1H, s), 9.66 (1H, s). | 447.1; >99% |
| 119 | 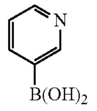 | 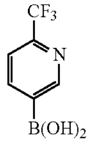 | $NH_3$ | 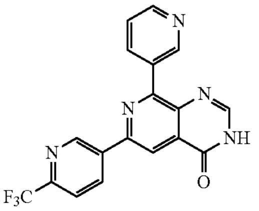 [SMILES: O=c1[nH]cnc2c(-c3cccnc3)nc(-c3ccc(C(F)(F)F)nc3)cc12] 8-(pyridin-3-yl)-6-(6-(trifluoromethyl)pyridin-3-yl)pyrido[3,4-d]pyrimidin-4(3H)-one | (DMSO-$d_6$, 400 MHz): δ H 7.57 (1H, t, J = 6.3 Hz), 8.04 (1H, d, J = 8.3 Hz), 8.33 (1H, s), 8.54 (1H, d, J = 8.0 Hz), 8.71-8.66 (2H, m), 8.92 (1H, d, J = 8.3 Hz), 9.33 (1H, s), 9.62 (1H, s), 12.86 (1H, s). | 370.1; >99% |

Preparation of (S)-6-(6-cyclopropylpyridin-3-yl)-8-(pyridin-3-yl)-3-(3,3,3-trifluoro-2-hydroxypropyl) pyrido[3,4-d]pyrimidin-4(3H)-one as a white solid (120)

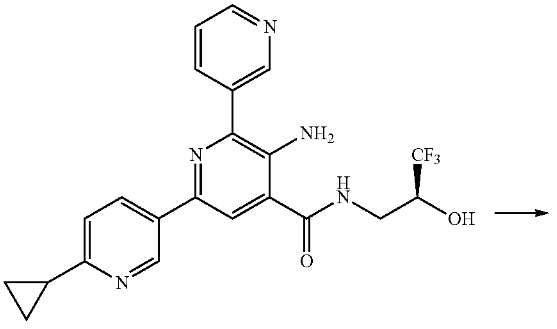

-continued

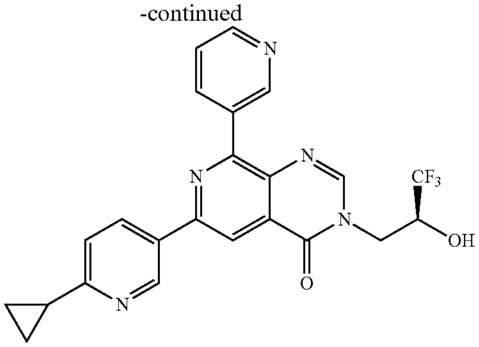

Triethylorthoformate (1.69 ml, 10.2 mmol) and p-toluenesulfonic acid (117 mg, 0.679 mmol) were added to a solution of (S)-3'-amino-6"-cyclopropyl-N-(3,3,3-trifluoro-2-hydroxypropyl)-[3,2':6',3"-terpyridine]-4'-carboxamide (301 mg, 0.679 mmol) in dioxane (3.4 ml). After 1 h DMF (0.5 ml) was added and the reaction mixture was heated to 40° C. and stirred for 48 h. The reaction mixture was quenched with sodium bicarbonate (pH>11). Water was added and the mixture was extracted with ethyl acetate. The combined organic layers were dried over anhydrous magnesium sulfate, concentrated and purified by silica gel column chromatography to afford the title compound (S)-6-(6-cyclopropylpyridin-3-yl)-8-(pyridin-3-yl)-3-(3,3,3-trifluoro-2-hydroxypropyl)pyrido[3,4-d]pyrimidin-4(3H)-one as a white solid (120, 115 mg, 37%). $^{1}$H NMR (DMSO-$d_6$, 400 MHz): δ 1.02 (4H, d, J=8.2 Hz), 2.23-2.17 (1H, m), 4.08 (1H, dd, J=14.1, 9.9 Hz), 4.45 (2H, d, J=12.5 Hz), 6.78 (1H, d, J=6.4 Hz), 7.47 (1H, d, J=8.2 Hz), 7.59 (1H, dd, J=7.9, 4.8 Hz), 8.49-8.47 (2H, m), 8.54 (2H, d, J=11.8 Hz), 8.70 (1H, d, J=4.8 Hz), 9.26 (1H, s), 9.32 (1H, s); MS (m/z): 454.2 $[M+H]^+$; >99% purity.

Table 12 lists compounds made via procedures similar to that described for 120, replacing reactant 4, 5 and 6 with the indicated groups.

TABLE 12

| Compound No. | Reactant 4 (step 1) | Reactant 5 (step 2) | Reactant 6 (step 3) | Compound Structure/Name | $^{1}$H-NMR | MS (m/z) $[M + H]^+$; Purity (%) |
|---|---|---|---|---|---|---|
| 121 | 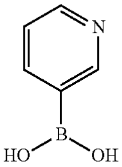 | 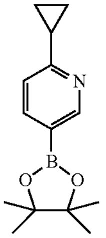 | 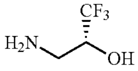 | 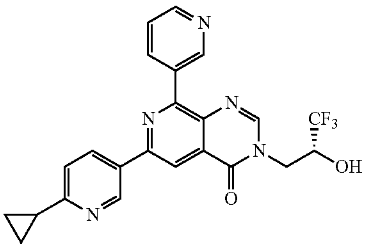 [SMILES: O=c1c2cc(-c3ccc(C4CC4)nc3)nc(-c3cccnc3)c2ncn1C[C@@H](O)C(F)(F)F] (R)-6-(6-cyclopropylpyridin-3-yl)-8-(pyridin-3-yl)-3-(3,3,3-trifluoro-2-hydroxypropyl)pyrido[3,4-d]pyrimidin-4(3H)-one | (DMSO-$d_6$, 400 MHz): δ 1.02 (4H, d, J = 8.1 Hz), 2.23-2.18 (1H, m), 4.11-4.05 (1H, m), 4.46-4.41 (2H, m), 6.79-6.77 (1H, m), 7.47 (1H, d, J = 8.3 Hz), 7.60 (1H, dd, J = 7.9, 4.8 Hz), 8.51-8.48 (2H, m), 8.56-8.52 (2H, m), 8.70 (1H, dd, J = 4.8, 1.6 Hz), 9.27 (1H, d, J = 2.2 Hz), 9.33 (1H, d, J = 2.2 Hz). | 454.1; 99 |

Preparation of (R)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one (108)

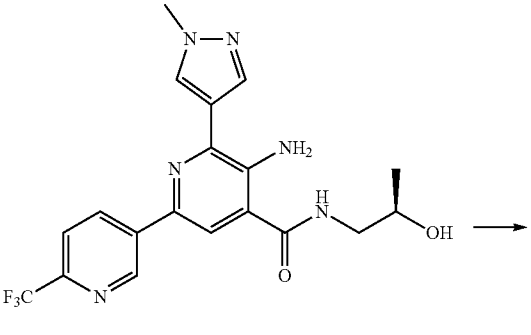

-continued

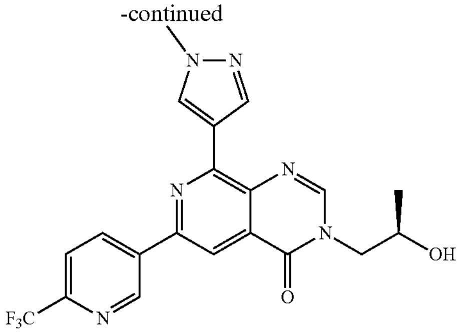

108 was prepared according to the procedure reported for Step 2 for the synthesis of 1 (synthesis of Intermediate B1). $^1$H NMR (DMSO-$d_6$, 400 MHz): $\delta_H$ 1.17 (3H, d, J=6.2 Hz), 3.76 (1H, dd, J=13.3, 8.6 Hz), 3.97 (3H, s), 4.16 (1H, dd, J=13.3, 3.2 Hz), 5.08 (1H, d, J=5.0 Hz), 8.03 (1H, d, J=8.3 Hz), 8.46 (1H, s), 8.49 (1H, s), 8.53 (1H, s), 8.86 (1H, s), 8.93 (1H, d, J=8.3 Hz), 9.65 (1H, s); MS (m/z): 431.1 $[M+H]^+$; >99% purity.

Table 13 lists compounds made via procedures similar to that described for 108, replacing reactant 4, 5, and 6 with the indicated groups.

TABLE 13

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| 109 | 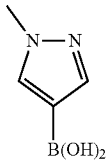 | 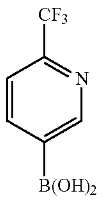 [SMILES: OB(O)c1ccc(C(F)(F)F)nc1] | 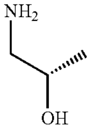 | 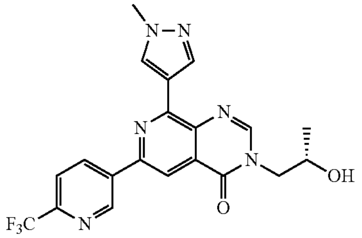 (S)-3-(2-hydroxypropyl)-8-(1-methyl-1H-pyrazol-4-yl)-6-(6-(trifluoromethyl)pyridin-3-yl)pyrido[3,4-d]pyrimidin-4(3H)-one | (DMSO-$d_6$, 400 MHz): δH 1.15 (3H, d, J = 6.2 Hz), 3.75 (1H, dd, J = 13.3, 8.6 Hz), 3.96 (3H, s), 4.15 (1H, dd, J = 13.2, 3.2 Hz), 5.06 (1H, d, J = 5.0 Hz), 8.02 (1H, d, J = 8.3 Hz), 8.45 (1H, s), 8.49 (1H, s), 8.52 (1H, s), 8.85 (1H, s), 8.92 (1H, d, J = 8.3 Hz), 9.64 (1H, s). | 431.1; >98 |
| 122 | 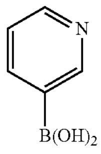 | 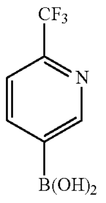 | 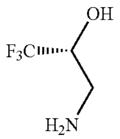 | 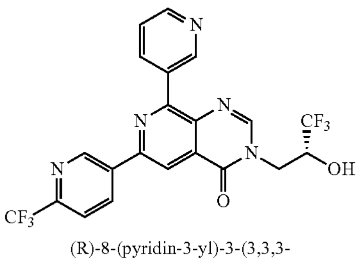 (R)-8-(pyridin-3-yl)-3-(3,3,3-trifluoro-2-hydroxypropyl)-6-(6-(trifluoromethyl)pyridin-3-yl)pyrido[3,4-d]pyrimidin-4(3H)-one | ($CH_3OH$-$d_4$, 400 MHz): δH 4.07-3.99 (1H, m), 4.48 (1H, br s), 4.65 (1H, d, J = 13.9 Hz), 7.64 (1H, t, J = 6.5 Hz), 8.00 (1H, d, J = 8.3 Hz), 8.42 (1H, s), 8.67 (2H, s), 8.74 (1H, d, J = 8.2 Hz), 8.78 (1H, s), 8.88 (1H, d, J = 8.4 Hz), 9.43 (1H, s), 9.57 (1H, s). | 481.9; 99% |
| 123 | 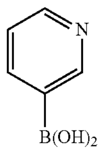 | 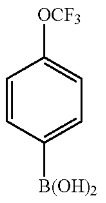 | 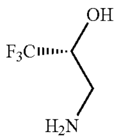 | 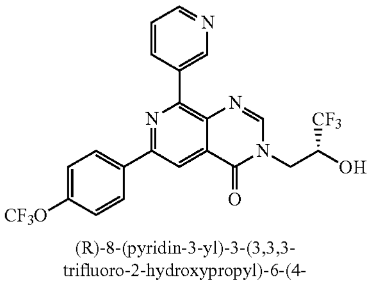 (R)-8-(pyridin-3-yl)-3-(3,3,3-trifluoro-2-hydroxypropyl)-6-(4- | ($CH_3OH$-$d_4$, 300 MHz): δH 4.00 (1H, dd, J = 13.7, 9.6 Hz), 4.46 (1H, t, J = 8.3 Hz), 4.63 (1H, dd, J = 13.8, 3.0 Hz), 7.46 (2H, d, J = 8.4 Hz), 7.62 (1H, dd, J = 8.1, 4.9 | 496.9; 99% |

TABLE 13-continued

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| | | | | (trifluoromethoxy)phenyl)pyrido [3,4-d]pyrimidin-4(3H)-one | Hz), 8.36 (3H, dd, J = 7.0, 1.9 Hz), 8.66-8.62 (2H, m), 8.72 (1H, dt, J = 8.0, 2.0 Hz), 9.40 (1H, s). | |
| 124 | 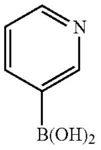 | 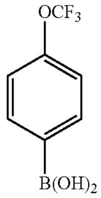 | 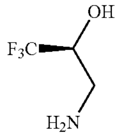 | 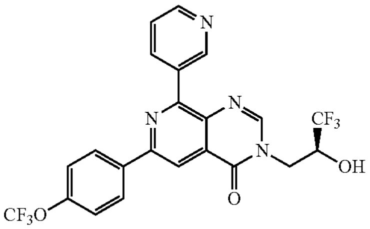 (S)-8-(pyridin-3-yl)-3-(3,3,3-trifluoro-2-hydroxypropyl)-6-(4-(trifluoromethoxy)phenyl)pyrido [3,4-d]pyrimidin-4(3H)-one | ($CH_3OH-d_4$, 400 MHz): δH 3.94 (1H, dd, J = 13.8, 9.7 Hz), 4.40 (1H, s), 4.57 (1H, dd, J = 13.8, 2.9 Hz), 7.39 (2H, d, J = 8.4 Hz), 7.55 (1H, dd, J = 8.0, 4.9 Hz), 8.30 (3H, d, J = 8.4 Hz), 8.56 (1H, s), 8.58 (1H, d, J = 4.8 Hz), 8.66 (1H, d, J = 8.1 Hz), 9.34 (1H, s). | 496.9; 99% |
| 125 | 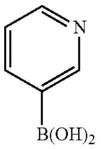 | 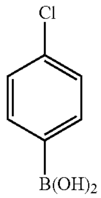 | 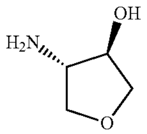 | 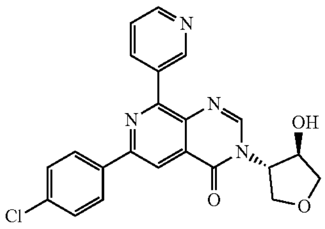 [SMILES: O=c1c2cc(-c3ccc(Cl)cc3)nc(-c3cccnc3)c2ncn1[C@H]1COC[C@@H]1O] 6-(4-chlorophenyl)-3-((3S,4R)-4-hydroxytetrahydrofuran-3-yl)-8-(pyridin-3-yl)pyrido[3,4-d]pyrimidin-4(3H)-one | ($CH_3OH-d_4$, 400 MHz): δH 3.77 (1H, dd, J = 10.0, 3.1 Hz), 4.23 (1H, d, J = 3.3 Hz), 4.29 (2H, dd, J = 10.6, 5.9 Hz), 4.61 (1H, s), 5.07 (1H, s), 7.53 (2H, d, J = 8.4 Hz), 7.60 (1H, t, J = 6.4 Hz), 8.23 (2H, d, J = 8.4 Hz), 8.32 (1H, s), 8.58 (1H, s), 8.63 (1H, s), 8.70 (1H, d, J = 8.0 Hz), 9.39 (1H, s). | 421.1; 99% |
| 126 | 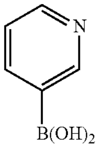 | 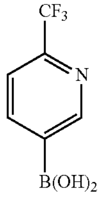 | 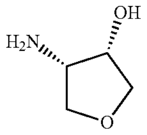 | 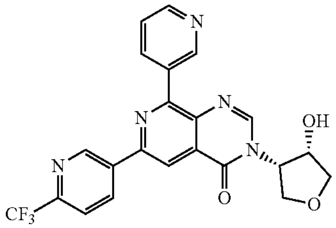 3-((3S,4S)-4-hydroxytetrahydrofuran-3-yl)-8-(pyridin-3-yl)-6-(6-(trifluoromethyl)pyridin-3-yl)pyrido[3,4-d]pyrimidin-4(3H)-one | ($DMSO-d_6$, 400 MHz): δH 3.78 (1H, d, J = 9.8 Hz), 4.03-3.93 (2H, m), 4.20 (1H, dd, J = 9.7, 5.9 Hz), 4.52 (1H, s), 5.42-5.37 (1H, m), 5.49 (1H, d, J = 4.4 Hz), 7.59 (1H, dd, J = 7.9, 4.8 Hz), 8.06 (1H, d, J = 8.3 Hz), 8.40 (1H, s), 8.59 (1H, d, | 456.1; 99% |

TABLE 13-continued

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| | | | | | J = 7.9 Hz), 8.70 (1H, dd, J = 4.7, 1.7 Hz), 8.77 (1H, s), 8.94 (1H, d, J = 8.3 Hz), 9.37 (1H, d, J = 2.1 Hz), 9.64 (1H, s). | |
| 127 | 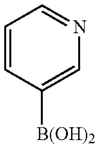 | 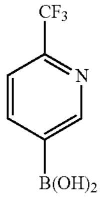 | 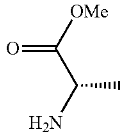 | 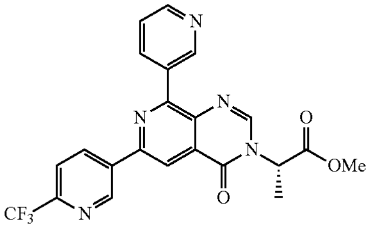 [SMILES: COC(=O)[C@H](C)n1cnc2c(-c3cccnc3)nc(-c3ccc(C(F)(F)F)nc3)cc2c1=O] methyl (S)-2-(4-oxo-8-(pyridin-3-yl)-6-(6-(trifluoromethyl)pyridin-3-yl)pyrido[3,4-d]pyrimidin-3(4H)-yl)propanoate | ($CH_3OH$-$d_4$, 400 MHz): δH 1.81 (3H, d, J = 7.2 Hz), 3.78 (3H, s), 5.40 (1H, d, J = 7.4 Hz), 7.63 (1H, s), 7.98 (1H, d, J = 8.3 Hz), 8.49 (1H, s), 8.65 (1H, s), 8.75 (2H, s), 8.86 (1H, d, J = 8.3 Hz), 9.43 (1H, s), 9.56 (1H, s). | 455.9; 95% |
| 128 | 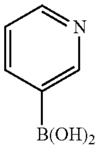 | 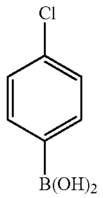 | 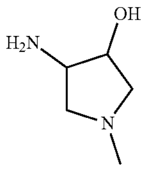 cis racemic | 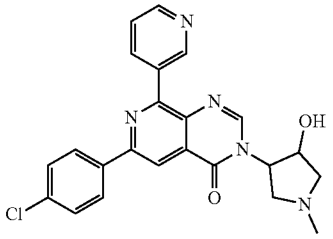 [SMILES: CN1CC(O)C(n2cnc3c(-c4cccnc4)nc(-c4ccc(Cl)cc4)cc3c2=O)C1] 6-(4-chlorophenyl)-3-(4-hydroxy-1-methylpyrrolidin-3-yl)-8-(pyridin-3-yl)pyrido[3,4-d]pyrimidin-4(3H)-one | ($CHCl_3$-d, 300 MHz): δH 1.86 (6H, bs), 3.07 (3H, s), 4.78 (1H, m), 7.49 (3H, m), 7.62-7.56 (1H, m), 8.14 (3H, m), 8.49 (1H, s), 8.73-8.69 (2H, m), 9.54 (1H, s). | 434.1; 99% |
| 129XX | 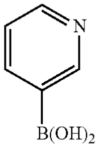 | 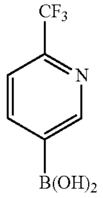 | 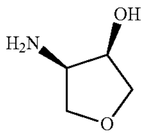 | 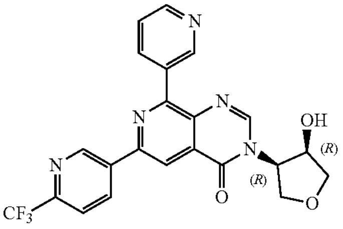 3-((3R,4R)-4-hydroxytetrahydrofuran-3-yl)-8-(pyridin-3-yl)-6-(6-(trifluoromethyl)pyridin-3-yl)pyrido[3,4-d]pyrimidin-4(3H)-one | (DMSO-$d_6$, 400 MHz): δH 3.78 (1H, d, J = 9.8 Hz), 4.03-3.93 (2H, m), 4.20 (1H, t, J = 7.7 Hz), 4.51 (1H, s), 5.38 (1H, t, J = 6.8 Hz), 5.49 (1H, d, J = 4.3 Hz), 7.59 (1H, t, J = 6.3 Hz), 8.05 (1H, d, J = 8.3 Hz), 8.40 (1H, s), 8.58 (1H, d, J = 8.0 Hz), 8.70 (1H, d, J = 4.7 Hz), 8.77 (1H, s), 8.94 (1H, d, J = 8.3 Hz), 9.36 (1H, s), 9.64 (1H, s). | 456.1; 99% |

TABLE 13-continued

| Compound No. | Reactant 4 (step 1) | Reactant 5 (step 2) | Reactant 6 (step 3) | Compound Structure/Name | $^1$H-NMR | MS (m/z) $[M + H]^+$; Purity (%) |
|---|---|---|---|---|---|---|
| 130 | 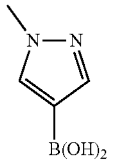 | 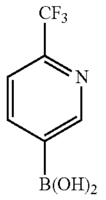 | 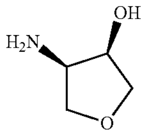 | 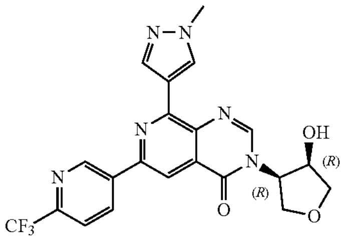 3-((3R,4R)-4-hydroxytetrahydrofuran-3-yl)-8-(1-methyl-1H-pyrazol-4-yl)-6-(6-(trifluoromethyl)pyridin-3-yl)pyrido[3,4-d]pyrimidin-4(3H)-one | (DMSO-$d_6$, 400 MHz): δH 3.79 (1H, d, J = 9.8 Hz), 4.02-3.95 (5H, m), 4.20 (1H, t, J = 7.2 Hz), 4.52 (1H, s), 5.41 (1H, d, J = 6.9 Hz), 5.51 (1H, s), 8.02 (1H, d, J = 8.3 Hz), 8.39 (1H, s), 8.51 (2H, d, J = 10.9 Hz), 8.88 (1H, s), 8.93 (1H, d, J = 8.2 Hz), 9.65 (1H, s). | 459.1 |
| 131 | 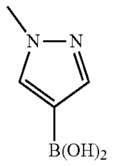 | 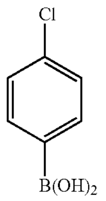 | 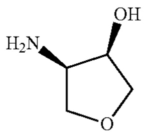 | 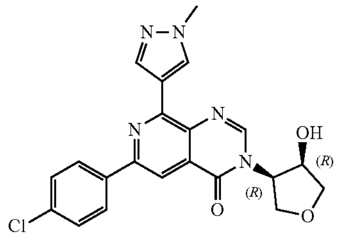 6-(4-chlorophenyl)-3-((3R,4R)-4-hydroxytetrahydrofuran-3-yl)-8-(1-methyl-1H-pyrazol-4-yl)pyrido[3,4-d]pyrimidin-4(3H)-one | (DMSO-$d_6$, 400 MHz): δH 3.78 (1H, d, J = 9.7 Hz), 4.01-3.91 (5H, m), 4.19 (1H, t, J = 7.4 Hz), 4.51 (1H, s), 5.40-5.37 (1H, m), 5.49 (1H, d, J = 4.3 Hz), 7.57 (2H, d, J = 8.3 Hz), 8.33-8.28 (4H, m), 8.48 (1H, s), 8.82 (1H, s). | 424.1 |
| 132 | 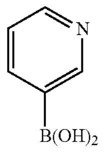 | 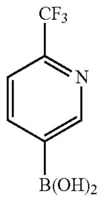 | 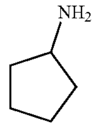 | 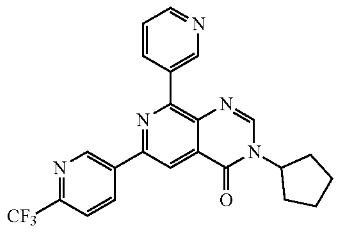 [SMILES: O=c1c2cc(-c3ccc(C(F)(F)F)nc3)nc(-c3cccnc3)c2ncn1C1CCCC1] 3-cyclopentyl-8-(pyridin-3-yl)-6-(6-(trifluoromethyl)pyridin-3-yl)pyrido[3,4-d]pyrimidin-4(3H)-one | (DMSO-$d_6$, 400 MHz): δH 1.67 (2H, s), 1.91 (4H, br s), 2.10 (2H, s), 5.01 (1H, d, J = 8.8 Hz), 7.58 (1H, t, J = 6.2 Hz), 8.04 (1H, d, J = 8.3 Hz), 8.56 (1H, d, J = 7.9 Hz), 8.63 (1H, s), 8.69 (1H, d, J = 4.6 Hz), 8.74 (1H, s), 8.92 (1H, d, J = 8.3 Hz), 9.35 (1H, s), 9.62 (1H, s). | 438.1; 99% |
| 133 | 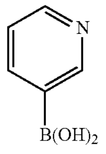 | 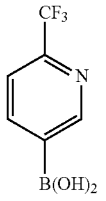 | 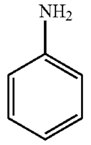 | 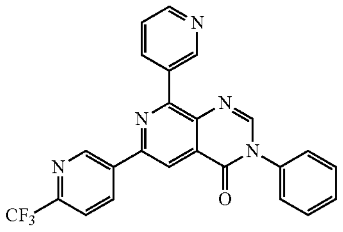 [SMILES: O=c1c2cc(-c3ccc(C(F)(F)F)nc3)nc(-c3cccnc3)c2ncn1-c1ccccc1] 3-phenyl-8-(pyridin-3-yl)-6-(6-(trifluoromethyl)pyridin-3-yl)pyrido[3,4-d]pyrimidin-4(3H)-one | (DMSO-$d_6$, 400 MHz): 7.59 (6H, s), 8.04 (1H, d, J = 8.3 Hz), 8.59-8.57 (2H, m), 8.70 (1H, s), 8.78 (1H, s), 8.94 (1H, d, J = 8.2 Hz), 9.38 (1H, s), 9.64 (1H, s). | 446.1; 99% |

Preparation of K-0004422 6-(4-chlorophenyl)-3-((3R,4R)-4-hydroxypyrrolidin-3-yl)-8-(pyridin-3-yl)pyrido[3,4-d]pyrimidin-4(3H)-one (134)

Step 1. Preparation of tert-butyl (3R,4R)-3-(6-(4-chlorophenyl)-4-oxo-8-(pyridin-3-yl)pyrido[3,4-d]pyrimidin-3(4H)-yl)-4-hydroxypyrrolidine-1-carboxylate (Precursor 5)

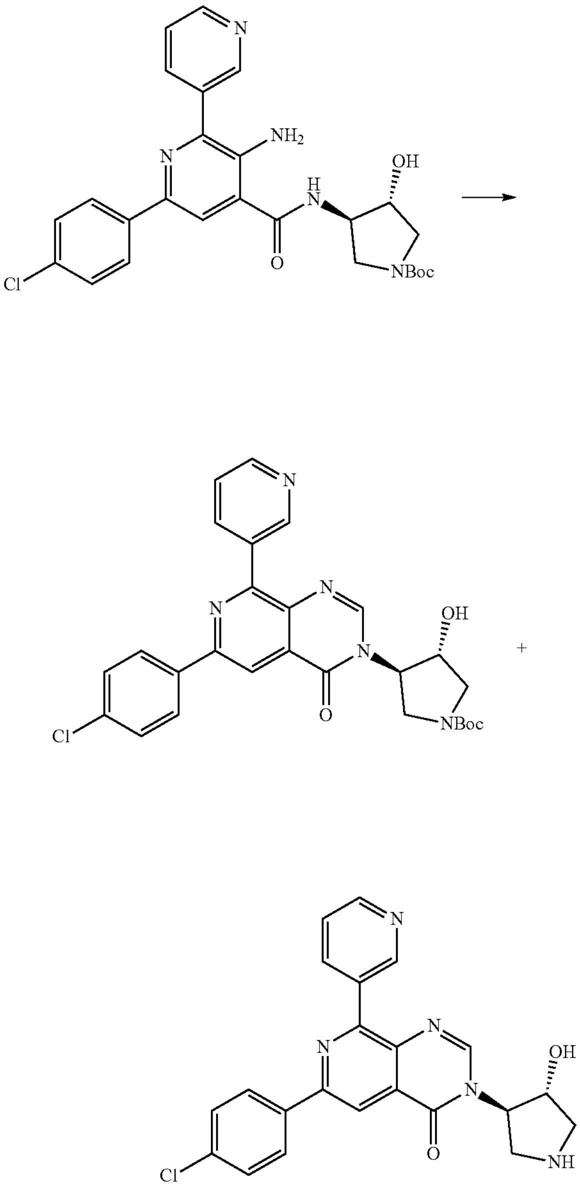

The above step was performed according to the procedure reported for 108 to afford a mixture of tert-butyl (3R,4R)-3-(6-(4-chlorophenyl)-4-oxo-8-(pyridin-3-yl)pyrido[3,4-d]pyrimidin-3(4H)-yl)-4-hydroxypyrrolidine-1-carboxylate (Precursor 5) and 6-(4-chlorophenyl)-3-((3R,4R)-4-hydroxypyrrolidin-3-yl)-8-(pyridin-3-yl)pyrido[3,4-d]pyrimidin-4(3H)-one (134)

Step 2. 6-(4-chlorophenyl)-3-((3R,4R)-4-hydroxypyrrolidin-3-yl)-8-(pyridin-3-yl)pyrido[3,4-d]pyrimidin-4(3H)-one (134)

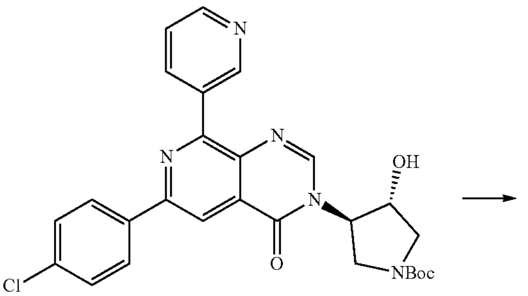

Precursor 5

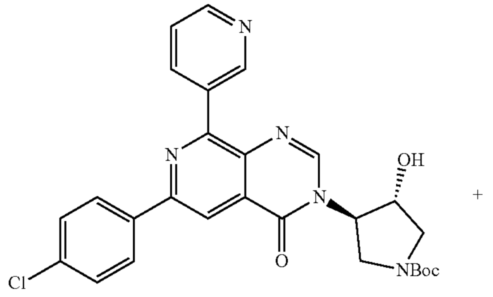

118

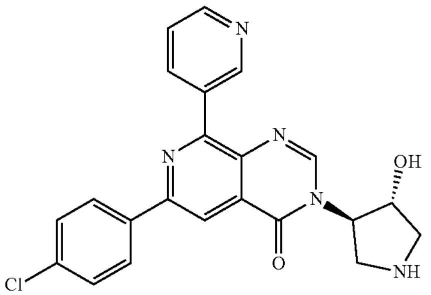

118

The mixture of Precursor 5 and 134 (218 mg, 0.43 mmol) was dissolved in 3.0 mL of 4M HCl in dioxane and was stirred at room temperature for 1 hour. Diethyl ether (2.0 ml) was added and the solid was centrifuged, decanted, triturated with ether and dried. The solid was purified by reverse phase column chromatography to provide the title compound 6-(4-chlorophenyl)-3-((3R,4R)-4-hydroxypyrrolidin-3-yl)-8-(pyridin-3-yl)pyrido[3,4-d]pyrimidin-4(3H)-one (134, 120 mg, 0.29, 67% yield) as a white solid. $^1H$ NMR (DMSO-$d_6$, 400 MHz): $\delta_H$ 2.70 (1H, dd, J=11.5, 4.7 Hz), 3.00 (1H, dd, J=11.8, 5.3 Hz), 3.23 (1H, dd, J=11.6, 6.1 Hz), 3.27 (1H, s), 3.34-3.31 (1H, m), 4.43-4.41 (1H, m), 4.83-4.80 (1H, m), 5.31 (1H, d, J=4.6 Hz), 7.60-7.55 (3H, m), 8.31 (2H, d, J=8.4 Hz), 8.54-8.51 (3H, m), 8.68 (1H, dd, J=4.8, 1.7 Hz), 9.32 (1H, d, J=2.1 Hz). MS (m/z): 420.1 $[M+H]^+$; 99% purity.

Preparation of (R)-6-(6-cyclopropylpyridin-3-yl)-8-(1-methyl-1H-pyrazol-4-yl)-3-(3,3,3-trifluoro-2-hydroxypropyl)pyrido[3,4-d]pyrimidin-4(3H)-one (135)

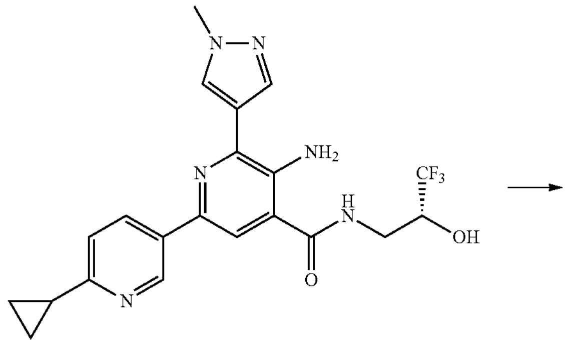

F19

-continued

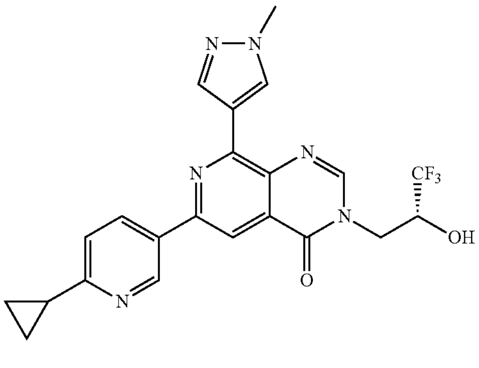

Triethylorthoformate (1.74 ml, 10.5 mmol) and 12.1 N HCl (115 μl, 1.39 mmol) were added to a solution of (R)-5-amino-6'-cyclopropyl-6-(1-methyl-1H-pyrazol-4-yl)-N-(3,3,3-trifluoro-2-hydroxypropyl)-[2,3'-bipyridine]-4-carboxamide (F19, 311 mg, 0.697 mmol) in dioxane (3.5 ml). After 1 h DMF (0.5 ml) was added and the reaction mixture was stirred for 24 h at room temperature. The reaction mixture was quenched with sodium bicarbonate (pH>11). Water was added and was extracted with ethyl acetate. The combined organic layers were dried over anhydrous magnesium sulfate, concentrated and purified by silica gel column chromatography to afford the title compound (R)-6-(6-cyclopropylpyridin-3-yl)-8-(1-methyl-1H-pyrazol-4-yl)-3-(3,3,3-trifluoro-2-hydroxypropyl)pyrido[3,4-d]pyrimidin-4(3H)-one (135, 152 mg, 48%). $^1$H NMR (DMSO-$d_6$, 400 MHz): δ 1.03-1.00 (4H, m), 2.23-2.18 (1H, m), 3.98 (3H, s), 4.10-4.03 (1H, m), 4.49-4.40 (2H, m), 6.79 (1H, t, J=6.1 Hz), 7.46 (1H, dd, J=8.1, 4.9 Hz), 8.31-8.30 (1H, m), 8.50-8.47 (3H, m), 8.84-8.82 (1H, m), 9.29-9.28 (1H, m); MS (m/z): 457.1 [M+H]$^+$; >99% purity.

Table 14 lists compounds made via procedures similar to that described for 139, replacing reactant 4, 5, and 6 with the indicated groups.

TABLE 14

| Compound No. | Reactant 4 (step 1) | Reactant 5 (step 2) | Reactant 6 (step 3) | Compound Structure/Name | $^1$H-NMR | MS (m/z) [M + H]$^+$; Purity (%) |
|---|---|---|---|---|---|---|
| 136 | 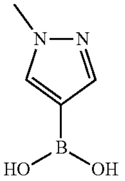 | 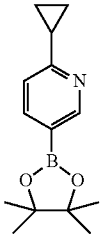 | 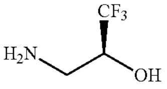 | 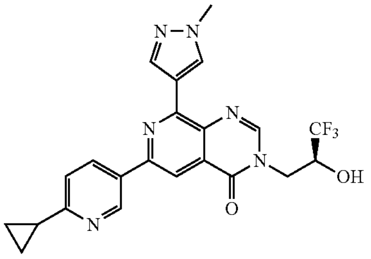 [SMILES: Cn1cc(-c2nc(-c3ccc(C4CC4)nc3)cc3c(=O)n(C[C@H](O)C(F)(F)F)cnc23)cn1] (S)-6-(6-cyclopropylpyridin-3-yl)-8-(1-methyl-1H-pyrazol-4-yl)-3-(3,3,3-trifluoro-2-hydroxypropyl)pyrido[3,4-d]pyrimidin-4(3H)-one | (DMSO-$d_6$, 400 MHz): δH 1.04-1.00 (4H, m), 2.22-2.17 (1H, m), 3.98-3.96 (3H, m), 4.10-4.04 (1H, m), 4.46-4.43 (2H, m), 6.79 (1H, d, J = 6.4 Hz), 7.46 (1H, d, J = 8.1 Hz), 8.31 (1H, s), 8.50 (3H, d, J = 6.7 Hz), 8.83 (1H, s), 9.29 (1H, s). | 457.1; >99 |

The compounds encompassed within the present disclosure can be prepared by the procedure outlined in Scheme III and described in the Examples herein below.

Scheme III

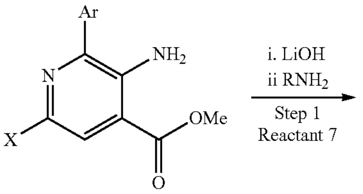

-continued

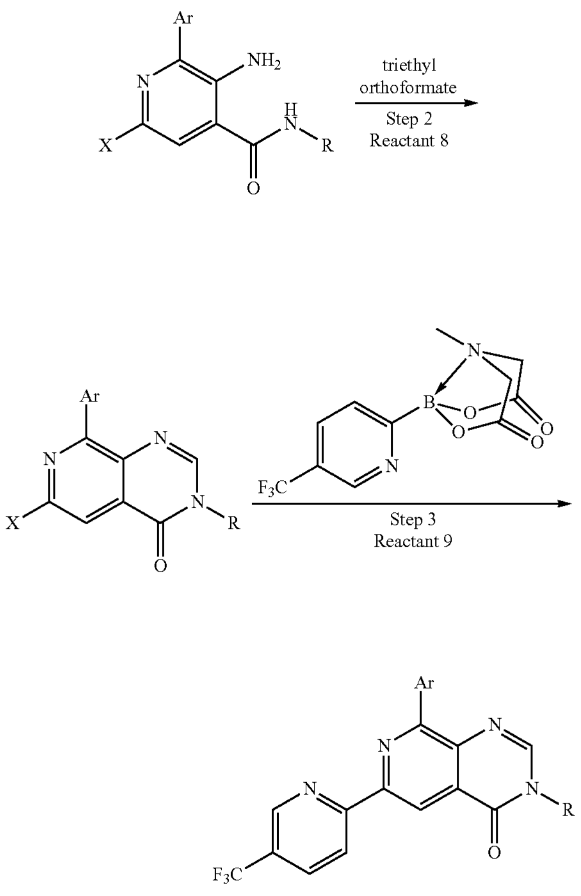

Preparation of 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (137)

Step 1. Preparation of 3-amino-6-chloro-N-((3S,4R)-4-hydroxytetrahydrofuran-3-yl)-2-(1-methyl-1H-pyrazol-4-yl)isonicotinamide (Intermediate G1)

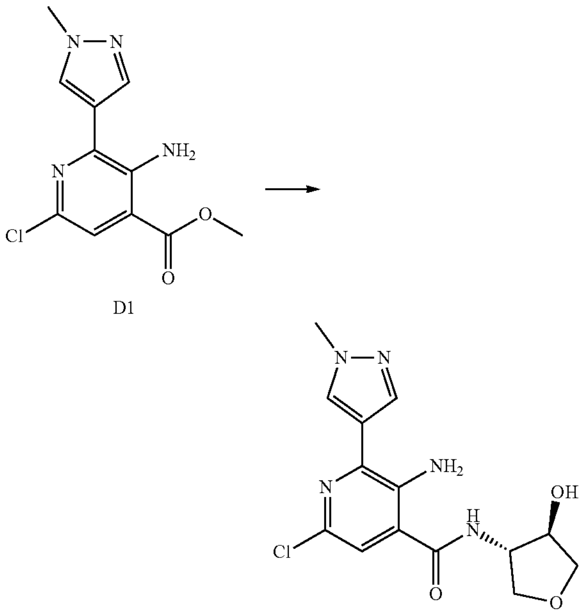

D1

G1

Intermediate G1 was prepared according to step 3 for the synthesis of 114. MS (m/z): 338.0 $[M+H]^+$.

Table 15 shows intermediates made according to the step shown above.

TABLE 15

| Intermediate Name | Structure and Name | $^1$H-NMR | MS (m/z) $[M + H]^+$; Purity (%) |
|---|---|---|---|
| G2 | 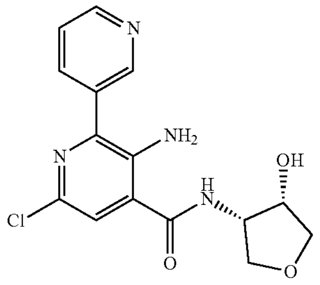 [SMILES: Nc1c(C(=O)N[C@H]2COC[C@H]2O)cc(Cl)nc1-c1cccnc1] 3-amino-6-chloro-N-((3S,4S)-4-hydroxytetrahydrofuran-3-yl)-[2,3'-bipyridine]-4-carboxamide | NA | 334.9 |

TABLE 15-continued

| Intermediate Name | Structure and Name | $^1$H-NMR | MS (m/z) [M + H]$^+$; Purity (%) |
|---|---|---|---|
| G3 | 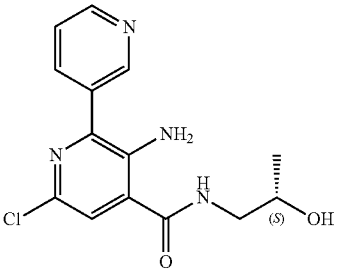 (S)-3-amino-6-chloro-N-(2-hydroxypropyl)-[2,3'-bipyridine]-4-carboxamide | NA | 307.0 |
| G4 | 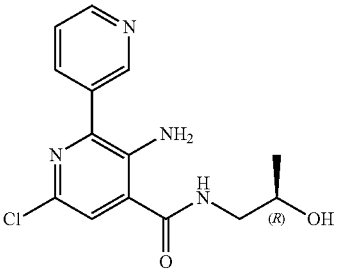 (R)-3-amino-6-chloro-N-(2-hydroxypropyl)-[2,3'-bipyridine]-4-carboxamide | NA | 307.1 |
| G5 | 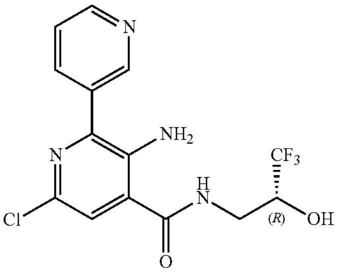 (R)-3-amino-6-chloro-N-(3,3,3-trifluoro-2-hydroxypropyl)-[2,3'-bipyridine]-4-carboxamide | NA | 360.9 |
| G6 | 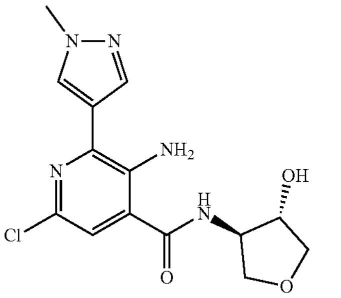 [SMILES: Cn1cc(-c2nc(Cl)cc(C(=O)N[C@@H]3COC[C@H]3O)c2N)cn1] 3-Amino-6-chloro-N-((3R,4S)-4-hydroxytetrahydrofuran-3-yl)-2-(1-methyl-1H-pyrazol-4-yl)isonicotinamide | NA | 338.0; NA |

TABLE 15-continued

| Inter-mediate Name | Structure and Name | $^1$H-NMR | MS (m/z) [M + H]$^+$; Purity (%) |
|---|---|---|---|
| G7 | 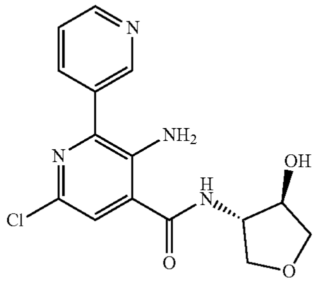 [SMILES: Nc1c(C(=O)N[C@H]2COC[C@@H]2O)cc(Cl)nc1-c1cccnc1] 3-Amino-6-chloro-N-((3S,4R)-4-hydroxytetrahydrofuran-3-yl)-[2,3'-bipyridine]-4-carboxamide | NA | 335.0 NA |
| G8 | 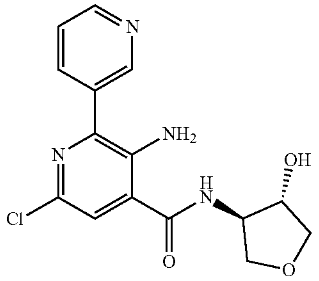 [SMILES: Nc1c(C(=O)N[C@@H]2COC[C@H]2O)cc(Cl)nc1-c1cccnc1] 3-Amino-6-chloro-N-((3R,4S)-4-hydroxytetrahydrofuran-3-yl)-[2,3'-bipyridine]-4-carboxamide | NA | 335.0 NA |
| G9 | 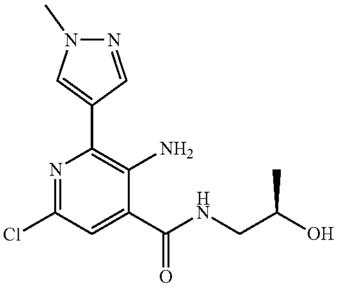 [SMILES: C[C@@H](O)CNC(=O)c1cc(Cl)nc(-c2cnn(C)c2)c1N] (R)-3-amino-6-chloro-N-(2-hydroxypropyl)-2-(1-methyl-1H-pyrazol-4-yl)isonicotinamide | NA | 310.1 NA |
| G10 | 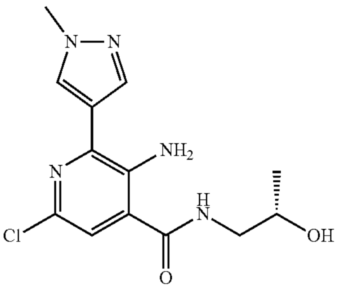 [SMILES: C[C@H](O)CNC(=O)c1cc(Cl)nc(-c2cnn(C)c2)c1N] (S)-3-amino-6-chloro-N-(2-hydroxypropyl)-2-(1-methyl-1H-pyrazol-4-yl)isonicotinamide | NA | 310.1 NA |

TABLE 15-continued

| Intermediate Name | Structure and Name | $^1$H-NMR | MS (m/z) $[M + H]^+$; Purity (%) |
| --- | --- | --- | --- |
| G11 | 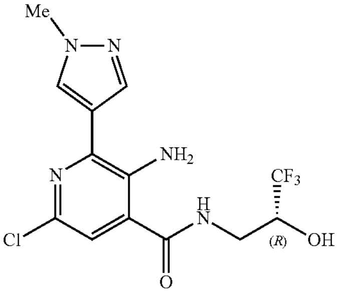 (R)-3-amino-6-chloro-2-(1-methyl-1H-pyrazol-4-yl)-N-(3,3,3-trifluoro-2-hydroxypropyl)isonicotinamide | (400 MHz, DMSO): δH 8.98 (1H, t, J 5.5), 8.24 (1H, s), 7.89 (1H, s), 7.41 (1H, s), 6.57 (1H, d, J 6.5), 6.21 (2H, s), 4.23-4.15 (1H, m), 3.90 (3H, s), 3.61-3.54 (1H, m), 3.29 (1H, dd, J 14.6, 6.8). | 364.1; NA |
| G12 | 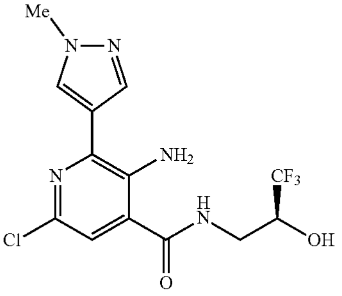 [SMILES: Cn1cc(-c2nc(Cl)cc(C(=O)NC[C@H](O)C(F)(F)F)c2N)cn1] (S)-3-amino-6-chloro-2-(1-methyl-1H-pyrazol-4-yl)-N-(3,3,3-trifluoro-2-hydroxypropyl)isonicotinamide | (400 MHz, DMSO): 8.98 (1H, t, J 5.5), 8.24 (1H, s), 7.89 (1H, s), 7.41 (1H, s), 6.57 (1H, d, J 6.5), 6.21 (2H, s), 4.23-4.15 (1H, m), 3.90 (3H, s), 3.61-3.54 (1H, m), 3.29 (1H, dd, J 14.6, 6.8). | 364.1; NA |
| G13 | 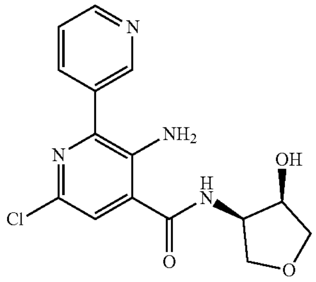 [SMILES: Nc1c(C(=O)N[C@@H]2COC[C@@H]2O)cc(Cl)nc1-c1cccnc1] 3-amino-6-chloro-N-((3R,4R)-4-hydroxytetrahydrofuran-3-yl)-[2,3'-bipyridine]-4-carboxamide | (DMSO-$d_6$, 400 MHz): δH 3.66-3.60 (2H, m), 3.93-3.86 (2H, m), 4.24 (1H, s), 4.36 (1H, t, J = 7.3 Hz), 5.28 (1H, d, J = 4.2 Hz), 6.23 (2H, s), 7.51 (1H, t, J = 6.2 Hz), 7.64 (1H, s), 7.99 (1H, d, J = 7.9 Hz), 8.53 (1H, d, J = 7.5 Hz), 8.62 (1H, d, J = 4.7 Hz), 8.76 (1H, s). | 335.1; NA |
| G14 | 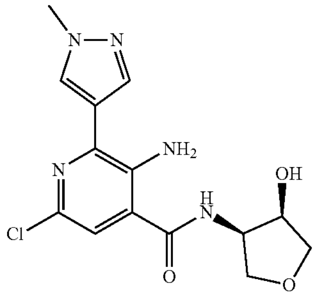 [SMILES: Cn1cc(-c2nc(Cl)cc(C(=O)N[C@@H]3COC[C@@H]3O)c2N)cn1] 3-amino-6-chloro-N-((3R,4R)-4-hydroxytetrahydrofuran-3-yl)-2-(1-methyl-1H-pyrazol-4-yl)isonicotinamide | NA | 338.0; NA |

Step 2. Preparation of 6-chloro-3-((3S,4R)-4-hydroxytetrahydrofuran-3-yl)-8-(1-methyl-1H-pyrazol-4-yl)pyrido[3,4-d]pyrimidin-4(3H)-one (Intermediate H1)

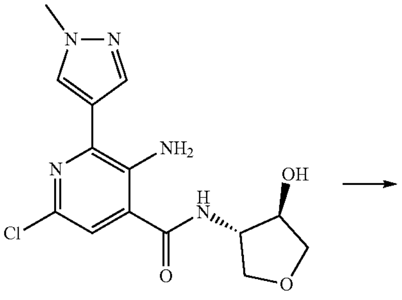

G1

-continued

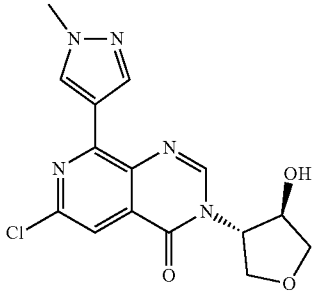

H1

Intermediate H1 was synthesized according to the last step for the synthesis of 98. $^1$H-NMR (DMSO-$d_6$, 400 MHz): $\delta_H$ 3.62-3.55 (1H, m), 3.92 (3H, s), 4.11-4.06 (2H, m), 4.16 (1H, dd, J=10.0, 5.6 Hz), 4.52 (1H, s), 4.92 (1H, s), 5.71 (1H, d, J=4.1 Hz), 7.79-7.76 (1H, m), 8.32 (1H, s), 8.33 (1H, s), 8.73 (1H, s); MS (m/z): 348.0 $[M+H]^+$; >90% purity.

Intermediates in Table 16 were synthesized according to the step described above.

TABLE 16

| Intermediate Name | Structure and Name | $^1$H NMR | MS (m/z) $[M + H]^+$; Purity (%) |
|---|---|---|---|
| H2 | 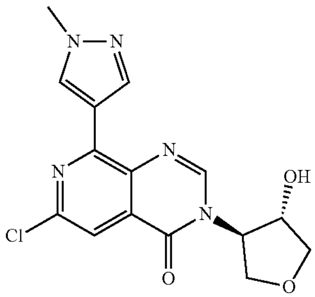 [SMILES: Cn1cc(-c2nc(Cl)cc3c(=O)n([C@@H]4COC[C@H]4O)cnc23)cn1] 6-Chloro-3-((3R,4S)-4-hydroxytetrahydrofuran-3-yl)-8-(1-methyl-1H-pyrazol-4-yl)pyrido[3,4-d]pyrimidin-4(3H)-one | (DMSO-$d_6$, 400 MHz): δH 3.60 (1H, dd, J = 9.7, 3.2 Hz), 3.92 (3H, s), 4.11-4.06 (2H, m), 4.16 (1H, dd, J = 10.1, 5.7 Hz), 4.52 (1H, s), 4.92 (1H, s), 5.72 (1H, s), 7.76 (1H, s), 8.32 (1H, s), 8.33 (1H, s), 8.72 (1H, s). | 348.0; >90% |
| H3 | 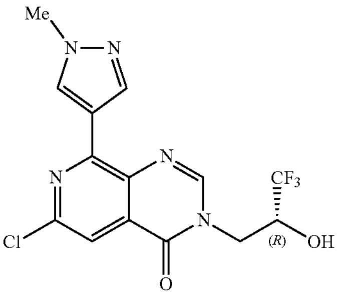 (R)-6-chloro-8-(1-methyl-1H-pyrazol-4-yl)-3-(3,3,3-trifluoro-2-hydroxypropyl)pyrido[3,4-d]pyrimidin-4(3H)-one | (400 MHz, DMSO) 8.74 (1H, s), 8.49 (1H, s), 8.33 (1H, s), 7.79 (1H, s), 6.77 (1H, d, J 6.6), 4.44-4.35 (2H, m), 4.06 (1H, dd, J 13.9, 9.8), 3.95 (3H, s). | 374.9; NA |

TABLE 16-continued

| Intermediate Name | Structure and Name | $^1$H NMR | MS (m/z) $[M + H]^+$; Purity (%) |
|---|---|---|---|
| H4 | 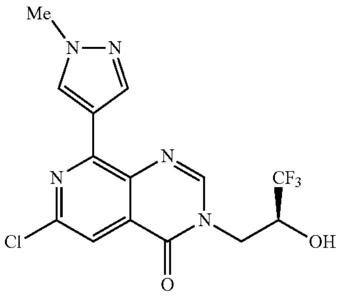 [SMILES: Cn1cc(-c2nc(Cl)cc3c(=O)n(C[C@H](O)C(F)(F)F)cnc23)cn1] (S)-6-chloro-8-(1-methyl-1H-pyrazol-4-yl)-3-(3,3,3-trifluoro-2-hydroxypropyl)pyrido[3,4-d]pyrimidin-4(3H)-one | (400 MHz, DMSO): 8.74 (1H, s), 8.49 (1H, s), 8.33 (1H, s), 7.79 (1H, s), 6.75 (1H, d, J 6.6), 4.44-4.38 (1H, m), 4.08 (2H, q, J 5.2), 3.95 (3H, s). | 374.0; NA |
| H5 | 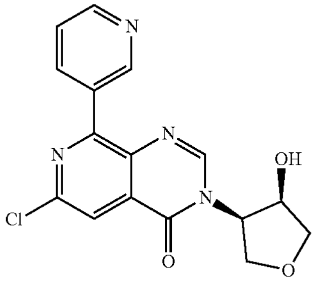 [SMILES: O=c1c2cc(Cl)nc(-c3cccnc3)c2ncn1[C@@H]1COC[C@@H]1O] 6-chloro-3-((3R,4R)-4-hydroxytetrahydrofuran-3-yl)-8-(pyridin-3-yl)pyrido[3,4-d]pyrimidin-4(3H)-one | ($DMSO-d_6$, 400 MHz): δ 3.75 (1H, d, J = 9.8 Hz), 3.99-3.90 (2H, m), 4.15 (1H, t, J = 7.6 Hz), 4.48 (1H, s), 5.33 (1H, d, J = 7.0 Hz), 5.46 (1H, s), 7.56 (1H, t, J = 6.2 Hz), 8.09 (1H, s), 8.34 (1H, s), 8.42 (1H, d, J = 7.9 Hz), 8.68 (1H, s), 9.21 (1H, s). | 345.1; NA |
| H6 | 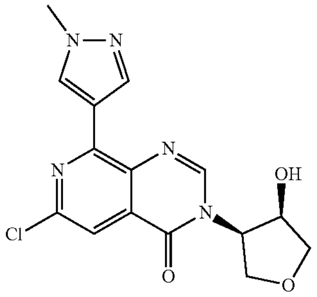 [SMILES: Cn1cc(-c2nc(Cl)cc3c(=O)n([C@@H]4COC[C@@H]4O)cnc23)cn1] 6-chloro-3-((3R,4R)-4-hydroxytetrahydrofuran-3-yl)-8-(1-methyl-1H-pyrazol-4-yl)pyrido[3,4-d]pyrimidin-4(3H)-one | ($DMSO-d_6$, 400 MHz): δH 3.77 (1H, d, J = 9.8 Hz), 3.97-3.92 (5H, m), 4.16 (1H, s), 4.49 (1H, s), 5.35 (1H, s), 5.47 (1H, s), 7.76 (1H, s), 8.32 (2H, s), 8.75 (1H, s). | 348.0; NA |

Table 17 shows intermediate was synthesized according to the last step for the synthesis of 108

TABLE 17

| Intermediate Name | Structure and Name | $^1$H NMR | MS (m/z) [M + H]$^+$; Purity (%) |
| --- | --- | --- | --- |
| Method C for 99 L1 | 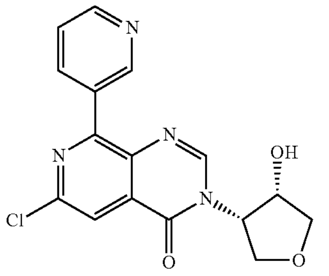 [SMILES: O=c1c2cc(Cl)nc(-c3cccnc3)c2ncn1[C@H]1COC[C@H]1O] 6-chloro-3-((3S,4S)-4-hydroxytetrahydrofuran-3-yl)-8-(pyridin-3-yl)pyrido[3,4-d]pyrimidin-4(3H)-one | NA | 344.9 |
| Method C for 99 L2 | 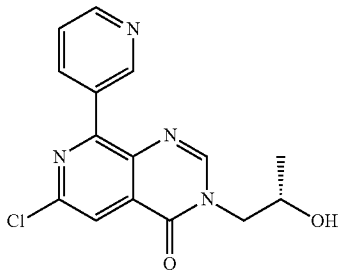 [SMILES: C[C@H](O)Cn1cnc2c(-c3cccnc3)nc(Cl)cc2c1=O] (S)-6-chloro-3-(2-hydroxypropyl)-8-(pyridin-3-yl)pyrido[3,4-d]pyrimidin-4(3H)-one | NA | 317.1 |
| Method C for 99 L3 | 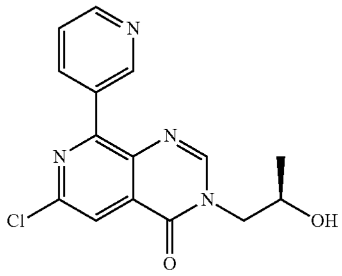 [SMILES: C[C@@H](O)Cn1cnc2c(-c3cccnc3)nc(Cl)cc2c1=O] (R)-6-chloro-3-(2-hydroxypropyl)-8-(pyridin-3-yl)pyrido[3,4-d]pyrimidin-4(3H)-one | NA | 317.1 |
| Method C for 99 L4 | 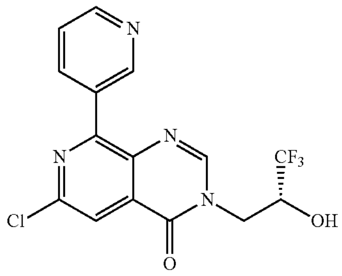 [SMILES: O=c1c2cc(Cl)nc(-c3cccnc3)c2ncn1C[C@@H](O)C(F)(F)F] (R)-6-chloro-8-(pyridin-3-yl)-3-(3,3,3-trifluoro-2-hydroxypropyl)pyrido[3,4-d]pyrimidin-4(3H)-one | NA | 370.9 |

TABLE 17-continued

| Intermediate Name | Structure and Name | $^1H$ NMR | MS (m/z) $[M + H]^+$; Purity (%) |
|---|---|---|---|
| Method C L5 | 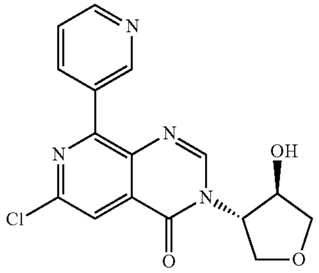 [SMILES: O=c1c2cc(Cl)nc(-c3cccnc3)c2ncn1[C@H]1COC[C@@H]1O] 6-Chloro-3-((3S,4R)-4-hydroxytetrahydrofuran-3-yl)-8-(pyridin-3-yl)pyrido[3,4-d]pyrimidin-4(3H)-one | $^1H$ NMR (DMSO-$d_6$, 400 MHz): $\delta_H$ 3.59 (1H, dd, J = 9.6, 3.3 Hz), 4.18-4.01 (3H, m), 4.53 (1H, s), 4.93 (1H, s), 5.69 (1H, d, J = 4.3 Hz), 7.56 (1H, dd, J = 7.9, 4.9 Hz), 8.08 (1H, s), 8.35 (1H, s), 8.40 (1H, d, J = 8.0 Hz), 8.68 (1H, d, J = 4.8 Hz), 9.20 (1H, s). | 345.0 >95% |
| Method C L6 | 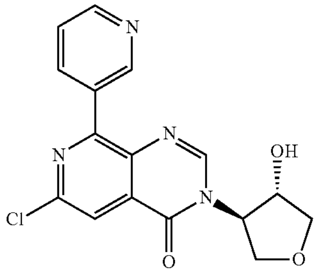 [SMILES: O=c1c2cc(Cl)nc(-c3cccnc3)c2ncn1[C@@H]1COC[C@H]1O] 6-Chloro-3-((3R,4S)-4-hydroxytetrahydrofuran-3-yl)-8-(pyridin-3-yl)pyrido[3,4-d]pyrimidin-4(3H)-one | $^1H$ NMR (DMSO-$d_6$, 400 MHz): $\delta_H$ 3.59 (1H, dd, J = 9.6, 3.3 Hz), 4.18-4.01 (3H, m), 4.53 (1H, s), 4.93 (1H, s), 5.69 (1H, d, J = 4.4 Hz), 7.56 (1H, dd, J = 7.9, 4.8 Hz), 8.08 (1H, s), 8.35 (1H, s), 8.40 (1H, d, J = 8.0 Hz), 8.68 (1H, d, J = 4.7 Hz), 9.20 (1H, s). | 345.0 >95% |
| Method C L7 | 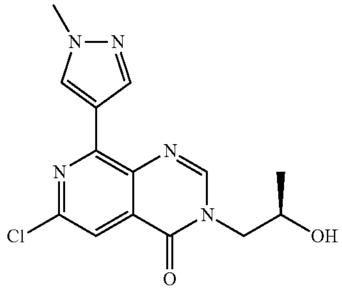 [SMILES: C[C@@H](O)Cn1cnc2c(-c3cnn(C)c3)nc(Cl)cc2c1=O] (R)-6-chloro-3-(2-hydroxypropyl)-8-(1-methyl-1H-pyrazol-4-yl)pyrido[3,4-d]pyrimidin-4(3H)-one | $^1H$ NMR (DMSO-$d_6$, 400 MHz): $\delta_H$ 1.12 (3H, d, J = 6.2 Hz), 3.70 (1H, dd, J = 13.2, 8.7 Hz), 3.93 (4H, s), 4.10 (1H, d, J = 13.2 Hz), 5.04 (1H, d, J = 5.0 Hz), 7.75 (1H, s), 8.31 (1H, s), 8.39 (1H, s), 8.73 (1H, s). | 320.0 >95 |
| Method C L8 | 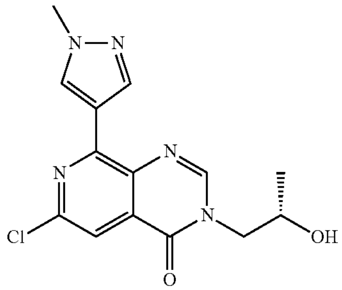 [SMILES: C[C@H](O)Cn1cnc2c(-c3cnn(C)c3)nc(Cl)cc2c1=O] (S)-6-chloro-3-(2-hydroxypropyl)-8-(1-methyl-1H-pyrazol-4-yl)pyrido[3,4-d]pyrimidin-4(3H)-one | $^1H$ NMR (DMSO-$d_6$, 400 MHz): $\delta_H$ 1.12 (3H, d, J = 6.2 Hz), 3.70 (1H, dd, J = 13.2, 8.7 Hz), 3.93 (4H, s), 4.10 (1H, dd, J = 13.2, 3.2 Hz), 5.04 (1H, d, J = 5.0 Hz), 7.75 (1H, s), 8.31 (1H, s), 8.39 (1H, s), 8.72 (1H, s). | 320.1; >95 |

Step 3. Method A: Preparation of 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (137)

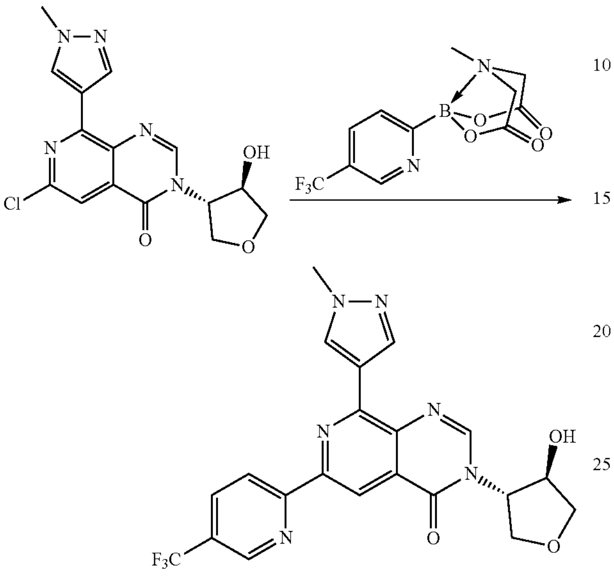

6-Chloro-3-((3S,4R)-4-hydroxytetrahydrofuran-3-yl)-8-(1-methyl-1H-pyrazol-4-yl)pyrido[3,4-d]pyrimidin-4(3H)-one (H1, 200 mg, 0.575 mmol), chloro(2-dicyclohexylphosphino-2',4',6'-triisopropyl-1,1'-biphenyl)[2-(2-aminoethyl)phenyl)]palladium(II) [Xphos Pd G1], (22.24 mg, 0.029 mmol), and 5-Trifluoromethyl-2-pyridylboronic acid MIDA ester (260 mg, 0.863 mmol) were added under air to a flame-dried 10 mL pressure vial equipped with stir bar. The vial was back-filled with argon, then 1-methyl-2-pyrrolidone (NMP) (4 mL) was added, followed by diethanolamine (0.055 ml, 0.575 mmol), $K_3PO_4$ (610 mg, 2.87 mmol) and $Cu(OAc)_2$ (52.2 mg, 0.288 mmol) and the vial was sealed with a cap. The reaction mixture was heated to 100° C. and stirred for 18 hours. The vial was then cooled. To the reaction mixture was added 8 mL of 2N HCl and the resulting solution was stirred for 10 min, then 1N NaOH (12 mL) was added and the resulting solution was stirred for 20 min. The formed precipitate was filtered, collected and dried. Purification of the precipitate by silica gel column chromatography afforded the title compound 3-((3S,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one (137, 151 mg, 57% yield). $^1$H-NMR (DMSO-$d_6$, 400 MHz): $\delta_H$ 3.64 (1H, d, J=9.3 Hz), 3.98 (4H, s), 4.15 (3H, s), 4.20 (1H, d, J=8.1 Hz), 4.57 (2H, s), 5.01 (2H, s), 5.75 (2H, s), 8.39 (3H, d, J=11.3 Hz), 8.55 (1H, s), 8.87-8.81 (4H, m), 9.14 (1H, s); MS (m/z): 459.1 $[M+H]^+$; >99% purity.

Table 18 lists compounds that were made via a procedure similar to that described for 137, replacing reactants 6 and 7 with the indicated groups.

TABLE 18

| Compound No. | Intemediate | Reactant 8 replacement | Compound Structure/Name | $^1$H-NMR | MS $[m/z]^+$; Purity (%) |
|---|---|---|---|---|---|
| 138 | 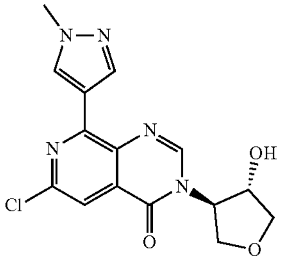 H2 | 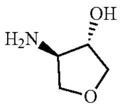 | 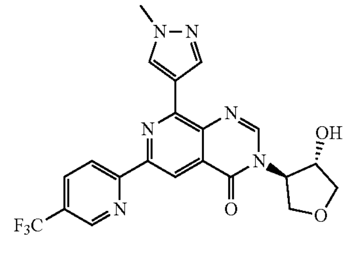 [SMILES: Cn1cc(-c2nc(-c3ccc(C(F)(F)F)cn3)cc3c(=O)n([C@@H]4COC[C@H]4O)cnc23)cn1] 3-((3R,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one | $^1$H NMR (DMSO-$d_6$, 400 MHz): $\delta_H$ 3.63 (1H, d, J = 6.8 Hz), 3.98 (3H, s), 4.15 (2H, s), 4.23-4.19 (1H, m), 4.57 (1H, s), 5.01 (1H, s), 5.75 (1H, s), 8.40 (2H, s), 8.56 (1H, s), 8.85 (3H, dd, J = 14.3, 8.1 Hz), 9.15 (1H, s). | 459.1; >99 |
| 139 | 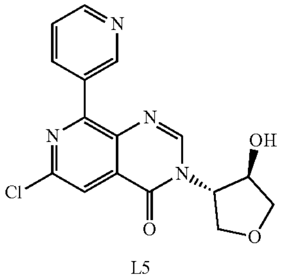 L5 | 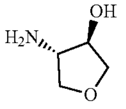 | 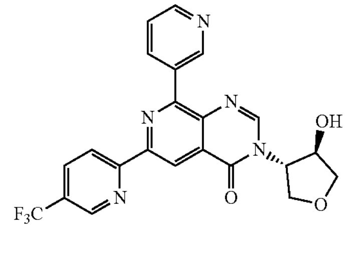 [SMILES: O=c1c2cc(-c3ccc(C(F)(F)F)cn3)nc(-c3cccnc3)c2ncn1[C@H]1COC[C@@H]1O] | $^1$H NMR (DMSO-$d_6$, 400 MHz): $\delta_H$ 3.62 (1H, dd, J = 9.6, 3.3 Hz), 4.21-4.06 (3H, m), 4.57 (1H, s), 5.00 (1H, s), 5.71 (1H, d, J = 4.4 Hz), 7.60 (1H, dd, J = 7.9, 4.8 Hz), 8.41-8.39 (2H, m), 8.57 (1H, d, J = 8.0 Hz), 8.74-8.69 (2H, m), 9.06 precurso(1H, s), 9.16 (1H, s), 9.36 (1H, s). | 456.1; >98 |

TABLE 18-continued

| Compound No. | Intemediate | Reactant 8 replacement | Compound Structure/Name | $^{1}$H-NMR | MS $[m/z]^+$; Purity (%) |
|---|---|---|---|---|---|
| | | | 3-((3S,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one | | |
| 140 | 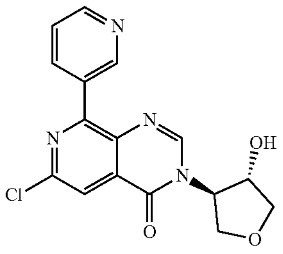<br>L6 | 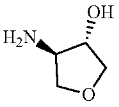 | 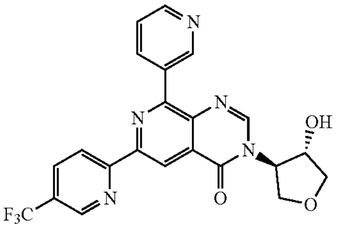 [SMILES: O=c1c2cc(-c3ccc(C(F)(F)F)cn3)nc(-c3cccnc3)c2ncn1[C@@H]1COC[C@H]1O]<br>3-((3R,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one | $^{1}$H NMR (DMSO-$d_6$, 400 MHz): $\delta_H$ 3.61 (1H, dd, J = 9.6, 3.3 Hz), 4.21-4.06 (3H, m), 4.57 (1H, s), 5.00 (1H, s), 5.71 (1H, d, J = 4.4 Hz), 7.59 (1H, dd, J = 7.9, 4.8 Hz), 8.40-8.38 (2H, m), 8.57 (1H, d, J = 8.0 Hz), 8.74-8.69 (2H, m), 9.06 (1H, s), 9.16 (1H, s), 9.36 (1H, s). | 456.1; >99 |
| 141 | 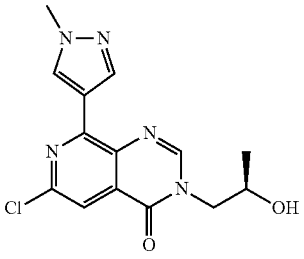<br>L7 | 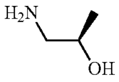 | 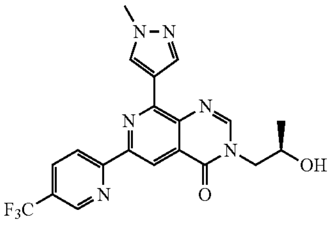<br>(R)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one | $^{1}$H NMR (DMSO-$d_6$, 400 MHz): $\delta_H$ 1.15 (3H, d, J = 6.2 Hz), 3.73 (1H, dd, J = 13.2, 8.7 Hz), 3.97 (3H, s), 4.15 (1H, d, J = 13.2 Hz), 5.06 (1H, d, J = 5.0 Hz), 8.36 (1H, d, J = 8.4 Hz), 8.45 (1H, s), 8.53 (1H, s), 8.81 (1H, d, J = 8.9 Hz), 8.84 (2H, d, J = 4.9 Hz), 9.12 (1H, s). | 431.1 >99 |
| 142 | 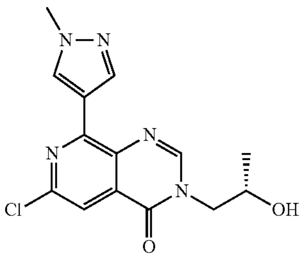<br>L8 | 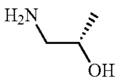 | 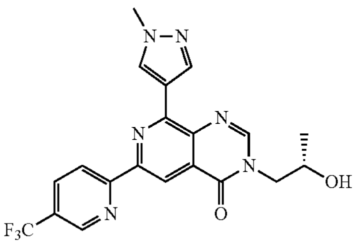 [SMILES: C[C@H](O)Cn1cnc2c(-c3cnn(C)c3)nc(-c3ccc(C(F)(F)F)cn3)cc2c1=O]<br>(S)-3-(2-hydroxypropyl)-8-(1-methyl-1H-pyrazol-4-yl)-6-(5-(trifluoromethyl)pyridin-2-yl)pyrido[3,4-d]pyrimidin-4(3H)-one | $^{1}$H NMR (DMSO-$d_6$, 400 MHz): $\delta_H$ 1.15 (3H, d, J = 6.2 Hz), 3.73 (1H, dd, J = 13.3, 8.7 Hz), 3.97 (3H, s), 4.15 (1H, d, J = 13.2 Hz), 5.05 (1H, d, J = 5.0 Hz), 8.36 (1H, d, J = 8.4 Hz), 8.44 (1H, s), 8.52 (1H, s), 8.79 (1H, d, J = 8.4 Hz), 8.83 (2H, d, J = 6.2 Hz), 9.11 (1H, s). | 431.1 >99 |

TABLE 18-continued

| Compound No. | Intemediate | Reactant 8 replacement | Compound Structure/Name | $^1$H-NMR | MS [m/z]$^+$; Purity (%) |
|---|---|---|---|---|---|
| 143 | 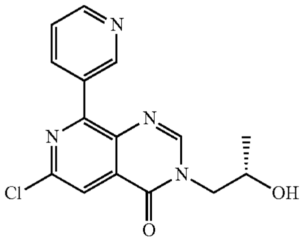 L2 | 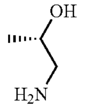 | 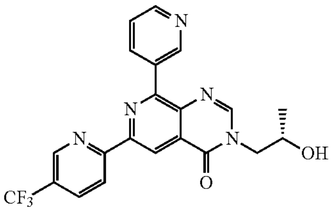 [SMILES: C[C@H](O)Cn1cnc2c(-c3cccnc3)nc(-c3ccc(C(F)(F)F)cn3)cc2c1=O] (S)-3-(2-hydroxypropyl)-8-(pyridin-3-yl)-6-(5-(trifluoromethyl)pyridin-2-yl)pyrido[3,4-d]pyrimidin-4(3H)-one | $^1$H NMR ($CH_3OH-d_4$, 400 MHz): $\delta_H$ 1.29 (3H, d, J = 6.3 Hz), 3.76 (1H, dd, J = 13.6, 8.9 Hz), 4.14 (1H, d, J = 7.5 Hz), 4.30 (1H, dd, J = 13.6, 3.0 Hz), 7.60 (1H, dd, J = 8.0, 5.0 Hz), 8.25 (1H, d, J = 8.5 Hz), 8.35 (1H, s), 8.63 (1H, d, J = 4.8 Hz), 8.73 (2H, dd, J = 8.1, 4.3 Hz), 9.01 (1H, s), 9.17 (1H, s), 9.41 (1H, s). | 428.1; 98% |
| 144 | 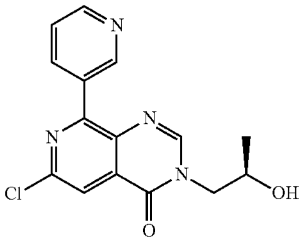 L3 | 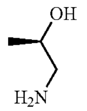 | 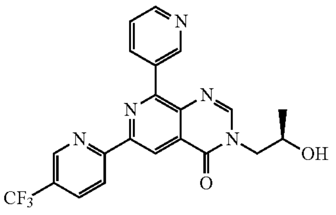 [SMILES: C[C@@H](O)Cn1cnc2c(-c3cccnc3)nc(-c3ccc(C(F)(F)F)cn3)cc2c1=O] (R)-3-(2-hydroxypropyl)-8-(pyridin-3-yl)-6-(5-(trifluoromethyl)pyridin-2-yl)pyrido[3,4-d]pyrimidin-4(3H)-one | $^1$H NMR ($CH_3OH-d_4$, 400 MHz): $\delta_H$ 1.29 (3H, d, J = 6.3 Hz), 3.74 (1H, dd, J = 13.6, 8.9 Hz), 4.14 (1H, t, J = 7.3 Hz), 4.28 (1H, dd, J = 13.6, 3.0 Hz), 7.64 (1H, dd, J = 8.0, 5.0 Hz), 8.22 (1H, d, J = 8.4 Hz), 8.33 (1H, s), 8.69-8.64 (2H, m), 8.78 (1H, d, J = 8.0 Hz), 8.98 (1H, s), 9.11 (1H, s), 9.43 (1H, s). | 428.1; 99% |
| 145 | 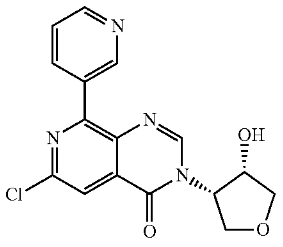 L1 | 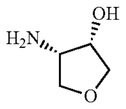 | 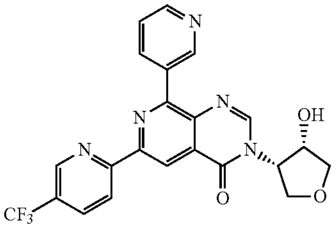 [SMILES: O=c1c2cc(-c3ccc(C(F)(F)F)cn3)nc(-c3cccnc3)c2ncn1[C@H]1COC[C@H]1O] 3-((3S,4S)-4-hydroxytetrahydrofuran-3-yl)-8-(pyridin-3-yl)-6-(5-(trifluoromethyl)pyridin-2-yl)pyrido[3,4-d]pyrimidin-4(3H)-one | $^1$H NMR (DMSO-$d_6$, 400 MHz): $\delta_H$ 3.78 (1H, d, J = 9.8 Hz), 4.02-3.92 (2H, m), 4.19 (1H, dd, J = 9.8, 5.9 Hz), 4.52 (1H, s), 5.40 (1H, d, J = 6.8 Hz), 5.47 (1H, d, J = 4.3 Hz), 7.60 (1H, dd, J = 7.9, 4.9 Hz), 8.41-8.39 (2H, m), 8.59 (1H, d, J = 8.0 Hz), 8.75-8.69 (2H, m), 9.07 (1H, s), 9.16 (1H, s), 9.37 (1H, s). | 456.1; 97% |
| 146 | 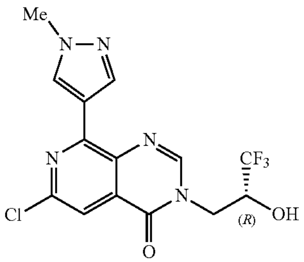 H3 | 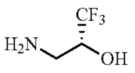 | 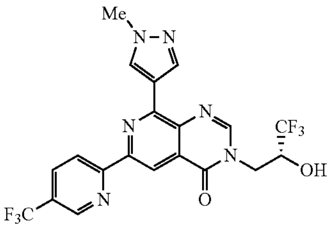 | $^1$H NMR (400 MHz, DMSO) 9.12 (1 H, s), 8.81 (3 H, t, J 9.7), 8.53 (2 H, d, J 6.3), 8.37 (1 H, dd, J 8.4, 1.8), 6.78 (1 H, d, J 6.4), 4.50-4.39 (2 H, m), 4.07 (1 H, dd, J 14.2, 9.9), 3.98 (3 H, s). | 485.1 99.1 |

TABLE 18-continued

| Compound No. | Intemediate | Reactant 8 replacement | Compound Structure/Name | $^1$H-NMR | MS [m/z]$^+$; Purity (%) |
|---|---|---|---|---|---|
| | | | (S)-3-(2-hydroxypropyl)-8-(pyridin-3-yl)-6-(6-(trifluoromethyl)pyridin-3-yl)pyrido[3,4-d]pyrimidin-4(3H)-one | | |
| 147 | 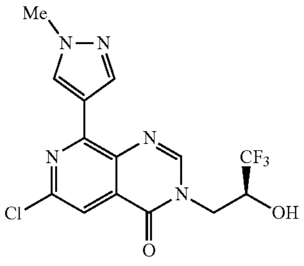 H4 | 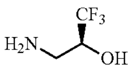 | 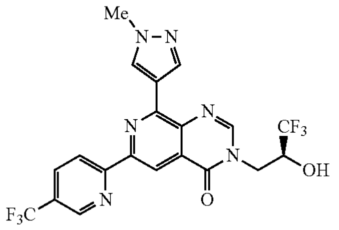 (S)-8-(1-methyl-1H-pyrazol-4-yl)-3-(3,3,3-trifluoro-2-hydroxypropyl)-6-(5-(trifluoromethyl)pyridin-2-yl)pyrido[3,4-d]pyrimidin-4(3H)-one | $^1$H NMR (400 MHz, DMSO) 9.13 (1 H, s), 8.82 (3 H, t, J 9.5), 8.53 (2 H, d, J 6.0), 8.37 (1 H, dd, J 8.3, 1.8), 6.80 (1 H, d, J 6.0), 4.50-4.40 (2 H, m), 4.07 (1 H, dd, J 14.0, 10.0), 3.98 (3 H, s). | 485.1 97.6 |
| 148 | 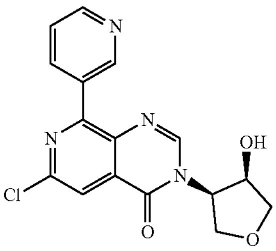 H5 | 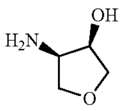 | 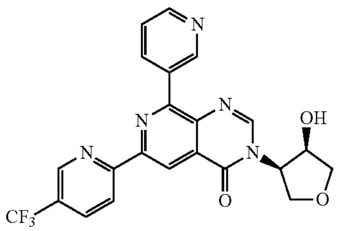 [SMILES: O=c1c2cc(-c3ccc(C(F)(F)F)cn3)nc(-c3cccnc3)c2ncn1[C@@H]1COC[C@@H]1O] 3-((3R,4R)-4-hydroxytetrahydrofuran-3-yl)-8-(pyridin-3-yl)-6-(5-(trifluoromethyl)pyridin-2-yl)pyrido[3,4-d]pyrimidin-4(3H)-one | (DMSO-$d_6$, 400 MHz): $\delta_H$ 3.77 (1H, d, J = 9.8 Hz), 4.02-3.92 (2H, m), 4.19 (1H, dd, J = 9.7, 5.9 Hz), 4.51 (1H, t, J = 5.6 Hz), 5.40 (1H, q, J = 6.6 Hz), 5.48 (1H, d, J = 4.3 Hz), 7.60 (1H, dd, J = 7.9, 4.8 Hz), 8.40 (2H, s), 8.59 (1H, d, J = 8.0 Hz), 8.75-8.69 (2H, m), 9.07 (1H, s), 9.16 (1H, s), 9.37 (1H, s). | 456.1; 99% |
| 149 | 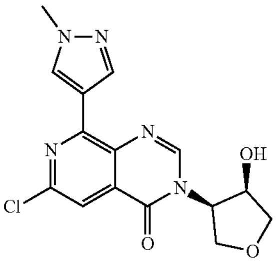 H6 | 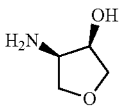 | 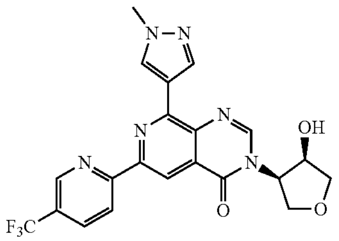 [SMILES: Cn1cc(-c2nc(-c3ccc(C(F)(F)F)cn3)cc3c(=O)n([C@@H]4COC[C@@H]4O)cnc23)cn1] 3-((3R,4R)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one | (DMSO-$d_6$, 400 MHz): $\delta_H$ 3.79 (1H, d, J = 9.8 Hz), 4.01-3.90 (6H, m), 4.20 (1H, dd, J = 9.9, 5.5 Hz), 4.52 (2H, s), 5.41 (1H, q, J = 6.5 Hz), 5.50 (1H, s), 8.36 (1H, d, J = 8.6 Hz), 8.40 (1H, s), 8.53 (1H, s), 8.81 (1H, d, J = 8.4 Hz), 8.86 (2H, d, J = 15.4 Hz), 9.12 (1H, s). | 459.1; >99% |

Scheme IV

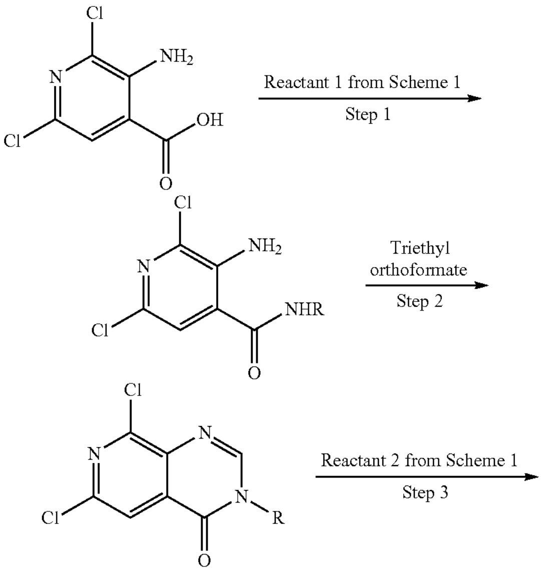

-continued

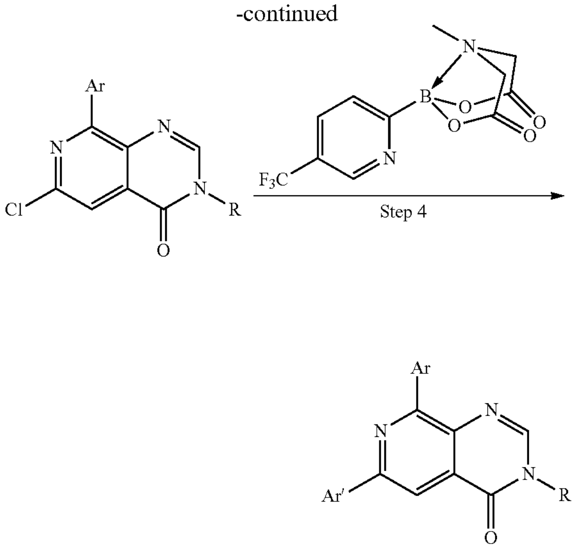

Table 19 lists compounds that were synthesized according to the procedure used for the last step for the synthesis of 137

TABLE 19

| Compound No. | Intermediate | Compound Structure/Name | $^1$H-NMR | MS $[m/z]^+$; Purity (%) |
|---|---|---|---|---|
| 150 | 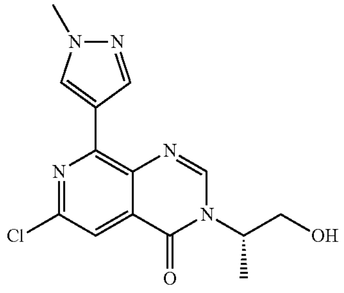 C10 | 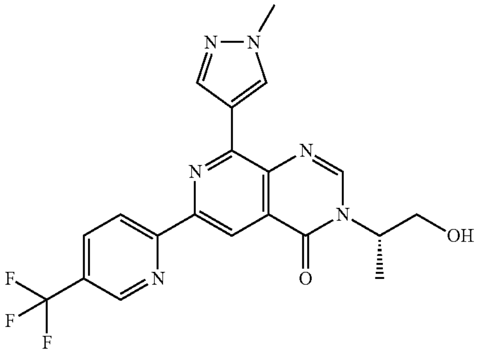 [SMILES: C[C@@H](CO)n1cnc2c(-c3cnn(C)c3)nc(-c3ccc(C(F)(F)F)cn3)cc2c1=O] (S)-3-(1-hydroxypropan-2-yl)-8-(1-methyl-1H-pyrazol-4-yl)-6-(5-(trifluoromethyl)pyridin-2-yl)pyrido[3,4-d]pyrimidin-4(3H)-one | (DMSO-$d_6$, 400 MHz): $\delta_H$ 1.43 (3H, d, J = 7.0 Hz), 3.69-3.64 (1H, m), 3.81-3.76 (1H, m), 3.96 (3H, s), 4.91-4.86 (1H, m), 5.10 (1H, t, J = 5.5 Hz), 8.37 (1H, dd, J = 8.5, 2.3 Hz), 8.55 (1H, s), 8.60 (1H, s), 8.82 (1H, d, J = 8.4 Hz), 8.84 (2H, d, J = 2.9 Hz), 9.13 (1H, s). | 431.2; 98 |
| 151 | 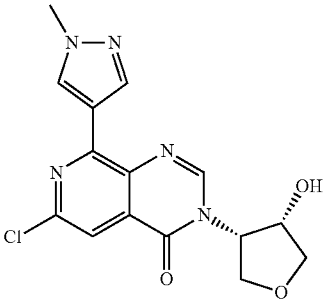 C33 | 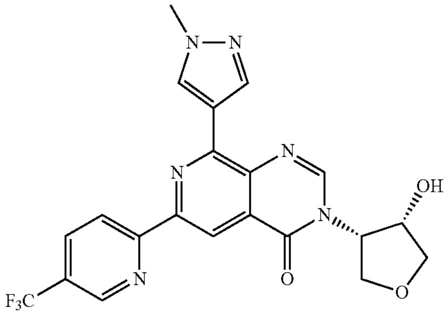 [SMILES: Cn1cc(-c2nc(-c3ccc(C(F)(F)F)cn3)cc3c(=O)n([C@H]4COC[C@H]4O)cnc23)cn1] 3-((3S,4S)-4-hydroxytetrahydrofuran-3-yl)-8-(1-methyl-1H-pyrazol-4-yl)-6-(5-(trifluoromethyl)pyridin-2-yl)pyrido[3,4-d]pyrimidin-4(3H)-one | (DMSO-$d_6$, 400 MHz): $\delta_H$ 3.80 (1H, d, J = 9.8 Hz), 4.03-3.93 (5H, m), 4.21 (1H, dd, J = 10.0, 5.5 Hz), 4.56-4.52 (1H, m), 5.43 (1H, q, J = 6.5 Hz), 5.50 (1H, d, J = 4.3 Hz), 8.38 (1H, d, J = 8.6 Hz), 8.42 (1H, s), 8.56 (1H, s), 8.83 (1H, d, J = 8.4 Hz), 8.87 (1H, s), 8.90 (1H, s), 9.14 (1H, s) | 459.1; 98 |

The compounds encompassed within the present disclosure can be prepared by the procedure outlined in Scheme V and described in the Examples herein below.

Scheme V

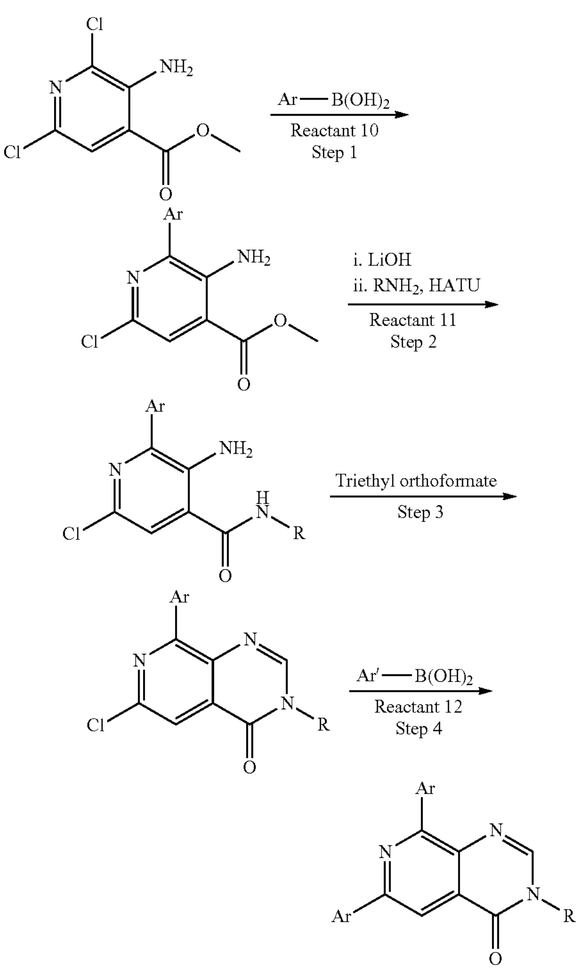

Preparation of 6-(4-chlorophenyl)-3-((3R,4S)-4-hydroxytetrahydrofuran-3-yl)-8-(pyridin-3-yl)pyrido[3,4-d]pyrimidin-4(3H)-one 18 (152)

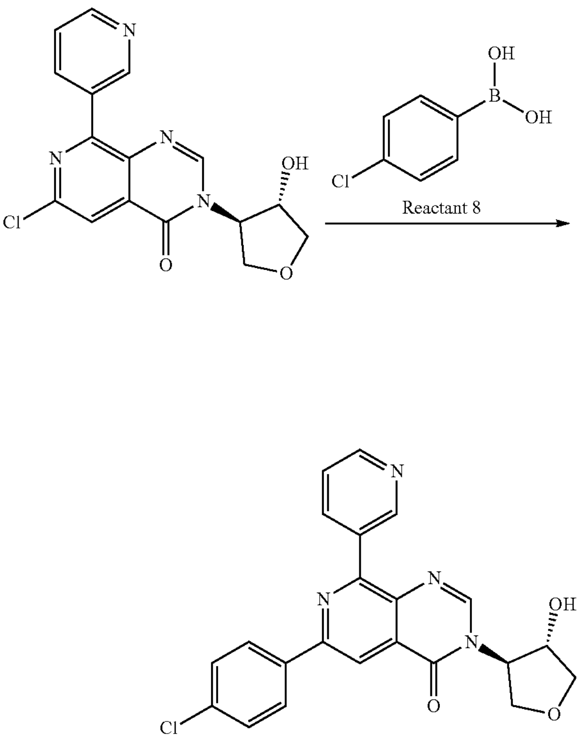

152 was synthesized according to step 4 for the synthesis of 1. $^{1}$H NMR (DMSO-$d_6$, 400 MHz): δ 3.63 (1H, dd, J=9.6, 3.3 Hz), 4.07 (1H, dd, J=10.0, 4.0 Hz), 4.22-4.13 (2H, m), 4.58 (1H, s), 5.00 (1H, s), 5.70 (1H, d, J=4.4 Hz), 7.60 (3H, m), 8.32 (2H, d, J=8.4 Hz), 8.37 (1H, s), 8.54 (1H, s), 8.56 (1H, s), 8.70 (1H, s), 9.34 (1H, s); MS (m/z): 421.1 $[M+H]^+$; >98% purity.

Table 20 lists compounds that were made via a procedure similar to that described for 152, replacing reactants 6, 7, and 8 with the indicated groups.

TABLE 20

| Compound No. | Reactant 6 replacement | Reactant 7 replacement | Reactant 8 replacement | Compound Structure/Name | $^{1}$H-NMR | MS $[m/z]^+$; Purity (%) |
|---|---|---|---|---|---|---|
| 153 | 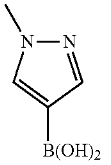 | 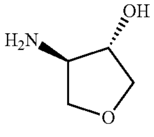 | 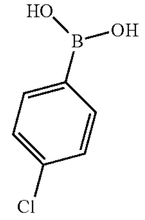 | 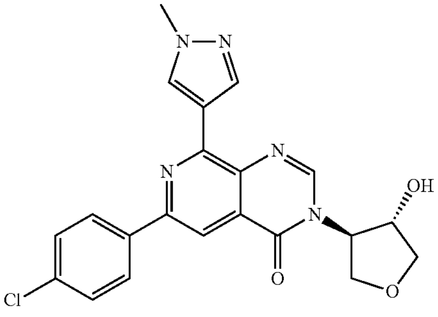 [SMILES: Cn1cc(-c2nc(-c3ccc(Cl)cc3)cc3c(=O)n([C@@H]4COC[C@H]4O)cnc23)cn1] | (DMSO-$d_6$, 400 MHz): $\delta_H$ 3.65 (1H, dd, J = 9.6, 3.3 Hz), 3.98 (3H, s), 4.24-4.12 (3H, m), 5.72 (1H, d, J = 4.3 Hz), 7.60 (2H, d, J = 8.3 Hz), 8.33 (2H, d, J = 2.9 Hz), 8.37 (2H, d, J = 11.7 Hz), 8.51 (1H, s), 8.83 (1H, s). | 424.1; >99 |

TABLE 20-continued

| Compound No. | Reactant 6 replacement | Reactant 7 replacement | Reactant 8 replacement | Compound Structure/Name | $^1$H-NMR | MS [m/z]$^+$; Purity (%) |
|---|---|---|---|---|---|---|
| | | | | 6-(4-Chlorophenyl)-3-((3R,4S)-4-hydroxytetrahydrofuran-3-yl)-8-(1-methyl-1H-pyrazol-4-yl)pyrido[3,4-d]pyrimidin-4(3H)-one | | |
| 154 | 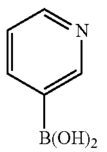 | 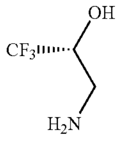 | 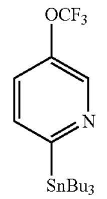 | 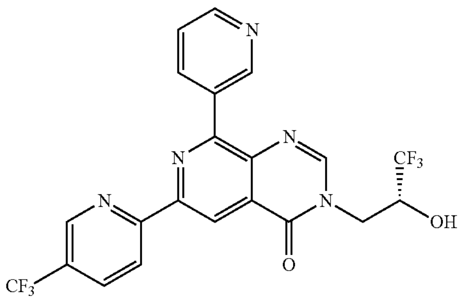 [SMILES: O=c1c2cc(-c3ccc(C(F)(F)F)cn3)nc(-c3cccnc3)c2ncn1C[C@@H](O)C(F)(F)F] (R)-8-(pyridin-3-yl)-3-(3,3,3-trifluoro-2-hydroxypropyl)-6-(5-(trifluoromethyl)pyridin-2-yl)pyrido[3,4-d]pyrimidin-4(3H)-one | ($CH_3OH$-$d_4$, 400 MHz): $\delta_H$ 3.99 (1H, dd, J = 13.7, 9.7 Hz), 4.46 (1H, s), 4.62 (1H, d, J = 14.0 Hz), 7.62 (1H, dd, J = 8.0, 5.0 Hz), 8.26 (1H, d, J = 8.5 Hz), 8.39 (1H, s), 8.65 (1H, d, J = 4.9 Hz), 8.73 (2H, d, J = 8.3 Hz), 9.01 (1H, s), 9.14 (1H, s), 9.41 (1H, s). | 481.9; 97 |

Preparation of (S)-2-(4-oxo-8-(pyridin-3-yl)-6-(6-(trifluoromethyl)pyridin-3-yl)pyrido[3,4-d]pyrimidin-3(4H)-yl)propanoic acid (155)

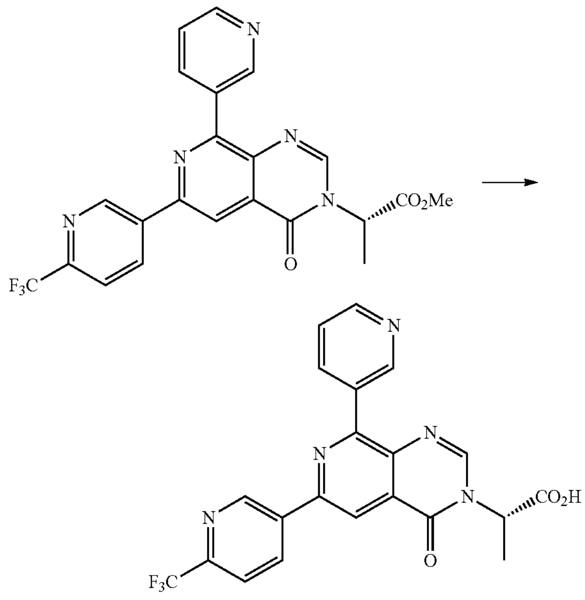

Methyl (S)-2-(4-oxo-8-(pyridin-3-yl)-6-(6-(trifluoromethyl)pyridin-3-yl)pyrido[3,4-d]pyrimidin-3(4H)-yl)propanoate (127, 70 mg, 0.15 mmol) was dissolved in 0.5 THE and 0.5 mL of 1M LiOH was added in dropwise. The reaction mixture was kept stirring at room temperature. After completion, the solution was acidified with Amberlite-IR120 [H], filtered, concentrated and the residue was purified by reverse phase chromatography to provide the title compound (S)-2-(4-oxo-8-(pyridin-3-yl)-6-(6-(trifluoromethyl)pyridin-3-yl)pyrido[3,4-d]pyrimidin-3(4H)-yl)propanoic acid (155, 32 mg, 0.073 mmol, 47% yield). $^1$H-NMR ($CH_3OH$-$d_4$, 400 MHz): $\delta_H$ 1.76 (3H, d, J=7.5 Hz), 5.42 (1H, d, J=7.5 Hz), 7.62 (1H, dd, J=8.0, 5.0 Hz), 7.98 (1H, d, J=8.3 Hz), 8.46 (1H, s), 8.64 (1H, d, J=4.8 Hz), 8.77-8.75 (2H, m), 8.86 (1H, d, J=8.3 Hz), 9.43 (1H, s), 9.56 (1H, s). MS (m/z): 442.1 [M+H]. Purity: 99%.

Preparation of (S)—N-methyl-2-(4-oxo-8-(pyridin-3-yl)-6-(6-(trifluoromethyl)pyridin-3-yl)pyrido[3,4-d]pyrimidin-3(4H)-yl)propanamide (156)

155

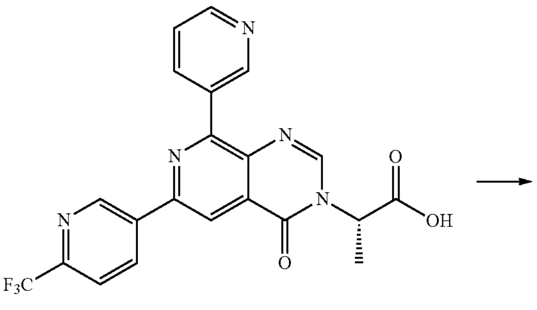

-continued

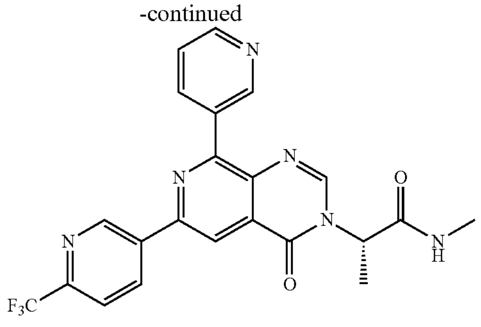

(S)-2-(4-oxo-8-(pyridin-3-yl)-6-(6-(trifluoromethyl)pyridin-3-yl)pyrido[3,4-d]pyrimidin-3(4H)-yl)propanoic acid (155, 150 mg, 0.34 mmol) and methylamine hydrochloride (35 mg, 0.51 mmol) were dissolved in 1.1 mL anhydrous NMP. N,N-Diisopropylethylamine (0.18 mL, 1.02 mmol) was added. The solution was cooled within an ice-water bath and HATU (155 mg, 0.408 mmol) was added. The reaction mixture was allowed to warm to room temperature and kept stirring at room temperature. After completion, reaction was quenched with water and diluted with EtOAc. The organic phase was washed with sat. $NaHCO_3$, brine, dried over anhydrous sodium sulfate and concentrated. The residue was purified by normal phase chromatography to provide the title compound (S)—N-methyl-2-(4-oxo-8-(pyridin-3-yl)-6-(6-(trifluoromethyl)pyridin-3-yl)pyrido[3,4-d]pyrimidin-3(4H)-yl)propanamide (156, 94 mg, 0.21 mmol, 61% yield). $^1$H-NMR ($CH_3OH$-$d_4$, 400 MHz): $\delta_H$ 1.78 (3H, d, J=7.3 Hz), 2.79 (3H, s), 5.48 (1H, d, J=7.3 Hz), 7.62 (1H, dd, J=7.9, 5.0 Hz), 7.97 (1H, d, J=8.3 Hz), 8.52 (1H, s), 8.65 (1H, d, J=4.8 Hz), 8.74-8.73 (2H, m), 8.85 (1H, d, J=8.4 Hz), 9.43 (1H, s), 9.55 (1H, s). MS (m/z): 455.1 [M+H]. Purity: 99%.

Preparation of (S)—N,N-dimethyl-2-(4-oxo-8-(pyridin-3-yl)-6-(6-(trifluoromethyl)pyridin-3-yl)pyrido[3,4-d]pyrimidin-3(4H)-yl)propenamide (157)

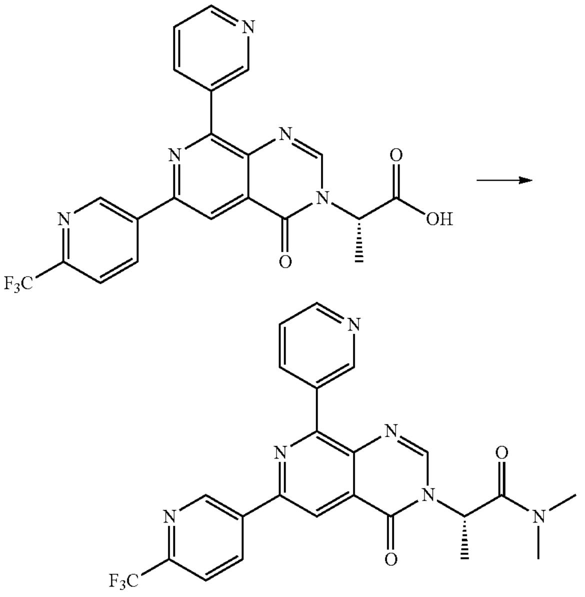

157 was synthesized according to the procedure reported for 156. $^1$H-NMR (DMSO-$d_6$, 400 MHz): $\delta_H$ 1.66 (3H, d, J=7.3 Hz), 2.87 (3H, s), 3.19 (3H, s), 5.88 (1H, d, J=7.5 Hz), 7.59 (1H, dd, J=7.9, 4.7 Hz), 8.06 (1H, d, J=8.3 Hz), 8.59-8.57 (1H, m), 8.64 (1H, s), 8.70-8.69 (1H, m), 8.74 (1H, s), 8.92 (1H, d, J=8.4 Hz), 9.37 (1H, s), 9.62 (1H, s). MS (m/z): 469.1 [M+H]. Purity: 99%.

Preparation of (S)—N-((3R,4S)-4-hydroxytetrahydrofuran-3-yl)-2-(4-oxo-8-(pyridin-3-yl)-6-(6-(trifluoromethyl)pyridin-3-yl)pyrido[3,4-d]pyrimidin-3(4H)-yl)propenamide (158)

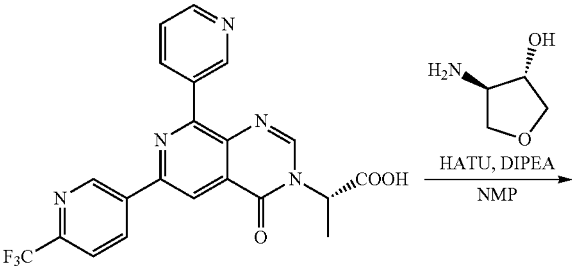

155

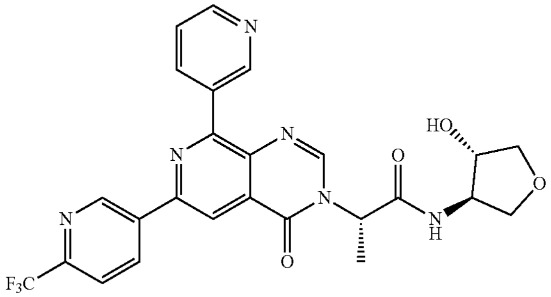

158

158 was synthesized according to the procedure reported for 138. $^1$H-NMR (DMSO-$d_6$, 400 MHz): δ 1.68 (3H, d, J=7.3 Hz), 3.53 (2H, dd, J=17.9, 9.2 Hz), 3.83 (1H, dd, J=9.3, 4.4 Hz), 3.91 (1H, t, J=7.3 Hz), 3.99 (1H, t, J=5.6 Hz), 4.06 (1H, s), 5.29 (1H, d, J=3.9 Hz), 5.46-5.40 (1H, m), 7.61 (1H, dd, J=7.9, 4.9 Hz), 8.07 (1H, d, J=8.3 Hz), 8.58 (2H, t, J=7.8 Hz), 8.64 (1H, s), 8.72 (1H, d, J=4.8 Hz), 8.76 (1H, s), 8.95 (1H, d, J=8.4 Hz), 9.38 (1H, s), 9.65 (1H, s). MS (m/z): 527.1 [M+H]. Purity: >99%

Preparation of 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one (159)

Step 1. Preparation of 6-chloro-3-(2-hydroxy-2-methylpropyl)-8-(1-((2-(trimethylsilyl)ethoxy)methyl)-1H-pyrazol-4-yl)pyrido[3,4-d]pyrimidin-4(3H)-one (Precursor 6)

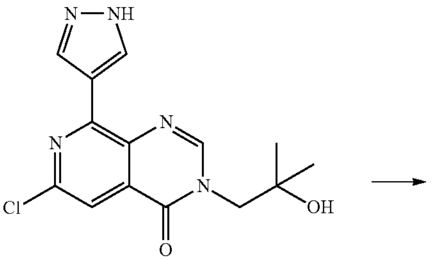

C23

-continued

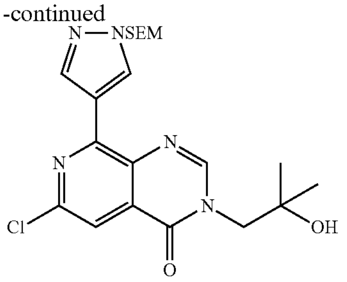

Precursor 6

6-chloro-3-(2-hydroxy-2-methylpropyl)-8-(1H-pyrazol-4-yl)pyrido[3,4-d]pyrimidin-4(3H)-one (C23, 140 mg, 0.44 mmol) was suspended in anhydrous THE (4.4 mL) and the mixture was cooled down by an ice-water bath. NaH (60% dispersion in oil, 26 mg, 1.10 mmol) was added and the mixture was stirred for 10 mins before addition of SEMCl (0.19 mL, 1.10 mmol). After completion, reaction was quenched with saturated aqueous $NH_4Cl$ (25 mL) and water (10 mL). The aqueous layer was separated and extracted with DCM. The combined organic layers were washed with brine, dried over anhydrous sodium sulfate, filtered and concentrated under reduced pressure. The residue was purified by normal phase chromatography, providing the title compound 6-chloro-3-(2-hydroxy-2-methylpropyl)-8-(1-((2-(trimethylsilyl)ethoxy)methyl)-1H-pyrazol-4-yl)pyrido[3,4-d]pyrimidin-4(3H)-one (6, 170 mg, 0.38 mmol, 86% yield). $^1$H-NMR ($CHCl_3$-d, 400 MHz): $\delta_H$-0.02 (9H, s), 0.94 (2H, t, J=8.2 Hz), 1.21 (1H, d, J=6.1 Hz), 1.33 (6H, s), 3.63 (2H, t, J=8.3 Hz), 4.10 (2H, s), 5.50 (2H, s), 7.92 (1H, s), 8.26 (1H, s), 8.54 (1H, s), 8.79 (1H, s). MS (m/z): 450.2 $[M+H]^+$.

Step 2. Preparation of 3-(2-hydroxy-2-methylpropyl)-6-(5-(trifluoromethyl)pyridin-2-yl)-8-(1-((2-(trimethylsilyl)ethoxy)methyl)-1H-pyrazol-4-yl)pyrido[3,4-d]pyrimidin-4(3H)-one (Precursor 7)

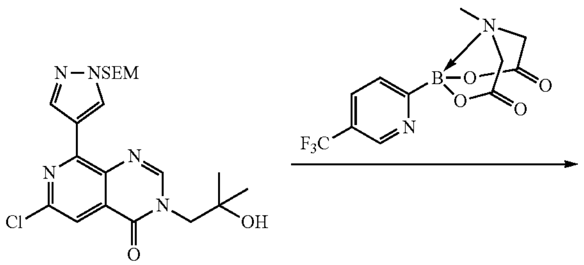

Precursor 6

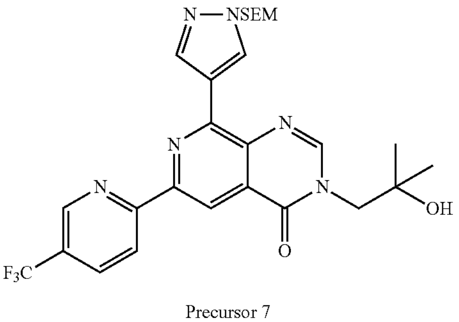

Precursor 7

Precursor 7 was prepared according to the procedure reported above. $^1$H-NMR ($CHCl_3$-d, 400 MHz): $\delta_H$-0.001 (9H, s), 0.96 (2H, t, J=8.3 Hz), 1.35-1.32 (6H, m), 2.12 (1H, s), 3.67 (2H, t, J=8.3 Hz), 4.15 (2H, s), 5.55 (2H, s), 8.10-8.08 (1H, m), 8.32 (1H, s), 8.62 (1H, s), 8.70 (1H, d, J=8.3 Hz), 8.89 (1H, s), 8.97 (1H, s), 9.09 (1H, s). MS (m/z): 561.2 $[M+H]^+$.

Step 3. Preparation of 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one (159)

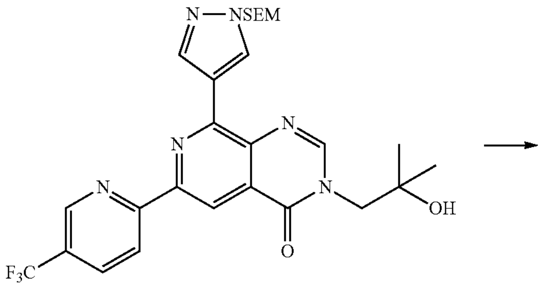

Precursor 7

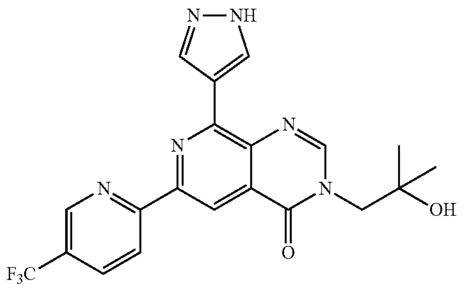

3-(2-hydroxy-2-methylpropyl)-6-(5-(trifluoromethyl)pyridin-2-yl)-8-(1-((2-(trimethylsilyl)ethoxy)methyl)-1H-pyrazol-4-yl)pyrido[3,4-d]pyrimidin-4(3H)-one (Precursor 7, 90 mg, 0.16 mmol) was dissolved in 1.6 mL anhydrous DCM and the solution was cooled down with an ice-water bath. Trifluoroacetic acid (0.61 mL, 8.0 mmol) was added. The reaction mixture was kept stirring at 0° C. for 30 mins, and warmed up to room temperature. After completion, volatiles were removed under reduced pressure. The residue was taken up in EtOAc, washed with sat. $NaHCO_3$, brine, dried over anhydrous sodium sulfate and concentrated. The residue was purified by normal phase chromatography, followed by re-crystallization in MeOH to afford the title compound 3-(2-hydroxy-2-methylpropyl)-8-(1H-pyrazol-4-yl)-6-(5-(trifluoromethyl)pyridin-2-yl)pyrido[3,4-d]pyrimidin-4(3H)-one (159, 35 mg, 51% yield). $^1$H-NMR ($CH_3OH$-$d_4$, 400 MHz): $\delta_H$ 1.27 (6H, s), 4.13 (2H, s), 8.27-8.25 (1H, m), 8.43 (1H, s), 8.67 (1H, s), 8.81-8.79 (1H, m), 8.90 (1H, s), 8.99-8.97 (2H, m). MS (m/z): 431.1 $[M+H]^+$. Purity: 98%.

Preparation of 3-(2-hydroxy-2-methylpropyl)-8-(1H-imidazol-1-yl)-6-(5-(trifluoromethyl)pyridin-2-yl)pyrido[3,4-d]pyrimidin-4(3H)-one (160)

Step 1. Preparation of 6-chloro-3-(2-hydroxy-2-methylpropyl)-8-(1H-imidazol-1-yl)pyrido[3,4-d]pyrimidin-4(3H)-one (Precursor 8)

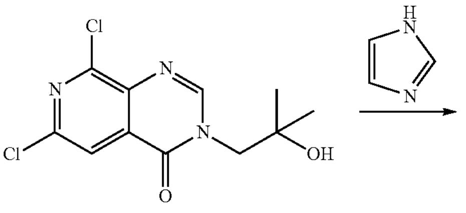

B2

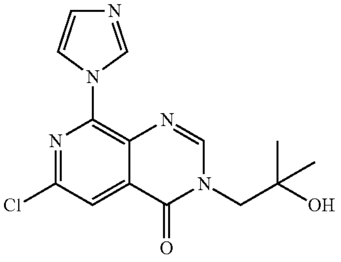

Precursor 8

An oven-dried screw-cap test tube was charged with CuI (53 mg, 0.28 mmol), 4,7-dimethoxy-1,10-phenanthroline (134 mg, 0.56 mmol), imidazole (95 mg, 1.4 mmol), 6,8-dichloro-3-(2-hydroxy-2-methylpropyl)pyrido[3,4-d]pyrimidin-4(3H)-one (B2, 400 mg, 1.4 mmol), poly(ethylene glycol) (233 mg, 0.07 mmol), $Cs_2CO_3$ (908 mg, 2.8 mmol) and a magnetic stir bar. Anhydrous NMP (7 mL) was then added and the reaction vessel was fitted with a rubber septum. The vessel was evacuated and refilled with argon for 3 cycles. The reaction mixture was heated at 108° C. for 2-3 hours. After completion, the reaction mixture was cooled to room temperature, diluted with dichloromethane, filtered through a plug of celite, and eluted with additional dichloromethane. The filtrate was washed with sat. $NaHCO_3$, brine, dried over anhydrous sodium sulfate, concentrated and the resulting residue was purified by normal phase chromatography to provide the title compound 6-chloro-3-(2-hydroxy-2-methylpropyl)-8-(1H-imidazol-1-yl)pyrido[3,4-d]pyrimidin-4(3H)-one (Precursor 8, 200 mg, 45% yield). $^1$H-NMR ($CH_3OH$-$d_4$, 300 MHz): $\delta_H$ 1.24-1.21 (6H, m), 3.65 (1H, s), 4.13 (1H, s), 7.18 (1H, s), 8.08 (1H, s), 8.26 (1H, s), 8.44 (1H, s), 9.11 (1H, s). MS (m/z): 319.9 $[M+H]^+$.

Step 2. Preparation of 3-(2-hydroxy-2-methylpropyl)-8-(1H-imidazol-1-yl)-6-(5-(trifluoromethyl)pyridin-2-yl)pyrido[3,4-d]pyrimidin-4(3H)-one (160)

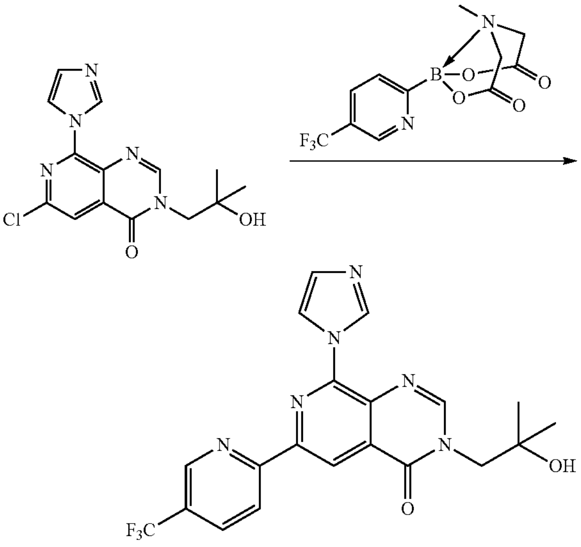

Compound 160 was prepared according to the procedure reported for 121. $^1$H-NMR ($CH_3OH$-$d_4$, 400 MHz): $\delta_H$ 1.27 (6H, s), 4.08 (2H, s), 7.11 (1H, s), 8.14 (1H, d, J=8.1 Hz), 8.27 (1H, s), 8.37 (1H, s), 8.44 (1H, d, J=8.3 Hz), 8.87 (2H, d, J=16.9 Hz), 9.06 (1H, s). MS (m/z): 430.9 [M+H]. Purity: 99%.

Preparation of 3-(2-hydroxy-2-methylpropyl)-8-(1H-imidazol-1-yl)-6-(6-(trifluoromethyl)pyridin-2-yl)pyrido[3,4-d]pyrimidin-4(3H)-one (161)

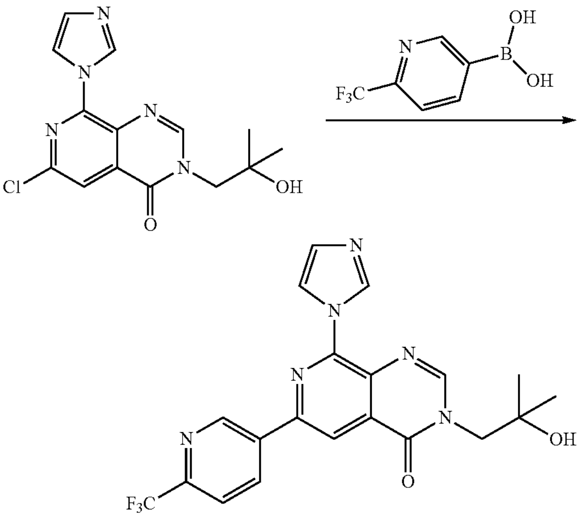

161 was synthesized according to step 4 for the synthesis of 1. $^1$H-NMR ($CH_3OH$-$d_4$, 300 MHz): $\delta_H$ 1.30 (6H, s), 4.16 (2H, s), 7.20 (1H, s), 7.98 (1H, d, J=8.3 Hz), 8.40 (1H, s), 8.48 (1H, s), 8.68 (1H, s), 8.82 (1H, d, J=8.3 Hz), 9.18 (1H, s), 9.51 (1H, s). MS (m/z): 430.9 [M+H]. Purity: 98%.

Preparation of (S)-3-(1-hydroxypropan-2-yl)-8-(1H-imidazol-1-yl)-6-(5-(trifluoromethyl)pyridin-2-yl) pyrido[3,4-d]pyrimidin-4(3H)-one (162)

Step 1. Preparation of (S)-3-(1-((tert-butyldimethylsilyl)oxy)propan-2-yl)-6,8-dichloropyrido[3,4-d] pyrimidin-4(3H)-one (Precursor 9)

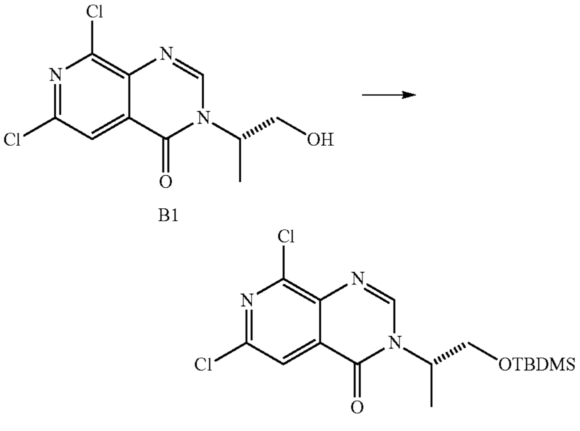

B1

Precursor 9

Imidazole (99 mg, 1.5 mmol) was added to a solution of (S)-6,8-dichloro-3-(1-hydroxypropan-2-yl)pyrido[3,4-d]pyrimidin-4(3H)-one (B1, 200 mg, 0.73 mmol) in anhydrous DMF. The solution was cooled down with an ice-water bath and TBDMSCl (132 mg, 0.88 mmol) was added. The reaction mixture was allowed to warm up to room temperature and kept stirring for 2 hours. After completion, reaction was quenched with methanol. The reaction mixture was diluted with EtOAc, washed with sat. $NaHCO_3$ and water sequentially. The organic phase was dried over anhydrous sodium sulfate and concentrated to provide the title compound (S)-3-(1-((tert-butyldimethylsilyl)oxy)propan-2-yl)-6,8-dichloropyrido[3,4-d]pyrimidin-4(3H)-one (Precursor 9, 280 mg, 99% yield). $^1$H-NMR (DMSO-$d_6$, 400 MHz): $\delta_H$ −0.07 (6H, d, J=10.7 Hz), 0.73 (9H, s), 1.41 (3H, d, J=7.0 Hz), 3.93-3.81 (2H, m), 4.87 (1H, s), 8.05 (1H, s), 8.61 (1H, s). MS (m/z): 387.9 $[M+H]^+$.

Step 2. Preparation of (S)-3-(1-((tert-butyldimethylsilyl)oxy)propan-2-yl)-6-chloro-8-(1H-imidazol-1-yl)pyrido[3,4-d]pyrimidin-4(3H)-one (P1)

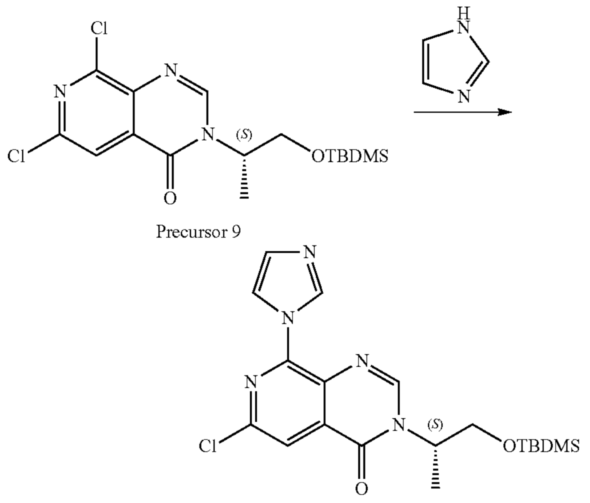

Precursor 9

Intermediate P1

Intermediate P1 was synthesized according to the procedure reported for step 1 for the synthesis of 160. MS (m/z): 420.0 [M+H].

Table 21 shows intermediates synthesized according to the step described above.

TABLE 21

| Intermediate Name | Structure and Name | $^1$H-NMR | MS (m/z) $[M + H]^+$; Purity (%) |
|---|---|---|---|
| P2 | 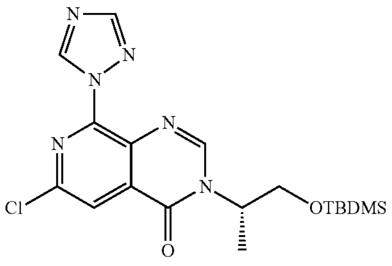 [SMILES: C[C@@H](CO[Si](C)(C)C(C)(C)C)n1cnc2c(-n3cncn3)nc(Cl)cc2c1=O] (S)-3-(1-((tert-butyldimethylsilyl)oxy)propan-2-yl)-6-chloro-8-(1H-1,2,4-triazol-1-yl)pyrido[3,4-d]pyrimidin-4(3H)-one | ($CHCl_3$-d, 300 MHz): $\delta_H$ 0.03 (6H, d, J = 11.3 Hz), 0.87 (9H, s), 1.59 (3H, d, J = 7.9 Hz), 3.91 (2H, s), 5.11 (1H, s), 8.19 (1H, s), 8.25 (1H, s), 8.40 (1H, s), 9.59 (1H, s). | 421.0; NA |

TABLE 21-continued

| Intermediate Name | Structure and Name | $^1$H-NMR | MS (m/z) $[M + H]^+$; Purity (%) |
|---|---|---|---|
| P3 | 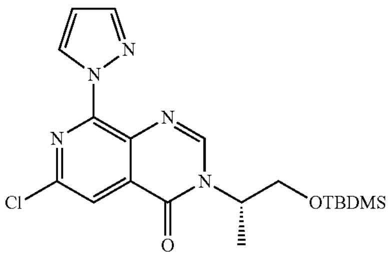 [SMILES: C[C@@H](CO[Si](C)(C)C(C)(C)C)n1cnc2c(-n3cccn3)nc(Cl)cc2c1=O] (S)-3-(1-((tert-butyldimethylsilyl)oxy)propan-2-yl)-6-chloro-8-(1H-pyrazol-1-yl)pyrido[3,4-d]pyrimidin-4(3H)-one | ($CHCl_3$-d, 300 MHz): $\delta_H$ 0.03 (6H, d, J = 7.6 Hz), 0.87 (9H, s), 1.58 (3H, m), 3.56-3.48 (1H, m), 3.91-3.89 (2H, m), 6.55-6.54 (1H, m), 7.94 (1H, t, J = 1.4 Hz), 8.10 (1H, t, J = 1.0 Hz), 8.38-8.37 (1H, m), 8.81-8.80 (1H, m) | 420.0; NA |

Step 3. Preparation of (S)-6-chloro-3-(1-hydroxy-propan-2-yl)-8-(1H-imidazol-1-yl)pyrido[3,4-d]py-rimidin-4(3H)-one (Q1)

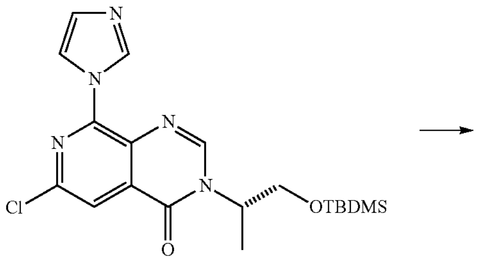

Intermediate P1

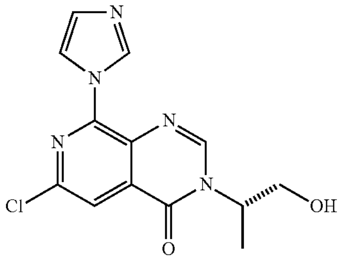

Intermediate Q1

(S)-3-(1-((tert-butyldimethylsilyl)oxy)propan-2-yl)-6-chloro-8-(1H-imidazol-1-yl)pyrido[3,4-d]pyrimidin-4(3H)-one (Intermediate P1, 460 mg, 1.1 mmol) was dissolved in anhydrous THE (11 mL) and cooled down with an ice-water bath. Tetrabutylammonium fluoride (1.0 M in THF, 1.3 mL, 1.3 mmol) was added in dropwise and the solution was stirred for 10 mins. After completion, the reaction mixture was quenched with sat. $NH_4Cl$, and was extracted with EtOAc. The organic phase was collected, washed with water, brine, dried over anhydrous sodium sulfate and concentrated. The residue was taken in MeOH, precipitates were collected and dried to provide the title compound which was taken into next step without further purification (S)-6-chloro-3-(1-hydroxypropan-2-yl)-8-(1H-imidazol-1-yl)pyrido[3,4-d]pyrimidin-4(3H)-one (Intermediate Q1, 340 mg, 1.1 mmol, quant. yield). $^1$H-NMR (DMSO-$d_6$, 300 MHz): $\delta_H$ 1.45-1.39 (3H, m), 3.84-3.62 (2H, m), 4.93-4.78 (1H, m), 5.06-5.11 (1H, m), 7.17-7.14 (1H, m), 8.03-8.00 (1H, m), 8.12-8.09 (1H, m), 8.66-8.62 (1H, m), 8.85-8.83 (1H, m). MS (m/z): 305.9 $[M+H]^+$.

Table 22 lists intermediates synthesized according to the step described above.

TABLE 22

| Intermediate Name | Structure and Name | $^1$H-NMR | MS (m/z) $[M + H]^+$; Purity (%) |
|---|---|---|---|
| Q2 | 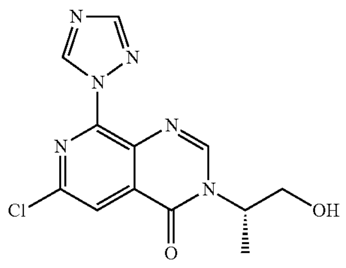 [SMILES: C[C@@H](CO)n1cnc2c(-n3cncn3)nc(Cl)cc2c1=O] (S)-6-chloro-3-(1-hydroxypropan-2-yl)-8-(1H-1,2,4-triazol-1-yl)pyrido[3,4-d]pyrimidin-4(3H)-one | $^1$H NMR ($CH_3OH$-$d_4$, 400 MHz): $\delta_H$ 1.64 (3H, d, J = 7.1 Hz), 3.94 (1H, dd, J = 11.9, 4.2 Hz), 4.04 (1H, dd, J = 11.9, 6.9 Hz), 5.09-5.04 (1H, m), 8.30 (1H, s), 8.41 (1H, s), 8.62 (1H, s), 9.78 (1H, s). | 307.0 |

TABLE 22-continued

| Intermediate Name | Structure and Name | $^1$H-NMR | MS (m/z) $[M + H]^+$; Purity (%) |
|---|---|---|---|
| Q3 | 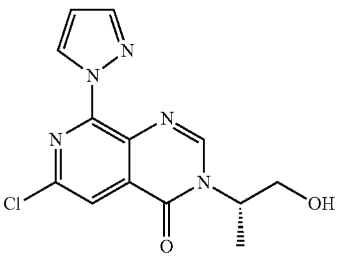 [SMILES: C[C@@H](CO)n1cnc2c(-n3cccn3)nc(Cl)cc2c1=O] (S)-6-chloro-3-(1-hydroxypropan-2-yl)-8-(1H-pyrazol-1-yl)pyrido[3,4-d]pyrimidin-4(3H)-one | $^1$H NMR ($CH_3OH$-$d_4$, 400 MHz): $\delta_H$ 1.52-1.35 (3H, m), 3.87-3.70 (2H, m), 4.89-4.73 (1H, m), 6.56-6.49 (1H, m), 7.84-7.76 (1H, m), 8.02-7.95 (1H, m), 8.43-8.32 (1H, m), 8.94-8.85 (1H, m). | 306.1 |

Step 4. Preparation of (S)-3-(1-hydroxypropan-2-yl)-8-(1H-imidazol-1-yl)-6-(5-(trifluoromethyl)pyridin-2-yl)pyrido[3,4-d]pyrimidin-4(3H)-one (162)

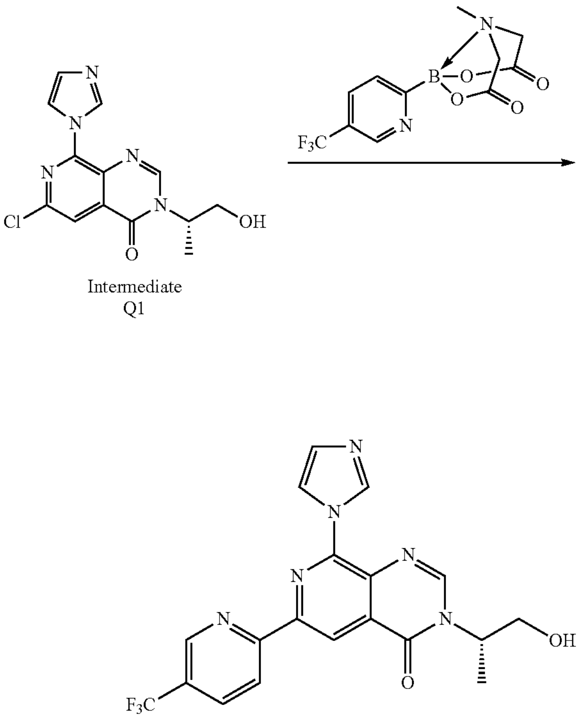

Intermediate Q1

143

162 was prepared according to the procedure reported for 137. $^1$H-NMR ($CH_3OH$-$d_4$, 400 MHz): $\delta_H$ 1.57 (3H, d, J=7.1 Hz), 3.87 (1H, dd, J=11.9, 4.3 Hz), 3.97 (1H, dd, J=11.9, 6.9 Hz), 5.01 (1H, td, J=7.1, 4.4 Hz), 7.19 (1H, s), 8.28 (1H, dd, J=8.3, 2.2 Hz), 8.43 (1H, s), 8.57 (1H, s), 8.70 (1H, d, J=8.4 Hz), 9.03 (1H, s), 9.15 (1H, s), 9.19 (1H, s). MS (m/z): 416.9 [M+H]. Purity: 98%.

Preparation of (S)-3-(1-hydroxypropan-2-yl)-8-(1H-imidazol-1-yl)-6-(6-(trifluoromethyl)pyridin-3-yl)pyrido[3,4-d]pyrimidin-4(3H)-one (163)

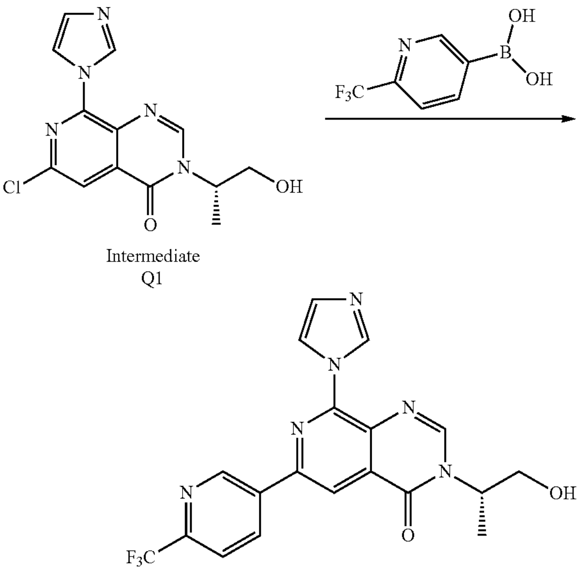

Intermediate Q1

(S)-6-chloro-3-(1-hydroxypropan-2-yl)-8-(1H-imidazol-1-yl)pyrido[3,4-d]pyrimidin-4(3H)-one (Intermediate Q1, 85 mg, 0.28 mmol) and 2-trifluoromethyl-pyridine-5-boronic acid (80 mg, 0.42 mmol) were dissolved in 2 mL toluene-EtOH (2:1), and sodium carbonate (118 mg, 1.1 mmol) were added. The suspension was degassed and refilled with argon (3 cycles). Tetrakis(triphenylphosphine) palladium (32 mg, 0.028 mmol) was added and the suspension was degassed and refilled with argon (3 cycles). The reaction mixture was heated to 85° C. under argon and kept stirring overnight. After completion, the reaction mixture was cooled down, diluted in EtOAc, washed with water and brine. The organic phase was dried over anhydrous sodium sulfate. The solution was concentrated and purified by normal phase column chromatography, followed by crystallization in MeOH providing the title compound (S)-3-(1-hydroxypropan-2-yl)-8-(1H-imidazol-1-yl)-6-(6-(trifluoromethyl)pyridin-3-yl)pyrido[3,4-d]pyrimidin-4(3H)-one (163, 52 mg, 45% yield). $^1$H-NMR ($CH_3OH$-$d_4$, 300 MHz): $\delta_H$ 0.08 (3H, d, J=7.1 Hz), 2.47-2.38 (2H, m), 3.53 (1H, s), 5.69 (1H, s), 6.48 (1H, d, J=8.3 Hz), 6.91 (1H, s), 7.08 (1H, s), 7.20 (1H, s), 7.34 (1H, d, J=8.4 Hz), 7.70 (1H, s), 8.03 (1H, s). MS (m/z): 416.9 [M+H], Purity: 99%.

Table 23 lists compounds that were synthesized according to the synthetic procedure reported for 163, replacing the reactant in step 2.

TABLE 23

| Compound No. | Reactant replacement for step 2 | Compound Structure/Name | $^1$H-NMR | MS (m/z) $[M + H]^+$; Purity (%) |
|---|---|---|---|---|
| 164 | 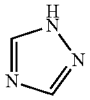 | 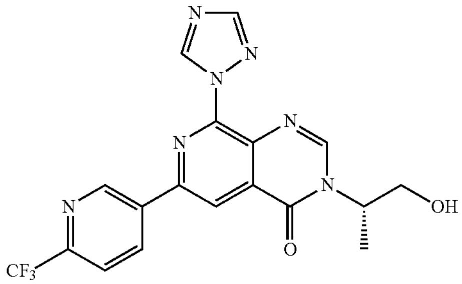 [SMILES: C[C@@H](CO)n1cnc2c(-n3cncn3)nc(-c3ccc(C(F)(F)F)nc3)cc2c1=O] (S)-3-(1-hydroxypropan-2-yl)-8-(1H-1,2,4-triazol-1-yl)-6-(6-(trifluoromethyl)pyridin-3-yl)pyrido[3,4-d]pyrimidin-4(3H)-one | (DMSO-$d_6$, 400 MHz): $\delta_H$ 0.81 (3H, d, J = 7.0 Hz), 3.09-3.05 (1H, m), 3.19-3.14 (1H, m), 4.31-4.26 (1H, m), 4.48 (1H, t, J = 5.5 Hz), 7.47-7.44 (1H, m), 7.75-7.74 (1H, m), 8.03 (1H, s), 8.27-8.25 (2H, m), 8.81-8.80 (1H, m), 8.97 (1H, s). | 418.1; 98% |
| 165 | 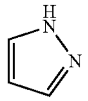 | 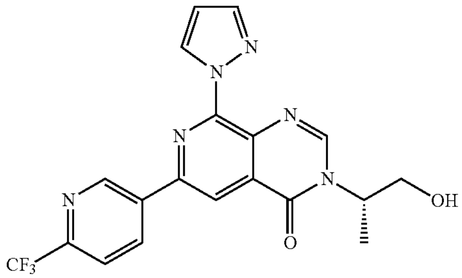 [SMILES: C[C@@H](CO)n1cnc2c(-n3cccn3)nc(-c3ccc(C(F)(F)F)nc3)cc2c1=O] (S)-3-(1-hydroxypropan-2-yl)-8-(1H-pyrazol-1-yl)-6-(6-(trifluoromethyl)pyridin-3-yl)pyrido[3,4-d]pyrimidin-4(3H)-one | $^1$H NMR (DMSO-$d_6$, 400 MHz): $\delta_H$ 1.44 (3H, d, J = 7.0 Hz), 3.68 (1H, d, J = 10.2 Hz), 3.80 (1H, s), 5.10 (1H, d, J = 5.9 Hz), 5.81 (1H, d, J = 5.9 Hz), 6.63 (1H, s), 7.90 (1H, s), 8.07 (1H, d, J = 8.3 Hz), 8.61 (1H, s), 8.75 (2H, d, J = 12.6 Hz), 8.87 (1H, d, J = 8.3 Hz), 9.59 (1H, s). | 417.1, 98% |
| 166 | 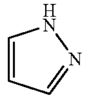 | 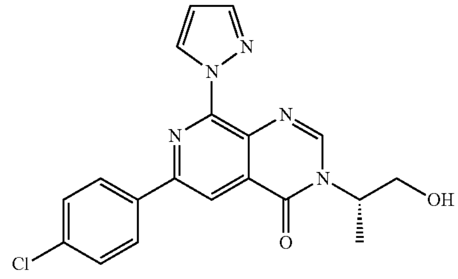 [SMILES: C[C@@H](CO)n1cnc2c(-n3cccn3)nc(-c3ccc(Cl)cc3)cc2c1=O] (S)-6-(4-chlorophenyl)-3-(1-hydroxypropan-2-yl)-8-(1H-pyrazol-1-yl)pyrido[3,4-d]pyrimidin-4(3H)-one | $^1$H NMR ($CH_3OH$-$d_4$, 400 MHz): $\delta_H$ 1.55 (3H, d, J = 7.1 Hz), 3.85 (1H, dd, J = 11.9, 4.2 Hz), 3.96 (1H, dd, J = 11.9, 6.9 Hz), 5.01-4.96 (1H, m), 6.63 (1H, s), 7.53 (2H, d, J = 8.3 Hz), 7.91 (1H, s), 8.25 (2H, d, J = 8.3 Hz), 8.44 (1H, s), 8.57 (1H, s), 8.86 (1H, s). | 382.1; 99% |
| 167 | 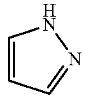 | 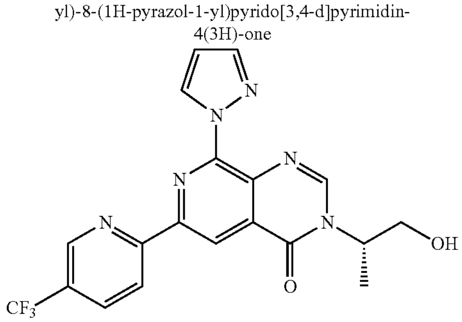 (S)-3-(1-hydroxypropan-2-yl)-8-(1H-pyrazol-1-yl)-6-(5-(trifluoromethyl)pyridin-2-yl)pyrido[3,4-d]pyrimidin-4(3H)-one | $^1$H NMR (DMSO-$d_6$, 400 MHz): $\delta_H$ 1.43 (3H, d, J = 7.0 Hz), 3.68 (1H, s), 3.78 (1H, s), 4.90 (1H, s), 5.10 (1H, s), 6.63 (1H, s), 7.90 (1H, s), 8.42 (1H, d, J = 8.4 Hz), 8.61 (2H, d, J = 11.1 Hz), 8.74 (1H, s), 9.04 (1H, s), 9.16 (1H, s). | 417.1; 99% |

Preparation of (S)-3-(1-hydroxypropan-2-yl)-8-(1-methyl-1H-pyrazol-4-yl)-6-(2-(trifluoromethyl)thiazol-5-yl)pyrido[3,4-d]pyrimidin-4(3H)-one (168)

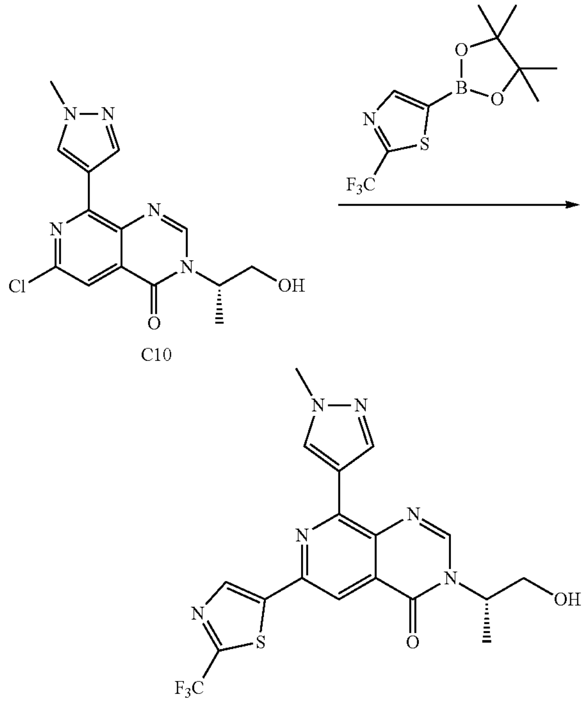

C10

(S)-6-Chloro-3-(1-hydroxypropan-2-yl)-8-(1-methyl-1H-pyrazol-4-yl)pyrido[3,4-d]pyrimidin-4(3H)-one (C10, 100 mg, 0.313 mmol) and 5-(4,4,5,5-tetramethyl-1,3,2-dioxaborolan-2-yl)-2-(trifluoromethyl)thiazole (96.0 mg, 0.344 mmol) were dissolved in dioxane. $Pd(OAc)_2$ (7.02 mg, 0.031 mmol), triphenylphosphine (16.4 mg, 0.063 mmol) and $K_3PO_4$ (266 mg, 1.25 mmol) were added to the solution. The suspension was degassed and refilled with argon (3 cycles). The reaction mixture was heated to 90° C. and stirred for 16 hours. The reaction mixture was extracted with ethyl acetate and washed with water and brine. The combined organic layers were dried over anhydrous magnesium sulfate, concentrated and purified by silica gel column chromatography to afford (S)-3-(1-hydroxypropan-2-yl)-8-(1-methyl-1H-pyrazol-4-yl)-6-(2-(trifluoromethyl)thiazol-5-yl)pyrido[3,4-d]pyrimidin-4(3H)-one (168, 28 mg, 20% yield). $^1$H NMR (DMSO-$d_6$, 400 MHz): δ 1.45 (3H, d, J=7.0 Hz), 3.71-3.66 (1H, m), 3.82-3.77 (1H, m), 3.97 (3H, s), 4.92-4.87 (1H, m), 5.10 (1H, t, J=5.4 Hz), 8.45 (1H, s), 8.51 (1H, s), 8.58 (1H, s), 8.77 (1H, s), 9.03 (1H, s). MS (m/z): 437.1 $[M+H]^+$; 98% purity.

Table 24 lists compounds that were synthesized according to the synthetic Scheme V wherein step is performed according to the procedure reported for 168.

TABLE 24

| Compound No. | Reactant 6 replacement | Reactant 7 replacement | Compound Structure/Name | $^1$H-NMR | MS $[m/z]^+$; Purity (%) |
|---|---|---|---|---|---|
| 169 | 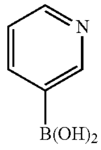 | 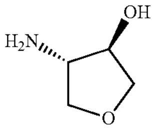 | 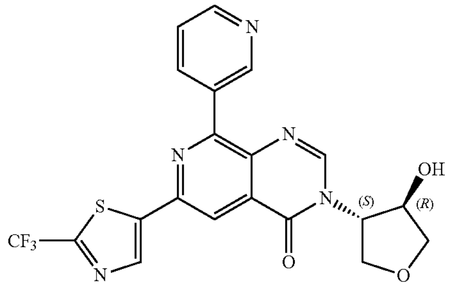 3-((3S,4R)-4-hydroxytetrahydrofuran-3-yl)-8-(pyridin-3-yl)-6-(2-(trifluoromethyl)thiazol-5-yl)pyrido[3,4-d]pyrimidin-4(3H)-one | $^1$H NMR ($CH_3OH$-$d_4$, 400 MHz): $\delta_H$ 3.77 (1H, dd, J = 10.0, 3.1 Hz), 4.31-4.21 (3H, m), 4.61 (1H, s), 5.06 (1H, s), 7.60 (1H, t, J = 6.4 Hz), 8.35 (1H, s), 8.70-8.64 (4H, m), 9.37 (1H, s). | 433.9; 99% |
| 170 | 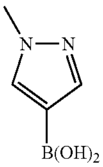 | 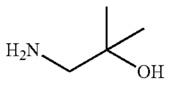 | 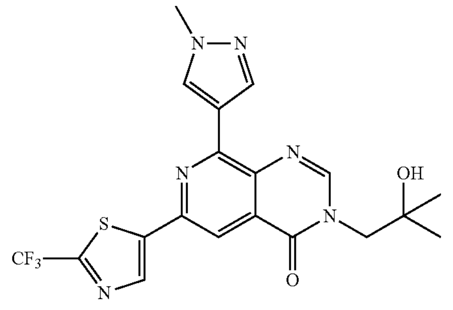 [SMILES: Cn1cc(-c2nc(-c3cnc(C(F)(F)F)s3)cc3c(=O)n(CC(C)(C)O)cnc23)cn1] 3-(2-hydroxy-2-methylpropyl)-8-(1-methyl-1H-pyrazol-4-yl)-6-(2- | $^1$H NMR (DMSO-$d_6$, 400 MHz): $\delta_H$ 1.14 (6H, s), 3.95 (3H, s), 4.03 (2H, s), 4.90 (1H, s), 8.41 (2H, s), 8.50 (1H, s), 8.77 (1H, s), 9.00 (1H, s). | 451.1; 93% |

TABLE 24-continued

| Compound No. | Reactant 6 replacement | Reactant 7 replacement | Compound Structure/Name | $^1$H-NMR | MS [m/z]$^+$; Purity (%) |
|---|---|---|---|---|---|
| | | | (trifluoromethyl)thiazol-5-yl)pyrido[3,4-d]pyrimidin-4(3H)-one | | |
| 171 | 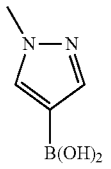 | 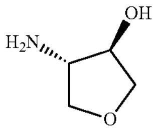 | 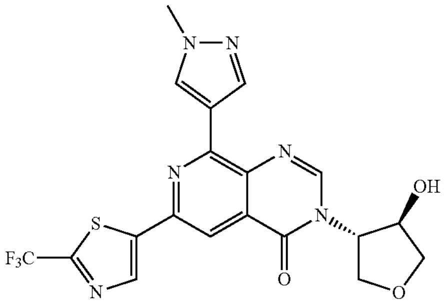 [SMILES: Cn1cc(-c2nc(-c3cnc(C(F)(F)F)s3)cc3c(=O)n([C@H]4COC[C@@H]4O)cnc23)cn1] 3-((3S,4R)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one | (DMSO-$d_6$, 400 MHz): $\delta_H$ 3.63 (1H, dd, J= 9.6, 3.2 Hz), 3.94 (3H, s), 4.21-4.09 (3H, m), 4.56 (1H, s), 4.97 (1H, s), 5.70 (1H, d, J = 4.3 Hz), 8.38 (2H, d, J = 15.4 Hz), 8.48 (1H, s), 8.74 (1H, s), 9.01 (1H, s). | 465.0; >98% |
| 172 | 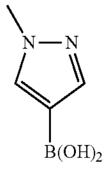 | 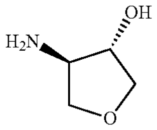 | 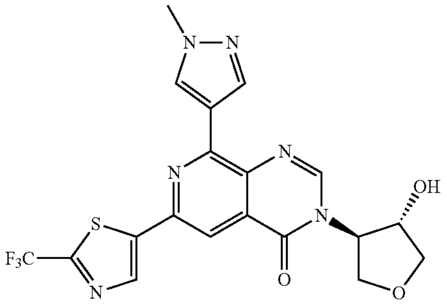 [SMILES: Cn1cc(-c2nc(-c3cnc(C(F)(F)F)s3)cc3c(=O)n([C@@H]4COC[C@H]4O)cnc23)cn1] 3-((3R,4S)-4-hydroxytetrahydrofuran-3-yl)-8-(1-methyl-1H-pyrazol-4-yl)-6-(2-(trifluoromethyl)thiazol-5-yl)pyrido[3,4-d]pyrimidin-4(3H)-one | (DMSO-$d_6$, 400 MHz): $\delta_H$ 3.62 (1H, d, J = 9.7 Hz), 3.95 (3H, s), 4.20-4.11 (3H, m), 4.56 (1H, s), 4.97 (1H, s), 5.71 (1H, d, J = 4.3 Hz), 8.37 (1H, s), 8.42 (1H, s), 8.50 (1H, s), 8.76 (1H, s), 9.02 (1H, s). | 465.1; >99% |
| 173 | 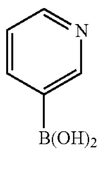 | 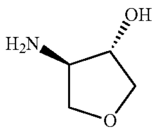 | 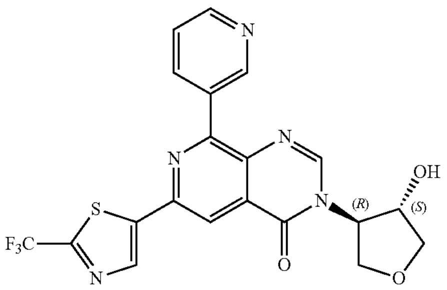 3-((3R,4S)-4-hydroxytetrahydrofuran-3-yl)-8-(pyridin-3-yl)-6-(2-(trifluoromethyl)thiazol-5-yl)pyrido[3,4-d]pyrimidin-4(3H)-one | (DMSO-$d_6$, 400 MHz): 3.61 (1H, dd, J = 9.6, 3.2 Hz), 4.06 (1H, dd, J = 10.1, 4.0 Hz), 4.21-4.12 (2H, m), 4.57 (1H, s), 4.97 (1H, s), 5.71 (1H, d, J = 4.3 Hz), 7.58 (1H, t, J = 6.2 Hz), 8.38 (1H, s), 8.48 (1H, d, J = 8.0 Hz), 8.69 (1H, s), 8.79 (1H, s), 9.11 (1H, s), 9.27 (1H, s). | 462.1; >98% |

The compounds encompassed within the present disclosure can be prepared by the procedure outlined in Scheme V and described in the Examples herein below.

Scheme V

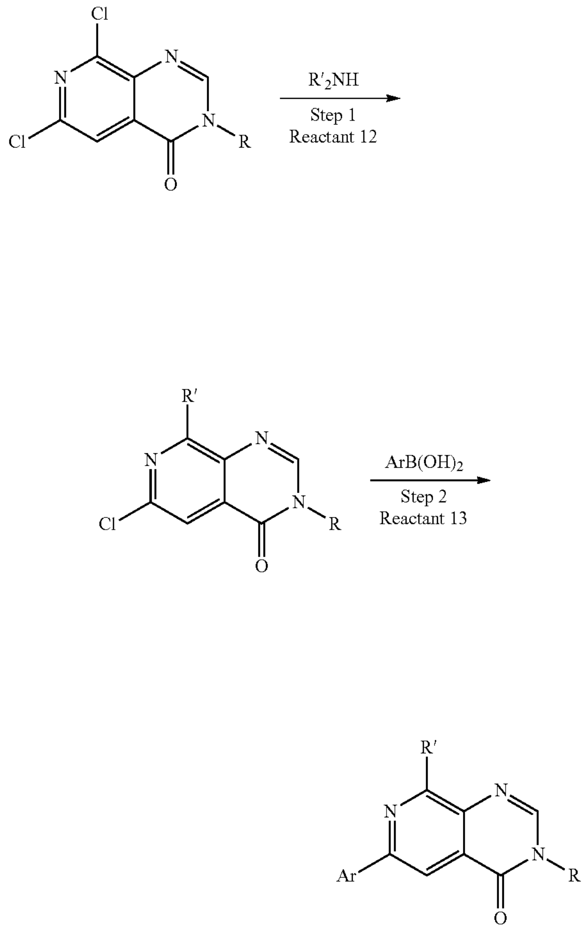

Preparation of (S)-8-(diethylamino)-3-(1-hydroxypropan-2-yl)-6-(6-(trifluoromethyl)pyridin-3-yl)pyrido[3,4-d]pyrimidin-4(3H)-one (174)

Step 1. Preparation of (S)-6-chloro-8-(diethylamino)-3-(1-hydroxypropan-2-yl)pyrido[3,4-d]pyrimidin-4(3H)-one (Intermediate S1)

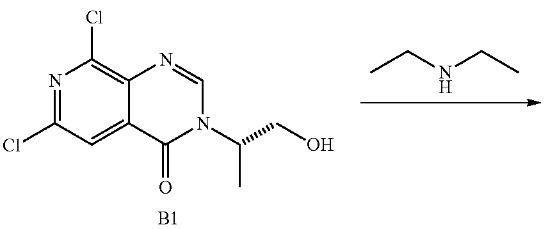

B1

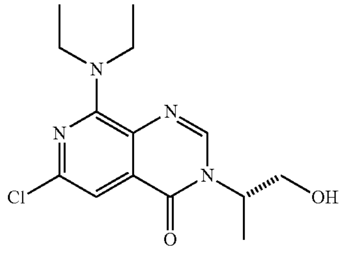

Intermediate S1

Dimethylformamide (2.0 ml) was added to (S)-6,8-Dichloro-3-(1-hydroxypropan-2-yl)pyrido[3,4-d]pyrimidin-4(3H)-one (B1, 0.200 g, 0.73 mmol) and potassium carbonate (0.403 g, 2.92 mmol) in a sealed tube. Diethylamine (0.0586 g, 0.803 mmol) was added and the reaction mixture stirred at 120° C. for 2 hours. The reaction mixture cooled to room temperature, water was added and the mixture was partitioned with ethyl acetate. The organic layer was separated, dried over anhydrous sodium sulphate and concentrated. Purification of the residue by silica gel column chromatography afforded the title compound (S)-6-chloro-8-(diethylamino)-3-(1-hydroxypropan-2-yl)pyrido[3,4-d]pyrimidin-4(3H)-one (Intermediate S1, 0.062 g, 27% yield). $^1$H-NMR (DMSO-$d_6$, 400 MHz): $\delta_H$ 1.21 (6H, t, J=6.9 Hz), 1.37 (3H, d, J=7.1 Hz), 3.64-3.60 (1H, m), 3.83-3.75 (5H, m), 4.82-4.76 (1H, m), 5.04 (1H, t, J=5.5 Hz), 7.03 (1H, s), 8.32 (1H, s); MS (m/z): 311.1 $[M+H]^+$.

Table 25 lists intermediates synthesized according to the step described above.

TABLE 25

| Intermediate Name | Structure and Name | $^1$H-NMR | MS (m/z) $[M + H]^+$; Purity (%) |
|---|---|---|---|
| S2 | 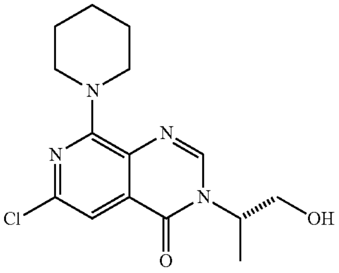 [SMILES: C[C@@H](CO)n1cnc2c(N3CCCCC3)nc(Cl)cc2c1=O] | (DMSO-$d_6$, 400 MHz): δ 1.37 (3H, d, J = 7.0 Hz), 1.64 (6H, br. s), 3.64-3.59 (1H, m), 3.77-3.71 (1H, m), 3.88-3.85 (4H, m), 4.83-4.77 (1H, m), 5.04 (1H, t, J = 5.6 Hz), 7.17 (1H, s), 8.38 (1H, s). | 323.0 |

TABLE 25-continued

| Intermediate Name | Structure and Name | $^1$H-NMR | MS (m/z) [M + H]$^+$; Purity (%) |
|---|---|---|---|
| | (S)-6-chloro-3-(1-hydroxypropan-2-yl)-8-(piperidin-1-yl)pyrido[3,4-d]pyrimidin-4(3H)-one | | |
| S3 | 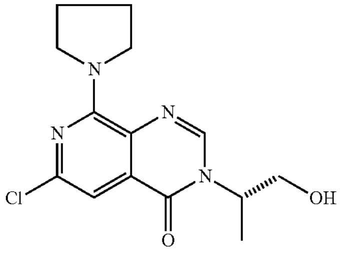 [SMILES: C[C@@H](CO)n1cnc2c(N3CCCC3)nc(Cl)cc2c1=O] (S)-6-chloro-3-(1-hydroxypropan-2-yl)-8-(pyrrolidin-1-yl)pyrido[3,4-d]pyrimidin-4(3H)-one | (DMSO-$d_6$, 400 MHz): δ 1.37 (3H, d, J = 7.0 Hz), 1.91-1.90 (4H, m), 3.64-3.59 (1H, m), 3.84-3.74 (5H, m), 4.83-4.78 (1H, m), 5.04 (1H, t, J = 5.6 Hz), 6.97 (1H, s), 8.31 (1H, s). | 309.1 |
| S4 | 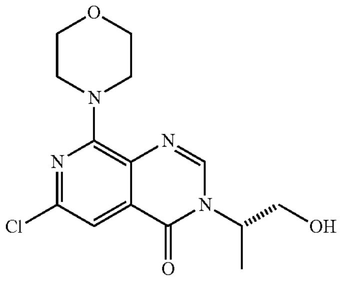 [SMILES: C[C@@H](CO)n1cnc2c(N3CCOCC3)nc(Cl)cc2c1=O] (S)-6-chloro-3-(1-hydroxypropan-2-yl)-8-morpholinopyrido[3,4-d]pyrimidin-4(3H)-one | (DMSO-$d_6$, 400 MHz): δ 1.37 (3H, d, J = 7.0 Hz), 3.64-3.59 (1H, m), 3.75-3.71 (5H, m), 3.90 (4H, t, J = 4.5 Hz), 4.83-4.78 (1H, m), 5.04 (1H, t, J = 5.6 Hz), 7.27 (1H, s), 8.41 (1H, s). | 325.1 |
| S5 | 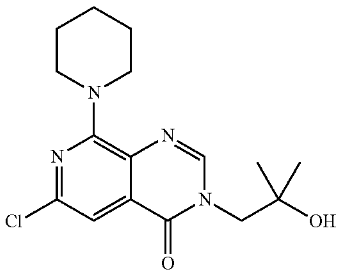 [SMILES: CC(C)(O)Cn1cnc2c(N3CCCCC3)nc(Cl)cc2c1=O] 6-chloro-3-(2-hydroxy-2-methylpropyl)-8-(piperidin-1-yl)pyrido[3,4-d]pyrimidin-4(3H)-one | (DMSO-$d_6$, 400 MHz): δ 1.10 (6H, s), 1.64 (6H, s), 3.86 (4H, s), 3.94 (2H, s), 4.84 (1H, s), 7.18 (1H, s), 8.20 (1H, s). | 337.1 |

Step 2. Preparation of (S)-8-(diethylamino)-3-(1-hydroxypropan-2-yl)-6-(6-(trifluoromethyl)pyridin-3-yl) pyrido[3,4-d]pyrimidin-4(3H)-one (174)

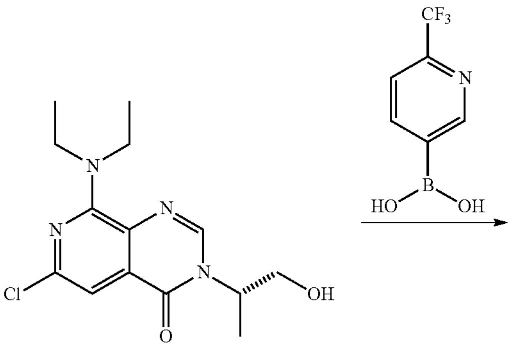

Intermediate S1

-continued

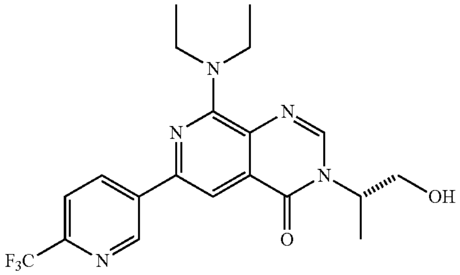

148

The above step to prepare 174 was performed according to the procedure reported for the last step 1.

Table 26 lists compounds that were synthesized according to the synthetic procedure reported for 174, replacing the reactants for step 1 and step 2.

TABLE 26

| Compound No. | Step 1 Reactant replacement | Step 2 Reactant replacement | Compound Structure/Name | $^1$H-NMR | MS (m/z) $[M + H]^+$; Purity (%) |
|---|---|---|---|---|---|
| 175 | 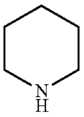 | 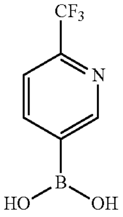 | 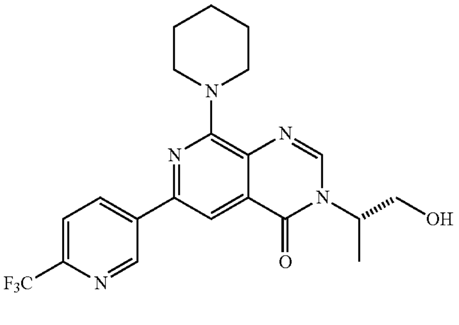 (S)-3-(1-hydroxypropan-2-yl)-8-(piperidin-1-yl)-6-(6-(trifluoromethyl)pyridin-3-yl)pyrido[3,4-d]pyrimidin-4(3H)-one | (DMSO-$d_6$, 400 MHz): δ 1.41 (3H, d, J = 7.0 Hz), 1.69 (6H, s), 3.65 (1H, dd, J = 11.6, 5.2 Hz), 3.78 (1H, dd, J = 11.9, 6.8 Hz), 3.93 (4H, s), 4.89-4.84 (1H, m), 5.05 (1H, t, J = 5.6 Hz), 8.01-7.98 (2H, m), 8.46 (1H, s), 8.74 (1H, d, J = 8.3 Hz), 9.47 (1H, s). | 434.1; 98 |
| 176 | 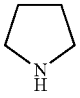 | 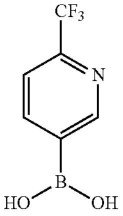 | 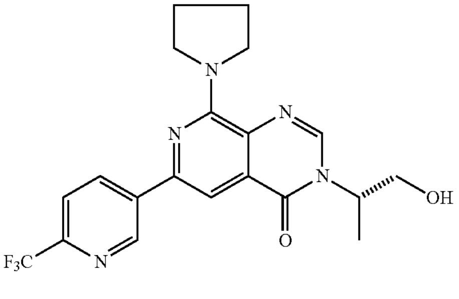 (S)-3-(1-hydroxypropan-2-yl)-8-(pyrrolidin-1-yl)-6-(6-(trifluoromethyl)pyridin-3-yl)pyrido[3,4-d]pyrimidin-4(3H)-one | (DMSO-$d_6$, 400 MHz): δ 1.41 (3H, d, J = 7.0 Hz), 1.96-1.93 (4H, m), 3.69-3.64 (1H, m), 3.83-3.77 (1H, m), 3.98-3.95 (4H, m), 4.91-4.83 (1H, m), 5.06 (1H, t, J = 5.5 Hz), 7.82 (1H, s), 7.98 (1H, d, J = 8.2 Hz), 8.38 (1H, s), 8.74 (1H, d, J = 8.3 Hz), 9.48 (1H, s). | 420.1; 98 |

TABLE 26-continued

| Compound No. | Step 1 Reactant replacement | Step 2 Reactant replacement | Compound Structure/Name | $^1$H-NMR | MS (m/z) $[M + H]^+$; Purity (%) |
|---|---|---|---|---|---|
| 177 | 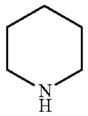 | 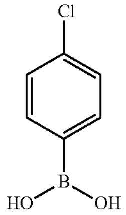 | 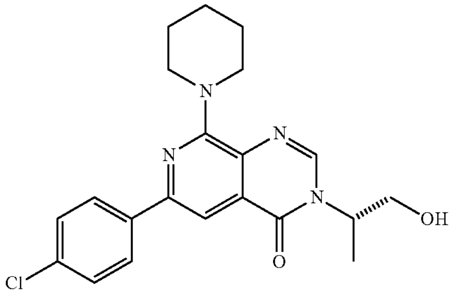 [SMILES: C[C@@H](CO)n1cnc2c(N3CCCCC3)nc(-c3ccc(Cl)cc3)cc2c1=O] (S)-6-(4-chlorophenyl)-3-(1-hydroxypropan-2-yl)-8-(piperidin-1-yl)pyrido[3,4-d]pyrimidin-4(3H)-one | (DMSO-$d_6$, 400 MHz): δ 1.40 (3H, d, J = 7.0 Hz), 1.68 (6H, s), 3.68-3.64 (1H, m), 3.81-3.75 (1H, m), 3.89 (4H, s), 4.89-4.84 (1H, m), 5.05 (1H, t, J = 5.6 Hz), 7.55-7.53 (2H, m), 7.83 (1H, s), 8.15 (2H, d, J = 8.4 Hz), 8.41 (1H, s). | 399.0; 98 |
| 178 | 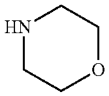 | 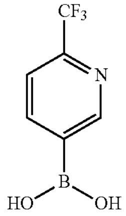 | 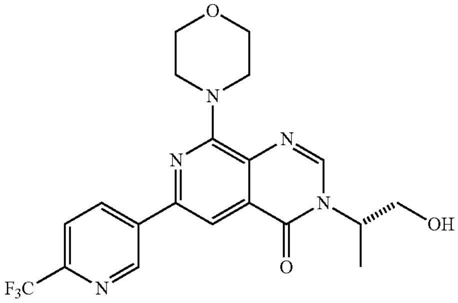 [SMILES: C[C@@H](CO)n1cnc2c(N3CCOCC3)nc(-c3ccc(C(F)(F)F)nc3)cc2c1=O] (S)-3-(1-hydroxypropan-2-yl)-8-morpholino-6-(6-(trifluoromethyl)pyridin-3-yl)pyrido[3,4-d]pyrimidin-4(3H)-one | (DMSO-$d_6$, 400 MHz): δ 1.41 (3H, d, J = 7.0 Hz), 3.68-3.63 (1H, m), 3.81-3.74 (5H, m), 3.95 (4H, d, J = 5.0 Hz), 4.89-4.84 (1H, m), 5.07 (1H, t, J = 5.6 Hz), 8.00 (1H, d, J = 8.3 Hz), 8.10 (1H, s), 8.48 (1H, s), 8.77 (1H, d, J = 8.3 Hz), 9.50 (1H, s). | 436.2; >99 |
| 179 | 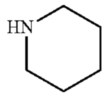 | 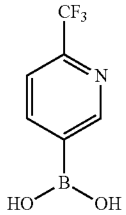 | 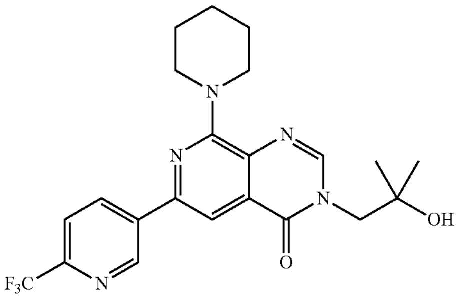 [SMILES: CC(C)(O)Cn1cnc2c(N3CCCCC3)nc(-c3ccc(C(F)(F)F)nc3)cc2c1=O] 3-(2-hydroxy-2-methylpropyl)-8-(piperidin-1-yl)-6-(6-(trifluoromethyl)pyridin-3-yl)pyrido[3,4-d]pyrimidin-4(3H)-one | (DMSO-$d_6$, 400 MHz): δ 1.13 (6H, s), 1.69 (6H, s), 3.92 (4H, s), 4.00 (2H, s), 4.87 (1H, s), 8.03-7.98 (2H, m), 8.29 (1H, s), 8.75 (1H, d, J = 8.2 Hz), 9.48 (1H, s). | 448.2; 99 |

Preparation of (S)-3-(1-hydroxypropan-2-yl)-8-(pyridin-2-yl)-6-(6-(trifluoromethyl)pyridin-3-yl)pyrido[3,4-d]pyrimidin-4(3H)-one (180)

Step 1. Preparation of (S)-6-chloro-3-(1-hydroxy-propan-2-yl)-8-(pyridin-2-yl)pyrido[3,4-d]pyrimidin-4(3H)-one (Precursor 10)

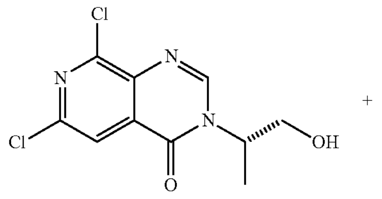

Intermediate B1

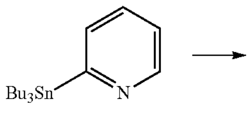

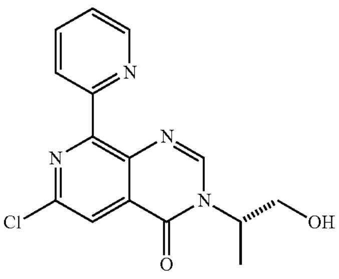

Precursor 10

(S)-6,8-dichloro-3-(1-hydroxypropan-2-yl)pyrido[3,4-d]pyrimidin-4(3H)-one (Intermediate B1, 200 mg, 0.73 mmol) was dissolved in toluene and degassed before addition of $PdCl_2$ (2.62 mg, 0.015 mmol), CsF (0.222 g, 1.46 mmol), CuI (0.056 g, 0.292 mmol), tri-tertiarybutyl phosphine (0.292 μl, 0.292 mmol, 1.0 M in THF) and 2-(tributylstannyl)pyridine (0.348 mg, 0.803 mmol). The solution was degassed again and stirred at 50° C. overnight. The reaction mixture was diluted with EtOAc, washed with water, brine and then dried over anhydrous sodium sulfate. Solvents were removed under vacuum and the residue was purified by silica gel column chromatography ($CH_2Cl_2$/MeOH) to afforded (S)-6-chloro-3-(1-hydroxypropan-2-yl)-8-(pyridin-2-yl)pyrido[3,4-d]pyrimidin-4(3H)-one (Precursor 10, 55.6 mg, 24% yield). $^1$H-NMR ($CHCl_3$-d, 400 MHz): $\delta_H$ 1.34 (3H, m), 3.92 (2H, t, J=4.4 Hz), 5.07-5.00 (1H, m), 7.41 (1H, dd, J=7.3, 1.9 Hz), 7.89-7.82 (1H, m), 8.03-7.98 (1H, m), 8.19-8.19 (1H, m), 8.34 (1H, t, J=1.6 Hz), 8.90-8.83 (1H, m); MS (m/z): 316.9 $[M+H]^+$.

Step 2. Preparation of (S)-3-(1-hydroxypropan-2-yl)-8-(pyridin-2-yl)-6-(6-(trifluoromethyl)pyridin-3-yl)pyrido[3,4-d]pyrimidin-4(3H)-one (180)

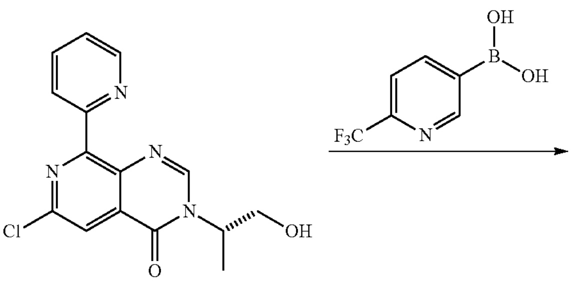

Precursor 10

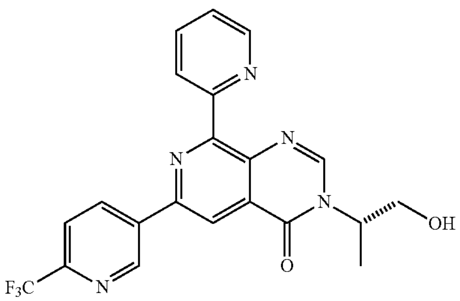

The above step to prepare 180 was performed according to the procedure reported for the last step of 1. $^1$H-NMR (DMSO-$d_6$, 300 MHz): $\delta_H$ 1.44-1.40 (3H, m), 3.79-3.64 (2H, m), 4.91 (1H, s), 5.09-5.04 (1H, m), 7.55-7.50 (1H, m), 7.92-7.89 (1H, m), 7.99-7.95 (1H, m), 8.07-8.02 (1H, m), 8.51 (1H, t, J=0.9 Hz), 8.77-8.74 (1H, m), 8.81 (1H, t, J=0.8 Hz), 8.89-8.85 (1H, m), 9.60-9.58 (1H, m); MS (m/z): 427.9 $[M+H]^+$; 99% purity.

Preparation of (S)-6-cyclohexyl-3-(1-hydroxypropan-2-yl)-8-(pyridin-3-yl)pyrido[3,4-d]pyrimidin-4(3H)-one (181)

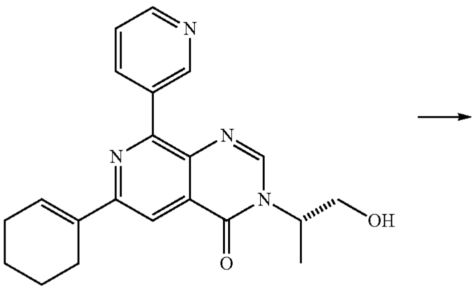

-continued

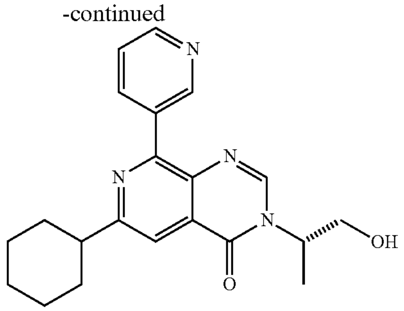

(S)-6-(Cyclohex-1-en-1-yl)-3-(1-hydroxypropan-2-yl)-8-(pyridin-3-yl)pyrido[3,4-d]pyrimidin-4(3H)-one (77, 76.2 mg, 0.210 mmol) and $PtO_2$ (4.77 mg, 0.021 mmol) were dissolved in EtOH (3 ml). The suspension was degassed and refilled with argon and purged with hydrogen gas. The reaction mixture was stirred under hydrogen atmosphere for 3 days at room temperature. The reaction mixture was filtered through Celite and the filtrate was concentrated and purified by silica gel column chromatography to afford (S)-6-cyclohexyl-3-(1-hydroxypropan-2-yl)-8-(pyridin-3-yl)pyrido[3,4-d]pyrimidin-4(3H)-one (181, 46.0 mg, 60% yield). $^1$H-NMR ($CHCl_3$-d, 300 MHz): δ 1.81-1.29 (9H, m), 1.93-1.87 (2H, m), 2.06 (2H, d, J=12.5 Hz), 2.95-2.85 (1H, m), 3.98 (2H, d, J=4.6 Hz), 5.06-4.97 (1H, m), 7.38 (1H, dd, J=7.8, 4.7 Hz), 7.91 (1H, s), 8.22 (1H, s), 8.41 (1H, d, J=8.0 Hz), 8.61 (1H, s), 9.34 (1H, s); MS (m/z): 365.0 [M+H]$^+$; 99% purity.

Preparation of (S)-3-(1-hydroxypropan-2-yl)-6-(pyridin-2-yl)-8-(pyridin-3-yl)pyrido[3,4-d]pyrimidin-4(3H)-one (182)

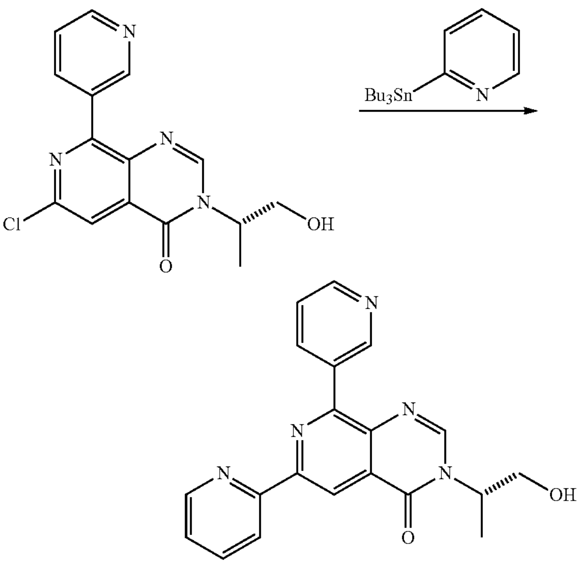

The above step was performed according to the procedure reported for the step 1 for the synthesis of 180 to afford (S)-3-(1-hydroxypropan-2-yl)-6-(pyridin-2-yl)-8-(pyridin-3-yl)pyrido[3,4-d]pyrimidin-4(3H)-one (182). $^1$H-NMR (DMSO-$d_6$, 300 MHz): $\delta_H$ 1.43 (3H, d, J=7.0 Hz), 3.84-3.64 (2H, m), 4.91 (1H, m), 5.07 (1H, t, J=5.6 Hz), 7.50 (1H, ddd, J=7.4, 4.8, 1.2 Hz), 7.59 (1H, dd, J=7.9, 4.8 Hz), 8.00 (1H, td, J=7.8, 1.7 Hz), 8.60-8.54 (3H, m), 8.69 (1H, dd, J=4.8, 1.7 Hz), 8.77-8.75 (1H, m), 9.02 (1H, s), 9.36 (1H, s); MS (m/z): 360.0 [M+H]$^+$; 99% purity.

Table 27 lists compounds that were synthesized according to the synthetic procedure reported for 180.

TABLE 27

| Compound No. | Reactant replacement | Compound Structure/Name | $^1$H-NMR | MS (m/z) [M + H]$^+$; Purity (%) |
|---|---|---|---|---|
| 183 | 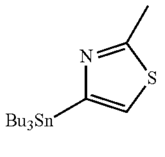 | 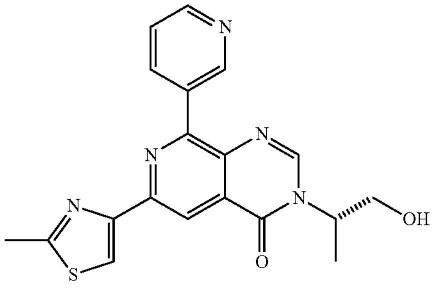 [SMILES: Cc1nc(-c2cc3c(=O)n([C@@H](C)CO)cnc3c(-c3cccnc3)n2)cs1] (S)-3-(1-hydroxypropan-2-yl)-6-(2-methylthiazol-4-yl)-8-(pyridin-3-yl)pyrido[3,4-d]pyrimidin-4(3H)-one | (DMSO-$d_6$, 400 MHz): δ 1.42 (3H, d, J = 7.0 Hz), 2.79 (3H, s), 3.69-3.64 (1H, m), 3.82-3.76 (1H, m), 4.93-4.87 (1H, m), 5.07 (1H, t, J = 5.6 Hz), 7.57 (1H, dd, J = 7.9, 4.8 Hz), 8.30 (1H, s), 8.56-8.54 (2H, m), 8.62 (1H, s), 8.68 (1H, dd, J = 4.8, 1.7 Hz), 9.33 (1H, d, J = 2.2 Hz). | 379.9; 92 |

Preparation of (S)-3-(1-hydroxypropan-2-yl)-6-(1-methyl-1H-1,2,3-triazol-5-yl)-8-(pyridin-3-yl)pyrido[3,4-d]pyrimidin-4(3H)-one (184)

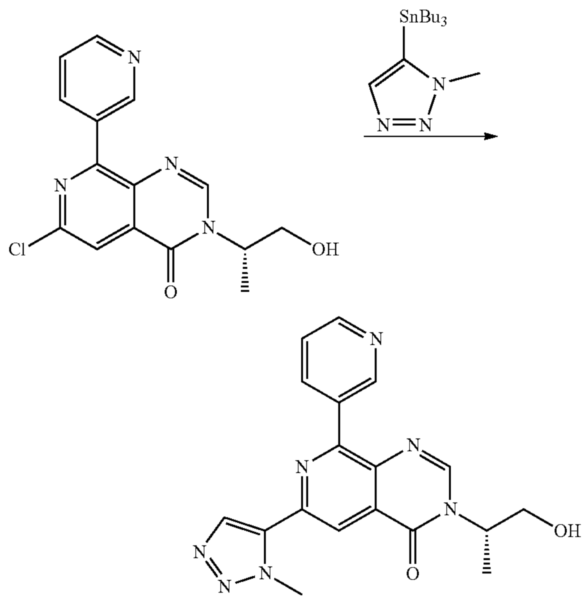

The above step was performed according to the procedure reported for the synthesis of 47 to afford (S)-3-(1-hydroxypropan-2-yl)-6-(1-methyl-1H-1,2,3-triazol-5-yl)-8-(pyridin-3-yl)pyrido[3,4-d]pyrimidin-4(3H)-one (184, 40 mg, 18%). $^1$H-NMR (DMSO-$d_6$, 300 MHz): δ 1.44 (3H, d, J=7.0 Hz), 3.84-3.66 (2H, m), 4.42 (3H, s), 4.90 (1H, td, J=7.1, 4.9 Hz), 5.09-5.06 (1H, m), 7.59 (1H, dd, J=8.0, 4.8 Hz), 8.54-8.50 (2H, m), 8.56 (1H, s), 8.60 (1H, s), 8.70 (1H, dd, J=4.8, 1.6 Hz), 9.31 (1H, d, J=2.1 Hz). MS (m/z): 364.0 [M+H]$^+$; 98% purity.

Preparation of (R)-6-(4-chlorophenyl)-8-(pyridin-3-yl)-3-(3,3,3-trifluoro-2-hydroxypropyl)pyrido[3,4-d]pyrimidin-4(3H)-one (185 enantiomer 1) and (S)-6-(4-chlorophenyl)-8-(pyridin-3-yl)-3-(3,3,3-trifluoro-2-hydroxypropyl)pyrido[3,4-d]pyrimidin-4(3H)-one (185 enantiomer 2)

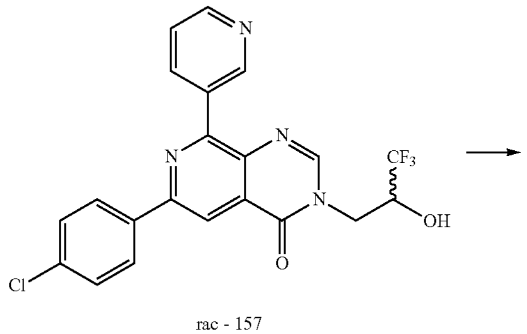

rac - 157

-continued

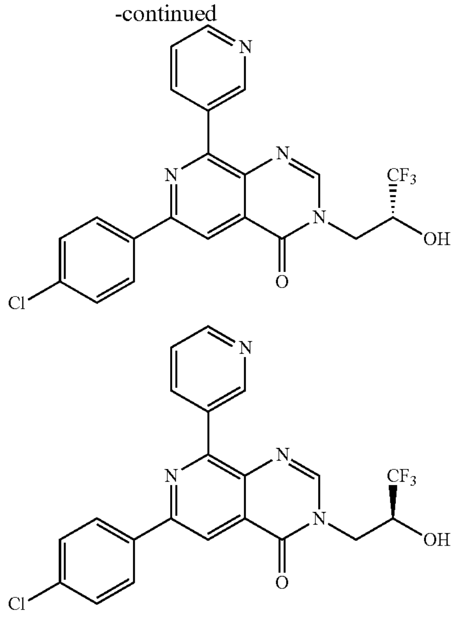

157 - enantiomer 1 and 157 enantiomer 2

Racemic 6-(4-chlorophenyl)-8-(pyridin-3-yl)-3-(3,3,3-trifluoro-2-hydroxypropyl)pyrido[3,4-d]pyrimidin-4(3H)-one (rac-185, 20 mg, 0.045 mmol) was purified by SFC to provide titled compounds. (R)-6-(4-chlorophenyl)-8-(pyridin-3-yl)-3-(3,3,3-trifluoro-2-hydroxypropyl)pyrido[3,4-d]pyrimidin-4(3H)-one (6.9 mg, 35% yield). $^1$H-NMR ($CH_3OH$-$d_4$, 400 MHz): $\delta_H$ 3.98 (1H, dd, J=13.7, 9.6 Hz), 4.45-4.41 (1H, m), 4.62 (1H, dd, J=13.8, 3.0 Hz), 7.53 (2H, d, J=8.4 Hz), 7.60 (1H, dd, J=7.9, 4.9 Hz), 8.23 (2H, d, J=8.4 Hz), 8.33 (1H, s), 8.58 (1H, s), 8.64-8.62 (1H, m), 8.70 (1H, d, J=8.0 Hz), 9.38 (1H, t, J=2.6 Hz). MS (m/z): 446.9 [M+H]. Purity: 99%. (S)-6-(4-chlorophenyl)-8-(pyridin-3-yl)-3-(3,3,3-trifluoro-2-hydroxypropyl)pyrido[3,4-d]pyrimidin-4(3H)-one (6.4 mg, 32% yield). $^1$H-NMR ($CH_3OH$-$d_4$, 400 MHz): $\delta_H$ 3.99 (1H, dd, J=13.7, 9.7 Hz), 4.46-4.41 (1H, m), 4.62 (1H, dd, J=13.6, 2.8 Hz), 7.54 (2H, d, J=8.4 Hz), 7.61 (1H, dd, J=8.0, 4.9 Hz), 8.24 (2H, d, J=8.4 Hz), 8.33 (1H, s), 8.60 (1H, s), 8.64-8.62 (1H, m), 8.72-8.70 (1H, m), 9.39 (1H, d, J=2.5 Hz). MS (m/z): 446.9 [M+H]. Purity: 99%.

Preparation of (S)-3-(1-hydroxypropan-2-yl)-6-(5-methylpyridin-2-yl)-8-(pyridin-3-yl)pyrido[3,4-d]pyrimidin-4(3H)-one (186)

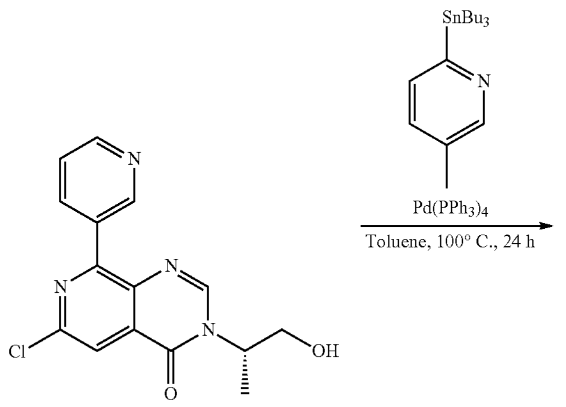

-continued

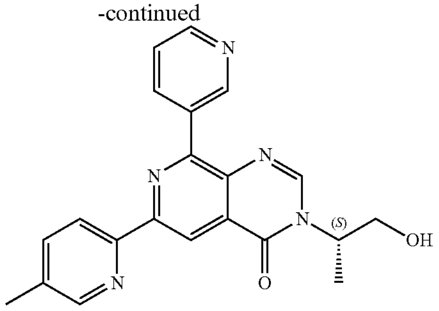

(S)-6-chloro-3-(1-hydroxypropan-2-yl)-8-(pyridin-3-yl)pyrido[3,4-d]pyrimidin-4(3H)-one (100 mg, 1 eq) and 5-Methyl-2-(tributylstannyl)pyridine (145 mg, 0.131 mL, 1.2 eq) was dissolved in Toluene (3 mL). The suspension was degassed and refilled with argon (3 cycles). Tetrakis (triphenylphosphine)palladium (73 mg, 0.2 eq) was added and the suspension was degassed and refilled with argon again (3 cycles). The reaction mixture was heated to 100° C. under argon and was monitored by LC-MS. After 24 hours to the reaction KF and water/MeOH were added and stirred overnight. The reaction mixture was filtered through celite and the filtrate was concentrated and purified by Combi-Flash using DCM/MeOH, from 0 to 10% MeOH over 25 min. Product obtained (100 mg, 84% yield) further purified by reverse phase chromatography to afford (S)-3-(1-hydroxypropan-2-yl)-6-(5-methylpyridin-2-yl)-8-(pyridin-3-yl)pyrido[3,4-d]pyrimidin-4(3H)-one (186) as a white solid. $^1$H NMR (DMSO-$d_6$, 400 MHz): $\delta_H$ 1.42 (3H, d, J=7.0 Hz), 2.38 (3H, s), 3.67-3.64 (1H, m), 3.77 (1H, t, J=7.5 Hz), 4.90 (1H, d, J=7.9 Hz), 5.07 (1H, t, J=5.6 Hz), 7.58 (1H, dd, J=7.9, 4.9 Hz), 7.81 (1H, d, J=8.1 Hz), 8.44 (1H, d, J=8.1 Hz), 8.55 (2H, t, J=3.9 Hz), 8.59 (1H, s), 8.68 (1H, d, J=4.7 Hz), 8.97 (1H, s), 9.34 (1H, s). MS (m/z): 374.1 [M+H]. Purity: >99%.

Table 28 lists compounds that were synthesized according to the synthetic procedure reported for 186.

TABLE 28

| Compound No. | Reactant replacement | Compound Structure/Name | $^1$H-NMR | MS (m/z) [M + H]$^+$; Purity (%) |
|---|---|---|---|---|
| 187 | 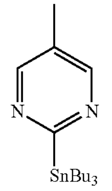 | 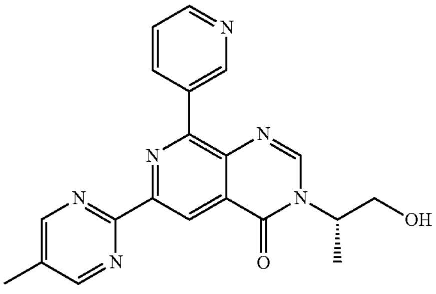 [SMILES: Cc1cnc(-c2cc3c(=O)n([C@@H](C)CO)cnc3c(-c3cccnc3)n2)nc1] (S)-3-(1-hydroxypropan-2-yl)-6-(5-methylpyrimidin-2-yl)-8-(pyridin-3-yl)pyrido[3,4-d]pyrimidin-4(3H)-one | $^1$H NMR (DMSO-$d_6$, 400 MHz): $\delta_H$ 1.42 (3H, d, J = 7.0 Hz), 2.36 (3H, s), 3.69-3.67 (1H, m), 3.80-3.76 (1H, m), 4.90 (1H, s), 7.60 (1H, t, J = 6.0 Hz), 8.50 (1H, d, J = 7.7 Hz), 8.60 (1H, s), 8.69 (1H, d, J = 4.6 Hz), 8.87 (2H, s), 9.02 (1H, s), 9.29 (1H, s). | 375.1; >99% |

Preparation of (S)-8-cyclohexyl-3-(1-hydroxypropan-2-yl)-6-(5-(trifluoromethyl)pyridin-2-yl)pyrido[3,4-d]pyrimidin-4(3H)-one (189)

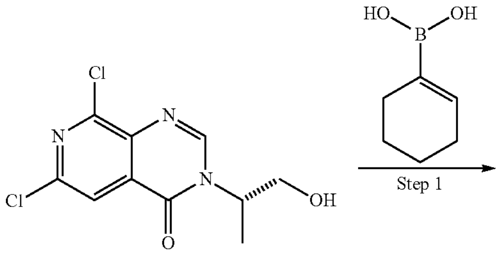

-continued

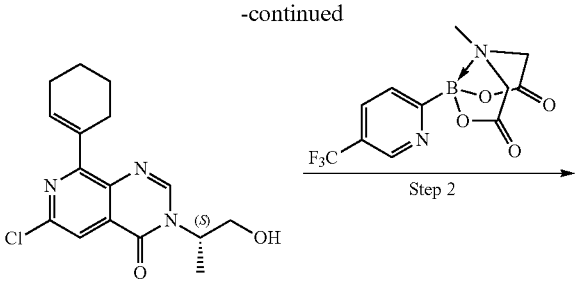

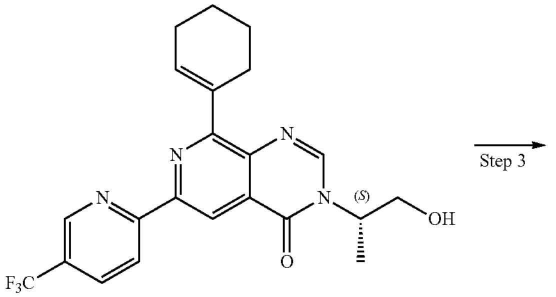

188

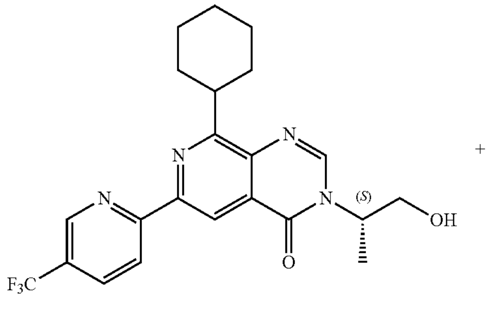

189

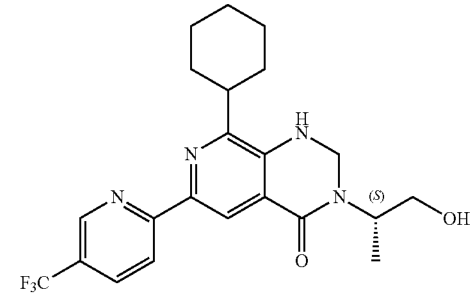

Step 1. Preparation of (S)-6-chloro-8-(cyclohex-1-en-1-yl)-3-(1-hydroxypropan-2-yl)pyrido[3,4-d]pyrimidin-4(3H)-one

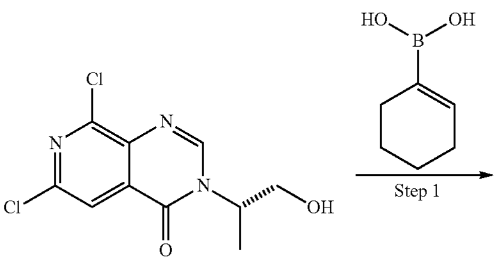

-continued

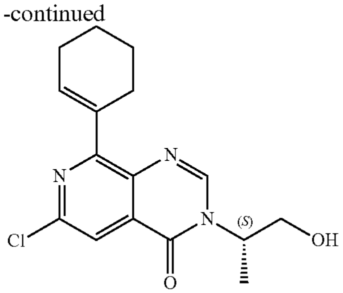

(S)-6,8-dichloro-3-(1-hydroxypropan-2-yl)pyrido[3,4-d]pyrimidin-4(3H)-one (Intermediate B1 200 mg, 0.73 mmol) and cyclohex-1-en-1-ylboronic acid (101 mg, 0.80 mmol) were dissolved in toluene-EtOH (3:1, 7 mL), and sodium carbonate (309 mg, 2.9 mmol) was added. The suspension was degassed and refilled with argon (3 cycles). Tetrakis (triphenylphosphine)palladium (84 mg, 0.07 mmol) was added and the suspension was degassed and refilled with argon again (3 cycles). The reaction mixture was heated to 75° C. under argon and was monitored by LC-MS. After reaction overnight, the reaction mixture was cooled down, diluted with EtOAc, filtered through celite and the filtrate was washed with water, brine, dried over sodium sulfate. The residue was purified by silica column to give the titled compound. (130 mg, 56% yield). 1H NMR (DMSO-d6, 400 MHz): δH 1.37 (3H, d, J=7.0 Hz), 1.68 (4H, d, J=30.1 Hz), 2.25 (2H, s), 3.76-3.60 (2H, m), 4.80 (1H, d, J=7.9 Hz), 5.03 (1H, t, J=5.5 Hz), 6.74 (1H, s), 7.82 (1H, d, J=4.1 Hz), 8.46 (1H, s). MS (m/z): 320.1[M+H]+.

Step 2. Preparation of(S)-8-(cyclohex-1-en-1-yl)-3-(1-hydroxypropan-2-yl)-6-(5-(trifluoromethyl)pyridin-2-yl)pyrido[3,4-d]pyrimidin-4(3H)-one (188)

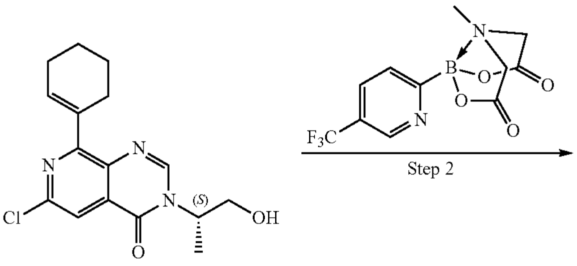

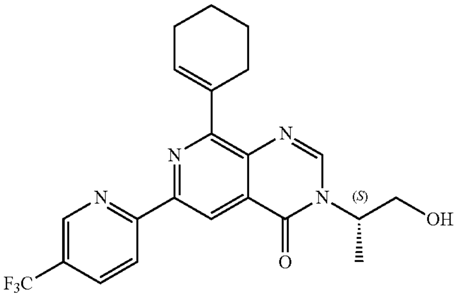

188

Under air to a flame-dried pressure vial equipped with stir bar was added (S)-6-chloro-8-(cyclohex-1-en-1-yl)-3-(1-hydroxypropan-2-yl)pyrido[3,4-d]pyrimidin-4(3H)-one (120 mg, 0.38 mmol), potassium phosphate (399 mg, 1.88 mmol), (2-Dicyclohexylphosphino-2',4',6'-triisopropyl-1,1'-biphenyl)[2-(2-aminoethyl)phenyl)]palladium(II) chloride[Xphos Pd G1](28 mg, 0.38 mmol), and 5-trifluoromethyl-2-pyridylboronic acid MIDA ester (170 mg, 0.56 mmol), diethanolamine (79 mg, 0.75 mmol). 2 mL NMP was added and the vial was degassed before addition of Cu(OAc)2 (68 mg, 0.38 mmol). The vial was heated to 108° C. with stirring for 15 h. The reaction mixture was then cooled down, diluted with EtOAc and filtered through a celite pad. The filtrate was washed with sat. $NaHCO_3$, water, concentrated and purified by normal phase plus reverse phase combi-flash to provide the titled compound. (100 mg, 62% yield). $^1H$ NMR ($CH_3OH$-d4, 400 MHz): δH 1.56 (3H, d, J=7.1 Hz), 1.78 (2H, d, J=7.1 Hz), 1.86 (2H, d, J=7.1 Hz), 2.34 (2H, s), 2.72 (2H, s), 3.84 (1H, dd, J=11.9, 4.1 Hz), 3.96 (1H, dd, J=11.8, 6.7 Hz), 4.96 (1H, d, J=7.8 Hz), 6.73 (1H, s), 8.19 (1H, d, J=8.4 Hz), 8.38 (1H, s), 8.60 (1H, d, J=8.4 Hz), 8.92 (1H, s), 8.95 (1H, s). MS (m/z): 431.2[M+H]+. 98% purity.

Step 3. Preparation of (S)-8-cyclohexyl-3-(1-hydroxypropan-2-yl)-6-(5-(trifluoromethyl)pyridin-2-yl)pyrido[3,4-d]pyrimidin-4(3H)-one (189)

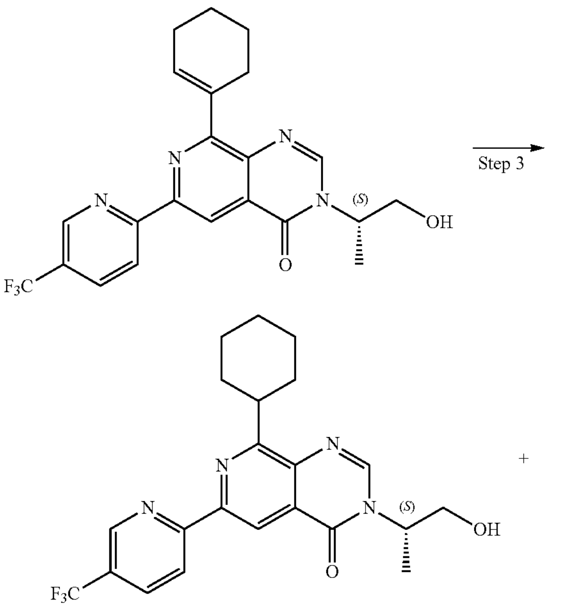

189

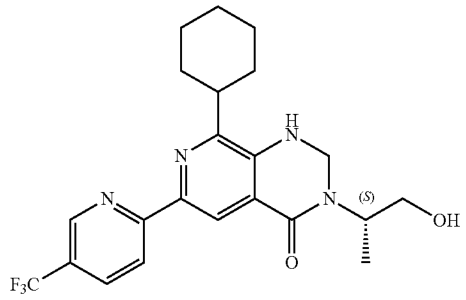

(S)-8-(cyclohex-1-en-1-yl)-3-(1-hydroxypropan-2-yl)-6-(5-(trifluoromethyl)pyridin-2-yl)pyrido[3,4-d]pyrimidin-4(3H)-one (76 mg, 0.18 mmol) and PtO2 (4 mg, 0.018 mmol) was dissolved in 17 mL EtOH. The suspension was degassed and refilled with $H_2$ gas (in a balloon) for 3 cycles. The reaction mixture was stirred under $H_2$ gas (in a balloon) at room temperature and was monitored by LC-MS. The reaction was stopped after 24 h and filtered through celite. The filtrate was concentrated and purified by normal phase and reverse phase combi-flash to provide the titled compounds: (S)-8-cyclohexyl-3-(1-hydroxypropan-2-yl)-6-(5-(trifluoromethyl)pyridin-2-yl)pyrido[3,4-d]pyrimidin-4(3H)-one (189) (18 mg, 24% yield). 1H NMR (DMSO-d6, 400 MHz): δH 1.34 (1H, s), 1.41 (3H, d, J=7.0 Hz), 1.47 (2H, d, J=13.5 Hz), 1.76 (3H, t, J=12.2 Hz), 1.89 (4H, t, J=14.9 Hz), 3.66-3.63 (1H, m), 3.76 (1H, s), 3.84 (1H, s), 4.88 (1H, s), 5.05 (1H, d, J=5.8 Hz), 8.39 (1H, d, J=8.4 Hz), 8.57 (1H, s), 8.66 (1H, d, J=8.4 Hz), 8.87 (1H, s), 9.11 (1H, s). MS (m/z): 433.2[M+H]+; 96% purity; (S)-8-cyclohexyl-3-(1-hydroxypropan-2-yl)-6-(5-(trifluoromethyl)pyridin-2-yl)-2,3-dihydropyrido[3,4-d]pyrimidin-4(1H)-one (22 mg, 29% yield). 1H NMR (DMSO-d6, 400 MHz): δH 1.14 (3H, d, J=6.9 Hz), 1.27 (1H, d, J=15.6 Hz), 1.44 (2H, d, J=14.2 Hz), 1.61 (2H, t, J=12.4 Hz), 1.73 (1H, br s), 1.82 (4H, br s), 2.90 (1H, s), 3.49 (2H, d, J=6.8 Hz), 4.54 (1H, d, J=8.2 Hz), 4.62 (2H, s), 4.85 (1H, d, J=5.8 Hz), 7.11 (1H, s), 8.24 (1H, d, J=8.5 Hz), 8.43 (1H, d, J=8.5 Hz), 8.52 (1H, s), 8.96 (1H, s). MS (m/z): 435.2 [M+H]+; 99% purity.

Preparation of (S)-3-(1-hydroxypropan-2-yl)-N,N-dimethyl-4-oxo-8-(pyridin-3-yl)-3,4-dihydropyrido[3,4-d]pyrimidine-6-carboxamide (190)

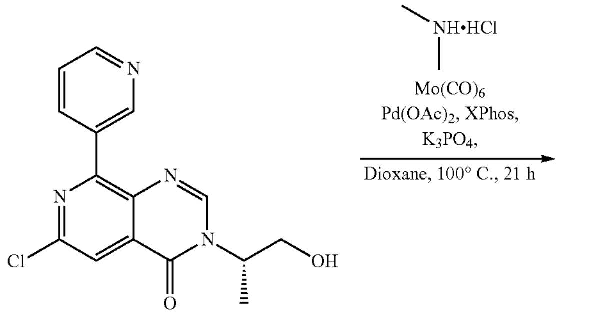

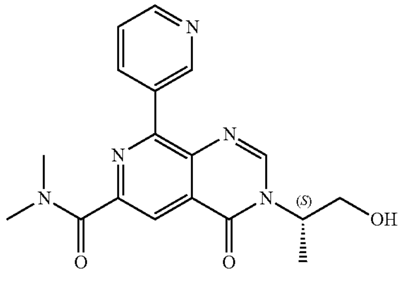

190

To a mixture of (S)-6-chloro-3-(1-hydroxypropan-2-yl)-8-(pyridin-3-yl)pyrido[3,4-d]pyrimidin-4(3H)-one (200 mg, 1 eq), dimethyl amine·HCl (77 mg, 1.5 eq), molybdenumhexacarbonyl (166 mg, 1 eq.) and XPhos (60 mg, 0.2 eq) was added dioxane (6 mL). The suspension was degassed and refilled with nitrogen (3 cycles). Palladium(II) acetate (15 mg, 0.1 eq) and $K_3PO_4$ were added and the suspension was degassed and refilled with nitrogen again (3 cycles). The reaction mixture was heated at 100° C. and was monitored by LC-MS. After overnight, the reaction mixture filtered through celite, wash with EtOAc, MeOH and the filtrate was concentrated. The crude product (190) was first purified by silica gel column chromatography eluting with DCM/MeOH, from 0 to 10% MeOH over 25 min, followed by reverse phase using water/Acetonitrile to give desired product (90 mg, 40%). $^1$H NMR (DMSO-$d_6$, 400 MHz): $\delta_H$ 1.40 (3H, d, J=7.0 Hz), 3.05 (7H, s), 3.66 (1H, s), 3.76 (1H, s), 4.88-4.83 (1H, m), 5.05 (1H, t, J=5.3 Hz), 7.55 (1H, t, J=6.3 Hz), 8.16 (1H, s), 8.41 (1H, d, J=8.0 Hz), 8.58 (1H, s), 8.66 (1H, d, J=4.8 Hz), 9.21 (1H, s). MS (m/z): 488.0 $[M+H]^+$; >99% purity.

Preparation of (S)-3-(1-hydroxypropan-2-yl)-8-(1H-pyrazol-4-yl)-6-(5-(trifluoromethyl)pyridin-2-yl)pyrido[3,4-d]pyrimidin-4(3H)-one (191)

Compound 191 was prepared according to the same procedure as general Scheme IV above and the following protection strategy.

Scheme VI

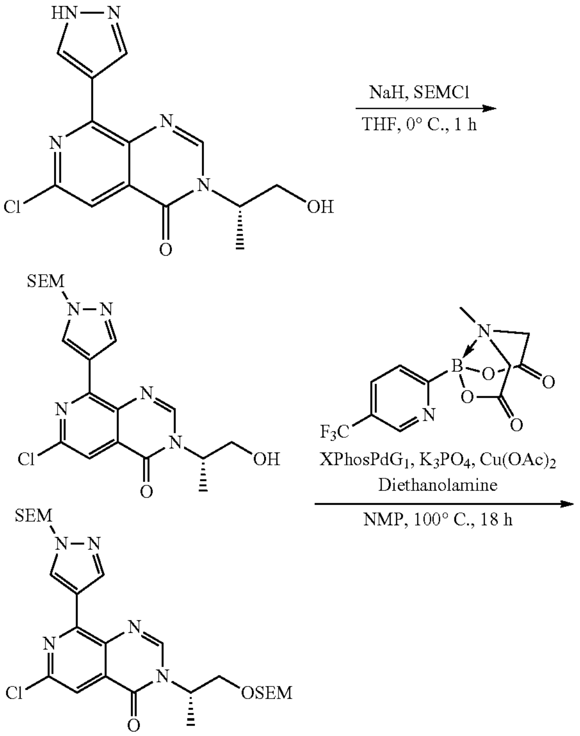

-continued

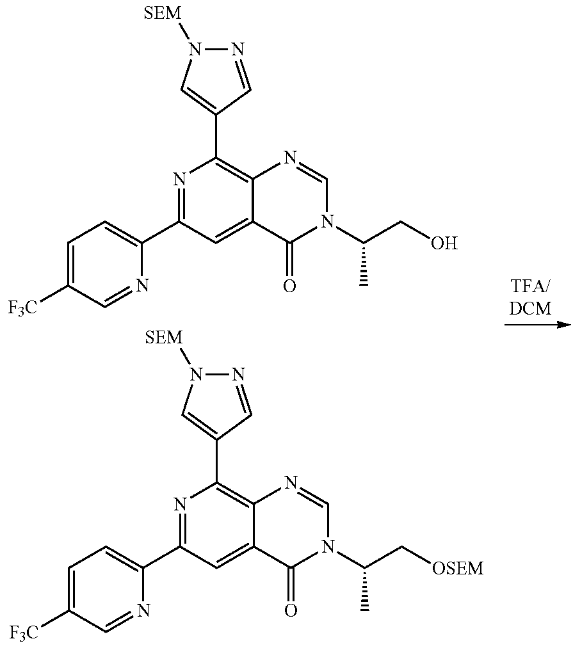

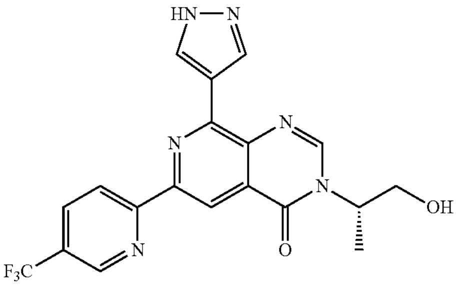

191

Table 29 describes intermediates synthesized via general Scheme VI.

TABLE 29

| Intermediate Name | Structure and Name | $^1$H-NMR | MS $[m/z]^+$; Purity (%) |
|---|---|---|---|
| T1 | 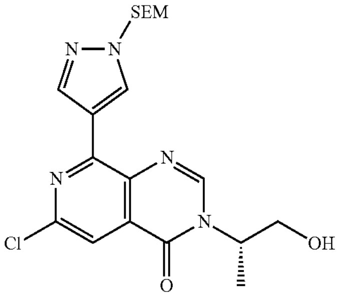<br>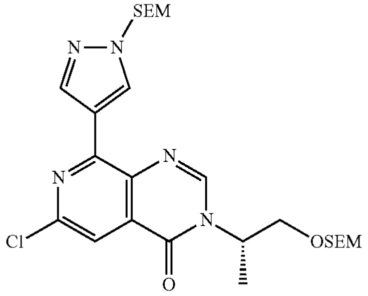 | NA | 436.1; 566.3 |
| T2A & T2B | 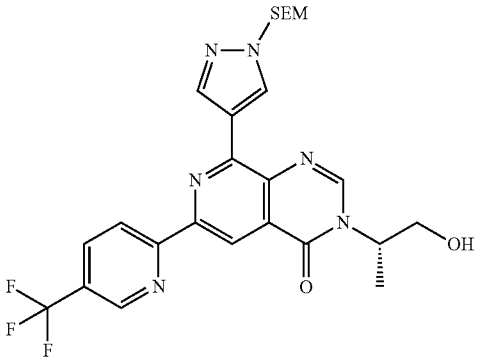 [SMILES: C[C@@H](CO)n1cnc2c(-c3cnn(COCC[Si](C)(C)C)c3)nc(-c3ccc(C(F)(F)F)cn3)cc2c1=O]<br>T2A: (S)-3-(1-hydroxypropan-2-yl)-6-(5-(trifluoromethyl)pyridin-2-yl)-8-(1-((2-(trimethylsilyl)ethoxy)methyl)-1H-pyrazol-4-yl)pyrido[3,4-d]pyrimidin-4(3H)-one | Mono SEM compound (T2A): $^1$H NMR ($CHCl_3$-d, 400 MHz): $\delta_H$ 0.98 (2H, t, J = 8.2 Hz), 3.53 (1H, s), 3.67 (2H, t, J = 8.2 Hz), 4.03-3.97 (1H, m), 4.07 (1H, s), 5.12 (1H, s), 5.53-5.47 (2H, m), 8.01 (1H, d, J = 8.4 Hz), 8.25 (1H, s), 8.31 (1H, s), 8.46 (1H, d, J = 8.3 Hz), 8.70 (1H, s), 8.82 (1H, s), 8.91 (1H, s). | Mono SEM (T2A): 547.2 |
| | 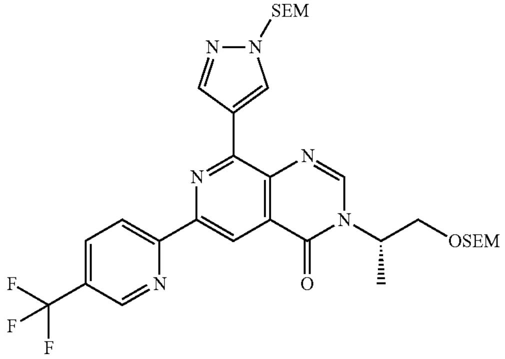<br>T2B: (S)-6-(5- | Bis SEM compound (T2B): $^1$H NMR ($CHCl_3$-d, 400 MHz): $\delta_H$ −0.07 (6H, s), 0.97-0.84 (4H, m), 3.68-3.46 (4H, m), 3.96-3.82 (2H, m), 4.68-4.67 (2H, m), 5.25 (1H, s), 5.55 (2H, s), 8.08 (1H, d, J = 8.4 Hz), 8.38-8.36 (1H, m), 8.63 (1H, s), 8.70 (1H, d, J = 8.4 Hz), 8.88 (1H, s), 8.97 (1H, s), 9.09-9.08 (1H, m). | |

TABLE 29-continued

| Interme-diate Name | Structure and Name | $^1$H-NMR | MS [m/z]$^+$; Purity (%) |
|---|---|---|---|
| | (trifluoromethyl)pyridin-2-yl)-3-(1-((2-(trimethylsilyl)ethoxy)methoxy)propan-2-yl)-8-(1-((2-(trimethylsilyl)ethoxy)methyl)-1H-pyrazol-4-yl)pyrido[3,4-d]pyrimidin-4(3H)-one | | |

Table 30 lists a compound that was synthesized according to the synthetic scheme VI above.

TABLE 30

| Compound No | Compound Structure/Name | $^1$H-NMR | MS (m/z) [M + H]$^+$; Purity (%) |
|---|---|---|---|
| 191 | 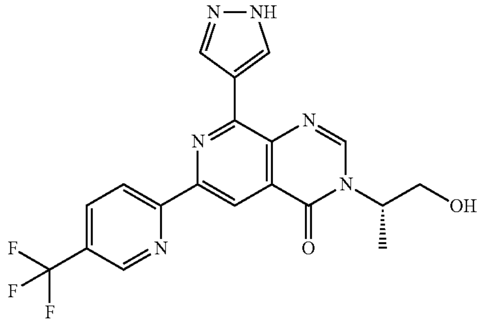 [SMILES: C[C@@H](CO)n1cnc2c(-c3cn[nH]c3)nc(-c3ccc(C(F)(F)F)cn3)cc2c1=O] (S)-3-(1-hydroxypropan-2-yl)-8-(1H-pyrazol-4-yl)-6-(5-(trifluoromethyl)pyridin-2-yl)pyrido[3,4-d]pyrimidin-4(3H)-one | $^1$H NMR (CHCl$_3$-d, 400 MHz): $\delta_H$ 1.44 (3H, d, J = 7.0 Hz), 3.68 (1H, s), 3.79 (1H, s), 4.90 (1H, s), 5.10 (1H, s), 8.37 (1H, d, J = 8.4 Hz), 8.62 (1H, s), 8.85 (3H, t, J = 7.9 Hz), 9.13 (1H, s), 13.24 (1H, s). | 417.1; >99% |

Preparation of (S)-3-(1-hydroxypropan-2-yl)-6-(2-methoxyethyl)-8-(pyridin-3-yl)pyrido[3,4-d]pyrimidin-4(3H)-one (192)

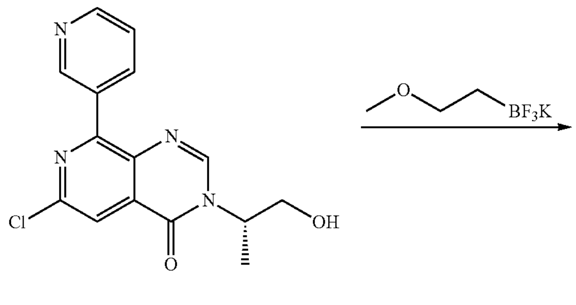

-continued

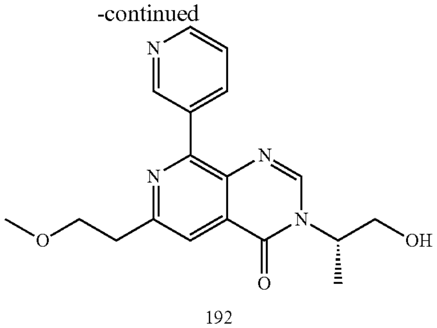

192

In an oven-dried microwave vial were introduced bis(di-tert-butyl(4-dimethylaminophenyl)phosphine)dichloropalladium(II) (5.6 mg, 0.05 mmol), trifluoro(2-methoxyethyl)-λ4-borane, potassium salt (40 mg, 0.24 mmol), Cs2CO3 (154 mg, 0.47 mmol) and (S)-6-chloro-3-(1-hydroxypropan-2-yl)-8-(pyridin-3-yl)pyrido[3,4-d]pyrimidin-4(3H)-one (50 mg, 0.16 mmol). The vial was sealed, degassed and refilled with N$^2$. Degassed dioxane-H2O (4:1, 1 mL) were added by syringe. The reaction mixture was then placed in an oil bath preheated at 100° C. and stirred for 24 h at this temperature. After completion, the reaction mixture was cooled to room temperature, diluted with EtOAc, filtered through a celite pad. The filtrate was washed with water, brine, dried over sodium sulfate, concentrated and purified by normal phase chromatography to provide the titled compound (192). $^1H$ NMR (DMSO-d6, 400 MHz): δH 1.39 (3H, d, J=7.0 Hz), 3.17 (2H, t, J=6.4 Hz), 3.24 (3H, s), 3.64-3.61 (1H, m), 3.77 (3H, t, J=6.7 Hz), 4.85 (1H, s), 5.03 (1H, t, J=5.5 Hz), 7.53 (1H, t, J=6.2 Hz), 7.93 (1H, s), 8.40 (1H, d, J=7.9 Hz), 8.47 (1H, s), 8.64 (1H, d, J=4.6 Hz), 9.20 (1H, s). MS (m/z): 341.1 [M+H]+; 96% purity.

Preparation of (S)-3-(1-hydroxypropan-2-yl)-8-(2-methoxyethyl)-6-(5-(trifluoromethyl)pyridin-2-yl)pyrido[3,4-d]pyrimidin-4(3H)-one (193)

Compound 193 was prepared according to the same procedure as general Scheme IV above and following the alkyl-aryl coupling step according to the procedure for Compound 192.

Scheme VII

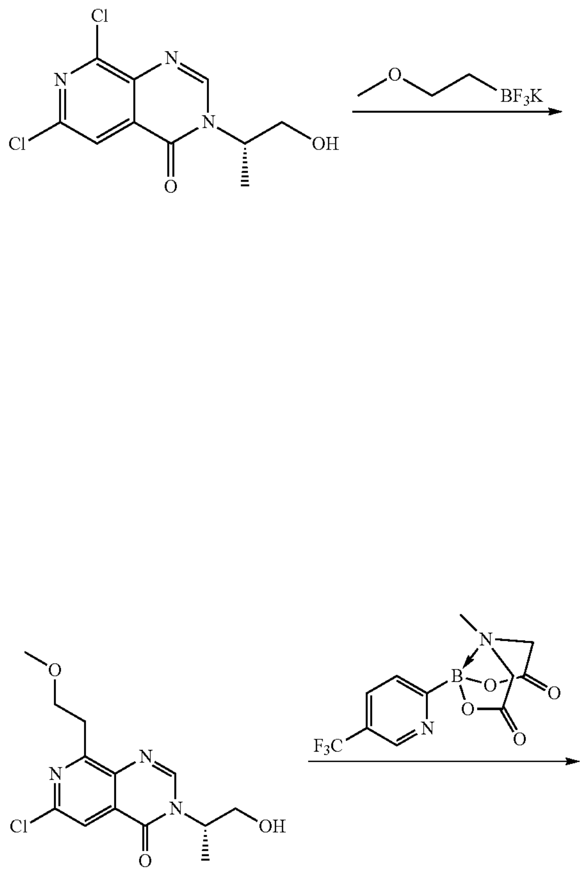

-continued

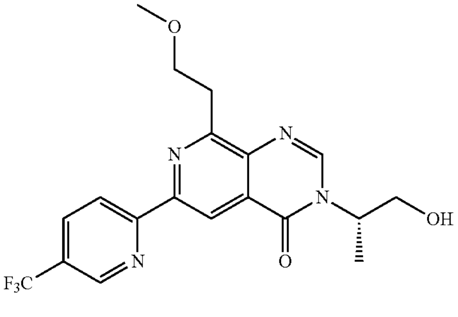

193

Table 31 describes the intermediate synthesized via general Scheme VII.

TABLE 31

| Intermediate Name | Structure and Name | $^1H$-NMR | MS $[m/z]^+$; Purity (%) |
|---|---|---|---|
| U1 | 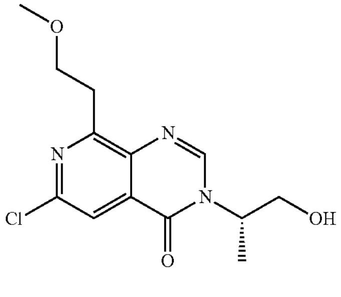 [SMILES: COCCc1nc(Cl)cc2c(=O)n([C@@H](C)CO)cnc12] (S)-6-chloro-3-(1-hydroxypropan-2-yl)-8-(2-methoxyethyl)pyrido[3,4-d]pyrimidin-4(3H)-one | NA | 298.0.0; NA |

Table 32 lists a compound that was synthesized according to the synthetic scheme VII above.

TABLE 32

| Compound No. | Compound Structure/Name | $^1$H-NMR | MS (m/z) [M + H]$^+$; Purity (%) |
|---|---|---|---|
| 193 | 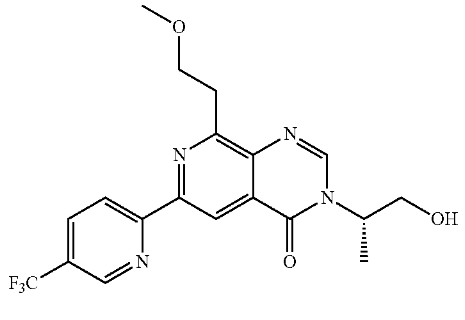 [SMILES: COCCc1nc(-c2ccc(C(F)(F)F)cn2)cc2c(=O)n([C@@H](C)CO)cnc12] (S)-3-(1-hydroxypropan-2-yl)-8-(2-methoxyethyl)-6-(5-(trifluoromethyl)pyridin-2-yl)pyrido[3,4-d]pyrimidin-4(3H)-one | $^1$H NMR ($CH_3OH$-$d_4$, 400 MHz): $\delta_H$ 1.54 (3H, d, J = 7.1 Hz), 3.39 (3H, s), 3.63 (2H, t, J = 6.8 Hz), 3.84 (1H, d, J = 12.1 Hz), 3.94 (1H, d, J = 7.5 Hz), 4.02 (2H, t, J = 6.9 Hz), 4.98 (2H, s), 8.25 (1H, d, J = 8.4 Hz), 8.46 (1H, s), 8.71 (1H, d, J = 8.4 Hz), 9.01 (2H, d, J = 17.4 Hz). | 409.1; >98% |

Example 2: DRE-Luciferase Reporter Assay

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter. 20000 Human HepG2 liver carcinoma—AhR-Lucia reporter cells or Human HT29 colon adenocarcinoma—AhR reporter cells or other cell line with a DRE-luciferase reporter stably transfected were plated in Eagle's Minimal Essential Medium, 10% heat-inactivated FBS, 1× non-essential amino acids Pen-Strep (10,000 U/mL) and Normocin (100 ug/mL) in plates (96-well, 384-well or other plates) and incubated overnight at 37° C. in a $CO_2$ incubator and treated with and without AhR antagonists at a log dilution starting at 100 uM.

After 1 hr that cells were plated an AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole) or other AHR ligands at their specific $EC_{50}$ concentration, were added to the cells with or without AHR antagonist.

Cells were incubated for 24 or 48 hours or another time point and then, supernatant was analyzed for determination of luciferase activity as a read-out of the AHR activation or inhibition. Luciferase was measured with the commercial kit QUANTI-Luc™ assay solution kit from Invivogen following the manufacturer's instructions.

The level of luciferase with only agonist ligand added was the maximum signal while the luciferase with no antagonist was the minimum signal. $IC_{50}$ values were determined as the concentration which inhibits half of the luciferase activity. The $IC_{50}$ level of luciferase of compounds of the disclosure is reported in Table 33. "A" indicates an $IC_{50}$ value less than 100 nM, "B" indicates an $IC_{50}$ between 100 and 500 nM, "C" indicates an $IC_{50}$ above 500 nM, and "D" indicates that an $IC_{50}$ value could not be generated from the data.

TABLE 33

| Compound No. | HepG2-Luc $IC_{50}$ (nM) |
|---|---|
| 1 | A |
| 2 | B |
| 3 | B |
| 4 | B |
| 5 | A |
| 6 | D |
| 7 | A |
| 8 | A |
| 9 | A |
| 10 | B |
| 11 | C |
| 12 | A |
| 13 | A |
| 14 | A |
| 15 | A |
| 16 | A |
| 17 | A |
| 18 | A |
| 19 | C |
| 20 | B |
| 21 | A |
| 22 | A |
| 23 | A |
| 24 | A |
| 25 | A |
| 26 | B |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | C |
| 41 | A |
| 42 | A |
| 43 | D |
| 44 | A |
| 45 | A |
| 46 | A |
| 47 | A |

TABLE 33-continued

| Compound No. | HepG2-Luc $IC_{50}$ (nM) |
|---|---|
| 48 | A |
| 49 | A |
| 50 | A |
| 51 | A |
| 52 | C |
| 53 | B |
| 54 | A |
| 55 | A |
| 56 | B |
| 57 | A |
| 58 | A |
| 59 | C |
| 60 | A |
| 61 | B |
| 62 | A |
| 63 | B |
| 64 | C |
| 65 | B |
| 66 | A |
| 67 | A |
| 68 | A |
| 69 | B |
| 70 | A |
| 71 | A |
| 72 | A |
| 73 | C |
| 74 | A |
| 75 | B |
| 76 | B |
| 77 | C |
| 78 | B |
| 79 | A |
| 80 | C |
| 81 | A |
| 82 | A |
| 83 | A |
| 84 | C |
| 85 | A |
| 86 | A |
| 87 | A |
| 88 | A |
| 89 | A |
| 90 | A |
| 91 | B |
| 92 | A |
| 93 | B |
| 94 | A |
| 95 | A |
| 96 | A |
| 97 | C |
| 98 | A |
| 99 | A |
| 100 | C |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 1123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | C |
| 156 | A |
| 157 | A |
| 158 | B |
| 159 | A |
| 160 | A |
| 161 | A |
| 162 | A |
| 163 | A |
| 164 | B |
| 165 | A |
| 166 | A |
| 167 | B |
| 168 | A |
| 169 | A |
| 170 | A |
| 171 | A |
| 172 | A |
| 173 | B |
| 174 | A |
| 175 | A |
| 176 | A |
| 177 | A |
| 178 | A |
| 179 | A |
| 180 | B |
| 181 | C |
| 182 | B |
| 183 | C |
| 184 | C |
| 185 enantiomer 1 | A |
| 185 enantiomer 2 | A |
| 186 | A |
| 187 | C |
| 188 | B |
| 189 | C |
| 190 | C |
| 191 | A |
| 192 | C |
| 193 | |

Example 3: CYP1A1 Gene Expression Assay

Human and mouse colorectal cancer (CRC) cell lines, HT29 and HT26 respectively, American Type Culture Collection (ATCC) are plated in a sterile tissue culture treated 96-well plate (ThermoFisher) at $8.0\times10^5$ cells per well, and grown overnight at 37° C., 5% $CO_2$ in DMEM complete (Gibco) in order to achieve confluence. After the incubation medium is aspirated off the cell monolayers, tissues are then washed with 200 µL of warmed PBS solution, and subsequently 190 µL of pre-warmed growth medium is added to each well. AhR antagonist of interest are diluted at a 20× concentration in growth medium containing 2% DMSO, and 10 µL of compound solutions are added to respective wells in triplicate. After 1 hr, AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole or other AHR ligands, is added with or without AHR antagonist for 24 hours, after which media will be removed and stored at −80 C for later cytokine analysis. At the end of the incubation, medium is aspirated off the CRC cells, and the cells washed with 100 µL of cold PBS solution. RNA is extracted via the TaqMan™ Gene Expression Cells-to-CT™ Kit (ThermoFisher) according to the manufacturer's protocol. The QuantStudio 6 Flex (Applied Biosciences) is used to analyze mRNA levels of CYP1A1 using GAPDH as the endogenous control. TaqMan™ probe sets for both genes are acquired from ThermoFisher. Samples are run in triplicate and data is analyzed using the QuantStudio software and reported as linear and log 2(ΔΔCT) values. Statistical analysis is performed using a two-tailed t-test comparing CYP1A1 levels in the presence of each individual compound to the vehicle negative control. Compounds with $IC_{50}$ in the range of the nanomolar concentration are considered for further evaluation. This assay can be used to confirm the inhibitory effect of the compounds prior to testing using an in vivo model.

Example 4: Human PBMC (CD8+) Assay

Human donor blood (8 mL) is collected in sodium citrate CPT tubes and centrifuged at 1,600×g for 20 minutes at room temperature. Buffy coat containing PBMCs is collected and transferred to a 50 mL conical tube containing 30 mL of RPMI-1640 medium at room temperature (supplemented with penicillin-streptomycin). PBMCs samples are centrifuged at 400×g for 10 minutes at 10° C. The pelleted PBMCs are washed twice in 10 ml of RPMI-1640 medium (supplemented with penicillin-streptomycin), then resuspended in RPMI-1640 medium (supplemented with penicillin-streptomycin, fetal bovine serum, and L-Glutamine: RPMI-1640 complete medium). PBMCs are filtered through a 70-micron mesh to remove any cellular debris. The volume is adjusted to achieve 1.66×106 cells/mL, from which 180 µl (300,000 PBMCs) are added into each well in a 96-well plate (sterile, tissue culture treated, round bottom). PBMCs in a 96-well plate are rested for 30 minutes in a 37° C., 5% $CO_2$ incubator, then subsequently treated with 10 µl of indicated compound. For CD8+ (Killing T cells) differentiation assay, PMBC are cultured ($1\text{-}10\times10^4$ cells) in RPMI-1640 complete medium for 2, 4 and 6 days and stimulated with 5 uL/ml ImmunoCult™ Human CD3/CD28/CD2 T Cell Activator; Stemcell #10990) with/without AhR antagonist Compounds. Cell viability was determined using a viability dye (eBioscience Fixable Viability Dye eFluor 780: ThermoFisher 65-0865-14) at 1:500 dilution. The cells were gated for CD8+, defined as Live, CD11c−, CD14−, CD19−, CD8+, CD4−, CD3+. Percent (%) CD8+ were calculated as percentage of CD8+ cells over total live T cells. Statistical analysis was performed with GraphPad Prism Software Using One-Way ANOVA.

Example 5: Human PBMC Cytokine Assay

Human donor blood (8 mL) is collected in sodium citrate CPT tubes and centrifuged at 1,600×g for 20 minutes at room temperature. Buffy coat containing PBMCs is collected and transferred to a 50 mL conical tube containing 30 mL of RPMI-1640 medium at room temperature (supplemented with penicillin-streptomycin). PBMCs samples are centrifuged at 400×g for 10 minutes at 10° C. The pelleted PBMCs are washed twice in 10 ml of RPMI-1640 medium (supplemented with penicillin-streptomycin), then resuspended in RPMI-1640 medium (supplemented with penicillin-streptomycin, fetal bovine serum, and L-Glutamine: RPMI-1640 complete medium). PBMCs are filtered through a 70 micron mesh to remove any cellular debris. The volume is adjusted to achieve 1.66×106 cells/mL, from which 180 µl (300,000 PBMCs) are added into each well in a 96-well plate (sterile, tissue culture treated, round bottom). PBMCs in a 96-well plate are rested for 30 minutes in a 37° C., 5% CO2 incubator, then subsequently treated with 10 µl of indicated compound. For cytokine secretion assay, PMBC are cultured (1-10×104 cells) in RPMI-1640 complete medium for 2, 4 and 6 days and stimulated with 5 uL/ml ImmunoCult™ Human CD3/CD28/CD2 T Cell Activator; Stemcell #10990) with/without AhR antagonist compounds. After 2, 4, and 6 days of incubation at 37° C., 5% CO2, 100 µL of cell supernatant is collected and transferred to a 96-well plate (non-tissue treated, flat bottom). The plate is centrifuged at 350×g for 5 minutes at room temperature, and then the clear supernatant transferred to a new 96-well plate (non-tissue treated, flat bottom). The remaining cells are tested for viability using CellTiter-Glo® Luminescent Cell Viability Assay (Promega). The supernatant is analyzed for IL22 and IFg), using Luminex Immunoassay Technology (MAGPIX System). Cytokine levels of PBMC treated DMSO control samples are set to 100%, and compound treated samples are expressed relative to this.

Example 6: Solubility Determination Assay

The stock solutions of test compounds and control compound progesterone were prepared in DMSO at the concentrations of 10 mM. 15 µL of stock solution (10 mM) of each sample was placed in order into their proper 96-well rack. 485 µL of PBS pH 1.6 and pH 7.4 were added into each vial of the cap-less Solubility Sample plate. The assay was performed in singlet. One stir stick was added to each vial and then the vial was sealed using a molded PTFE/Silicone plug. The solubility sample plates were then transferred to the Eppendorf Thermomixer Comfort plate shaker and shaken at 25° C. at 1100 rpm for 2 hours. After completion of the 2 hours, plugs were removed and the stir sticks were removed using a big magnet. The samples from the Solubility Sample plate were transferred into the filter plate. Using the Vacuum Manifold, all the samples were filtered. An aliquot of 5 µL was taken from the filtrate followed by addition of 495 µL of a mixture of $H_2O$ and acetonitrile containing internal standard (1:1). A certain proportion of ultrapure water was used to dilute the diluent according to the peak shape. The dilution factor was changed according to the solubility values and the LC-MS signal response.

From the 10 mM DMSO STD plate, 6 μL was transferred into the remaining empty plate, and then 194 μL of DMSO were added to that plate to have a STD concentration of 300 μM. From the 300 μM DMSO STD plate, 5 μL were transferred into the remaining empty plate, and then 495 μL of a mixture of H2O and acetonitrile containing internal standard (1:1) were added to that plate to have a final STD concentration of 3 μM. A certain proportion of ultrapure water was used to dilute the diluent according to the peak shape. The concentrations of the standard samples were changed according to the LC-MS signal response.

The plate was placed into the well plate autosampler. The samples were evaluated by LC-MS/MS analysis.

All calculations were carried out using Microsoft Excel.

The filtrate was analyzed and quantified against a standard of known concentration using LC coupled with mass spectral peak identification and quantitation. Solubility values of the test compound and control compound were calculated as follows:

$$[\text{Sample}] = \frac{\text{Area ratio Sample} \times INJ\ VOL\ STD \times DF\ \text{Sample} \times [STD]}{\text{Area ratio } STD \times INJ\ VOL\ \text{Sample}}$$

Any value of the compounds that was not within the specified limits was rejected and the experiment was repeated.

The solubility of compounds of the disclosure in pH 1.6 and 7.4 buffers is reported in Table 34. "+++" indicates a solubility value equal to or greater than 1 μM, "++" indicates a solubility value between 0.1 and 1 μM, and "+" indicates a solubility value less than 0.1 μM.

TABLE 34

| Compound No. | Aq. Solubility at pH = 1.6 (μM) | Aq. Solubility at pH = 7.4 (μM) |
|---|---|---|
| 1 | | ++ |
| 7 | ++ | + |
| 8 | | +++ |
| 9 | +++ | +++ |
| 12 | +++ | +++ |
| 16 | +++ | +++ |
| 17 | +++ | +++ |
| 18 | +++ | +++ |
| 21 | +++ | +++ |
| 22 | +++ | +++ |
| 23 | +++ | +++ |
| 24 | +++ | +++ |
| 25 | ++ | + |
| 27 | ++ | ++ |
| 30 | | ++ |
| 31 | | ++ |
| 33 | | + |
| 34 | +++ | +++ |
| 36 | +++ | + |
| 37 | +++ | + |
| 38 | + | + |
| 44 | | ++ |
| 46 | +++ | +++ |
| 47 | | ++ |
| 48 | +++ | ++ |
| 49 | + | + |
| 50 | +++ | +++ |
| 51 | ++ | ++ |
| 54 | +++ | +++ |
| 55 | +++ | +++ |
| 57 | +++ | +++ |
| 58 | + | + |
| 60 | +++ | +++ |
| 66 | +++ | +++ |

TABLE 34-continued

| Compound No. | Aq. Solubility at pH = 1.6 (μM) | Aq. Solubility at pH = 7.4 (μM) |
|---|---|---|
| 68 | +++ | +++ |
| 70 | +++ | +++ |
| 71 | +++ | +++ |
| 74 | +++ | +++ |
| 79 | +++ | +++ |
| 81 | +++ | +++ |
| 82 | +++ | +++ |
| 83 | +++ | +++ |
| 85 | +++ | +++ |
| 86 | +++ | +++ |
| 88 | +++ | ++ |
| 89 | +++ | +++ |
| 92 | ++ | + |
| 95 | +++ | +++ |
| 99 | +++ | ++ |
| 101 | ++ | + |
| 102 | ++ | ++ |
| 103 | ++ | + |
| 104 | +++ | +++ |
| 105 | +++ | +++ |
| 109 | ++ | ++ |
| 110 | + | + |
| 111 | ++ | + |
| 112 | +++ | +++ |
| 114 | ++ | ++ |
| 115 | ++ | ++ |
| 116 | ++ | ++ |
| 117 | +++ | +++ |
| 120 | +++ | +++ |
| 122 | +++ | +++ |
| 123 | +++ | + |
| 124 | +++ | + |
| 125 | +++ | +++ |
| 126 | +++ | +++ |
| 129 | +++ | +++ |
| 136 | +++ | ++ |
| 139 | +++ | +++ |
| 140 | +++ | +++ |
| 142 | ++ | ++ |
| 143 | +++ | +++ |
| 144 | +++ | +++ |
| 145 | +++ | ++ |
| 148 | +++ | +++ |
| 151 | ++ | ++ |
| 152 | +++ | +++ |
| 154 | +++ | +++ |
| 156 | +++ | +++ |
| 160 | +++ | +++ |
| 161 | +++ | +++ |
| 162 | +++ | +++ |
| 163 | +++ | +++ |
| 177 | +++ | ++ |
| 183 | +++ | +++ |
| 185 enantiomer 1 | +++ | ++ |
| 185 enantiomer 2 | +++ | ++ |

BLD: Below limit of detection.

Example 7: Hepatocyte Stability Assay

Preparation of working solutions: 10 mM stock solutions of test compound and positive control were prepared in DMSO. In separate conical tubes, the 10 mM solution of test compound and the positive control were diluted to 100 μM by combining 198 μL of 50% acetonitrile/50% water and 2 μL of 10 mM stock.

Preparation of Hepatocytes: Incubation medium (William's E Medium supplemented with GlutaMAX) and hepatocyte thawing medium were placed in a 37° C. water bath and allowed warming for at least 15 minutes prior to use. A vial of cryopreserved hepatocytes was transferred from storage, ensuring that vials remained at cryogenic temperatures until thawing process ensued. Cells were thawed by placing the vial in a 37° C. water bath and gently shaking the vials for 2 minutes. After thawing was completed, vial was sprayed with 70% ethanol and transferred to a biosafety cabinet. Wide-bore pipette tip were used to transfer hepatocytes into 50 mL conical tube containing thawing medium. The 50 mL conical tube were placed into a centrifuge and spun at 100 g for 10 minutes. Upon completion of spin, thawing medium was aspirated and resuspended hepatocytes in enough incubation medium to yield ~$1.5\times10^6$ cells/mL. Using an AO/PI Staining, cells were counted and the viable cell density was determined. Cells with poor viability (<75% viability) were determined to be not acceptable for use. Cells were diluted with incubation medium to a working cell density of $0.5\times10^6$ viable cells/mL.

Procedure for Stability Determination: 198 μL of hepatocytes were pipetted into each wells of a 96-well non-coated plate. The plate was placed in the incubator to allow the hepatocytes to warm for 10 minutes. 2 μL of the 100 μM test compound or positive control solutions were pipetted into respective wells of the 96-well non-coated plate to start the reaction. The plate was returned to the incubator for the designed time points. Well contents was transferred in 25 μL aliquots at time points of 0, 15, 30, 60, 90 and 120 minutes. The aliquots were then mixed with 6 volumes (150 μL) of acetonitrile containing internal standard, IS (100 nM alprazolam, 200 nM caffeine and 100 nM tolbutamide) to terminate the reaction. The mixture was vortex for 5 minutes. Samples were centrifuged for 45 minutes at 3,220 g. An aliquot of 100 μL of the supernatant was diluted by 100 μL ultra-pure water, and the mixture was used for LC/MS/MS analysis. All incubations were performed in duplicate.

Data Analysis: All calculations were carried out using Microsoft Excel. Peak areas were determined from extracted ion chromatograms. In vitro half-life ($t_{1/2}$) of parent compound was determined by regression analysis of the percent parent disappearance vs. time curve.

The in vitro half-life (in vitro $t_{1/2}$) was determined from the slope value:

$$\text{in vitro } t_{1/2}=0.693/k$$

Conversion of the in vitro $t_{1/2}$ (in min) into the in vitro intrinsic clearance (in vitro $CL_{int}$, in μL/min/$1\times10^6$ cells) was done using the following equation (mean of duplicate determinations):

$$\text{in vitro } CL_{int}=kV/N$$

$$V=\text{incubation volume}(0.2\text{ mL});$$

$$N=\text{number of hepatocytes per well}(0.1\times10^6\text{ cells}).$$

Data Processing Rules: The rules for data processing are shown in Table 35.

TABLE 35

| Remaining % | |
|---|---|
| ≥80% at 120 min | If T-test with $p < 0.05$ is obtained, report the calculated $CL_{int}$ value; When the calculated $CL_{int}$ value <3.73, then report <3.73 instead of calculated value. If T-test with $p < 0.05$ is not obtained, then report <3.73 for $CL_{int}$ value and >371.12 for $t_{1/2}$ value when all the other data points fall in the range of 80%~120% (one data point within the range of 70%~130% is accepted, otherwise the experiment should be repeated). |
| <80% at 120 min | Always remove from the calculation all points with <10% left of 0.5 min sample, but leave at least 2 points If T-test with $p < 0.05$ is obtained, report the calculated $CL_{int}$ value. If T-test with $p < 0.05$ is not obtained, the experiment must be repeated. |

The human and rat liver hepatocyte clearance of compounds of the disclosure is reported in Table 36. "+++" indicates a $CL_{int}$ value less than 20 mL/min/Kg, "++" indicates a $CL_{int}$ between 20 and 50 mL/min/Kg, and "+" indicates an $CL_{int}$ above 50 mL/min/Kg.

TABLE 36

| Compound No. | Human hepatocyte clearance (mL/min/Kg) | Human hepatocyte clearance (mL/min/Kg) Plated hepatocyte Pharmaron assay | Human hepatocyte clearance (mL/min/Kg) Plated hepatocyte Alliance assay | Rat hepatocyte clearance (mL/min/Kg) | Mouse hepatocyte clearance (mL/min/Kg) |
|---|---|---|---|---|---|
| 1 | +++ | | | ++ | |
| 7 | ++ | | | ++ | ++ |
| 8 | +++ | | | ++ | |
| 9 | +++ | +++ | +++ | +++ | |
| 12 | +++ | | +++ | +++ | ++ |
| 16 | +++ | +++ | | +++ | ++ |
| 17 | ++ | | | + | + |
| 18 | +++ | +++ | | +++ | + |
| 21 | +++ | | | +++ | ++ |
| 22 | +++ | | | ++ | ++ |
| 23 | +++ | +++ | | | |
| 25 | +++ | | | | |
| 27 | +++ | | | +++ | |
| 30 | +++ | +++ | | ++ | ++ |
| 31 | +++ | | | ++ | |
| 33 | +++ | | | ++ | |
| 34 | +++ | | | | |
| 44 | +++ | | | +++ | |
| 46 | +++ | +++ | +++ | +++ | ++ |
| 47 | +++ | | | +++ | |
| 50 | ++ | | | | |

TABLE 36-continued

| Compound No. | Human hepatocyte clearance (mL/min/Kg) | Human hepatocyte clearance (mL/min/Kg) Plated hepatocyte Pharmaron assay | Human hepatocyte clearance (mL/min/Kg) Plated hepatocyte Alliance assay | Rat hepatocyte clearance (mL/min/Kg) | Mouse hepatocyte clearance (mL/min/Kg) |
|---|---|---|---|---|---|
| 51 | +++ | | | | |
| 54 | +++ | | | | |
| 55 | ++ | | | | |
| 57 | +++ | | +++ | | |
| 58 | +++ | | | | ++ |
| 60 | +++ | +++ | | +++ | ++ |
| 66 | ++ | | | | |
| 68 | +++ | | +++ | +++ | |
| 70 | +++ | | | | |
| 71 | +++ | | | | |
| 74 | +++ | | | ++ | + |
| 79 | +++ | +++ | | +++ | |
| 81 | +++ | | | | |
| 82 | +++ | | | | |
| 83 | +++ | | +++ | | |
| 85 | +++ | | | | |
| 86 | +++ | | | | |
| 88 | +++ | | | | |
| 89 | +++ | | | | |
| 92 | +++ | | | | |
| 95 | +++ | | | | |
| 99 | +++ | | | | |
| 101 | +++ | | | | |
| 102 | +++ | | | | |
| 103 | +++ | | | ++ | |
| 104 | +++ | | | | |
| 105 | +++ | +++ | | +++ | ++ |
| 109 | +++ | | | | |
| 110 | +++ | | | | |
| 111 | +++ | | | | |
| 112 | +++ | | | | |
| 114 | +++ | | | | |
| 115 | +++ | | | | |
| 116 | +++ | | | | |
| 117 | +++ | | | | |
| 120 | +++ | | | | |
| 122 | +++ | | | | |
| 123 | +++ | | | | |
| 124 | +++ | | | | |
| 125 | +++ | +++ | | + | |
| 126 | +++ | | | | |
| 134 | +++ | | | | |
| 136 | +++ | | | | |
| 139 | +++ | | | | |
| 140 | +++ | | | | |
| 142 | +++ | | | | |
| 143 | +++ | | | | |
| 144 | +++ | | | | |
| 145 | +++ | | | | |
| 150 | +++ | | | | |
| 151 | +++ | | | | |
| 152 | ++ | | | | |
| 154 | +++ | | | | |
| 156 | +++ | | | | |
| 160 | +++ | | | | |
| 161 | +++ | +++ | | | |
| 162 | +++ | | | | |
| 163 | +++ | | +++ | | |
| 177 | ++ | | | | |
| 183 | +++ | | | | |
| 185 enantiomer 1 | +++ | | | ++ | + |
| 185 enantiomer 2 | +++ | | | ++ | + |

Example 8: Liver Microsome Stability Assay

TABLE 37

| Reagent | Stock Concentration | Volume | Final Concentration |
|---|---|---|---|
| Phosphate buffer | 100 mM | 210 μL | 100 mM |
| Microsomes | 20 mg/mL | 6.25 μL | 0.5 mg/mL |

Two separate experiments were performed as follows.

With Cofactors (NADPH): 25 μL of 10 mM NADPH was added to the incubations. The final concentrations of microsomes and NADPH were 0.5 mg/mL and 1 mM, respectively. The final concentration of microsomes was 0.5 mg/mL. The mixture was pre-warmed at 37° C. for 10 minutes. The reaction was started with the addition of 2.5 μL of 100 μM control compound or test compound solutions. Verapamil was used as positive control in this study. The final concentration of test compound or control compound was 1 μM. The incubation solution was incubated in water batch at 37° C. Aliquots of 25 μL were taken from the reaction solution at 0.5, 5, 15, 30 and 60 minutes. The reaction was stopped by the addition of 5 volumes of cold acetonitrile with IS (200 nM caffeine and 100 nM tolbutamide). Samples were centrifuged at 3, 220 g for 40 minutes. Aliquot of 100 μL of the supernatant was mixed with 100 μL of ultra-pure H2O and then used for LC-MS/MS analysis.

Data Analysis: All calculations were carried out using Microsoft Excel. Peak areas were determined from extracted ion chromatograms. The slope value, k, was determined by linear regression of the natural logarithm of the remaining percentage of the parent drug vs. incubation time curve.

The in vitro half-life (in vitro $t_{1/2}$) was determined from the slope value:

$$\text{in vitro } t_{1/2} = -(0.693/k)$$

Conversion of the in vitro $t_{1/2}$ (min) into the in vitro intrinsic clearance (in vitro $CL_{int}$, in μL/min/mg protein) was done using the following equation (mean of duplicate determinations):

$$\text{in vitro } CL_{int} = \left(\frac{0.693}{(t_{1/2})}\right) * \left(\frac{\text{volume of incubation } (\mu L)}{\text{amount of proteins(mg)}}\right)$$

The calculations of Scaled-up $CL_{int}$(mL/min/kg), Predicted CLH (mL/min/kg) and EH were done using the following equation:

$$\text{Scaled-up } CL_{int} = (0.693/t_{1/2}) \times (1/(\text{microsomal protein concentration } (0.5 \text{ mg/mL}))) \times \text{Scaling Factors};$$

$$\text{Predicted } CLH = (QH \times \text{Scaled-up } CL_{int} \times f_{ub})/(QH + \text{Scaled-up } CL_{int} \times f_{ub});$$

$$EH = \text{Predicted } CLH/QH$$

where QH is the hepatic blood flow (mL/min/kg) (Table 32), $f_{ub}$ is the fraction of unbound drug in plasma which is assumed to be 1.

The scaling factors for intrinsic clearance prediction in the human and mouse microsomes are reported in Table 38.

TABLE 38

| Species | Microsomal protein per gram of liver | Liver weight per Kg of body weight | Scaling factor* | Hepatic blood flow |
|---|---|---|---|---|
| Human | 48.8 | 25.7 (human) | 1254.2 human) | 20.7 (human) |
| | | 40.0 (rat) | 1792 (rat) | 55.2 (rat) |

*Scaling Factor = (microsomal protein per gram of liver) × (liver weight per kilogram of body weight)

Data Processing Rules: The rules for data processing are shown in Table 39.

TABLE 39

| Remaining % | Processing Rules |
|---|---|
| ≥80% at 60 min | If T-test with $p < 0.05$ is obtained, report the calculated $CL_{int}$ value<br>If T-test with $p < 0.05$ is obtained, report the calculated $CL_{int}$ value;<br>When the calculated $CL_{int}$ value <7.50, then report <7.50 instead of calculated value.<br>If T-test with $p < 0.05$ is not obtained, then report <7.50 for $CL_{int}$ value and >184.78 for $t_{1/2}$ value when all the other data points fall in the range of 80%~120% (one data point within the range of 70%~130% is accepted, otherwise the experiment should be repeated). |
| <80% at 60 min | Always remove from the calculation all points with <10% left of 0.5 min sample, but leave at least 2 points<br>If T-test with $p < 0.05$ is obtained, report the calculated $CL_{int}$ value.<br>If T-test with $p < 0.05$ is not obtained, the experiment must be repeated. |

The human and rat liver microsome clearance of compounds of the disclosure is reported in Table 40. "+++" indicates a $Cl_{int}$ value less than 10 mL/min/Kg, "C++" indicates a $Cl_{int}$ between 10 and 20 mL/min/Kg, and "+" indicates a $Cl_{int}$ above 20 mL/min/Kg.

TABLE 40

| Compound No. | Human liver microsome clearance (mL/min/Kg) |
|---|---|
| 7 | +++ |
| 12 | +++ |
| 16 | +++ |
| 17 | + |
| 18 | +++ |
| 21 | +++ |
| 22 | +++ |
| 23 | +++ |
| 24 | ++ |
| 25 | +++ |
| 27 | +++ |
| 34 | +++ |
| 36 | +++ |
| 48 | +++ |
| 49 | +++ |

Example 9: Caco-2 Permeability Assay

Preparation of Caco-2 Cells: 50 μL and 25 mL of cell culture medium were added to each well of the Transwell insert and reservoir, respectively. The HTS transwell plates were incubated at 37° C., 5% $CO_2$ for 1 hour before cell seeding. Caco-2 cells were diluted to $6.86\times10^5$ cells/mL with culture medium and 50 μL of cell suspension were dispensed into the filter well of the 96-well HTS Transwell plate. Cells were cultivated for 14-18 days in a cell culture incubator at 37° C., 5% $CO_2$, 95% relative humidity. Cell culture medium was replaced every other day, beginning no later than 24 hours after initial plating.

Assessment of Cell Monolayer Integrity: Medium was removed from the reservoir and each Transwell insert and replaced with prewarmed fresh culture medium. Transepithelial electrical resistance (TEER) across the monolayer was measured using Millicell Epithelial Volt-Ohm measuring system (Millipore, USA). The Plate was returned to the incubator once the measurement was done. The TEER value was calculated according to the following equation:

TEER measurement (ohms)×Area of membrane ($cm^2$)=TEER value (ohm·$cm^2$)

TEER value should be greater than 230 ohm·$cm^2$, which indicates the well-qualified Caco-2 monolayer.

Preparation of Solutions: 2 mM stock solutions in DMSO of control compounds were prepared and diluted with HBSS (10 mM HEPES, pH 7.4) to get 10 μM working solution. 0.2 mM stock solutions of test compounds in DMSO were prepared and diluted with HBSS (10 mM HEPES, pH 7.4 with 0.5% BSA) to get 1 μM working solution. Metoprolol, erythromycin and cimetidine were used as control compounds.

Performing the Drug Transport Assay: The Caco-2 plate was removed from the incubator. The monolayer was washed twice with pre-warmed HBSS (10 mM HEPES, pH 7.4). The plate was incubated at 37° C. for 30 minutes. To determine the rate of drug transport in the apical to basolateral direction, 125 μL of the working solution was added to the Transwell insert (apical compartment). A 50 μL sample was transferred immediately from the apical compartment to 200 μL of acetonitrile containing IS (100 nM alprazolam, 200 nM Caffeine and 100 nM tolbutamide) in a new 96-well plate as the initial donor sample (A-B) and it was vortexed at 1000 rpm for 10 minutes. The wells in the receiver plate (basolateral compartment) were filled with 235 μL of transport buffer. To determine the rate of drug transport in the basolateral to apical direction, 285 μL of the working solution were added to the receiver plate wells (basolateral compartment). A 50 μL sample was transferred immediately from the basolateral compartment to 200 μL of acetonitrile containing IS (100 nM alprazolam, 200 nM Caffeine and 100 nM tolbutamide) in a new 96-well plate as the initial donor sample (B-A) and it was vortexed at 1000 rpm for 10 minutes. The Transwell insert (apical compartment) was filled with 75 μL of transport buffer. The apical to basolateral direction and the basolateral to apical direction need to be done at the same time. The plates were incubated at 37° C. for 2 hours. At the end of the incubation, 50 μL samples from donor sides (apical compartment for Ap→B1 flux, and basolateral compartment for B1→Ap) and receiver sides (basolateral compartment for Ap→B1 flux, and apical compartment for B1→Ap) were transferred to wells of a new 96-well plate, followed by the addition of 4 volume of acetonitrile containing IS (100 nM alprazolam, 200 nM Caffeine and 100 nM tolbutamide). Samples were vortexed for 10 minutes, 50 μL samples were transferred to wells of a new 96-well plate, followed by the addition of 50 μL Hepes and 200 μL IS. A11 samples were vortexed for 10 minutes, and then centrifuged at 3,220 g for 40 minutes. An aliquot of 150 μL of the supernatant was mixed with an appropriate volume of ultra-pure water before LC-MS/MS analysis.

Data analysis: All calculations were carried out using Microsoft Excel. Peak areas were determined from extracted ion chromatograms. Lucifer yellow leakage of monolayer can be calculated using the following equation:

$$LY\text{ Leakage} = \left(\frac{I_{acceptor}\times 0.3}{I_{acceptor}\times 0.3 + I_{donor}\times 0.1}\right)\times 100\%$$

where $I_{acceptor}$ is the fluorescence intensity in the acceptor well (0.3 mL), and $I_{donor}$ is the fluorescence intensity in the donor well (0.1 mL) and expressed as % leakage.

Lucifer yellow percentage amount transported values should be less than 1.5%. However, if the lucifer yellow percentage amount transported value for a particular transwell is higher than 1.5 but the determined digoxin $P_{app}$ in that transwell is qualitatively similar to that determined in the replicate transwells then, based upon the scientific judgement of the responsible scientist, the monolayer is considered acceptable.

Apparent permeability (Papp) can be calculated for drug transport assays using the following equation:

where $P_{app}$ is $$p_{app} = \frac{dQ/DT}{A\times D_o}$$

apparent permeability (cm/s×$10^{-6}$);

dQ/dt is the rate of drug transport (pmol/second);

A is the surface area of the membrane (cm2);

$D_o$ is the initial donor concentration (nM; pmol/$cm_3$).

Efflux ratio can be determined using the following equation:

$$\text{Efflux Ratio} = \frac{P_{app(B-A)}}{P_{app(A-B)}}$$

where $P_{app(B-A)}$ indicates the apparent permeability coefficient in basolateral to apical direction, and $P_{app(A-B)}$ indicates the apparent permeability coefficient in apical to basolateral direction.

The apparent permeability ratio of compounds of the disclosure is reported in Table 41. "A" indicates a $P_{app}$ value greater than $10*10^{-6}$ cm/s, "B" indicates an $P_{app}$ between 2 and $10*10^{-6}$ cm/s, and "C" indicates an $P_{app}$ below $2*10^{-6}$ cm/s.

TABLE 41

| Compound No. | Caco2 $P_{app}$ (AB)/(BA) ($10^{-6}$ cm/s) |
|---|---|
| 1 | B/C |
| 7 | C/C |
| 8 | B/B |

TABLE 41-continued

| Compound No. | Caco2 $P_{app}$ (AB)/(BA) ($10^{-6}$ cm/s) |
|---|---|
| 9 | B/A |
| 12 | B/A |
| 16 | B/B |
| 17 | A/B |
| 18 | B/B |
| 21 | B/C |
| 22 | B/B |
| 27 | B/C |
| 30 | B/C |
| 31 | B/C |
| 33 | B/B |
| 34 | B/A |
| 44 | B/B |
| 46 | A/A |
| 47 | C/C |
| 60 | A/B |
| 74 | B/A |
| 103 | B/C |
| 105 | A/B |

Example 10: Plasma Protein Binding Determination with Ultracentrifugation Method The frozen plasma (stored at −80° C.) was thawed in a 37° C. water bath, followed by centrifugation at 3,220 g for 10 minutes to remove clots. The supernatant was removed into a new tube as the spun plasma. The spun plasma was pre-warmed in a 37° C. water bath for 10 minutes. The stock solutions of test compounds were diluted to 200 μM in DMSO, and then spiked into the plasma. Duplicate samples were prepared. The final concentration of compound was 1.0 μM. The final concentration of organic solvent was 0.5%. Warfarin was used as positive control in the assay. 1.0 mL of the spiked plasma was transferred to a new balance ultracentrifuge tube. Samples were incubated at 37° C., 5% $CO_2$ for 30 minutes. After incubation, the balance ultracentrifuge tubes were centrifuged at 600,000 g for 5.5 hours at 37° C. After centrifugation, 50 μL solution was removed from the center of the ultracentrifuge tubes as the post-ultracentrifugation samples, followed by the addition of 50 μL blank plasma and 400 μL quench solution (acetonitrile containing internal standards (IS, 100 nM Alprazolam, 500 nM Labetalol and 2 μM Ketoprofen)) to precipitate protein and release compounds. Samples were vortexed for 2 minutes, followed by centrifugation at 20,000 g for 15 minutes at room temperature. The supernatant was diluted with ultrapure water and then used for LC-MS/MS analysis. Stability samples was prepared by transferring 50 μL of the spiked plasma to 0.6 mL tubes and incubated at 37° C., 5% $CO_2$ for 0.5 and 6 hours. After incubation, 50 μL PBS (100 mM, pH7.4) and 400 μL quench solution were added to the stability samples. And then stability samples were treated the same way as the post-ultracentrifugation samples. The supernatant was diluted with ultrapure water and then used for LC-MS/MS analysis. 0.5 hour time point samples were also used as no-spun controls. Time 0 samples were prepared by transferring 50 μL spiked plasma to 0.6 mL tubes containing 50 μL PBS, followed by the addition of 400 μL quench solution to precipitate protein and release compound. And then these samples were treated the same way as the post-ultracentrifugation samples. The supernatant was diluted with ultrapure water and then used for LC-MS/MS analysis.

Data Analysis: All calculations were carried out using Microsoft Excel. The concentrations of test compound in plasma samples and post-ultracentrifugation plasma was determined from peak areas. The percentages of test compound bound was calculated as follows:

$$\%\ \text{Unbound} = (\text{Peak Area post-ultracentrifugation/Peak Area non-spun control}) \times 100\%$$

$$\%\ \text{Bound} = 100\% - \%\ \text{Unbound}$$

$$\text{Remaining}\ \%\ \text{at}\ 0.5\ hr = \text{Area ratio}\ 0\ hr \times 100\%$$

$$\text{Remaining}\ \%\ \text{at}\ 6\ hr = \text{Area ratio}\ 6\ hr/\text{Area ratio}\ 0\ hr \times 100\%$$

$$LogK = \text{Log}\left(\frac{\%\ \text{Bound}}{100 - \%\ \text{Bound}}\right)$$

The level of binding to human, rat and mouse plasma protein of compounds of the disclosure is reported in Table 42. "+++" indicates a % bound value less than 50, "++" indicates a % bound value between 50 and 75, and "+" indicates a % bound value above 75.

TABLE 42

| Compound No. | Human plasma protein binding (% bound) | Rat plasma protein binding (% bound) | Mouse plasma protein binding (% bound) |
|---|---|---|---|
| 1 | + | | |
| 7 | + | + | + |
| 8 | + | | |
| 9 | + | + | + |
| 12 | + | | + |
| 16 | + | | + |
| 17 | + | | + |
| 18 | + | | + |
| 21 | + | | + |
| 22 | + | | + |
| 27 | + | | |
| 30 | | + | + |
| 31 | | | |
| 33 | + | | |
| 44 | + | | |
| 46 | + | + | + |
| 47 | + | | |
| 60 | + | | + |
| 68 | + | | + |
| 74 | + | | |
| 79 | + | | + |
| 103 | + | | + |
| 105 | + | | + |
| 125 | + | | + |

Example 11: CYP Inhibition Assay

Stock solutions of test compounds were prepared in DMSO at the concentrations of 10 mM. Stock solution was diluted to 2 mM with acetonitrile. The final concentration of test compounds was 10 μM. The concentration of positive inhibitor is listed in Table 43. For the stock solution preparation, if the positive control could not be well dissolved in the mixture of DMSO and acetonitrile (1:4) at the highest concentration, another mixture of acetonitrile and DMSO, the mixture of acetonitrile and H2O or DMSO will be used to dissolve the compound.

TABLE 43

| Table 4. Positive inhibitor nominal concentration | | | |
|---|---|---|---|
| CYP Isoform | Positive control | Conc. of stock solution (μM) | Final conc. in system (μM) |
| CYP2D6, 3A4 | Quinidine, Ketoconazole | 100 μM | 0.5 μM |

Preparation details of these substrates are given in Table 44. The substrate solutions are stored in a −20° C. freezer and warmed to room temperature prior to use.

TABLE 44

| Table 5. Preparation of Substrate Stock Solution | | | | |
|---|---|---|---|---|
| CYP Isoform | Substrate | Conc. of stock solution (mM) | Final conc. in system (μM) | Incubation Time |
| 2D6 | Dextromethorphan | 0.4 (in ACN) | 2 | 20 min |
| 3A4 | Midazolam | 0.2 (in MeOH + ACN) | 1 | 5 min |

Preparation of Phosphate Buffer (100 mmol/L, pH 7.4): To prepare the Solution A, 7.098 g of disodium hydrogen phosphate were weighed out and added into 500 mL of pure water, then sonicated to dissolve the content. To prepare the Solution B, 3.400 g of potassium dihydrogen phosphate were weighed out and added into 250 mL of pure water, then sonicated to dissolve the content. Solution A was placed on a stirrer and slowly Solution B was added into Solution A until the pH reached 7.4. Preparation of 10 mmol/L NADPH Solution: NADPH was dissolved at 8.334 mg/mL in phosphate buffer; the solution was freshly prepared prior to use.

The master solution was prepared according to Table 45. The incubation was carried out in 96 deep well plates. The following volumes were dispensed into each well of the incubation plate: 179 μL of the substrate and HLM mixture in phosphate buffer, 1 μL of the compound working solution, or vehicle (mixture of DMSO and acetonitrile (1:4)). The incubation plate was placed into the water bath and pre-warmed at 37° C. for 15 minutes before the reactions was started by the addition of 20 μL of 10 mmol/L NADPH solution in phosphate buffer. After the addition of NADPH, the incubation plate was incubated at 37° C. for corresponding time. The assay was performed in duplicate.

TABLE 45

| Table 6. Preparation of master solution | | | |
|---|---|---|---|
| Buffer | Stock Concentration | Volume | Final Concentration |
| Microsomes | 20 mg/mL | 2 μL | 0.2 mg/mL |
| Phosphate buffer | 100 mM | 176 μL | 100 mM |
| Substrate | — | 1 μL | — |

The reaction was quenched by the addition of 1.5 volume (300 μL) of cold acetonitrile containing 3% formic acid and internal standards (200 nM Labetalol, 200 nM Alprazolam and 200 nM tolbutamide). The plate was centrifuged at 3,220 g for 40 minutes. 100 μL of the supernatant was transferred to a new plate. The supernatant was diluted with 100 μL pure water. The samples were mixed well and analyzed using UPLC/MS/MS.

Data Analysis: The automatic peak integration areas are checked for all the samples. The Analyte Peak Area and Internal Standard Peak Area are exported into excel spreadsheet. The inhibition of each P450 enzyme in human liver microsomes is measured as the percentage decrease in the activity of marker metabolite formation compared to non-inhibited controls (=100% activity).

The percentage of remaining activity was calculated as follows:

Area Ratio=Peak Area Analyte/Peak Area Internal Standard

Remaining Activity (%)=Area Ratio test compound/Area Ratio vehicle*100%

Inhibition %=100−Remaining Activity (%)

The % inhibition of compounds of the disclosure for CYP2D6 and CYP3A4 is reported in Table 46.

TABLE 46

| Compound No. | CYP2D6% inhibition at 10 μM | CYP3A4% inhibition at 10 μM |
|---|---|---|
| 7 | 6.78 | NA |
| 9 | 7.19 | NA |
| 12 | 8.45 | NA |
| 16 | 15.6 | NA |
| 18 | 12.1 | 35.2 |
| 27 | 8.96 | NA |
| 30 | 11.2 | 12.2 |
| 46 | 7.43 | 2.26 |
| 68 | 10.9 | NA |
| 74 | 7.27 | NA |
| 79 | 8 | NA |
| 103 | 8.7 | NA |
| 105 | 2.73 | NA |
| 125 | 20.6 | 23.8 |

NA = Not available

Example 12: hERG Inhibition Assay hERG stably expressed HEK 293 cell line (Cat #K1236) was purchased from Invitrogen. The cells are cultured in 85% DMEM, 10% dialyzed FBS, 0.1 mM NEAA, 25 mM HEPES, 100 U/mL Penicillin-Streptomycin and 5 μg/mL Blasticidin and 400 μg/mL Geneticin. Cells are split using TrypLE™ Express about three times a week and maintained between ~40% to ~80% confluence. Before the assay, the cells were onto the coverslips at 5×105 cells/per 6 cm cell culture dish and induced with doxycycline at 1 μg/mL for 48 hours.

External solution (in mM): 132 NaCl, 4 KCl, 3 CaCl2), 0.5 MgCl2, 11.1 glucose, and 10 HEPES (pH adjusted to 7.35 with NaOH). Internal solution (in mM): 140 KCl, 2 MgCl2, 10 EGTA, 10 HEPES and 5 MgATP (pH adjusted to 7.35 with KOH). Working solution preparation for test compound: test compounds were initially prepared in DMSO with final concentration of 10 mM as stock solution. Stock solution of each compound was serial-diluted by ratio of 1:3 with DMSO to prepare additional 3 intermediate solutions including 3.33, 1.11 and 0.37 mM.

Before performing the hERG assay, the working solutions were prepared by dilution of 10, 3.33, 1.11, and 0.37 mM intermediate solutions in 1000 folds using extracellular solution, while 30 μM working solution was prepared by 333.333-folds dilution of 10 mM DMSO stock. so that the final concentration of working solution was 30, 10, 3.33, 1.11 and 0.37 μM. The final DMSO concentration in working solutions was maintained in range of 0.1-0.3% (v/v).

Experimental procedure: the coverslip was removed from the cell culture dish and placed it on the microscope stage in bath chamber. A desirable cell was located using the ×10 objective. The tip of the electrode was located under the microscope using the ×10 objective by focusing above the plane of the cells. Once the tip was in focus, the electrode was advanced downwards towards the cell using the coarse controls of the manipulator, while simultaneously moving the objective to keep the tip in focus. When directly over the cell, the fine controls of the manipulator were used to approach the surface of the cell in small steps, by using the ×40 objective. Gentle suction was applied through the side-port of the electrode holder to form a gigaohm seal.

Cfast was used to remove the capacity current that is in coincidence with the voltage step. The whole cell configuration was obtained by applying repetitive, brief, strong suction until the membrane patch has ruptured. membrane potential was set to −60 mV at this point to ensure that hERG channels were not open. The spikes of capacity current was then cancelled using the Cslow on the amplifier.

Holding potential was set to −90 mV for 500 ms; current was recorder at 20 kHz and filtered at 10 kHz. Leaking current was tested at −80 mV for 500 ms.

The hERG current was elicited by depolarizing at +30 mV for 4.8 seconds and then the voltage was taken back to −50 mV for 5.2 seconds to remove the inactivation and observe the deactivating tail current. The maximum amount of tail current size was used to determine hERG current amplitude. Current was recorded for 120 seconds to assess current stability. Only stable cells with recording parameters above threshold were proceeded with further drug administrations. Vehicle control was applied to the cells to establish the baseline. Once the hERG current was found to be stabilized for 5 minutes, working solution was applied. hERG current in the presence of test compound were recorded for approximately 5 minutes to reach steady state and then 5 sweeps were captured. For dose response testing, 5 doses of test compound was applied to the cells cumulatively from low to high concentrations. In order to ensure the good performance of cultured cells and operations, the positive control, Dofetilide, with 5 doses was also used to test the same batch of cells.

The following criteria were used to determine data acceptability: initial seal resistance>1 GΩ; leak currents<50% of the control peak tail currents at any time; the peak tail amplitude>300 pA; membrane resistance Rm>500 MΩ; access resistance (Ra)<15 MΩ; apparent run-down of peak current<2.5% per min.

Data that met the above criteria for hERG current quality were further analyzed as the following steps. Percent current inhibition was calculated using the following equation: (Note: PatchMaster or Clampfit software were used to extract the peak current from the original data).

$$\text{Peak current inhibition} = \left(1 - \frac{\text{Peak tail current}_{compound}}{(\text{Peak tail current})_{blank\ vehicle}}\right) \times 100$$

The dose response curve of test compounds was plotted with % inhibition against the concentration of test compounds using Graphpad Prism 6.0, and fit the data to a sigmoid dose-response curve with a variable slope.

The $IC_{50}$ of compounds of the disclosure is reported in Table 47.

TABLE 47

| Compound No. | hERG channel: $IC_{50}$ (uM) |
|---|---|
| 7 | >30.0 |
| 9 | 12.1 |
| 12 | >10.0 |
| 16 | 4.31 |
| 18 | 5.28 |
| 27 | >10.0 |
| 30 | >30.0 |
| 46 | 8.63 |
| 60 | >30.0 |
| 68 | >30.0 |
| 74 | 4.84 |
| 79 | >30.0 |
| 103 | >10.0 |
| 105 | 11.8 |
| 125 | 7.67 |
| 160 | 11.5 |

Example 13: In Vivo Rat PK Studies

The studies were conducted in male Sprague Dawley rats, three rats per group, or male CD1 mice, three mice per group. Compounds were dosed 1.0 mg/Kg i.v. (vehicle ethanol: % PEG400 in deionized water, in proportions suitable for dosing a clear solution) and 3.0 mg/kg or 10 mg/kg p.o. (vehicle: 1% methyl cellulose: 1,500 cP in DI water (w/v)). A11 animals had free access to food and water. Rat i.v. PK time points: Plasma: 0.083, 0.25, 0.5, 1, 2, 4, 8 and 24 h; Rat p.o. PK time points: Plasma: 0.25, 0.5, 1, 2, 4, 8 and 24 h. Mouse i.v. PK time points: Plasma: 0.083, 0.25, 0.5, 1, 2, 4, 8, 24, and 48 h; Mouse p.o. PK time points: Plasma: 0.25, 0.5, 1, 2, 4, 8, 24, and 48 h. Concentrations of compound in the plasma samples were analyzed using a LC-MS/MS method. WinNonlin (Phoenix™, version 6.1) or other similar software was used for pharmacokinetic calculations.

The data pharmacokinetic data from the mouse and rat PK studies are shown in Tables 48 to 51 below. The PK data in mice dosed with 1 mg/mL IV of compounds of the disclosure is reported in Table 48. The PK data in mice dosed with 10 mg/mL PO of compounds of the disclosure is reported in Table 49. The PK data in rats dosed with 1 mg/mL IV of compounds of the disclosure is reported in Table 50. The PK data in rats dosed with 3 or 10 mg/mL PO of compounds of the disclosure is reported in Table 51.

TABLE 48

| Compound No. | $C_0$ Mean (nmol/L) | $C_0$ CV (%) | $C_I$ Mean (L/h/kg) | $C_I$ CV (%) | $T_{1/2}$ Mean (h) | $T_{1/2}$ CV (%) | $AUC_{Last}$ Mean (h * nmol/L) | $AUC_{Last}$ CV (%) | $AUC_{Inf}$ Mean (h * nmol/L) | $AUC_{Inf}$ CV (%) |
|---|---|---|---|---|---|---|---|---|---|---|
| 9 | 5.37 | 9.68 | 3.42 | 8.19 | 5.37 | 9.68 | 4880 | 7.76 | 4900 | 7.88 |
| 17 | 601 | 14.9 | 72.2 | 8.24 | 0.504 | 5.23 | 231 | 8.67 | 232 | 8.62 |
| 18 | 333 | 23 | 2.02 | 13.9 | 20.7 | 8.54 | 6770 | 11.1 | 8330 | 13 |
| 30 | 457 | 29.1 | 2.6 | 15.2 | 8.6 | 9.79 | 6380 | 16.3 | 6510 | 16.5 |
| 46 | 470 | 8.33 | 1.76 | 10.2 | 15.7 | 5.7 | 8400 | 8.94 | 9540 | 10.3 |
| 60 | 350 | 5.87 | 2.42 | 10.2 | 11.8 | 10.9 | 6520 | 9.06 | 6930 | 10.8 |
| 103 | 349 | 23.4 | 0.64 | 26.9 | 69.5 | 23.5 | 10400 | 11.9 | 27500 | 29.1 |
| 105 | 412 | 12.7 | 0.682 | 2.99 | 55.9 | 11 | 11300 | 7.07 | 24500 | 2.99 |

TABLE 49

| Compound No. | $C_{Max}$ Mean (nmol/L) | $C_{Max}$ CV (%) | $T_{Max}$ Mean (h) | $T_{Max}$ CV (%) | $T_{1/2}$ Mean (h) | $T_{1/2}$ CV (%) | $AUC_{Last}$ Mean (h * nmol/L) | $AUC_{Last}$ CV (%) | $AUC_{Inf}$ Mean (h * nmol/L) | $AUC_{Inf}$ CV (%) | Bioavailability (%) |
|---|---|---|---|---|---|---|---|---|---|---|---|
| 9 | 1470 | 12.4 | 5.67 | 71.3 | NA | NA | 1470 | 12.4 | 34200 | 11.4 | 70.3 |
| 17 | 349 | 6.62 | 0.417 | 34.6 | 1.15 | NA | 497 | 6.66 | 519 | NA | 21.6 |
| 18 | 1310 | 8.66 | 6.67 | 34.6 | 23.4 | NA | 45800 | 6.51 | NA | NA | 67.6 |
| 30 | 2160 | 11.8 | 8 | 0 | NA | NA | 72800 | 3.5 | NA | NA | 114 |
| 46 | 2370 | 4.26 | NA | NA | 8 | 0 | 67700 | 7.88 | NA | NA | 80.6 |
| 60 | 1120 | 4.72 | 8 | 0 | NA | NA | 29800 | 10.5 | NA | NA | 45.7 |
| 103 | 152 | 18.4 | 13.3 | 69.3 | NA | NA | 6060 | 24.4 | NA | NA | 5.82 |
| 105 | 2350 | 14.4 | 12 | 88.2 | 48.5 | NA | 96100 | 11.6 | NA | NA | 85 |

NA not available

TABLE 50

| Compound No. | $C_0$ Mean (nmol/L) | $C_0$ CV (%) | $C_I$ Mean (L/h/kg) | $C_I$ CV (%) | $T_{1/2}$ Mean (h) | $T_{1/2}$ CV (%) | $AUC_{Last}$ Mean (h * nmol/L) | $AUC_{Last}$ CV (%) | $AUC_{Inf}$ Mean (h * nmol/L) | $AUC_{Inf}$ CV (%) |
|---|---|---|---|---|---|---|---|---|---|---|
| 7 | 212 | 19.8 | 17.7 | 28.1 | 5.31 | 33.8 | 659 | 15 | 1000 | 33.4 |
| 30 | 311 | 7.86 | 8.59 | 26.7 | 3.62 | 19.8 | 2010 | 23.8 | 2030 | 24.4 |
| 46 | 301 | 11.4 | 6.73 | 7.43 | 5.65 | 24.9 | 2350 | 4.25 | 2490 | 7.12 |
| 60 | 425 | 12.4 | 5.48 | 8.91 | 5.61 | 15.9 | 2910 | 9.18 | 3050 | 8.68 |
| 79 | 663 | 10.1 | 13.7 | 9.99 | 1.38 | 7.1 | 1200 | 9.38 | 1220 | 9.61 |
| 103 | 199 | 18.1 | 1.56 | 39.4 | 63 | 39.6 | 2790 | 15 | 12300 | 50.8 |
| 105 | 411 | 21.5 | 1.77 | 11.6 | 27.1 | 12.6 | 4410 | 3.91 | 9520 | 11 |

TABLE 51

| Compound No. | $C_{Max}$ Mean (nmol/L) | $C_{Max}$ CV (%) | $T_{Max}$ Mean (h) | $T_{Max}$ CV (%) | $T_{1/2}$ Mean (h) | $T_{1/2}$ CV (%) | $AUC_{Last}$ Mean (h * nmol/L) | $AUC_{Last}$ CV (%) | $AUC_{Inf}$ Mean (h * nmol/L) | $AUC_{Inf}$ CV (%) | Bioavailability (%) |
|---|---|---|---|---|---|---|---|---|---|---|---|
| 7[a] | 224 | 30.7 | 3.33 | 34.6 | NA | NA | 2400 | 30.5 | NA | NA | 110 |
| 7[b] | 610 | 50.5 | 3.33 | 34.6 | NA | NA | 7820 | 58.4 | NA | NA | 105 |
| 30[a] | 276 | 27.5 | 3.33 | 34.6 | NA | NA | 3250 | 21.5 | NA | NA | 53.9 |
| 46[a] | 462 | 7.53 | 3.33 | 34.6 | 5.73 | NA | 6280 | 3.68 | NA | NA | 89 |
| 60[a] | 152 | 14.2 | 5.33 | 43.3 | NA | NA | 2430 | 15.9 | NA | NA | 27.9 |
| 79[a] | 508 | 34.5 | 1 | 0 | 2.53 | 22.4 | 2270 | 28.4 | 2420 | 26.6 | 65.9 |
| 103[a] | 40.2 | 14.8 | 8 | 0 | NA | NA | 794 | 13.6 | NA | NA | 9.49 |
| 105[a] | 592 | 6.15 | 6.67 | 34.6 | NA | NA | 11900 | 2.68 | NA | NA | 90.2 |

[a]Dosage of 3 mg/kg;
[b]Dosage of 10 mg/kg;
NA not available

In Vivo Models

Efficacy Study AHR Antagonist and Checkpoint Inhibitor Anti-PD-1 in the Mouse Colorectal Cancer Model CT26 in Balb/c Mice Female mice between six and eight weeks of age were obtained from Charles River Laboratory (C57BL/6NCrl). Mouse tumor cell lines WT-CT26 were obtained from American Type Culture Collection, tested for *mycoplasma* and other pathogens at Charles River Research Animal Diagnostics services, and cultured according to their guidelines. All studies were conducted in accordance with the CRADL Policy on the Care, Welfare and Treatment of Laboratory Animals. Mice from the day the tumor were inoculated, were monitored a minimum of three times per week by the investigator or veterinary staff for clinical abnormalities which may require euthanasia. These included chronic and/or severe diarrhea leading to moderate to severe dehydration, evidence of infection that is not readily treatable, hunched posture in conjunction with other clinical signs if debilitating or prolonged for greater than three days, inability/unwillingness to ambulate to reach food or water, or other clinical signs judged by experienced technical staff to be indicative of morbidity or being in a moribund condition. Mice showing a net body weight loss>20% compared to baseline weight measurement were euthanized.

CT26 is a murine colon carcinoma cell line obtained from ATCC. CT26 cells were cultured in RPMI supplemented with 10% FBS. Low passage CT26 cells were resuspended at $5\times10^5$ cells/ml in in 100 μL PBS were implanted subcutaneously on the shaved right lower flank of 6-8-week-old Balb/c mice. The day of the subcutaneous tumor cell implant was defined as Day 0.

Once enrollment criteria was been achieved, animals were distributed into treatment groups such that the mean tumor burden in each group is within 10% of the overall mean. Mice were dosed individually by body weight on the day of treatment.

After 1 week from inoculation, mice with an average size of tumor of ~60 $mm^3$ were randomized and available to start treatment. (FIG. 1) AhR antagonist was dosed orally, every day (QD) at 1 mg/kg, 3 mg/kg, or 10 mg/kg for 14 days. Anti-PD-1 (BioXcell RMPl-14) or anti-PD-L1 was dosed, three times intraperitoneally at 100 μg/kg every three days starting at day 14.

Tumors were monitored via perpendicular tumor diameter measurements and calculated using the formula ($mm^3$) $=0.52\times(\text{length})\times(\text{width})^2$ and by caliper measurement every day and body weight was measured three times per week. At the end point, tumors were recovered and analyzed by Flowcytometry and or IHC for infiltrated tumor immune cells.

AHR-Dependent Gene Expression in Tumor, Spleen and Liver

AHR-dependent gene expression will be measured in tissue samples such as tumor or liver. RNA will be extracted from the tissue via RNA isolation kit such as Qiagen. The RNA extraction will be done from total cells or cells post-sorting for specific populations of cells such as tumor cells, tumor associated-T cells, tumor associated-myeloid cells, Tumor associate-macrophages or others. Gene expression will be determined by quantitative RT-PCR using probes for specific genes including a housekeeping gene such as Gapdh for normalization. AHR-dependent genes will be examined include but are not limited to: CYP1A1, CYP1B1, AHRR, IDO1, IDO2, IL22, IL6, VEGFA, STAT3, cdc2, MMP13, MMP-9.

Example 14: Drug Metabolism and Pharmacokinetic Profiles for Compound Nos. 9 and 46

Compound Nos. 9 and 46 have the following in vitro DMPK profiles.

TABLE 52

| Compound No. | 46 | 9 |
|---|---|---|
| Human hepatocyte intrinsic clearance, suspension Hheps $Cl_{Int}$ (% Qh) Plated heps (% Qh) | <31<br><1 (1.0 All) | <31<br>2.1 (0.6 All) |
| Suspension Rat/mou. heps $Cl_{int}$ (% Qh) | <24/<33 | <24/<33 |
| Suspension Monkey heps $Cl_{Int}$ (% Qh) | <24 (@1 and 0.1 mM) | <24 (@1 and 0.1 mM) |
| Plasma Protein Binding PPB (h/m/r/d/mon) % | 89.2/92.5/89.8/ 89.0/88.7 | 89.1/89.6/90.2/ 87.6/85.1 |
| Caco 2 apparent permeability $P_{app\ (A-B)/(B-A)}$ ($10^{-6}$, cm/s) (+0.5% BSA) | 12.6/16.4 | 9.6/25 |
| CYP Inhibition | Negative | Negative |

Compound Nos. 9 and 46 have the following in vivo DMPK profiles.

TABLE 53

| Compound No. | 46 | 9 |
|---|---|---|
| Mouse $T_{1/2}$ (h) | 15.7 | 5.4 |
| Mouse CL (ml/min/kg) | 1.8 (2% Qh) | 3.4 (3.85% Qh) |
| Mouse Vss (L/kg) | 2.3 | 1.9 |
| Mouse % F | 80.6 | 70.3 |
| Rat $T_{1/2}$ (h) | 5.6 | 5.4 |
| Rat CL (ml/min/kg) | 6.7 (9% Qh) | 4.1 (5.8% Qh) |
| Rat Vss (L/kg) | 3.1 | 1.75 |
| Rat % F | 89 | 77 |

Figure 14:
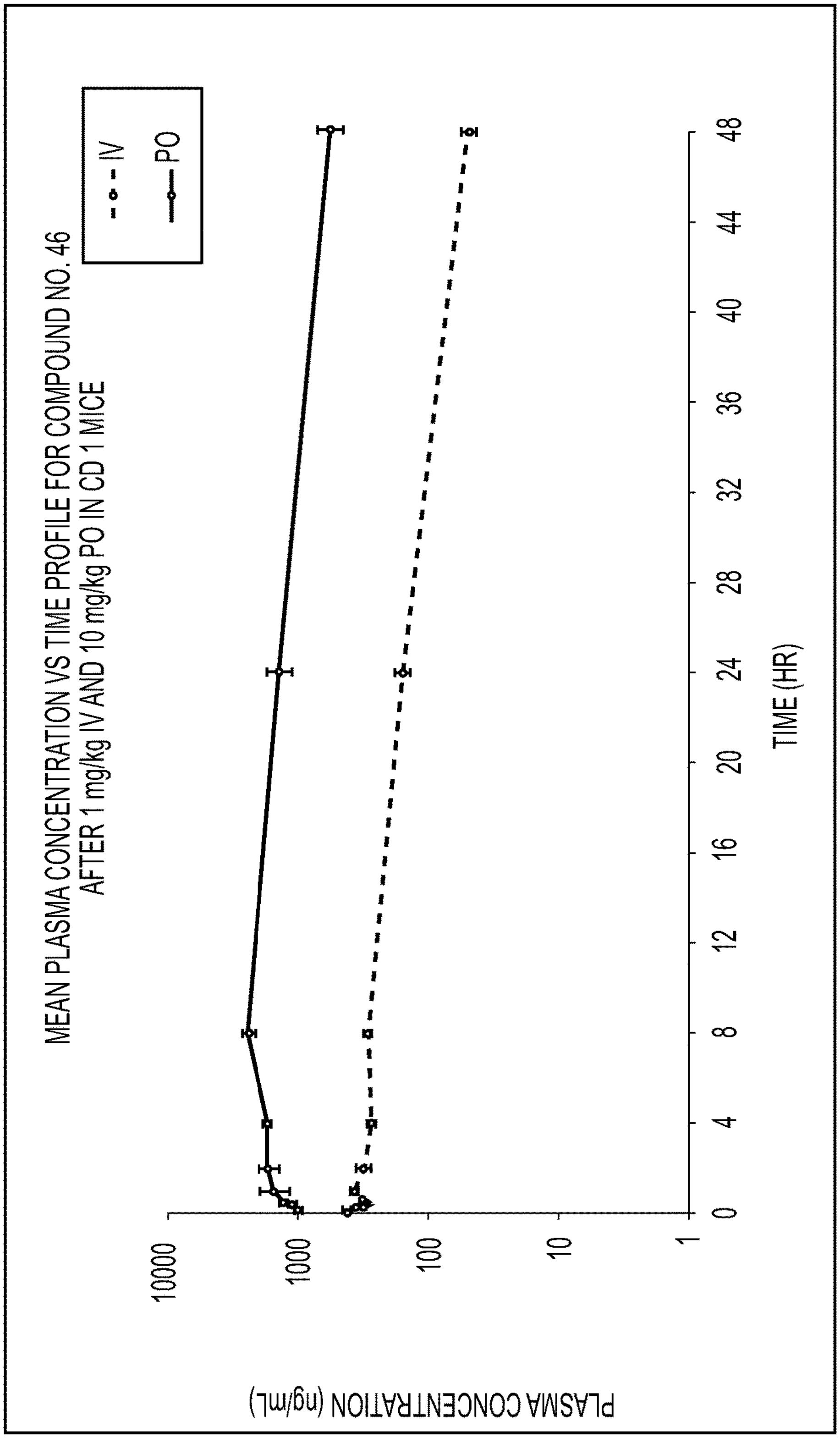
FIG. 14 shows a plot of the mean plasma concentration over time for Compound No. 46 after 1 mg/kg IV and 10 mg/kg PO in CD1 mice.
Figure 15:
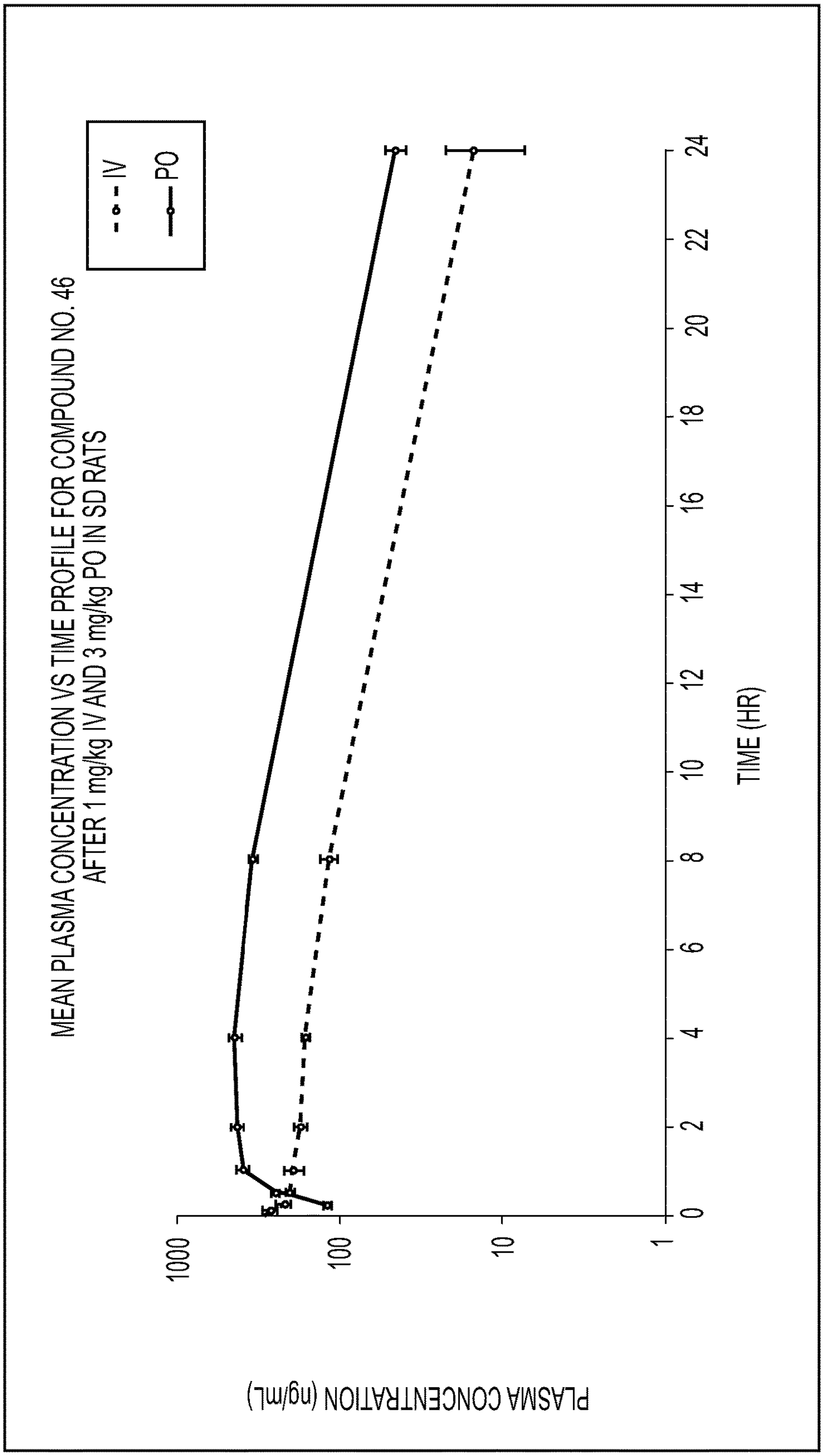
FIG. 15 shows a plot of the mean plasma concentration over time for Compound No. 46 after 1 mg/kg IV and 3 mg/kg PO in SD rats.

A plot of the mean plasma concentration over time for Compound No. 46 after 1 mg/kg IV and 10 mg/kg PO in CD1 mice is shown in FIG. 14. A plot of the mean plasma concentration over time for Compound No. 46 after 1 mg/kg IV and 3 mg/kg PO in SD rats is shown in FIG. 15.

Figure 16:
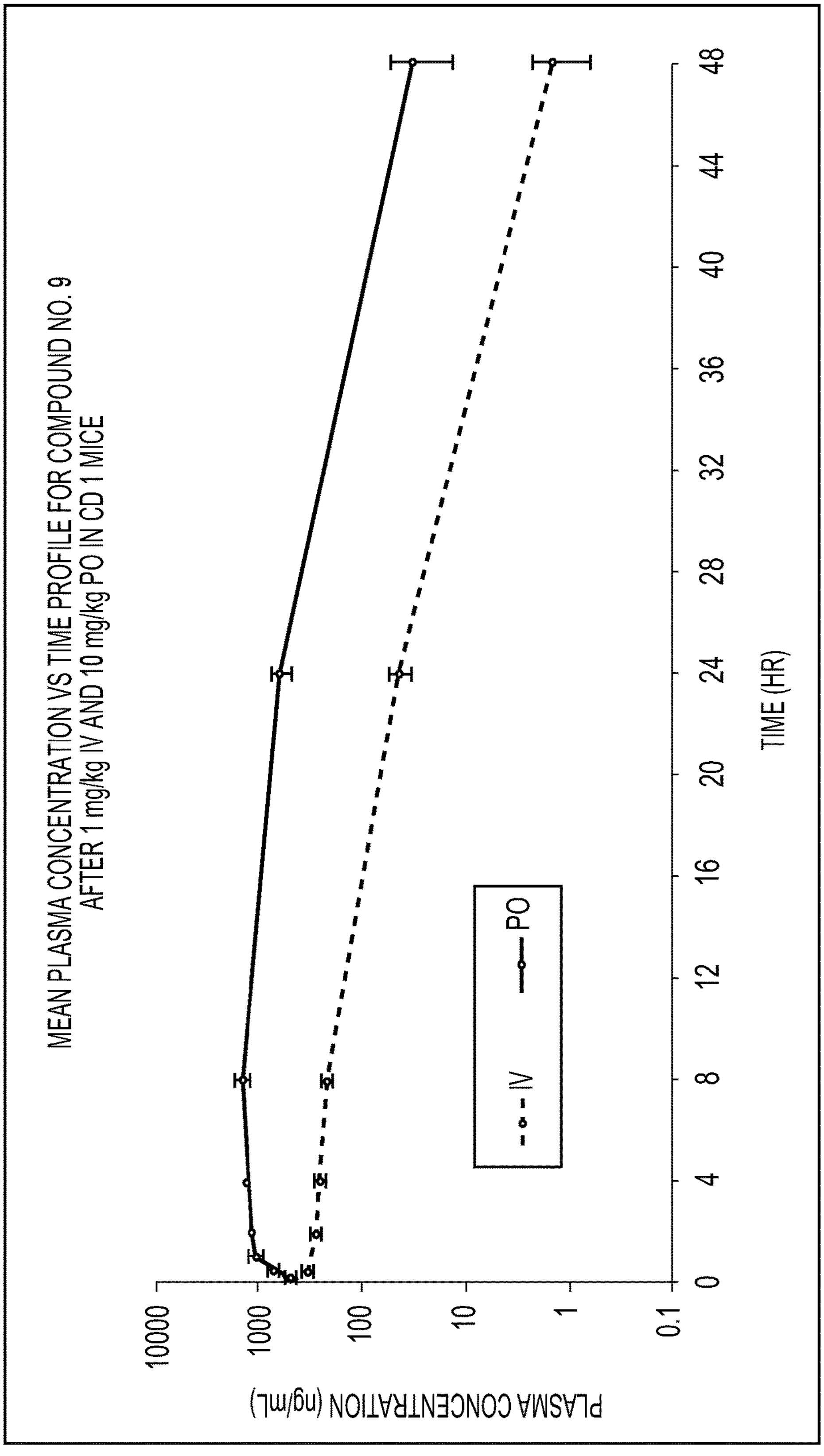
FIG. 16 shows a plot of the mean plasma concentration over time for Compound No. 9 after 1 mg/kg IV and 10 mg/kg PO in CD1 mice.
Figure 17:
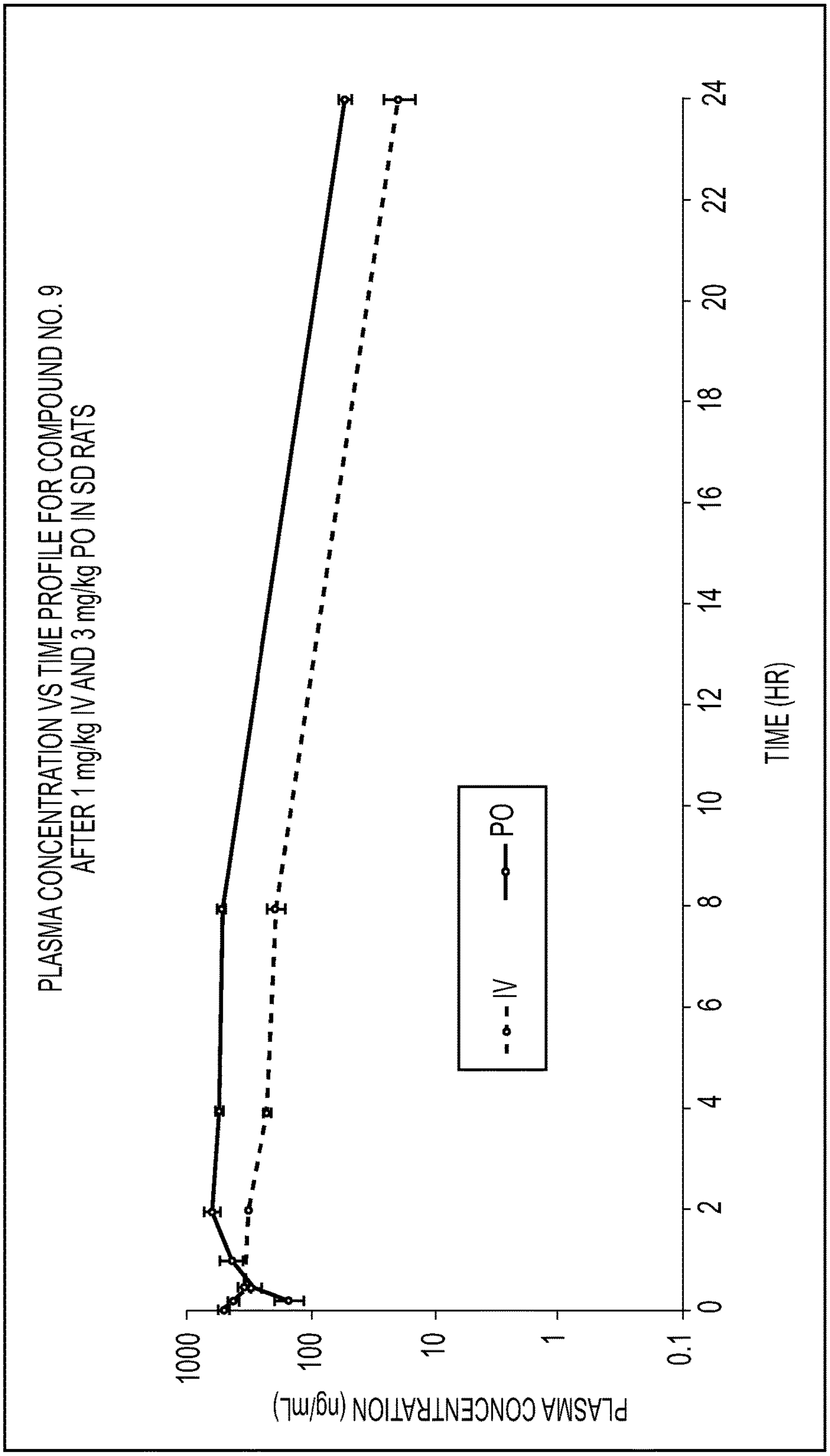
FIG. 17 shows a plot of the mean plasma concentration over time for Compound No. 9 after 1 mg/kg IV and 3 mg/kg PO in SD rats.

A plot of the mean plasma concentration over time for Compound No. 9 after 1 mg/kg IV and 10 mg/kg PO in CD1 mice is shown in FIG. 16. A plot of the mean plasma concentration over time for Compound No. 9 after 1 mg/kg IV and 3 mg/kg PO in SD rats is shown in FIG. 17.

Example 15: Combination Therapy with Immune Checkpoint Inhibitors (ICIs)

Studies were conducted to identify potent selective, low dose modulators of the aryl hydrocarbon receptor that antagonized the activity of tryptophan metabolites alone or in combination with checkpoint inhibitors (ICIs) for multiple types of cancer.

Figure 2:
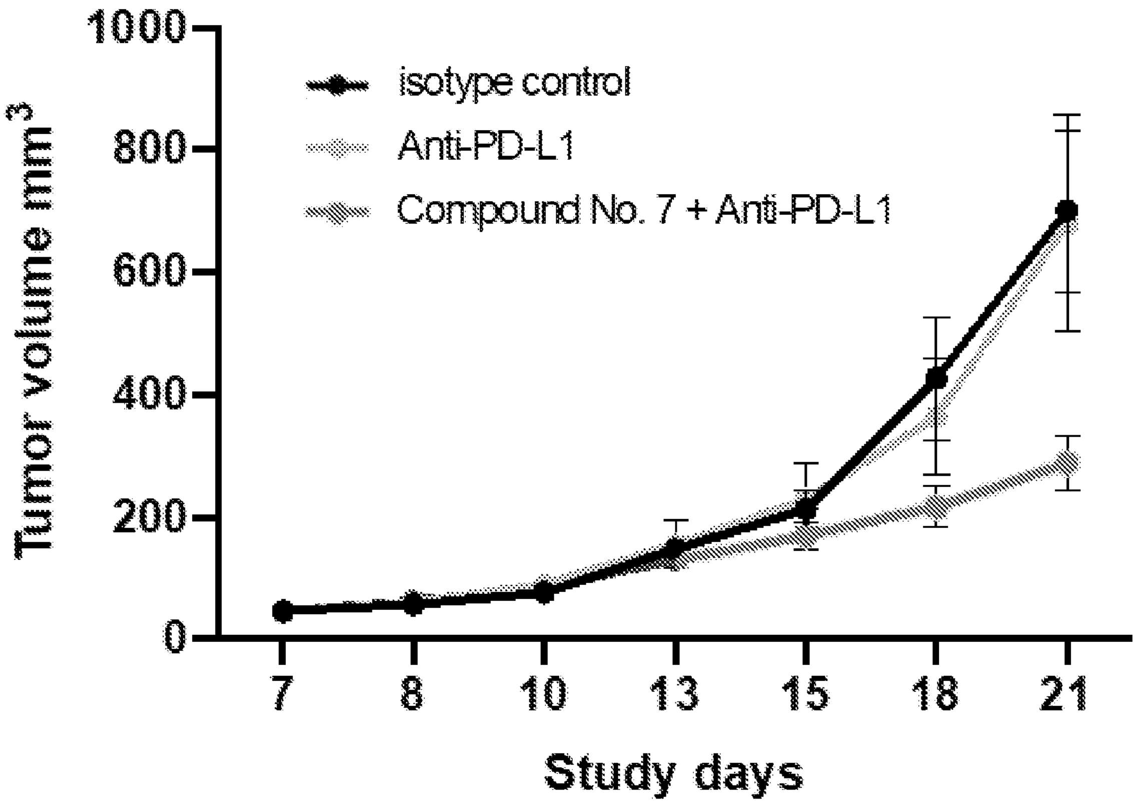
FIG. 2 shows the tumor growth curves of the vehicle versus single agent PD-L1 antibody or PD-L1 antibody with Compound No. 7 in a syngeneic colon cancer mouse model resistant to anti-PD-L1 therapy.
Figure 3:
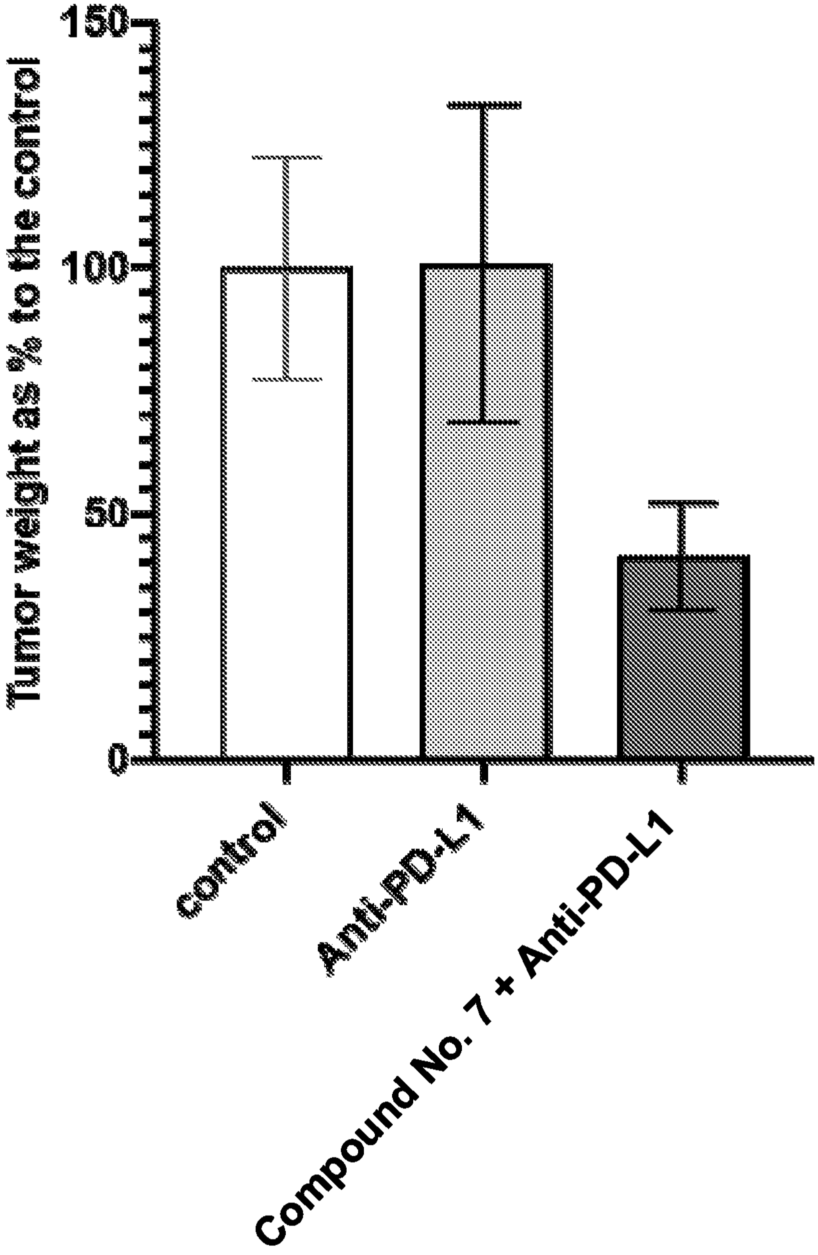
FIG. 3 shows tumor weight upon termination of study of the vehicle versus single agent PD-L1 antibody or PD-L1 antibody with Compound No. 7 in a syngeneic colon cancer mouse model resistant to anti-PD-L1 therapy.

The antitumor efficacy of Compound No. 7 in the CT26 syngeneic model. CT26 cells were implanted subcutaneously into Balb/c mice which were then randomized and treated either with a PD-L1 antibody alone or with a PD-L1 antibody in combination with Compound No. 7. Compound No. 7 was dosed PO, 3 mg/kg, p.o. once a day over 14 days of dosing combined with anti-PD-L1 antibody dosed at 10 mg/kg IP every 3 days. The tumor growth curves of the vehicle versus single agent PD-L1 antibody or PD-L1 antibody with Compound No. 7 are shown in FIG. 2. The coadministration of Compound No. 7 with PD-L1 antibody showed a reduction in tumor volume p=0.0039 (Mann-Whitney, non-parametric test). Also, the tumor weight upon termination of study of the vehicle versus single agent PD-L1 antibody or PD-L1 antibody with Compound No. 7 are shown in FIG. 3. Coadministration of Compound No. 7 with PD-L1 antibody showed a reduction in tumor weight p=0.041 (Mann-Whitney, non-parametric test).

Figure 4:
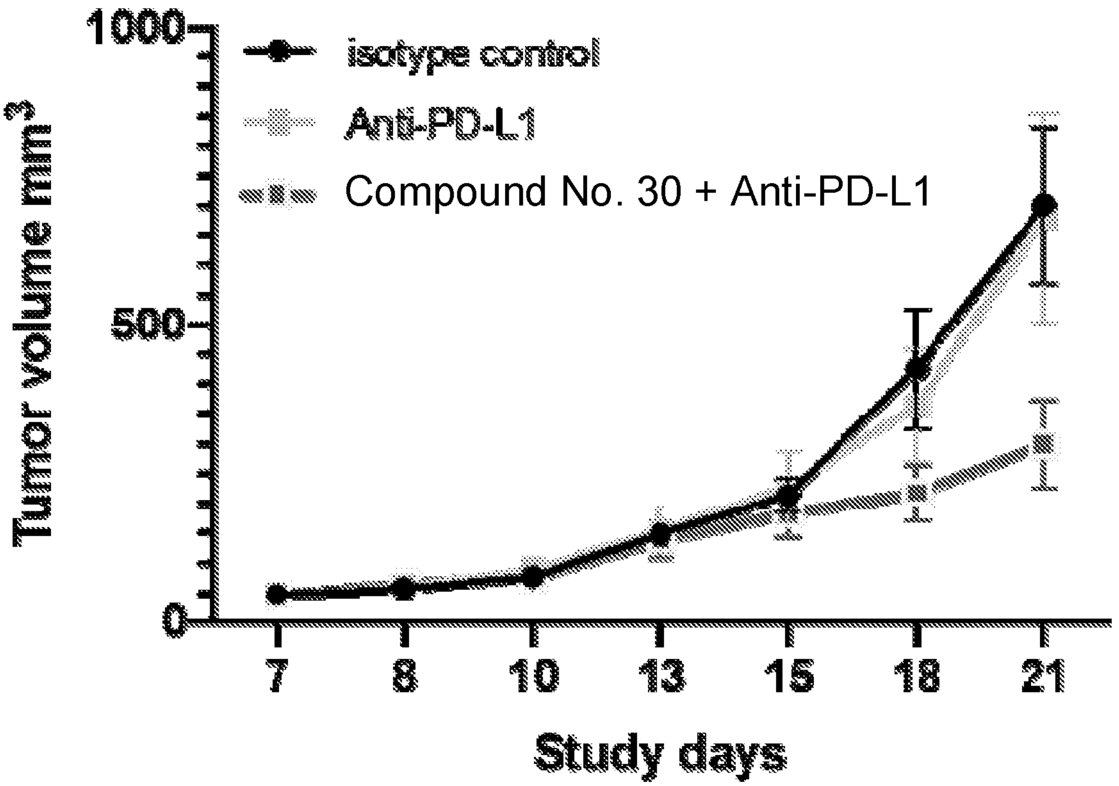
FIG. 4 shows the tumor growth curves of the vehicle versus single agent PD-L1 antibody or PD-L1 antibody with Compound No. 30 in a syngeneic colon cancer mouse model resistant to anti-PD-L1 therapy.
Figure 5:
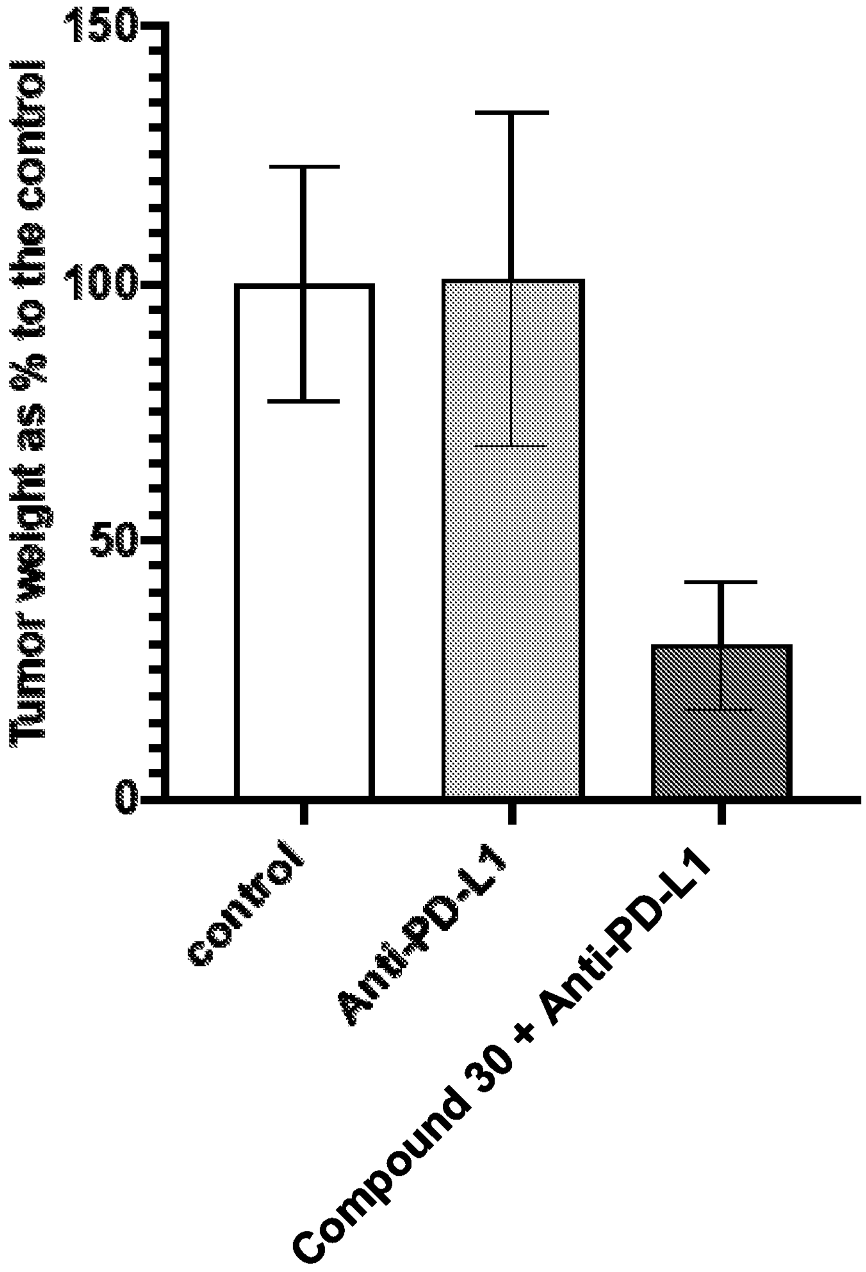
FIG. 5 shows tumor weight upon termination of study of the vehicle versus single agent PD-L1 antibody or PD-L1 antibody with Compound No. 30 in a syngeneic colon cancer mouse model resistant to anti-PD-L1 therapy.
Figure 6:
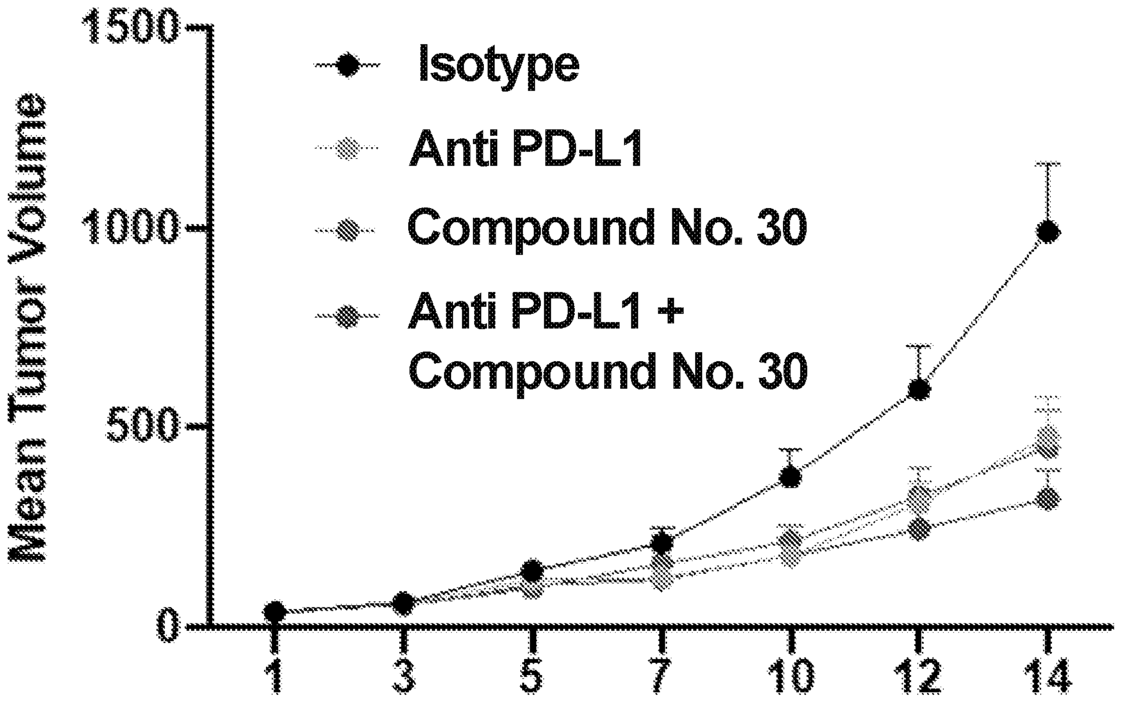
FIG. 6 shows the tumor growth curves of the vehicle versus single agent PD-L1 antibody or PD-L1 antibody with Compound No. 30 in a syngeneic colon cancer mouse model resistant to anti-PD-L1 therapy.
Figure 7:
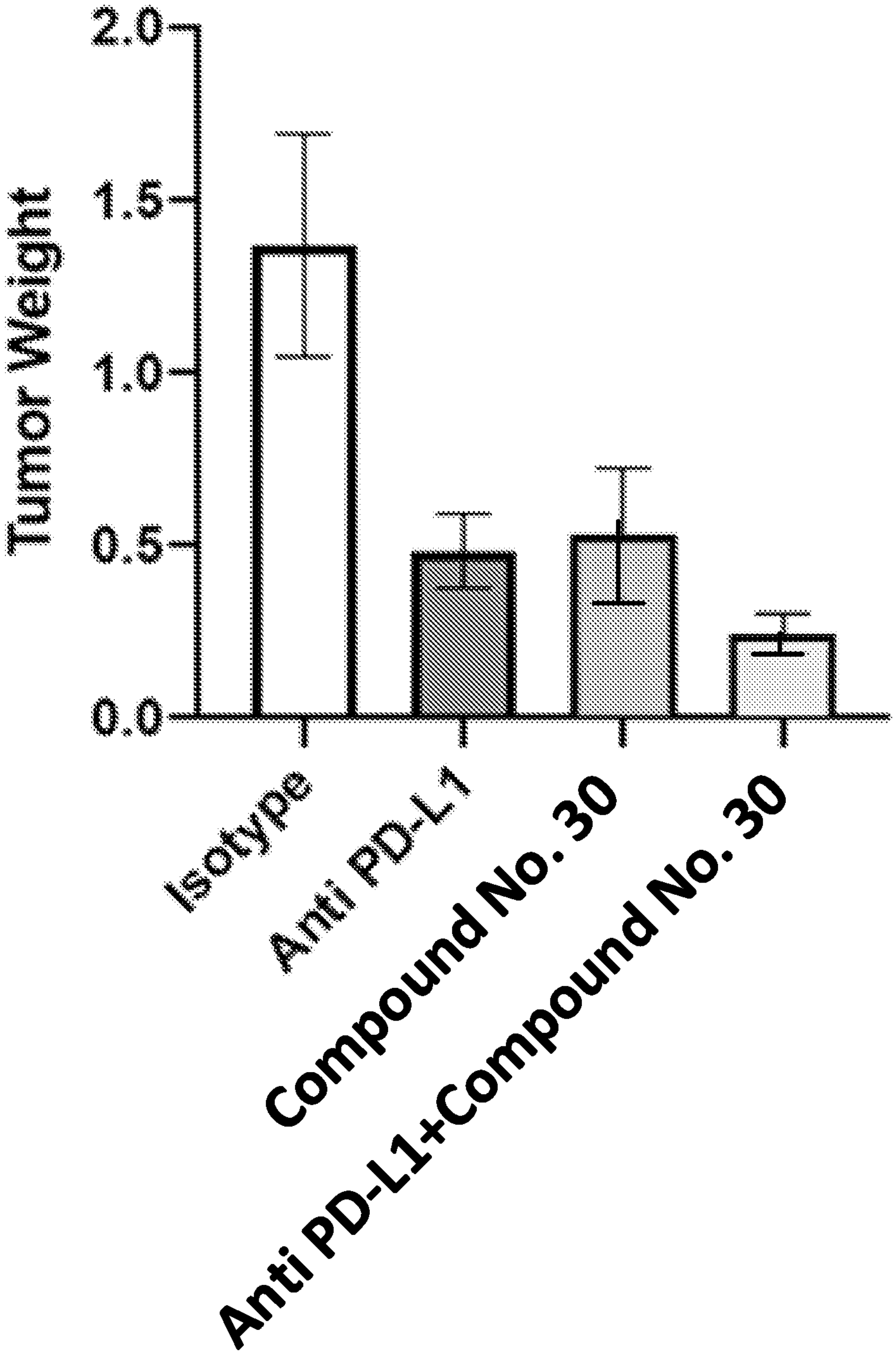
FIG. 7 shows tumor weight upon termination of study of the vehicle versus single agent PD-L1 antibody or PD-L1 antibody with Compound No. 30 in a syngeneic colon cancer mouse model resistant to anti-PD-L1 therapy.

The antitumor efficacy of Compound No. 30 in the CT26 syngeneic model. CT26 cells were implanted subcutaneously into Balb/c mice which were then randomized and treated either with Compound No. 30 alone, PD-L1 antibody alone, or a PD-L1 antibody in combination with Compound No. 30. Compound No. 30 was dosed PO, 10 mg/kg, p.o. once a day over 14 days of dosing combined with anti-PD-L1 antibody dosed at 10 mg/kg IP every 3 days. The tumor growth curves of the vehicle versus single agent PD-L1 antibody or Compound No. 30 alone or PD-L1 antibody with Compound No. 30 are shown in FIGS. 4 and 6. The coadministration of Compound No. 30 with PD-L1 antibody showed a reduction in tumor volume p=0.039 (FIG. 4, Mann-Whitney, non-parametric test) and p=0.350 (FIG. 6, Kruskal Wallis test followed by non-parametric Dunn's multiple comparison test). Also, the tumor weight upon termination of study of the vehicle versus single agent PD-L1 antibody or Compound No. 30 alone, or PD-L1 antibody with Compound No. 30 are shown in FIGS. 5 and 7. Coadministration of Compound No. 30 with PD-L1 antibody showed a reduction in tumor weight p=0.067 (FIG. 5, Mann-Whitney, non-parametric test) and p=0.0004 (FIG. 7, Kruskal Wallis test followed by non-parametric Dunn's multiple comparison test).

Figure 8:
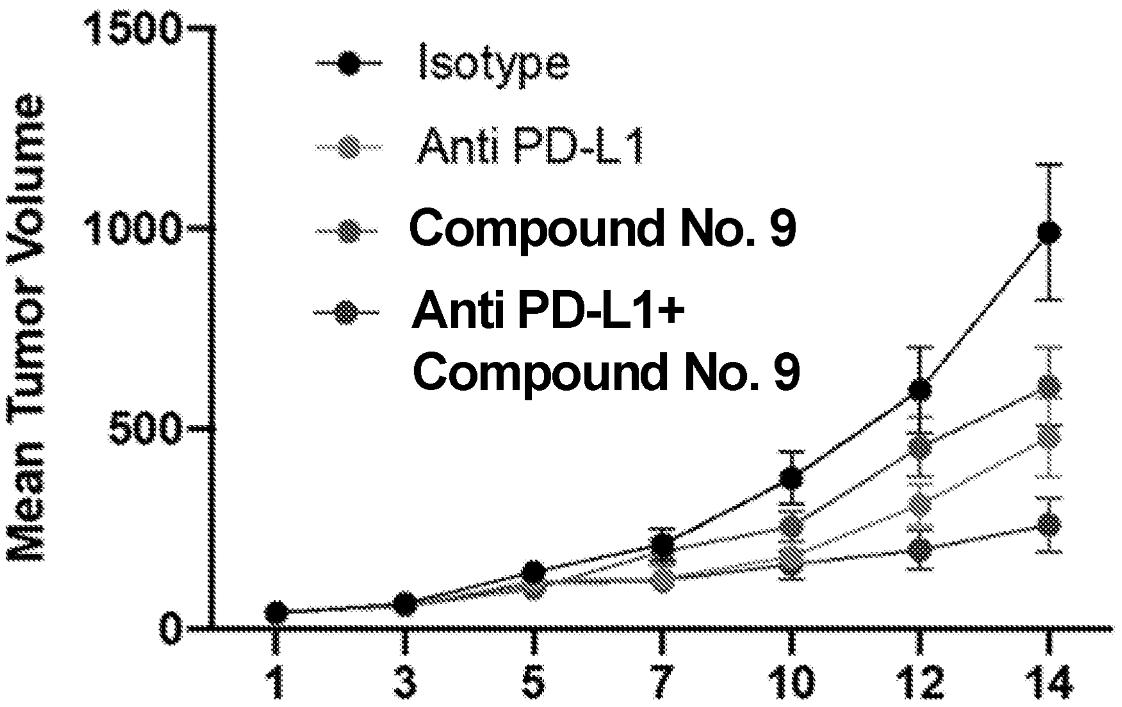
FIG. 8 shows the tumor growth curves of the vehicle versus single agent PD-L1 antibody or PD-L1 antibody with Compound No. 9 in a syngeneic colon cancer mouse model resistant to anti-PD-L1 therapy.
Figure 9:
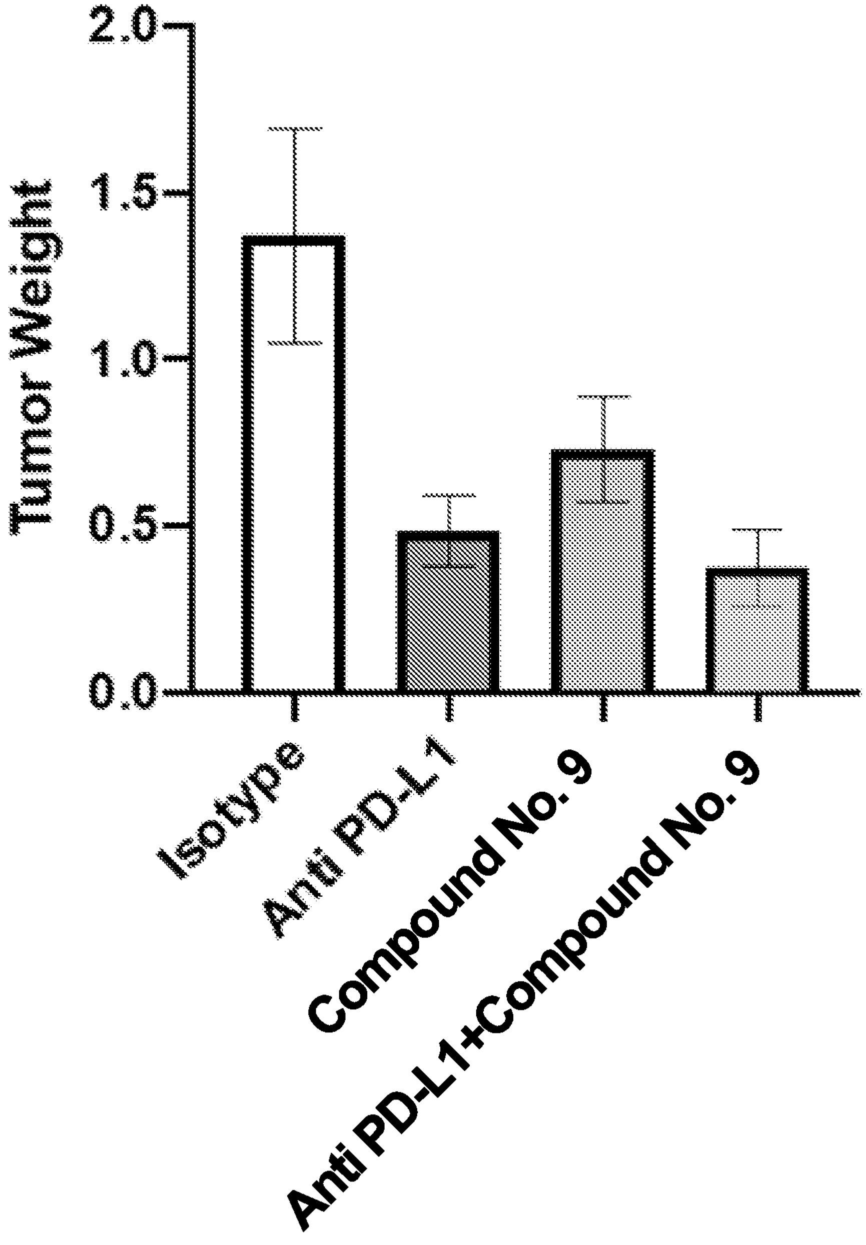
FIG. 9 shows tumor weight upon termination of study of the vehicle versus single agent PD-L1 antibody or PD-L1 antibody with Compound No. 9 in a syngeneic colon cancer mouse model resistant to anti-PD-L1 therapy.
Figure 10:
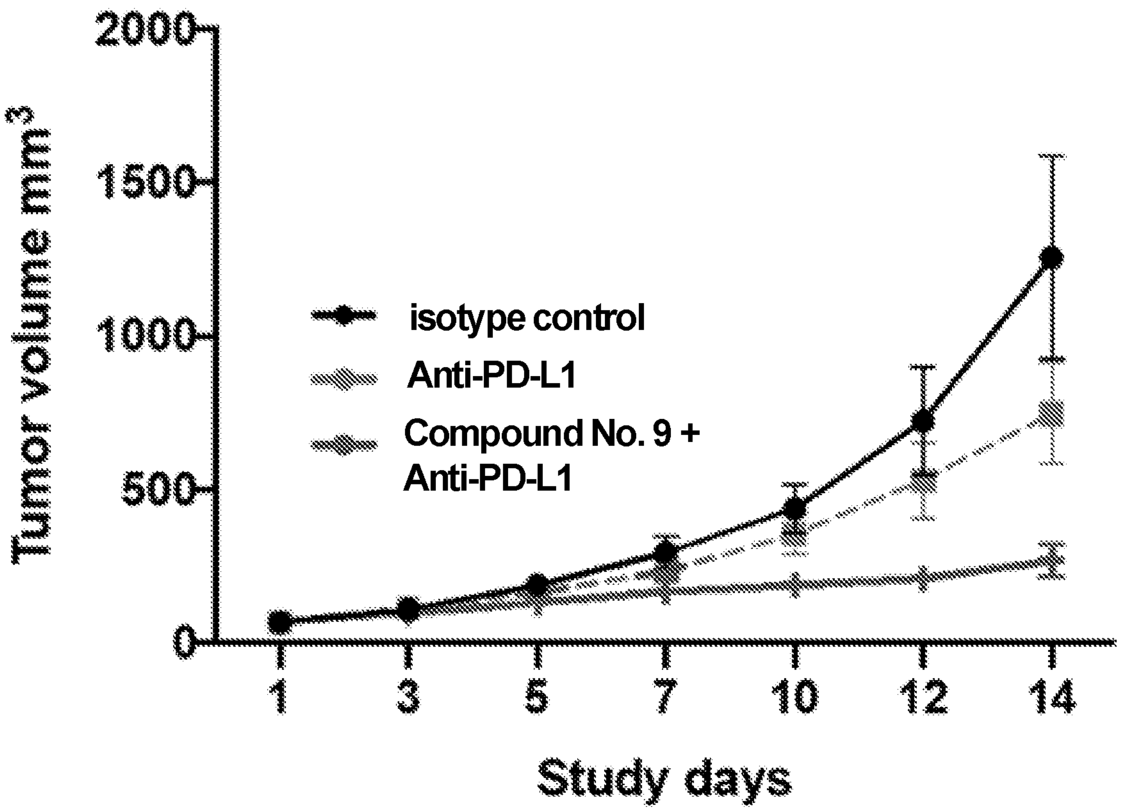
FIG. 10 shows the tumor growth curves of the vehicle versus single agent PD-L1 antibody or PD-L1 antibody with Compound No. 9 in a syngeneic colon cancer mouse model resistant to anti-PD-L1 therapy.
Figure 11:
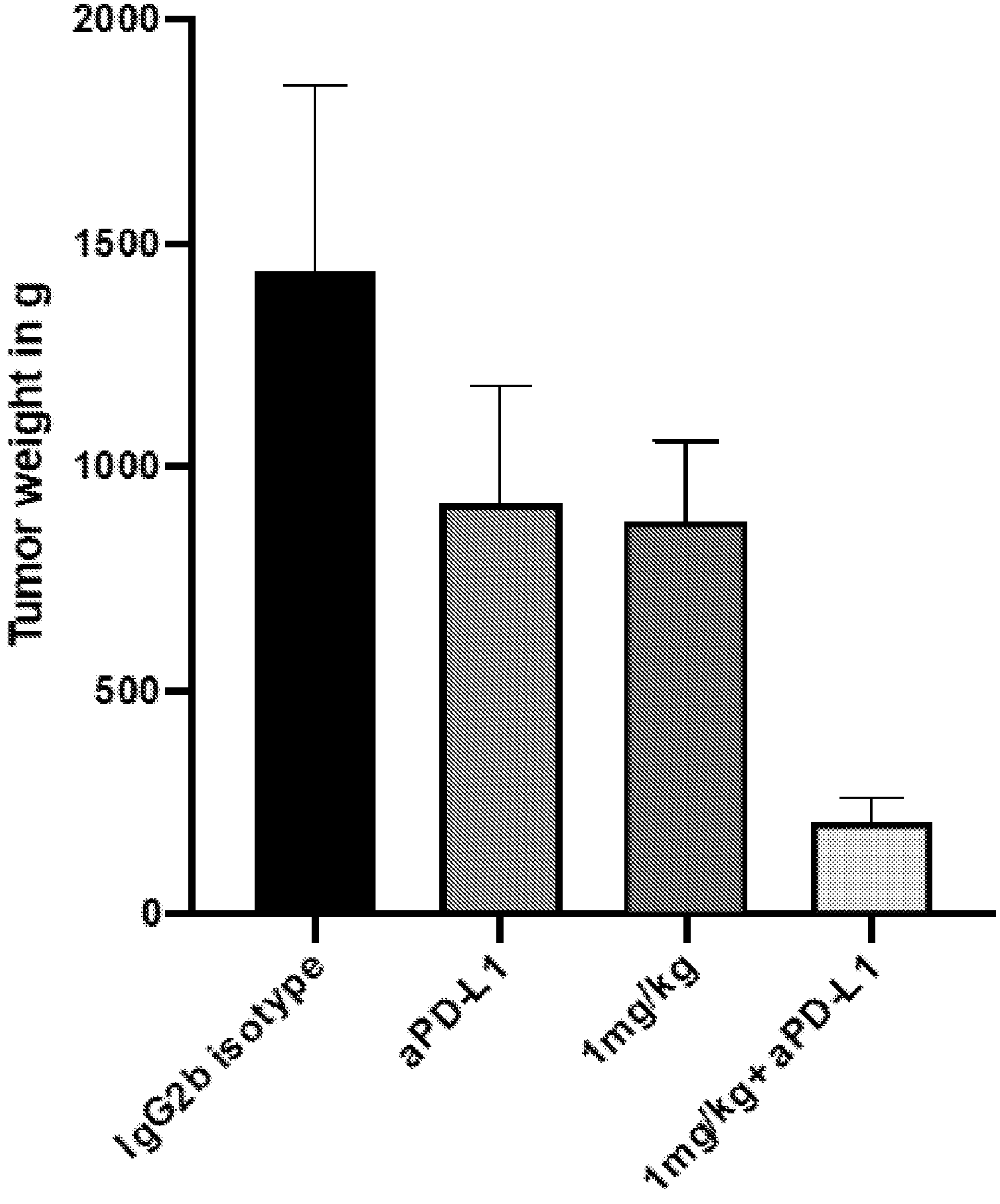
FIG. 11 shows tumor weight upon termination of study of the vehicle versus single agent PD-L1 antibody or PD-L1 antibody with Compound No. 9 in a syngeneic colon cancer mouse model resistant to anti-PD-L1 therapy.

The antitumor efficacy of Compound No. 9 in the CT26 syngeneic model. CT26 cells were implanted subcutaneously into Balb/c mice which were then randomized and treated wither with Compound No. 9 alone, PD-L1 antibody alone, or a PD-L1 antibody in combination with Compound No. 9. Compound No. 9 was dosed PO, 10 mg/kg (FIG. 8) or 1 mg/kg (FIG. 10), p.o. once a day over 14 days of dosing combined with anti-PD-L1 antibody dosed at 10 mg/kg IP every 3 days. The tumor growth curves of the vehicle versus single agent PD-L1 antibody or Compound No. 9 alone or PD-L1 antibody with Compound No. 9 are shown in FIGS. 8 and 10. The coadministration of Compound No. 9 with PD-L1 antibody showed a reduction in tumor volume p=0.0070 (FIG. 8, Mann-Whitney, non-parametric test) and p=0.0039 (FIG. 10, Kruskal Wallis test followed by non-parametric Dunn's multiple comparison test). Also, the tumor weight upon termination of study of the vehicle versus single agent PD-L1 antibody or Compound No. 9 alone, or PD-L1 antibody with Compound No. 9 are shown in FIGS. 9 and 11. Coadministration of Compound No. 9 with PD-L1 antibody showed a reduction in tumor weight p=0.0114 (FIG. 9, Mann-Whitney, non-parametric test) and p=0.0029 (FIG. 11, Kruskal Wallis test followed by non-parametric Dunn's multiple comparison test). Overall, Compound No. 9 in combination with PD-L1 decreases tumor volume and weight compared to PD-L1 alone.

Figure 12:
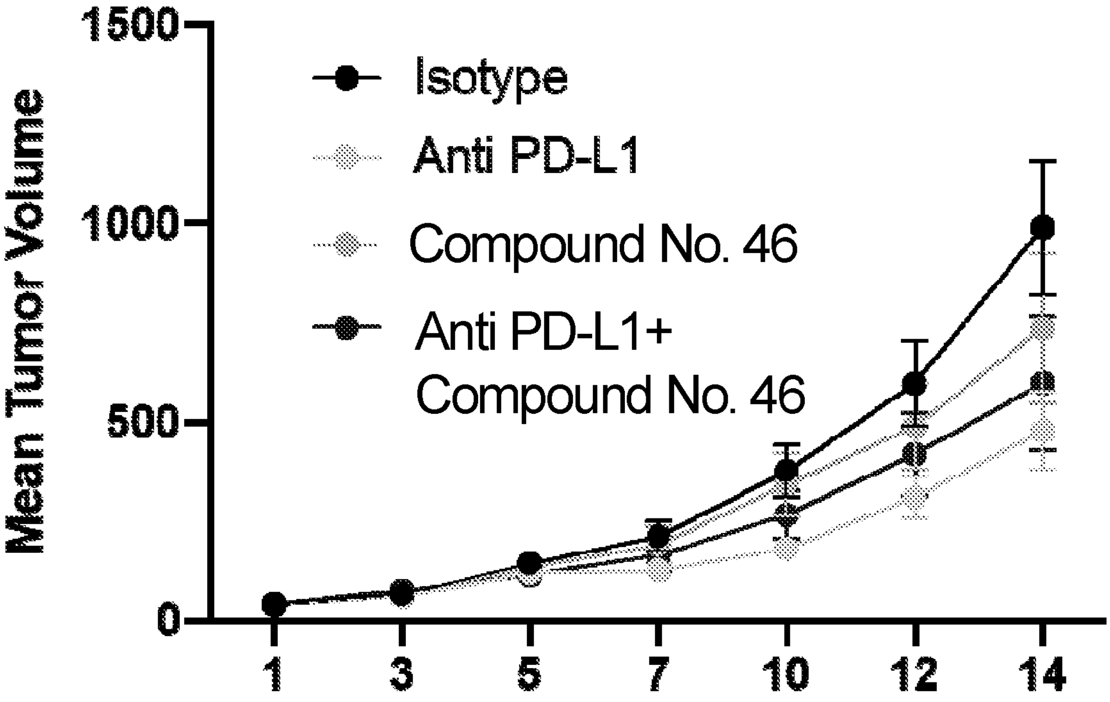
FIG. 12 shows the tumor growth curves of the vehicle versus single agent PD-L1 antibody or PD-L1 antibody with Compound No. 46 in a syngeneic colon cancer mouse model resistant to anti-PD-L1 therapy.
Figure 13:
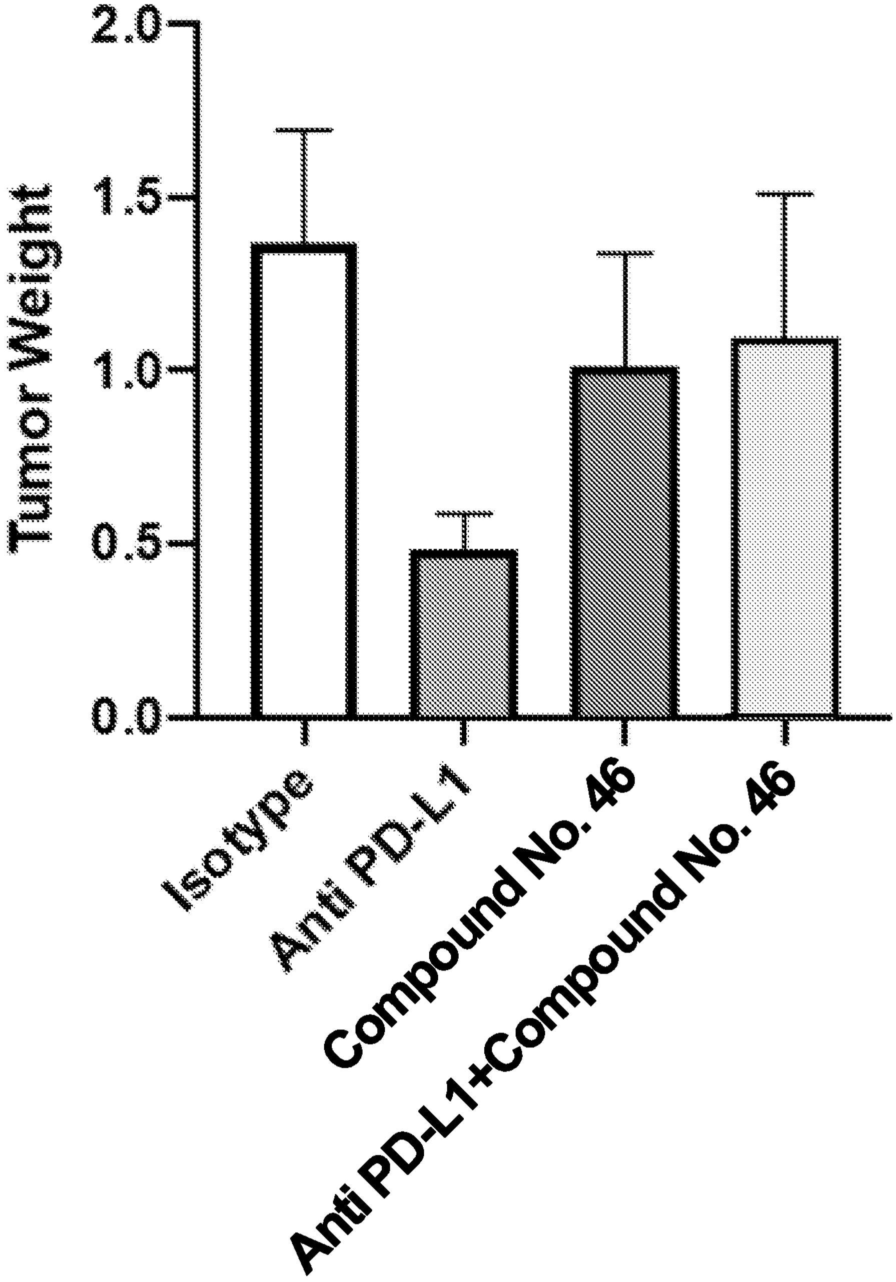
FIG. 13 shows tumor weight upon termination of study of the vehicle versus single agent PD-L1 antibody or PD-L1 antibody with Compound No. 46 in a syngeneic colon cancer mouse model resistant to anti-PD-L1 therapy.

The antitumor efficacy of Compound No. 46 in the CT26 syngeneic model. CT26 cells were implanted subcutaneously into Balb/c mice which were then randomized and treated wither with Compound No. 46 alone, PD-L1 antibody alone, or a PD-L1 antibody in combination with Compound No. 46. Compound No. 46 was dosed PO, 10 mg/kg, p.o. once a day over 14 days of dosing combined with anti-PD-L1 antibody dosed at 10 mg/kg IP every 3 days. The tumor growth curves of the vehicle versus single agent PD-L1 antibody or Compound No. 46 alone or PD-L1 antibody with Compound No. 46 are shown in FIG. 12. The coadministration of Compound No. 46 with PD-L1 antibody showed a reduction in tumor volume. Also, the tumor weight upon termination of study of the vehicle versus single agent PD-L1 antibody or Compound No. 46 alone, or PD-L1 antibody with Compound No. 46 are shown in FIG. 13. Coadministration of Compound No. 46 with PD-L1 antibody showed a reduction in tumor weight.

TABLE 54

Data for in vivo pharmacology for CT26 model

| Compound No. | Dose (mg/kg) | $C_{max}$ (nM) | $C_{min}$ (nm) | Mouse CYP1A1 $IC_{50}$ |
|---|---|---|---|---|
| 30 | 10 | 5,880 | 1,725 | 2.9 nM (~56% eff) (n = 3) |
| 9 | 10 | 4,964 | 849 | 2.7 nM (~55% eff) (n = 3) |
| 46 | 10 | 17,339 | 12,350 | 18.5 nM (~96% eff) (n = 4) |

The invention claimed is:

1. A compound of Formula Ia (Ia)

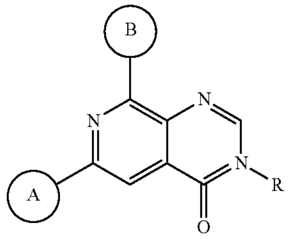

or a pharmaceutically acceptable salt thereof, wherein:

ring A is chosen from optionally substituted aryls, optionally substituted heteroaryls, optionally substituted cycloalkyls, and optionally substituted heterocycloalkyls;

ring B is chosen from optionally substituted aryls, optionally substituted heteroaryls, optionally substituted cycloalkyls, and optionally substituted heterocycloalkyls; and R is chosen from hydrogen, optionally substituted alkyls, optionally substituted acyls, optionally substituted amides, optionally substituted aryls, optionally substituted cycloalkyls, optionally substituted esters, optionally substituted heteroalkyls, optionally substituted heteroaryls, optionally substituted heterocycloalkyls, amino, cyano, halos, hydroxy, and —C(O)H.

2. The compound of claim 1, or a pharmaceutically acceptable salt thereof, wherein:

ring A is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^A$, ring B is chosen from 6-10 membered aryls, 5-10 membered heteroaryls, 3-10 membered cycloalkyls, and 3-10 membered heterocycloalkyls, wherein each 6-10 membered aryl, 5-10 membered heteroaryl, 3-10 membered cycloalkyl, and 3-10 membered heterocycloalkyl is independently optionally substituted with 1 to 5 instances of $R^B$;

R is chosen from hydrogen, $C_1$-$C_{10}$ alkyls, 6-10 membered aryls, —C(O)R', —C(O) NR'R', 3-10 membered cycloalkyls, —C(O) OR', $C_1$-$C_{10}$ heteroalkyls, 5-10 membered heteroaryls, 3-10 membered heterocycloalkyls, amino, cyano, halos, hydroxy, and —C(O)H, wherein each $C_1$-$C_{10}$ alkyl, 6-10 membered aryl, 3-10 membered cycloalkyl, $C_1$-$C_{10}$ heteroalkyl, 5-10 membered heteroaryl, and 3-10 membered heterocycloalkyl is independently optionally substituted with 1 to 5 instances of $R^C$;

each R' is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls;

each $R^A$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^B$ is independently chosen from halos, hydroxy, $C_1$-$C_{10}$ alkyls, $C_1$-$C_{10}$ haloalkyls, $C_1$-$C_{10}$ alkoxys, $C_1$-$C_{10}$ haloalkoxys, $C_1$-$C_{10}$ hydroxyalkyls, and NR"R";

each $R^C$ is independently chosen from halos, hydroxy, cyano, $C_1$-$C_{10}$ alkyls, $C_1$-$C_{10}$ alkoxys, $C_1$-$C_{10}$ haloalkyls, 3-10 membered cycloalkyls, 3-10 membered heterocycloalkyls, 6-10 membered aryls, and 5-10 membered heteroaryls; and each R" is independently chosen from hydrogen, $C_1$-$C_{10}$ alkyls, $C_1$-$C_{10}$ haloalkyls, $C_1$-$C_{10}$ hydroxyalkyls, and $C_1$-$C_{10}$ heteroalkyls.

3. The compound of claim 2, or a pharmaceutically acceptable salt thereof, wherein ring A is chosen from 5-8 membered heteroaryls optionally substituted with 1 to 5 instances of $R^A$.

4. The compound of claim 3, or a pharmaceutically acceptable salt thereof, wherein ring A is chosen from pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl, wherein each of pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^A$.

5. The compound of claim 4, or a pharmaceutically acceptable salt thereof, wherein ring A is pyridinyl optionally substituted with 1 to 3 instances of $R^A$.

6. The compound of claim 2, or a pharmaceutically acceptable salt thereof, wherein ring B is chosen from benzodioxolyl and 5-8 membered heteroaryls optionally substituted with 1 to 5 instances of $R^B$.

7. The compound of claim 6, or a pharmaceutically acceptable salt thereof, wherein ring B is chosen from benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, pyridinonyl, and pyrimidinyl, wherein each of benzodioxolyl, pyrrolyl, furanyl, furazanyl, thiophenyl, imidazolyl, isothiazoyl, isoxazolyl, oxazolyl, oxadiazolyl, tetrazolyl, thiazolyl, triazolyl, pyrazolyl, pyridinyl, pyrazinyl, pyridazinyl, and pyrimidinyl is independently optionally substituted with 1 to 3 instances of $R^B$.

8. The compound of claim 7, or a pharmaceutically acceptable salt thereof, wherein ring B is chosen from pyrazolyl, isothiazoyl, isoxazolyl, pyridinyl, pyrimidinyl, and thiophenyl, wherein each of pyrazolyl, isothiazoyl, isoxazolyl, pyridinyl, pyrimidinyl, and thiophenyl is independently optionally substituted with 1 to 3 instances of $R^B$.

9. The compound of claim 2, or a pharmaceutically acceptable salt thereof, wherein:

each $R^A$ is independently chosen from halos, $C_1$-$C_{10}$ alkyls, $C_1$-$C_{10}$ haloalkyls, $C_1$-$C_{10}$ alkoxys, $C_1$-$C_{10}$ haloalkoxys, and NR"R";

each $R^B$ is independently chosen from halos, $C_1$-$C_{10}$ alkyls, and $C_1$-$C_{10}$ haloalkyls;

each $R^C$ is independently chosen from halos, hydroxy, cyano, $C_1$-$C_{10}$ alkyls, $C_1$-$C_{10}$ alkoxys, 3-8 membered cycloalkyls, 3-8 membered heterocycloalkyls, and 6-8 membered aryls; and each R" is independently chosen from hydrogen and $C_1$-$C_{10}$ alkyls.

10. The compound of claim 1, or a pharmaceutically acceptable salt thereof, wherein ring A is chosen from

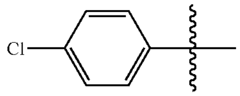, 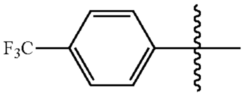,

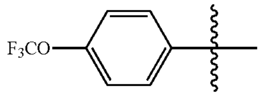, 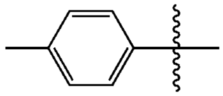,

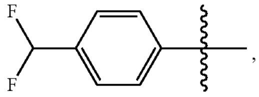, 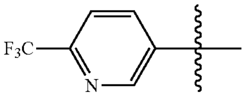,

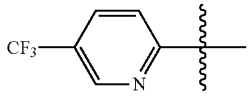, 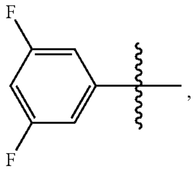,

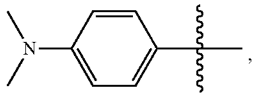, 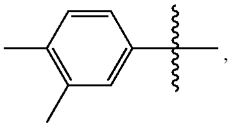,

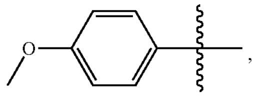,

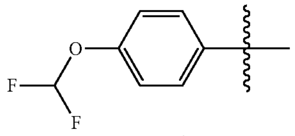,

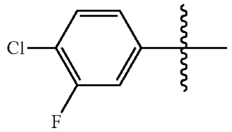, 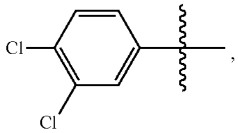,

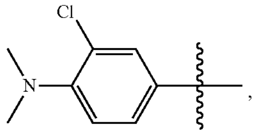, 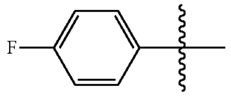,

-continued
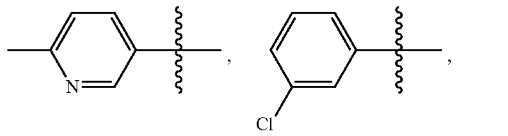
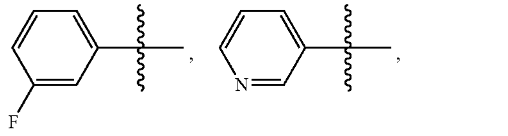
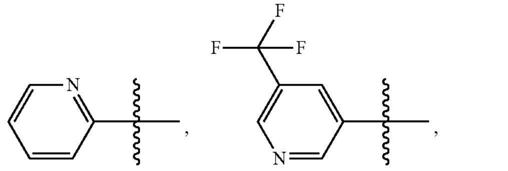
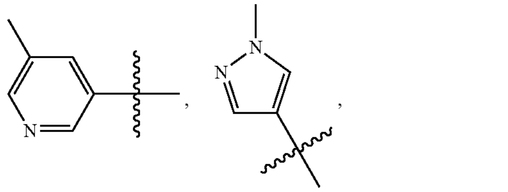
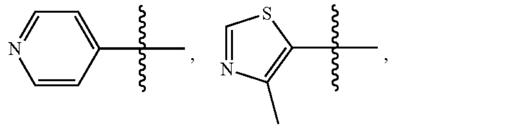
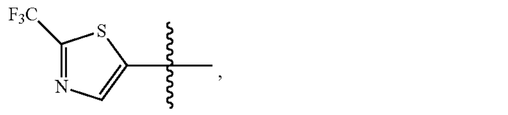
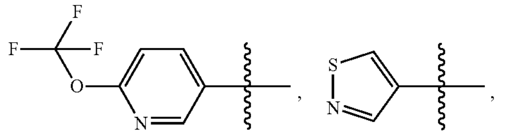
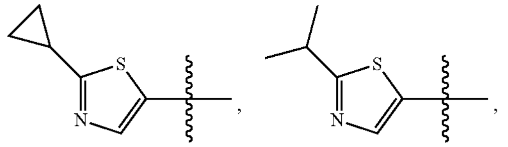
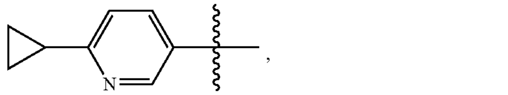
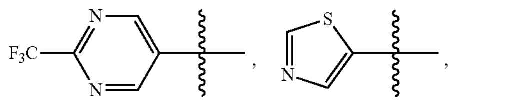
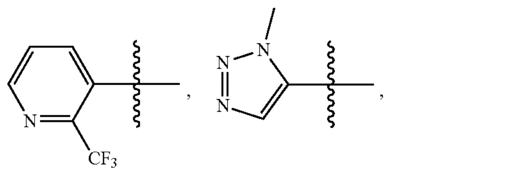
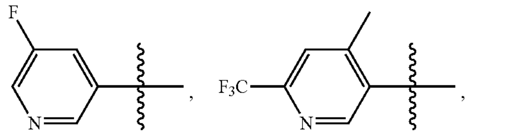
-continued
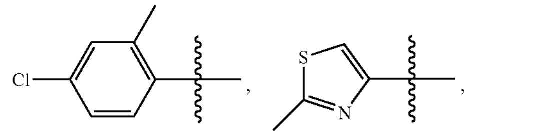
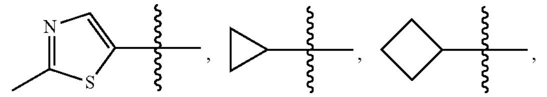
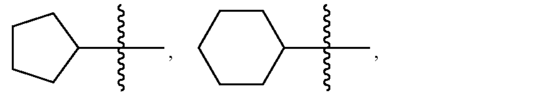
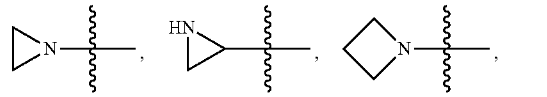
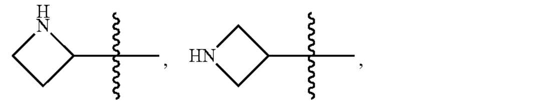
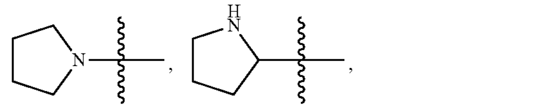
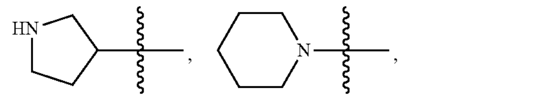
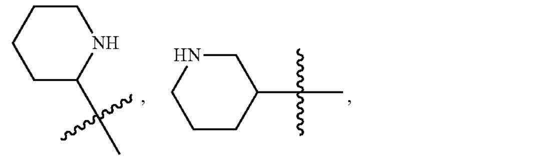
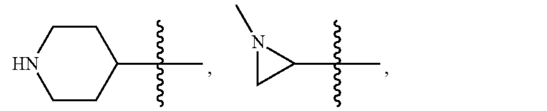
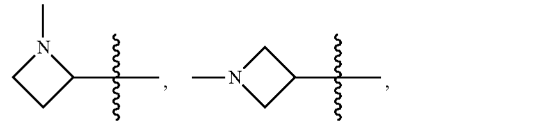
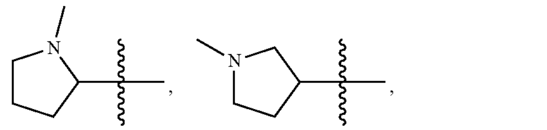
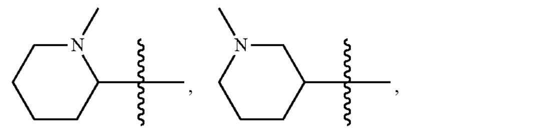
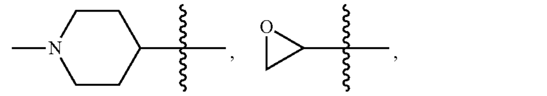
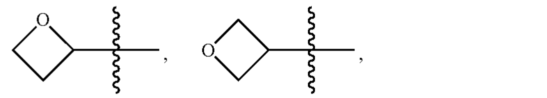
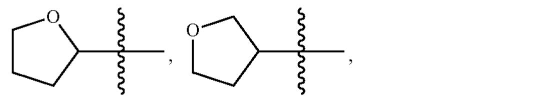

-continued
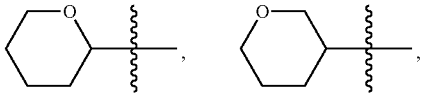
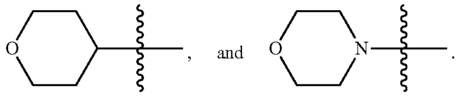
and
11. The compound of claim 10, or a pharmaceutically acceptable salt thereof, wherein ring A is chosen from
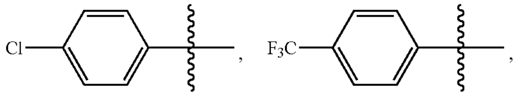
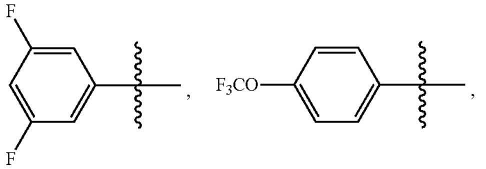
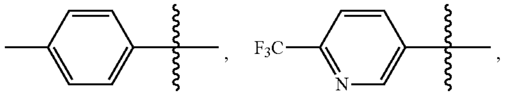
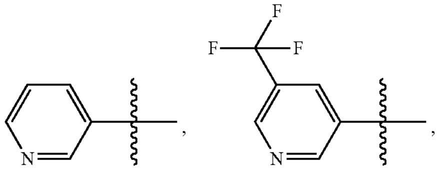
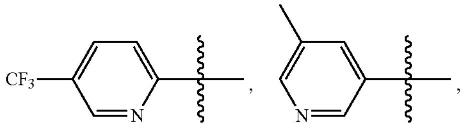
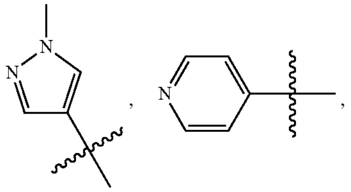
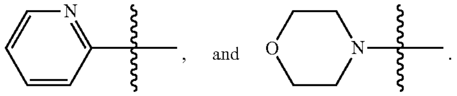
and
12. The compound of claim 1, or a pharmaceutically acceptable salt thereof, wherein ring B is chosen from
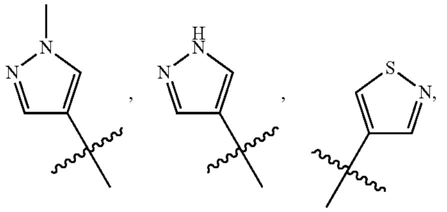
-continued
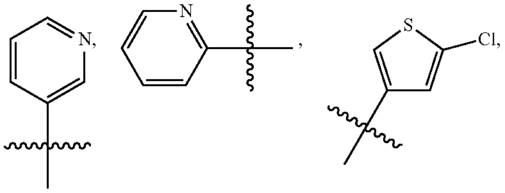
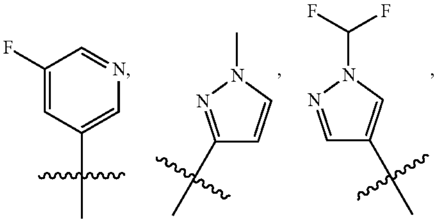
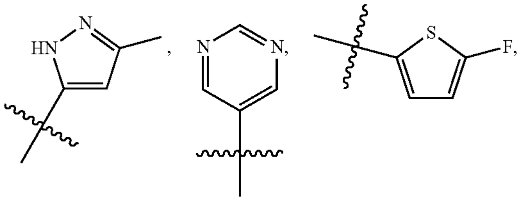
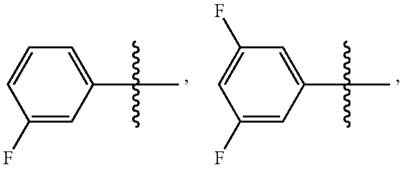
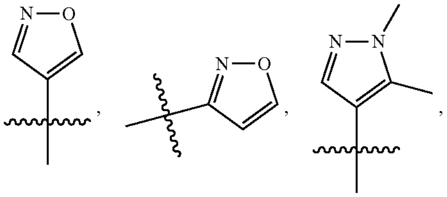
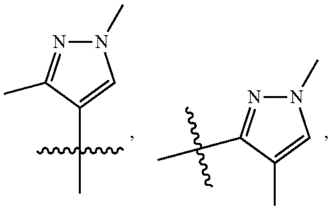
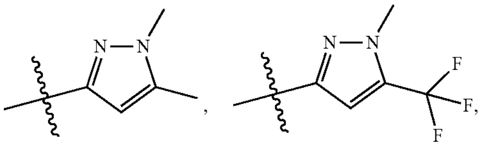
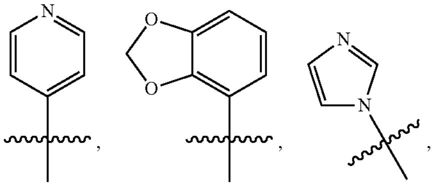

-continued
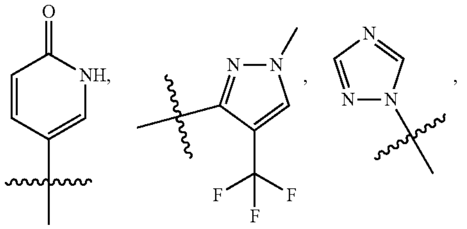
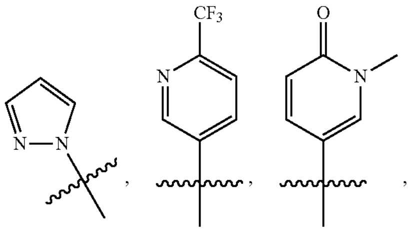
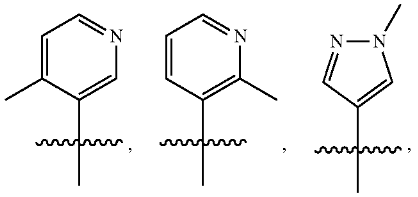
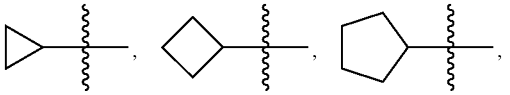
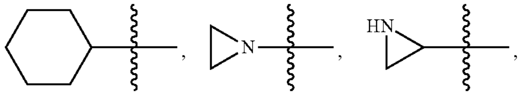
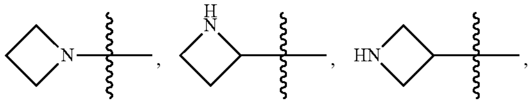
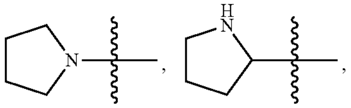
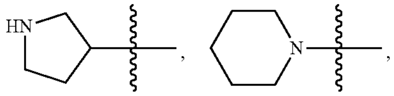
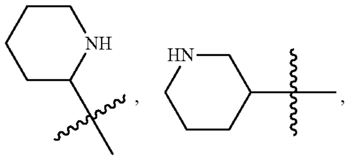
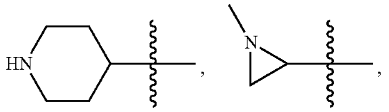
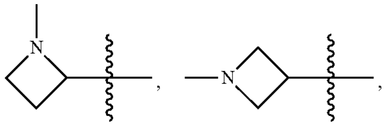
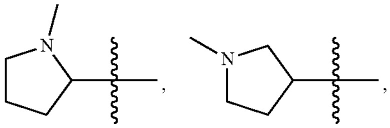
-continued
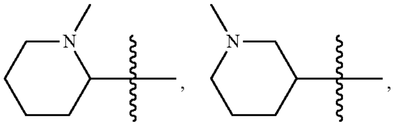
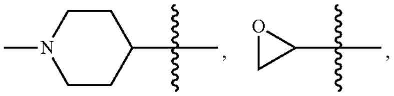
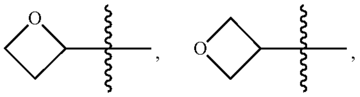
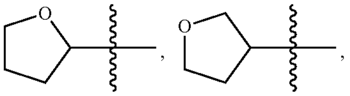
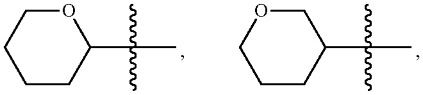
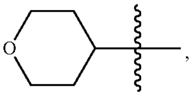
and
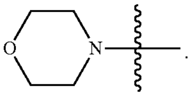
13. The compound of claim 12, or a pharmaceutically acceptable salt thereof, wherein ring B is chosen from
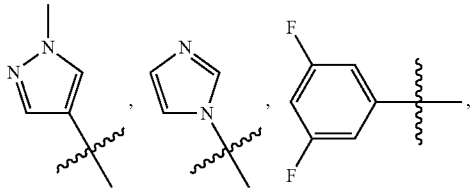
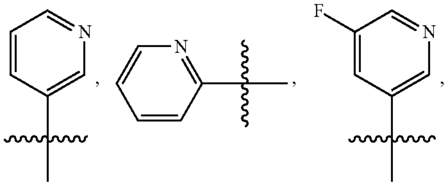
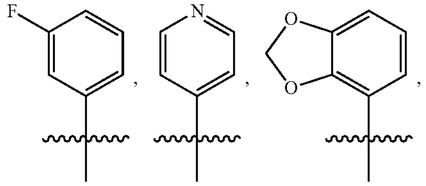
and
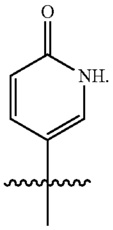
14. The compound of claim 1, or a pharmaceutically acceptable salt thereof, wherein R is chosen from methyl, -continued
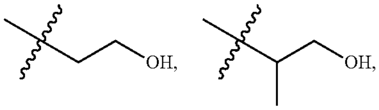
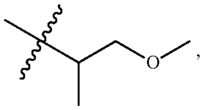
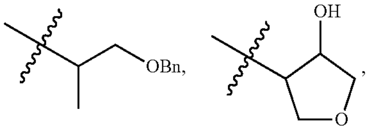
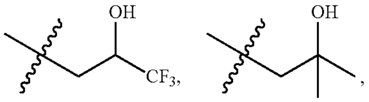
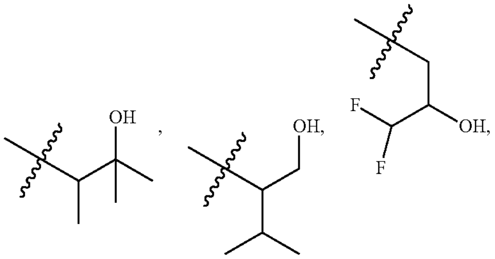
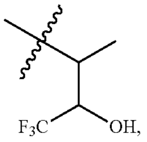
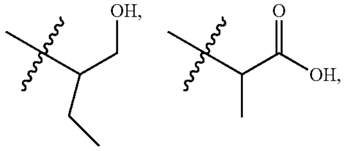
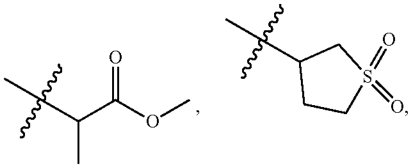
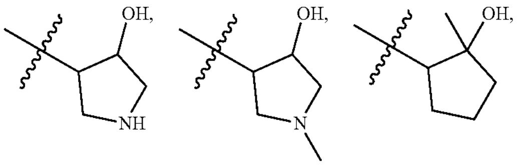
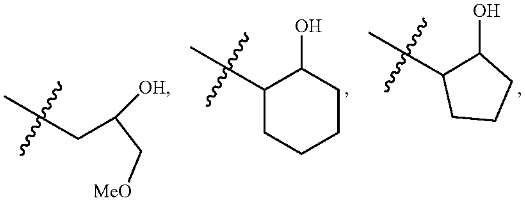
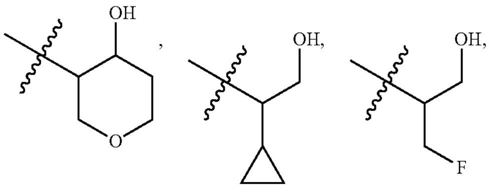
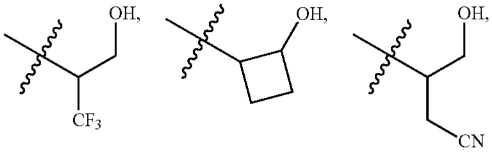
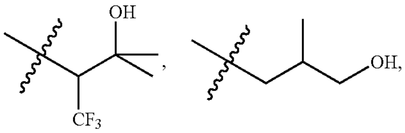
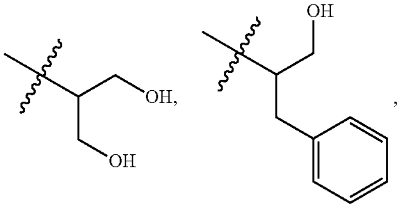
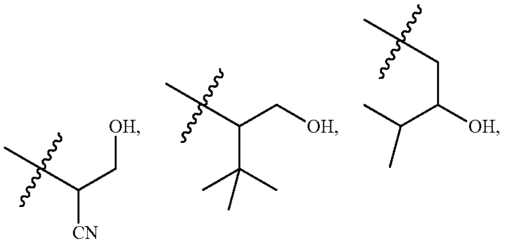
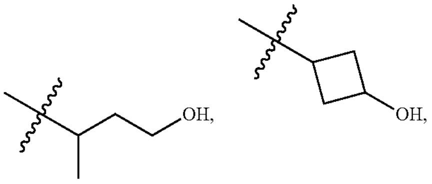
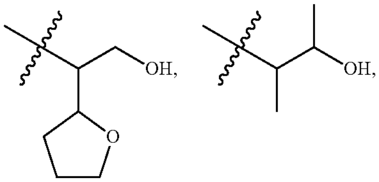
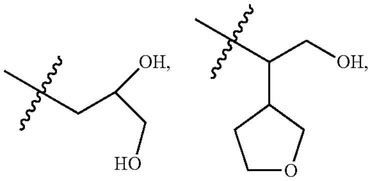
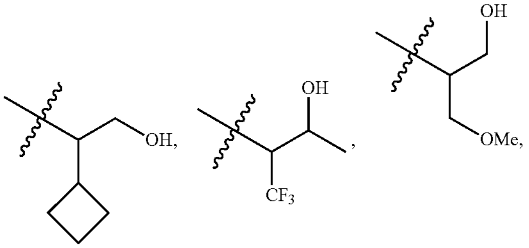
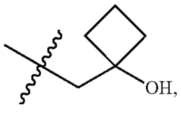
and
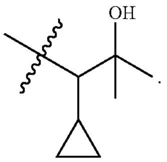

15. The compound of claim 14, or a pharmaceutically acceptable salt thereof, wherein R is chosen from methyl,

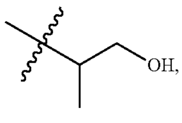
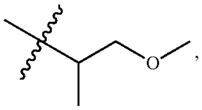,
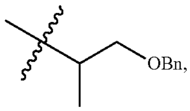
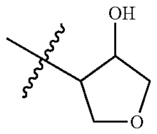,
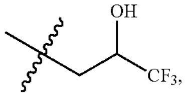
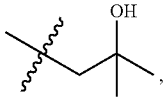,
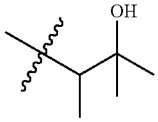, and
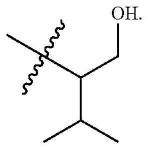

16. A compound or pharmaceutically acceptable salt thereof, selected from:

(i) (S)-8-(5-fluoropyridin-3-yl)-3-(1-hydroxypropan-2-yl)-6-(4-(trifluoromethoxy) phenyl) pyrido[3,4-d]pyrimidin-4 (3H)-one;

(ii) (S)-6-(4-chlorophenyl)-3-(1-hydroxypropan-2-yl)-8-(6-oxo-1,6-dihydropyridin-3-yl) pyrido[3,4-d]pyrimidin-4 (3H)-one;

(iii) (S)-8-(benzo[d][1,3]dioxol-4-yl)-6-(4-chlorophenyl)-3-(1-hydroxypropan-2-yl) pyrido[3,4-d]pyrimidin-4 (3H)-one;

(iv) (S)-3-(1-hydroxypropan-2-yl)-8-(pyridin-4-yl)-6-(6-(trifluoromethyl) pyridin-3-yl) pyrido[3,4-d]pyrimidin-4 (3H)-one;

(v) (S)-8-(5-fluoropyridin-3-yl)-3-(1-hydroxypropan-2-yl)-6-(4-(trifluoromethyl) phenyl) pyrido[3,4-d]pyrimidin-4 (3H)-one;

(vi) (S)-3-(1-hydroxypropan-2-yl)-6,8-di(pyridin-4-yl) pyrido[3,4-d]pyrimidin-4 (3H)-one;

(vii) (S)-6-(4-chlorophenyl)-8-(3-fluorophenyl)-3-(1-hydroxypropan-2-yl) pyrido[3,4-d]pyrimidin-4 (3H)-one;

(viii) (S)-8-(3-fluorophenyl)-3-(1-hydroxypropan-2-yl)-6-(6-(trifluoromethyl) pyridin-3-yl) pyrido[3,4-d]pyrimidin-4 (3H)-one;

(ix) 3-(2-hydroxy-2-methylpropyl)-8-(pyridin-3-yl)-6-(6-(trifluoromethyl) pyridin-3-yl) pyrido[3,4-d]pyrimidin-4 (3H)-one;

(x) 6,8-di(pyridin-3-yl)-3-(3,3,3-trifluoro-2-hydroxypropyl) pyrido[3,4-d]pyrimidin-4 (3H)-one;

(xi) (S)-6-chloro-3-(1-hydroxypropan-2-yl)-8-(pyridin-3-yl) pyrido[3,4-d]pyrimidin-4 (3H)-one;

(xii) (S)-3-(1-hydroxypropan-2-yl)-8-(pyridin-3-yl)-6-(6-(trifluoromethyl) pyridin-3-yl) pyrido[3,4-d]pyrimidin-4 (3H)-one;

(xiii) 6-(4-chlorophenyl)-8-(pyridin-3-yl)-3-(3,3,3-trifluoro-2-hydroxypropyl) pyrido[3,4-d]pyrimidin-4 (3H)-one;

(xiv) 8-(pyridin-3-yl)-3-(3,3,3-trifluoro-2-hydroxypropyl)-6-(4-(trifluoromethoxy) phenyl) pyrido[3,4-d]pyrimidin-4 (3H)-one;

(xv) 6-(4-chlorophenyl)-8-(1-methyl-1H-pyrazol-4-yl)-3-(3,3,3-trifluoro-2-hydroxypropyl) pyrido[3,4-d]pyrimidin-4 (3H)-one;

(xvi) 3-(2-hydroxy-2-methylpropyl)-8-(pyridin-3-yl)-6-(4-(trifluoromethyl) phenyl) pyrido[3,4-d]pyrimidin-4 (3H)-one;

(xvii) (S)-3-(1-hydroxypropan-2-yl)-8-(pyridin-3-yl)-6-(p-tolyl) pyrido[3,4-d]pyrimidin-4 (3H)-one;

(xviii) 6-(4-chlorophenyl)-3-(2-hydroxy-2-methylpropyl)-8-(pyridin-3-yl) pyrido[3,4-d]pyrimidin-4 (3H)-one;

(xix) 3-(2-hydroxy-2-methylpropyl)-6,8-bis(1-methyl-1H-pyrazol-4-yl) pyrido[3,4-d]pyrimidin-4 (3H)-one;

(xx) (S)-3-(1-hydroxypropan-2-yl)-6,8-di(pyridin-3-yl) pyrido[3,4-d]pyrimidin-4 (3H)-one;

(xxi) 6-(4-chlorophenyl)-3-(2-hydroxy-2-methylpropyl)-8-(1-methyl-1H-pyrazol-4-yl) pyrido[3,4-d]pyrimidin-4 (3H)-one;

(xxii) (S)-3-(1-hydroxypropan-2-yl)-8-(pyridin-3-yl)-6-(4-(trifluoromethoxy) phenyl) pyrido[3,4-d]pyrimidin-4 (3H)-one;

(xxiii) (S)-3-(1-hydroxypropan-2-yl)-8-(pyridin-3-yl)-6-(4-(trifluoromethyl) phenyl) pyrido[3,4-d]pyrimidin-4 (3H)-one;

(xxiv) (S)-6-(4-chlorophenyl)-3-(1-hydroxypropan-2-yl)-8-(pyridin-3-yl) pyrido[3,4-d]pyrimidin-4 (3H)-one;

(xxv) (S)-3-(1-hydroxypropan-2-yl)-8-(1-methyl-1H-pyrazol-4-yl)-6-(4-(trifluoromethoxy) phenyl) pyrido [3,4-d]pyrimidin-4 (3H)-one;

(xxvi) (S)-3-(1-hydroxypropan-2-yl)-8-(1-methyl-1H-pyrazol-4-yl)-6-phenylpyrido[3,4-d]pyrimidin-4 (3H)-one;

(xxvii) (S)-6-(4-chlorophenyl)-3-(1-hydroxypropan-2-yl)-8-(1-methyl-1H-pyrazol-4-yl) pyrido[3,4-d]pyrimidin-4 (3H)-one;

(xxviii) 3-methyl-8-(pyridin-3-yl)-6-(4-(trifluoromethoxy) phenyl) pyrido[3,4-d]pyrimidin-4 (3H)-one;

(xxix) Rac-6-(4-chlorophenyl)-3-((trans)-4-hydroxytetrahydrofuran-3-yl)-8-(pyridin-3-yl) pyrido[3,4-d]pyrimidin-4 (3H)-one;

(xxx) (S)-6-(4-chlorophenyl)-3-(3-hydroxy-3-methylbutan-2-yl)-8-(1-methyl-1H-pyrazol-4-yl) pyrido[3,4-d] pyrimidin-4 (3H)-one;

(xxxi) (R)-6-(4-chlorophenyl)-3-(3-hydroxy-3-methylbutan-2-yl)-8-(1-methyl-1H-pyrazol-4-yl) pyrido[3,4-d] pyrimidin-4 (3H)-one;

(xxxii) rac-6-(4-chlorophenyl)-3-((cis)-4-hydroxytetrahydrofuran-3-yl)-8-(pyridin-3-yl) pyrido[3,4-d]pyrimidin-4 (3H)-one;

(xxxiii) (R)-6-(4-chlorophenyl)-3-(3-hydroxy-3-methylbutan-2-yl)-8-(pyridin-3-yl) pyrido[3,4-d]pyrimidin-4 (3H)-one;

(xxxiv) (S)-3-(3-hydroxy-3-methylbutan-2-yl)-6,8-di (pyridin-3-yl) pyrido[3,4-d]pyrimidin-4 (3H)-one;

(xxxv) (S)-6,8-bis(3,5-difluorophenyl)-3-(1-hydroxy-3-methylbutan-2-yl) pyrido[3,4-d]pyrimidin-4 (3H)-one;

(xxxvi) (S)-6-(4-chlorophenyl)-3-(3-hydroxy-3-methylbutan-2-yl)-8-(pyridin-3-yl) pyrido[3,4-d]pyrimidin-4 (3H)-one;

(xxxvii) (S)-8-(3,5-difluorophenyl)-3-(1-hydroxy-3-methylbutan-2-yl)-6-(p-tolyl) pyrido[3,4-d]pyrimidin-4 (3H)-one;

(xxxviii) 6-(4-chlorophenyl)-8-(3-fluorophenyl)-3-(2-hydroxy-2-methylpropyl) pyrido[3,4-d]pyrimidin-4 (3H)-one;

(xxxix) (R)-6-(4-chlorophenyl)-8-(3-fluorophenyl)-3-(3-hydroxy-3-methylbutan-2-yl) pyrido[3,4-d]pyrimidin-4 (3H)-one;

(xl) (S)-3-(1-(benzyloxy) propan-2-yl)-8-(3-fluorophenyl)-6-(p-tolyl) pyrido[3,4-d]pyrimidin-4 (3H)-one;

(xli) (R)-6-(4-chlorophenyl)-8-(3-fluorophenyl)-3-(3,3,3-trifluoro-2-hydroxypropyl) pyrido[3,4-d]pyrimidin-4 (3H)-one;

(xlii) (S)-6-(4-chlorophenyl)-8-(3-fluorophenyl)-3-(3,3,3-trifluoro-2-hydroxypropyl) pyrido[3,4-d]pyrimidin-4 (3H)-one;

(xliii) (S)-3-(1-hydroxypropan-2-yl)-6-morpholino-8-(pyridin-3-yl) pyrido[3,4-d]pyrimidin-4 (3H)-one;

(xliv) (S)-3-(1-hydroxypropan-2-yl)-8-(1H-imidazol-1-yl)-6-(4-(trifluoromethoxy) phenyl) pyrido[3,4-d]pyrimidin-4 (3H)-one;

(xlv) (S)-3-(1-methoxypropan-2-yl)-8-(pyridin-3-yl)-6-(p-tolyl) pyrido[3,4-d]pyrimidin-4 (3H)-one;

(xlvi) (S)-3-(1-hydroxypropan-2-yl)-8-(pyridin-3-yl)-6-(5-(trifluoromethyl) pyridin-2-yl) pyrido[3,4-d]pyrimidin-4 (3H)-one;

(xlvii) (S)-8-(3-fluorophenyl)-3-(1-hydroxypropan-2-yl)-6-(5-(trifluoromethyl) pyridin-2-yl) pyrido[3,4-d]pyrimidin-4 (3H)-one;

(xlviii) (S)-8-(3-fluorophenyl)-3-(1-hydroxypropan-2-yl)-6-(p-tolyl) pyrido[3,4-d]pyrimidin-4 (3H)-one;

(xlix) (S)-8-(3-fluorophenyl)-3-(1-hydroxypropan-2-yl)-6-(4-(trifluoromethoxy) phenyl) pyrido[3,4-d]pyrimidin-4 (3H)-one;

(l) (S)-3-(1-hydroxypropan-2-yl)-8-(pyridin-3-yl)-6-(6-(trifluoromethoxy) pyridin-3-yl) pyrido[3,4-d]pyrimidin-4 (3H)-one (li) (S)-3-(2-hydroxy-2-methylpropyl)-8-(1H-pyrazol-4-yl)-6-(6-(trifluoromethyl) pyridin-3-yl) pyrido[3,4-d] pyrimidin-4 (3H)-one (lii) methyl(S)-5-(3-(1-hydroxypropan-2-yl)-4-oxo-8-(pyridin-3-yl)-3,4-dihydropyrido[3,4-d]pyrimidin-6-yl) picolinate (liii) (S)-3-(1-hydroxypropan-2-yl)-6-(isothiazol-4-yl)-8-(pyridin-3-yl) pyrido[3,4-d]pyrimidin-4 (3H)-one (liv) 3-(2-hydroxy-2-methylpropyl)-8-(isothiazol-4-yl)-6-(6-(trifluoromethyl) pyridin-3-yl) pyrido[3,4-d]pyrimidin-4 (3H)-one (lv) (S)-3-(1-hydroxypropan-2-yl)-8-(isothiazol-4-yl)-6-(6-(trifluoromethyl) pyridin-3-yl) pyrido[3,4-d]pyrimidin-4 (3H)-one (lvi) (S)-3-(1-hydroxypropan-2-yl)-6,8-di(isothiazol-4-yl) pyrido[3,4-d]pyrimidin-4 (3H)-one (lvii) (S)-8-(pyridin-3-yl)-3-(3,3,3-trifluoro-2-hydroxypropyl)-6-(6-(trifluoromethyl) pyridin-3-yl) pyrido[3,4-d]pyrimidin-4 (3H)-one (lviii) (S)-6-(4-chlorophenyl)-3-(1-hydroxypropan-2-yl)-8-(isothiazol-4-yl) pyrido[3,4-d]pyrimidin-4 (3H)-one (lix) 3-(2-hydroxy-2-methylpropyl)-6,8-di(pyridin-3-yl) pyrido[3,4-d]pyrimidin-4 (3H)-one (lx) 3-(2-hydroxy-2-methylpropyl)-8-(1-methyl-1H-pyrazol-4-yl)-6-(6-(trifluoromethyl) pyridin-3-yl) pyrido[3,4-d]pyrimidin-4 (3H)-one (lxi) 6-(4-chloro-2-methylphenyl)-3-(2-hydroxy-2-methylpropyl)-8-(1-methyl-1H-pyrazol-4-yl) pyrido[3,4-d] pyrimidin-4 (3H)-one (lxii) (S)-3-(1-hydroxypropan-2-yl)-8-(1H-pyrazol-4-yl)-6-(6-(trifluoromethyl) pyridin-3-yl) pyrido[3,4-d]pyrimidin-4 (3H)-one (lxiii) (S)-3-(1-hydroxypropan-2-yl)-8-(2-methylpyridin-3-yl)-6-(6-(trifluoromethyl) pyridin-3-yl) pyrido[3,4-d] pyrimidin-4 (3H)-one (lxiv) (S)-3-(1-hydroxypropan-2-yl)-8-(4-methylpyridin-3-yl)-6-(6-(trifluoromethyl) pyridin-3-yl) pyrido[3,4-d] pyrimidin-4 (3H)-one (lxv) (S)-3-(1-hydroxypropan-2-yl)-6-(4-methylthiazol-5-yl)-8-(pyridin-3-yl) pyrido[3,4-d]pyrimidin-4 (3H)-one (lxvi) (S)-6-(2-cyclopropylthiazol-5-yl)-3-(1-hydroxypropan-2-yl)-8-(pyridin-3-yl) pyrido[3,4-d]pyrimidin-4 (3H)-one (lxvii) (S)-3-(1-hydroxypropan-2-yl)-6-(2-isopropylthiazol-5-yl)-8-(pyridin-3-yl) pyrido[3,4-d]pyrimidin-4 (3H)-one (lxviii) (S)-3-(1-hydroxypropan-2-yl)-8-(1-methyl-1H-pyrazol-4-yl)-6-(6-(trifluoromethyl) pyridin-3-yl) pyrido[3,4-d]pyrimidin-4 (3H)-one (lxix) (S)-3-(1-hydroxypropan-2-yl)-6,8-bis(6-(trifluoromethyl) pyridin-3-yl) pyrido[3,4-d]pyrimidin-4 (3H)-one (lxx) 6-(4-chlorophenyl)-3-((3S,4S)-4-hydroxytetrahydrofuran-3-yl)-8-(pyridin-3-yl) pyrido[3,4-d]pyrimidin-4 (3H)-one (lxxi) 6-(4-chlorophenyl)-3-((3R,4R)-4-hydroxytetrahydrofuran-3-yl)-8-(pyridin-3-yl) pyrido[3,4-d]pyrimidin-4 (3H)-one (lxxii) 3-(2-hydroxyethyl)-8-(pyridin-3-yl)-6-(4-(trifluoromethoxy) phenyl) pyrido[3,4-d]pyrimidin-4 (3H)-one (lxxiii) (S)-6-(4-chlorophenyl)-3-(1-hydroxypropan-2-yl)-8-(1-methyl-6-oxo-1,6-dihydropyridin-3-yl) pyrido [3,4-d]pyrimidin-4 (3H)-one (lxxiv) (S)-6-(6-cyclopropylpyridin-3-yl)-3-(1-hydroxypropan-2-yl)-8-(pyridin-3-yl) pyrido[3,4-d]pyrimidin-4 (3H)-one (lxxv) (S)-3-(1-hydroxypropan-2-yl)-6-(4-methyl-6-(trifluoromethyl) pyridin-3-yl)-8-(pyridin-3-yl) pyrido[3,4-d]pyrimidin-4 (3H)-one (lxxvi) (S)-3-(1-hydroxypropan-2-yl)-8-(1-methyl-1H-pyrazol-4-yl)-6-(pyridin-3-yl) pyrido[3,4-d]pyrimidin-4 (3H)-one (lxxvii) (S)-6-(cyclohex-1-en-1-yl)-3-(1-hydroxypropan-2-yl)-8-(pyridin-3-yl) pyrido[3,4-d]pyrimidin-4 (3H)-one (lxxviii) (S)-6,8-bis(5-fluoropyridin-3-yl)-3-(1-hydroxypropan-2-yl) pyrido[3,4-d]pyrimidin-4 (3H)-one (lxxix) 3-((3R,4S)-4-hydroxytetrahydrofuran-3-yl)-8-(pyridin-3-yl)-6-(6-(trifluoromethyl) pyridin-3-yl) pyrido[3,4-d]pyrimidin-4 (3H)-one (lxxx) 3-(2-hydroxy-2-methylpropyl)-8-(pyridin-3-yl)-6-(2-(trifluoromethyl) pyridin-3-yl) pyrido[3,4-d]pyrimidin-4 (3H)-one (lxxxi) 6-(6-cyclopropylpyridin-3-yl)-3-(2-hydroxy-2-methylpropyl)-8-(pyridin-3-yl) pyrido[3,4-d]pyrimidin-4 (3H)-one (lxxxii) 6-(6-cyclopropylpyridin-3-yl)-3-(2-hydroxy-2-methylpropyl)-8-(1-methyl-1H-pyrazol-4-yl) pyrido[3,4-d]pyrimidin-4 (3H)-one (lxxxiii) (S)-6-(6-cyclopropylpyridin-3-yl)-3-(1-hydroxypropan-2-yl)-8-(1-methyl-1H-pyrazol-4-yl) pyrido[3,4-d]pyrimidin-4 (3H)-one (lxxxiv) (S)-3-(1-hydroxypropan-2-yl)-8-(pyridin-3-yl)-6-(thiazol-5-yl) pyrido[3,4-d]pyrimidin-4 (3H)-one (lxxxv) (S)-3-(1-hydroxypropan-2-yl)-8-(pyridin-3-yl)-6-(2-(trifluoromethyl) thiazol-5-yl) pyrido[3,4-d]pyrimidin-4 (3H)-one (lxxxvi) (S)-3-(1-hydroxypropan-2-yl)-8-(pyridin-3-yl)-6-(2-(trifluoromethyl) pyrimidin-5-yl) pyrido[3,4-d] pyrimidin-4 (3H)-one (lxxxvii) 3-(2-hydroxy-2-methylpropyl)-8-(pyridin-3-yl)-6-(2-(trifluoromethyl) thiazol-5-yl) pyrido[3,4-d]pyrimidin-4 (3H)-one (lxxxviii) 3-((3S,4S)-4-hydroxytetrahydrofuran-3-yl)-8-(1-methyl-1H-pyrazol-4-yl)-6-(6-(trifluoromethyl) pyridin-3-yl) pyrido[3,4-d]pyrimidin-4 (3H)-one (lxxxix) (S)-3-(1-hydroxypropan-2-yl)-6-(2-methylthiazol-5-yl)-8-(pyridin-3-yl) pyrido[3,4-d]pyrimidin-4 (3H)-one (xc) (S)-6-(4-chlorophenyl)-8-(3-fluorophenyl)-3-(1-hydroxy-3-methylbutan-2-yl) pyrido[3,4-d]pyrimidin-4 (3H)-one (xci) (S)-3-(1-hydroxypropan-2-yl)-6-(piperidin-1-yl)-8-(pyridin-3-yl) pyrido[3,4-d]pyrimidin-4 (3H)-one (xcii) 3-(2-hydroxy-2-methylpropyl)-8-(isothiazol-4-yl)-6-(5-(trifluoromethyl) pyridin-2-yl) pyrido[3,4-d]pyrimidin-4 (3H)-one (xciii) (S)-3-(1-hydroxypropan-2-yl)-8-(isothiazol-4-yl)-6-(5-(trifluoromethyl) pyridin-2-yl) pyrido[3,4-d]pyrimidin-4 (3H)-one (xciv) 3-(2-hydroxy-2-methylpropyl)-8-(1-methyl-1H-pyrazol-4-yl)-6-(5-(trifluoromethyl) pyridin-2-yl) pyrido[3,4-d]pyrimidin-4 (3H)-one (xcv) (S)-8-(pyridin-3-yl)-3-(3,3,3-trifluoro-2-hydroxypropyl)-6-(5-(trifluoromethyl) pyridin-2-yl) pyrido[3,4-d]pyrimidin-4 (3H)-one (xcvi) 3-(2-hydroxy-2-methylpropyl)-8-(pyridin-3-yl)-6-(5-(trifluoromethyl) pyridin-2-yl) pyrido[3,4-d]pyrimidin-4 (3H)-one (xcvii) 3-(1,1-dioxidotetrahydrothiophen-3-yl)-8-(pyridin-3-yl)-6-(6-(trifluoromethyl) pyridin-3-yl) pyrido[3,4-d]pyrimidin-4 (3H)-one (xcviii) (R)-3-(1,1-dioxidotetrahydrothiophen-3-yl)-8-(pyridin-3-yl)-6-(6-(trifluoromethyl) pyridin-3-yl) pyrido[3,4-d]pyrimidin-4 (3H)-one (xcix) (R)-8-(1-methyl-1H-pyrazol-4-yl)-3-(3,3,3-trifluoro-2-hydroxypropyl)-6-(6-(trifluoromethyl) pyridin-3-yl) pyrido[3,4-d]pyrimidin-4 (3H)-one (c) (S)-8-(1-methyl-1H-pyrazol-4-yl)-3-(3,3,3-trifluoro-2-hydroxypropyl)-6-(6-(trifluoromethyl) pyridin-3-yl) pyrido[3,4-d]pyrimidin-4 (3H)-one (ci) (R)-3-(2-hydroxypropyl)-8-(pyridin-3-yl)-6-(6-(trifluoromethyl) pyridin-3-yl) pyrido[3,4-d]pyrimidin-4 (3H)-one (cii) (R)-8-(1-methyl-1H-pyrazol-4-yl)-3-(3,3,3-trifluoro-2-hydroxypropyl)-6-(5-(trifluoromethyl) pyridin-2-yl) pyrido[3,4-d]pyrimidin-4 (3H)-one (ciii) 3-((3S,4R)-4-hydroxytetrahydrofuran-3-yl)-8-(1-methyl-1H-pyrazol-4-yl)-6-(6-(trifluoromethyl) pyridin-3-yl) pyrido[3,4-d]pyrimidin-4 (3H)-one (civ) 3-((3R,4S)-4-hydroxytetrahydrofuran-3-yl)-8-(1-methyl-1H-pyrazol-4-yl)-6-(6-(trifluoromethyl) pyridin-3-yl) pyrido[3,4-d]pyrimidin-4 (3H)-one (cv) 6-(4-chlorophenyl)-3-((3S,4R)-4-hydroxytetrahydrofuran-3-yl)-8-(1-methyl-1H-pyrazol-4-yl) pyrido[3,4-d]pyrimidin-4 (3H)-one (cvi) 3-((3S,4R)-4-hydroxytetrahydrofuran-3-yl)-8-(pyridin-3-yl)-6-(6-(trifluoromethyl) pyridin-3-yl) pyrido[3,4-d]pyrimidin-4 (3H)-one (cvii) (S)-6-(6-cyclopropylpyridin-3-yl)-8-(pyridin-3-yl)-3-(3,3,3-trifluoro-2-hydroxypropyl) pyrido[3,4-d]pyrimidin-4 (3H)-one (cviii) (R)-6-(6-cyclopropylpyridin-3-yl)-8-(pyridin-3-yl)-3-(3,3,3-trifluoro-2-hydroxypropyl) pyrido[3,4-d] pyrimidin-4 (3H)-one (cix) (R)-8-(pyridin-3-yl)-3-(3,3,3-trifluoro-2-hydroxypropyl)-6-(6-(trifluoromethyl) pyridin-3-yl) pyrido[3,4-d]pyrimidin-4 (3H)-one (cx) (R)-8-(pyridin-3-yl)-3-(3,3,3-trifluoro-2-hydroxypropyl)-6-(4-(trifluoromethoxy) phenyl) pyrido[3,4-d] pyrimidin-4 (3H)-one (cxi) (S)-8-(pyridin-3-yl)-3-(3,3,3-trifluoro-2-hydroxypropyl)-6-(4-(trifluoromethoxy) phenyl) pyrido[3,4-d] pyrimidin-4 (3H)-one (cxii) 6-(4-chlorophenyl)-3-((3S,4R)-4-hydroxytetrahydrofuran-3-yl)-8-(pyridin-3-yl) pyrido[3,4-d]pyrimidin-4 (3H)-one (cxiii) 3-((3S,4S)-4-hydroxytetrahydrofuran-3-yl)-8-(pyridin-3-yl)-6-(6-(trifluoromethyl) pyridin-3-yl) pyrido[3,4-d]pyrimidin-4 (3H)-one (cxiv) methyl(S)-2-(4-oxo-8-(pyridin-3-yl)-6-(6-(trifluoromethyl) pyridin-3-yl) pyrido[3,4-d]pyrimidin-3 (4H)-yl) propanoate (cxv) 6-(4-chlorophenyl)-3-(4-hydroxy-1-methylpyrrolidin-3-yl)-8-(pyridin-3-yl) pyrido[3,4-d]pyrimidin-4 (3H)-one (cxvi) 6-(4-chlorophenyl)-3-((3R,4R)-4-hydroxypyrrolidin-3-yl)-8-(pyridin-3-yl) pyrido[3,4-d]pyrimidin-4 (3H)-one (cxvii) (R)-6-(6-cyclopropylpyridin-3-yl)-8-(1-methyl-1H-pyrazol-4-yl)-3-(3,3,3-trifluoro-2-hydroxypropyl) pyrido[3,4-d]pyrimidin-4 (3H)-one (cxviii) (S)-6-(6-cyclopropylpyridin-3-yl)-8-(1-methyl-1H-pyrazol-4-yl)-3-(3,3,3-trifluoro-2-hydroxypropyl) pyrido[3,4-d]pyrimidin-4 (3H)-one (cxix) 3-((3S,4R)-4-hydroxytetrahydrofuran-3-yl)-8-(1-methyl-1H-pyrazol-4-yl)-6-(5-(trifluoromethyl) pyridin-2-yl) pyrido[3,4-d]pyrimidin-4 (3H)-one (cxx) 3-((3R,4S)-4-hydroxytetrahydrofuran-3-yl)-8-(1-methyl-1H-pyrazol-4-yl)-6-(5-(trifluoromethyl) pyridin-2-yl) pyrido[3,4-d]pyrimidin-4 (3H)-one (cxxi) 3-((3S,4R)-4-hydroxytetrahydrofuran-3-yl)-8-(pyridin-3-yl)-6-(5-(trifluoromethyl) pyridin-2-yl) pyrido[3,4-d]pyrimidin-4 (3H)-one (cxxii) 3-((3R,4S)-4-hydroxytetrahydrofuran-3-yl)-8-(pyridin-3-yl)-6-(5-(trifluoromethyl) pyridin-2-yl) pyrido[3,4-d]pyrimidin-4 (3H)-one (cxxiii) (R)-3-(2-hydroxypropyl)-8-(1-methyl-1H-pyrazol-4-yl)-6-(5-(trifluoromethyl) pyridin-2-yl) pyrido[3,4-d]pyrimidin-4 (3H)-one (cxxiv) (S)-3-(2-hydroxypropyl)-8-(1-methyl-1H-pyrazol-4-yl)-6-(5-(trifluoromethyl) pyridin-2-yl) pyrido[3,4-d]pyrimidin-4 (3H)-one (cxxv) (S)-3-(2-hydroxypropyl)-8-(pyridin-3-yl)-6-(5-(trifluoromethyl) pyridin-2-yl) pyrido[3,4-d]pyrimidin-4 (3H)-one (cxxvi) (R)-3-(2-hydroxypropyl)-8-(pyridin-3-yl)-6-(5-(trifluoromethyl) pyridin-2-yl) pyrido[3,4-d]pyrimidin-4 (3H)-one (cxxvii) 3-((3S,4S)-4-hydroxytetrahydrofuran-3-yl)-8-(pyridin-3-yl)-6-(5-(trifluoromethyl) pyridin-2-yl) pyrido[3,4-d]pyrimidin-4 (3H)-one (cxxviii) (S)-3-(2-hydroxypropyl)-8-(pyridin-3-yl)-6-(6-(trifluoromethyl) pyridin-3-yl) pyrido[3,4-d]pyrimidin-4 (3H)-one (cxxix) (S)-8-(1-methyl-1H-pyrazol-4-yl)-3-(3,3,3-trifluoro-2-hydroxypropyl)-6-(5-(trifluoromethyl) pyridin-2-yl) pyrido[3,4-d]pyrimidin-4 (3H)-one (cxxx) (S)-3-(1-hydroxypropan-2-yl)-8-(1-methyl-1H-pyrazol-4-yl)-6-(5-(trifluoromethyl) pyridin-2-yl) pyrido[3,4-d]pyrimidin-4 (3H)-one (cxxxi) 3-((3S,4S)-4-hydroxytetrahydrofuran-3-yl)-8-(1-methyl-1H-pyrazol-4-yl)-6-(5-(trifluoromethyl) pyridin-2-yl) pyrido[3,4-d]pyrimidin-4 (3H)-one (cxxxii) 6-(4-chlorophenyl)-3-((3R,4S)-4-hydroxytetrahydrofuran-3-yl)-8-(pyridin-3-yl) pyrido[3,4-d]pyrimidin-4 (3H)-one (cxxxiii) 6-(4-Chlorophenyl)-3-((3R,4S)-4-hydroxytetrahydrofuran-3-yl)-8-(1-methyl-1H-pyrazol-4-yl) pyrido [3,4-d]pyrimidin-4 (3H)-one (cxxxiv) (R)-8-(pyridin-3-yl)-3-(3,3,3-trifluoro-2-hydroxypropyl)-6-(5-(trifluoromethyl) pyridin-2-yl) pyrido[3,4-d]pyrimidin-4 (3H)-one (cxxxv) (S)-2-(4-oxo-8-(pyridin-3-yl)-6-(6-(trifluoromethyl) pyridin-3-yl) pyrido[3,4-d]pyrimidin-3 (4H)-yl) propanoic acid (cxxxvi) (S)—N-methyl-2-(4-oxo-8-(pyridin-3-yl)-6-(6-(trifluoromethyl) pyridin-3-yl) pyrido[3,4-d]pyrimidin-3 (4H)-yl) propanamide (cxxxvii) (S)—N,N-dimethyl-2-(4-oxo-8-(pyridin-3-yl)-6-(6-(trifluoromethyl) pyridin-3-yl) pyrido[3,4-d]pyrimidin-3 (4H)-yl) propanamide (cxxxviii) 3-(2-hydroxy-2-methylpropyl)-8-(1H-pyrazol-4-yl)-6-(5-(trifluoromethyl) pyridin-2-yl) pyrido[3,4-d] pyrimidin-4 (3H)-one (cxxxix) 3-(2-hydroxy-2-methylpropyl)-8-(1H-imidazol-1-yl)-6-(5-(trifluoromethyl) pyridin-2-yl) pyrido[3,4-d] pyrimidin-4 (3H)-one (cxl) 3-(2-hydroxy-2-methylpropyl)-8-(1H-imidazol-1-yl)-6-(6-(trifluoromethyl) pyridin-2-yl) pyrido[3,4-d] pyrimidin-4 (3H)-one (cxli) (S)-3-(1-hydroxypropan-2-yl)-8-(1H-imidazol-1-yl)-6-(5-(trifluoromethyl) pyridin-2-yl) pyrido[3,4-d] pyrimidin-4 (3H)-one (cxlii) (S)-3-(1-hydroxypropan-2-yl)-8-(1H-imidazol-1-yl)-6-(6-(trifluoromethyl) pyridin-3-yl) pyrido[3,4-d] pyrimidin-4 (3H)-one (cxliii) (S)-3-(1-hydroxypropan-2-yl)-8-(1H-1,2,4-triazol-1-yl)-6-(6-(trifluoromethyl) pyridin-3-yl) pyrido [3,4-d]pyrimidin-4 (3H)-one (cxliv) (S)-3-(1-hydroxypropan-2-yl)-8-(1H-pyrazol-1-yl)-6-(6-(trifluoromethyl) pyridin-3-yl) pyrido[3,4-d] pyrimidin-4 (3H)-one (cxlv) (S)-3-(1-hydroxypropan-2-yl)-8-(1-methyl-1H-pyrazol-4-yl)-6-(2-(trifluoromethyl) thiazol-5-yl) pyrido[3,4-d]pyrimidin-4 (3H)-one (cxlvi) (S)-8-(diethylamino)-3-(1-hydroxypropan-2-yl)-6-(6-(trifluoromethyl) pyridin-3-yl) pyrido[3,4-d]pyrimidin-4 (3H)-one (cxlvii) (S)-3-(1-hydroxypropan-2-yl)-8-(piperidin-1-yl)-6-(6-(trifluoromethyl) pyridin-3-yl) pyrido[3,4-d]pyrimidin-4 (3H)-one (cxlviii) (S)-3-(1-hydroxypropan-2-yl)-8-(pyrrolidin-1-yl)-6-(6-(trifluoromethyl) pyridin-3-yl) pyrido[3,4-d] pyrimidin-4 (3H)-one (cxlix) (S)-6-(4-chlorophenyl)-3-(1-hydroxypropan-2-yl)-8-(piperidin-1-yl) pyrido[3,4-d]pyrimidin-4 (3H)-one (cl) (S)-3-(1-hydroxypropan-2-yl)-8-(pyridin-2-yl)-6-(6-(trifluoromethyl) pyridin-3-yl) pyrido[3,4-d]pyrimidin-4 (3H)-one (cli) (S)-6-cyclohexyl-3-(1-hydroxypropan-2-yl)-8-(pyridin-3-yl) pyrido[3,4-d]pyrimidin-4 (3H)-one (clii) (S)-3-(1-hydroxypropan-2-yl)-6-(pyridin-2-yl)-8-(pyridin-3-yl) pyrido[3,4-d]pyrimidin-4 (3H)-one (cliii) (S)-3-(1-hydroxypropan-2-yl)-6-(2-methylthiazol-4-yl)-8-(pyridin-3-yl) pyrido[3,4-d]pyrimidin-4 (3H)-one (cliv) (S)-3-(1-hydroxypropan-2-yl)-6-(1-methyl-1H-1,2,3-triazol-5-yl)-8-(pyridin-3-yl) pyrido[3,4-d]pyrimidin-4 (3H)-one (clv) (R)-6-(4-chlorophenyl)-8-(pyridin-3-yl)-3-(3,3,3-trifluoro-2-hydroxypropyl) pyrido[3,4-d]pyrimidin-4 (3H)-one;

(clvi) (S)-6-(4-chlorophenyl)-8-(pyridin-3-yl)-3-(3,3,3-trifluoro-2-hydroxypropyl) pyrido[3,4-d]pyrimidin-4 (3H)-one;

(clvii) (S)-3-(1-hydroxypropan-2-yl)-8-(1-methyl-1,2,5,6-tetrahydropyridin-3-yl)-6-(6-(trifluoromethyl) pyridin-3-yl) pyrido[3,4-d]pyrimidin-4 (3H)-one (clviii) 6-(4-chlorophenyl)-3-((3S,4S)-4-hydroxytetrahydrofuran-3-yl)-8-(1-methyl-1H-pyrazol-4-yl) pyrido[3,4-d]pyrimidin-4 (3H)-one (clix) (S)-3-(1-hydroxypropan-2-yl)-6-(2-methylpyrimidin-5-yl)-8-(pyridin-3-yl) pyrido[3,4-d]pyrimidin-4 (3H)-one (clx) 3-(2-hydroxy-2-methylpropyl)-8-(1-(trifluoromethyl)-1H-pyrazol-4-yl)-6-(6-(trifluoromethyl) pyridin-3-yl) pyrido[3,4-d]pyrimidin-4 (3H)-one (clxi) (S)-3-(1-hydroxypropan-2-yl)-8-(1-methyl-1H-pyrazol-4-yl)-6-(2-(trifluoromethyl) pyrimidin-5-yl) pyrido[3,4-d]pyrimidin-4 (3H)-one (clxii) 3-(2-hydroxy-2-methylpropyl)-8-(pyridin-3-yl)-6-(2-(trifluoromethyl) pyrimidin-5-yl) pyrido[3,4-d]pyrimidin-4 (3H)-one (clxiii) (S)-5-(3-(1-hydroxypropan-2-yl)-4-oxo-8-(pyridin-3-yl)-3,4-dihydropyrido[3,4-d]pyrimidin-6-yl) picolinic acid (clxiv) (S)-3-(1-hydroxypropan-2-yl)-6-(6-methylpyridin-3-yl)-8-(pyridin-3-yl) pyrido[3,4-d]pyrimidin-4 (3H)-one (clxv) 3-(2-hydroxy-2-methylpropyl)-8-(1-methyl-1H-pyrazol-4-yl)-6-(2-(trifluoromethyl) pyrimidin-5-yl) pyrido[3,4-d]pyrimidin-4 (3H)-one (clxvi) 3,8-di(pyridin-3-yl)-6-(6-(trifluoromethyl) pyridin-3-yl) pyrido[3,4-d]pyrimidin-4 (3H)-one (clxvii) 8-(pyridin-3-yl)-6-(6-(trifluoromethyl) pyridin-3-yl) pyrido[3,4-d]pyrimidin-4 (3H)-one (clxviii) 3-((3R,4R)-4-hydroxytetrahydrofuran-3-yl)-8-(pyridin-3-yl)-6-(6-(trifluoromethyl) pyridin-3-yl) pyrido[3,4-d]pyrimidin-4 (3H)-one (clxix) 3-((3R,4R)-4-hydroxytetrahydrofuran-3-yl)-8-(1-methyl-1H-pyrazol-4-yl)-6-(6-(trifluoromethyl) pyridin-3-yl) pyrido[3,4-d]pyrimidin-4 (3H)-one (clxx) 6-(4-chlorophenyl)-3-((3R,4R)-4-hydroxytetrahydrofuran-3-yl)-8-(1-methyl-1H-pyrazol-4-yl) pyrido[3,4-d]pyrimidin-4 (3H)-one (clxxi) 3-cyclopentyl-8-(pyridin-3-yl)-6-(6-(trifluoromethyl) pyridin-3-yl) pyrido[3,4-d]pyrimidin-4 (3H)-one (clxxii) 3-phenyl-8-(pyridin-3-yl)-6-(6-(trifluoromethyl) pyridin-3-yl) pyrido[3,4-d]pyrimidin-4 (3H)-one (clxxiii) 3-((3R,4R)-4-hydroxytetrahydrofuran-3-yl)-8-(pyridin-3-yl)-6-(5-(trifluoromethyl) pyridin-2-yl) pyrido[3,4-d]pyrimidin-4 (3H)-one (clxxiv) 3-((3R,4R)-4-hydroxytetrahydrofuran-3-yl)-8-(1-methyl-1H-pyrazol-4-yl)-6-(5-(trifluoromethyl) pyridin-2-yl) pyrido[3,4-d]pyrimidin-4 (3H)-one (clxxv) (S)—N-((3R,4S)-4-hydroxytetrahydrofuran-3-yl)-2-(4-oxo-8-(pyridin-3-yl)-6-(6-(trifluoromethyl) pyridin-3-yl) pyrido[3,4-d]pyrimidin-3 (4H)-yl) propanamide (clxxvi) 3-(2-hydroxy-2-methylpropyl)-8-(1H-pyrazol-4-yl)-6-(5-(trifluoromethyl) pyridin-2-yl) pyrido[3,4-d] pyrimidin-4 (3H)-one (clxxvii) (S)-6-(4-chlorophenyl)-3-(1-hydroxypropan-2-yl)-8-(1H-pyrazol-1-yl) pyrido[3,4-d]pyrimidin-4 (3H)-one (clxxviii) (S)-3-(1-hydroxypropan-2-yl)-8-(1H-pyrazol-1-yl)-6-(5-(trifluoromethyl) pyridin-2-yl) pyrido[3,4-d] pyrimidin-4 (3H)-one (clxxix) 3-((3S,4R)-4-hydroxytetrahydrofuran-3-yl)-8-(pyridin-3-yl)-6-(2-(trifluoromethyl) thiazol-5-yl) pyrido[3,4-d]pyrimidin-4 (3H)-one (clxxx) 3-(2-hydroxy-2-methylpropyl)-8-(1-methyl-1H-pyrazol-4-yl)-6-(2-(trifluoromethyl) thiazol-5-yl) pyrido[3,4-d]pyrimidin-4 (3H)-one (clxxxi) 3-((3S,4R)-4-hydroxytetrahydrofuran-3-yl)-8-(1-methyl-1H-pyrazol-4-yl)-6-(2-(trifluoromethyl) thiazol-5-yl) pyrido[3,4-d]pyrimidin-4 (3H)-one (clxxxii) 3-((3R,4S)-4-hydroxytetrahydrofuran-3-yl)-8-(1-methyl-1H-pyrazol-4-yl)-6-(2-(trifluoromethyl) thiazol-5-yl) pyrido[3,4-d]pyrimidin-4 (3H)-one (clxxxiii) 3-((3R,4S)-4-hydroxytetrahydrofuran-3-yl)-8-(pyridin-3-yl)-6-(2-(trifluoromethyl) thiazol-5-yl) pyrido[3,4-d]pyrimidin-4 (3H)-one (clxxxiv) (S)-3-(1-hydroxypropan-2-yl)-8-morpholino-6-(6-(trifluoromethyl) pyridin-3-yl) pyrido[3,4-d]pyrimidin-4 (3H)-one (clxxxv) 3-(2-hydroxy-2-methylpropyl)-8-(piperidin-1-yl)-6-(6-(trifluoromethyl) pyridin-3-yl) pyrido[3,4-d] pyrimidin-4 (3H)-one (clxxxvi) (S)-3-(1-hydroxypropan-2-yl)-6-(5-methylpyridin-2-yl)-8-(pyridin-3-yl) pyrido[3,4-d]pyrimidin-4 (3H)-one (clxxxvii) (S)-3-(1-hydroxypropan-2-yl)-6-(5-methylpyrimidin-2-yl)-8-(pyridin-3-yl) pyrido[3,4-d]pyrimidin-4 (3H)-one (clxxxviii) (S)-8-(cyclohex-1-en-1-yl)-3-(1-hydroxypropan-2-yl)-6-(5-(trifluoromethyl) pyridin-2-yl) pyrido [3,4-d]pyrimidin-4 (3H)-one (clxxxix) (S)-8-cyclohexyl-3-(1-hydroxypropan-2-yl)-6-(5-(trifluoromethyl) pyridin-2-yl) pyrido[3,4-d]pyrimidin-4 (3H)-one (cxc) (S)-3-(1-hydroxypropan-2-yl)-N,N-dimethyl-4-oxo-8-(pyridin-3-yl)-3,4-dihydropyrido[3,4-d]pyrimidine-6-carboxamide (cxci) (S)-3-(1-hydroxypropan-2-yl)-8-(1H-pyrazol-4-yl)-6-(5-(trifluoromethyl) pyridin-2-yl) pyrido[3,4-d] pyrimidin-4 (3H)-one (cxcii) (S)-3-(1-hydroxypropan-2-yl)-6-(2-methoxyethyl)-8-(pyridin-3-yl) pyrido[3,4-d]pyrimidin-4 (3H)-one (cxciii) (S)-3-(1-hydroxypropan-2-yl)-8-(2-methoxyethyl)-6-(5-(trifluoromethyl) pyridin-2-yl) pyrido[3,4-d]pyrimidin-4 (3H)-one.

17. A compound selected from the following structural formulas:

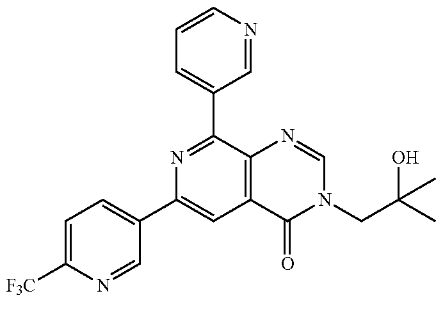 [SMILES: CC(C)(O)Cn1cnc2c(-c3cccnc3)nc(-c3ccc(C(F)(F)F)nc3)cc2c1=O]

(3-(2-hydroxy-2-methylpropyl)-8-(pyridin-3-yl)-6-(6-trifluoromethyl) pyridin-3-yl) pyrido[3,4-d]pyrimidin-4 (3H)-one),

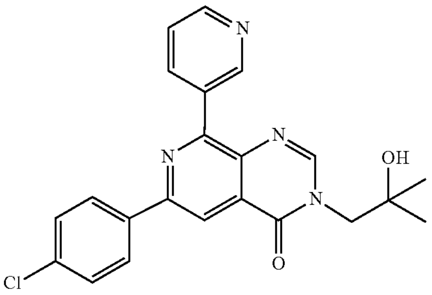 [SMILES: CC(C)(O)Cn1cnc2c(-c3cccnc3)nc(-c3ccc(Cl)cc3)cc2c1=O]

(6-(4-chlorophenyl)-3-(2-hydroxy-2-methylpropyl)-8-(pyridin-3-yl) pyrido[3,4-d]pyrimidin-4 (3H)-one);

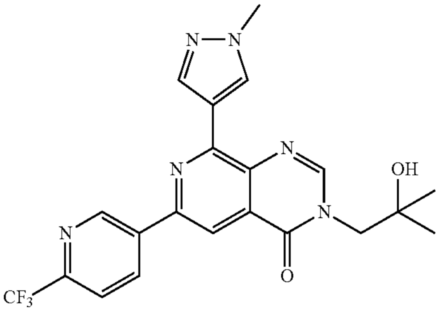

(3-(2-hydroxy-2-methylpropyl)-8-(1-methyl-1H-pyrazol-4-yl)-6-(6-(trifluoromethyl) pyridin-3-yl) pyrido[3,4-d] pyrimidin-4 (3H)-one);

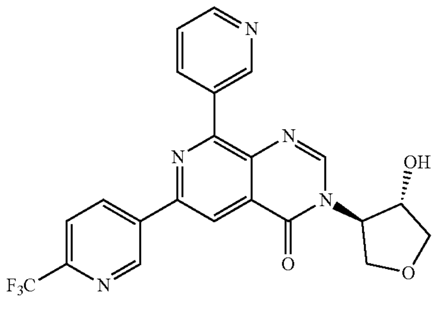 [SMILES: O=c1c2cc(-c3ccc(C(F)(F)F)nc3)nc(-c3cccnc3)c2ncn1[C@@H]1COC[C@H]1O]

(3-((3R,4S)-4-hydroxytetrahydrofuran-3-yl)-8-(pyridin-3-yl)-6-(6-(trifluoromethyl) pyridin-3-yl) pyrido[3,4-d] pyrimidin-4 (3H)-one);

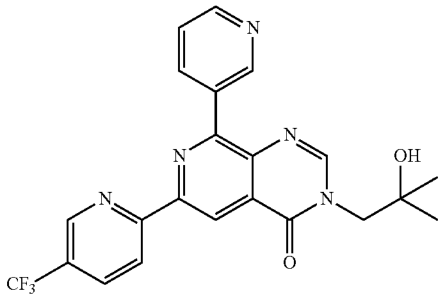 [SMILES: CC(C)(O)Cn1cnc2c(-c3cccnc3)nc(-c3ccc(C(F)(F)F)cn3)cc2c1=O]

(3-(2-hydroxy-2-methylpropyl)-8-(pyridin-3-yl)-6-(5-(trifluoromethyl) pyridin-2-yl) pyrido[3,4-d]pyrimidin-4 (3H)-one); or

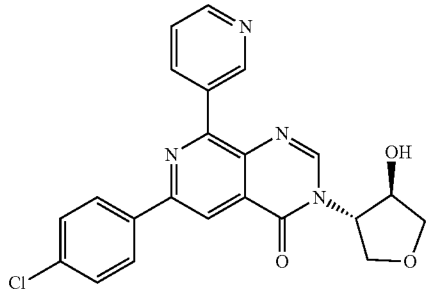 [SMILES: O=c1c2cc(-c3ccc(Cl)cc3)nc(-c3cccnc3)c2ncn1[C@H]1COC[C@@H]1O]

(6-(4-chlorophenyl)-3-((3S,4R)-4-hydroxytetrahydrofuran-3-yl)-8-(pyridin-3-yl) pyrido[3,4-d]pyrimidin-4 (3H)-one), or a pharmaceutically acceptable salt thereof.

18. A pharmaceutical composition comprising the compound of claim 1, or a pharmaceutically acceptable salt thereof, and at least one pharmaceutically acceptable excipient.

19. A method of treating a disease or condition mediated by AhR signaling or associated with aberrant AhR signaling in a subject in need thereof, comprising administering to the subject a therapeutically effective amount of the compound of claim 1 or a pharmaceutically acceptable salt thereof, wherein the disease or condition is selected from colorectal cancer, hepatocellular carcinoma, or liver cancer.

20. A method of inhibiting cancer cell proliferation mediated by AhR signaling in a subject in need thereof comprising administering to the subject a therapeutically effective amount of the compound of claim 1 or a pharmaceutically acceptable salt thereof, wherein the cancer is selected from colorectal cancer, hepatocellular carcinoma, or liver cancer.

21. A method of treating cancer in a subject in need thereof comprising administering to the subject a therapeutically effective amount of the compound of claim 1 or a pharmaceutically acceptable salt thereof wherein the compound, or pharmaceutically acceptable salt thereof, is administrable with at least one additional therapy, wherein the additional therapy is chosen from checkpoint inhibitors that target ligand for PD-1 (PD-L1) and the cancer is selected from colorectal cancer, hepatocellular carcinoma, or liver cancer.

22. The method of claim 21, wherein the checkpoint inhibitor that targets PD-L1 is an anti-PD-L1 antibody.

23. The method of claim 22, wherein the anti-PD-L1 antibody is selected from atezolizumab, avelumab, durvalumab, or KN035.

* * * * *